US011273168B2

(12) United States Patent
Ito et al.

(10) Patent No.: US 11,273,168 B2
(45) Date of Patent: *Mar. 15, 2022

(54) METHODS OF TREATING ANXIETY BY ADMINISTERING A SUBSTITUTED QUINOLONE

(71) Applicant: OTSUKA PHARMACEUTICAL CO., LTD., Tokyo (JP)

(72) Inventors: Nobuaki Ito, Osaka (JP); Hirofumi Sasaki, Osaka (JP); Kuninori Tai, Osaka (JP); Tomoichi Shinohara, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/820,652

(22) Filed: Mar. 16, 2020

(65) Prior Publication Data

US 2020/0281951 A1 Sep. 10, 2020

Related U.S. Application Data

(60) Continuation of application No. 16/118,376, filed on Aug. 30, 2018, now Pat. No. 10,603,331, which is a (Continued)

(30) Foreign Application Priority Data

Sep. 13, 2010 (JP) ................................ 2010-204747

(51) Int. Cl.

| | |
|---|---|
| *C07D 241/40* | (2006.01) |
| *A61K 31/695* | (2006.01) |
| *C07D 241/38* | (2006.01) |
| *C07D 243/10* | (2006.01) |
| *C07D 401/04* | (2006.01) |
| *C07D 403/04* | (2006.01) |
| *C07D 403/10* | (2006.01) |
| *C07D 405/04* | (2006.01) |
| *C07D 405/10* | (2006.01) |
| *C07D 409/04* | (2006.01) |
| *C07D 409/10* | (2006.01) |
| *C07D 413/10* | (2006.01) |
| *C07D 417/04* | (2006.01) |

(Continued)

(52) U.S. Cl.

CPC .......... *A61K 31/695* (2013.01); *A61K 31/498* (2013.01); *A61K 31/499* (2013.01); *A61K 31/501* (2013.01); *A61K 31/502* (2013.01); *A61K 31/506* (2013.01); *A61K 31/517* (2013.01); *A61K 31/538* (2013.01); *A61K 31/5377* (2013.01); *A61K 31/551* (2013.01); *A61K 31/5513* (2013.01); *C07D 241/38* (2013.01); *C07D 241/42* (2013.01); *C07D 243/10* (2013.01); *C07D 243/12* (2013.01); *C07D 401/04* (2013.01); *C07D 401/10* (2013.01); *C07D 403/04* (2013.01); *C07D 403/10* (2013.01); *C07D 405/04* (2013.01); *C07D 405/10* (2013.01); *C07D 409/04* (2013.01); *C07D 409/10* (2013.01); *C07D 413/10* (2013.01); *C07D 417/04* (2013.01); *C07D 417/10* (2013.01); *C07D 471/04* (2013.01); *C07D 491/04* (2013.01); *C07D 495/04* (2013.01); *C07D 498/04* (2013.01); *C07F 7/10* (2013.01); *C07F 7/1804* (2013.01); *Y02P 20/55* (2015.11)

(58) Field of Classification Search

CPC .................................................. C07D 241/40
USPC ........................................................ 544/353
See application file for complete search history.

(56) References Cited

FOREIGN PATENT DOCUMENTS

| | | |
|---|---|---|
| CA | 2093108 | 3/1993 |
| EP | 0 952 154 | 10/1999 |

(Continued)

OTHER PUBLICATIONS

English-language International Search Report from the European Patent Office, dated Dec. 14, 2011, for International Application No. PCT/JP2011/071174.

(Continued)

*Primary Examiner* — Douglas M Willis

(74) *Attorney, Agent, or Firm* — Finnegan, Henderson, Farabow, Garrett & Dunner, LLP

(57) ABSTRACT

A heterocyclic compound represented by the general formula (1) or a salt thereof:

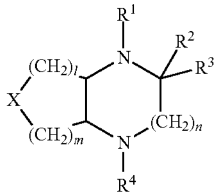

wherein m, l, and n respectively represent an integer of 1 or 2; X represents —O— or —$CH_2$—;

$R^1$ represents hydrogen, a lower alkyl group, a hydroxy-lower alkyl group, a protecting group, or a tri-lower alkylsilyloxy-lower alkyl group;

$R^2$ and $R^3$, which are the same or different, each independently represent hydrogen or a lower alkyl group; or $R_2$ and $R_3$ are bonded to form a cyclo-C3-C8 alkyl group; and $R^4$ represents an aromatic group or a heterocyclic group, wherein the aromatic or heterocyclic group may have one or more arbitrary substituent(s).

6 Claims, No Drawings

Related U.S. Application Data continuation of application No. 15/495,862, filed on Apr. 24, 2017, now Pat. No. 10,064,879, which is a continuation of application No. 14/705,870, filed on May 6, 2015, now abandoned, which is a division of application No. 13/822,589, filed as application No. PCT/JP2011/071174 on Sep. 12, 2011, now Pat. No. 9,090,572.

(51) Int. Cl.

| | |
|---|---|
| *C07D 417/10* | (2006.01) |
| *C07D 471/04* | (2006.01) |
| *C07D 491/04* | (2006.01) |
| *C07D 495/04* | (2006.01) |
| *C07F 7/10* | (2006.01) |
| *C07D 241/42* | (2006.01) |
| *C07D 243/12* | (2006.01) |
| *C07D 401/10* | (2006.01) |
| *C07D 498/04* | (2006.01) |
| *C07F 7/18* | (2006.01) |
| *A61K 31/498* | (2006.01) |
| *A61K 31/499* | (2006.01) |
| *A61K 31/501* | (2006.01) |
| *A61K 31/502* | (2006.01) |
| *A61K 31/506* | (2006.01) |
| *A61K 31/517* | (2006.01) |
| *A61K 31/5377* | (2006.01) |
| *A61K 31/538* | (2006.01) |
| *A61K 31/5513* | (2006.01) |
| *A61K 31/551* | (2006.01) |

(56) References Cited

FOREIGN PATENT DOCUMENTS

| | | |
|---|---|---|
| EP | 0 726 899 | 1/2000 |
| JP | 6-49074 | 2/1994 |
| JP | 2000-26385 | 1/2000 |
| JP | 2000-500775 | 1/2000 |
| SU | 390 391 | 7/1973 |
| WO | WO 97/25318 | 7/1997 |
| WO | WO 00/67735 | 11/2000 |
| WO | WO 2004/056784 | 7/2004 |
| WO | WO 2008/019372 | 2/2008 |
| WO | WO 2008/023239 | 2/2008 |
| WO | WO 2009/061879 | 5/2009 |
| WO | WO 2010/141540 | 12/2010 |

OTHER PUBLICATIONS

Giardina, D., et al., "Doxazosin-Related $\alpha_1$-Adrenoceptor Antagonists With Prostate Antitumor Activity", Journal Medicinal Chemistry, vol. 52, No. 15, 2009, pp. 4951-4954.
Giardina, D., et al., "Searching for cyclazosin analogues as $\alpha_{1B}$-adrenoceptor antagonists", IL Farmaco, vol. 58, 2003, pp. 477-487.
Miura, S., "Emergence of SNRI and its historical background", Japanese Journal of Clinical Psychopharmacology, vol. 3, pp. 311-318, (2000).
Regnier, et al. Journal of Medicinal Chemistry, 15, 1972, 295-301.
Sagratini, G., et al., "Synthesis and $\alpha_1$-adrenoceptor antagonist activity of derivatives and isosters of the furan portion of (+)-cyclazosin", Bioorganic & Medicinal Chemistry, vol. 15, No. 6, 2007, pp. 2334-2345.
Savel'ev, V., et al., "Synthesis and Pharmacological Activity of 4-Amino-3-Nitrocoumarins", Pharmaceutical Chemistry Journal, vol. 9. No. 6, 1975, pp. 360-362.
Skolnick, P., "Antidepressants for the new millennium", European Journal of Pharmacology, vol. 375, 1999, pp. 31-40.

METHODS OF TREATING ANXIETY BY ADMINISTERING A SUBSTITUTED QUINOLONE

This application is a continuation of application Ser. No. 16/118,376, filed Aug. 30, 2018, now U.S. Pat. No. 10,603,331, issued Mar. 31, 2020, which is a continuation of application Ser. No. 15/495,862, filed Apr. 24, 2017, now U.S. Pat. No. 10,064,879, issued Sep. 4, 2018, which is a continuation of application Ser. No. 14/705,870, filed May 6, 2015, abandoned, which is a divisional of application Ser. No. 13/822,589, filed May 29, 2013, now U.S. Pat. No. 9,090,572, issued Jul. 28, 2015, which is a National Stage of PCT/JP2011/071174, filed Sep. 12, 2011, and claims foreign priority to JP 2010-204747, filed Sep. 13, 2010, all of which are incorporated herein by reference.

TECHNICAL FIELD

The present invention relates to a novel heterocyclic compound.

BACKGROUND ART

Three monoamines known as serotonin, norepinephrine, and dopamine function as neurotransmitters in vivo. Therefore, drugs having inhibitory effects on the reuptake of these monoamines have been used widely as therapeutic drugs for diseases associated with the central or peripheral nervous system.

Most of drugs previously used in the treatment of depression selectively inhibit the reuptake of norepinephrine or serotonin. Examples of such drugs include imipramine (first-generation antidepressant), maprotiline (second-generation antidepressant), selective serotonin reuptake inhibitors (SSRIs, third-generation antidepressants) typified by fluoxetine, and serotonin and/or norepinephrine reuptake inhibitors (SNRIs, fourth-generation antidepressants) typified by venlafaxine (S. Miura, Japanese Journal of Clinical Psychopharmacology, 2000, 3: 311-318).

However, all of these drugs require a period as long as 3 weeks or longer for exerting their therapeutic effects and, in addition, fail to exert sufficient therapeutic effects on approximately 30% of patients with depression (Phil Skolnick, European Journal of Pharmacology, 1999, 375: 31-40).

DISCLOSURE OF INVENTION

An object of the present invention is to provide a drug that has a wide therapeutic spectrum and can exert sufficient therapeutic effects in a short period, compared with antidepressants known in the art.

The present inventors have conducted diligent studies to attain the object and have consequently found that a heterocyclic compound represented by the general formula (1) shown below can be used in the production of the desired drug. The present invention has been completed based on these findings.

The present invention provides a heterocyclic compound or a salt thereof according to any one of Items 1 to 15 shown below, a pharmaceutical composition comprising the compound or an use of the compounds, a method for treating or preventing diseases or a methods for producing the compounds.

Item 1. A heterocyclic compound represented by the general formula (1) or a salt thereof:

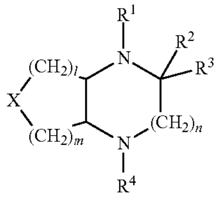

wherein m, l, and n respectively represent an integer of 1 or 2; X represents —O— or —$CH_2$—;

$R^1$ represents hydrogen, a lower alkyl group, a hydroxy-lower alkyl group, a protecting group, or a tri-lower alkylsilyloxy-lower alkyl group;

$R^2$ and $R^3$, which are the same or different, each independently represent hydrogen or a lower alkyl group; or $R_2$ and $R_3$ are bonded to form a cyclo-C3-C8 alkyl group; and $R^4$ represents an aromatic group or a heterocyclic group, wherein the aromatic or heterocyclic group may have one or more arbitrary substituent(s).

Item 2. The heterocyclic compound represented by the general formula (1) or a salt thereof according to item 1, wherein $R^4$ represents any of (1) a phenyl group,
(2) an indolyl group,
(3) a benzothienyl group,
(4) a naphthyl group,
(5) a benzofuryl group,
(6) a quinolyl group,
(7) an isoquinolyl group,
(8) a pyridyl group,
(9) a thienyl group,
(10) a dihydrobenzoxazinyl group,
(11) a dihydrobenzodioxinyl group,
(12) a dihydroquinolyl group,
(13) a chromanyl group,
(14) a quinoxalinyl group,
(15) a dihydroindenyl group,
(16) a dihydrobenzofuryl group,
(17) a benzodioxolyl group,
(18) an indazolyl group,
(19) a benzothiazolyl group,
(20) an indolinyl group,
(21) a thienopyridyl group,
(22) a tetrahydrobenzazepinyl group,
(23) a tetrahydrobenzodiazepinyl group,
(24) a dihydrobenzodioxepinyl group,
(25) a fluorenyl group,
(26) a pyridazinyl group,
(27) a tetrahydroquinolyl group,
(28) a carbazolyl group,
(29) a phenanthryl group,
(30) a dihydroacenaphthylenyl group,
(31) a pyrrolopyridyl group,
(32) an anthryl group,
(33) a benzodioxinyl group,
(34) a pyrrolidinyl group,
(35) a pyrazolyl group,
(36) an oxadiazolyl group,
(37) a pyrimidinyl group,
(38) a tetrahydronaphthyl group,

(39) a dihydroquinazolinyl group,
(40) a benzoxazolyl group,
(41) a thiazolyl group,
(42) a quinazolinyl group,
(43) a phthalazinyl group,
(44) a pyrazinyl group, and
(45) a chromenyl group, wherein
these aromatic or heterocyclic groups may have one or more substituent(s) selected from
(1-1) a halogen atom,
(1-2) a lower alkyl group,
(1-3) a lower alkanoyl group,
(1-4) a halogen-substituted lower alkyl group,
(1-5) a halogen-substituted lower alkoxy group,
(1-6) a cyano group,
(1-7) a lower alkoxy group,
(1-8) a lower alkylthio group,
(1-9) an imidazolyl group,
(1-10) a tri-lower alkylsilyl group,
(1-11) an oxadiazolyl group which may have a lower alkyl group(s),
(1-12) a pyrrolidinyl group which may have an oxo group(s),
(1-13) a phenyl group which may have a lower alkoxy group(s),
(1-14) a lower alkylamino-lower alkyl group,
(1-15) an oxo group,
(1-16) a pyrazolyl group which may have a lower alkyl group(s),
(1-17) a thienyl group,
(1-18) a furyl group,
(1-19) a thiazolyl group which may have a lower alkyl group(s),
(1-20) a lower alkylamino group,
(1-21) a pyrimidyl group which may have a lower alkyl group(s),
(1-22) a phenyl-lower alkenyl group,
(1-23) a phenoxy group which may have a halogen atom(s),
(1-24) a phenoxy-lower alkyl group,
(1-25) a pyrrolidinyl-lower alkoxy group,
(1-26) a lower alkylsulfamoyl group,
(1-27) a pyridazinyloxy group which may have a lower alkyl group(s),
(1-28) a phenyl-lower alkyl group,
(1-29) a lower alkylamino-lower alkoxy group,
(1-30) an imidazolyl-lower alkyl group,
(1-31) a phenyl-lower alkoxy group,
(1-32) a hydroxy group,
(1-33) a lower alkoxycarbonyl group,
(1-34) a hydroxy-lower alkyl group,
(1-35) an oxazolyl group,
(1-36) a piperidyl group,
(1-37) a pyrrolyl group,
(1-38) a morpholinyl-lower alkyl group,
(1-39) a piperazinyl-lower alkyl group which may have a lower alkyl group(s),
(1-40) a piperidyl-lower alkyl group,
(1-41) a pyrrolidinyl-lower alkyl group,
(1-42) a morpholinyl group, and
(1-43) a piperazinyl group which may have a lower alkyl group(s).

Item 3. The heterocyclic compound represented by the general formula (1) or a salt thereof according to item 2, wherein
$R^4$ represents any of
(1) a phenyl group,
(2) an indolyl group,
(3) a benzothienyl group,
(4) a naphthyl group,
(5) a benzofuryl group,
(6) a quinolyl group,
(7) an isoquinolyl group,
(8) a pyridyl group,
(9) a thienyl group,
(10) a dihydrobenzoxazinyl group,
(11) a dihydrobenzodioxinyl group,
(12) a dihydroquinolyl group,
(13) a chromanyl group,
(14) a quinoxalinyl group,
(15) a dihydroindenyl group,
(16) a dihydrobenzofuryl group,
(17) a benzodioxolyl group,
(18) an indazolyl group,
(19) a benzothiazolyl group,
(20) an indolinyl group,
(21) a thienopyridyl group,
(22) a tetrahydrobenzazepinyl group,
(23) a tetrahydrobenzodiazepinyl group,
(24) a dihydrobenzodioxepinyl group,
(25) a fluorenyl group,
(26) a pyridazinyl group,
(27) a tetrahydroquinolyl group,
(28) a carbazolyl group,
(29) a phenanthryl group,
(30) a dihydroacenaphthylenyl group,
(31) a pyrrolopyridyl group,
(32) an anthryl group,
(33) a benzodioxinyl group,
(34) a pyrrolidinyl group,
(35) a pyrazolyl group,
(36) an oxadiazolyl group,
(37) a pyrimidinyl group,
(38) a tetrahydronaphthyl group,
(39) a dihydroquinazolinyl group,
(40) a benzoxazolyl group,
(41) a thiazolyl group,
(42) a quinazolinyl group,
(43) a phthalazinyl group,
(44) a pyrazinyl group, and
(45) a chromenyl group, wherein
these aromatic or heterocyclic groups may have 1 to 4 substituent(s) selected from
(1-1) a halogen atom,
(1-2) a lower alkyl group,
(1-3) a lower alkanoyl group,
(1-4) a halogen-substituted lower alkyl group,
(1-5) a halogen-substituted lower alkoxy group,
(1-6) a cyano group,
(1-7) a lower alkoxy group,
(1-8) a lower alkylthio group,
(1-9) an imidazolyl group,
(1-10) a tri-lower alkylsilyl group,
(1-11) an oxadiazolyl group which may have 1 lower alkyl group,
(1-12) a pyrrolidinyl group which may have 1 oxo group,
(1-13) a phenyl group which may have 1 lower alkoxy group,
(1-14) a lower alkylamino-lower alkyl group,
(1-15) an oxo group,
(1-16) a pyrazolyl group which may have 1 lower alkyl group,
(1-17) a thienyl group,
(1-18) a furyl group,
(1-19) a thiazolyl group which may have 1 lower alkyl group, (1-20) a lower alkylamino group,
(1-21) a pyrimidyl group which may have 1 lower alkyl group,
(1-22) a phenyl-lower alkenyl group,
(1-23) a phenoxy group which may have 1 halogen atom,
(1-24) a phenoxy-lower alkyl group,
(1-25) a pyrrolidinyl-lower alkoxy group,
(1-26) a lower alkylsulfamoyl group,
(1-27) a pyridazinyloxy group which may have 1 lower alkyl group,
(1-28) a phenyl-lower alkyl group,
(1-29) a lower alkylamino-lower alkoxy group,
(1-30) an imidazolyl-lower alkyl group,
(1-31) a phenyl-lower alkoxy group,
(1-32) a hydroxy group,
(1-33) a lower alkoxycarbonyl group,
(1-34) a hydroxy-lower alkyl group,
(1-35) an oxazolyl group,
(1-36) a piperidyl group,
(1-37) a pyrrolyl group,
(1-38) a morpholinyl-lower alkyl group,
(1-39) a piperazinyl-lower alkyl group which may have 1 lower alkyl group,
(1-40) a piperidyl-lower alkyl group,
(1-41) a pyrrolidinyl-lower alkyl group,
(1-42) a morpholinyl group, and
(1-43) a piperazinyl group which may have 1 lower alkyl group.

Item 4. The heterocyclic compound represented by the general formula (1) or a salt thereof according to item 3, wherein
m represents 2; l and n respectively represent an integer of 1; X represents $—CH_2—$;
$R^1$ represents hydrogen, a lower alkyl group, a hydroxy-lower alkyl group, a benzyl group, or
a tri-lower alkylsilyloxy-lower alkyl group; and
$R^4$ represents any of
(1) a phenyl group,
(2) an indolyl group,
(4) a naphthyl group,
(5) a benzofuryl group, and
(31) a pyrrolopyridyl group, wherein
these aromatic or heterocyclic groups may have 1 to 4 substituent(s) selected from
(1-1) a halogen atom,
(1-2) a lower alkyl group,
(1-3) a lower alkanoyl group,
(1-4) a halogen-substituted lower alkyl group,
(1-5) a halogen-substituted lower alkoxy group,
(1-6) a cyano group,
(1-7) a lower alkoxy group,
(1-8) a lower alkylthio group,
(1-9) an imidazolyl group,
(1-10) a tri-lower alkylsilyl group,
(1-11) an oxadiazolyl group which may have 1 lower alkyl group,
(1-12) a pyrrolidinyl group which may have 1 oxo group,
(1-13) a phenyl group which may have 1 lower alkoxy group,
(1-14) a lower alkylamino-lower alkyl group,
(1-15) an oxo group,
(1-16) a pyrazolyl group which may have 1 lower alkyl group,
(1-17) a thienyl group,
(1-18) a furyl group,
(1-19) a thiazolyl group which may have 1 lower alkyl group,
(1-20) a lower alkylamino group,
(1-21) a pyrimidyl group which may have 1 lower alkyl group,
(1-22) a phenyl-lower alkenyl group,
(1-23) a phenoxy group which may have 1 halogen atom,
(1-24) a phenoxy-lower alkyl group,
(1-25) a pyrrolidinyl-lower alkoxy group,
(1-26) a lower alkylsulfamoyl group,
(1-27) a pyridazinyloxy group which may have 1 lower alkyl group,
(1-28) a phenyl-lower alkyl group,
(1-29) a lower alkylamino-lower alkoxy group,
(1-30) an imidazolyl-lower alkyl group,
(1-31) a phenyl-lower alkoxy group,
(1-32) a hydroxy group,
(1-34) a hydroxy-lower alkyl group,
(1-35) an oxazolyl group,
(1-36) a piperidyl group,
(1-37) a pyrrolyl group,
(1-38) a morpholinyl-lower alkyl group,
(1-39) a piperazinyl-lower alkyl group which may have a lower alkyl group(s),
(1-40) a piperidyl-lower alkyl group,
(1-41) a pyrrolidinyl-lower alkyl group,
(1-42) a morpholinyl group, and
(1-43) a piperazinyl group which may have 1 lower alkyl group.

Item 5. The heterocyclic compound represented by the general formula (1) or a salt thereof according to item 4, wherein
$R^1$ represents hydrogen;
$R^2$ and $R^3$, which are the same or different, each independently represent a lower alkyl group; or $R^2$ and $R^3$ are bonded to form a cyclo-C3-C8 alkyl group; and
$R^4$ represents any of
(1) a phenyl group,
(2) an indolyl group,
(4) a naphthyl group,
(5) a benzofuryl group, and
(31) a pyrrolopyridyl group, wherein
these aromatic or heterocyclic groups may have 1 to 2 substituent(s) selected from
(1-1) a halogen atom,
(1-2) a lower alkyl group,
(1-5) a halogen-substituted lower alkoxy group,
(1-6) a cyano group, and
(1-7) a lower alkoxy group.

Item 6. The heterocyclic compound represented by the general formula (1) or a salt thereof according to item 5, which is selected from
(4aS,8aR)-1-(4-chlorophenyl)-3,3-dimethyldecahydroquinoxaline,
2-chloro-4-((4aS,8aS)-3,3-dimethyloctahydroquinoxalin-1(2H)-yl)benzonitrile
(4aS,8aR)-1-(3-chloro-4-fluorophenyl)-3,3-dimethyldecahydroquinoxaline,
(4aS,8aR)-1-(7-fluorobenzofuran-4-yl)-3,3-dimethyldecahydroquinoxaline,
5-((4aR,8aS)-3,3-dimethyloctahydroquinoxalin-1(2H)-yl)-1-methyl-1H-indole-2-carbonitrile
(4a'R,8a'S)-4'-(7-methoxybenzofuran-4-yl)octahydro-1'H-spiro[cyclobutane-1,2'-quinoxaline],
(4aS,8aR)-2-(6,7-diflurobenzofuran-4-yl)-3,3-dimethyldecahydroquinoxaline,
5-((4aS,8aS)-3,3-dimethyloctahydroquinoxalin-1(2H)-yl)-1H-indole-2-carbonitrile, (4aS,8aR)-1-(7-chloro-2,3-dihydro-1H-inden-4-yl)-3,3-dimethyldecahydroquinoxaline, 6-((4aS,8aS)-3,3-dimethyloctahydroquinoxalin-1(2H)-yl)-2-naphthonitrile, (4aS,8aS)-3,3-dimethyl-1-(1H-pyrrolo[2,3-b]pyridin-4-yl)decahydroquinoxaline, and (4aS,8aS)-1-(4-(difluoromethoxy)-3-fluorophenyl)-3,3-dimethyldecahydroquinoxaline.

Item 7. A pharmaceutical composition comprising a heterocyclic compound represented by the general formula (1) or a salt thereof according to item 1 as an active ingredient and a pharmaceutically acceptable carrier.

Item 8. A prophylactic and/or therapeutic agent for disorders caused by reduced neurotransmission of serotonin, norepinephrine or dopamine, comprising as an active ingredient a heterocyclic compound of general formula (I) or a salt thereof according to item 1.

Item 9. a prophylactic and/or therapeutic agent according to item 8, wherein the disorder is selected from the group consisting of depression, depression status caused by adjustment disorder, anxiety caused by adjustment disorder, anxiety caused by various diseases, generalized anxiety disorder, phobia, obsessive-compulsive disorder, panic disorder, posttraumatic stress disorder, acute stress disorder, hypochondria, dissociative amnesia, avoidant personality disorder, body dysmorphic disorder, eating disorder, obesity, chemical dependence, pain, fibromyalgia, Alzheimer's disease, memory deficit, Parkinson's disease, restless leg syndrome, endocrine disorder, vasospasm, cerebellar ataxia, gastrointestinal disorder, negative syndrome of schizophrenia, premenstrual syndrome, stress urinary incontinence, Tourette's disorder, attention deficit hyperactivity disorder (ADHD), autism, Asperger syndrome, impulse control disorder, trichotillomania, kleptomania, gambling disorder, cluster headache, migraine, chronic paroxysmal hemicrania, chronic fatigue syndrome, precocious ejaculation, male impotence, narcolepsy, primary hypersomnia, cataplexy, sleep apnea syndrome and headache.

Item 10. a prophylactic and/or therapeutic agent according to item 9, wherein the depression is selected from the group consisting of major depressive disorder; bipolar I disorder; bipolar II disorder; mixed state; dysthymic disorder; rapid cycler; atypical depression; seasonal affective disorder; postpartum depression; hypomelancholia; recurrent brief depressive disorder; refractory depression; chronic depression; double depression; alcohol-induced mood disorder; mixed anxiety-depressive disorder; depression caused by various physical diseases such as Cushing('s) syndrome, hypothyroidism, hyperparathyroidism, Addison's disease, amenorrhea-galactorrhea syndrome, Parkinson's disease, Alzheimer's disease, cerebrovascular dementia, brain infarct, brain hemorrhage, subarachnoid hemorrhage, diabetes millitus, virus infection, multiple sclerosis, chronic fatigue syndrome, coronary artery disease, pain, cancer, etc.; presenile depression; senile depression; depression in children and adolescents; depression induced by drugs such as interferon, etc.

Item 11. A prophylactic and/or therapeutic agent according to item 9, wherein the anxiety caused by various diseases is selected from the group consisting of anxiety caused by head injury, brain infection, inner ear impairment, cardiac failure, cardiac dysrhythmia, hyperadrenalism, hyperthyroidism, asthma and chronic obstructive pulmonary disease.

Item 12. A prophylactic and/or therapeutic agent according to item 9, wherein the pain is selected from the group consisting of chronic pain, psychogenic pain, neuropathic pain, phantom limb pain, postherpetic neuralgia, traumatic cervical syndrome, spinal cord injury pain, trigeminal neuralgia, diabetic neuropathy.

Item 13. Use of a heterocyclic compound of the general formula (1) or a salt thereof according to any one of items 1 to 6 as a drug.

Item 14. Use of a heterocyclic compound of the general formula (1) or a salt thereof according to any one of items 1 to 6 as a serotonine reuptake inhibitor and/or a norepinephrine reuptake inhibitor and/or a dopamine reuptake inhibitor.

Item 15. A method for treating and/or preventing disorders caused by reduced neurotransmission of serotonin, norephnephrine or dopamine, comprising administering a heterocyclic compound of general formula (1) or a salt thereof according to items 1 to 6 to a human or an animal.

Item 16. A process for producing a heterocyclic compound of general formula (1):

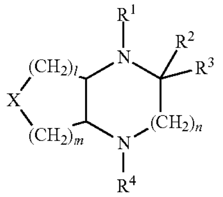

or salts thereof, wherein m, l and n respectively represent an integer of 1 or 2; X, $R^1$, $R^2$, and $R^3$ are defined in the above in item 1, the process comprising reacting the compound represented by the general formula;

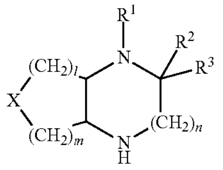

wherein m, l and n respectively represent an integer of 1 or 2; X, $R^1$, $R^2$, and $R^3$ are defined in the above in item 1 and the compound represented by the general formula;

$R^4$—$X_1$ wherein $R^4$ and $X^1$ are defined in the below.

Each group shown in the general formula is specifically as shown below.

The term "lower" means a group having 1 to 6 (preferably 1 to 4, more preferably 1 to 3) carbon atoms, unless otherwise specified.

A heterocyclic ring group includes saturated or unsaturated monocyclic or polycyclic heterocyclic rings comprising at least one hetero atoms selected from an oxygen atom(s), a sulfur atom(s) and nitrogen atom(s). More preferably, it includes the following heterocyclic ring:

3 to 8 unsaturated-membered, preferably 5 or 6-membered heteromonocyclic ring containing 1 to 4 nitrogen atoms, for example, pyrrolyl, pyrroliny, imidazolyl, pyrazolyl, pyridyl groups and N-oxide thereof, pyrimidinyl, pyrazinyl, pyridazinyl, triazolyl (e.g., 4H-1, 2, 4-triazolyl, 1H-1, 2, 3-triazolyl, 2H-1, 2, 3-triazolyl groups etc.), tetrazolyl group (e.g., 1H-tetrazolyl, 2H-tetrazolyl groups, etc.), dihydrotriazinyl (e.g., 4, 5-dihydro-1, 2, 4-triazinyl, 2, 5-dihydro-1, 2, 4-triazinyl groups) groups, etc. can be mentioned. Preferably, imidazolyl, pyridazinyl, pyridyl, pyrazinyl, pyrimidinyl, pyrazolyl groups, etc. can be mentioned.

3 to 8-membered, preferably 5 or 6-membered unsaturated heteromonocyclic ring containing 1 to 4 nitrogen atoms, for example, azetidinyl, pyrrolidinyl, imidazolidinyl, piperidinyl, pyrazolidinyl, pyperazinyl groups, etc. can be mentioned. Preferably, pyrrolidinyl group can be mentioned.

7 to 12-membered partially saturated or unsaturated condensed hetero ring group containing 1 to 5 nitrogen atoms, for example, indolyl, dihydroindolyl, (e.g., 2, 3-dihydro-1H-dihydroindolyl group, etc.), isoindolyl, indolizinyl, benzimidazolyl, quinolyl, isoquinolyl, dihydroisoquinolyl (e.g., 3, 4-dihydro-1H-isoquinolyl group, etc.), tetrahydroquinolyl, tetrahydroisoquinolyl (e.g., 1, 2, 3, 4-tetrahydro-1H-isoquinolyl, 5, 6, 7, 8-tetrahydroisoquinolyl groups, etc.), carbostyril, dihydrocarbostyril (e.g., 3, 4-dihydrocarbostyril group, etc.), indazolyl, benzotriazolyl, tetrazolopyridyl, tetrazolopyridazinyl (e.g., tetrazolo[, 5-b]pyridazinyl group, etc.), dihydrotriazolopyridazinyl, imidazopyridyl (e.g., imidazo[1, 2-a]pyridyl group, etc.), naphthyridyl, cinnolinyl, quinoxalinyl, pyrazolopyridyl (e.g., pyrazolo[2, 3-a]pyridyl group, etc.), pyrrolopyridyl, carbazolyl, Indolinyl, tetrahydrobenzodiazepinyl, tetrahydrobenzoazepinyl, quinazolinyl, phthalazinyl groups, etc. can be mentioned. Preferably, quinolyl, isoquinolyl, quinoxalinyl, indolyl, indazolyl, pyrrolopyridyl, tetrahydroquinolyl, carbazolyl, indolinyl, quinazolyl, phthalazinyl, tetrahydrobenzodiazepinyl, or tetrahydrobenzoazepinyl groups, etc. can be mentioned.

3 to 8 membered, preferably 5 or 6 membered unsaturated heteromono ring containing 1 to 2 oxygen atoms, for example, furyl group, etc. can be mentioned.

7 to 12-membered partially saturated or unsaturated condensed hetero ring group containing 1 to 3 oxygen atoms, for example, benzofuryl, dihydrobenzofuyl (e.g., 2, 3-dihydrobenzo [b] furyl group, etc.), chromanyl, benzodioxanyl (e.g., 1,4-benzodioxanyl group, etc.), dihydrobenzoxadinyl (e.g, 2, 3-dihydrobenzo-1,4-oxadinyl), benzodioxolyl (e.g., benzo[1,3] dioxolyl group, etc.), benzodioxynyl, dihydrobenzodioxynyl, dihydrobenzodioxepinyl groups, etc. can be mentioned. Preferably, benzofuryl, benzodioxynyl, benzodioxolyl, dihydrobenzofuryl, dihydrobenzodioxepinyl, dihydrobenzodioxsepinylyl, chromenyl, or chromanyl groups can be mentioned.

3 to 8-membered, preferably 5 or 6-membered unsaturated heteromonocyclic ring containing 1 to 2 oxygen atoms and 1 to 3 nitrogen atoms, for example, oxazolyl, isoxazolyl, oxadiazolyl (e.g., 1, 2, 4-oxadiazolyl, 1, 3, 4-oxadiazoyl, 1, 2, 5-oxadiazoyl groups, etc.) groups, etc. can be mentioned. Preferably, oxazolyl, oxadiazolyl groups can be mentioned.

3 to 8-membered, preferably 5 or 6-membered saturated heteromonocyclic ring containing 1 to 2 oxygen atoms and 1 to 3 nitrogen atoms, for example, morpholinyl group, etc. can be mentioned.

7 to 12-membered partially saturated or unsaturated condensed hetero ring containing 1 to 2 oxygen atoms and 1 to 3 nitrogen atoms, for example, benzoxazoly, benzoxazdiazolyl, benzisoxazolyl, furopyridyl (e.g., furo[2, 3-b] pyridyl, furo[3, 2-c]pyridyl groups, etc.), dihydrobenzoxadinyl groups, etc. can be mentioned. Preferably, benzoxazolyl, dihydrobenzoxadinyl groups can be mentioned.

3 to 8-membered, preferably 5 or 6-membered unsaturated heteromonocyclic ring containing 1 to 2 sulfur atoms and 1 to 3 nitrogen atoms, for example, thiazolyl, 1, 2-thiazolyl, thiazolynyl, thiadiazolyl (e.g., 1,2,4-tiadiazolyl, 1,3, 4-thiadiazolyl, 1,2,5-thiadiazolyl, 1, 2, 3-thiadiazolyl groups, etc.) groups, etc. can be mentioned. Preferably, thiazolyl group can be mentioned.

3 to 8-membered, preferably, 5 or 6-membered saturated heteromonocyclic ring containing 1 to 2 sulfur atoms and 1 to 3 nitrogen atoms, for example, thiazolydinyl group, etc. can be mentioned.

3 to 8-membered, preferably, 5 or 6-membered unsaturated heteromonocyclic ring containing 1 sulfur atom, for example, thienyl group, etc. can be mentioned.

7 to 12-membered unsaturated condensed hetero ring containing 1 to 3 sulfur atoms, for example, benzothienyl group (e.g., benzo [b] thienyl group, etc.), etc. can be mentioned.

7 to 12-membered partially saturated or unsaturated condensed hetero ring group containing 1 to 2 sulfur atoms and 1 to 3 nitrogen atoms, for example, benzothiazolyl, benzothadiazolyl, thienopyridyl (e.g., thieno[2, 3-b] pyridyl, thieno[2, 3-c] pyridyl, thieno[3, 2-c]pyridyl groups, etc.), imidazothiazolyl (e.g., imidazo[2, 1-b] thiazolyl group, etc.), dihydroimidazothiazolyl (e.g., 2, 3-dihydroimidazo[2, 1-b] thiazolyl group, etc.), thienopyradinyl (e.g., thieno[2, 3-b] pyradinyl group, etc.), groups, etc. can be mentioned. Preferably, thienopyridyl or benzothiazolyl groups can be mentioned.

The above heterocyclic ring can be substituted by one or more optional substituents.

As an aromatic ring, it includes, for example, $C_{6-14}$ aryl groups can be mentioned. The preferable examples of the aryl groups are a phenyl, naphthyl, anthryl, phenanthryl, acenaphthylenyl, biphenyl, indenyl groups. Among them, phenyl, naphtyl, anthryl, phenanthryl groups are preferable. The aryl groups can be partially saturated. As the partially unsaturated aryl groups are, for example, dihydroindenyl, fluorenyl, dihydroacenaphthylenyl, tetrahydronaphthyl groups. Here, the above heterocyclic rings can be substituted by one or more optional substituents.

As a saturated hydrocarbon group, it includes, for example, lower alkyl, cyclo C3-C8 alkyl groups, etc.

As an unsaturated hydrocarbon group, it includes, for example, lower alkenyl, lower alkynyl, phenyl groups, etc.

A characteristic group is a generic term used to refer to groups bind directly to a mother structure other than a carbon-carbon binding (atoms or atomic groups other than hydrogen), and —C≡N and >C═X (X=O, S, Se, Te, NH, NR). As the characteristic group, it includes, for example, carboxy, carbamoyl, cyano, hydroxy, amino groups, etc.

The optional substituents are the above heterocyclic rings, aromatic ring groups, saturated hydrocarbon groups, unsaturated hydrocarbon groups, characteristic groups, etc. Preferably, the substituents (1-1) to (1-43) described in item 2 above can be mentioned.

Examples of the lower alkyl group can include linear or branched alkyl groups having 1 to 6 carbon atoms (preferably 1 to 4 carbon atoms), unless otherwise specified. More specifically, it includes methyl, ethyl, n-propyl, isopropyl, n-butyl, isobutyl, tert-butyl, sec-butyl, n-pentyl, 1-ethylpropyl, isopentyl, neopentyl, n-hexyl, 1,2,2-trimethylpropyl, 3,3-dimethylbutyl, 2-ethylbutyl, isohexyl, and 3-methylpentyl groups, etc.

Examples of a lower alkoxy group can include linear or branched alkoxy groups having 1 to 6 carbon atoms (preferably 1 to 4 carbon atoms), unless otherwise specified. More specifically, it includes methoxy, ethoxy, n-propoxy, isopropoxy, n-butoxy, isobutoxy, tert-butoxy, sec-butoxy, n-pentyloxy, 1-ethylpropoxy, isopentyloxy, neopentyloxy, n-hexyloxy, 1,2,2-trimethylpropoxy, 3,3-dimethylbutoxy, 2-ethylbutoxy, isohexyloxy, and 3-methylpentyloxy groups, etc.

Examples of a halogen atom include fluorine, chlorine, bromine, and iodine atoms, unless otherwise specified.

Examples of a halogen-substituted lower alkyl group can include the lower alkyl groups exemplified above which are substituted by 1 to 7 (more preferably 1 to 3) halogen atoms, unless otherwise specified. More specifically, it includes fluoromethyl, difluoromethyl, trifluoromethyl, chloromethyl, dichloromethyl, trichloromethyl, bromomethyl, dibromomethyl, dichlorofluoromethyl, 2,2-difluoroethyl, 2,2,2-trifluoroethyl, pentafluoroethyl, 2-fluoroethyl, 2-chloroethyl, 3,3,3-trifluoropropyl, heptafluoropropyl, 22,3,3,3-pentafluoropropyl, heptafluoroisopropyl, 3-chloropropyl, 2-chloropropyl, 3-bromopropyl, 4,4,4-trifluorobutyl, 4,4,4,3,3-pentafluorobutyl, 4-chlorobutyl, 4-bromobutyl, 2-chlorobutyl, 5,5,5-trifluoropentyl, 5-chloropentyl, 6,6,6-trifluorohexyl, 6-chlorohexyl, and perfluorohexyl groups, etc.

Examples of a halogen-substituted lower alkoxy group can include the lower alkoxy groups exemplified above which are substituted by 1 to 7 (preferably 1 to 3) halogen atoms, unless otherwise specified. More specifically, it includes fluoromethoxy, difluoromethoxy, trifluoromethoxy, chloromethoxy, dichloromethoxy, trichloromethoxy, bromomethoxy, dibromomethoxy, dichlorofluoromethoxy, 2,2-difluoroethoxy, 2,2,2-trifluoroethoxy, pentafluoroethoxy, 2-fluoroethoxy, 2-chloroethoxy, 3,3,3-trifluoropropoxy, heptafluoropropoxy, heptafluoroisopropoxy, 3-chloropropoxy, 2-chloropropoxy, 3-bromopropoxy, 4,4,4-trifluorobutoxy, 4,4,4,3,3-pentafluorobutoxy, 4-chlorobutoxy, 4-bromobutoxy, 2-chlorobutoxy, 5,5,5-trifluoropentyloxy, 5-chloropentyloxy, 6,6,6-trifluorohexyloxy, 6-chlorohexyloxy, and perfluorohexyloxy groups, etc.

Examples of a cyclo-C3-C8 alkyl group include cyclopropyl, cyclobutyl, cyclopentyl, cyclohexyl, cycloheptyl, and cyclooctyl groups, etc., unless otherwise specified.

Examples of a lower alkanoyl group can include linear or branched alkanoyl groups having 1 to 6 carbon atoms (preferably 1 to 4 carbon atoms), unless otherwise specified. More specifically, it includes formyl, acetyl, propionyl, butyryl, isobutyryl, pentanoyl, tert-butylcarbonyl, and hexanoyl groups, etc.

Examples of a lower alkylthio group can include thio groups which are substituted by linear or branched alkyl groups having 1 to 6 carbon atoms (preferably 1 to 4 carbon atoms), unless otherwise specified. More specifically, it includes methylthio, ethylthio, n-propylthio, isopropylthio, n-butylthio, isobutylthio, tert-butylthio, sec-butylthio, n-pentylthio, 1-ethylpropylthio, isopentylthio, neopentylthio, n-hexylthio, 1,2,2-trimethylpropylthio, 3,3-dimethylbutylthio, 2-ethylbutylthio, isohexylthio, and 3-methylpentylthio groups, etc.

Examples of a lower alkenyl group can include linear or branched alkenyl groups having 1 to 3 double bonds and 2 to 6 carbon atoms (preferably 2 to 4 carbon atoms), unless otherwise specified, and the lower alkenyl group encompasses both trans and cis forms. More specifically, it includes vinyl, 1-propenyl, 2-propenyl, 1-methyl-1-propenyl, 2-methyl-1-propenyl, 2-methyl-2-propenyl, 2-butenyl, 1-butenyl, 3-butenyl, 2-pentenyl, 1-pentenyl, 3-pentenyl, 4-pentenyl, 1,3-butadienyl, 1,3-pentadienyl, 2-penten-4-yl, 2-hexenyl, 1-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, and 1,4-hexadienyl groups, etc.

Examples of a hydroxy-lower alkyl group can include the lower alkyl groups exemplified above (preferably, linear or branched alkyl groups having 1 to 6 carbon atoms (more preferably 1 to 4 carbon atoms)) which have 1 to 5, preferably 1 to 3 hydroxy groups, unless otherwise specified. More specifically, it includes hydroxymethyl, 2-hydroxyethyl, 2-hydroxypropyl, 1-hydroxyethyl, 3-hydroxypropyl, 2,3-dihydroxypropyl, 4-hydroxybutyl, 3,4-dihydroxybutyl, 1,1-dimethyl-2-hydroxyethyl, 5-hydroxypentyl, 6-hydroxyhexyl, 3,3-dimethyl-3-hydroxypropyl, 2-methyl-3-hydroxypropyl, 2,3,4-trihydroxybutyl, and perhydroxyhexyl groups, etc.

Examples of a lower alkylamino group can include amino groups having 1 to 2 of the lower alkyl groups (preferably linear or branched alkyl groups having 1 to 6 (more preferably 1 to 4, even more preferably 1 to 3) carbon atoms) exemplified above, unless otherwise specified. More specifically, it includes methylamino, dimethylamino, diethylamino, and diisopropylamino groups, etc.

Examples of a lower alkylsulfamoyl group can include sulfamoyl groups having 1 to 2 of the lower alkyl groups (preferably linear or branched alkyl groups having 1 to 6 (more preferably 1 to 4, even more preferably 1 to 3) carbon atoms) exemplified above, unless otherwise specified. More specifically, it includes methylsulfamoyl, ethylsulfamoyl, dimethylsulfamoyl, diethylsulfamoyl, and ethylmethylsulfamoyl groups, etc.

A tri-lower alkylsilyl group can be exemplified by silyl groups which are substituted by 3 linear or branched alkyl groups having 1 to 6 carbon atoms, such as triisopropylsilyl, tert-butyldimethylsilyl, trimethylsilyl, n-butylethylmethylsilyl, tert-butyldipropylsilyl, n-pentyldiethylsilyl, and n-hexyl-n-propylmethylsilyl groups, etc.

Examples of a tri(lower alkyl)silyloxy-lower alkyl group can include tri(lower alkyl)silyloxy-lower alkyl groups whose lower alkyl moiety is any of the lower alkyl groups exemplified above (preferably, linear or branched alkyl groups having 1 to 6 carbon atoms (more preferably 1 to 4 carbon atoms)), unless otherwise specified. More specifically, it includes trimethylsilyloxymethyl, 1-(or 2-)trimethylsilyloxyethyl, 1-(or 2- or 3-)trimethylsilyloxypropyl, triethylsilyloxymethyl, 1-(or 2-)triethylsilyloxyethyl, 1-(or 2- or 3-)triethylsilyloxypropyl, triisopropylsilyloxymethyl, 1-(or 2-)triisopropylsilyloxyethyl, and 1-(or 2- or 3-)triisopropylsilyloxypropyl groups, etc.

Examples of a phenoxy-lower alkyl group can include the lower alkyl groups (preferably linear or branched alkyl groups having 1 to 6 (more preferably 1 to 4, even more preferably 1 to 3) carbon atoms) exemplified above which have 1 to 3, preferably 1 phenoxy group, unless otherwise specified. More specifically, it includes phenoxymethyl, 1-phenoxyethyl, 2-phenoxyethyl, 3-phenoxypropyl, 2-phenoxypropyl, 4-phenoxybutyl, 5-phenoxypentyl, 4-phenoxypentyl, 6-phenoxyhexyl, 2-methyl-3-phenoxypropyl, and 1,1-dimethyl-2-phenoxyethyl groups, etc.

Examples of a phenyl-lower alkoxy group can include the lower alkoxy groups (preferably linear or branched alkoxy groups having 1 to 6 (more preferably 1 to 4, even more preferably 1 to 3) carbon atoms) exemplified above which have 1 to 3, preferably 1 phenyl group, unless otherwise specified. More specifically, it includes benzyloxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, and 2-methyl-3-phenylpropoxy groups, etc.

Examples of a phenyl-lower alkenyl group can include the lower alkenyl groups (preferably linear or branched alkenyl groups having 2 to 6 (more preferably 2 to 4) carbon atoms)

exemplified above which have 1 to 3, preferably 1 phenyl group, unless otherwise specified. More specifically, it includes styryl, 3-phenyl-2-propenyl (commonly called cinnamyl), 4-phenyl-2-butenyl, 4-phenyl-3-butenyl, 5-phenyl-4-pentenyl, 5-phenyl-3-pentenyl, 6-phenyl-5-hexenyl, 6-phenyl-4-hexenyl, 6-phenyl-3-hexenyl, 4-phenyl-1,3-butadienyl, and 6-phenyl-1,3,5-hexatrienyl groups, etc.

Examples of a lower alkylamino-lower alkyl group can include lower alkyl groups which have 1 to 2 of the lower alkylamino groups exemplified above, unless otherwise specified. More specifically, it includes methylaminomethyl, ethylaminomethyl, dimethylaminomethyl, 1-(or 2-)dimethylaminoethyl, 1-(or 2- or 3-)dimethylaminopropyl, diisopropylaminomethyl, 1-(or 2-)diethylaminoethyl, and bis(dimethylamino)methyl groups, etc.

Examples of a lower alkylamino-lower alkoxy group can include lower alkoxy groups which have 1 to 2 of the lower alkylamino groups exemplified above, unless otherwise specified. More specifically, it includes methylaminomethoxy, ethylaminomethoxy, dimethylaminomethoxy, 1-(or 2-)dimethylaminoethoxy, 1-(or 2- or 3-)dimethylaminopropoxy, diisopropylaminomethoxy, 1-(or 2-)diethylaminoethoxy, and bis(dimethylamino)methoxy groups, etc.

Examples of a dihydrobenzodioxinyl group include 2,3-dihydrobenzo[b][1,4]dioxinyl, 3,4-dihydrobenzo[c][1,2]dioxinyl, and 2,4-dihydrobenzo[d][1,3] dioxinyl groups, etc.

Examples of an imidazolyl-lower alkyl group can include the lower alkyl groups (preferably linear or branched alkyl groups having 1 to 6 (more preferably 1 to 4) carbon atoms) exemplified above which have 1 to 3, preferably 1 imidazolyl group. More specifically, it includes 1-(or 2- or 4- or 5-)imidazolylmethyl, 1-(or 2-) {1-(or 2- or 4- or 5-)imidazolyl}ethyl, and 1-(or 2- or 3-){1-(or 2- or 4- or 5-)imidazolyl}propyl groups, etc.

A dihydroindenyl group includes (1-, 2-, 4-, or 5-)-1,2-dihydroindenyl groups, etc.

A dihydroquinolyl group includes 1,2-dihydroquinolyl, 3,4-dihydroquinolyl, 1,4-dihydroquinolyl, 4a,8a-dihydroquinolyl, 5,6-dihydroquinolyl, 7,8-dihydroquinolyl, and 5,8-dihydroquinolyl groups, etc.

A fluorenyl group includes 1H-fluorenyl, 2H-fluorenyl, 3H-fluorenyl, 4aH-fluorenyl, 5H-fluorenyl, 6H-fluorenyl, 7H-fluorenyl, 8H-fluorenyl, 8aH-fluorenyl, and 9H-fluorenyl groups, etc.

A dihydrobenzofuryl group includes 2,3-dihydro-(2-, 3-, 4-, 5-, 6-, or 7-)benzofuryl groups, etc.

A dihydrobenzoxazinyl group includes (2-, 3-, 4-, 5-, 6-, 7-, or 8-)3,4-dihydro-2H-benzo[b][1.4]oxazinyl and (1-, 2-, 4-, 5-, 6-, 7-, or 8-)2,4-dihydro-1H-benzo[d][1.3]oxazinyl groups, etc.

A tetrahydrobenzodiazepinyl group includes (1-, 2-, 3-, 4-, 5-, 6-, 7-, 8-, or 9-) 2,3,4,5-tetrahydro-1H-benzo[b][1.4] diazepinyl and (1-, 2-, 3-, 4-, 5-, 6-, 7-, 8-, or 9-)2,3,4,5-tetrahydro-1H-benzo[e][1.4]diazepinyl groups, etc.

Examples of a tetrahydrobenzodiazepinyl group can include (1-, 2-, 3-, 4-, 5-, 6-, 7-, 8-, or 9-)2,3,4,5-tetrahydro-1H-benzo[b][1.4]diazepinyl and (1-, 2-, 3-, 4-, 5-, 6-, 7-, 8-, or 9-)2,3,4,5-tetrahydro-1H-benzo[e][1.4]diazepinyl groups, etc.

A dihydrobenzodioxepinyl group includes 3,4-dihydro-2H-1,5-benzodioxepinyl, 4,5-dihydro-3H-1,2-benzodioxepinyl, and 3,5-dihydro-2H-1,4-benzodioxepinyl groups, etc.

Examples of a pyrrolidinyl group which may have an oxo group(s) include pyrrolidinyl group which may have 1 to 2 (preferably 1) oxo groups, unless otherwise specified. More specifically, it includes (1-, 2-, or 3-)pyrrolidinyl, (2- or 3-)oxo-1-pyrrolidinyl, (3-, 4-, or 5-)oxo-2-pyrrolidinyl, and (2-, 4-, or 5-)oxo-3-pyrrolidinyl groups, etc.

Examples of an oxadiazolyl group which may have a lower alkyl group(s) can include oxadiazolyl group which may have 1 to 2 (preferably 1) of the lower alkyl groups exemplified above, unless otherwise specified. More specifically, it includes 5-methyl-1,3,4-oxadiazolyl, 5-ethyl-1,3,4-oxadiazolyl, 5-propyl-1,3,4-oxadiazolyl, 5-butyl-1,3,4-oxadiazolyl, 5-pentyl-1,3,4-oxadiazolyl, and 5-hexyl-1,3,4-oxadiazolyl groups, etc.

Examples of a pyrazolyl group which may have a lower alkyl group(s) can include pyrazolyl group which may have 1 to 2 (preferably 1) of the lower alkyl groups exemplified above, unless otherwise specified. More specifically, it includes 1-methyl-1H-pyrazolyl, 1-ethyl-1H-pyrazolyl, 1-propyl-1H-pyrazolyl, 1-isopropyl-1H-pyrazolyl, 1-butyl-1H-pyrazolyl, 1-tert-butyl-1H-pyrazolyl, and 1,3-dimethyl-1H-pyrazolyl groups, etc.

Examples of a thiazolyl group which may have a lower alkyl group(s) can include thiazolyl group which may have 1 to 2 (preferably 1) of the lower alkyl groups exemplified above, unless otherwise specified. More specifically, it includes 2-methylthiazolyl, 2-ethylthiazolyl, 2-propylthiazolyl, 2-isopropylthiazolyl, 2-butylthiazolyl, 2-tert-butylthiazolyl, and 2,5-dimethylthiazolyl groups, etc.

Examples of a pyrimidyl group which may have a lower alkyl group(s) can include pyrimidyl group which may have 1 to 2 (preferably 1) of the lower alkyl groups exemplified above, unless otherwise specified. More specifically, it includes 2-methylpyrimidyl, 2-ethylpyrimidyl, 2-propylpyrimidyl, 2-isopropylpyrimidyl, 2-butylpyrimidyl, 2-tert-butylpyrimidyl, and 2,4-dimethylpyrimidyl groups, etc.

Examples of a pyridazinyl group which may have a lower alkyl group(s) can include pyridazinyl group which may have 1 to 2 (preferably 1) of the lower alkyl groups exemplified above, unless otherwise specified. More specifically, it includes 3-methylpyridazinyl, 3-ethylpyridazinyl, 3-propylpyridazinyl, 3-isopropylpyridazinyl, 3-butylpyridazinyl, 3-tert-butylpyridazinyl, and 3,4-dimethylpyridazinyl groups, etc.

Examples of a pyridazinyloxy group which may have a lower alkyl group(s) can include oxy group which is substituted by pyridazinyl which may have 1 to 2 (preferably 1) of the lower alkyl groups exemplified above, unless otherwise specified. More specifically, it includes 6-methylpyridazinyl-3-yloxy and 4-methylpyridazinyl-3-yloxy groups, etc.

Examples of a pyrrolidinyl-lower alkoxy group can include lower alkoxy groups (preferably linear or branched alkoxy groups having 1 to 6 (more preferably 1 to 4, even more preferably 1 to 3) carbon atoms) exemplified above which have 1 to 3, preferably 1 pyrrolidinyl group, unless otherwise specified. Specific examples thereof include (1-, 2-, or 3-) pyrrolidinylmethoxy, 2-[(1-, 2-, or 3-)pyrrolidinyl] ethoxy, 1-[(1-, 2-, or 3-)pyrrolidinyl]ethoxy, 3-[(1-, 2-, or 3-)pyrrolidinyl]propoxy, 4-[(1-, 2-, or 3-)pyrrolidinyl]butoxy, 5-[(1-, 2-, or 3-) pyrrolidinyl]pentyloxy, 6-[(1-, 2-, or 3-)pyrrolidinyl]hexyloxy, 1,1-dimethyl-2-[(1-, 2-, or 3-) pyrrolidinyl]ethoxy, and 2-methyl-3-[(1-, 2-, or 3-)pyrrolidinyl] propoxy groups, etc.

Examples of a protecting group include protecting groups routinely used, such as substituted or unsubstituted lower alkanoyl [e.g., formyl, acetyl, propionyl, and trifluoroacetyl], phthaloyl, lower alkoxycarbonyl [e.g., tertiary butoxycarbonyl and tertiary amyloxycarbonyl], substituted or unsubstituted aralkyloxycarbonyl [e.g., benzyloxycarbonyl and p-nitrobenzyloxycarbonyl], 9-fluorenylmethoxycarbonyl, substituted or unsubstituted arenesulfonyl [e.g., benzenesulfonyl and tosyl], nitrophenylsulfenyl, aralkyl [e.g., trityl and benzyl], and lower alkylsilyl groups [e.g., triisopropylsilyl].

Examples of a phenyl-lower alkyl group can include the lower alkyl groups (preferably linear or branched alkyl groups having 1 to 6 (more preferably 1 to 4 carbon atoms) exemplified above which have 1 to 3, preferably 1 phenyl group, unless otherwise specified. More specifically, it includes benzyl, phenethyl, 3-phenylpropyl, benzhydryl, trityl, 4-phenylbutyl, 5-phenylpentyl, and 6-phenylhexyl groups, etc.

Examples of a morpholinyl-lower alkyl group can include the lower alkyl groups (preferably linear or branched alkyl groups having 1 to 6 carbon atoms) exemplified above which have 1 to 2 (preferably 1) morpholinyl groups, unless otherwise specified. More specifically, it includes 2-morpholinyl methyl, 3-morpholinyl methyl, 4-morpholinyl methyl, 2-(2-morpholinyl)ethyl, 2-(3-morpholinyl)ethyl, 2-(4-morpholinyl)ethyl), 1-(2-morpholinyl)ethyl, 1-(3-morpholinyl)ethyl, 1-(4-morpholinyl)ethyl, 3-(2-morpholinyl) propyl, 3-(3-morpholinyl)propyl, 3-(4-morpholinyl)propyl, 4-(2-morpholinyl)butyl, 4-(3-morpholinyl)butyl, 4-(4-morpholinyl)butyl, 5-(2-morpholinyl)pentyl, 5-(3-morpholinyl) pentyl, 5-(4-morpholinyl)pentyl, 6-(2-morpholinyl)hexyl, 6-(3-morpholinyl)hexyl, 6-(4-morpholinyl)hexyl, 3-methyl-3-(2-morpholinyl)propyl, 3-methyl-3-(3-morpholinyl)propyl, 1, 1-dimethyl-2-(2-morpholinyl)ethyl, 1,1-dimethyl-2-(3-morpholinyl)ethyl, and 1,1-dimethyl-2-(4-morpholinyl) ethyl groups, etc.

Examples of a pyrrolidinyl-lower alkyl group can include the lower alkyl groups exemplified above which have 1 to 3 (preferably 1) pyrrolidinyl groups, unless otherwise specified. More specifically, it includes (1-, 2-, or 3-) pyrrolidinylmethyl, 2-[(1-, 2- or 3-) pyrrolidinyl]ethyl, 1-[(1-, 2- or 3-)] pyrrolidinyl]ethyl, 3-[(1-, 2- or 3-)]pyrrolidinyl]propyl, 4-[(1-, 2- or 3-)] pyrrolidinyl]butyl, 5-[(1-, 2- or 3-)] pyrrolidinyl]pentyl, 6-[(1-, 2- or 3-)] pyrrolidinyl]hexyl, 1, 1-dimethyl-2-[(1-, 2- or 3-)] pyrrolidinyl]ethyl, and 2-methyl-3-[(1-, 2- or 3-)] pyrrolidinyl]propyl groups, etc.

Examples of a piperidyl-lower alkyl group can include the lower alkyl groups (preferably linear or branched alkyl groups having 1 to 6 carbon atoms) exemplified above which have 1 to 2 (preferably 1) piperidyl groups, unless otherwise specified. More specifically, it includes (1-, 2-, 3- or 4-) piperidylmethyl, 2-[(1-, 2-, 3- or 4-)piperidyl]ethyl, 1-[(1-, 2-, 3- or 4-)piperidyl]ethyl, 3-[(1-, 2-, 3- or 4-)piperidyl]propyl, 4-[(1-, 2-, 3- or 4-)piperidyl]butyl, 1,1-dimethyl-2-[(1-, 2-, 3- or 4-)piperidyl]ethyl, 5-[(1-, 2-, 3- or 4-)piperidyl]pentyl, 6-[(1-, 2-, 3- or 4-)piperidyl]hexyl, 1-[(1-, 2-, 3- or 4-)piperidyl]isopropyl, and 2-methyl-3-[(1-, 2-, 3- or 4-)piperidyl]propyl groups, etc.

Examples of a lower alkoxycarbonyl group can include linear or branched alkoxy groups having preferably 1 to 6 carbon atoms and having a lower alkoxycarbonyl moiety as exemplified above. More specifically, it includes methoxycarbonyl, ethoxycarbonyl, n-propxycarbonyl, isopropoxycarbonyl, n-butoxycarbonyl, isobutoxycarbonyl, tert-butoxycarbonyl, sec-butoxycarbonyl, n-pentyloxycarbonyl, neopentyloxycarbonyl, n-hexyloxycarbonyl, isohexyloxycarbonyl, 3-methylpentyloxycarbonyl groups, etc.

Examples of a piperazinyl group which may have a lower alkyl group(s) include piperazinyl groups which may have 1 to 2 (preferably 1) lower alkyl groups, unless otherwise specified. More specifically, it includes 2-methylpiperazinyl, 4-methylpiperazinyl, 2-ethylpiperazinyl, 2-propylpiperazinyl, 2-isopropylpiperazinyl, 2-butylpiperazinyl, 2-tert butylpiperazinyl, and 2, 4-dimethylpiperazinyl groups, etc.

Examples of a piperazinyl-lower alkyl group which may have a lower alkyl group(s) include piperazinyl groups exemplified above which may have 1 to 2 (preferably 1) lower alkyl groups, unless otherwise specified. More specifically, it includes 1-(4-methylpiperazinyl)methyl, 1-(2-methyl piperazinyl)methyl, 2-(1-methyl piperazinyl)ethyl, 3-(1-methyl piperazinyl)propyl, 4-(1-methyl piperazinyl) butyl groups, etc.

Examples of a phenyl group which may have a lower alkoxy group(s) include phenyl groups exemplified above which may have 1 to 2 (preferably 1) lower alkoxy groups, unless otherwise specified. More specifically, it includes 4-methoxyphenyl, 4-ethoxyphenyl, 4-propoxyphenyl, 4-isopropylphenyl, 4-butoxyphenyl, 4-tert butoxyphenyl groups, etc. can be mentioned. As a phenoxy group exemplified above which may have a halogen atom(s) include phenoxy groups which may have 1 to 4 (preferably 1) halogen atoms, unless otherwise specified. More specifically, it includes 4-fluorophenoxy, 3, 4-difluorophenoxy, 3, 4, 5-trifluorophenoxy, and 3-chloro-4,5-difluorophenoxy groups, etc.

A tetrahydroquinolyl group includes, for example, 1, 2, 3, 4-tetrahydroquinolyl, 5, 6, 7, 8-tetrahydroquinolyl, 4a, 5, 8, 8a-tetrahydroquinolyl, 3, 4, 4a, 8a-tetrahydroquinolyl, 4a, 5, 8, 8a-tetrahydroquinolyl, and 4a, 5, 6, 7-tetrahydroquinolyl groups, etc.

A dihydroacenaphthylenyl group includes, for example, 1, 2-dibydroacenaphthylenyl, 2a', 3-dihydroacenaphthylenyl, 5, 6-dihydroacenaphthylenyl, 3, 7-dihydroacenaphthylenyl, 2a', 6-dihydroacenaphthylenyl, 1, 2a'-dihydroacenaphthylenyl, and 6, 8a-dihydroacenaphthylenyl groups, etc. More preferably, it is 1, 2-dihydroacenaphthylenyl group can be mentioned.

A tetrahydronaphthyl group includes, for example, 1, 2, 3, 4-tetrahydronaphthyl, 1, 2, 3, 5-tetrahydronaphthyl, and 5, 6, 7, 8-tetrahydronaphthyl, 2, 3, 7, 8-tetrahydronaphthyl groups, etc. can be mentioned.

A dihydroquinazolinyl group includes, for example, 1, 2-dihydroquinazolinyl, 3, 4-dihydroquinazolinyl, 4a, 5-dihydroquinazolinyl, 5, 6-dihydroquinazolinyl, 6, 7-dihydroquinazolinyl, 7,8-dihydroquinazolinyl, 8,8a-dihydroquinazolinyl, and 4a, 8a-dihydroquinazolinyl groups, etc. can be mentioned.

The heterocyclic compound represented by the general formula (1) can be produced by various methods. As an example, the heterocyclic compound represented by the general formula (1) is produced by methods represented by the reaction formulas shown below.

Reaction Formula-1

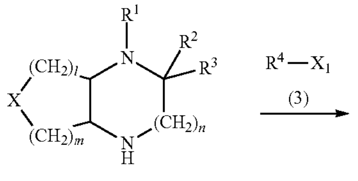

(2)

-continued

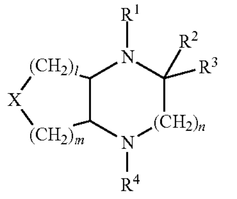

(1)

wherein $R^1$, $R^2$, $R^3$, $R^4$, X, l, m, and n are defined as above; and $X_1$ represents a leaving group.

In the general formula (3), the leaving group represented by $X_1$ can be exemplified by halogen atoms, lower alkanesulfonyloxy groups, arylsulfonyloxy groups, aralkylsulfonyloxy groups, trihalomethanesulfonyloxy groups, sulfonio groups, and toluenesulfoxy groups. Preferable examples of the leaving groups for the present reaction include halogen atoms.

Examples of the halogen atoms represented by $X_1$ can include fluorine, chlorine, bromine, and iodine atoms.

The lower alkanesulfonyloxy groups represented by $X_1$ can be exemplified specifically by linear or branched alkanesulfonyloxy groups having 1 to 6 carbon atoms, such as methanesulfonyloxy, ethanesulfonyloxy, n-propanesulfonyloxy, isopropanesulfonyloxy, n-butanesulfonyloxy, tert-butanesulfonyloxy, n-pentanesulfonyloxy, and n-hexanesulfonyloxy groups.

Examples of the arylsulfonyloxy groups represented by $X_1$ can include: phenylsulfonyloxy groups which may have 1 to 3 groups selected from the group consisting of linear or branched alkyl groups having 1 to 6 carbon atoms, linear or branched alkoxy groups having 1 to 6 carbon atoms, nitro groups, and halogen atoms as substituents on the phenyl ring; and naphthylsulfonyloxy groups. The phenylsulfonyloxy groups which may have the substituents can be exemplified specifically by phenylsulfonyloxy, 4-methylphenylsulfonyloxy, 2-methylphenylsulfonyloxy, 4-nitrophenylsulfonyloxy, 4-methoxyphenyisulfonyloxy, 2-nitrophenylsulfonyloxy, and 3-chlorophenylsulfonyloxy groups. The naphthylsulfonyloxy groups can be exemplified specifically by α-naphthylsulfonyloxy and β-naphthylsulfonyloxy groups.

Examples of the aralkylsulfonyloxy groups represented by $X_1$ can include: linear or branched alkanesulfonyloxy groups having 1 to 6 carbon atoms, which are substituted by a phenyl group which may have 1 to 3 groups selected from the group consisting of linear or branched alkyl groups having 1 to 6 carbon atoms, linear or branched alkoxy groups having 1 to 6 carbon atoms, nitro groups, and halogen atoms as substituents on the phenyl ring; and linear or branched alkanesulfonyloxy groups having 1 to 6 carbon atoms, which are substituted by a naphthyl group. The alkanesulfonyloxy groups which are substituted by the phenyl group can be exemplified specifically by benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, and 3-chlorobenzylsulfonyloxy. The alkanesulfonyloxy groups which are substituted by the naphthyl group can be exemplified specifically by α-naphthylmethylsulfonyloxy and β-naphthylmethylsulfonyloxy groups.

The perhaloalkanesulfonyloxy groups represented by $X_1$ can be exemplified specifically by trifluoromethanesulfonyloxy groups.

Examples of the sulfonio groups represented by $X_1$ can specifically include dimethylsulfonio, diethylsulfonio, dipropylsulfonio, di-(2-cyanoethyl)sulfonio, di-(2-nitroethyl)sulfonio, di-(aminoethyl)sulfonio, di-(2-methylaminoethyl)sulfonio, di-(2-dimethylaminoethyl)sulfonio, di-(2-hydroxyethyl)sulfonio, di-(3-hydroxypropyl)sulfonio, di-(2-methoxyethyl)sulfonio, di-(2-carbamoylethyl)sulfonio, di-(2-carbamoylethyl)sulfonio, di-(2-carboxyethyl)sulfonio, and di-(2-methoxycarbonylethyl)sulfonio, and diphenylsulfonio groups.

A compound represented by the general formula (2) and the compound represented by the general formula (3) can be reacted in the presence of a palladium catalyst in the presence or absence of a basic compound without or in an inert solvent to thereby produce the compound (1).

Examples of the inert solvent can include, for example: water; ether solvents such as dioxane, tetrahydrofuran, diethyl ether, 1,2-dimethoxyethane, diethylene glycol dimethyl ether, and ethylene glycol dimethyl ether; aromatic hydrocarbon solvents such as benzene, toluene, and xylene; lower alcohol solvents such as methanol, ethanol, and isopropanol; ketone solvents such as acetone and methyl ethyl ketone; and polar solvents such as N,N-dimethylformamide (DMF), dimethyl sulfoxide (DMSO), hexamethylphosphoric triamide, and acetonitrile. These inert solvents are used alone or as a mixture of two or more of them.

The palladium compound used in the present reaction is not particularly limited. Examples thereof include: tetravalent palladium catalysts such as sodium hexachloropalladium (IV) acid tetrahydrate and potassium hexachloropalladium (IV) acid; divalent palladium catalysts such as palladium (II) chloride, palladium (II) bromide, palladium (II) acetate, palladium (II) acetylacetonate, dichlorobis(benzonitrile)palladium (II), dichlorobis(acetonitrile)palladium (11), dichlorobis(triphenylphosphine)palladium (II), dichlorotetraammine palladium (II), dichloro(cycloocta-1,5-diene) palladium (11), and palladium (II) trifluoroacetate 1,1'-bis (diphenylphosphino)ferrocenedichloropalladium (II)-dichloromethane complex; and zerovalent palladium catalysts such as tris(dibenzylideneacetone)dipalladium (0), tris(dibenzylideneacetone)dipalladium (0)-chloroform complex, and tetrakis(triphenylphosphine)palladium (0). These palladium compounds are used alone or as a mixture of two or more of them.

In the present reaction, the amount of the palladium catalyst used is not particularly limited and usually ranges from 0.000001 to 20 mol in terms of palladium with respect to 1 mol of the compound of the general formula (2). More preferably, the amount of the palladium compound used ranges from 0.0001 to 5 mol in terms of palladium with respect to 1 mol of the compound of the general formula (2).

The present reaction proceeds advantageously in the presence of an appropriate ligand. For example, 2,2'-bis (diphenylphosphino)-1,1'-binaphthyl (BINAP), tri-o-tolylphosphine, bis(diphenylphosphino)ferrocene, triphenylphosphine, tri-t-butylphosphine, tricyclohexylphosphine, and 9,9-dimethyl-4,5-bis(diphenylphosphino)xanthene (XANTPHOS) can be used as the ligand for the palladium catalyst. These ligands are used alone or as a mixture of two or more of them.

Furthermore, in the present invention, the tertiary phosphine may be prepared in a complex form in advance and added thereto. Examples of the complex can include tri-t-butylphosphonium tetrafluoroborate and tri-t-butylphosphonium tetraphenylborate.

The ratio between the palladium catalyst and the ligand used is not particularly limited. The amount of the ligand used is approximately 0.1 to 100 mol, preferably approximately 0.5 to 15 mol, with respect to 1 mol of the palladium catalyst.

Inorganic and organic bases known in the art can be used widely as the basic compound.

Examples of the inorganic bases can include: alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metal bicarbonates such as lithium bicarbonate, sodium bicarbonate, and potassium bicarbonate; alkali metals such as sodium and potassium; phosphates such as sodium phosphate and potassium phosphate; amides such as sodium amide; and alkali metal hydrides such as sodium hydride and potassium hydride.

Examples of the organic bases can include: alkali metal lower alkoxides such as sodium methoxide, sodium ethoxide, sodium t-butoxide, potassium methoxide, potassium ethoxide, and potassium t-butoxide; and amines such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]non-5-ene (DBN), 1,8-diazabicyclo[5.4.0]undec-7-ene (DBU), and 1,4-diazabicyclo[2.2.2]octane (DABCO).

These basic compounds are used alone or as a mixture of two or more of them. More preferable examples of the basic compound used in the present reaction include alkali metal carbonates such as sodium carbonate, potassium carbonate, cesium carbonate, and lithium carbonate, and sodium t-butoxide.

The amount of the basic compound used is usually 0.5 to 10 mol, preferably 0.5 to 6 mol, with respect to 1 mol of the compound of the general formula (2).

The ratio between the compound of the general formula (2) and the compound of the general formula (3) used in the Reaction Formula-1 may be at least 1 mol, preferably approximately 1 to 5 mol of the latter compound with respect to 1 mol of the former compound.

The reaction can be performed in an atmosphere of inert gas such as nitrogen or argon under the atmospheric pressure or can be performed under increased pressure.

The present reaction is usually performed under temperature conditions involving room temperature to 200° C., preferably room temperature to 150° C., and generally completed in approximately 1 to 30 hours. It is also achieved by heating at 100 to 200° C. for 5 minutes to 1 hour using a microwave reactor.

After the completion of the reaction, the reaction product can be treated by a standard method to obtain the compound of interest.

The compound represented by the general formula (2) used as a starting material in the Reaction Formula-1 is produced from compounds known in the art, for example, by methods represented by Reaction Formulas-3 and 4 shown below. The compound represented by the general formula (3) is an easily obtainable compound known in the art or a compound easily produced by a method known in the art.

Reaction Formula -2

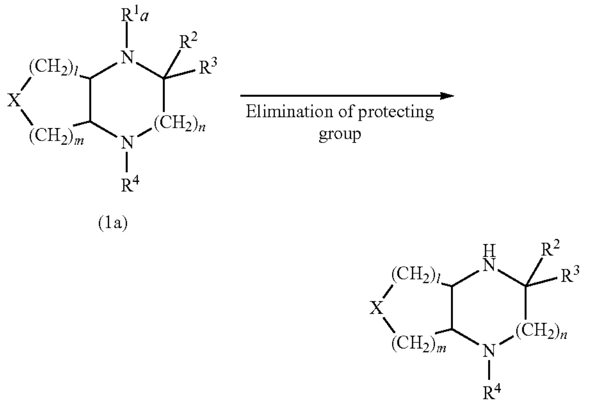

(1a)

(1b)

wherein $R^2$, $R^3$, $R^4$, X, l, m, and n are defined as above; and $R^{1a}$ represents a protecting group.

Examples of the protecting group include the protecting groups exemplified above.

The compound represented by the general formula (1b) can be produced by subjecting a compound represented by the general formula (1a) to the elimination reaction of the protecting group.

A method routinely used such as hydrolysis or hydrogenolysis can be applied to the elimination reaction of the protecting group.

The present reaction is usually performed in a solvent routinely used that does not adversely affect the reaction. Examples of the solvent include: water; alcohol solvents such as methanol, ethanol, isopropanol, n-butanol, trifluoroethanol, and ethylene glycol; ketone solvents such as acetone and methyl ethyl ketone; ether solvents such as tetrahydrofuran, dioxane, diethyl ether, dimethoxyethane, and diglyme; ester solvents such as methyl acetate and ethyl acetate; aprotic polar solvents such as acetonitrile, N,N-dimethylformamide, dimethyl sulfoxide, and N-methylpyrrolidone; halogenated hydrocarbon solvents such as methylene chloride and ethylene chloride; and other organic solvents.

(i) Hydrolysis:

The hydrolysis is preferably performed in the presence of a base or an acid (including Lewis acids).

Inorganic and organic bases known in the art can be used widely as the base. Preferable examples of the inorganic bases include alkali metals (e.g., sodium and potassium), alkaline earth metals (e.g., magnesium and calcium), and hydrides, carbonates, or bicarbonates thereof. Preferable examples of the organic bases include trialkylamines (e.g., trimethylamine and triethylamine), picoline, and 1,5-diazabicyclo[4.3.0]non-5-ene.

Organic and inorganic acids known in the art can be used widely as the acid. Preferable examples of the organic acids include: fatty acids such as formic acid, acetic acid, and propionic acid; and trihaloacetic acids such as trichloroacetic acid and trifluoroacetic acid. Preferable examples of the inorganic acids include hydrochloric acid, hydrobromic acid, sulfuric acid, hydrogen chloride, and hydrogen bromide. Examples of the Lewis acids include boron trifluoride-ether complexes, boron tribromide, aluminum chloride, and ferric chloride.

When trihaloacetic acid or Lewis acid is used as the acid, the reaction is preferably performed in the presence of a cation scavenger (e.g., anisole and phenol).

The amount of the base or the acid used is not particularly limited as long as it is an amount necessary for hydrolysis.

The reaction temperature is usually 0 to 120° C., preferably room temperature to 100° C., more preferably room temperature to 80° C. The reaction time is usually 30 minutes to 24 hours, preferably 30 minutes to 12 hours, more preferably 1 to 8 hours.

(ii) Hydrogenolysis:

Hydrogenolysis methods known in the art can be applied widely to the hydrogenolysis. Examples of such hydrogenolysis methods include chemical reduction and catalytic reduction.

Preferable reducing agents used in chemical reduction are the combinations of hydrides (e.g., hydrogen iodide, hydrogen sulfide, lithium aluminum hydride, sodium borohydride, and sodium cyanoborohydride), metals (e.g., tin, zinc, and iron), or metal compounds (e.g., chromium chloride and chromium acetate) with organic or inorganic acids (e.g., formic acid, acetic acid, propionic acid, trifluoroacetic acid, p-toluenesulfonic acid, hydrochloric acid, and hydrobromic acid).

Preferable catalysts used in catalytic reduction are platinum catalysts (e.g., platinum plates, platinum sponge, platinum black, colloidal platinum, platinum oxide, and platinum wires), palladium catalysts (e.g., palladium sponge, palladium black, palladium oxide, palladium-carbon, palladium/barium sulfate, and palladium/barium carbonate), nickel catalysts (e.g., reduced nickel, nickel oxide, and Raney nickel), cobalt catalysts (e.g., reduced cobalt and Raney cobalt), iron catalysts (e.g., reduced iron), etc.

When these acids used in chemical reduction are in a liquid state, they can also be used as solvents.

The amount of the reducing agent used in chemical reduction or the catalyst used in catalytic reduction is not particularly limited and may be an amount usually used.

The reaction of the present invention can be performed in an atmosphere of inert gas such as nitrogen or argon under the atmospheric pressure or can be performed under increased pressure.

The reaction temperature is usually 0 to 120° C., preferably room temperature to 100° C., more preferably room temperature to 80° C. The reaction time is usually 30 minutes to 24 hours, preferably 30 minutes to 10 hours, more preferably 30 minutes to 4 hours.

After the completion of the reaction, the reaction product can be treated by a standard method to obtain the compound of the general formula (1 b) of interest.

The deprotection reaction of the protecting group is not limited to the reaction conditions described above. For example, reaction described in T. W. Green, P. G. M. Wuts, “Protective Groups in Organic Synthesis”, 4th ed., or John Wiley & Sons; New York, 1991, P. 309 can also be applied to the present reaction step.

The compound represented by the general formula (2) is a novel compound, which is useful as an intermediate for the compound represented by the general formula (1), as described above.

The compound of the general formula (2) is produced according to, for example, Reaction Formulas-3, 4, or 5 shown below.

Hereinafter, each reaction formula will be described.

Reaction Formula-3

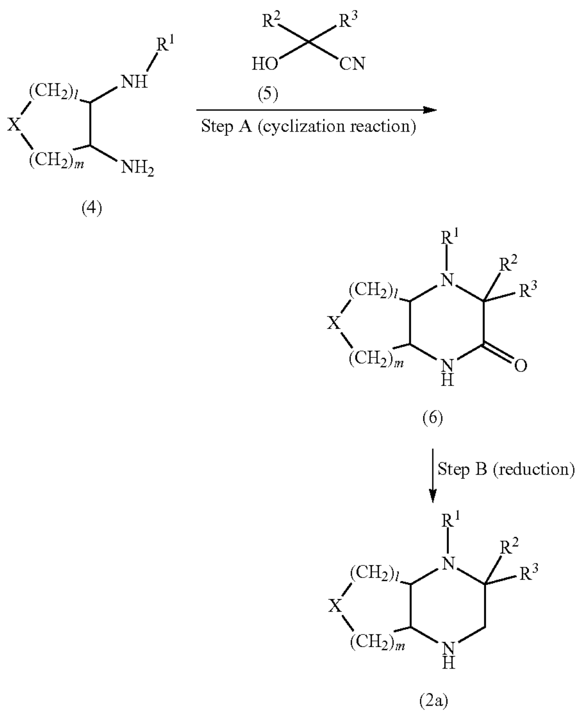

wherein $R^1$, $R^2$, R, X, l, m, and n are defined as above.

The compound represented by the general formula (2a) is produced by subjecting a compound represented by the general formula (4) and a compound represented by the general formula (5) to cyclization reaction to form a compound represented by the general formula (6) (Step A), which is then reduced (Step B).

Step A

The reaction between the compound represented by the general formula (4) and the compound represented by the general formula (5) can be performed in the presence or absence of a base without or in an inert solvent.

Examples of the inert solvent can include, for example: water; ethers such as dioxane, tetrahydrofuran, diethyl ether, diethylene glycol dimethyl ether, and ethylene glycol dimethyl ether; aromatic hydrocarbons such as benzene, toluene, and xylene; lower alcohols such as methanol, ethanol, and isopropanol; ketones such as acetone and methyl ethyl ketone; and polar solvents such as N,N-dimethylformamide (DMF), dimethyl sulfoxide (DMSO), hexamethylphosphoric triamide, and acetonitrile.

Basic compounds known in the art can be used widely. Examples thereof can include: alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metals such as sodium and potassium; other inorganic bases such as sodium amide, sodium hydride, and potassium hydride; alkali metal alcoholates such as sodium methoxide, sodium ethoxide, potassium methoxide, and potassium ethoxide; and other organic bases such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazacyclo[4.3.0]non-5-ene (DBN), 1,8-diazabicyclo[5.4.0]undec-7-ene (DBU), and 1,4-diazabicyclo[2.2.2]octane (DABCO).

These basic compounds are used alone or as a mixture of two or more of them.

The amount of the basic compound used is usually 0.5 to 10 mol, preferably 0.5 to 6 mol, with respect to the compound of the general formula (4).

The reaction can be performed by adding, if necessary, alkali metal iodide (e.g., potassium iodide and sodium iodide) as a reaction promoter.

The ratio between the compound of the general formula (4) and the compound of the general formula (5) used in the reaction formula may be usually at least 0.5 mol, preferably approximately 0.5 to 5 mol of the latter compound with respect to 1 mol of the former compound.

The reaction of the present invention can be performed in an atmosphere of inert gas such as nitrogen or argon under the atmospheric pressure or can be performed under increased pressure.

The reaction is usually performed under temperature conditions involving 0° C. to 200° C., preferably room temperature to 150° C., and generally completed in approximately 1 to 30 hours.

The compound of the general formula (4) and the compound of the general formula (5) used as starting materials in the Step A are easily obtainable compounds known in the art or compounds easily produced by a method known in the art.

Step B

The compound represented by the general formula (2a) can be produced by subjecting the compound represented by the general formula (6) to reduction reaction without or in an inert solvent.

Examples of such reduction methods include chemical reduction and catalytic reduction.

Examples of the inert solvent can include: water; ethers such as dioxane, tetrahydrofuran, diethyl ether, diethylene glycol methyl ether, and ethylene glycol dimethyl ether; aromatic hydrocarbons such as benzene, toluene, and xylene; lower alcohols such as methanol, ethanol, and isopropanol; ketones such as acetone and methyl ethyl ketone; and polar solvents such as N,N-dimethylformamide (DMF), dimethyl sulfoxide (DMSO), hexamethylphosphoric triamide, and acetonitrile.

Preferable reducing agents used in chemical reduction are the combinations of hydrides (e.g., hydrogen iodide, hydrogen sulfide, lithium aluminum hydride, boron hydride, sodium borohydride, and sodium cyanoborohydride), metals (e.g., tin, zinc, and iron), or metal compounds (e.g., chromium chloride and chromium acetate) with organic or inorganic acids (e.g., formic acid, acetic acid, propionic acid, trifluoroacetic acid, p-toluenesulfonic acid, hydrochloric acid, and hydrobromic acid).

Preferable catalysts used in catalytic reduction are platinum catalysts (e.g., platinum plates, platinum sponge, platinum black, colloidal platinum, platinum oxide, and platinum wires), palladium catalysts (e.g., palladium sponge, palladium black, palladium oxide, palladium-carbon, palladium/barium sulfate, and palladium/barium carbonate), nickel catalysts (e.g., reduced nickel, nickel oxide, and Raney nickel), cobalt catalysts (e.g., reduced cobalt and Raney cobalt), iron catalysts (e.g., reduced iron), etc.

When these acids used in chemical reduction are in a liquid state, they can also be used as solvents.

The amount of the reducing agent used in chemical reduction or the catalyst used in catalytic reduction is not particularly limited and may be an amount usually used.

The reaction of the present invention can be performed in an atmosphere of inert gas such as nitrogen or argon under the atmospheric pressure or can be performed under increased pressure.

The reaction temperature is usually 0 to 120° C., preferably room temperature to 100° C., more preferably room temperature to 80° C. The reaction time is usually 30 minutes to 24 hours, preferably 30 minutes to 10 hours, more preferably 30 minutes to 4 hours.

After the completion of the reaction, the reaction product can be treated by a standard method to obtain the compound of the general formula (2a) of interest.

Reaction Formula-4

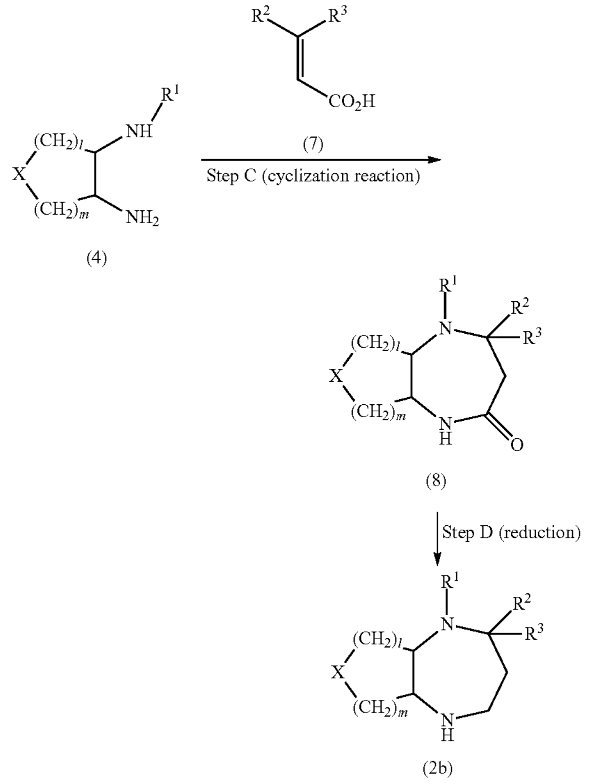

(7) (4) (8) (2b)

wherein $R^1$, $R^2$, $R^3$, X, l, m, and n are defined as above.

The compound represented by the general formula (2b) is produced by subjecting the compound represented by the general formula (4) and a compound represented by the general formula (7) to cyclization reaction to form a compound represented by the general formula (8) (Step C), which is then reduced (Step D). The reaction conditions are the same reaction conditions as in the Reaction Formula-3.

Reaction Formula-5

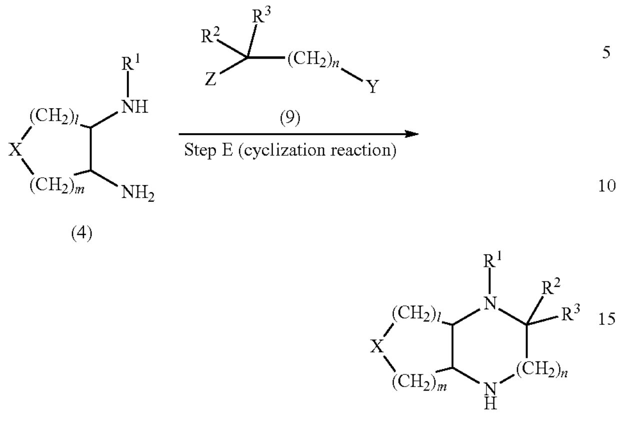

(4) (9) (2)

wherein $R^1$, $R^2$, $R^3$, $R^4$, l, m, n, and X are defined as above; and Y and Z, which are the same or different, each independently represent a leaving group.

Examples of the leaving groups represented by Y and Z in the general formula (9) include the leaving groups exemplified above.

Step E

The compound represented by the general formula (2) can be produced by subjecting the compound represented by the general formula (4) and a compound represented by the general formula (9) to cyclization reaction. The cyclization reaction is usually performed in the presence or absence of a basic compound.

The present reaction is usually performed in a solvent routinely used that does not adversely affect the reaction. Examples of the solvent include: water, alcohol solvents such as methanol, ethanol, isopropanol, n-butanol, trifluoroethanol, and ethylene glycol; ketone solvents such as acetone and methyl ethyl ketone; ether solvents such as tetrahydrofuran, dioxane, diethyl ether, dimethoxyethane, and diglyme; ester solvents such as methyl acetate and ethyl acetate; aprotic polar solvents such as acetonitrile, N,N-dimethylformamide, dimethyl sulfoxide, and N-methylpyrrolidone; halogenated hydrocarbon solvents such as methylene chloride and ethylene chloride; and other organic solvents.

A transition metal catalyst and a ligand may be used in this reaction. Examples of the transition metal include ruthenium chloride, dichlorotris(triphenylphosphine)ruthenium, dibromotris(triphenylphosphine)ruthenium, dihydridotetrakis(triphenylphosphine)ruthenium, ($\eta^4$-cyclooctadiene)($\eta^6$-cyclooctatriene)ruthenium, dichlorotricarbonylruthenium dimers, dodecacacarbonyltriruthenium, ($\eta^5$-pentamethylcyclopentadienyl)chloro($\eta^4$-cyclooctatriene)ruthenium, palladium acetate, palladium chloride, dichlorobis(triphenylphosphine)palladium, tetrakis(triphenylphosphine)palladium, bis(dibenzylideneacetone) palladium, rhodium chloride, chlorotris(triphenylphosphine) rhodium, hydridocarbonyltris(triphenylphosphine)rhodium, hydridotris(triphenylphosphine)rhodium, di-t-chlorotetracarbonyldirhodium, chlorocarbonylbis(triphenylphosphine)iridium, ($\eta^5$-pentamethylcyclopentadienyl)dichloroiridium dimers, nickel tetrakis(triphenylphosphine), dicobaltoctacarbonyl, and ($\eta^5$-cyclopentadienyl)dicarbonylcobalt.

Examples of the ligand include: unidentate phosphine ligands typified by trimethylphosphine, triethylphosphine, tri-n-propylphosphine, tri-1-propylphosphine, tri-n-butyiphosphine, tri-t-butylphosphine, tricyclohexylphosphine, triphenylphosphine, and tri(o-tolyl)phosphine; bidentate phosphine ligands typified by 1,2-bis(diphenylphosphino) ethane, 1,3-bis(diphenylphosphino)propane, 1,4-bis(diphenylphosphino)butane, and 1,2-(diethylphosphino)ethane; and phosphite ligands typified by triethyl phosphite, tributyl phosphite, triphenyl phosphite, and tri(o-tolyl) phosphite.

This reaction may be performed in the presence of a base. Inorganic and organic bases known in the art can be used widely as the base. Examples of the inorganic bases include alkali metals (e.g., sodium and potassium), alkali metal bicarbonates (e.g., lithium bicarbonate, sodium bicarbonate, and potassium bicarbonate), alkali metal hydroxides (e.g., lithium hydroxide, sodium hydroxide, potassium hydroxide, and cesium hydroxide), alkali metal carbonates (e.g., lithium carbonate, sodium carbonate, potassium carbonate, and cesium carbonate), alkali metal lower alkoxides (e.g., sodium methoxide and sodium ethoxide), and alkali metal hydrides (e.g., sodium hydride and potassium hydride). Examples of the organic bases include trialkylamines (e.g., trimethylamine, triethylamine, and N-ethyldiisopropylamine), pyridine, quinoline, piperidine, imidazole, picoline, dimethylaminopyridine, dimethylaniline, N-methylmorpholine, 1,5-diazabicyclo[4.3.0]non-5-ene (DBN), 1,4-diazabicyclo[2.2.2]octane (DABCO), and 1,8-diazabicyclo[5.4.0]undec-7-ene (DBU). When these bases are in a liquid state, they can also be used as solvents. These bases are used alone or as a mixture of two or more of them. The amount of the base used is usually 0.1 to 10 mol, preferably 0.1 to 3 mol, with respect to 1 mol of the compound of the general formula (7).

The reaction can also be performed in the presence of a mixture of an oxidizing agent and a reducing agent.

Examples of the oxidizing agent include manganese dioxide, chromic acid, lead tetraacetate, silver oxide, copper oxide, halogen acid, dimethyl sulfoxide (Swern oxidation), organic peroxides, and oxygen. A method such as electrode oxidation may be used.

Examples of the reducing agent include borohydride reagents such as sodium borohydride and aluminum hydride reagents such as lithium aluminum hydride.

The ratio between the compound of the general formula (9) and the compound of the general formula (4) used in the reaction formula is usually at least 1 mol, preferably approximately 1 to 5 mol of the former compound with respect to 1 mol of the latter compound.

The reaction of the present invention can be performed in an atmosphere of inert gas such as nitrogen or argon under the atmospheric pressure or can be performed under increased pressure.

The reaction temperature is not particularly limited. The reaction is usually performed under cooling, at room temperature, or under heating. The reaction is preferably performed under temperature conditions involving room temperature to 100° C., for 30 minutes to 30 hours, preferably 30 minutes to 5 hours.

After the completion of the reaction, the reaction product can be treated by a standard method to obtain the compound of the general formula (2) of interest.

Examples of preferable salts of the compound of the general formula (1) include pharmacologically acceptable salts, for example: metal salts such as alkali metal salts (e.g., sodium salt and potassium salt) and alkaline earth metal salts (e.g., calcium salt and magnesium salt); ammonium salt;

salts of inorganic bases such as alkali metal carbonates (e.g., lithium carbonate, potassium carbonate, sodium carbonate, and cesium carbonate), alkali metal bicarbonates (e.g., lithium bicarbonate, sodium bicarbonate, and potassium bicarbonate), and alkali metal hydroxides (e.g., lithium hydroxide, sodium hydroxide, potassium hydroxide, and cesium hydroxide); salts of organic bases such as tri-(lower) alkylamine (e.g., trimethylamine, triethylamine, and N-ethyldiisopropylamine), pyridine, quinoline, piperidine, imidazole, picoline, dimethylaminopyridine, dimethylaniline, N-(lower) alkyl-morpholine (e.g., N-methylmorpholine), 1,5-diazabicyclo[4.3.0]non-5-ene (DBN), 1,8-diazabicyclo [5.4.0]undec-7-ene (DBU), and 1,4-diazabicyclo [2.2.2] octane (DABCO); inorganic acid salts such as hydrochloride, hydrobromide, hydroiodide, sulfate, nitrate, and phosphate; and organic acid salts such as formate, acetate, propionate, oxalate, malonate, succinate, fumarate, maleate, lactate, malate, citrate, tartrate, carbonate, picrate, methanesulfonate, ethanesulfonate, p-toluenesulfonate, and glutamate.

Moreover, compounds in a form of a solvate (e.g., a hydrate or an ethanolate) added to the raw material or the compound of interest shown in each reaction formula are also included in each general formula. Preferable examples of the solvate include hydrates.

Each compound of interest obtained according to each of the reaction formulas can be isolated and purified from the reaction mixture, for example, by separating, after cooling, the reaction mixture into a crude reaction product by isolation procedures such as filtration, concentration, and extraction and subjecting the crude reaction product to usual purification procedures such as column chromatography and recrystallization.

The compound represented by the general formula (1) of the present invention also encompasses isomers such as geometric isomers, stereoisomers, and optical isomers, of course.

Various isomers can be isolated by a standard method using difference in physicochemical properties among the isomers. For example, racemic compounds can be converted to sterically pure isomers by a general optical resolution method [e.g., method involving conversion to diastereomeric salts with a general optically active acid (tartaric acid, etc.) and subsequent optical resolution]. Diastereomeric mixtures can be separated by, for example, fractional crystallization or chromatography. Optically active compounds can also be produced using appropriate optically active starting materials.

The present invention also encompasses isotope-labeled compounds which are the same as the compound represented by the general formula (1) except that one or more atom(s) is substituted by one or more atoms(s) having a particular atomic mass or mass number. Examples of the isotope that can be incorporated in the compound of the present invention include hydrogen, carbon, nitrogen, oxygen, sulfur, fluorine, and chlorine isotopes such as $^{2}H$, $^{3}H$, $^{13}C$, $^{14}C$, $^{15}N$, $^{18}O$, $^{17}O$, $^{18}F$, and $^{36}Cl$. These particular isotope-labeled compounds of the present invention containing any of the isotopes and/or other isotopes of other atoms, for example, radioisotope (e.g., $^{3}H$ and $^{14}C$)-incorporated compounds, are useful in assay for the distribution of drugs and/or substrates in tissues. Tritiated (i.e., $^{3}H$) and carbon-14 (i.e., $^{14}C$) isotopes are particularly preferable because of their easy preparation and detectability. Furthermore, substitution by heavier isotopes such as heavy hydrogen (i.e., $^{2}H$) can be expected to bring about particular therapeutic advantages attributed to improved metabolic stability, for example, increased in-vivo half-life, or reduced necessary doses. The isotope-labeled compounds of the present invention can be prepared generally by substituting an unlabeled reagent by an easily obtainable isotope-labeled reagent by a method disclosed in the reaction formulas and/or Examples below.

A pharmaceutical preparation comprising the compound of the present invention as an active ingredient will be described.

The pharmaceutical preparation is obtained by making the compound of the present invention into usual dosage forms of pharmaceutical preparations and prepared using a diluent and/or an excipient usually used, such as fillers, extenders, binders, humectants, disintegrants, surfactants, and lubricants.

Such a pharmaceutical preparation can be selected from among various forms according to a therapeutic purpose. Typical examples thereof include tablets, pills, powders, solutions, suspensions, emulsions, granules, capsules, suppositories, and injections (solutions, suspensions, etc.).

Carries known in the art for use for forming a tablet form can be used widely. Examples thereof include: excipients such as lactose, sucrose, sodium chloride, glucose, urea, starch, calcium carbonate, kaolin, and crystalline cellulose; binders such as water, ethanol, propanol, simple syrup, glucose solutions, starch solutions, gelatin solutions, carboxymethylcellulose, shellac, methylcellulose, potassium phosphate, and polyvinyl pyrrolidone; disintegrants such as dry starch, sodium alginate, agar powder, laminaran powder, sodium bicarbonate, calcium carbonate, polyoxyethylene sorbitan fatty acid esters, sodium lauryl sulfate, stearic acid monoglyceride, starch, and lactose; disintegration inhibitors such as sucrose, stearin, cacao butter, and hydrogenated oil; absorption promoters such as quaternary ammonium bases and sodium lauryl sulfate; humectants such as glycerin and starch; adsorbents such as starch, lactose, kaolin, bentonite, and colloidal silicic acid; and lubricants such as purified talc, stearate, boric acid powder, and polyethylene glycol.

Furthermore, the tablets can be coated, if necessary, with a usual coating material to prepare, for example, sugar-coated tablets, gelatin-coated tablets, enteric coated tablets, film-coated tablets, and bilayer or multilayer tablets.

Carries known in the art for use for forming a pill form can be used widely. Examples thereof include: excipients such as glucose, lactose, starch, cacao butter, hydrogenated plant oil, kaolin, and talc; binders such as gum arabic powder, powdered tragacanth, gelatin, and ethanol; and disintegrants such as laminaran and agar.

Carries known in the art for use for forming a suppository form can be used widely. Examples thereof include polyethylene glycol, cacao butter, higher alcohol, esters of higher alcohol, gelatin, and semisynthetic glyceride.

When the compound represented by the general formula (1) is prepared as injections, solutions, emulsions, and suspensions are preferably sterile and isotonic with blood. Diluents known in the art for use for forming forms of these solutions, emulsions, and suspensions can be used widely. Examples thereof include water, ethanol, propylene glycol, ethoxylated isostearyl alcohol, polyoxylated isostearyl alcohol, and polyoxyethylene sorbitan fatty acid esters. In this case, the pharmaceutical preparation may contain common salt, glucose, or glycerin in an amount sufficient for preparing an isotonic solution and may contain usual solubilizers, buffers, soothing agents, and the like, and if necessary, coloring agents, preservatives, perfumes, flavoring agents, sweetening agents, and the like, and/or other drugs.

The amount of the compound of the present invention contained in the pharmaceutical preparation is not particularly limited and can be selected appropriately from within a wide range. The compound of the present invention is usually contained in an amount of preferably approximately 1 to 70% by weight in the pharmaceutical preparation.

A method for administering the pharmaceutical preparation according to the present invention is not particularly limited. The pharmaceutical preparation is administered by a method according to various dosage forms, the age, sex, and disease state of a patient, and other conditions. For example, tablets, pills, solutions, suspensions, emulsions, granules, and capsules are orally administered. Moreover, injections can be administered through an intravenous route alone or as a mixture with a usual replacement fluid such as glucose or amino acid or can be administered alone through intramuscular, intradermal, hypodermic, or intraperitoneal route, if necessary. Suppositories are rectally administered.

The dose of the pharmaceutical preparation may be selected appropriately according to use, the age, sex, and disease state of a patient, and other conditions. The pharmaceutical preparation is usually administered once or several times a day at a daily dose of approximately 0.001 to 100 mg, preferably approximately 0.001 to 50 mg, per kg of body weight.

The dose varies depending on various conditions. Thus, in some cases, a dose smaller than this range suffices. In other cases, a dose exceeding this range is required.

A heterocyclic compound of the present invention has reuptake inhibitory effects on 1, 2, or 3 monoamines (serotonin, norepinephrine, and dopamine).

The heterocyclic compound of the present invention has remarkably strong uptake inhibitory activity in in-vitro or ex-vivo tests on any one, any two, or all of the 3 monoamines, compared with existing compounds having monoamine uptake inhibitory activity. Moreover, the heterocyclic compound of the present invention exhibits remarkably strong activity in brain microdialysis study against increase in any one, any two, or all of the 3 monoamines, compared with existing compounds having monoamine uptake inhibitory activity.

The heterocyclic compound of the present invention has a wide therapeutic spectrum, compared with antidepressants known in the art.

The heterocyclic compound of the present invention exerts sufficient therapeutic effects even in short-term administration.

The heterocyclic compound of the present invention has excellent bioavailability, weak inhibitory activity on metabolic enzymes in the liver, few side effects, and excellent safety.

The heterocyclic compound of the present invention is excellent in transfer into the brain.

The heterocyclic compound of the present invention also exerts strong activity in a mouse forced swimming test used in depression screening. Moreover, the heterocyclic compound of the present invention also exerts strong activity in a rat forced swimming test used in depression screening. Moreover, the heterocyclic compound of the present invention also exerts strong activity in a reserpine-induced hypothermia test used in depression screening.

The heterocyclic compound of the present invention exerts strong activity in a marble burying behavior test of anxiety or stress disease model mice and in fear-conditioned stress models.

The heterocyclic compound of the present invention has reuptake inhibitory effects on 1, 2, or 3 monoamines (serotonin, norepinephrine, and dopamine) and is therefore effective for treating various disorders associated with the reduced neurotransmission of serotonin, norepinephrine, or dopamine.

Such disorders include depression (e.g.: major depressive disorder; bipolar I disorder; bipolar II disorder; mixed state; dysthymic disorder; rapid cycler; atypical depression; seasonal affective disorder; postpartum depression; hypomelancholia; recurrent brief depressive disorder; refractory depression/chronic depression; double depression; alcohol-induced mood disorder; mixed anxiety-depressive disorder; depression caused by various physical diseases such as Cushing syndrome, hypothyroidism, hyperparathyroidism, Addison's disease, amenorrhea-galactorrhea syndrome, Parkinson's disease, Alzheimer's disease, cerebrovascular dementia, brain infarct, brain hemorrhage, subarachnoid hemorrhage, diabetes mellitus, virus infection, multiple sclerosis, chronic fatigue syndrome, coronary artery disease, pain, and cancer, etc.; presenile depression; senile depression; depression in children and adolescents; depression induced by drugs such as interferon, etc.); depression status caused by adjustment disorder, anxiety caused by adjustment disorder, anxiety caused by various diseases [e.g.: nerve disorders (head injury, brain infection, and inner ear impairment); cardiovascular disorders (cardiac failure and arrhythmia); endocrine disorders (hyperadrenalism and hyperthyroidism); and respiratory disorders (asthma and chronic obstructive pulmonary disease)], generalized anxiety disorder, phobia (e.g., agoraphobia, social fear, simple phobia, social phobia, social anxiety disorder, ereuthrophobia, anthrophobia, acrophobia, odontophobia, trypanophobia, specific phobia, simple phobia, animal phobia, claustrophobia, nyctophobia and phobic anxiety), obsessive-compulsive disorder, panic disorder, posttraumatic stress disorder, acute stress syndrome, hypochondriasis disorder, dissociative amnesia, avoidant personality disorder, body dysmorphic disorder, eating disorders (e.g., anorexia nervosa and bulimia nervosa), obesity, chemical dependence (e.g., addition to alcohol, cocaine, heroin, phenobarbital, nicotine, and benzodiazepines), pain (e.g., chronic pain, psychogenic pain, neuropathic pain, phantom limb pain, postherpetic neuralgia, traumatic cervical syndrome, spinal cord injury (SCI) pain, trigeminal neuralgia, diabetic neuropathy), fibromyalgia (FMS), Alzheimer's disease, memory deficit (e.g., dementia, amnestic disorder, and age-related cognitive decline (ARCD)), Parkinson's disease (e.g., non-motor/psychotic symptoms, dementia in Parkinson disease, neuroleptic-induced Parkinson's syndrome, and tardive dyskinesia), restless leg diseases, endocrine disorders (e.g., hyperprolactinemia), vasospasm (particularly, in the cerebral vasculature), cerebellar ataxia, gastrointestinal disorders (which encompass changes in secretion and motility), negative syndromes of schizophrenia, premenstrual syndrome, stress urinary incontinence, Tourette's Disorder, attention deficit hyperactivity disorder (ADHD), autism, Asperger syndrome, impulse control disorder, trichotillomania, kleptomania, gambling disorder, cluster headache, migraine, chronic paroxysmal hemicrania, chronic fatigue syndrome, precocious ejaculation, male impotence, narcolepsy, primary hypersomnia, cataplexy, sleep apnea syndrome and headache (associated with angiopathy).

EXAMPLES

Hereinafter, the present invention will be described more specifically with reference to Reference Examples, Examples, and Pharmacological Tests. The chemical structures of racemic bodies and optically active forms are indicated, for example, as shown below.

Racemic Body

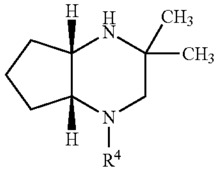

Relative configuration

Optically Active Form

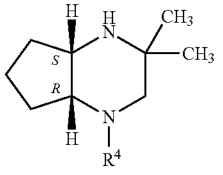

Absolute configuration

Reference Example 1

Production of cis-3,3-dimethyloctahydrocyclopentapyrazin-2-one

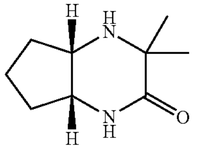

Relative configuration

90% acetone cyanohydrin (9.79 g, 104 mmol) was added to an aqueous (100 mL) solution of cis-cyclopentane-1,2-diamine (9.88 g, 98.6 mmol) at room temperature, and the mixture was stirred under reflux for 16 hours. The solvent was removed from the reaction mixture under reduced pressure, followed by azeotropy with ethanol. The obtained residue was purified by silica gel column chromatography (methylene chloride/methanol=1/10) to obtain cis-3,3-dimethyloctahydrocyclopentapyrazin-2-one (5.00 g, 30%) in a white powder form.

$^1$H-NMR ($CDCl_3$) δ ppm: 1.20 (1H, brs), 1.34 (3H, s), 1.39 (3H, s), 1.40-2.20(6H, m), 3.50-3.70 (2H, m), 5.89 (1H, brs).

Compounds of Reference Examples 2 to 12 shown below were produced in the same way as in Reference Example 1 using appropriate starting materials.

Reference Example 2

Trans-3,3-dimethyloctahydrocyclopentapyrazin-2-one

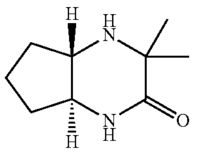

Relative configuration $^1$H-NMR ($CDCl_3$) δ ppm: 1.26-1.55 (9H, m), 1.75-2.00 (4H, m), 2.85-3.02 (1H, m), 3.05-3.20 (1H, m), 6.02 (1H, brs).

Reference Example 3

Cis-3,3-dimethylhexahydrofuro[3,4-b]pyrazin-2-one

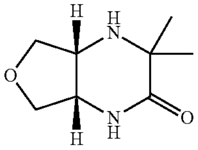

Relative configuration $^1$H-NMR ($CDCl_3$) δ ppm: 1.37 (3H, s), 1.40 (3H, s), 1.50-1.85 (1H, br), 3.73-4.10 (6H, m), 6.02-6.22 (1H, br).

Reference Example 4

Trans-3,3-dimethylhexahydrofuro[3,4-b]pyrazin-2-one

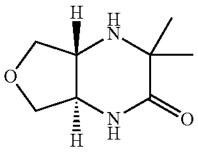

Relative configuration $^1$H-NMR ($CDCl_3$) δ ppm: 1.38-1.43 (1H, br), 1.44 (3H, s), 1.47 (3H, s), 3.38-3.52 (1H, m), 3.52-3.65 (3H, m), 4.00-4.14 (2H, m), 6.28-6.45 (1H, br).

Reference Example 5

(4aS,8aS)-3,3-dimethyloctahydroquinoxalin-2-one

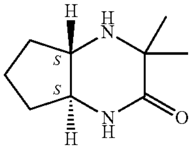

Absolute configuration $^1$H-NMR ($CDCl_3$) δ ppm: 1.14-1.37 (61H, m), 1.38 (3H, s), 1.42 (3H, s), 1.69 (1H, brs), 1.74-1.84 (2H, m), 2.57-2.65 (1H, m), 2.96-3.04 (1H, m), 5.61 (1H, s)

Reference Example 6

(4aR,8aR)-3,3-dimethyloctahydroquinoxalin-2-one

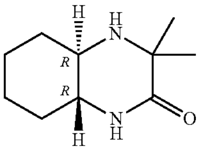

Absolute configuration $^1$H-NMR ($CDCl_3$) δ ppm: 1.14-1.37 (6H, m), 1.38 (3H, s), 1.42 (3H, s), 1.63 (1H, brs), 1.73-1.83 (2H, m), 2.57-2.66 (1H, m), 2.95-3.04 (1H, m), 5.55 (1H, s)

Reference Example 7

Trans-3,3-diethyloctahydroquinoxalin-2-one

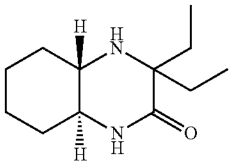

Relative configuration $^1$H-NMR ($CDCl_3$) δ ppm: 0.92 (3H, t, J=7.5 Hz), 0.93 (3H, t, J=7.3 Hz), 1.13-1.49 (7H, m), 1.60-1.99 (6H, m), 2.55-2.60 (1H, m), 2.91-3.00 (1H, m), 5.69 (1H, brs)

Reference Example 8

Trans-octahydro-1$^1$H-spiro[cyclobutane-1,2'-quinoxalin]-3'-one

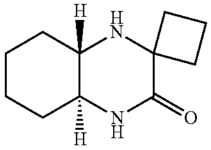

Relative configuration $^1$H-NMR ($CDCl_3$) δ ppm: 1.14-1.46 (4H, m), 1.70-2.17 (9H, m), 2.43-2.52 (1H, m), 2.55-2.66 (1H, m), 2.78-2.88 (1H, m), 2.97-3.06 (1H, m), 5.65 (1H, brs)

Reference Example 9

Cis-octahydro-1$^1$H-spiro[cyclobutane-1,2'-quinoxalin]-3'-one

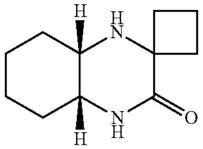

Relative configuration $^1$H-NMR ($CDCl_3$) δ ppm: 1.1-1.3 (1H, m), 1.35-2.15 (12H, m), 2.5-2.6 (1H, m), 2.75-2.85 (1H, m), 3.15-3.3(2H, m), 5.65 (1H, br).

Reference Example 10

Trans-octahydro-1'H-spiro[cyclohexane-1,2'-quinoxalin]-3'-one

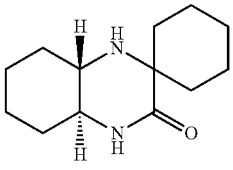

Relative configuration $^1$H-NMR ($CDCl_3$) δ ppm: 1.18-1.88 (18H, m), 2.03-2.13 (1H, m), 2.47-2.58 (1H, m), 2.92-3.00 (1H, m), 5.59 (1H, s)

Reference Example 11

Cis-3,3-dimethyldecahydrocycloheptapyrazin-2-one

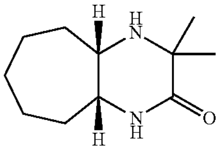

Relative configuration $^1$H-NMR ($CDCl_3$) δ ppm: 1.12-2.00 (16H, m), 2.03-2.20 (1H, m), 3.35-3.55 (2H, m), 5.88 (1H, brs).

Reference Example 12

Trans-3,3-dimethyldecahydrocycloheptapyrazin-2-one

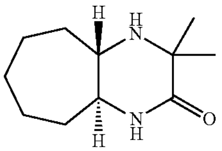

Relative configuration $^1$H-NMR ($CDCl_3$) δ ppm: 1.35 (3H, s), 1.39 (3H, s), 1.42-1.90 (11H, m), 2.73-2.85 (1H, m), 3.13-3.26 (1H, m), 5.51 (1H, brs).

Reference Example 13

Production of cis-4,4-dimethyloctahydrocyclopenta[b][1,4]diazepin-2-one

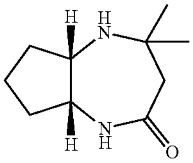

Relative configuration

A toluene (200 mL) suspension of cis-cyclopentane-1,2-diamine (19.7 g, 197 mmol) and 3-methyl-2-butenoic acid (19.7 g, 197 mmol) was stirred under reflux for 24 hours under azeotropic conditions using a Dean-Stark apparatus. The reaction mixture was cooled to room temperature and then concentrated under reduced pressure, and the deposited crystal was collected by filtration. The obtained crystal was washed with ether and then dried to obtain cis-4,4-dimethyloctahydrocyclopenta[b][1,4]diazepin-2-one (8.60 g, 24%) in a light brown powder form.

$^1$H-NMR ($CDCl_3$) δ ppm: 1.10-1.56 (10H, m), 1.65-1.80 (1H, m), 2.02-2.30 (3H, m), 2.60 (1H, d, J=12.8 Hz), 3.18-3.37 (1H, m), 3.68-3.85 (1H, m), 5.73 (1H, brs).

Compounds of Reference Examples 14 and 15 below were produced in the same way as in Reference Example 13 using appropriate starting materials.

Reference Example 14

(5aS,9aS)-4,4-dimethyldecahydro[b][1,4]diazepin-2-one

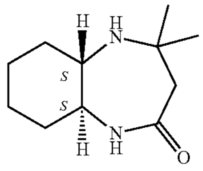

Absolute configuration

$^1$H-NMR ($CDCl_3$) δ ppm: 1.00-1.45 (11H, m), 1.63-1.83 (3H, m), 1.83-2.00 (1H, m), 2.31-2.43 (1H, m), 2.65-2.81 (2H, m), 3.00-3.16 (1H, m), 5.54-5.90 (1H, br).

Reference Example 15

(5aR,9aR)-4,4-dimethyldecahydro[b][1,4]diazepin-2-one

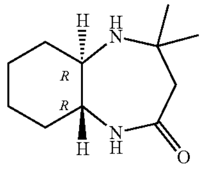

Absolute configuration

$^1$H-NMR ($CDCl_3$) δ ppm: 1.02-1.36 (11H, m), 1.64-1.83 (3H, m), 1.83-1.97 (1H, m), 2.37 (1H, dd, J=2.4, 13.9 Hz), 2.66-2.81 (2H, m), 3.01-3.15 (1H, m), 5.75-5.92 (1H, brs).

Reference Example 16

Production of cis-2,2-dimethyloctahydro-1H-cyclopenta[b]pyrazine

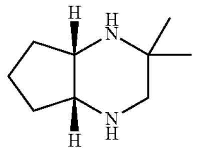

Relative configuration

Lithium aluminum hydride (541 mg, 14.3 mmol) was added to an anhydrous dioxane (40 mL) solution of cis-3,3-dimethyloctahydrocyclopentapyrazin-2-one (2.00 g, 11.9 mmol) with stirring at room temperature, and the mixture was gradually heated and stirred for 10 minutes under reflux. The reaction mixture was cooled to ice temperature. Then, sodium sulfate decahydrate was added thereto in small portions until no hydrogen gas was generated. Then, the mixture was stirred at room temperature for 1 hour. Insoluble matter was filtered through celite, and the filtrate was concentrated. The obtained residue was purified by basic silica gel column chromatography (ethyl acetate/hexane=l/l 0) to obtain cis-2,2-dimethyloctahydro-1H-cyclopenta[b]pyrazine (1.67 g, 91%) in a pale yellow oil form.

$^1$H-NMR ($CDCl_3$) δ ppm: 1.04 (3H, s), 1.16 (3H, s), 1.28-2.02 (8H, m), 2.37 (1H, d, J=12.9 Hz), 2.70 (1H, d, J=12.9 Hz), 3.00-3.15 (1H, m), 3.15-3.32 (1H, m).

Compounds of Reference Examples 17 to 34 below were produced in the same way as in Reference Example 16 using appropriate starting materials.

Reference Example 17

Trans-2,2-dimethyloctahydro-1H-cyclopenta[b]pyrazine

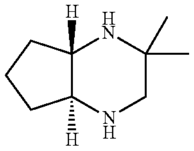

Relative configuration

$^1$H-NMR ($CDCl_3$) δ ppm: 1.08 (3H, s), 1.19-1.92 (11H, m), 2.15-2.30 (1H, m), 2.55-2.74 (2H, m), 2.77 (1H, d, J=12.2 Hz).

Reference Example 18

Cis-2,2-dimethyldecahydrocyclopenta[b][1,4]diazepine

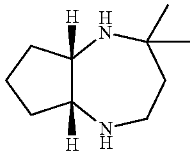

Relative configuration

$^1$H-NMR ($CDCl_3$) δ ppm: 1.11 (3H, s), 1.14 (3H, s), 1.15-1.45 (6H, m), 1.55-1.67 (1H, m), 1.67-1.77 (1H, m), 1.97-2.12 (2H, m), 2.68-2.80 (1H, m), 2.98-3.11 (2H, m), 3.16-3.28 (1H, m).

Reference Example 19

Cis-2,2-dimethyloctahydrofuro[3,4-b]pyrazine

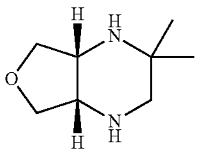

Relative configuration

$^1$H-NMR ($CDCl_3$) δ ppm: 1.08 (3H, s), 1.18 (3H, s), 1.40-1.80 (2H, br), 2.41 (1H, d, J=13.2 Hz), 2.69 (1H, d, J=13.2 Hz), 3.33-3.43 (1H, m), 3.43-3.55 (1H, m), 3.63-3.72 (1H, m), 3.75-3.96 (3H, m).

Reference Example 20

Trans-2,2-dimethyloctahydrofuro[3,4-b]pyrazine

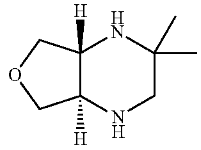

Relative configuration $^1$H-NMR ($CDCl_3$) δ ppm: 1.13 (3H, s), 1.30 (3H, s), 1.44-1.65 (2H, m), 2.64-2.78 (2H, m), 2.83 (1H, d, J=12.2 Hz), 3.11-3.22 (1H, m), 3.46 (1H, dd, J=7.3, 10.5 Hz), 3.55 (1H, dd, J=7.4, 10.5 Hz), 3.94 (1H, t, J=7.1 Hz), 4.00 (1H, t, J=7.2 Hz).

Reference Example 21

Cis-2,2-dimethyldecahydro-1H-benzo[b][1,4]diazepine

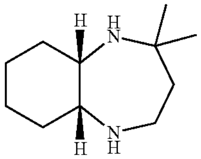

Relative configuration $^1$H-NMR ($CDCl_3$) δ ppm: 1.08 (3H, s), 1.13 (3H, s), 1.18-1.84 (12H, m), 2.65-2.93 (3H, m), 3.14-3.22 (1H, m).

Reference Example 22

(5aS,9aS)-2,2-dimethyldecahydro-1H-benzo[b][1,4] diazepine

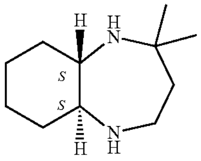

Absolute configuration $^1$H-NMR ($CDCl_3$) δ ppm: 1.00-1.35 (11H, m), 1.50-1.85 (7H, m), 2.20-2.31 (1H, m), 2.31-2.43 (1H, m), 2.79-2.90 (1H, m), 2.90-3.04 (1H, m).

Reference Example 23

(5aR,9aR)-2,2-dimethyldecahydro-1H-benzo[b][,4] diazepine

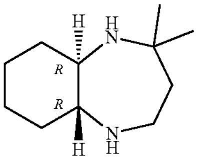

Absolute configuration $^1$H-NMR ($CDCl_3$) δ ppm: 1.00-1.35 (11H, m), 1.50-1.85 (7H, m), 2.20-2.31 (1H, m), 2.31-2.43 (1H, m), 2.79-2.90 (1H, m), 2.90-3.04 (1H, m).

Reference Example 24

Cis-2,2-dimethyldecahydroquinoxaline

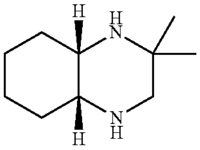

Relative configuration $^1$H-NMR ($CDCl_3$) δ ppm: 1.06 (3H, s), 1.19 (3H, s), 1.20-1.40 (5H, m), 1.53-1.60 (3H, m), 1.70-1.77 (1H, m), 1.92-2.15 (1H, m), 2.36 (1H, d, J=12.7 Hz), 2.66-2.72 (1H, m), 2.72 (1H, d, J=12.7 Hz), 3.16-3.28 (1H, m).

Reference Example 25

Trans-2,2-dimethyldecahydroquinoxaline

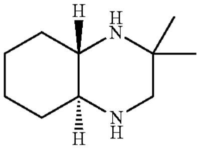

Relative configuration $^1$H-NMR ($CDCl_3$) δ ppm: 1.05 (3H, s), 1.08-1.74 (10H, m), 1.23 (3H, s), 2.02-2.12 (1H, m), 2.40-2.50 (1H, m), 2.60 (1H, d, J=12.1 Hz), 2.73 (1H, d, J=12.1 Hz).

Reference Example 26

(4aS,8aS)-2,2-dimethyldecahydroquinoxaline

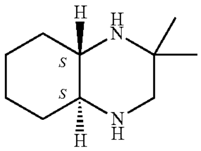

Absolute configuration

$^1$H-NMR ($CDCl_3$) δ ppm: 1.01-1.43 (6H, m), 1.05 (3H, s), 1.23 (3H, s), 1.58-1.63 (1H, m), 1.68-1.74 (3H, m), 2.03-2.19 (1H, m), 2.40-2.49 (1H, m), 2.60 (1H, d, J=12.1 Hz), 2.73 (1H, d, J=12.1 Hz).

Reference Example 27

(4aR,8aR)-2,2-dimethyldecahydroquinoxaline

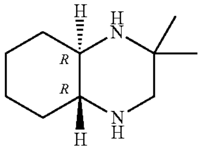

Absolute configuration

$^1$H-NMR ($CDCl_3$) δ ppm: 1.05 (3H, s), 1.09-1.56 (6H, m), 1.23 (3H, s), 1.58-1.63 (1H, m), 1.66-1.75 (3H, m), 2.03-2.12 (1H, m), 2.41-2.50 (1H, m), 2.61 (1H, d, J=12.1 Hz), 2.75 (1H, d, J=12.1 Hz).

Reference Example 28

Trans-2,2-diethyldecahydroquinoxaline

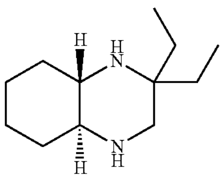

Relative configuration

$^1$H-NMR ($CDCl_3$) δ ppm: 0.79 (3H, t, J=7.5 Hz), 0.81 (3H, t, J=7.5 Hz), 0.86-1.02 (1H, m), 1.08-1.40 (8H, m), 1.47-1.60 (2H, m), 1.67-1.87 (3H, m), 2.06-2.15 (1H, m), 2.33-2.42 (1H, m), 2.57 (1H, d, J=12.1 Hz), 2.81 (1H, d, J=12.1 Hz).

Reference Example 29

Trans-octahydro-1 [1]H-spiro[cyclobutane-12'-quinoxaline]

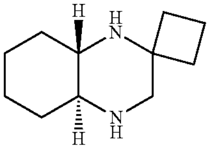

MS(M+1) 181

Relative configuration

Reference Example 30

Cis-octahydro-1'H-spiro[cyclobutane-1,2'-quinoxaline]

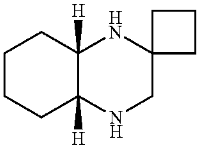

MS(M+1) 181

Relative configuration

Reference Example 31

Trans-octahydro-1'H-spiro[cyclopentane-1,2'-quinoxaline]

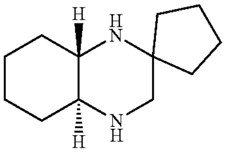

Relative configuration

$^1$H-NMR ($CDCl_3$) δ ppm: 1.10-1.97 (18H, m), 2.10-2.21 (1H, m), 2.29-2.38 (111H, m), 2.71 (1H, d, J=12.2 Hz), 2.76 (1H, d, J=12.2 Hz).

Reference Example 32

Trans-octahydro-1'H-spiro[cyclohexane-1,2'-quinoxaline]

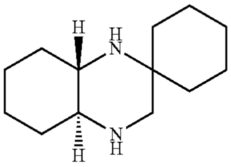

Relative configuration

$^1$H-NMR ($CDCl_3$) δ ppm: 1.12-1.76 (20H, m), 2.12-2.20 (1H, m), 2.44-2.53 (1H, m), 2.55 (1H, d, J=12.2 Hz), 2.98 (1H, d, J=12.2 Hz).

Reference Example 33

Cis-2,2-dimethyldecahydro-1H-cyclohepta[b]pyrazine

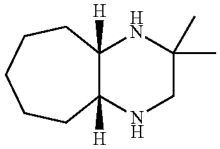

Relative configuration $^1$H-NMR ($CDCl_3$) δ ppm: 1.00-2.02 (18H, m), 2.42 (1H, d, J=12.4 Hz), 2.58 (1H, d, J=12.4 Hz), 2.75-2.86 (1H, m), 3.13-3.25 (1H, m).

Reference Example 34

Trans-2,2-dimethyldecahydro-1H-cyclohepta[b] pyrazine

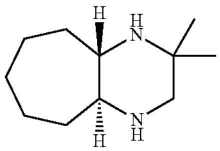

Relative configuration $^1$H-NMR ($CDCl_3$) δ ppm: 1.05 (3H, s), 1.21 (3H, s), 1.23-1.80 (12H, m), 2.09-2.20 (1H, m), 2.46-2.60 (2H, m), 2.68 (1H, d, J=11.8 Hz).

Reference Example 35

Production of (2RS,4aSR,8aSR)-2-ethyldecahydroquinoxaline

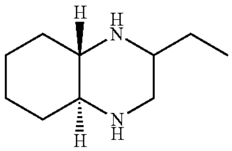

Relative configuration

Dichloro(pentamethylcyclopentadienyl)iridium (111) dimer (70 mg, 0.090 mmol) and sodium bicarbonate (73 mg, 0.87 mmol) were added to an aqueous (20 mL) solution of trans-cyclohexane-1,2-diamine (2.00 g. 17.5 mmol) and (±)-1,2-butanediol (1.69 mL, 18.4 mmol) with stirring at room temperature. Degassing and argon substitution were repeated 3 times, and the mixture was then stirred for 24 hours under reflux. The reaction mixture was concentrated under reduced pressure. The obtained residue was purified by basic silica gel column chromatography (methylene chloride/methanol) to obtain (2R*,4aS*,8aS*)-2-ethyldecahydroquinoxaline (2.03 g, yield: 69%) in a yellow solid form.

$^1$H-NMR ($CDCl_4$) δ ppm: 0.92 (3H, t, J=7.5 Hz), 1.10-1.60 (71, m), 1.64-1.83 (5H, m), 2.16-2.31 (2H, m), 2.44 (1H, dd, J=11.5, 10.4 Hz), 2.58-2.67 (1H, m), 3.02 (1H, dd, J=11.5, 2.7 Hz).

Reference Example 36

Production of (4aS,8aS)-1-benzyldecahydroquinoxaline

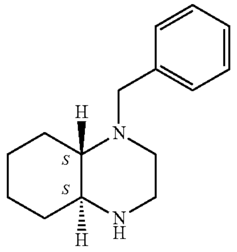

Absolute configuration

Benzaldehyde (3.05 mL, 30.0 mmol) was added to a methanol (300 mL) solution of (1S,2S)-cyclohexane-1,2-diamine (3.43 g, 30.0 mmol) with stirring at room temperature, and the mixture was stirred overnight at the same temperature. The reaction mixture was cooled to 0° C. Sodium borohydride (2.27 g, 60.0 mmol) was added thereto, and the mixture was stirred at 0° C. for 2 hours. To the reaction mixture, water (30 mL) was added, and the product was extracted twice with methylene chloride (50 mL). The organic layers were combined and dried over magnesium sulfate, and the solvent was then distilled off under reduced pressure. The obtained residue was purified by basic silica gel column chromatography (ethyl acetate/hexane) to obtain (1S,2S)—N-benzylcyclohexane-1,2-diamine (cas no. 207450-11-1) (2.95 g, yield: 48%) in a pale yellow oil form.

The obtained (1 S,2S)—N-benzylcyclohexane-1,2-diamine (2.90 g, 14.2 mmol) was dissolved in methylene chloride (284 nL). To the solution, 60% sodium hydride (1.99 g, 49.7 mmol) was added with ice-cooling and stirring in a nitrogen atmosphere. After 5 minutes, (2-bromoethyl) diphenylsulfonium trifluoromethanesulfonate (6.92 g, 15.6 mmol) was added to the reaction mixture with ice-cooling and stirring, and the mixture was stirred overnight at room temperature. To the reaction mixture, a saturated aqueous solution of ammonium chloride was added dropwise in small portions, and the product was then extracted twice with methylene chloride (100 mL). The organic layers were combined and dried over magnesium sulfate, and the solvent was then distilled off under reduced pressure. The obtained residue was purified by NH-silica gel column chromatography (ethyl acetate/hexane) to obtain (4aS,8aS)-1-benzyldecahydroquinoxaline (2.28 g, 70%) in a light brown solid form.

$^1$H-NMR ($CDCl_3$) δ ppm: 1.05-1.4 (4H, m), 1.50 (1H, br), 1.6-1.9 (4H, m), 2.05-2.2 (1H, m), 2.2-2.3 (1H, m), 2.4-2.5 (1H, m), 2.65-2.75 (1, m), 2.8-2.95 (2H, m), 3.14 (1H, d, J=13.4 Hz), 4.11 (1H, d, J 13.4 Hz), 7.15-7.4 (5H, m).

Compounds of Reference Examples 37 to 39 below were produced in the same way as in Reference Example 36 using appropriate starting materials.

Reference Example 37

(4aS,8aS)-1-benzyldecahydroquinoxaline

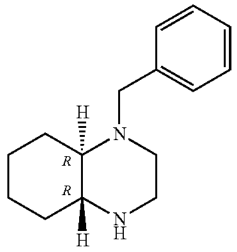

Absolute configuration $^1$H-NMR ($CDCl_3$) δ ppm: 1.05-1.4 (4H, m), 1.50 (1H, br), 1.6-1.9 (4H, m), 2.05-2.2 (1H, m), 2.2-2.3 (111H, m), 2.4-2.5 (1H, m), 2.65-2.75 (1H, m), 2.8-2.95(2H, m), 3.13 (1H, d, J=13.4 Hz), 4.11 (1H, d, J=13.4 Hz), 7.15-7.4 (5H, m).

Reference Example 38

Cis-decahydroquinoxaline-1-carboxylic acid tert-butyl ester

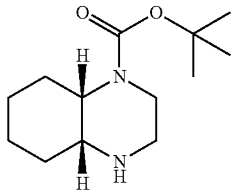

Relative configuration $^1$H NMR ($CDCl_3$) δ ppm: 1.05-1.15 (I H m), 1.2-1.75 (19H, m), 1.75-1.85 (1H, m), 1.85-2.2 (1H, m), 3.70 (1H, br), 4.83 (1H, br).

Reference Example 39

Cis-1-benzyldecahydroquinoxaline

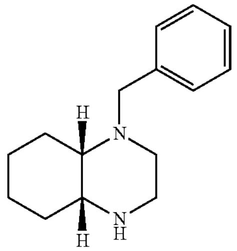

Relative configuration $^1$H-NMR ($CDCl_3$) δ ppm: 1.0-2.0 (10H, m), 2.2-2.4 (1H, m), 2.45-2.7 (2H, m), 2.75-3.1 (2H, m), 3.63 (2H, br), 7.05-7.45 (5H, m).

Reference Example 40

Production of (4aR,8aS)-2,2-dimethyldecahydroquinoxaline

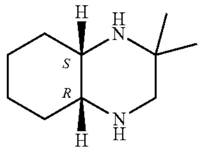

Absolute configuration

Reference Example 41

(4aS,8aR)-2,2-dimethyldecabydroquinoxaline

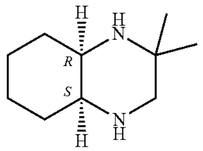

Absolute configuration (−)-dibenzoyl-L-tartaric acid monohydrate (13.8 g, 36.7 mmol) in ethanol (140 mL) was added to an ethanol (140 mL) solution of cis-2,2-dimethyldecahydroquinoxaline (13.7 g, 81.4 mmol) with stirring at room temperature. The reaction mixture was stirred for 30 minutes under reflux and cooled to room temperature, and the deposited white crystal was then collected by filtration. The obtained crystal was washed with ethanol (20 mL) and then dried to obtain a white solid <1>(13.1 g). The filtrate and washes obtained in obtaining the solid <1> were concentrated under reduced pressure. The obtained residue was dissolved in ethanol (100 mL). To the solution, an ethanol (130 mL) solution of (+)-dibenzoyl-D-tartaric acid (13.1 g, 36.6 mmol) was added with stirring at room temperature, and the deposited crystal was collected by filtration. The obtained crystal was washed with ethanol (20 mL) and then dried to obtain a light brown solid <2>(16.6 g).

A methanol (130 mL)water (10 mL) suspension of the solid <1> was stirred for 30 minutes under reflux. Then, the reaction mixture was cooled to room temperature, and the deposited crystal was collected by filtration. The deposited crystal was washed with methanol (10 mL) and then dried to obtain (4aR,8aS)-2,2-dimethyldecahydroquinoxaline dibenzoyl-L-tartrate (11.4 g, 21.6 mmol) in a white solid form (the absolute configuration of cis-2.2-dimethyldecahydroquinoxaline was determined by the X-ray crystallographic analysis of the white solid). This solid was dissolved in a 1 N aqueous sodium hydroxide solution (44 mL), and the product was extracted with ether (100 mL) three times and with methylene chloride (100 mL) three times. The extracted organic layers were combined, dried over magnesium sulfate, and then concentrated under reduced pressure to obtain (4aR,8aS)-2,2-dimethyldecahydroquinoxaline (3.44 g, yield: 25%) in a white solid form.

$^1$H-NMR ($CDCl_3$) δ ppm: 1.06 (3H, s), 1.20 (3H, s, 1.2-1.4 (4H, m), 1.45-1.95 (5H, m), 1.95-2.15 (1H, m), 2.36 (1H, d, J=12.7 Hz), 2.65-2.75(2H, m), 3.15-3.25 (1H, m).

A methanol (130 mL)/water (10 mL) suspension of the solid <2> was stirred for 1 hour under reflux. Then, the reaction mixture was cooled to room temperature, and the deposited crystal was collected by filtration. The deposited crystal was washed with methanol (10 mL) and then dried to obtain (4aS,8aR)-2,2-dimethyldecahydroquinoxaline dibenzoyl-D-tartrate (16.0 g, 30.4 mmol) in a white solid form. This solid was dissolved in a 1 N aqueous sodium hydroxide solution (65 mL), and the product was extracted with methylene chloride (100 mL) three times. The extracted organic layers were combined, dried over magnesium sulfate, and then concentrated under reduced pressure to obtain (4aS,8aR)-2,2-dimethyldecahydroquinoxaline (4.63 g, yield: 34%) in a light brown solid form.

$^1$H-NMR ($CDCl_3$) δ ppm: 1.06 (3H, s), 1.19 (3H, s), 1.2-1.45 (5H, m), 1.45-1.65 (3H, m), 1.65-1.8 (1H, m), 1.95-2.15 (1H, m), 2.36 (1H, d, J=12.7 Hz), 2.6-2.8(2H, m), 3.15-3.25 (1H, m).

Compounds of Reference Examples 42 to 45 below were produced in the same way as in Reference Examples 40 and 41 using appropriate starting materials.

Reference Example 42

(4a'R,8a'S)-octahydro-1'H-spiro[cyclobutane-1,2'-quinoxaline]

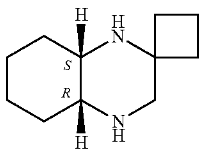

Absolute configuration
MS (M + 1) 181

$^1$H-NMR ($CDCl_3$) δ ppm: 1.20-2.20 (16H, m), 2.69 (1H, d, J=12.4 Hz), 2.72-2.82 (1H, m), 2.87-3.02 (2H, m).

Reference Example 43

(4a'S,8a'R)-octahydro-1'H-spiro[cyclobutane-1,2'-quinoxaline]

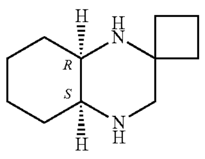

Absolute configuration
MS (M + 1) 181

$^1$H-NMR ($CDCl_3$) δ ppm: 1.20-2.20 (16H, m), 2.68 (1H, d, J=12.5 Hz), 2.72-2.82 (1H, m), 2.87-3.02 (2H, m).

Reference Example 44

(4aR,8aS)-1-benzyldecahydroquinoxaline

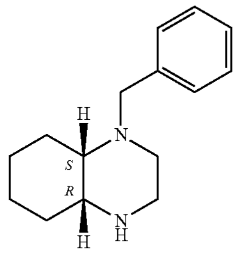

Absolute configuration $^1$H-NMR ($CDCl_3$) δ ppm: 1.0-1.25 (1H, m), 1.25-1.65 (5H, m), 1.65-2.05 (3H, m), 2.2-2.4 (1H, m), 2.45-2.7 (2H, m), 2.75-3.1 (3H, m), 3.63 (2H, br), 7.15-7.4 (5H, m).

Reference Example 45

(4aS,8aR)-1-benzyldecahydroquinoxaline

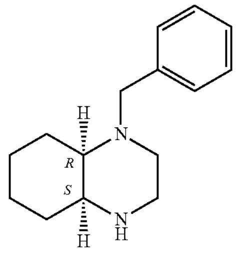

Absolute configuration $^1$H-NMR ($CDCl_3$) δ ppm: 1.05-1.25 (1H, m), 1.25-1.65 (5H, m), 1.65-2.05 (3H, m), 2.2-2.4 (H, m), 2.5-2.7 (2H, m), 2.75-3.1 (3H, m), 3.63 (21, br), 7.15-7.4(5H, m).

Reference Example 46

Production of (trans-3-oxodecahydroquinoxalin-1-yl)acetic acid ethyl ester

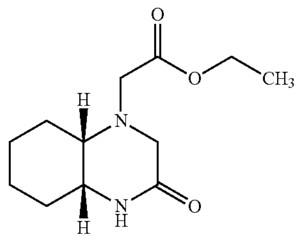

Relative configuration

Trans-cyclohexane-1,2-diamine (3.00 g, 26.3 mmol) was diluted with ethanol (15 ml). To the solution, bromoethyl acetate (6.12 mL, 55.2 mmol) was added dropwise with ice-cooling, and the mixture was then stirred overnight at room temperature.

To the reaction solution, water was added, and the mixture was stirred. The product was extracted with methylene chloride. The organic layer was washed with saturated saline and dried over magnesium sulfate, followed by filtration. The filtrate was concentrated under reduced pressure. The obtained residue was separated and purified by silica gel column chromatography (methylene chloride/methanol) to obtain (trans-3-oxodecahydroquinoxalin-1-yl)acetic acid ethyl ester (2.35 g, yield: 74.4%) in an orange particulate solid form.

$^1$H-NMR ($CDCl_3$) δ ppm: 1.13-1.41 (4H, m), 1.28 (3H, t, J=7.1 Hz), 1.72-1.97 (4H, m), 2.59-2.67 (1H, m), 3.06-3.13 (1H, m), 3.35 (1H, d, J=17.4 Hz), 3.48 (1H, d, J=16.8 Hz), 3.52 (1H, d, J=17.4 Hz), 3.60 (1H, d, J 16.8 Hz), 4.17(2H, q, J=7.1 Hz), 6.79 (1H, brs).

[Reference Example 47] Production of 2-(trans-decahydroquinoxalin-1-yl)ethanol

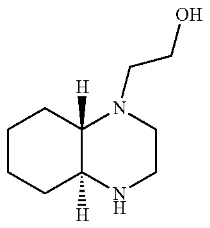

Relative configuration

Lithium aluminum hydride (1.00 g, 26.4 mmol) was suspended in anhydrous dioxane (40 ml). To the suspension, an anhydrous dioxane (10 ml) solution of (trans-3-oxodecahydroquinoxalin-1-yl)acetic acid ethyl ester (2.35 g, 9.78 mmol) was added dropwise with stirring at room temperature, and the mixture was then stirred under reflux for 10 minutes. The reaction mixture was cooled on ice, and sodium sulfate decahydrate was added thereto in small portions until no gas was generated. This mixture was filtered through celite and washed with methylene chloride, and the filtrate was then concentrated under reduced pressure to obtain 2-(trans-decahydroquinoxalin-1-yl)ethanol (1.74 g, yield: 97%) in a brown oil form.

$^1$H-NMR ($CDCl_3$) δ ppm: 0.95-1.11 (1H, m), 1.15-1.44 (3H, m), 1.68-1.80 (5H, m), 1.85-1.94 (1H, m), 2.05-2.44 (4H, m), 2.87-2.97 (3H, m), 3.04-3.16 (1]H, m), 3.46-3.54 (1H, m), 3.60-3.69 (1H, m).

Reference Example 48

Production of trans-1-[2-(tert-butyldimethylsilyloxy) ethyl]decahydroquinoxaline

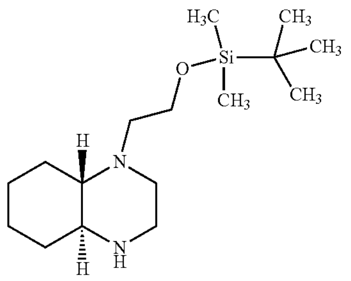

Relative configuration

Triethylamine (4.61 mL, 33.0 mmol) and subsequently tert-butyldimethylsilyl chloride (4.27 g, 28.3 mmol) were added to a methylene chloride (40 mL) solution of 2-(trans-decahydroquinoxalin-1-yl)ethanol (1.74 g, 9.44 mmol) with ice-cooling and stirring, and the mixture was stirred overnight at room temperature. To the reaction mixture, water (100 mL) was added to terminate the reaction. The product was extracted with methylene chloride (100 mL). The organic layer was washed with water twice and with saturated saline once, then dried over magnesium sulfate, and concentrated under reduced pressure. The obtained residue was purified by silica gel column chromatography (methylene chloride/methanol) to obtain trans-1-[2-(tert-butyldimethylsilyloxy)ethyl]decahydroquinoxaline (2.00 g, yield: 71%) in a light brown oil form.

$^1$H-NMR ($CDCl_3$) δ ppm: 0.06 (6H, s), 0.89 (9H, s), 0.98-1.36 (4H, m), 1.65-1.79 (4H, m), 1.85-1.95 (1H, m), 2.08-2.14 (1H, m), 2.24-2.39 (1H, m), 2.45-2.61 (2H, m), 2.79-3.03 (4H, m), 3.62-3.80 (2H, m).

Compounds of Reference Examples 50 and 51 below were produced in the same way as in Reference Example 1 using appropriate starting materials.

Reference Example 50

(4a'S,8a'S)-octahydro-1'H-spiro[cyclobutane-1,2'-quinoxalin]-3'-one

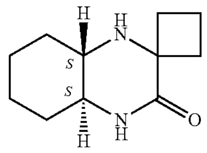

Absolute configuration $^1$H-NMR ($CDCl_3$) δ ppm: 0.99-1.38 (4H, m), 1.55-1.78 (5H, m), 1.78-1.94 (3H, m), 2.21-2.33 (2H, m), 2.48-2.59 (1H, m), 2.63 (1H, brs), 2.76-2.87 (1H, m), 7.36 (1H, s).

Reference Example 51

(4a'R,8a'R)-octahydro-1'H-spiro[cyclobutane-1,2'-quinoxalin]-3'-one

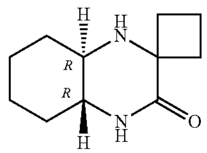

Absolute configuration $^1$H-NMR ($CDCl_3$) δ ppm: 0.97-1.36 (4H, m), 1.55-1.77 (5H, m), 1.77-1.92 (3H, m), 2.20-2.32 (2H, m), 2.47-2.57 (1H, m), 2.63 (1H, brs), 2.76-2.86 (1H, m), 7.36 (1H, s).

Compounds of Reference Examples 52 and 53 below were produced in the same way as in Reference Example 16 using appropriate starting materials.

Reference Example 52

(4a'S,8a'S)-octahydro-1$^{1}$H-spiro[cyclobutane-1,2'-quinoxaline]

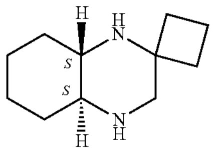

Absolute configuration $^{1}$H-NMR ($CDCl_3$) δ ppm: 1.05-1.90 (15H, m), 2.15-2.30 (3H, m), 2.69 (1H, dd, J=1.5, 12.2 Hz), 3.01 (1H, d, J=12.2 Hz).

Reference Example 53

(4a'R,8a'R)-octahydro-1'H-spiro[cyclobutane-1,2'-quinoxaline]

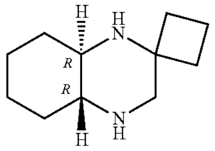

Absolute configuration $^{1}$H-NMR ($CDCl_3$) δ ppm: 1.05-1.91 (15H, m), 2.15-2.30 (3H, m), 2.69 (1H, d, J=12.2 Hz), 3.01 (1H, d, J=12.2 Hz).

Reference Example 54

Production of (4aS,8aR)-tert-butyl 4-benzyldecahydroquinoxaline-1-carboxylate

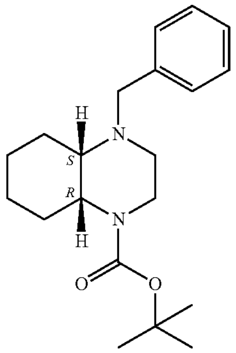

Absolute configuration

Di-tert-butyl dicarbonate (1.70 g, 7.79 mmol) was added to a MeOH (16 ml) solution of (4aR,8aS)-1-benzyldecahydroquinoxaline (1.63 g, 7.08 mmol), and the mixture was stirred at room temperature for 2 hours. The solvent was distilled off, and the residue was then purified by basic silica gel column chromatography (Hex-AcOEt) to obtain (4aS,8aR)-tert-butyl 4-benzyldecahydroquinoxaline-1-carboxylate (2.38 g, yield: quantitative) in a colorless oil form.

$^{1}$H-NMR ($CDCl_3$) δ ppm: 1.26-1.66 (14H, m), 1.79-1.96 (2H, m), 2.14-2.33 (2H, m), 2.40-2.45 (1H, m), 2.66 (1H, brs), 2.86 (1H, d, J=13.2 Hz), 3.03 (1H, brs), 3.50-4.10 (2H, br), 4.16 (1, d, J=13.2 Hz), 7.21-7.36 (5H, m).

A compound of Reference Example 55 below was produced in the same way as in Reference Example 54 using appropriate starting materials.

Reference Example 55

(4aR,8aS)-tert-butyl 4-benzyldecahydroquinoxaline-1-carboxylate

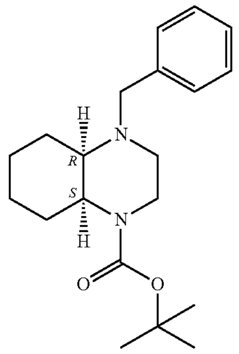

Absolute configuration $^{1}$H-NMR ($CDCl_3$) δ ppm: 1.26-1.66 (14H, m), 1.79-1.96 (2H, m), 2.14-2.33 (2H, m), 2.40-2.45 (1H, m), 2.65 (1H, brs), 2.86 (1H, d, J=13.2 Hz), 3.03 (1H, brs), 3.51-4.10 (2H, br), 4.16 (1H, d, J=13.2 Hz), 7.21-7.36 (5H, m).

Reference Example 56

Production process of (4aS,8aR)-tert-butyl decahydroquinoxaline-1-carboxylate

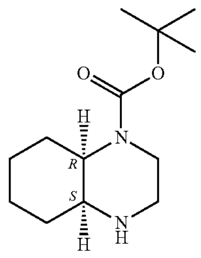

Absolute configuration

Pearlman's catalyst (0.24 g) was added to an EtOH (25 ml) solution of (4aS,8aR)-tert-butyl 4-benzyldecahydroquinoxaline-1-carboxylate (2.4 g, 7.26 mmol). This suspension was stirred at room temperature for 1 hour in a hydrogen atmosphere. The catalyst was filtered through celite, and the residue was washed with EtOH. Then, the filtrate was concentrated under reduced pressure to obtain (4aS,8aR)-tert-butyl decahydroquinoxaline-1-carboxylate (1.67 g, yield: 96%) in a colorless oil form.

$^1$H-NMR ($CDCl_3$) δ ppm: 1.16-1.53 (14H, m), 1.53-1.82 (3H, m), 1.83-2.00 (1H, m), 2.68-2.83 (1H, m), 2.85-3.10 (3H, m), 3.65-4.06 (2H, m).

A compound of Reference Example 57 below was produced in the same way as in Reference Example 56 using appropriate starting materials.

Reference Example 57

(4aR,8aS)-tert-butyl decahydroquinoxaline-1-carboxylate

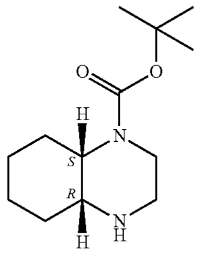

Absolute configuration $^1$H-NMR ($CDCl_3$) δ ppm: 1.18-1.55 (14H, m), 1.55-1.82 (3H, m), 1.85-2.00 (1H, m), 2.68-2.82 (1H, m), 2.85-3.10 (3H, m), 3.65-4.04 (2H, m).

Reference Example 58

Production process of cis tert-butyl 4-(4-chlorophenyl)decahydroquinoxaline-1-carboxylate

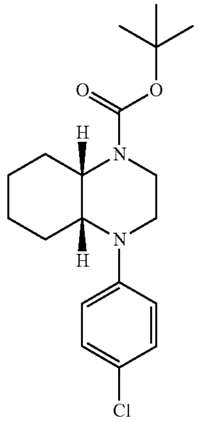

Relative configuration

A toluene (4 mil) suspension of cis tert-butyl decahydroquinoxaline-1-carboxylate (240 mg, 0.999 mmol), 1-bromo-4-chlorobenzene (211 mg, 1.10 mmol), $Pd(OAc)_2$ (11.2 mg, 0.0499 mmol), t-$Bu_3P.HBF_4$ (14.5 mg, 0.0500 mmol), and NaOt-Bu (135 mg, 1.40 mmol) was stirred for 5 hours under reflux in a nitrogen atmosphere. The reaction solution was cooled to room temperature. Then, water (0.5 mL) and AcOEt (10 mL) were added thereto, and the mixture was stirred. $MgSO_4$ was further added thereto, and the mixture was stirred. Insoluble matter was filtered through celite, and the celite layer was washed with AcOEt (5 ml×2). Then, the filtrate was concentrated under reduced pressure. The obtained residue was purified by basic silica gel column chromatography (Hex-AcOEt) to obtain a white solid (87 mg, yield: 25%).

$^1$H-NMR ($CDCl_3$) δ ppm: 1.10-1.40 (41H, m), 1.40-1.52 (10H, m), 1.63-1.71 (1l, m), 1.73-1.82 (1H, m), 2.15-2.28 (1H, m), 2.74 (1H, dt, J=3.6, 11.8 Hz), 2.90-2.97 (1H, m), 3.05-3.11 (1M, m), 3.27 (1H, dt, J=3.4, 12.6 Hz), 3.77-3.86 (1H, m), 4.01-4.10 (1H, m), 7.08-7.13 (2H, m), 7.25-7.30 (2H, m).

Compounds of Reference Examples 59 to 63 below were produced in the same way as in Reference Example 35 using appropriate starting materials.

Reference Example 59

(4aS,8aS)-decahydroquinoxaline

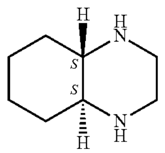

Absolute configuration $^1$H-NMR ($CDCl_3$) δ ppm: 1.12-1.58 (6H, m), 1.62-1.78 (41H, m), 2.20-2.29 (2H, m), 2.82-3.02 (4H, m).

Reference Example 60

(4aR,5aR)-decahydroquinoxaline

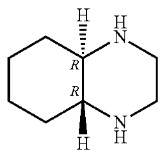

Absolute configuration $^1$H-NMR ($CDCl_3$) δ ppm: 1.14-1.27 (2H, m), 1.27-1.57 (4H, m), 1.62-1.79 (4H, m), 2.19-2.30 (2H, m), 2.83-3.03 (4H, m).

Reference Example 61

(2R,4aS,8aS)-2-methyldecahydroquinoxaline

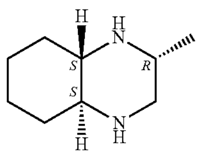

Absolute configuration $^1$H-NMR ($CDCl_3$) δ ppm: 1.02 (3H, d, J=6.3 Hz), 1.11-1.51 (6H, m), 1.62-1.79 (4H, m), 2.14-2.22 (11H, m), 2.24-2.33 (1H, m), 2.44 (1H, dd, J=10.2, 11.7 Hz), 2.81-2.91 (1H, m), 2.94 (1H, dd, J=2.9, 11.7 Hz).

Reference Example 62

(2S,4aR,8aR)-2-methyldecahydroquinoxaline

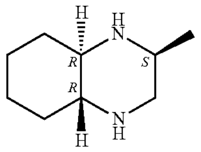

Absolute configuration

$^1$H-NMR ($CDCl_3$) δ ppm: 1.02 (3H, d, J=6.3 Hz), 1.10-1.49 (6H, m), 1.62-1.80 (4H, m), 2.14-2.22 (1H, m), 2.24-2.33 (1H, m), 2.44 (1H, dd, J=10.3, 11.7 Hz), 2.80-2.91 (1H, m), 2.94 (1H, dd, J=2.9, 11.7 Hz).

Reference Example 63

(2R,4aS,8aS)-2-ethyldecahydroquinoxaline

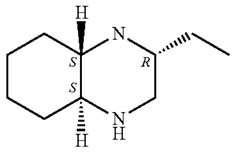

Absolute configuration

$^1$H-NMR ($CDCl_3$) δ ppm: 0.92 (3H, t, J=7.5 Hz), 1.1-1.55 (8H, m), 1.6-1.8(4H, m), 2.14-2.32 (2H, m), 2.39-2.5 (1H, m), 2.57-2.68 (1H, m), 3.01 (1H, dd, J=2.6, 11.6 Hz).

Example 1

Production of (4aR,8aS)-3,3-dimethyl-1-(1-(triisopropylsilyl)-1H-indol-6-yl)decahydroquinoxaline

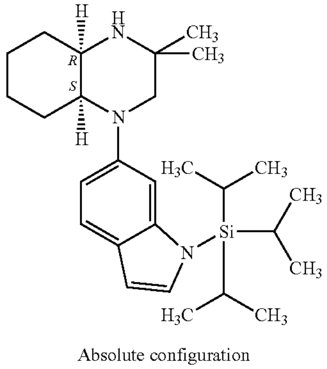

Absolute configuration

A toluene (8 mL) suspension of (4aS,8aR)-2,2-dimethyldecahydroquinoxaline (337 mg, 2.00 mmol), 6-bromo-1-(triisopropylsilyl)-1H-indole (846 mg, 2.40 mmol), sodium tert-butoxide (269 mg, 2.80 mmol), palladium (11) acetate (22.5 mg, 0.0902 mmol), and tri-tert-butylphosphine tetrafluoroborate (29.1 mg, 0.101 mmol) was stirred for 5 hours under reflux in a nitrogen atmosphere. The reaction mixture was cooled to room temperature. Then, water (0.5 mL) and ethyl acetate (10 mL) were added thereto, and the mixture was stirred, followed by addition of magnesium sulfate. Insoluble matter was filtered through celite, and the filtrate was then concentrated under reduced pressure. The obtained residue was purified by NH-silica gel column chromatography (n-hexane:ethyl acetate) to obtain colorless, amorphous (4aR,8aS)-3,3-dimethyl-1-(1-(triisopropylsilyl)-1H-indol-6-yl)decahydroquinoxaline (0.75 g, yield: 85%).

$^1$H-NMR ($CDCl_3$) δ ppm: 1.1-1.2(18H, m), 1.21 (3H, s), 1.29 (3H, s), 1.3-1.55(5H, m), 1.55-1.8(7H, m), 2.79 (1H, d, J=11.6 Hz), 2.91 (1H, d, J=11.6 Hz), 3.45-3.6(2H, m), 6.49 (1H, dd, J=0.7, 3.2 Hz), 6.82 (1H, dd, J=2.0, 8.6 Hz), 6.93 (1H, s), 7.08 (1H, d, J 3.2 Hz), 7.45 (1H, d, J=8.6 Hz).

Example 2

Production of (4aR,8aS)-1-(1H-indol-6-yl)-3,3-dimethyldecahydroquinoxaline

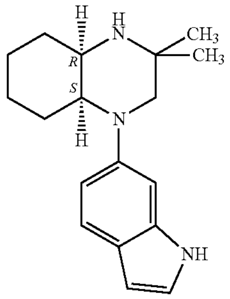

Absolute configuration

Tetra-n-butyl ammonium fluoride (1 M in THF) (3.41 mL, 3.41 mol) was added to a tetrahydrofuran (15 mL) solution of (4aR,8aS)-3,3-dimethyl-1-(1-(triisopropylsilyl)-1H-indol-6-yl)decahydroquinoxaline (0.750 g, 1.71 mmol) with stirring at room temperature, and the mixture was stirred at room temperature for 1 hour. The solvent was distilled off from the reaction mixture under reduced pressure. The obtained residue was purified by NH-silica gel column chromatography (ethyl acetate/hexane) to obtain a white solid. The obtained solid was recrystallized from diisopropyl ether/hexane to obtain (4aR,8aS)-1-(1H-indol-6-yl)-3,3-dimethyldecahydroquinoxaline (305 mg, yield: 63%).

$^1$H-NMR ($CDCl_3$) δ ppm: 1.0-1.55 (11H, m), 1.55-1.85 (4H, m), 2.79 (1H, d, J=11.6 Hz), 2.94 (1H, d, J=11.6 Hz), 3.45-3.55 (1H, m), 3.6-3.75 (1H, m), 6.35-6.5 (1H, m), 6.79 (1H, s), 6.86 (1H, dd, J=2.1, 8.7 Hz), 7.03 (1H, dd, J=2.7, 2.7 Hz), 7.47 (1H, d, J=8.6 Hz), 7.92 (1H, br).

Example 3

Production of (4aS,8aS)-1-(4-chlorophenyl)decahydroquinoxaline

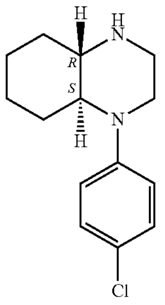

Absolute configuration 1-chloroethyl chloroformate (229 μL, 2.10 mmol) was added to a methylene chloride (6.5 mL) solution of (4aS, 8aS)-1-benzyl-4-(4-chlorophenyl)decahydroquinoxaline (0.650 g, 1.91 mmol) with ice-cooling and stirring. The mixture was stirred at room temperature for 15 hours, and the reaction mixture was then concentrated under reduced pressure. The obtained residue was dissolved in methanol (6.5 mL), and this solution was stirred for 1 hour under reflux. The solvent was distilled off from the reaction mixture. To the obtained residue, acetone (5 mL) was added, and the mixture was stirred. The deposited crystal was collected by filtration. The obtained crystal was washed with acetone (1 mL) and then dried to obtain (4aS,8aS)-1-(4-chlorophenyl)decahydroquinoxaline (253 mg, yield: 53%) in a white powder form.

$^1$H-NMR (DMSO-$d_6$) δ ppm: 0.85-1.05 (1H, m), 1.1-1.4 (2H, m), 1.4-1.65 (3H, m), 1.65-1.8 (1H, m), 1.9-2.05 (1H, m), 2.8-3.0 (2H, m), 3.05-3.2 (3H, m), 3.2-3.5 (1H, m), 7.1-7.2 (2H, m), 7.35-7.45 (2H, m), 9.2-9.65(2H, m).

Example 4

Production of cis-4-(benzo[b]thiophen-5-yl)-1,2,2-trimethyldecahydroquinoxaline hydrochloride

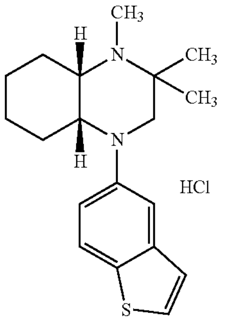

Relative configuration

A 37% aqueous formaldehyde solution (0.81 mL, 9.9 mmol) was added to a methanol (10 mL) solution of cis-1-(benzo[b]thiophen-5-yl)-3,3-dimethyldecahydroquinoxaline (298 mg, 0.992 mmol) with stirring at room temperature. After 30 minutes, sodium cyanoborohydride (311 mg, 4.96 mmol) and acetic acid (0.30 mL) were added to the reaction solution at room temperature, and the mixture was stirred overnight. The solvent was distilled off from the reaction mixture under reduced pressure. Then, a saturated aqueous solution of sodium bicarbonate (50 mL) was added thereto, followed by extraction with ethyl acetate (50 mL) twice. The organic layer was washed with water twice and with saturated saline once, then dried over magnesium sulfate, and concentrated under reduced pressure. The obtained residue was purified by silica gel column chromatography (methylene chloride:methanol=10:1) to obtain a brown oil. 4 N hydrochloric acid/ethyl acetate (0.6 mL) was added to an ethanol solution of the obtained oil with stirring at room temperature, and the deposited crystal was collected by filtration. The obtained crystal was washed with ethyl acetate and then dried under reduced pressure to obtain cis-4-(benzo[b]thiophen-5-yl)-1,2,2-trimethyldecahydroquinoxaline hydrochloride (258 mg, yield: 74%) in a white powder form.

$^1$H-NMR ($CDCl_3$) δ ppm: 1.17-1.34 (1H, m), 1.37-1.74 (2H, m), 1.47 (3H, s), 1.87-2.04 (1H, m), 1.90 (3H, s), 2.20-2.30 (1H, m), 2.39-2.54 (1H, m), 2.64-2.88 (2H, m), 2.75 (3H, d, J=4.9 Hz), 3.12 (1H, d, J=13.2 Hz), 3.69-3.74 (1H, m), 3.85-3.93 (1H, m), 3.87 (1H, d, J=13.2 Hz), 7.01 (1H, dd, J=8.8, 2.3 Hz), 7.21-7.32 (2H, m), 7.44 (1H, d, J=5.4 Hz), 7.75 (1H, d, J=8.8 Hz), 11.20 (1H, brs).

Example 5

Production of 2-(trans-4-(naphthalen-2-yl)decahydroquinoxalin-1-yl)ethanol dihydrochloride

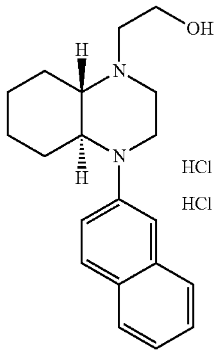

Relative configuration

Tetra-n-butyl ammonium fluoride (1 M in THF) (2.1 mL, 2.1 mmol) was added to a THF (10 mL) solution of trans-1-(2-(tert-butyldimethylsilyloxy)ethyl)-4-(naphthalen-2-yl)decahydroquinoxaline (820 mg, 1.93 mmol) with stirring at room temperature, and the mixture was stirred overnight. To the reaction mixture, ethyl acetate was added, and the resultant mixture was washed with water twice and with saturated saline once, then dried over magnesium sulfate, and concentrated under reduced pressure. The obtained residue was purified by silica gel column chromatography (methylene chloride:methanol=10:1) to obtain a colorless, amorphous solid (534 mg). A 319 mg aliquot of the obtained solid was dissolved in ethanol. To the solution, 4 N hydrochloric acid/ethyl acetate (1.0 mL) was added with stirring at room temperature, and the deposited crystal was collected by filtration. The obtained crystal was washed with ethyl acetate and then dried under reduced pressure to obtain 2-(trans-4-(naphthalen-2-yl)decahydroquinoxalin-1-yl)ethanol dihydrochloride (365 mg, yield: 49%) in a white powder form.

$^1$H-NMR ($CDCl_3$) δ ppm: 1.23-1.76 (4H, m), 1.86-2.08 (3H, m), 2.43-2.48 (1H, m), 3.18-3.25 (1H, m), 3.72-3.77 (2H, m), 3.93-3.98 (1H, m), 3.93-4.78 (1H, br), 4.08-4.20 (2H, m), 4.39-4.55 (1H, m), 4.57-4.78 (2H, m), 4.97-5.06 (1H, m), 7.61-7.68 (3H, m), 7.81-8.07 (3H, m), 8.17-8.69 (1H, br), 12.73 (1H, brs), 14.91 (1H, brs).

Example 77

Production of (4aS,8aR)-1-(7-fluorobenzofuran-4-yl)-3,3-dimethyldecahydroquinoxaline

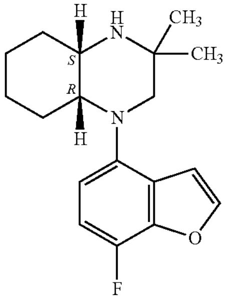

Absolute configuration

A toluene (4 ml) suspension of (4aR,8aS)-2,2-dimethyldecahydroquinoxaline (168 mg, 0.998 mmol), 4-bromo-7-fluorobenzofuran (258 mg, 1.20 mmol), $Pd(OAc)_2$ (11.2 mg, 0.0499 mmol), t-$Bu_3P.HBF_4$ (14.5 mg, 0.0500 mmol), and NaOt-Bu (135 mg, 1.40 mmol) was stirred for 4 hours under reflux in a nitrogen atmosphere. The reaction solution was cooled to room temperature. Then, water (0.5 mL) and AcOEt (10 mL) were added thereto, and the mixture was stirred. $MgSO_4$ was further added thereto, and the mixture was stirred. Insoluble matter was filtered, and the residue was washed with AcOEt (5 ml×2). Then, the filtrate was concentrated under reduced pressure. The obtained residue was purified by basic silica gel column chromatography (Hex-AcOEt) to obtain a colorless oil (167 mg). This oil was crystallized from hexane (1 mL) to obtain (4aS,8aR)-1-(7-fluorobenzofuran-4-yl)-3,3-dimethyldecahydroquinoxaline (107 mg, yield: 35%) in a white powder form.

$^1$H-NMR ($CDCl_3$) δ ppm: 1.0-1.45 (11H, m), 1.6-1.8 (3H, m), 1.8-1.95 (1H, m), 2.70 (1H, d, J=11.3 Hz), 3.04 (1H, d, J 11.3 Hz), 3.50 (1H, ddd, J=3.8, 3.8, 12.1 Hz), 3.55-3.65 (1H, m), 6.47 (1H, dd, J=3.4, 8.6 Hz), 6.84 (1H, dd, J=2.5, 2.5 Hz), 6.89 (1H, dd, J=8.6, 10.4 Hz), 7.60 (1H, d, J=2.2 Hz).

Example 106

Production of (4aS,8aR)-1-(4-chlorophenyl)-3,3-dimethyldecahydroquinoxaline hydrochloride

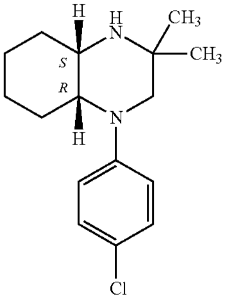

Absolute configuration

A toluene (10 ml) suspension of (4aR,8aS)-2,2-dimethyldecahydroquinoxaline (252 mg, 1.50 mmol), 1-bromo-4-chlorobenzene (345 mg, 1.80 mmol), $Pd(OAc)_2$ (16.8 mg, 0.0748 mmol), t-$Bu_3P.HBF_4$ (21.8 mg, 0.0751 mmol), and NaOt-Bu (202 mg, 2.10 mmol) was stirred for 5 hours under reflux in a nitrogen atmosphere. The reaction solution was cooled to room temperature. Then, water (0.5 mL) and AcOEt (10 mL) were added thereto, and the mixture was stirred. $MgSO_4$ was further added thereto, and the mixture was stirred. Then, insoluble matter was filtered through celite. The filtrate was concentrated under reduced pressure, and the obtained residue was purified by basic silica gel column chromatography (Hex-AcOEt). The obtained oil was dissolved in 1 N HCl-EtOH (3 mL), and the solvent was distilled off under reduced pressure. The deposited crystal was recrystallized from ethanol/acetone to obtain (4aS,8aR)-1-(4-chlorophenyl)-3,3-dimethyldecahydroquinoxaline hydrochloride (262 mg, yield: 55%) in a white powder form.

$^1$H-NMR (DMSO-$d_6$) δ ppm: 1.2-1.45 (6H, m), 1.51 (3H, s), 1.6-2.1 (5H, m), 2.93 (1H, d, J=13.6 Hz), 3.40 (1H, d, J=13.8 Hz), 3.65-3.85 (1H, m), 3.9-4.1 (1H, m), 6.8-7.05 (2H, m), 7.1-7.35(2H, m), 8.14 (1H, br), 9.77 (1H, br).

Example 112

Production of (4aS,8aR)-1-(3-chloro-4-fluorophenyl)-3,3-dimethyldecahydroquinoxaline hydrochloride

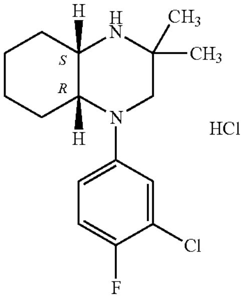

Absolute configuration

A toluene (10 ml) suspension of (4aR,8aS)-2,2-dimethyldecahydroquinoxaline (168 mg, 0.998 mmol), 4-bromo- 2-chloro-1-fluorobenzene (251 mg, 1.20 mmol), $Pd(OAc)_2$ (11.2 mg, 0.0500 mmol), $t\text{-}Bu_3P.HBF_4$ (14.5 mg, 0.0500 mmol), and NaOt-Bu (135 mg, 1.40 mmol) was stirred for 5 hours under reflux in a nitrogen atmosphere. The reaction solution was cooled to room temperature. Then, water (0.5 mL) and AcOEt (10 mL) were added thereto, and the mixture was stirred. $MgSO_4$ was further added thereto, and the mixture was stirred. Then, insoluble matter was filtered. The filtrate was concentrated under reduced pressure, and the obtained residue was purified by basic silica gel column chromatography (Hex-AcOEt). The obtained oil was dissolved in 1 N HCl-EtOH (3 mL), and ethanol was distilled off under reduced pressure. The deposited crystal was recrystallized from ethanol/acetone to obtain (4aS,8aR)-1-(3-chloro-4-fluorophenyl)-3,3-dimethyldecahydroquinoxaline hydrochloride (153 mg, yield: 46%) in a white powder form.

$^1$H-NMR (DMSO-$d_6$) δ ppm: 1.15-1.45 (6H, m), 1.51 (3H, s), 1.6-1.9 (4H, m), 1.9-2.05 (1H, m), 2.94 (1H, d, J=13.5 Hz), 3.3-3.45 (1H, m), 3.65-3.8 (1H, m), 3.95-4.1 (1H, m), 6.85-7.0 (1H, m), 7.12 (1H, dd, J=3.0, 6.2 Hz), 7.25 (1H, dd, J=9.1, 9.1 Hz), 8.13 (1H, br), 9.86 (1H, br).

Example 150

Production of 5-((4aR,8aS)-3,3-dimethyldecahydroquinoxalin-1-yl)-1-methyl-1H-indole-2-carbonitrile

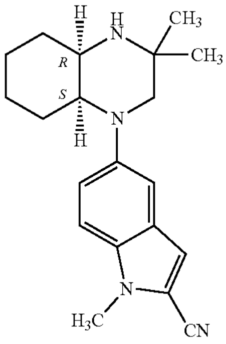

Absolute configuration

A toluene (4 ml) suspension of (4aS,8aR)-2,2-dimethyldecahydroquinoxaline (168 mg, 0.998 mmol), 5-bromo-1-methyl-1H-indole-2-carbonitrile (259 mg, 1.10 mmol), $Pd(OAc)_2$ (11.2 mg, 0.0499 mmol), $t\text{-}Bu_3P.HBF_4$ (14.5 mg, 0.0500 mmol), and NaOt-Bu (135 mg, 1.40 mmol) was stirred for 4 hours under reflux in a nitrogen atmosphere. The reaction solution was cooled to room temperature. Then, water (0.5 mL) and AcOEt (10 mL) were added thereto, and the mixture was stirred. $MgSO_4$ was further added thereto, and the mixture was stirred. Insoluble matter was filtered through celite, and the residue was washed with $CH_2Cl_2$:MeOH (3:1) (5 mL×2). Then, the filtrate was concentrated under reduced pressure. The obtained residue was purified by basic silica gel column chromatography (Hex-AcOEt) to obtain a colorless oil. This oil was crystallized from hexane (1 mL) to obtain (4aS,8aR)-1-(7-fluorobenzofuran-4-yl)-3,3-dimethyldecahydroquinoxaline (148 mg, yield: 46%) in a pale yellow powder form.

$^1$H-NMR ($CDCl_3$) δ ppm: 0.7-2.3 (15H, m), 2.7-3.2 (2H, m), 3.5-3.8 (2H, m), 3.85 (3H, s), 6.95-7.05 (2H, m), 7.15-7.3 (2H, m).

Example 237

Production of (4aS,8aS)-1-(3-chloro-4-cyanophenyl)-3,3-dimethyldecahydroquinoxaline hydrochloride

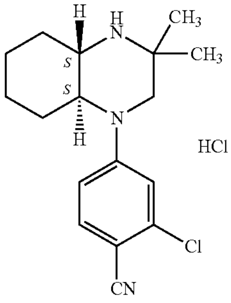

Absolute configuration

A toluene (10 ml) suspension of (4aS,8aS)-2,2-dimethyldecahydroquinoxaline (400 mg, 2.38 mmol), 4-bromo-2-chlorobenzonitrile (669 mg, 3.09 mmol), $Pd(OAc)_2$ (53 mg, 0.24 mmol), $t\text{-}Bu_3P.HBF_4$ (70 mg, 0.24 mmol), and t-BuONa (320 mg, 3.33 mmol) was stirred for 5 hours under reflux in a nitrogen atmosphere. The reaction solution was cooled. Then, insoluble matter was filtered through celite, and the filtrate was concentrated. The obtained residue was purified by silica gel column chromatography ($CH_2Cl_2$/MeOH) to obtain an orange amorphous solid. This amorphous solid was dissolved in ethyl acetate (5 mL). A crystal deposited by the addition of 4 N HCl/AcOEt (0.6 mL) was collected by filtration and dried under reduced pressure to obtain (4aS,8aS)-1-(3-chloro-4-cyanophenyl)-3,3-dimethyldecahydroquinoxaline (304 mgm, 48%) in a pale orange powder form.

$^1$H-NMR ($CDCl_3$) δ ppm: 1.05-1.20 (1H, m), 1.23-1.44 (2H, m), 1.54-2.10 (4H, m), 1.63 (3H, s), 1.68 (3H, s), 2.35-2.40 (1H, m), 2.89 (1H, d, J=12.7 Hz), 3.19 (2H, br), 3.34 (1H, d, J=12.7 Hz), 7.06 (1H, dd, J=8.4, 2.0 Hz), 7.20 (1H, d, J=2.0 Hz), 7.61 (1H, d, J=8.4 Hz), 9.62 (1H, brs), 9.90 (1H, br)

Example 579

Production of (4a'R,8a'S)-4'-(7-methoxybenzofuran-4-yl)octahydro-1'H-spiro[cyclobutane-1,2'-quinoxaline]

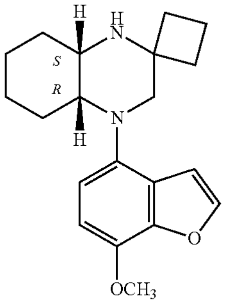

Absolute configuration

A toluene (4 ml) suspension of (4a'R,8a'S)-octahydro-1'H-spiro[cyclobutane-1,2'-quinoxaline] (180 mg, 0.998 mmol), 4-bromo-7-methoxybenzofuran (250 mg, 1.10 mmol), $Pd(OAc)_2$ (11.2 mg, 0.0499 mmol), t-$Bu_3P.HBF_4$ (14.5 mg, 0.0500 mmol), and NaOt-Bu (135 mg, 1.40 mmol) was stirred for 4 hours under reflux in a nitrogen atmosphere. The reaction solution was cooled to room temperature. Then, water (0.5 mL) and AcOEt (10 mL) were added thereto, and the mixture was stirred. $MgSO_4$ was further added thereto, and the mixture was stirred. Insoluble matter was filtered, and the residue was washed with AcOEt (5 mL×2). Then, the filtrate was concentrated under reduced pressure. The obtained residue was purified by basic silica gel column chromatography (Hex-AcOEt) to obtain a colorless amorphous solid. This solid was crystallized from hexane (1 mL) to obtain (4a'R,8a'S)-4'-(7-methoxybenzofuran-4-yl)octahydro-1 $^1$H-spiro[cyclobutane-1,2'-quinoxaline] (107 mg, yield: 35%) in a white powder form.

$^1$H-NMR ($CDCl_3$) δ ppm: 0.95-1.1 (2H, m), 1.3-1.4 (1H, m), 1,4-2.1 (11H, m), 2.25-2.4 (1H, m), 3.01 (1H, d, J=1.0 Hz), 3.17 (1H, d, J=11.1 Hz), 3.40 (1H, br), 3.45-3.5 (1H, m), 3.97 (3H, s), 6.58 (1H, d, J=8.4 Hz), 6.70 (1H, d, J=8.4 Hz), 6.80 (1H, d, J=2.1 Hz), 7.58 (1H, d, J=2.1 Hz).

Example 580

Production of (4aS,8aR)-1-(6,7-difluorobenzofuran-4-yl)-3,3-dimethyldecahydroquinoxaline hydrochloride

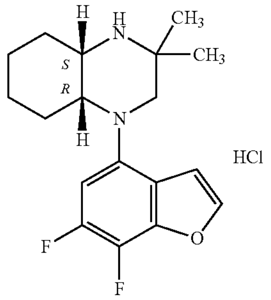

Absolute configuration

A toluene (6 ml) suspension of (4aR,8aS)-2,2-dimethyldecahydroquinoxaline (252 mg, 1.50 mmol), 4-bromo-6,7-difluorobenzofuran (384 mg, 1.65 mmol), $Pd(OAc)_2$ (16.8 mg, 0.0748 mmol), t-$Bu_3P.HBF_4$ (21.8 mg, 0.0751 mmol), and NaOt-Bu (202 mg, 2.10 mmol) was stirred for 3 hours under reflux in a nitrogen atmosphere. The reaction solution was cooled to room temperature. Then, water (0.5 mL) and AcOEt (10 mL) were added thereto, and the mixture was stirred. $MgSO_4$ was further added thereto, and the mixture was stirred. Then, insoluble matter was filtered through celite. The filtrate was concentrated under reduced pressure, and the obtained residue was purified by basic silica gel column chromatography (Hex-AcOEt) to obtain a pale yellow oil (193 mg). This oil was dissolved in ethanol (2 mL). To the solution, 1 N HCl-EtOH (1.2 mL) was added, and the mixture was stirred. The deposited crystal was collected by filtration, washed with ethyl acetate, and then dried under reduced pressure to obtain (4aS,8aR)-1-(6,7-difluorobenzofuran-4-yl)-3,3-dimethyldecahydroquinoxaline hydrochloride (167 mg, yield: 31%) in a white powder form.

$^1$H-NMR (DMSO-$d_6$) δ ppm: 1.01-1.17 (2H, m), 1.34-1.44 (1H, m), 1.48 (3H, s), 1.52 (3H, s), 1.59-2.07 (5H, m), 3.00 (1H, d, J=13.0 Hz), 3.28 (1H, d, J=13.2 Hz), 3.75-3.9 (1H, m), 4.0-4.15 (1H, m), 6.83 (1H, dd, J=5.9, 13.5 Hz), 7.36 (1H, dd, J=2.6, 2.6 Hz), 8.0-8.2(2H, m), 9.7-9.9 (1H, m).

Example 581

Production of (4aS,8aS)-1-(2-cyano-1-(triisopropylsilyl)-1H-indol-5-yl) 3,3-dimethyldecahydroquinoxaline

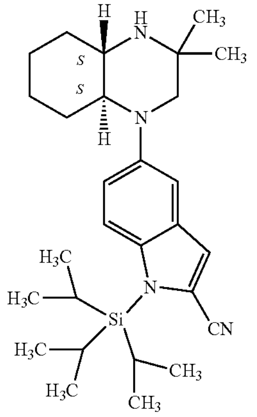

Absolute configuration

A toluene (5 ml) suspension of (4aS,8aS)-2,2-dimethyldecahydroquinoxaline (200 mg, 1.19 mmol), 5-bromo-1-(triisopropylsilyl)-1H-indole-2-carbonitrile (493 mg, 1.31 mmol), $Pd(OAc)_2$ (13.3 mg, 0.0594 mmol), $tBu_3P.HBF_4$ (17.2 mg, 0.0594 mmol), and t-BuONa (137 mg, 1.43 mmol) was stirred at 100° C. for 4 hours in a nitrogen atmosphere. Insoluble matter was filtered through celite, and the filtrate was concentrated. The obtained residue was purified by basic silica gel column chromatography (AcOEt/hexane) to obtain (4aS,8aS)-1-(2-cyano-1-(triisopropylsilyl)-1H-indol-5-yl) 3,3-dimethyldecahydroquinoxaline (430 mg, 78%) in a white amorphous solid form.

$^1$H-NMR ($CDCl_3$) δ ppm: 0.75-1.38 (26H, m), 1.41 (3H, s), 1.54-1.77 (4H, m), 2.01 (3H, quintet, J=7.5 Hz), 2.25-2.32 (11H, m), 2.65 (1H, d, J=11.2 Hz), 2.75-2.85 (2H, m), 7.11 (1H, dd, J=2.0, 9.1 Hz), 7.32 (1H, d, J=2.0 Hz), 7.33 (1H, d, J=0.5 Hz), 7.50 (1H, d, J=9.1 Hz).

Example 582

Production of (4aS,8aS)-1-(2-cyano-1H-indol-5-yl) 3,3-dimethyldecahydroquinoxaline

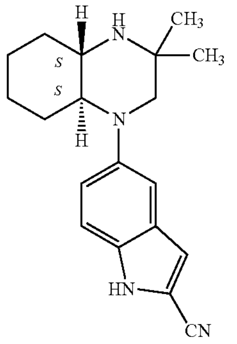

absolute configuration

Tetrabutylammonium fluoride (1 M THF solution, 0.73 mL, 0.73 mmol) was added to an anhydrous tetrahydrofuran (5 mL) solution of (4aS,8aS)-1-(2-cyano-1-(triisopropylsilyl)-1H-indol-5-yl) 3,3-dimethyldecahydroquinoxaline (170 mg, 0.366 mmol) at room temperature, and the reaction solution was stirred at room temperature for 1 hour. The reaction solution was concentrated under reduced pressure, and the obtained residue was purified by basic silica gel column chromatography (AcOEt/hexane=1/10→1/1). The solvent was removed under reduced pressure. The obtained residue was recrystallized from ethyl acetate/n-hexane to obtain (4aS,8aS)-1-(2-cyano-1H-indol-5-yl) 3,3-dimethyldecahydroquinoxaline (30 mg, yield: 27%) in a white powder form.

$^1$H-NMR (DMSO-$d_6$) δ ppm: 0.82-1.00 (4H, m), 1.08-1.34 (6H, m), 1.42-1.67 (5H, m), 2.19-2.27 (1H, m), 2.55 (1H, d, J=10.9 Hz), 2.59-2.69 (2H, m), 7.11 (1H, dd, J=1.8, 8.8 Hz), 7.26 (1H, d, J=0.8 Hz), 7.32 (1H, d, J=1.8 Hz), 7.36 (1H, d, J=8.8 Hz) 12.25 (1H, brs).

Example 583

Production of (4aS,8aR)-1-(7-chloro-2,3-dihydro-1H-inden-4-yl)-3,3-dimethyldecahydroquinoxaline

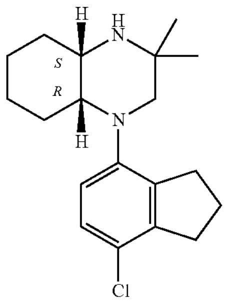

Absolute configuration

A toluene (1 mL) solution of bis(tri-tert-butylphosphine) palladium (25.6 mg, 0.0501 mmol) was added to a toluene (4 ml) suspension of (4aR,8aS)-2,2-dimethyldecahydroquinoxaline (168 mg, 0.998 mmol), 4-bromo-7-chloro-2,3-dihydro-1H-indene (255 mg, 1.10 mmol), and NaOt-Bu (135 mg, 1.40 mmol), and the mixture was stirred for 4 hours under reflux in a nitrogen atmosphere. The reaction solution was cooled to room temperature. Then, water (0.5 mL) and AcOEt (10 mL) were added thereto, and the mixture was stirred. $MgSO_4$ was further added thereto, and the mixture was stirred. Insoluble matter was filtered through celite, and the residue was washed with AcOEt (5 mL×2). Then, the filtrate was concentrated under reduced pressure. The obtained residue was purified by basic silica gel column chromatography (Hex-AcOEt) to obtain a white solid (167 mg). This solid was recrystallized from ethanol/water to obtain (4aS,8aR)-1-(7-chloro-2,3-dihydro-1H-inden-4-yl)-3,3-dimethyldecahydroquinoxaline (136 mg, yield: 43%) in a white powder form.

1H-NMR ($CDCl_3$) δ ppm: 0.97-1.12 (3H, m), 1.16 (3H, s), 1.27 (3H, s), 1.31-1.44 (2H, m), 1.45-1.76 (3H, m), 1.78-1.92 (1H, m), 1.94-2.06 (1H, m), 2.12-2.23 (1H, m), 2.51 (1H, d, J=11.2 Hz), 2.85-3.05 (5H, m), 3.1-3.2 (1H, m), 3.45-3.55 (1H, m), 6.58 (1H, d, J=8.4 Hz), 7.03 (1H, d, J=8.4 Hz).

Example 584

Production of (4aS,8aS)-1-(6-cyanonaphthalen-2-yl)-3,3-dimethyldecahydroquinoxaline dihydrochloride

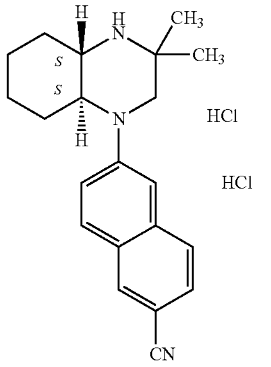

absolute configuration

A toluene (5 mL) suspension of (4aR,8aS)-2,2-dimethyldecahydroquinoxaline (200 mg, 1.19 mmol), 6-bromo-2-naphthonitrile (303 mg, 1.31 mmol), $Pd(OAc)_2$ (13.3 mg, 0.0594 mmol), $tBu_3P.HBF_4$ (17.2 mg, 0.0594 mmol), and t-BuONa (137 mg, 1.43 mmol) was stirred at 100° C. for 4 hours. Insoluble matter was filtered through celite, and the filtrate was concentrated. The obtained residue was purified by basic silica gel column chromatography (AcOEt/hexane). The solvent was removed under reduced pressure. The obtained residue was dissolved in ethyl acetate. To this solution, 1 N hydrochloric acid-ethanol was added, and the deposited crystal was collected by filtration. The obtained crystal was dried under reduced pressure to obtain (4aS, 8aS)-1-(6-cyanonaphthalen-2-yl)-3,3-dimethyldecahydroquinoxaline dihydrochloride (303 mg, yield: 65%) in a white powder form.

$^1$H-NMR (DMSO-d&) δ ppm: 1.10-1.50 (6H, m), 1.56-1.90 (7H, m), 2.00-2.14 (1H, m), 3.08-3.45 (4H, m), 4.68-5.32 (1H, br), 7.45 (1H, dd, J=2.0, 8.9 Hz), 7.64 (1H, d, J=1.8 Hz), 7.73 (1H, dd, J=1.6, 8.6 Hz), 8.00 (1H, d, J=8.6 Hz), 8.04 (1H, d, J=8.6 Hz), 8.49 (1H, s), 9.10-9.28 (1H, br), 10.04-10.28 (1H, br).

Example 585

Production of (4aS,8aS)-3,3-dimethyl-1-(1-(triisopropylsilyl)-1H-pyrrolo[2,3-b]pyridin-4-yl)decahydroquinoxaline

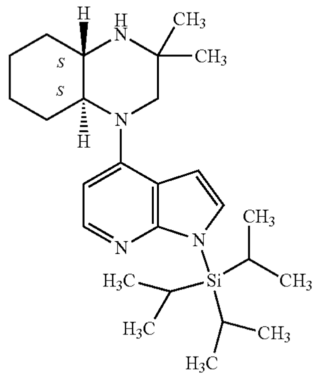

Absolute configuration

A toluene (5 mL) suspension of (4aS,8aS)-2,2-dimethyldecahydroquinoxaline (200 mg, 1.19 mmol), 4-bromo-1-

(triisopropylsilyl)-1H-pyrrolo[2,3-b]pyridine (462 mg, 1.31 mmol), $Pd(OAc)_2$ (13.3 mg, 0.0594 mmol), $tBu_3P.HBF_4$ (17.2 mg, 0.0594 mmol), and t-BuONa (137 mg, 1.43 mmol) was stirred at 100° C. for 4 hours in a nitrogen atmosphere. Insoluble matter was filtered through celite, and the filtrate was concentrated. The obtained residue was purified by basic silica gel column chromatography (AcOEt/hexane) to obtain (4aS,8aS)-3,3-dimethyl-1-(1-(triisopropylsilyl)-1H-pyrrolo[2,3-b]pyridin-4-yl)decahydroquinoxaline (439 mg, 84%) in a white amorphous solid form.

$^1$H-NMR ($CDCl_3$) δ ppm: 0.95-1.20 (22H, m), 1.36-1.45 (3H, m), 1.52 (3H, s), 1.65-1.92 (7H, m), 2.11-2.20 (1H, m), 2.57-2.67 (2H, m), 2.83-2.95 (1H, m), 3.26- (1H, d, J=11.7 Hz), 6.55 (1H, d, J=3.5 Hz), 6.63 (1H, d, J=5.3 Hz), 7.18 (1H, d, J=3.5 Hz), 8.12 (1H, d, J=5.3 Hz).

Example 586

Production of (4aS,8aS)-3,3-dimethyl-1-(1H-pyrrolo[2,3-b]pyridin-4-yl)decahydroquinoxaline fumarate

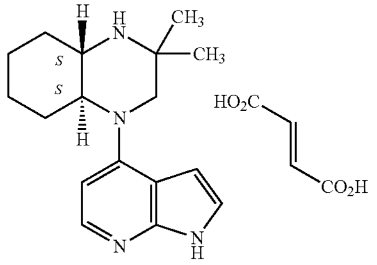

Absolute configuration

Tetrabutylammonium fluoride (1 M THF solution, 1.95 mL, 1.95 mmol) was added to an anhydrous tetrahydrofuran (5 mL) solution of (4aS,8aS)-3,3-dimethyl-1-(1-(triisopropylsilyl)-1H-pyrrolo[2,3-b]pyridin-4-yl)decahydroquinoxaline (430 mg, 0.976 nmol), and the mixture was stirred at room temperature for 1 hour. The reaction solution was concentrated under reduced pressure, and the obtained residue was purified by basic silica gel column chromatography (AcOEt/hexane=1/10→1/1) to obtain a product (370 mg, 1.30 mmol) in an oil form. This oil was dissolved in ethanol (5 mL). To this solution, an ethanol (5 mL) solution of fumaric acid (151 mg) was added, and ethanol was removed under reduced pressure. The obtained solid was recrystallized from ethanol/ethyl acetate to obtain 5-((4aS,8aS)-3,3-dimethyl-decahydroquinoxalin-1-yl)-1H-indole-2-carbonitrile (246 mg, yield: 63%) in a white powder form.

$^1$H-NMR (DMSO-$d_6$) δ ppm: 0.94-1.09 (1H, m), 1.20 (3H, s), 1.26-1.55 (7H, m), 1.68-1.78 (1H, m), 1.85-2.04 (2H, m), 2.81-2.93 (1H, m), 2.95-3.23 (3H, m), 6.36-6.42 (1H, m), 6.49 (2H, s), 6.71 (1H, d, J=5.2 Hz), 7.32-7.38 (1H, m), 8.09 (1H, d, J=5.2 Hz), 8.50-11.20 (1H, br), 11.59 (1H, s).

Example 587

Production of (4aS,8aS)-1-(4-(difluoromethoxy)-3-fluorophenyl)-3,3-dimethyldecahydroquinoxaline dihydrochloride

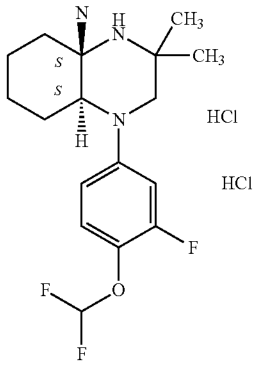

Absolute configuration

A toluene (5 mL) suspension of (4aR,8aS)-2,2-dimethyl-decahydroquinoxaline (200 mg, 1.19 mmol), 4-bromo-1-difluoromethoxy-2-fluorobenzene (315 mg, 1.31 mmol), $Pd(OAc)_2$ (13.3 mg, 0.0594 mmol), $tBu_3P.HBF_4$ (17.2 mg, 0.0594 mmol), and t-BuONa (137 mg, 1.43 mmol) was stirred at 100° C. for 4 hours. Insoluble matter was filtered through celite, and the filtrate was concentrated. The obtained residue was purified by basic silica gel column chromatography (AcOEt/hexane). The solvent was removed under reduced pressure. The obtained residue was dissolved in ethyl acetate. To this solution, 1 N hydrochloric acid-ethanol was added, and the deposited crystal was collected by filtration. The obtained crystal was dried under reduced pressure to obtain (4aS,8aS)-1-(4-difluoromethoxy-3-fluorophenyl)-3,3-dimethyldecahydroquinoxaline dihydrochloride (193 mg, yield: 40%) in a white powder form.

$^1$H-NMR (DMSO-$d_6$) δ ppm: 1.01-1.39 (6H, m), 1.49-1.67 (6H, m), 1.67-1.77 (1H, m), 1.96-2.05 (1H, m), 2.81-2.95 (2H, m), 3.02 (1H, d, J=12.5 Hz), 3.10-3.23 (1H, m), 4.30-4.80 (1H, br), 6.96-7.01 (1H, m), 7.02 (0.25H, s), 7.17 (1H, dd, J=2.5, 12.1 Hz), 7.20 (0.5H, s), 7.33 (1H, t, J=8.9 Hz), 7.39 (0.25H, s), 9.04-9.21 (1H, m), 9.70-9.85 (1H, m).

Compounds of Examples 6 to 76, 78 to 105, 107 to 111, 113 to 149, 151 to 236, 238 to 578, 588 to 1656 shown in tables below were produced in the same way as in the Examples using corresponding appropriate starting materials. In these tables, for example, the produced compounds have physical properties such as a crystalline form, m.p. (melting point), salt, $^1$H-NMR, and MS (mass spectrum).

TABLE 1

Relative configuration

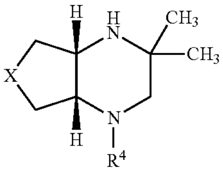

| Example | X | $R^4$ | 1H-NMR | Salt |
|---|---|---|---|---|
| 6 | —$CH_3$— | 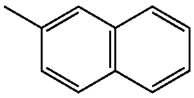 | 1H-NMR (DMSO-d6) δ ppm: 1.39 (3H, s), 1.49 (3H, s), 1.56-2.20 (6 H, m), 3.04 (1H, d, J = 13.3 Hz), 3.61 (1H, d, J = 13.3 Hz), 3.75-3.90 (1H, m), 4.40-4.55 (1 H, m), 7.17-7.30 (2 H, m), 7.33-7.45 (2 H, m), 7.65-7.63 (3 H, m), 8.35-8.80 (1 H, brr), 9.70-9.95 (1 H, brr). | Hydro-chloride |
| 7 | —$CH_3$— | 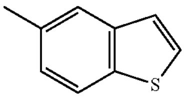 | 1H-NMR (DMSO-d6) δ ppm: 1.39 (3H, s), 1.48 (3H, s), 1.55-2.19 (5H, m), 3.01 (1H, d, J = 13.2 Hz), 3.45 (1H, d, J = 13.2 Hz), 3.70-3.87 (1H, m), 4.25-4.45 (1H, m), 7.17 (1H, dd, J = 2.2, 9.0 Hz), 7.29 (1H, d, J = 6.4 Hz), 7.37 (1H, d, J = 2.2 Hz), 7.67 (1H, d, J = 6.4 Hz), 7.81 (1H, J =8.9 Hz), 8.42-8.65 (1H, br), 9.80-10.05 (1H, br). | Hydro-chloride |
| 8 | —O— | 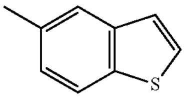 | 1H-NMR (DMSO-d6) δ ppm: 1.42 (3H, s), 1.49 (3H, s), 3.07 (1H, d, J = 13.4 Hz), 3.53 (1H, d, J = 13.4 Hz), 3.72 (1H, t, J = 8.6 Hz), 3.90-4.17 (4H, m), 4.79-4.94 (1H, m), 7.19 (1H, dd, J = 2.4, 5.9 Hz), 7.30 (1H, dd, J = 0.5, 5.4 Hz), 7.41 (1H, d, J = 2.4 Hz), 7.69 (1H, d, J = 5.4 Hz), 7.83 (1H, d, J = 6.9 Hz), 8.60-8.85 (1H, br), 10.41-10.65 (1H, br). | Hydro-chloride |
| 9 | —$CH_3$— | 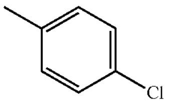 | 1H-NMR (DMSO-d6) δ ppm: 1.33 (3H, s), 1.44 (3H, s), 1.55-2.19 (6H, m), 2.92 (1H, d, J = 13.5 Hz), 3.45 (1H, d, J = 13.5 Hz), 3.68-3.82 (1H, m), 4.20-4.35 (1H, m), 6.98 (2H, d, J = 9.0 Hz), 7.23 (2H, d, J = 9.0 Hz), 8.40-8.86 (1H, br), 9.75-10.05 (1H, br). | Hydro-chloride |
| 10 | —$CH_3$— | 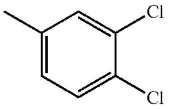 | 1H-NMR (DMSO-d6) δ ppm: 1.32 (3H, s), 1.43 (3H, s), 1.55-2.15 (6H, m), 2.95 (1H, d, J = 13.6 Hz), 3.58 (1H, d, J = 13.8 Hz), 3.65-3.82 (1H, m), 4.20-4.40 (1H, m), 5.97 (1H, dd, J = 2.9, 9.0 Hz), 7,19 (1H, d, J = 2.9 Hz), 7.40 (1H, d, J = 9.0 Hz), 8.40-8.52 (1H, br), 9.70-9.95 (1H, br). | Hydro-chloride |
| 11 | —O— | 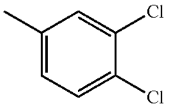 | 1H-NMR (DMSO-d6) δ ppm: 1.34 (3H, s), 1.44 (3H, s), 2.99 (1H, d, J = 13.5 Hz), 3.50-3.73 (2H, m), 3.85-4.11 (4H, m), 4.71-4.90 (1H, m), 6.95-7.08 (1H, m), 7.20-7.30 (1H, m), 7.42 (1H, d, J 9.0 Hz), 8.60-8.89 (1H, br), 10.20-10.61 (1H, br). | Hydro-chloride |

TABLE 2

Relative configuration

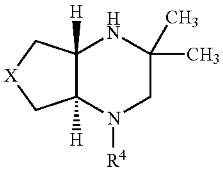

| Example | X | $R^4$ | NMR | Salt |
|---|---|---|---|---|
| 12 | —$CH_3$— | 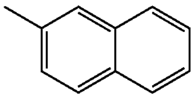 | 1H-NMR (DMSO-d6) δ ppm: 1.30-1.50 (4H, m), 1.80 (3H, s), 1.55-2.05 (4H, m), 2.05-2.23 (1H, m), 2.82-2.96 (1H, m), 3.06-3.25 (1H, m), 3.25-3.45 (2H, m), 4.00-5.25 (1H, br), 7.29 (1H, dd, J = 2.1, 8.8 Hz), 7.35-7.60 (3H, m), 7.76-7.94 (3H, m), 9.29-9.57 (1H, br), 9.78-10.08 (1H, br). | Dihydro-chloride |
| 13 | —$CH_3$— | 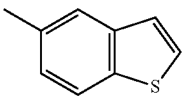 | 1H-NMR (DMSO-d6) δ ppm: 1.30-1.50 (4H, m), 1.80 (3H, s), 1.55-2.07 (6H, m), 2.94 (1H, d, J = 12.4 Hz), 3.05-3.45 (3H, m), 4.40-5.88 (1H, br), 7.18 (1H, dd, J = 1.7, 8.7 Hz), 7.42 (1H, d, J = 5.4 Hz), 7.55 (1H, d, J = 1.7 Hz), 7.76 (1H, d, J = 5.4 Hz), 7.93 (1H, d, J = 5.7 Hz), 9.40-9.70 (1H, br), 9.80-10.12 (1H, br). | Dihydro-chloride |

TABLE 2-continued

Relative configuration

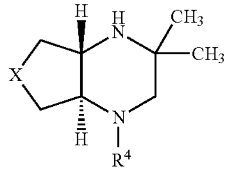

| Example | X | $R^4$ | NMR | Salt |
|---|---|---|---|---|
| 14 | —O— | 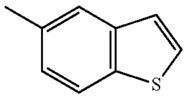 | 1H-NMR (DMSO-d6) δ ppm: 1.44 (3H, s), 1.62 (3H, s), 2.90 (1H, d, J = 12.7 Hz), 3.34 (1H, d, J = 12.7 Hz), 3.48-3.51 (2H, m), 3.75-9.95 (2H, m), 4.00-4.10 (1H, m), 4.11-4.28 (1H, m), 4.75-5.01 (1H, br), 7.12 (1H, dd, J = 2.1, 8.7 Hz), 7.40 (1H, d, J = 5.4 Hz), 7.62 (1H, d, J = 2.1 Hz), 7.75 (1H, d, J = 5.4 Hz), 7.91 (1H, d, J = 5.7 Hz), 9.88-10.08 (1H, br), 10.08-10.80 (1H, br). | Dihydro-chloride |
| 15 | —$CH_3$— | 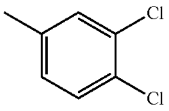 | 1H-NMR (DMSO-d6) δ ppm: 1.25-1.45 (4H, m), 1.52 (3H, s), 1.65-1.88 (3H, m), 1.88-2.10 (2H, m), 2.84 (1H, d, J = 12.8 Hz), 2.94-3.10 (1H, m), 3.18-3.39 (2H, m), 4.03-4.70 (1H, br), 7.09 (1H, dd, J = 2.6, 6.7 Hz), 7.33 (1H, d, J = 2.6 Hz), 7.52 (1H, d, J = 8.7 Hz), 9.25-9.83 (1H, br), 9.72-10.04 (1H, br). | Dihydro-chloride |
| 16 | —$CH_3$— | 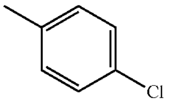 | 1H-NMR (DMSO-d6) δ ppm: 1.24-1.45 (4H, m), 1.56 (3H, s), 1.83-2.04 (6H, m), 2.82 (1H, d, J = 12.8 Hz), 2.90-3.08 (1H, m), 3.13 (1H, d, J = 12.8 Hz), 3.26-3.28 (1H, m), 4.35-5.05 (1H, br), 7.05-7.18 (2H, m), 7.30-7.40 (2H, m), 9.30-9.55 (1H, br), 9.75-10.02 (1H, br). | Dihydro-chloride |
| 17 | —O— | 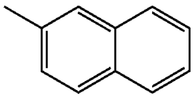 | 1H-NMR (DMSO-d6) δ ppm: 1.46 (3H, s), 1.84 (3H, s), 2.89 (1H, d, J = 12.9 Hz), 3.47-3.88 (3H, m), 3.81-3.97 (2H, m), 4.01-4.15 (1H, m), 4.34-4.46 (1H, m), 7.28 (1H, dd, J = 2.3, 5.8 Hz), 7.38-7.44 (1H, m), 7.44-7.50 (1H, m), 7.50-7.54 (1H, m), 7.80-7.87 (2H, m), 7.59 (1H, d, J = 8.1 Hz), 9.84-10.04 (1H, br), 10.04-10.20 (1H, br). | Hydro-chloride |

TABLE 3

Relative configuration

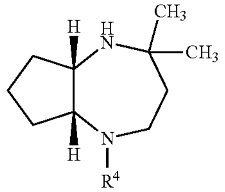

| Example | $R^4$ | NMR | Salt |
|---|---|---|---|
| 18 | 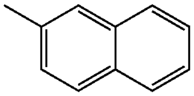 | 1H-NMR (DMSO-d6) δ ppm (80° C.): 1.40 (3 H, s), 1.43-1.70 (5 H, m), 1.72-1.92 (2 H, m), 1.95-2.23 (4 H, m), 3.39-3.52 (2 H, m), 3.55-4.02 (1 H, br), 4.02-4.14 (1 H, m), 5.64-6.00 (1 H, br), 7.31-7.38 (1 H, m), 7.38-7.47 (2 H, m), 7.50-7.57 (1H, m), 7.72-7.85 (3 H, m), 8.44-8.80 (1 H, br), 9.04-9.40 (1 H, br). | Dihydro-chloride |
| 19 | 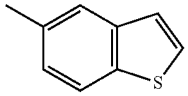 | 1H-NMR (DMSO-d6) δ ppm (80° C.): 1.31-1.51 (5H, m), 1.54 (3H, s), 1.83-1.76 (2H, m), 1.87-2.12 (3H, m), 2.12-2.23 (1H, m), 3.22-3.44 (2H, m), 3.85-4.02 (2H, m), 5.00-5.90 (1H, br), 7.33 (1H, d, J = 6.6 Hz), 7.36 (1H, d, J = 5.4 Hz), 7.70 (1H, d, J = 5.4 Hz), 7.77 (1H, s), 7.89 (1H, d, J = 8.8 Hz), 8.25-8.74 (1H, br), 9.00-9.54 (1H, br). | Dihydro-chloride |
| 20 | 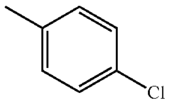 | 1H-NMR (DMSO-d6) δ ppm: 1.34 (3H, s), 1.39-1.55 (5H, m), 1.67-1.90 (3H, m), 1.90-2.15 (3H, m), 3.17-3.35 (2H, m), 3.75-4.02 (2H, m), 7.10-7.20 (2H, m), 7.25-7.37 (2H, m), 7.37-7.90 (1H, br), 5.45-6.69 (1H, br), 5.59-9.19 (1H, br). | Dihydro-chloride |

TABLE 4

Relative configuration

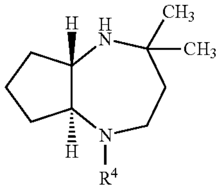

| Example | $R^4$ | NMR | Salt |
| --- | --- | --- | --- |
| 21 | 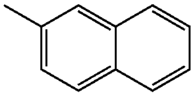 | 1H-NMR (DMSO-d6) δ ppm (80° C.): 1.43 (3H, s), 1.47 (3H, s), 1.61-1.65 (1H, m), 1.72-1.90 (3H, m), 1.93-2.09 (2H, m), 2.12-2.29 (2H, m), 3.59-3.80 (1H, m), 3.81-3.92 (1H, m), 3.98-4.11 (1H, m), 4.11-4.70 (2H, br), 7.22-7.45 (4H, m), 7.70-7.85 (3H, m), 9.15-9.49 (1H, br), 9.49-9.58 (1H, br). | Dihydro-chloride |
| 22 | 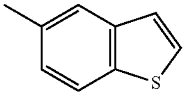 | 1H-NMR (DMSO-d6) δ ppm (80° C.): 1.48 (3H, s), 1.49 (3H, s), 1.85-1.94 (5H, m), 2.10-2.44 (3H, m), 3.89-3.90 (1H, m), 3.85-4.00 (1H, m), 4.00-4.20 (1H, m), 4.80-4.96 (1H, m), 4.95-6.06 (1H, br), 7.36-7.55 (2H, m), 7.76 (1H, d, J = 5.4 Hz), 7.78 (1H, brs), 7.98 (1H, d, J = 6.8 Hz), 9.40-9.65 (1H, br), 9.86-10.11 (1H, br). | Dihydro-chloride |
| 23 | 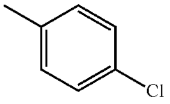 | 1H-NMR (DMSO-d6) δ ppm (80° C.): 1.44 (6H, m), 1.47-1.84 (1H, m), 1.67-1.54 (3H, m), 1.85-2.13 (3H, m), 2.14-2.30 (1H, m), 3.60-3.80 (2H, m), 3.92-4.07 (1H, m), 5.80-5.70 (1H, br), 7.04 (1H, d, J = 6.9 Hz), 7.25 (1H, d, J = 5.9 Hz), 9.40-9.75 (2H, br). | Dihydro-chloride |

TABLE 5

Relative configuration

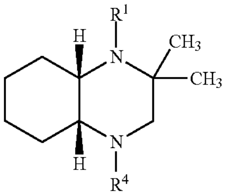

| Example | $R^1$ | $R^4$ | NMR | Salt |
| --- | --- | --- | --- | --- |
| 24 | —H | 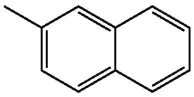 | 1H-NMR (DMSO) δ ppm: 1.29-1.67 (3H, m), 1.46 (3H, s), 1.57 (3H, s), 1.89-1.91 (4H, m), 1.98-2.09 (1H, m), 3.07 (1H, d, J = 13.5 Hz), 3.51 (1H, d, J = 13.5 Hz), 3.73-3.92 (1H, m), 4.11-4.30 (1H, m), 7.18 (1H, d, J = 2.2 Hz), 7.22-7.28 (1H, m), 7.36-7.43 (2H, m), 7.88-7.50 (3H, m), 5.02-8.51 (1H, m), 9.52-9.91 (1H, br) | Hydro-chloride |
| 25 | —$CH_3$ | 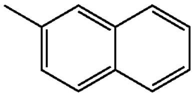 | 1H-NMR (CDCl3) δ ppm: 1.21-1.35 (1H, m), 1.40-1.53 (1H, m), 1.48 (3H, s), 1.55-1.77 (2H, m), 1.93 (3H, s), 1.98-2.05 (1H, m), 2.18-2.34 (1H, m), 2.37-2.58 (1H, m), 2.87-2.58 (1H, m), 2.82 (3H, d, J = 4.9 Hz), 3.26 (1H, d, J = 13.4 Hz), 3.64-3.77 (1H, m), 3.91 (1H, d, J = 13.4 Hz), 3.97-4.04 (1H, m), 7.07-7.09 (1H, m), 7.17-7.22 (1H, m), 7.30-7.35 (1H, m), 7.40-7.46 (1H, m), 7.68-7.53 (3H, m), 11.27 (1H, brs) | Hydro-chloride |
| 26 | —H | 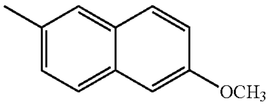 | 1H-NMR (DMSO-d6) δ ppm: 1.2-1.5 (6H, m), 1.57 (3H, s), 1.6-1.95 (4H, m), 1.95-2.15 (1H, m), 3.05 (1H, d, J = 13.3 Hz), 3.40 (1H, d, J = 13.4 Hz), 3.75-3.9 (4H, m), 4.05-4.2 (1H, m), 4.93 (1H, br), 7.07 (1H, dd, J = 2.5, 8.9 Hz), 7.1-7.2 (2H, m), 7.36 (1H, dd, J = 2.3, 9.1 Hz), 7.65 (1H, d, J = 9.0 Hz), 7.70 (1H, d, J = 9.1 Hz), 6.06-8.3 (1H, m), 9.76-10.05 (1H, m). | Dihydro-chloride |
| 27 | —H | 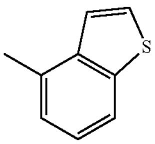 | 1H-NMR (DMSO-d6) δ ppm: 0.9-1.1 (2H, m), 1.25-1.45 (1H, m), 1.45-1.7 (7H, m), 1.7-2.1 (4H, m), 2.55 (1H, d, J = 12.7 Hz), 3.43 (1H, d, J = 12.5 Hz), 3.55-3.7 (1H, m), 4.1-4.3 (1H, m), 6.02 (1H, d, J = 7.7 Hz), 7.28 (1H, dd, J = 7.8, 7.6 Hz), 7.5-7.7 (2H, m), 7.74 (1H, d, J = 5.5 Hz), 7.9-8.2 (1H, m), 9.55-9.85 (1H, m). | Hydro-chloride |

TABLE 5-continued

Relative configuration

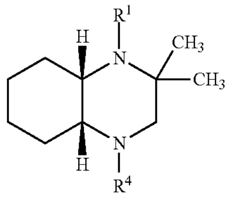

| Example | $R^1$ | $R^4$ | NMR | Salt |
|---|---|---|---|---|
| 28 | —H | 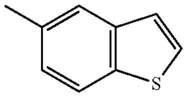 | 1H-NMR (CDCl3) δ ppm: 1.18-1.28 (1H, m), 1.38-1.50 (2H, m), 1.55 (3H, s), 1.72-2.00 (2H, m), 1.90 (3H, s), 2.07-2.22 (1H, m), 2.39-2.52 (2H, m), 3.05 (1H, d, J = 12.8 Hz), 8.43 (1H, d, J = 1.25 Hz), 3.77-3.90 (1H, m), 3.91-4.01 (1H, m), 7.04 (1H, dd, J = 8.8, 2.2 Hz), 7.21-7.25 (2H, m), 7.43 (1H, d, J = 5.4 Hz), 7.75 (1H, d, J = 8.5 Hz), 8.55-8.97 (1H, br), 9.99-10.37 (1H, br) | Hydro-chloride |
| 29 | —$CH_3$ | 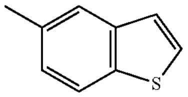 | 1H-NMR (CDCl3) δ ppm: 1.17-1.34 (1H, m), 1.37-1.74 (2H, m), 1.47 (3H, s), 1.57-2.04 (1H, m), 1.90 (3H, s), 2.20-2.30 (1H, m), 2.39-2.54 (1H, m), 2.84-2.88 (2H, m), 2.75 (3H, d, J = 4.9 Hz), 3.12 (1H, d, J = 13.2 Hz), 3.89-3.74 (1H, m), 3.85-3.93 (1H, m), 3.87 (1H, d, J = 13.2 Hz), 7.01 (1H, dd, J = 5.6, 2.2 Hz), 7.21-7.32 (2H, m), 7.44 (1H, d, J = 5.4 Hz), 7.75 (1H, d, J = 5.8 Hz), 11.20 (1H, brs) | Hydro-chloride |
| 30 | —H | 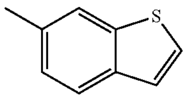 | 1H-NMR (CDCl3) δ ppm: 1.11-1.33 (1H, m), 1.35-1.54 (2H, m), 1.85 (3H, s), 1.72-2.00 (2H, m), 1.90 (3H, s), 2.07-2.29 (1H, m), 2.34-2.50 (2H, m), 3.03 (1H, d, J = 13.2 Hz), 3.42 (1H, d, J = 13.2 Hz), 3.76-4.02 (2H, m), 7.02 (1H, dd, J = 8.7, 2.2 Hz), 7.17-7.31 (3H, m), 7.70 (1H, d, J = 5.7 Hz), 8.64-9.00 (1H, br), 10.08-10.37 (1H, br) | Hydro-chloride |
| 31 | —$CH_3$ | 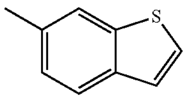 | 1H-NMR (CDCl3) δ ppm: 1.20-1.35 (1H, m), 1.38-1.74 (3H, m), 1.45 (3H, s), 1.90 (3H, s), 1.97-2.11 (1H, m), 2.20-2.30 (1H, m), 2.41-2.56 (1H, m), 2.85-2.89 (1H, m), 2.81 (3H, d, J = 4.5 Hz), 3.16 (1H, d, J = 13.3 Hz), 3.61-3.74 (1H, m), 3.88 (1H, d, J = 13.3 Hz), 3.89-3.99 (1H, m), 6.99 (1H, dd, J = 5.7, 2.1 Hz), 7.20-7.31 (3H, m), 7.70 (1H, d, J = 8.7 Hz), 11.04-11.44 (1H, br) | Hydro-chloride |
| 32 | —H | 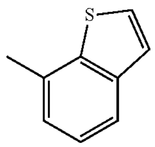 | 1H-NMR (DMSO-d6) δ ppm: 0.9-1.2 (2H, m), 1.25-1.45 (1H, m), 1.53 (5H, s), 1.8-1.7 (1H, m), 1.7-1.9 (2H, m), 1.9-2.15 (2H, m), 2.92 (1H, d, J = 2.8 Hz), 3.46 (1H, d, J = 12.7 Hz), 3.75-4.0 (2H, m), 7.02 (1H, d, J = 7.5 Hz), 7.34 (1H, dd, J = 7.7, 7.7 Hz), 7.48 (1H, d, J = 5.4 Hz), 7.51 (1H, d, J = 7.8 Hz), 7.78 (1H, d, J = 5.4 Hz), 8.17 (1H, br), 9.75 (1H, br). | Hydro-chloride |
| 33 | —H | 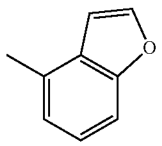 | 1H-NMR (DMSO-d6) δ ppm: 0.95-1.15 (2H, m), 1.3-1.45 (1H, m), 1.51 (3H, s), 1.53 (3H, s), 1.6-2.1 (8H, m), 3.04 (1H, d, J = 12.9 Hz), 3.2-3.45 (1H, m), 3.75-3.95 (1H, m), 3.95-4.15 (1H, m), 8.6-8.8 (1H, m), 7.1-7.3 (3H, m), 7.94 (1H, d, J = 2.1 Hz), 8.07 (1H, br), 9.77 (1H, br). | Hydro-chloride |

TABLE 6

Relative configuration

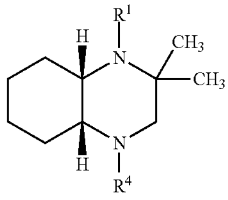

| Example | $R^1$ | $R^4$ | NMR | Salt |
|---|---|---|---|---|
| 34 | —H | 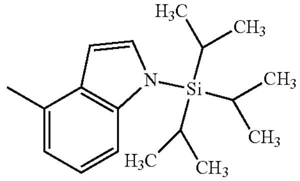 | 1H-NMR (CDCl3) δ ppm: 1.15 (18H, d, J = 7.5 Hz), 1.20 (3H, s), 1.25-1.45 (8H, m), 1.45-1.8 (8H, m), 1.8-2.0 (1H, m), 2.83 (1H, d, J = 11.5 Hz), 3.11 (1H, d, J = 11.5 Hz), 3.6-3.65 (1H, m), 3.67-3.8 (1H, m), 6.50 (1H, d, J = 7.2 Hz), 8.64 (1H, d, J = 2.7 Hz), 7.00 (1H, dd, J = 7.9, 7.9 Hz), 7.11 (1H, d, J = 8.3 Hz), 7.16 (1H, d, J = 3.2 Hz). | — |
| 35 | —H | 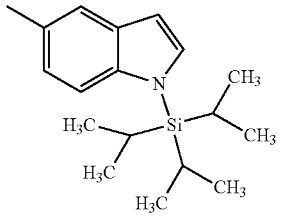 | 1H-NMR (CDCl3) δ ppm: 1.13 (18H, d, J = 7.5 Hz), 1.21 (3H, s), 1.25-1,3 (5H, m), 1.35-1.45 (2H, m), 1.53 (1H, br), 1.6-1.8 (7H, m), 2.80 (1H, d, J = 11.7 Hz), 2.93 (1H, d, J = 11.5 Hz), 3.45-3.55 (1H, m), 3.55-3.65 (1H, m), 5.48 (1H, d, J = 2.6 Hz), 6.85 (1H, dd, J = 2.4, 9.0 Hz), 7.02 (1H, d, J = 2.4 Hz), 7.16 (1H, d, J = 3.2 Hz), 7.36 (1H, d, J = 9.1 Hz). | — |
| 36 | —H | 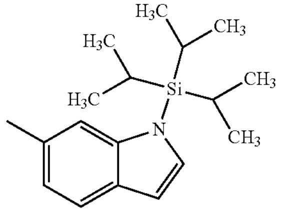 | 1H-NMR (CDCl3) δ ppm: 1.1-1.2 (1H, m), 1.21 (3H, s), 1.25-1.3 (4H, m), 1.3-1.85 (11H, m), 2.79 (1H, d, J = 11.6 Hz), 2.91 (1H, d, J = 11.5 Hz), 3.45-3.65 (2H, m), 5.45-6.5 (1H, m), 6.82 (1H, dd, J = 2.0, 8.8 Hz), 6.93 (1H, s), 7.08 (1H, d, J = 3.2 Hz), 7.45 (1H, d, J = 8.6 Hz). | — |

TABLE 7

Relative configuration

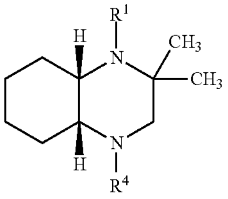

| Example | $R^1$ | $R^4$ | NMR | Salt |
|---|---|---|---|---|
| 37 | —H | 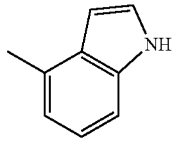 | 1H-NMR (CDCl3) δ ppm: 0.95-1.15 (3H, m), 1.21 (3H, s), 1.25-1.45 (6H, m), 1.45-1.8 (2H, m), 1.6-1.95 (1H, m), 2.83 (1H, d, J = 11.5 Hz), 3.11 (1H, d, J = 11.5 Hz), 3.6-3.7 (1H, m), 3.75-3.85 (1H, m), 6.50 (1H, dd, J = 0.9, 7.4 Hz), 6.55-6.6 (1H, m), 7.00 (1H, d, J = 8.1 Hz), 7.07 (1H, dd, J = 7.7, 7.7 Hz), 7.14 (1H, dd, J = 2.8, 2.8 Hz), 8.18 (1H, br). | — |
| 38 | —$CH_3$ | 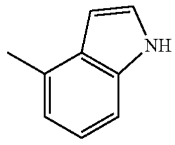 | 1H-NMR (CDCl3) δ ppm: 1.0-1.15 (5H, m), 1.19 (3H, s), 1.2-1.5 (3H, m), 1.6-1.7 (1H, m), 2.8-2.3 (5H, m), 2.76 (1H, d, J = 11.5 Hz), 3.05-3.15 (1H, m), 3.38 (1H, d, J = 11.4 Hz), 3.8-3.9 (1H, m), 8.49 (1H, d, J = 7.4 Hz), 6.55-6.6 (1H, m), 6.99 (1H, d, J = 7.4 Hz), 7.07 (1H, dd, J = 7.8, 7.8 Hz), 7.13 (1H, dd, J = 2.8, 2.8 Hz), 8.11 (1H, br). | — |

TABLE 7-continued

Relative configuration

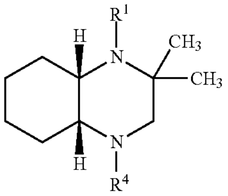

| Example | $R^1$ | $R^4$ | NMR | Salt |
|---|---|---|---|---|
| 39 | —H | 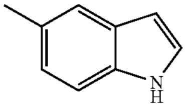 | 1H-NMR (CDCl3) δ ppm: 1.0-1.85 (15H, m), 2.82 (1H, d, J = 11.5 Hz), 2.88 (1H, d, J = 11.5 Hz), 3.45-3.55 (1H, m), 3.55-3.65 (1H, m), 8.4-6.45 (1H, m), 6.95 (1H, dd, J = 2.3, 8.8 Hz), 7.04 (1H, d, J = 2.2 Hz), 7.13 (1H, dd, J = 2.8, 2.8 Hz), 7.25-7.3 (1H, m), 7.98 (1H, br). | — |
| 40 | —$CH_3$ | 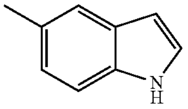 | 1H-NMR (CDCl3) δ ppm: 1.06 (3H, s), 1.1-1.55 (8H, m), 1.6-1.75 (1H, m), 1.95-2.15 (2H, m), 2.16 (3H, s), 2.80 (1H, d, J = 11.4 Hz), 2.95-3.0 (1H, m), 3.10 (1H, d, J = 11.4 Hz), 3.55-3.7 (1H, m), 6.35-5.45 (1H, m), 6.94 (1H, dd, J = 2.3, 5.6 Hz), 7.03 (1H, d, J = 2.0 Hz), 7.12 (1H, dd, J = 2.8, 2.8 Hz), 7.2-7.3 (1H, m), 7.94 (1H, br). | — |
| 41 | —H | 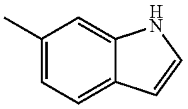 | 1H-NMR (DMSO-d6) δ ppm: 1.0-1.4 (9H, m), 1.4-1.9 (5H, m), 2.62 (1H, d, J = 11.9 Hz), 2.95 (1H, d, J = 12.0 Hz), 3.0-4.5 (4H, m), 6.25 (1H, dd, J = 2.4, 2.4 Hz), 6.47 (1H, s), 6.7-8.8 (2H, m), 7.10 (1H, dd, J = 2.7, 2.7 Hz), 7.34 (1H, d, J = 9.3 Hz), 10.65 (1H, s). | Hemi-fumarate |
| 42 | —$CH_3$ | 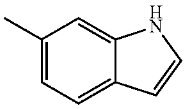 | 1H-NMR (DMSO-d6) δ ppm: 0.95-1.5 (1H, m), 1.55-1.7 (1H, m), 1.55-2.1 (2H, m), 2.16 (3H, s), 2.65-4.2 (6H, m), 6.2-6.25 (1H, m), 6.80 (2H, s), 5.7-6.6 (2H, s), 7.09 (1H, dd, J = 2.4, 3.0 Hz), 7.33 (1H, d, J = 6.6 Hz), 10.80 (1H, s). | Fumarate |
| 43 | —H | 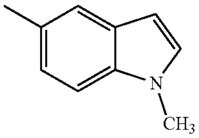 | 1H-NMR (DMSO-d6) δ ppm: 0.95-1.4 (9H, m), 1.45-1.9 (5H, m), 2.88 (2H, dd, J = 12.3, 15.1 Hz), 3.5-3.8 (1H, m), 3.6-3.75 (4H, m), 6.24 (1H, dd, J = 0.6, 3.0 Hz), 6.47 (1H, s), 6.85-7.0 (2H, m), 7.18 (1H, d, J = 3.0 Hz), 7.27 (1H, d, J = 9.5 Hz). | Hemi-fumarate |
| 44 | —H | 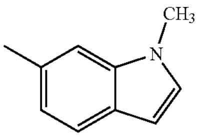 | 1H-NMR (DMSO-d6) δ ppm: 1.1-1.4 (9H, m), 1.4-1.9 (6H, m), 2.65 (1H, d, J = 12.1 Hz), 3.03 (1H, d, J = 12.1 Hz), 3.5-3.6 (1H, m), 3.69 (3H, s), 3.75-3.85 (1H, m), 6.24 (1H, d, J = 3.1 Hz), 6.49 (2H, s), 6.7-6.85 (2H, m), 7.07 (1H, d, J = 3.1 H), 7.34 (1H, d, J = 5.6 Hz). | Fumarate |
| 45 | —H | 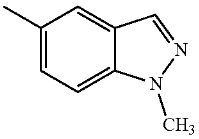 | 1H-NMR (DMSO-d6) δ ppm: 1.0-1.3 (2H, m), 1.3-1.45 (7H, m), 1.5-1.95 (5H, m), 2.9-3.1 (2H, m), 3.71 (1H, br), 3.8-3.95 (1H, m), 3.98 (3H, s), 6.54 (3H, s), 7.04 (1H, s), 7.27 (1H, dd, J = 1.9, 9.2 Hz), 7.51 (1H, d, J = 9.1 Hz), 7.83 (1H, s), 10.8 (4H, br). | 3/2 Fumarate |
| 46 | —H | 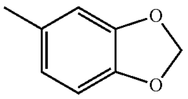 | 1H-NMR (DMSO-d6) δ ppm: 1.1-1.35 (2H, m), 1.35-1.45 (4H, m), 1.50 (3H, s), 1.6-1.9 (4H, m), 1.9-2.1 (1H, m), 2.92 (1H, d, J = 13.2 Hz), 3.11 (1H, d, J = 13.2 Hz), 3.5-4.05 (3H, m), 5.91 (2H, d, J = 1.0 Hz), 6.32 (1H, dd, J = 2.4, 8.5 Hz), 6.71 (1H, d, J = 2.3 Hz), 6.76 (1H, d, J = 8.4 Hz), 8.06 (1H, br), 9.83 (1H, br). | Dihydro-chloride |

TABLE 8

Relative configuration

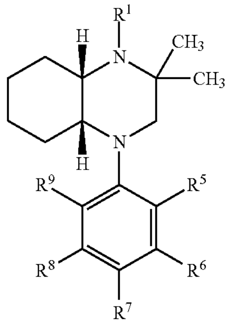

| Example | $R^1$ | $R^5$ | $R^6$ | $R^7$ | $R^8$ | $R^9$ | NMR | Salt |
|---|---|---|---|---|---|---|---|---|
| 47 | —H | —H | —H | —F | —H | —H | 1H-NMR (DMSO-d6) δ ppm: 1.1-1.35 (2H, m), 1.35-1.5 (4H, m), 1.53 (3H, s), 1.6-1.95 (4H, m), 1.95-2.15 (1H, m), 2.94 (1H, d, J = 13.3 Hz), 3.24 (1H, d, J = 13.2 Hz), 3.65-3.85 (1H, m), 3.85-4.0 (1H, m), 5.30 (1H, br), 6.9-7.0 (2H, m), 7.0-7.1 (2H, m), 8.0-8.35 (1H, m), 10.03 (1H, d, J = 10.5 Hz). | Dihydrochloride |
| 48 | —H | —H | —H | —F | —F | —H | 1H-NMR (DMSO-d6) δ ppm: 1.2-1.35 (6H, m), 1.52 (3H, s), 1.6-1.95 (4H, m), 1.96-2.15 (1H, m), 2.93 (1H, d, J = 13.5 Hz), 3.36 (1H, d, J = 13.5 Hz), 3.65-3.8 (1H, m), 3.9-4.1 (1H, m), 5.5-6.5 (1H, m), 6.9-7.1 (1H, m), 7.25 (1H, dd, J = 9.5, 19.7 Hz), 8.0-8.4 (1H, m), 10.02 (1H, d, J = 11.3 Hz). | Hydrochloride |
| 49 | —H | —H | —F | —H | —F | —H | 1H-NMR (DMSO-d6) δ ppm: 1.25-1.6 (9H, m), 1.8-2.05 (5H, m), 2.95 (1H, d, J = 14.5 Hz), 3.56 (1H, d, J = 13.9 Hz), 3.6-3.75 (1H, m), 4.0-4.15 (1H, m), 6.35-6.55 (1H, m), 8.5-8.75 (2H, m), 5.05-8.4 (1H, m), 9.65-10.2 (1H, m). | Hydrochloride |
| 50 | —H | —H | —F | —$OCH_3$ | —F | —H | 1H-NMR (DMSO-d6) δ ppm: 1.21-1.45 (6H, m), 1.80 (3H, s), 1.8-1.9 (4H, m), 1.9-2.05 (1H, m), 2.90 (1H, d, J = 13.7 Hz), 3.42 (1H, d, J = 13.7 Hz), 3.8-3.75 (1H, m), 3.78 (3H, s), 3.9-4.05 (1H, m), 6.65-6.8 (2H, m), 8.17 (1H, br), 9.86 (1H, br). | Hydrochloride |
| 51 | —$CH_3$ | —H | —F | —$OCH_3$ | —F | —H | 1H-NMR (DMSO-d6) δ ppm: 0.96 (3H, s), 1.05-1.2 (4H, m), 1.2-1.5 (4H, m), 1.55-1.75 (1H, m), 1.85-2.1 (2H, m), 2.16 (3H, s), 2.75-2.9 (2H, m), 3.12 (1H, d, J = 12.4 Hz), 3.65-3.85 (4H, m), 8.55-8.85 (5H, m). | ½ Fumarate |
| 52 | —H | —H | —Cl | —H | —H | —H | 1H-NMR (DMSO-d6) δ ppm: 1.2-1.45 (6H, m), 1.51 (3H, s), 1.6-2.05 (5H, m), 2.94 (1H, d, J = 13.7 Hz), 3.48 (1H, d, J = 14.0 Hz), 3.65-3.8 (1H, m), 4.0-4.15 (1H, m), 6.77 (1H, dd, J = 1.5, 7.8 Hz), 6.90 (1H, dd, J = 2.3, 8.4 Hz), 6.95-7.0 (1H, m), 7.21 (1H, dd, J = 8.1, 8.1 Hz), 8.14 (1H, br), 9.55-10.0 (1H, m). | Hydrochloride |
| 53 | —$CH_3$ | —H | —Cl | —H | —H | —H | 1H-NMR (DMSO-d6) δ ppm: 0.97 (3H, s), 1.05-1.2 (4H, m), 1.2-1.8 (4H, m), 1.6-1.75 (1H, m), 1.9-2.1 (2H, m), 2.15 (3H, s), 2.85-5.05 (6H, m), 6.61 (2H, s), 6.86 (1H, dd, J = 1.2, 7.8 Hz), 6.75-6.9 (2H, m), 7.15 (1H, dd, J = 8.1, 8.1 Hz). | Fumarate |
| 54 | —H | —H | —H | —Cl | —H | —H | 1H-NMR (DMSO-d6) δ ppm: 1.15-1.45 (8H, m), 1.62 (3H, s), 1.6-2.1 (5H, m), 2.93 (1H, d, J = 13.5 Hz), 3.39 (1H, d, J = 13.9 Hz), 3.65-3.8 (1H, m), 3.9-4.1 (1H, m), 5.9-7.0 (2H, m), 7.15-7.3 (2H, m), 7.95-8.4 (1H, m), 9.65-10.1 (1H, m). | Hydrochloride |
| 55 | —$CH_3$ | —H | —H | —Cl | —H | —H | 1H-NMR (DMSO-d6) δ ppm: 0.99 (3H, s), 1.06-1.5 (8H, m), 1.55-1.75 (1H, m), 1.54-2.1 (2H, m), 2.17 (3H, s), 2.8-2.95 (2H, m), 3.12 (1H, d, J = 12.3 Hz), 3.7-3.85 (1H, m), 6.61 (2H, s), 6.6-6.9 (2H, m), 7.1-7.2 (2H, m). | Fumarate |
| 56 | —H | —H | —Cl | —Cl | —H | —H | 1H-NMR (DMSO-d6) δ ppm: 1.21-1.62 (2H, m), 1.38 (3H, s), 1.53 (3H, s), 1.67-2.09 (6H, m), 2.95 (1H, d, J = 13.6 Hz), 3.48 (1H, d, J = 13.6 Hz), 3.70-3.74 (1H, m), 4.04-4.10 (1H, m), 6.95 (1H, dd, J = 8.7, 2.6 Hz), 7.17 (1H, d, J = 2.8 Hz), 7.40 (1H, d, J = 6.7 Hz), 8.03-8.52 (1H, br), 9.77-10.21 (1H, br) | Hydrochloride |
| 57 | —$CH_3$ | —H | —Cl | —Cl | —H | —H | 1H-NMR (CDCl3) δ ppm: 1.23-1.72 (4H, m), 1.42 (3H, s), 1.89 (3H, s), 2.01-2.11 (1H, m), 2.20-2.29 (1H, m), 2.37-2.65 (1H, m), 2.68-2.83 (1H, m), 2.79 (3H, d, J =4.8 Hz), 3.09 (1H, d, J = 13.5 Hz), 3.54-3.65 (1H, m), 3.75-3.83 (1H, m), 3.76 (1H,d, J = 13.5 Hz), 8.88 (1H, dd, J = 9.0, 2.9 Hz), 6.92 (1H, d, J = 2.9 Hz), 7.30 (1H, d, J = 9.0 Hz), 11.48 (1H, brs) | Hydrochloride |
| 58 | —H | —H | —Cl | —F | —H | —H | 1H-NMR (DMSO) δ ppm: 1.24-1.57 (3H, m), 1.37 (3H, s), 1.52 (3H, s), 1.64-1.81 (4H, m), 1.87-2.01 (1H, m), 2.92 (1H, d, J = 13.1 Hz), 3.45 (1H, d, J = 13.1 Hz), 3.65-3.79 (1H, m), 3.90-4.06 (1H, m), 6.89-6.94 (1H, m), 7.08-7.11 (1H, m), 7.20-7.27 (1H, m), 7.90-8.21 (1H, br), 9.55-9.81 (1H, br) | Hydrochloride |

TABLE 9

Absolute configuration

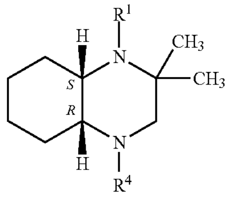

| Example | $R^1$ | $R^4$ | NMR | Salt |
|---|---|---|---|---|
| 59 | —H | 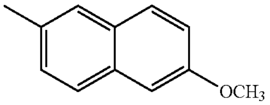 | 1H-NMR (CDCl3) δ ppm: 1.15-1.35 (5H, m), 1.35-1.86 (7H, m), 2.82 (1H, d, J = 11.7 Hz), 3.05 (1H, d, J = 11.8 Hz), 3.45-3.55 (1H, m), 3.7-3.8 (1H, m), 3.88 (3H, s), 8.97 (1H, d, J = 2.4 Hz), 7.0-7.1 (2H, m), 7.22-7.29 (1H, m), 7.55 (1H, d, J = 8.8 Hz), 7.61 (1H, d, J = 9.0 Hz). | — |
| 60 | —H | 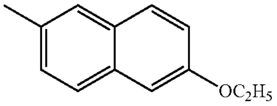 | 1H-NMR (CDCl3) δ ppm: 1.15-1.3 (8H, m), 1.3-1.5 (6H, m), 1.85-1.86 (4H, m), 2.82 (1H, d, J = 11.7 Hz), 3.04 (1H, d, J = 11.7 Hz), 3.45-3.85 (1H, m), 3.7-3.78 (1H, m), 4.11 (2H, q, J = 7.0 Hz), 8.96 (1H, d, J = 2.4 Hz), 7.03 (1H, d, J = 2.4 Hz), 7.08 (1H, dd, J = 2.5, 5.8 Hz), 7.2-7.3 (1H, m), 7.55 (1H, d, J = 8.9 Hz), 7.59 (1H, d, J = 9.0 Hz). | — |
| 61 | —H | 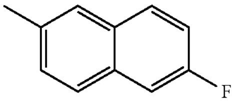 | 1H-NMR (DMSO-d6) δ ppm: 1.26-1.5 (8H, m), 1.56 (3H, s), 1.85-2.1 (5H, m), 3.06 (1H, d, J = 13.4 Hz), 3.46 (1H, d, J = 13.4 Hz), 3.8-3.9 (1H, m), 4.1-4.2 (1H, m), 4.42 (1H, br), 7.24 (1H, d, J = 2.3 Hz), 7.31 (1H, ddd, J = 4.5, 12.6, 12.5 Hz), 7.47 (1H, dd, J = 2.3, 9.2 Hz), 7.54 (1H, dd, J = 2.8, 10.2 Hz), 7.75-7.8 (2H, m), 8.1-8.25 (1H, m), 9.75-9.95 (1H, m). | Dihydro-chloride |
| 62 | —H | 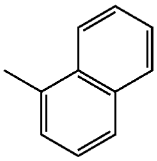 | 1H-NMR (DMSO-d6) δ ppm: 0.9-1.1 (2H, m), 1.3-1.4 (1H, m), 1.5-1.86 (7H, m), 1.65-1.85 (2H, m), 1.9-2.1 (2H, m), 2.81 (1H, d, J = 1.25 Hz), 3.4-3.5 (2H, m), 4.2-4.35 (1H, m), 7.13 (1H, d, J = 7.0 Hz), 7.43 (1H, dd, J = 7.8, 7.5 Hz), 7.5-7.8 (2H, m), 7.65 (1H, d, J = 8.2 Hz), 7.55-7.95 (1H, m), 7.95-8.15 (1H, m), 5.2-8.3 (1H, m), 9.65-9.85 (1H, m). | Hydro-chloride |
| 63 | —H | 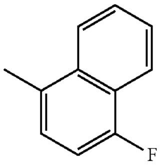 | 1H-NMR (DMSO-d6) δ ppm: 0.9-1.15 (2H, m), 1.3-1.4 (1H, m), 1.5-1.7 (7H, m), 1.7-1.85 (2H, m), 1.9-2.1 (2H, m), 2.77 (1H, d, J = 12.5 Hz), 3.3-3.45 (1H, m), 3.52 (1H, d, J = 12.5 Hz), 4.2-4.3 (1H, m), 7.05-7.15 (1H, m), 7.25 (1H, dd, J = 8.2, 10.5 Hz), 7.6-7.7 (2H, m), 8.0-8.15 (2H, m), 8.3-8.4 (1H, m), 9.7-9.95 (1H, m). | Hydro-chloride |

TABLE 10

Absolute configuration

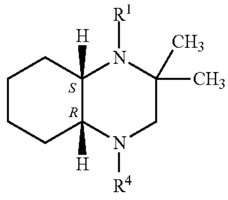

| Example | $R^1$ | $R^4$ | NMR | Salt |
|---|---|---|---|---|
| 64 | —H | 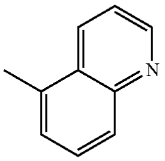 | 1H-NMR (DMSO-d6) δ ppm: 0.9-1.1 (2H, m), 1.3-1.4 (1H, m), 1.5-1.7 (7H, m), 1.7-1.9 (2H, m), 1.95-2.15 (2H, m), 2.89 (1H, d, J = 12.7 Hz), 3.0-4.2 (4H, m), 4.3-4.4 (1H, m), 7.35-7.5 (1H, m), 7.8-8.05 (3H, m), 8.05-8.3 (1H, m), 9.1-9.4 (2H, m), 10.0-10.25 (1H, m). | Trihydro-chloride |

TABLE 10-continued

Absolute configuration

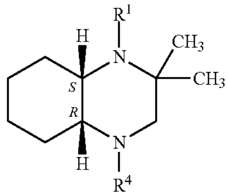

| Example | $R^1$ | $R^4$ | NMR | Salt |
|---|---|---|---|---|
| 65 | —H | 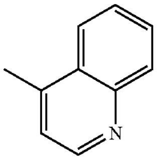 | 1H-NMR (CDCl3) δ ppm: 0.9-1.05 (3H, m), 1.24 (3H, s), 1.36-1.45 (5H, m), 1.55-1.8 (3H, m), 1.9-2.05 (1H, m), 2.71 (1H, d, J = 11.3 Hz), 3.25 (1H, d, J = 11.3 Hz), 3.85-3.75 (1H, m), 3.75-3.85 (1H, m), 8.76 (1H, d, J = 5.0 Hz), 7.45-7.8 (1H, m), 7.5-7.7 (1H, m), 8.0-8.1 (2H, m), 8.88 (1H, d, J = 5.0 Hz). | — |
| 66 | —H | 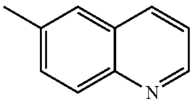 | 1H-NMR (DMSO-d6) δ ppm: 1.36-1.5 (5H, m), 1.82 (3H, s), 1.7-2.0 (3H, m), 2.6-2.15 (2H, m), 2.7-4.3 (4H, m), 4.25-4.4 (1H, m), 7.67 (1H, d, J = 2.5 Hz), 7.80 (1H, d, J = 5.2, 5.6 Hz), 5.04 (1H, dd, J = 2.7, 9.6 Hz), 8.24 (1H, d, J = 9.5 Hz), 8.5-8.8 (1H, m), 8.79 (1H, d, J = 8.4 Hz), 8.98 (1H, dd, J = 1.5, 6.2 Hz), 10.22 (1H, d, J = 10.1 Hz). | Dihydro-chloride |
| 67 | —H | 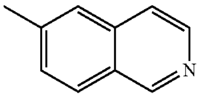 | 1H-NMR (DMSO-d6) δ ppm: 1.41 (3H, s), 1.45-1.8 (3H, m), 1.82 (3H, s), 1.7-1.85 (2H, m), 1.55-2.0 (1H, m), 2.05-2.25 (2H, m), 3.27 (1H, d, J = 14.5 Hz), 3.37 (1H, br), 3.75-3.85 (1H, m), 4.09 (1H, d, J = 14.4 Hz), 4.4-4.5 (1H, m), 7.80 (1H, d, J = 2.1 Hz), 7.85 (1H, dd, J = 2.4, 9.5 Hz), 7.93 (1H, d, J = 8.8 Hz), 8.25-5.35 (2H, m), 8.6-8.75 (1H, m), 9.36 (1H, s), 10.2-10.4 (1H, m). | Dihydro-chloride |

TABLE 11

Absolute configuration

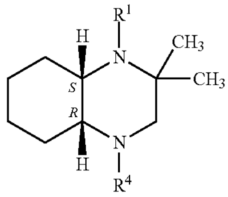

| Example | $R^1$ | $R^4$ | NMR | Salt |
|---|---|---|---|---|
| 68 | —H | 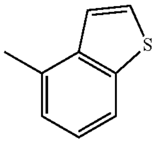 | 1H-NMR (CDCl3) δ ppm: 0.9-1.1 (2H, m), 1.22 (3H, s), 1.3-1.45 (6H, m), 1.45-1.8 (3H, m), 1.8-2.0 (1H, m), 2.65 (1H, d, J = 11.3 Hz), 3.19 (1H, d, J = 11.3 Hz), 3.45-3.85 (1H, m), 3.65-3.75 (1H, m), 6.79 (1H, d, J = 7.6 Hz), 7.15-7.3 (1H, m), 7.38 (1H, d, J = 5.8 Hz), 7.44 (1H, d, J = 5.5 Hz), 7.51 (1H, d, J = 8.0 Hz). | — |
| 69 | —H | 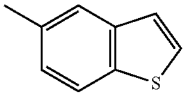 | 1H-NMR (DMDO-d6) δ ppm: 1.1-1.35 (2H, m), 1.35-1.5 (4H, m), 1.65 (3H, s), 1.8-2.15 (5H, m), 3.08 (1H, d, J = 13.2 Hz), 3.35 (1H, d, J = 13.2 Hz), 3.71 (1H, br), 3.75-3.9 (1H, m), 3.95-4.15 (1H, m), 7.18 (1H, dd, J = 2.1, 9.0 Hz), 7.29 (1H, d, J = 5.4 Hz), 7.35 (1H, d, J = 2.0 Hz), 7.68 (1H, d, J = 5.4 Hz), 7.82 (1H, d, J = 8.9 Hz), 6.05-8.25 (1H, m), 9.75-10.0 (1H, m). | Dihydro-chloride |
| 70 | —$CH_3$ | 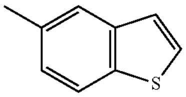 | 1H-NMR (DMDO-d6) δ ppm: 0.95-1.5 (11H, m), 1.55-1.75 (1H, m), 1.85-2.1 (2H, m), 2.19 (3H, s), 2.85-5.05 (5H, m), 6.61 (2H, s), 7.10 (1H, dd, J = 2.4, 9.0 Hz), 7.24 (1H, d, J = 2.3 Hz), 7.27 (1H, dd, J = 0.5, 5.4 Hz), 7.62 (1H, d, J = 5.4 Hz), 7.75 (1H, d, J = 8.9 Hz). | Fumarate |
| 71 | —H | 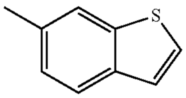 | 1H-NMR (DMDO-d6) δ ppm: 1.2-1.5 (6H, m), 1.54 (3H, s), 1.8-2.1 (5H, m), 3.03 (1H, d, J = 13.4 Hz), 3.43 (1H, d, J = 13.5 Hz), 3.7-3.9 (1H, m), 4.0-4.2 (1H, m), 7.14 (1H, dd, J = 2.2, 8.9 Hz), 7.27 (1H, d, J = 5.4 Hz), 7.4-7.55 (2H, m), 7.71 (1H, d, J = 5.8 Hz), 8.14 (1H, br), 9.84 1H, br). | Hydro-chloride |

TABLE 11-continued

Absolute configuration

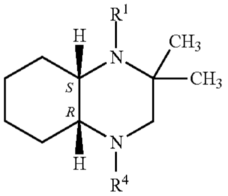

| Example | $R^1$ | $R^4$ | NMR | Salt |
|---|---|---|---|---|
| 72 | —H | 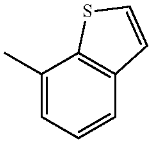 | 1H-NMR (DMDO-d6) δ ppm: 0.95-1.2 (2H, m), 1.3-1.45 (1H, m), 1.45-1.7 (7H, m), 1.7-1.9 (2H, m), 1.9-2.2 (2H, m), 2.91 (1H, d, J = 12.8 Hz), 3.48 (1H, d, J = 12.9 Hz), 3.75-4.0 (2H, m), 7.01 (1H, d, J = 7.5 Hz), 7.34 (1H, dd, J = 7.7, 7.7 Hz), 7.48 (1H, d, J = 5.4 Hz), 7.61 (1H, d, J = 7.7 Hz), 7.76 (1H, d, J = 5.4 Hz), 8.24 (1H, br), 9.94 (1H, br). | Hydro-chloride |

TABLE 12

Absolute configuration

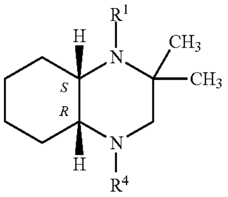

| Example | $R^1$ | $R^4$ | NMR | Salt |
|---|---|---|---|---|
| 73 | —H | 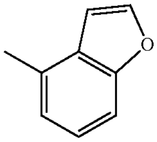 | 1H-NMR (DMDO-d6) δ ppm: 0.95-1.15 (2H, m), 1.3-1.45 (1H, m), 1.51 (3H, s), 1.53 (3H, s), 1.65-2.05 (5H, m), 3.04 (1H, d, J = 1.29 Hz), 3.2-.34 (1H, m), 3.75-3.9 (1H, m), 4.0-4.15 (1H, m), 6.71 (1H, dd, J = 3.0, 5.5 Hz), 7.15-7.25 (3H, m), 7.94 (1H, d, J = 2.2 Hz), 8.08 (1H, br), 9.80 (1H, br). | Hydro-chloride |
| 74 | —H | 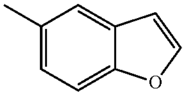 | 1H-NMR (DMDO-d6) δ ppm: 1.1-1.35 (2H, m), 1.35-1.5 (4H, m), 1.54 (3H, s), 1.6-1.86 (4H, m), 1.35-2.1 (1H, m), 3.03 (1H, d, J = 13.1 Hz), 3.21 (1H, d, J = 13.1 Hz), 3.75-3.9 (1H, m), 3.9-4.0 (1H, m), 4.53 (1H, br), 5.5-5.85 (1H, m), 7.03 (1H, dd, J = 2.5, 9.0 Hz), 7.18 (1H, d, J = 2.4 Hz), 7.46 (1H, d, J = 9.0 Hz), 7.90 (1H, d, J = 2.2 Hz), 8.11 (1H, br), 9.91 (1H, br). | Dihydro-chloride |
| 75 | —H | 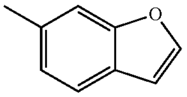 | 1H-NMR (DMDO-d6) δ ppm: 1.15-1.5 (8H, m), 1.65 (3H, s), 1.6-1.95 (4H, m), 1.95-2.15 (1H, m), 3.01 (1H, d, J = 13.4 Hz), 3.36 (1H, d, J = 13.1 Hz), 3.7-3.85 (1H, m), 3.95-4.05 (1H, m), 4.50 (1H, br), 6.80 (1H, d, J = 2.1 Hz), 6.96 (1H, dd, J = 1.9, 8.7 Hz), 7.13 (1H, s), 7.47 (1H, d, J = 6.6 Hz), 7.79 (1H, d, J = 0.7H), 8.20 (1H, br), 9.85-10.2 (1H, m). | Dihydro-chloride |
| 76 | —H | 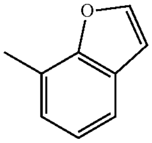 | 1H-NMR (DMDO-d6) δ ppm: 1.1-1.3 (2H, m), 1.35-1.45 (1H, m), 1.50 (3H, s), 1.54 (3H, s), 1.6-1.9 (3H, m), 1.9-2.1 (2H, m), 3.2-3.4 (2H, m), 3.9-4.0 (1H, m), 4.15-4.25 (1H, m), 6.50 (1H, d, J = 7.2 Hz), 6.93 (1H, d, J = 2.2 Hz), 7.12 (1H, dd, J = 7.7, 7.7 Hz), 7.21 (1H, dd, J = 0.8, 7.7 Hz), 7.97 (1H, d, J = 2.2 Hz), 8.1-8.35 (1H, m), 9.7-9.9 (1H, m). | Hydro-chloride |
| 77 | —H | 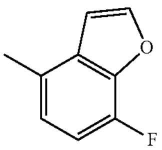 | 1H-NMR (CDCl3) δ ppm: 1.0-1.45 (11H, m), 1.6-1.8 (3H, m), 1.6-1.95 (1H, m), 2.70 (1H, d, J = 11.3 Hz), 3.04 (1H, d, J = 11.3 Hz), 3.50 (1H, ddd, J = 3.8, 3.8, 12.1 Hz), 3.55-3.85 (1H, m), 8.47 (1H, dd, J = 3.4, 8.6 Hz), 6.84 (1H, dd, J = 2.5, 2.5 Hz), 6.89 (1H, dd, J = 8.8, 10.4 Hz), 7.60 (1H, d, J = 2.2 Hz). | — |

TABLE 12-continued

Absolute configuration

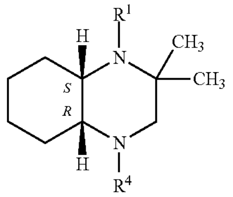

| Example | $R^1$ | $R^4$ | NMR | Salt |
|---|---|---|---|---|
| 78 | —H | 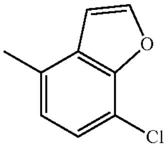 | 1H-NMR (CDCl3) δ ppm: 1.0-1.15 (2H, m), 1.20 (3H, s), 1.25-1.45 (5H, m), 1.6-1.8 (3H, m), 1.8-1.95 (1H, m), 2.79 (1H, d, J = 11.5 Hz), 3.05 (1H, d, J = 11.4 Hz), 3.55-3.64 (2H, m), 6.53 (1H, d, J = 8.4 Hz), 6.84 (1H, d, J = 2.2 Hz), 7.14 (1H, d, J = 8.4 Hz), 7.51 (1H, d, J = 2.2 Hz). | — |
| 79 | —H | 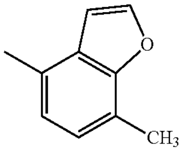 | 1H-NMR (DMDO-d6) δ ppm: 0.95-1.1 (2H, m), 1.3-1.4 (1H, m), 1.51 (3H, s), 1.52 (3H, s), 1.5-1.7 (1H, m), 1.7-1.95 (3H, m), 1.95-2.05 (1H, m), 2.39 (3H, s), 2.95 (1H, d, J = 12.8 Hz), 3.28 (1H, d, J = 12.9 Hz), 3.7-3.8 (1H, m), 4.0-4.15 (1H, m), 8.61 (1H, d, J = 7.9 Hz), 6.99 (1H, d, J = 8.0 Hz), 7.20 (1H, d, J = 2.2 Hz), 7.95 (1H, d, J = 2.2 Hz), 7.95-5.16 (1H, m), 9.7-9.9 (1H, m). | Hydro-chloride |
| 80 | —H | 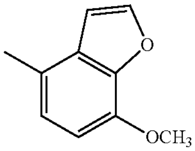 | 1H-NMR (DMDO-d6) δ ppm: 0.95-1.1 (2H, m), 1.3-1.4 (1H, m), 1.52 (8H, s), 1.55-1.65 (1H, m), 1.55-1.95 (3H, m), 1.95-2.1 (1H, m), 2.85 (1H, d, J = 12.7 Hz), 3.27 (1H, d, J = 12.8 Hz), 3.6-3.7 (1H, m), 3.87 (3H s), 4.0-4.15 (1H, m), 6.51 (1H, d, J = 8.4 Hz), 8.79 (1H, d, J = 8.4 Hz), 7.21 (1H, d, J = 2.2 Hz), 7.95 (1H, d, J = 2.2 Hz), 7.95-8.15 (1H, m), 9.75-10.0 (1H, m). | Hydro-chloride |
| 81 | —H | 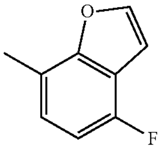 | 1H-NMR (DMDO-d6) δ ppm: 1.05-1.25 (2H, m), 1.35-1.45 (1H, m), 1.50 (3H, s), 1.53 (3H, s), 1.6-1.9 (3H, m), 1.9-2.1 (2H, m), 3.17 (1H, d, J = 13.0 Hz), 3.29 (1H, d, J = 13.2 Hz), 3.9-4.0 (1H, m), 4.0-4.1 (1H, m), 6.80 (1H, dd, J = 4.4, 8.7 Hz), 6.98 (1H, dd, J = 8.9, 5.9 Hz), 7.06 (1H, d, J = 2.2 Hz), 5.06 (1H, d, J = 2.2 Hz), 8.1-8.3 (1H, m), 9.7-9.9 (1H, m). | Hydro-chloride |

TABLE 13

Absolute configuration

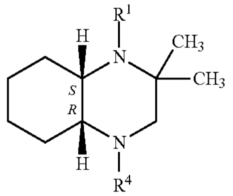

| Example | $R^1$ | $R^4$ | NMR | Salt |
|---|---|---|---|---|
| 82 | —H | 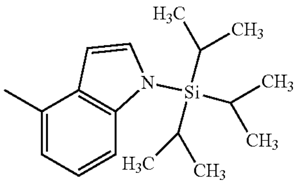 | 1H-NMR (CDCl3) δppm: 1.1-1.2 (20H, m), 1.20 (3H, s), 1.3-1.45 (6H, m), 1.55-1.8 (6H, m), 1.8-2.0 (1H, m), 2.83 (1H, d, J = 11.5 Hz), 3.11 (1H, d, J = 11.5 Hz), 3.6-3.7 (1H, m), 3.7-3.8 (1H, m), 6.50 (1H, d, J = 7.4 Hz), 6.64 (1H, d, J = 3.1 Hz), 7.00 (1H, dd, J = 7.9, 7.9 Hz), 7.11 (1H, d, J = 8.3 Hz), 7.16 (1H, d, J = 3.2 Hz). | — |

TABLE 13-continued

Absolute configuration

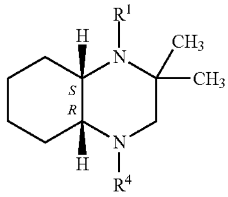

| Example | $R^1$ | $R^4$ | NMR | Salt |
|---|---|---|---|---|
| 83 | —H | 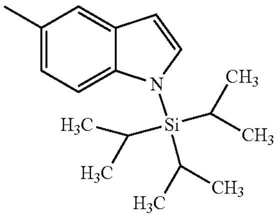 | 1H-NMR (CDCl3) δppm: 1.13 (18H, d, J = 7.5 Hz), 1.21 (3H, s), 1.28 (3H, s), 1.3-1.6 (5H, m), 1.55-1.8 (7H, m), 2.80 (1H, d, J = 11.6 Hz), 2.93 (1H, d, J = 11.6 Hz), 3.45-3.55 (1H, m), 3.55-3.65 (1H, m), 6.48 (1H, d, J = 3.1 Hz), 6.55 (1H, dd, J = 2.4, 9.0 Hz), 7.02 (1H, d, J = 2.4 Hz), 7.16 (1H, d, J = 3.1 Hz), 7.35 (1H, d, J = 9.0 Hz). | — |
| 84 | —H | 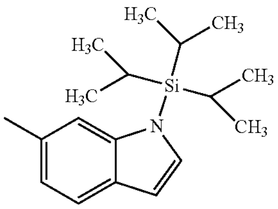 | 1H-NMR (CDCl3) δppm: 1.1-1.2 (18H, m), 1.21 (3H, s), 1.29 (3H, s), 1.3-1.5 (5H, m), 1.55-1.8 (7H, m), 2.79 (1H, d, J = 11.6 Hz), 2.91 (1H, d, J = 11.6 Hz), 3.45-3.6 (2H, m), 6.46 (1H, d, J = 3.2 Hz), 6.82 (1H, dd, J = 2.0, 8.6 Hz), 6.93 (1H, s), 7.08 (1H, d, J = 3.2 Hz), 7.45 (1H, d, J = 8.8 Hz). | — |

TABLE 14

Absolute configuration

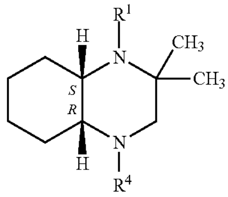

| Example | $R^1$ | $R^4$ | NMR | Salt |
|---|---|---|---|---|
| 85 | —H | 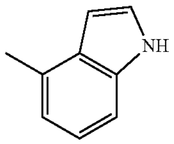 | 1H-NMR (CDCl3) δppm: 0.9-1.15 (2H, m), 1.21 (3H, s), 1.25-1.45 (5H, m), 1.5-1.8 (4H, m), 1.8-2.0 (1H, m), 2.83 (1H, d, J = 11.5 Hz), 3.11 (1H, d, J = 11.5 Hz), 3.6-3.75 (1H, m), 3.75-3.85 (1H, m), 6.50 (1H, dd, J = 0.9, 7.4 Hz), 6.55-6.6 (1H, m), 6.95-7.05 (1H, m), 7.07 (1H, dd, J = 7.7, 7.7 Hz), 7.14 (1H, dd, J = 2.8, 2.8 Hz), 8.15 (1H, br). | — |
| 86 | —H | 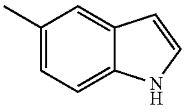 | 1H-NMR (DMSO-d6) δppm: 1.0-1.25 (2H, m), 1.35 (7H, bs), 1.45-1.9 (5H, m), 2.93 (2H, s), 3.6-3.8 (2H, m), 6.2-6.3 (1H, m), 6.50 (2H, s), 6.86 (1H, dd, J = 2.1, 8.8 Hz), 6.95 (1H, d, J = 1.8 Hz), 7.15-7.3 (2H, m), 10.80 (1H, s). | Fumarate |
| 87 | —H | 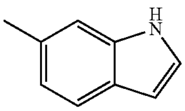 | 1H-NMR (CDCl3) δppm: 1.05-1.85 (15H, m), 2.79 (1H, d, J = 11.6 Hz), 2.94 (1H, d, J = 11.6 Hz), 3.45-3.55 (1H, m), 3.6-3.75 (1H, m), 6.35-8.45 (1H, m), 6.79 (1H, s), 6.86 (1H, dd, J = 2.1, 8.7 Hz), 7.03 (1H, dd, J = 2.4, 3.2 Hz), 7.47 (1H, d, J = 8.7 Hz), 7.89 (1H, br). | — |

TABLE 15

Absolute configuration

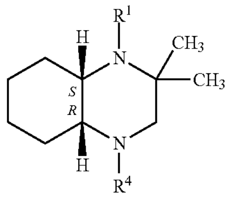

| Example | R1 | R4 | NMR | Salt |
|---|---|---|---|---|
| 88 | —H | 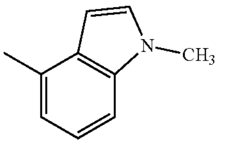 | 1H-NMR (DMSO-d6) δppm: 0.85-1.05 (2H, m), 1.25-1.4 (4H, m), 1.40 (3H, s), 1.5-2.0 (5H, m), 2.82 (1H, d, J = 8.2 Hz), 3.21 (1H, d, J = 12.2 Hz), 3.74 (3H, s), 3.8-3.9 (2H, m), 6.44 (1H, dd, J = 2.5, 5.8 Hz), 6.5-6.55 (3H, m), 6.95-7.05 (2H, m), 7.22 (1H, d, J = 3.1 Hz). | Fumarate |
| 89 | —H | 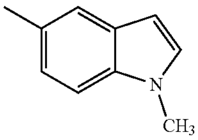 | 1H-NMR (DMSO-d6) δppm: 1.0-1.2 (2H, m), 1.32 (7H, bs), 1.45-1.85 (6H, m), 2.85-2.95 (2H, m), 3.63 (1H, br), 3.65-3.8 (4H, m), 6.24 (1H, dd, J = 0.6, 3.0 Hz), 6.50 (2H, s), 6.9-7.0 (2H, m), 7.19 (1H, d, J = 3.0 Hz), 7.28 (1H, d, J = 8.6 Hz). | Fumarate |
| 90 | —H | 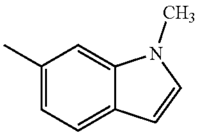 | 1H-NMR (DMSO-d6) δppm: 1.05-1.3 (2H, m), 1.3-1.45 (7H, m), 1.5-1.9 (5H, m), 2.90 (1H, d, J = 12.4 Hz), 3.08 (1H, d, J = 12.3 Hz), 3.62 (1H, br), 3.70 (3H, s), 3.8-3.9 (1H, m), 6.25 (1H, d, J = 3.0 Hz), 6.52 (2H, s), 6.75-6.85 (2H, m), 7.09 (1H, d, J = 3.1 Hz), 7.35 (1H, d, J = 8.6 Hz). | Fumarate |
| 91 | —H | 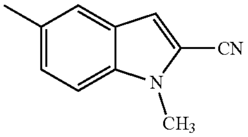 | 1H-NMR (CDCl3) δppm: 0.6-2.4 (15H, m), 2.7-3.3 (2H, m), 3.4-3.6 (2H, m), 3.65 (3H, s), 6.95-7.05 (2H, m), 7.15-7.3 (2H, m). | — |

TABLE 16

Absolute configuration

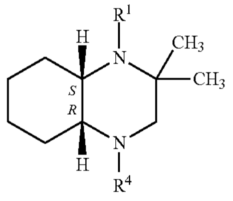

| Example | R1 | R4 | NMR | Salt |
|---|---|---|---|---|
| 92 | —H | 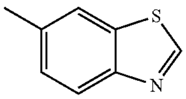 | 1H-NMR (DMSO-d6) δppm: 1.1-1.4 (9H, m), 1.45-1.75 (4H, m), 1.8-1.95 (1H, m), 2.80 (1H, d, J = 12.3 Hz), 3.20 (1H, d, J = 12.3 Hz), 3.4-3.5 (1H, m), 3.8-3.9 (1H, m), 6.51 (1H, s), 7.20 (1H, dd, J = 2.5, 9.1 Hz), 7.51 (1H, d, J = 2.4 Hz), 7.85 (1H, d, J = 9.1 Hz), 9.01 (1H, s). | Hemifumarate |
| 93 | —H | 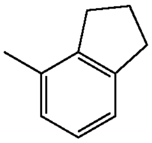 | 1H-NMR (DMSO-d6) δppm: 1.0-1.2 (2H, m), 1.3-1.45 (1H, m), 1.48 (3H, s), 1.50 (3H, s), 1.55-1.7 (1H, m), 1.7-2.15 (6H, m), 2.7-2.95 (6H, m), 3.28 (1H, d, J = 12.8 Hz), 3.35-3.45 (1H, m), 3.75-3.95 (1H, m), 6.68 (1H, d, J = 7.8 Hz), 6.90 (1H, d, J = 7.2 Hz), 7.05 (1H, dd, J = 7.6, 7.6 Hz), 7.95-8.2 (1H, m), 9.75-10.0 (1H, m). | Hydrochloride |

TABLE 16-continued

Absolute configuration

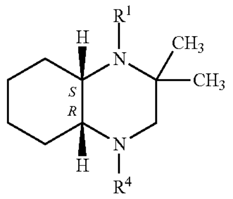

| Example | $R^1$ | $R^4$ | NMR | Salt |
|---|---|---|---|---|
| 94 | —H | 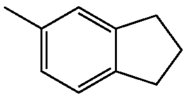 | 1H-NMR (DMSO-d6) δppm: 1.15-1.3 (2H, m), 1.3-1.5 (4H, m), 1.53 (3H, s), 1.6-1.9 (4H, m), 1.9-2.1 (3H, m), 2.74 (2H, t, J = 7.3 Hz), 2.79 (2H, t, J = 7.4 Hz), 2.93 (1H, d, J = 13.2 Hz), 3.22 (1H, d, J = 13.3 Hz), 3.65-3.8 (1H, m), 3.85-4.0 (1H, m), 6.70 (1H, dd, J = 2.2, 8.2 Hz), 6.8-6.85 (1H, m), 7.05 (1H, d, J = 5.2 Hz), 7.8-8.4 (2H, m), 9.85-10.2 (1H, m). | Dihydrochloride |
| 95 | —H | 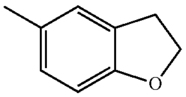 | 1H-NMR (DMSO-d6) δppm: 1.1-1.3 (2H, m), 1.35-1.5 (4H, m), 1.51 (3H, s), 1.6-1.9 (4H, m), 2.0-2.1 (1H, m), 2.95 (1H, d, J = 13.0 Hz), 3.02 (1H, d, J = , 13.0 Hz), 3.11 (2H, t, J = 8.6 Hz), 3.7-3.85 (2H, m), 4.44 (2H, t, J = 8.6 Hz), 4.7-5.5 (1H, m), 6.6-6.7 (2H, m), 6.85-6.95 (1H, m), 8.09 (1H, br), 9.94 (1H, br). | Dihydrochloride |

TABLE 17

Absolute configuration

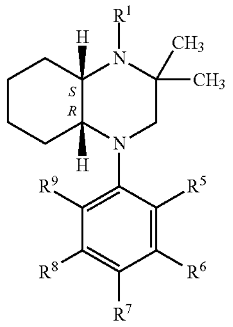

| Example | $R^1$ | $R^5$ | $R^6$ | $R^7$ | $R^8$ | $R^9$ | NMR | Salt |
|---|---|---|---|---|---|---|---|---|
| 96 | —H | —F | —H | —H | —H | —H | 1H-NMR (DMSO-d6) δppm: 1.1-1.25 (2H, m), 1.35-1.45 (1H, m), 1.46 (3H, s), 1.49 (3H, s), 1.6-1.85 (3H, m), 1.85-2.05 (2H, m), 2.93 (1H, d, J = 13.1 Hz), 3.27 (1H, d, J = 13.2 Hz), 3.55-3.65 (1H, m), 3.8-3.9 (1H, m), 6.95-7.05 (1H, m), 7.05-7.2 (3H, m), 8.0-8.2 (1H, m), 9.55-9.75 (1H, m). | Hydrochloride |
| 97 | —H | —H | —H | —F | —H | —H | 1H-NMR (DMSO-d6) δppm: 1.1-1.35 (2H, m), 1.35-1.45 (4H, m), 1.53 (3H, s), 1.6-1.95 (4H, m), 1.95-2.15 (1H, m), 2.94 (1H, d, J = 13.3 Hz), 3.24 (1H, d, J = 13.3 Hz), 3.65-3.85 (1H, m), 3.85-4.0 (1H, m), 4.2-5.8 (1H, m), 6.85-7.0 (2H, m), 7.0-7.1 (2H, m), 8.19 (1H, br), 10.05 (1H, br). | Dihydrochloride |
| 98 | —H | —H | —F | $—OCH_3$ | —H | —H | 1H-NMR (DMSO-d6) δppm: 1.2-1.35 (2H, m), 1.35-1.45 (4H, m), 1.52 (3H, s), 1.6-1.9 (4H, m), 2.0-2.1 (1H, m), 2.90 (1H, d, J = 13.3 Hz), 3.22 (1H, d, J = 13.2 Hz), 3.65-3.8 (4H, m), 3.85-3.95 (1H, m), 6.6-6.7 (1H, m), 6.89 (1H, dd, J = 2.9, 14.7 Hz), 7.02 (1H, dd, J = 9.5, 9.5 Hz), 8.05-8.25 (1H, m), 9.94 (1H, br). | Dihydrochloride |
| 99 | —H | —H | $—OCH_3$ | —F | —H | —H | 1H-NMR (DMSO-d6) δppm: 1.2-1.45 (6H, m), 1.55 (3H, s), 1.6-1.95 (4H, m), 2.0-2.15 (1H, m), 2.95 (1H, d, J = 13.2 Hz), 3.24 (1H, d, J = 13.2 Hz), 3.7-3.8 (1H, m), 3.82 (3H, s), 3.9-4.0 (1H, m), 6.4-6.5 (1H, m), 6.70 (1H, dd, J = 2.8, 7.6 Hz), 7.03 (1H, dd, J = 8.9, 11.3 Hz), 8.0 (1H, br), 8.15-8.35 (1H, m), 10.0-10.15 (1H, m). | Dihydrochloride |
| 100 | —H | —F | —F | —H | —H | —H | 1H-NMR (DMSO-d6) δppm: 1.15-1.3 (2H, m), 1.35-1.45 (1H, m), 1.46 (3H, s), 1.50 (3H, s), 1.6-1.85 (3H, m), 1.9-2.05 (2H, m), 3.00 (1H, d, J = 13.2 Hz), 3.28 (1H, d, J = 13.2 Hz), 3.6-3.7 (1H, m), 3.8-3.9 (1H, m), 6.85-6.95 (1H, m), 6.95-7.05 (1H, m), 7.05-7.15 (1H, m), 8.08-8.35 (1H, m), 9.7-9.9 (1H, m). | Hydrochloride |

TABLE 17-continued

Absolute configuration

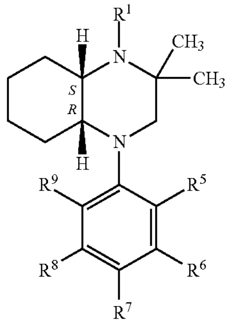

| Example | $R^1$ | $R^5$ | $R^6$ | $R^7$ | $R^8$ | $R^9$ | NMR | Salt |
|---|---|---|---|---|---|---|---|---|
| 101 | —H | —H | —H | —F | —F | —H | 1H-NMR (DMSO-d6) δppm: 1.05-1.4 (9H, m), 1.4-1.9 (5H, m), 2.72 (1H, d, J = 12.5 Hz), 2.8-4.6 (6H, m), 6.54 (2H, s), 6.6-6.7 (1H, m), 6.85-7.0 (1H, m), 7.20 (1H, dd, J = 9.5, 19.9 Hz). | Fumarate |
| 102 | —H | —H | —F | —F | —F | —H | 1H-NMR (DMSO-d6) δppm: 1.25-1.5 (6H, m), 1.51 (3H, s), 1.65-2.1 (5H, m), 2.92 (1H, d, J = 13.8 Hz), 3.46 (1H, d, J = 13.8 Hz), 3.65-3.75 (1H, m), 4.0-4.1 (1H, m), 6.8-6.95 (2H, m), 8.15-8.35 (1H, m), 9.85-10.1 (1H, m). | Hydrochloride |
| 103 | —H | —H | —F | —$OCH_3$ | —F | —H | 1H-NMR (DMSO-d6) δppm: 1.25-1.55 (9H, m), 1.6-1.85 (4H, m), 1.85-2.05 (1H, m), 2.90 (1H, d, J = 13.8 Hz), 3.43 (1H, d, J = 12.8 Hz), 3.65-3.75 (1H, m), 3.78 (3H, s), 3.95-4.05 (1H, m), 6.6-6.8 (2H, m), 8.06 (1H, br), 9.57 (1H, br). | Hydrochloride |
| 104 | —H | —Cl | —H | —H | —H | —H | 1H-NMR (DMSO-d6) δppm: 1.0-1.2 (2H, m), 1.3-1.4 (1H, m), 1.48 (3H, s), 1.50 (3H, s), 1.6-1.85 (3H, m), 1.85-2.1 (2H, m), 2.74 (1H, d, J = 12.8 Hz), 3.41 (1H, d, J = 13.1 Hz), 3.5-3.6 (1H, m), 3.8-3.9 (1H, m), 7.05-7.15 (1H, m), 7.17 (1H, dd, J = 1.4, 8.0 Hz), 7.25-7.35 (1H, m), 7.44 (1H, d, J = 1.5, 7.9 Hz), 8.02 (1H, br), 9.63 (1H, br). | Hydrochloride |
| 105 | —H | —H | —Cl | —$OCH_3$ | —H | —H | 1H-NMR (DMSO-d6) δppm: 1.15-1.45 (6H, m), 1.51 (3H, s), 1.6-1.9 (4H, m), 1.95-2.1 (1H, m), 2.92 (1H, d, J = 13.3 Hz), 3.20 (1H, d, J = 13.1 Hz) 3.7-3.8 (4H, m), 3.9-4.0 (1H, m), 5.9 (1H, br), 6.88 (1H, dd, J = 2.9, 9.1 Hz), 7.0-7.05 (1H, m), 8.11 (1H, br), 9.90 (1H, br). | Dihydrochloride |
| 106 | —H | —H | —H | —Cl | —H | —H | 1H-NMR (DMSO-d6) δppm: 1.2-1.45 (6H, m), 1.51 (3H, s), 1.6-2.1 (5H, m), 2.93 (1H, d, J = 13.5 Hz), 3.40 (1H, d, J = 13.8 Hz), 3.65-3.85 (1H, m), 3.9-4.1 (1H, m), 6.8-7.05 (2H, m), 7.1-7.35 (2H, m), 8.14 (1H, br), 9.77 (1H, br). | Hydrochloride |
| 107 | —$CH_3$ | —H | —H | —Cl | —H | —H | 1H-NMR (DMSO-d6) δppm: 0.98 (3H, s), 1.05-1.2 (4H, m), 1.2-1.45 (4H, m), 1.55-1.75 (1H, m), 1.85-2.1 (2H, m), 2.16 (3H, s), 2.85-4.2 (4H, m), 6.61 (2H, s), 6.8-6.9 (2H, m), 7.1-7.2 (2H, m), 12.8 (2H, br). | Fumarate |
| 108 | —H | —H | —$OCH_3$ | —Cl | —H | —H | 1H-NMR (DMSO-d6) δppm: 1.2-1.5 (6H, m), 1.5-1.6 (3H, m), 1.8-1.95 (4H, m), 2.0-2.1 (1H, m), 2.95 (1H, d, J = 13.5 Hz), 3.3-3.5 (1H, m), 3.7-3.8 (1H, m), 3.84 (3H, s), 4.0-4.1 (1H, m), 6.52 (1H, dd, J = 2.6, 8.9 Hz), 6.63 (1H, d, J = 2.6 Hz), 7.19 (1H, d, J = 8.8 Hz), 8.19 (1H, br), 9.75-10.1 (1H, m). | Hydrochloride |
| 109 | —H | —Cl | —Cl | —H | —H | —H | 1H-NMR (DMSO-d6) δppm: 1.05-1.25 (2H, m), 1.35-1.45 (1H, m), 1.47 (3H, s), 1.49 (3H, s), 1.6-1.85 (3H, m), 1.85-2.05 (2H, m), 2.76 (1H, d, J = 12.8 Hz), 3.42 (1H, d, J = 13.0 Hz), 3.5-3.6 (1H, m), 3.8-3.9 (1H, m), 7.18 (1H, dd, J = 1.6, 7.9 Hz), 7.31 (1H, dd, J = 8.0, 5.0 Hz), 7.37 (1H, dd, J = 1.5, 8.0 Hz), 8.01 (1H, br), 9.5-9.7 (1H, m). | Hydrochloride |
| 110 | —H | —H | —Cl | —Cl | —H | —H | 1H-NMR (DMSO-d6) δppm: 1.2-1.45 (6H, m), 1.52 (3H, s), 1.6-2.15 (5H, m), 2.95 (1H, d, J = 13.7 Hz), 3.49 (1H, d, J = 13.4 Hz), 3.6-3.8 (1H, m), 3.95-4.15 (1H, m), 6.95 (1H, dd, J = 2.6, 9.1 Hz), 7.05-7.25 (1H, m), 7.40 (1H, d, J = 9.0 Hz), 7.95-8.4 (1H, m), 9.6-10.15 (1H, m). | Hydrochloride |
| 111 | —$CH_3$ | —H | —Cl | —Cl | —H | —H | 1H-NMR (DMSO-d6) δppm: 0.96 (3H, s), 1.05-1.2 (4H, m), 1.2-1.5 (4H, m), 1.6-1.75 (1H, m), 1.85-2.05 (2H, m), 2.14 (3H, s), 2.76-2.95 (2H, m), 3.17 (1H, d, J = 12.4 Hz), 3.7-3.9 (1H, m), 6.62 (3H, s), 6.67 (1H, dd, J = 2.9, 9.1 Hz), 7.04 (1H, d, J = 2.9 Hz), 7.33 (1H, d, J = 9.0 Hz), 11.0 (3H, br), | ½ Fumarate |
| 112 | —H | —H | —Cl | —F | —H | —H | 1H-NMR (DMSO-d6) δppm: 1.15-1.45 (6H, m), 1.51 (3H, s), 1.6-1.9 (4H, m), 1.9-2.05 (1H, s), 2.01 (1H, d, J = 8.2 Hz), 3.3-3.45 (1H, m), 3.65-3.8 (1H, m), 3.95-4.1 (1H, m), 6.85-7.0 (1H, m), 7.12 (1H, dd, J = 3.0, 6.2 Hz), 7.25 (1H, dd, J = 9.1, 9.1 Hz), 6.13 (1H, br), 9.86 (1H, br). | Hydrochloride |
| 113 | —H | —H | —F | —Cl | —H | —H | 1H-NMR (DMSO-d6) δppm: 1.2-1.45 (6H, m), 1.51 (3H, s), 1.6-2.1 (5H, m), 2.94 (1H, d, J = 13.7 Hz), 3.50 (1H, d, J = 13.6 Hz), 3.65-3.8 (1H, m), 3.95-4.15 (1H, m), 6.80 (1H, dd, J = 2.6 , 9.1 Hz), 7.01 (1H, dd, J = 2.7, 13.4 Hz), 7.34 (1H, dd, J = 9.0, 9.0 Hz), 8.22 (1H, br), 9.90 (1H, br). | Hydrochloride |

TABLE 18

Absolute configuration

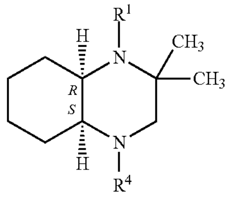

| Example | $R^1$ | $R^4$ | NMR | Salt |
|---|---|---|---|---|
| 114 | —H | 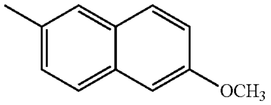 | 1H-NMR (CDCl3) δppm: 1.15-1.35 (8H, m), 1.35-1.85 (7H, m), 2.82 (1H, d, J = 11.7 Hz), 3.05 (1H, d, J = 11.7 Hz), 3.45-3.55 (1H, m), 3.7-3.8 (1H, m), 3.88 (3H, s), 6.97 (1H, d, J = 2.3 Hz), 7.03 (1H, d, J = 2.4 Hz), 7.06 (1H, dd, J = 2.8, 8.8 Hz), 7.26 (1H, dd, J = 2.5, 9.0 Hz), 7.55 (1H, d, J = 8.8 Hz), 7.61 (1H, d, J = 9.0 Hz). | — |
| 115 | $—CH_3$ | 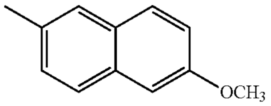 | 1H-NMR (CDCl3) δppm: 1.05 (3H, s), 1.15-1.5 (8H, m), 1.65-1.8 (1H, m), 2.0-2.15 (2H, m), 2.18 (3H, s), 2.9-3.0 (2H, m), 3.09 (1H, d, J = 11.7 Hz), 3.7-3.8 (1H, m), 3.88 (3H, s), 6.95 (1H, d, J = 2.4 Hz), 7.0-7.1 (2H, m), 7.15-7.3 (1H, m), 7.55 (1H, d, J = 8.7 Hz), 7.59 (1H, d, J = 9.1 Hz). | — |
| 116 | —H | 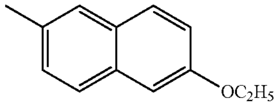 | 1H-NMR (CDCl3) δppm: 1.15-1.3 (8H, m), 1.3-1.85 (10H, m), 2.82 (1H, d, J = 11.7 Hz), 3.04 (1H, d, J = 11.7 Hz), 3.45-3.55 (1H, m), 3.7-3.8 (1H, m), 4.11 (2H, q, J = 7.0 Hz), 6.96 (1H, d, J = 2.4 Hz), 7.03 (1H, d, J = 2.4 Hz), 7.08 (1H, dd, J = 2.5, 8.8 Hz), 7.2-7.3 (1H, m), 7.55 (1H, d, J = 8.9 Hz), 7.59 (1H, d, J = 9.0 Hz). | — |
| 117 | —H | 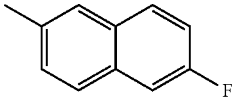 | 1H-NMR (DMSO-d6) δppm: 1.25-1.5 (6H, m), 1.57 (3H, s), 1.85-2.15 (5H, m), 3.06 (H, d, J = 13.4 Hz), 3.47 (1H, d, J = 13.5 Hz), 3.8-3.9 (1H, m), 4.15-4.25 (1H, m), 5.02 (1H, br), 7.24 (1H, d, J = 2.2 Hz), 7.31 (1H, ddd, J = 4.5, 12.8, 12.8 Hz), 7.47 (1H, dd, J = 2.2, 9.2 Hz), 7.54 (1H, dd, J = 2.6, 10.2 Hz), 7.75-7.8 (2H, m), 8.15-8.3 (1H, m), 9.9-10.0 (1H, m). | Dihydrochloride |
| 118 | —H | 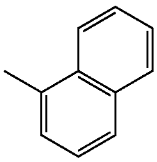 | 1H-NMR (DMSO-d6) δppm: 0.85-1.1 (2H, m), 1.3-1.45 (1H, m), 1.46-1.7 (7H, m), 1.7-1.9 (2H, m), 1.9-2.1 (2H, m), 2.81 (1H, d, J = 12.6 Hz), 3.45-3.6 (2H, m), 4.15-4.3 (1H, m), 7.12 (1H, d, J = 7.1 Hz), 7.43 (1H, dd, J = 7.8, 7.8 Hz), 7.5-7.6 (2H, m), 7.65 (1H, d, J = 8.2 Hz), 7.85-7.95 (1H, m), 8.0-8.2 (1H, m), 8.2-8.3 (1H, m), 9.7-9.95 (1H, m). | Hydrochloride |
| 119 | —H | 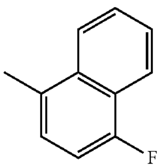 | 1H-NMR (DMSO-d6) δppm: 0.9-1.16 (2H, m), 1.3-1.4 (1H, m), 1.5-1.7 (7H, m), 1.7-1.9 (2H, m), 1.9-2.1 (2H, m), 2.77 (1H, d, J = 12.6 Hz), 3.3-3.45 (1H, m), 3.52 (1H, d, J = 12.6 Hz), 4.2-4.3 (1H, m), 7.05-7.15 (1H, m), 7.25 (1H, dd, J = 8.2, 10.5 Hz), 7.6-7.7 (2H, m), 8.0-8.2 (2H, m), 8.3-8.4 (1H, m), 9.8-10.0 (1H, m). | Hydrochloride |

TABLE 19

Absolute configuration

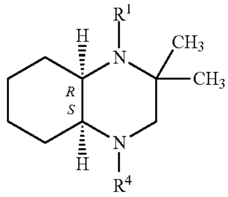

| Example | $R^1$ | $R^4$ | NMR | Salt |
|---|---|---|---|---|
| 120 | —H | 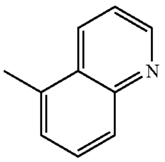 | 1H-NMR (DMSO-d6) δppm: 0.9-1.1 (2H, m), 1.3-1.4 (1H, m), 1.5-1.7 (7H, m), 1.7-1.85 (2H, m), 1.95-2.1 (2H, m), 2.89 (1H, d, J = 12.8 Hz), 3.0-3.9 (4H, m), 4.3-4.4 (1H, m), 7.41 (1H, d, J = 7.0 Hz), 7.8-7.9 (1H, m), 7.9-8.0 (2H, m), 8.1-8.2 (1H, m), 9.1-9.25 (2H, m), 9.98 (1H, br). | Trihydrochloride |
| 121 | —H | 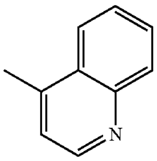 | 1H-NMR (CDCl3) δppm: 0.9-1.05 (3H, m), 1.24 (3H, s), 1.35-1.45 (5H, m), 1.65-1.8 (3H, m), 1.9-2.05 (1H, m), 2.71 (1H, d, J = 11.3 Hz), 3.25 (1H, d, J = 11.4 Hz), 3.65-3.75 (1H, m), 3.75-3.85 (1H, m), 6.76 (1H, d, J = 5.0 Hz), 7.45-7.5 (1H, m), 7.6-7.7 (1H, m), 8.0-8.1 (2H, m), 8.68 (1H, d, J = 5.0 Hz). | — |
| 122 | —H | 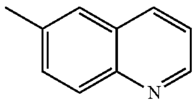 | 1H-NMR (DMSO-D6) δppm: 1.35-1.5 (5H, m), 1.61 (3H, s), 1.7-2.0 (3H, m), 2.0-2.15 (2H, m), 2.8-4.2 (4H, m), 4.25-4.4 (1H, m), 7.56 (1H, d, J = 2.6 Hz), 7.89 (1H, d, J = 5.2, 8.5 Hz), 8.04 (1H, dd, J = 2.7, 9.8 Hz), 8.23 (1H, d, J = 9.5 Hz), 8.45-8.8 (1H, m), 8.78 (1H, d, J = 8.3 Hz), 8.92 (1H, dd, J = 1.3, 5.2 Hz), 10.21 (1H, d, J = 10.6 Hz). | Dihydrochloride |
| 123 | —H | 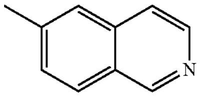 | 1H-NMR (DMSO-d6) δppm: 1.41 (3H, s), 1.45-1.6 (3H, m), 1.63 (3H, s), 1.7-1.85 (2H, m), 1.95-2.05 (1H, m), 2.05-2.25 (2H, m), 3.28 (1H, d, J = 14.5 Hz), 3.39 (1H, br), 3.75-3.85 (1H, m), 4.10 (1H, d, J = 14.4 Hz), 4.4-4.5 (1H, m), 7.51 (1H, d, J = 2.0 Hz), 7.66 (1H, dd, J = 2.4, 9.6 Hz), 7.94 (1H, d, J = 8.8 Hz), 8.25-8.35 (2H, m), 8.65-8.85 (1H, m), 9.37 (1H, s), 10.3-10.45 (1H, m). | Dihydrochloride |

TABLE 20

Absolute configuration

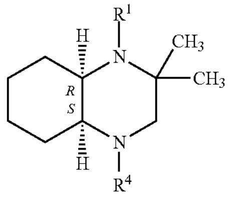

| Example | $R^1$ | $R^4$ | NMR | Salt |
|---|---|---|---|---|
| 124 | —H | 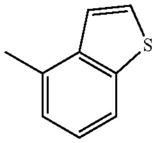 | 1H-NMR (CDCl3) δppm: 0.9-1.15 (2H, m), 1.21 (3H, s), 1.3-1.45 (5H, m), 1.45-1.8 (4H, m), 1.8-2.0 (1H, m), 2.64 (1H, d, J = 11.2 Hz), 3.18 (1H, d, J = 11.2 Hz), 3.45-3.55 (1H, m), 3.65-3.75 (1H, m), 6.78 (1H, d, J = 7.7 Hz), 7.15-7.3 (1H, m), 7.37 (1H, d, J = 5.5 Hz), 7.45 (1H, d, J = 5.6 Hz), 7.51 (1H, d, J = 8.0 Hz). | — |
| 125 | —$CH_3$ | 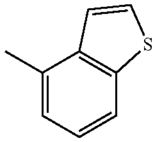 | 1H-NMR (DMSO-d6) δppm: 0.8-1.05 (2H, m), 1.13 (3H, s), 1.15-1.45 (6H, m), 1.5-1.65 (1H, m), 2.0-2.2 (2H, m), 2.23 (3H, s), 2.51 (1H, d, J = 11.8 Hz), 2.8-3.9 (3H, m), 6.61 (4H, s), 6.81 (1H, d, J = 7.6 Hz), 7.24 (1H, dd, J = 7.8, 7.8 Hz), 7.46 (1H, d, J = 5.6 Hz), 7.58 (1H, d, J = 8.0 Hz), 7.69 (1H, d, J = 5.5 Hz), 13.0 (4H, br). | Difumarate |

TABLE 20-continued

Absolute configuration

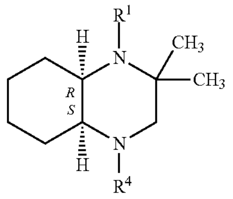

| Example | $R^1$ | $R^4$ | NMR | Salt |
|---|---|---|---|---|
| 126 | —H | 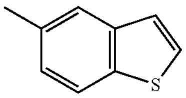 | 1H-NMR (DMSO-d6) δppm: 1.2-1.35 (2H, m), 1.35-1.5 (4H, m), 1.54 (3H, s), 1.6-2.1 (5H, m), 3.03 (1H, d, J = 13.2 Hz), 3.25-3.4 (1H, m), 3.75-3.9 (1H, m), 3.95-4.15 (1H, m), 7.16 (1H, dd, J = 2.2, 8.9 Hz), 7.29 (1H, d, J = 5.4 Hz), 7.35 (1H, d, J = 2.1 Hz), 7.68 (1H, d, J = 5.4 Hz), 7.82 (1H, d, J = 8.9 Hz), 7.95-8.3 (1H, m), 9.65-9.95 (1H, m). | Hydrochloride |
| 127 | —$CH_3$ | 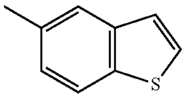 | 1H-NMR (DMSO-d6) δppm: 0.95-1.5 (11H, m), 1.55-1.75 (1H, m), 1.85-2.1 (1H, m), 2.18 (3H, s), 2.8-4.75 (6H, m), 6.61 (2H, s), 7.10 (1H, dd, J = 2.4, 9.0 Hz), 7.24 (1H, d, J = 2.3 Hz), 7.27 (1H, d, J = 5.4 Hz), 7.62 (1H, d, J = 5.3 Hz), 7.75 (1H, d, J = 8.9 Hz). | Fumarate |
| 128 | —H | 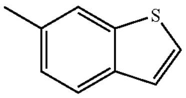 | 1H-NMR (DMSO-d6) δppm: 1.2-1.5 (6H, m), 1.53 (3H, s), 1.6-2.05 (5H, m), 3.03 (1H, d, J = 13.5 Hz), 3.44 (1H, d, J = 13.5 Hz), 3.75-3.9 (1H, m), 4.0-4.15 (1H, m), 7.14 (1H, dd, J = 2.2, 8.9 Hz), 7.27 (1H, d, J = 5.4 Hz), 7.44 (1H, d, J = 5.4 Hz), 7.48 (1H, d, J = 1.8 Hz), 7.71 (1H, d, J = 8.8 Hz), 7.95-8.2 (1H, m), 9.55-9.8 (1H, m). | Hydrochloride |
| 129 | —$CH_3$ | 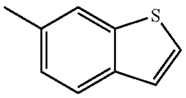 | 1H-NMR (DMSO-d6) δppm: 1.25-1.5 (6H, m), 1.61 (3H, s), 1.59-1.9 (3H, m), 2.05-2.3 (2H, m), 2.74 (3H, d, J = 4.7 Hz), 3.27 (1H, d, J = 13.9 Hz), 3.58 (1H, d, J = 13.8 Hz), 3.7-3.85 (1H, m), 4.1-4.25 (1H, m), 7.15 (1H, dd, J = 2.3, 8.9 Hz), 7.28 (1H, d, J = 5.4 Hz), 7.44 (1H, d, J = 5.4 Hz), 7.49 (1H, d, J = 1.9 Hz), 7.72 (1H, d, J = 8.8 Hz), 9.42 (1H, br). | Hydrochloride |
| 130 | —H | 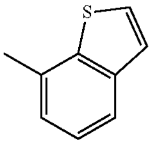 | 1H-NMR (DMSO-d6) δppm: 0.95-1.2 (2H, m), 1.3-1.45 (1H, m), 1.53 (5H, s), 1.55-1.7 (1H, m), 1.7-1.9 (2H, m), 1.9-2.15 (2H, m), 2.92 (1H, d, J = 12.9 Hz), 3.48 (1H, d, J = 12.8 Hz), 3.75-4.0 (2H, m), 7.02 (1H, d, J = 7.6 Hz), 7.35 (1H, dd, J = 7.7, 7.7 Hz), 7.48 (1H, d, J = 5.4 Hz), 7.81 (1H, d, J = 7.9 Hz), 7.76 (1H, d, J = 6.4 Hz), 8.18 (1H, br), 9.81 (1H, br). | Hydrochloride |

TABLE 21

Absolute configuration

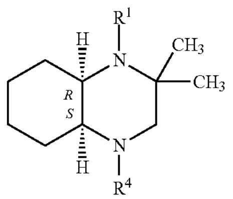

| Example | $R^1$ | $R^4$ | NMR | Salt |
|---|---|---|---|---|
| 131 | —H | 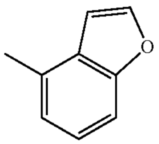 | 1H-NMR (DMSO-d6) δppm: 0.95-1.15 (2H, m), 1.3-1.45 (1H, m), 1.52 (3H, s), 1.54 (3H, s), 1.6-2.1 (5H, m), 3.03 (1H, d, J = 13.0 Hz), 3.30 (1H, d, J = 13.4 Hz), 3.75-3.9 (1H, m), 4.0-4.15 (1H, m), 6.65-6.75 (1H, m), 7.1-7.25 (3H, m), 7.94 (1H d, J = 2.2 Hz), 8.0-8.25 (1H, m), 9.7-10.05 (1H, m). | Hydrochloride |

TABLE 21-continued

Absolute configuration

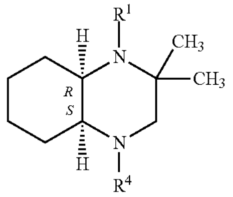

| Example | $R^1$ | $R^4$ | NMR | Salt |
|---|---|---|---|---|
| 132 | —$CH_3$ | 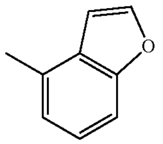 | 1H-NMR (DMSO-d6) δppm: 1.0-1.25 (2H, m), 1.3-1.4 (1H, m), 1.43 (3H, s), 1.55-1.9 (8H, m), 2.1-2.35 (2H, m), 2.75 (3H, d, J = 4.7 Hz), 3.21 (1H, d, J = 13.3 Hz), 3.55 (1H, d, J = 13.3 Hz), 3.85-4.1 (2H, m), 6.65-6.75 (1H, m), 7.15-7.25 (3H, m), 7.95 (1H, d, J = 2.2 Hz), 9.48 (1H, br). | Hydrochloride |
| 133 | —H | 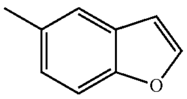 | 1H-NMR (DMSO-d6) δppm: 1.1-1.35 (2H, m), 1.35-1.5 (4H, m), 1.55 (3H, s), 1.6-1.95 (4H, m), 1.95-2.1 (1H, m), 3.03 (1H, d, J = 13.1 Hz), 3.20 (1H, d, J = 12.9 Hz), 3.75-3.9 (1H, m), 3.8-4.0 (1H, m), 5.29 (1H, br), 6.8-6.85 (1H, m), 7.03 (1H, dd, J = 2.4, 9.0 Hz), 7.13 (1H, d, J = 2.3 Hz), 7.45 (1H, d, J = 9.0 Hz), 7.89 (1H, d, J = 2.2 Hz, 8.15 (1H, br), 9.99 (1H, br). | Dihydrochloride |
| 134 | —H | 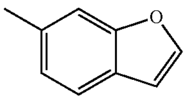 | 1H-NMR (DMSO-d6) δppm: 1.2-1.5 (6H, m), 1.56 (3H, s), 1.6-2.0 (4H, m), 2.0-2.15 (1H, m), 3.01 (1H, d, J = 13.4 Hz), 3.35 (1H, d, J = 13.3 Hz), 3.65-3.85 (1H, m), 3.95-4.15 (1H, m), 6.75-6.85 (1H, m), 6.98 (1H, dd, J = 2.1, 8.7 Hz), 7.13 (1H, s), 7.47 (1H, d, J = 8.6 Hz), 7.5-8.0 (2H, m), 8.15-8.35 (1H, m), 10.0-10.2 (1H, m). | Dihydrochloride |
| 135 | —H | 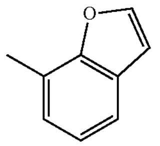 | 1H-NMR (DMSO-d6) δppm: 1.1-1.3 (2H, m), 1.35-1.45 (1H, m), 1.50 (3H, s), 1.55 (3H, s), 1.6-1.9 (3H, m), 1.92-2.1 (2H, m), 3.2-3.4 (2H, m), 3.85-4.0 (1H, m), 4.15-4.25 (1H, m), 6.80 (1H, d, J = 7.0 Hz), 6.94 (1H, d, J = 2.2 Hz), 7.12 (1H, dd, J = 7.7, 7.7 Hz), 7.21 (1H, dd, J = 0.8, 7.7 Hz), 7.97 (1H, d, J = 2.2 Hz), 8.1-8.35 (1H, m), 9.75-9.95 (1H, m). | Hydrochloride |
| 136 | —H | 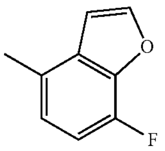 | 1H-NMR (CDCl3) δppm: 1.0-1.45 (11H, m), 1.6-1.8 (3H, m), 1.8-1.95 (1H, m), 2.70 (1H, d, J = 11.3 Hz), 3.04 (1H, d, J = 11.4 Hz), 3.45-3.55 (1H, m), 3.55-3.65 (1H, m), 6.47 (1H, dd, J = 3.4, 8.6 Hz), 6.84 (1H, dd, J = 2.5, 2.5 Hz), 6.89 (1H, dd, J = 8.6, 10.4 Hz), 7.60 (1H, d, J = 2.1 Hz). | — |
| 137 | —H | 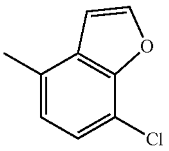 | 1H-NMR (CDCl3) δppm: 1.0-1.15 (2H, m), 1.20 (3H, s), 1.25-1.45 (6H, m), 1.6-1.8 (3H, m), 1.8-1.95 (1H, m), 2.79 (1H, d, J = 11.5 Hz), 3.05 (1H, d, J = 11.4 Hz), 3.55-3.65 (2H, m), 6.53 (1H, d, J = 8.4 Hz), 6.84 (1H, d, J = 2.2 Hz), 7.14 (1H, d, J = 8.4 Hz), 7.61 (1H, d, J = 2.2 Hz). | — |
| 138 | —H | 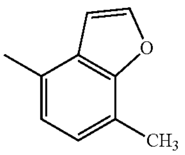 | 1H-NMR (DMSO-d6) δppm: 0.95-1.1 (2H, m), 1.3-1.4 (1H, m), 1.51 (3H, s), 1.53 (3H, s), 1.6-1.7 (1H, m), 1.7-2.0 (3H, m), 2.0-2.05 (1H, m), 2.39 (3H, s), 2.95 (1H, d, J = 12.8 Hz), 3.28 (1H, d, J = 12.9 Hz), 3.7-3.8 (1H, m), 4.0-4.15 (1H, m), 6.61 (1H, d, J = 7.9 Hz), 6.99 (1H, d, J = 8.1 Hz), 7.20 (1H, d, J = 2.2 Hz), 7.95 (1H, d, J = 2.2 Hz), 8.0-8.15 (1H, m), 9.57-9.95 (1H, m). | Hydrochloride |

TABLE 21-continued

Absolute configuration

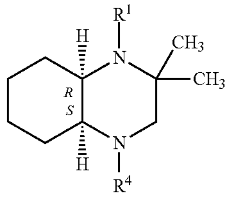

| Example | $R^1$ | $R^4$ | NMR | Salt |
|---|---|---|---|---|
| 139 | —H | 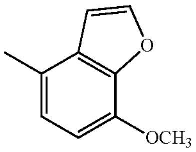 | 1H-NMR (DMSO-d6) δppm: 0.9-1.1 (2H, m), 1.3-1.4 (1H, m), 1.52 (6H, s), 1.55-1.65 (1H, m), 1.65-1.95 (3H, m), 1.95-2.1 (1H, m), 2.86 (1H, d, J = 12.8 Hz), 3.27 (1H, d, J = 12.8 Hz), 3.6-3.7 (1H, m), 3.87 (3H, s), 4.0-4.15 (1H, m), 6.61 (1H, d, J = 8.4 Hz), 6.79 (1H, d, J = 8.4 Hz), 7.21 (1H, d, J = 2.2 Hz), 7.95 (1H, d, J = 2.1 Hz), 7.95-8.15 (1H, m), 9.7-9.9 (1H, m). | Hydrochloride |
| 140 | —H | 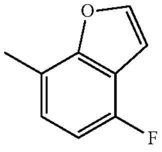 | 1H-NMR (DMSO-d6) δppm: 1.05-1.25 (2H, m), 1.35-1.45 (1H, m), 1.50 (3H, s), 1.54 (3H, s), 1.6-1.9 (3H, m), 1.9-2.1 (2H, m), 3.17 (1H, d, J = 13.1 Hz), 3.29 (1H, d, J = 13.2 Hz), 3.9-4.0 (1H, m), 4.0-4.1 (1H, m), 6.80 (1H, dd, J = 4.4, 8.7 Hz), 8.98 (1H, dd, J = 8.9, 8.9 Hz), 7.06 (1H, d, J = 2.2 Hz), 8.06 (1H, , J = 2.2 Hz), 8.1-8.3 (1H, m), 9.75-9.95 (1H, m). | Hydrochloride |

TABLE 22

Absolute configuration

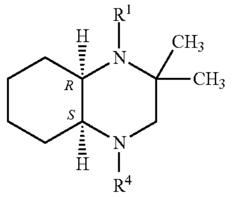

| Example | $R^1$ | $R^4$ | NMR | Salt |
|---|---|---|---|---|
| 141 | —H | 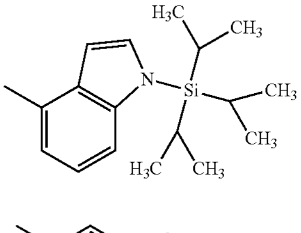 | 1H-NMR (CDCl3) δppm: 1.1-1.2 (20H, m), 1.20 (3H, s), 1.3-1.45 (6H, m), 1.55-1.8 (6H, m), 1.8-2.0 (1H, m), 2.83 (1H, d, J = 11.5 Hz), 3.11 (1H, d, J = 11.6 Hz), 3.6-3.7 (1H, m), 3.7-3.8 (1H, m), 6.50 (1H, d, J = 7.5 Hz), 6.64 (1H, d, J = 3.2 Hz), 7.00 (1H, dd, J = 7.9, 7.9 Hz), 7.11 (1H, d, J = 8.3 Hz), 7.16 (1H, d, J = 3.2 Hz). | — |
| 142 | —H | 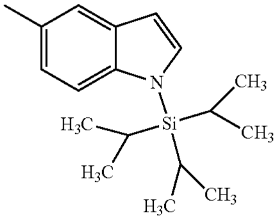 | 1H-NMR (CDCl3) δppm: 1.13 (16H, d, J = 7.5 Hz), 1.21 (3H, s), 1.28 (3H, s), 1.3-1.6 (5H, m), 1.6-1.8 (7H, m), 2.80 (1H, d, J = 11.7 Hz), 2.93 (1H, d, J = 11.6 Hz), 3.45-3.55 (1H, m), 3.55-3.65 (1H, m), 6.48 (1H, dd, J = 0.7, 3.1 Hz), 6.85 (1H, dd, J = 2.4, 9.0 Hz), 7.02 (1H, d, J = 2.3 Hz), 7.18 (1H, d, J = 3.1 Hz), 7.36 (1H, d, J = 9.0 Hz). | — |

TABLE 23

Absolute configuration

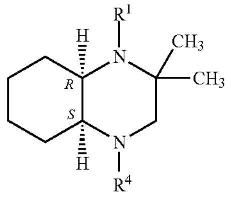

| Example | $R^1$ | $R^4$ | NMR | Salt |
|---|---|---|---|---|
| 143 | —H | 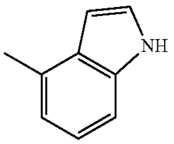 | 1H-NMR (CDCl3) δppm: 0.9-1.15 (2H, m), 1.21 (3H, s), 1.25-1.45 (5H, m), 1.45-1.8 (4H, m), 1.8-2.0 (1H, m), 2.83 (1H, d, J = 11.5 Hz), 3.11 (1H, d, J = 11.5 Hz), 3.6-3.75 (1H, m), 3.75-3.9 (1H, m), 6.50 (1H, d, J = 7.3 Hz), 6.55-6.65 (1H, m), 7.00 (1H, d, J = 8.0 Hz), 7.07 (1H, dd, J = 7.7, 7.7 Hz), 7.14 (1H, dd, J = 2.8, 2.8 Hz), 8.16 (1H, br). | — |
| 144 | —H | 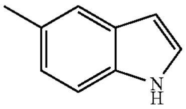 | 1H-NMR (DMSO-d6) δppm: 1.0-1.25 (2H, m), 1.33 (7H, bs), 1.45-1.9 (5H, m), 2.8-3.0 (2H, m), 3.0-4.05 (5H, m), 6.2-6.3 (1H, m), 6.50 (2H, s), 6.86 (1H, dd, J = 2.2, 8.8 Hz), 6.95 (1H, d, J = 1.9 Hz), 7.15-7.3 (2H, m), 10.79 (1H, s). | Fumarate |
| 145 | —H | 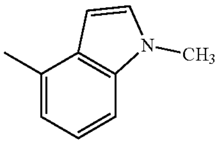 | 1H-NMR (DMSO-d6) δppm: 0.85-1.05 (2H, m), 1.25-1.4 (4H, m), 1.42 (3H, s), 1.5-2.0 (5H, m), 2.84 (1H, d, J = 12.3 Hz), 3.24 (1H, d, J = 12.3 Hz), 3.74 (3H, s), 3.8-3.95 (2H, m), 6.45 (1H, dd, J = 2.2, 6.2 Hz), 6.5-6.55 (3H, m), 6.95-7.05 (2H, m), 7.23 (1H, d, J = 3.1 Hz). | Fumarate |
| 146 | $—CH_3$ | 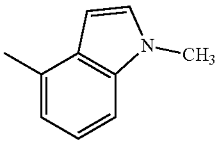 | 1H-NMR (CDCl3) δppm: 1.0-1.5 (11H, m), 1.6-1.7 (1H, m), 2.05-2.3 (6H, m), 2.75 (1H, d, J = 11.4 Hz), 3.05-3.15 (1H, m), 3.38 (1H, d, J = 11.5 Hz), 3.75 (3H, s), 3.8-3.9 (1H, m), 6.45-6.55 (2H, m), 6.92 (1H, d, J = 8.2 Hz), 6.96 (1H, d, J = 3.1 Hz), 7.10 (1H, dd, J = 0.7, 3.1 Hz). | — |
| 147 | —H | 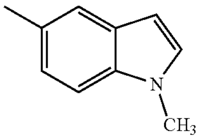 | 1H-NMR (DMSO-d6) δppm: 1.0-1.2 (2H, m), 1.33 (7H, bs), 1.45-1.85 (6H, m), 2.85-2.95 (2H, m), 3.64 (1H, br), 3.7-3.8 (4H, m), 6.24 (1H, dd, J = 0.7, 3.0 Hz), 6.51 (2H, s), 6.9-7.0 (2H, m), 7.19 (1H, d, J = 3.0 Hz), 7.28 (1H, d, J = 8.6 Hz). | Fumarate |
| 148 | —H | 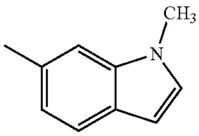 | 1H-NMR (DMSO-d6) δppm: 1.05-1.3 (2H, m), 1.3-1.45 (7H, m), 1.5-1.9 (5H, m), 2.93 (1H, d, J = 12.3 Hz), 3.09 (1H, d, J = 12.4 Hz), 3.65 (1H, br), 3.70 (3H, s), 3.8-3.95 (1H, m), 6.25 (1H, d, J = 3.0 Hz), 6.51 (2H, s), 6.75-6.85 (2H, m), 7.09 (1H, d, J = 3.1 Hz), 7.36 (1H, d, J = 9.2 Hz). | Fumarate |
| 149 | $—CH_3$ | 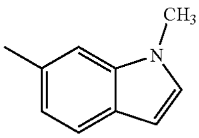 | 1H-NMR (CDCl3) δppm: 1.06 (3H, s), 1.1-1.5 (8H, m), 1.65-1.75 (1H, m), 2.0-2.15 (2H, m), 2.18 (3H, s), 2.87 (1H, d, J = 11.4 Hz), 2.95-3.0 (1H, m), 3.10 (1H, d, J = 11.4 Hz), 3.65-3.75 (4H, m), 6.34 (1H, dd, J = 0.7, 3.1 Hz), 6.62 (1H, d, J = 1.8 Hz), 6.8-6.9 (2H, m), 7.44 (1H, d, J = 8.7 Hz). | — |
| 150 | —H | 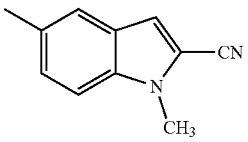 | 1H-NMR (CDCl3) δppm: 0.7-2.3 (15H, m), 2.7-3.2 (2H, m), 3.5-3.6 (2H, m), 3.85 (3H, s), 6.95-7.05 (2H, m), 7.15-7.3 (2H, m). | — |

TABLE 24

Absolute configuration

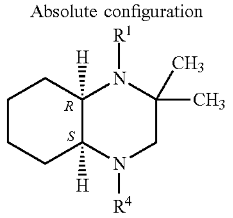

| Example | $R^1$ | $R^4$ | NMR | Salt |
|---|---|---|---|---|
| 151 | —H | 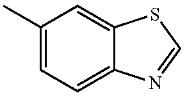 | 1H-NMR (DMSO-d6) δppm: 1.1-1.4 (9H, m), 1.45-1.8 (4H, m), 1.8-1.95 (1H, m), 2.81 (1H, d, J = 12.3 Hz), 3.22 (1H, d, J = 12.4 Hz), 3.45-3.5 (1H, m), 3.85-3.95 (1H, m), 6.52 (1H, s), 7.20 (1H, dd, J = 2.5, 9.1 Hz), 7.51 (1H, d, J = 2.4 Hz), 7.85 (1H, d, J = 9.1 Hz), 9.02 (1H, s). | Hemifumarate |
| 152 | —H | 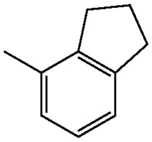 | 1H-NMR (DMSO-d6) δppm: 1.0-1.2 (2H, m), 1.3-1.45 (1H, m), 1.48 (3H, s), 1.50 (3H, s), 1.55-1.7 (1H, m), 1.7-2.15 (6H, m), 2.7-2.95 (5H, m), 3.28 (1H, d, J = 12.8 Hz), 3.35-3.45 (1H, m), 3.8-3.9 (1H, m), 8.68 (1H, d, J = 7.8 Hz), 6.90 (1H, d, J = 7.3 Hz), 7.05 (1H, dd, J = 7.6, 7.6 Hz), 7.95-8.2 (1H, m), 9.7-9.96 (1H, m). | Hydrochloride |
| 153 | —H | 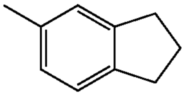 | 1H-NMR (DMSO-d6) δppm: 1.16-1.3 (2H, m), 1.35-1.5 (1H, m), 1.53 (3H, s), 1.6-1.9 (4H, m), 1.9-2.1 (3H, m), 2.74 (2H, t, J = 7.3 Hz), 2.79 (2H, t, J = 7.4 Hz), 2.93 (1H, d, J = 13.3 Hz), 3.22 (1H, d, J = 13.3 Hz), 3.65-3.8 (1H, m), 3.85-4.0 (1H, m), 6.70 (1H, dd, J = 2.2, 8.2 Hz), 6.8-6.85 (1H, m), 7.05 (1H, d, J = 8.2 Hz), 7.33 (1H, br), 8.0-8.3 (1H, m), 9.9-10.1 (1H, m). | Dihydrochloride |
| 154 | —H | 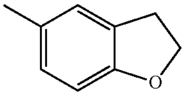 | 1H-NMR (DMSO-d6) δppm: 1.1-1.3 (2H, m), 1.35-1.5 (4H, m), 1.52 (3H, s), 1.6-1.9 (4H, m), 2.0-2.1 (1H, m), 2.95 (1H, d, J = 13.0 Hz), 3.02 (1H, d, J = , 13.0 Hz), 3.11 (2H, t, J = 8.6 Hz), 3.7-3.85 (2H, m), 4.44 (2H, t, J = 8.6 Hz), 6.96 (1H, br), 6.6-6.7 (2H, m), 6.85-6.95 (1H, m), 8.0-8.25 (1H, m), 9.9-10.2 (1H, m). | Dihydrochloride |

TABLE 25

Absolute configuration

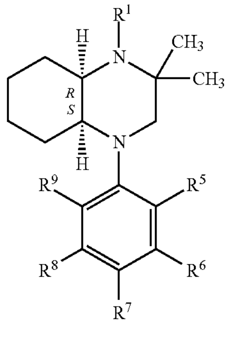

| Example | $R^1$ | $R^5$ | $R^6$ | $R^7$ | $R^8$ | $R^9$ | NMR | Salt |
|---|---|---|---|---|---|---|---|---|
| 155 | —H | —F | —H | —H | —H | —H | 1H-NMR (DMSO-d6) δppm: 1.1-1.25 (2H, m), 1.3-1.45 (1H, m), 1.45 (3H, s), 1.49 (3H, s), 1.65-1.85 (3H, m), 1.85-2.05 (2H, m), 2.93 (1H, d, J = 13.0 Hz), 3.27 (1H, d, J = 13.1 Hz), 3.55-3.65 (1H, m), 3.8-3.9 (1H, m), 6.95-7.05 (1H, m), 7.05-7.2 (3H, m), 8.09 (1H, br), 9.68 (1H, br). | Hydrochloride |
| 156 | —H | —H | —H | —F | —H | —H | 1H-NMR (DMSO-d6) δppm: 1.15-1.45 (6H, m), 1.52 (3H, s), 1.6-2.15 (5H, m), 2.94 (1H, d, J = 13.3 Hz), 3.25 (1H, d, J = 13.1 Hz), 3.35-3.4 (3H, m), 6.85-7.0 (2H, m), 7.0-7.1 (2H, m), 8.16 (1H, br), 9.94 (1H, br). | Dihydrochloride |
| 157 | $—CH_3$ | —H | —H | —F | —H | —H | 1H-NMR (DMSO-d6) δppm: 0.98 (3H, s), 1.0-11 (1H, m), 1.16 (3H, s), 1.2-1.45 (4H, m), 1.55-1.7 (1H, m), 1.85-2.05 (2H, s), 2.15 (3H, s), 2.35-4.55 (4H, m), 6.59 (2H, s), 6.8-6.9 (2H, m), 6.9-7.05 (2H, m), 12.9 (2H, br). | Fumarate |

TABLE 25-continued

Absolute configuration

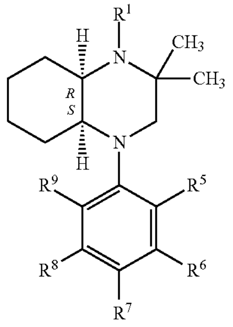

| Example | $R^1$ | $R^5$ | $R^6$ | $R^7$ | $R^8$ | $R^9$ | NMR | Salt |
|---|---|---|---|---|---|---|---|---|
| 158 | —H | —H | —F | —$OCH_3$ | —H | —H | 1H-NMR (DMSO-d6) δppm: 1.2-1.35 (2H, m), 1.35-1.45 (4H, m), 1.51 (3H, s), 1.6-1.9 (4H, m), 1.95-2.1 (1H, m), 2.90 (1H, d, J = 13.4 Hz), 3.22 (1H, d, J = 13.3 Hz), 3.65-3.8 (4H, m), 3.85-3.95 (1H, m), 6.6-6.7 (1H, m), 6.89 (1H, dd, J = 2.9, 14.7 Hz), 7.02 (1H, dd, J = 9.5, 9.5 Hz), 8.12 (1H, m), 9.90 (1H, br). | Hydrochloride |
| 159 | —H | —H | —$OCH_3$ | —F | —H | —H | 1H-NMR (DMSO-d6) δppm: 1.2-1.5 (6H, m), 1.54 (3H, s), 1.6-1.95 (4H, m), 2.0-2.15 (1H, m), 2.95 (1H, d, J = 13.3 Hz), 3.24 (1H, d, J = 13.2 Hz), 3.7-3.8 (1H, m), 3.82 (3H, s), 3.9-4.05 (1H, m), 6.4-6.5 (1H, m), 6.70 (1H, dd, J = 2.8, 7.6 Hz), 7.03 (1H, dd, J = 8.9, 11.3 Hz), 7.75 (1H, br), 8.15-8.35 (1H, m), 10.0-10.15 (1H, m). | Hydrochloride |
| 160 | —H | —F | —F | —H | —H | —H | 1H-NMR (DMSO-d6) δppm: 1.15-1.3 (2H, m), 1.35-1.45 (1H, m), 1.46 (3H, s), 1.50 (3H, s), 1.8-1.85 (4H, m), 1.9-2.05 (3H, m), 3.00 (1H, d, J = 13.2 Hz), 3.28 (1H, d, J = 13.4 Hz), 3.6-3.7 (1H, m), 3.8-3.9 (1H, m), 6.85-6.95 (1H, m), 6.95-7.05 (1H, m), 7.05-7.15 (1H, m), 8.1-8.3 (1H, m), 9.7-9.9 (1H, m). | Hydrochloride |
| 161 | —H | —H | —F | —F | —H | —H | 1H-NMR (DMSO-d6) δppm: 1.2-1.5 (6H, m), 1.52 (3H, s), 1.6-2.15 (5H, m), 2.93 (1H, d, J = 13.5 Hz), 3.2-3.45 (1H, m), 3.65-3.8 (1H, m), 3.9-4.1 (1H, m), 6.55-6.8 (1H, m), 6.95-7.1 (1H, m), 7.25 (1H, dd, J = 9.4, 19.8 Hz), 8.0-8.35 (1H, m), 9.75-10.1 (1H, m). | Hydrochloride |
| 162 | —$CH_3$ | —H | —F | —F | —H | —H | 1H-NMR (DMSO-d6) δppm: 0.97 (3H, s), 1.05-1.2 (4H, m), 1.2-1.45 (4H, m), 1.6-1.75 (1H, m), 1.85-2.05 (2H, s), 2.14 (3H, s), 2.66-4.05 (4H, m), 6.55-6.7 (3H, m), 6.8-6.95 (1H, m), 7.18 (1H, dd, J = 9.5, 20.0 Hz), 13.0 (2H, br). | Fumarate |
| 163 | —H | —H | —F | —F | —F | —H | 1H-NMR (DMSO-d6) δppm: 1.25-1.5 (6H, m), 1.50 (3H, s), 1.65-1.9 (4H, m), 1.95-2.05 (1H, m), 2.92 (1H, d, J = 13.8 Hz), 3.47 (1H, d, J = 13.8 Hz), 3.65-3.8 (1H, m), 4.0-4.1 (1H, m), 6.8-6.95 (2H, m), 8.1-8.3 (1H, m), 9.75-9.95 (1H, m). | Hydrochloride |
| 164 | —H | —H | —F | —$OCH_3$ | —F | —H | 1H-NMR (DMSO-d6) δppm: 1.2-1.45 (6H, m), 1.50 (3H, s), 1.6-1.9 (4H, m), 1.9-2.1 (1H, m), 2.90 (1H, d, J = 13.6 Hz), 3.42 (1H, d, J = 13.8 Hz), 3.8-3.75 (1H, m), 3.78 (3H, s), 3.95-4.05 (1H, m), 6.6-6.85 (2H, m), 8.16 (1H, br), 9.85 (1H, br). | Hydrochloride |
| 165 | —H | —Cl | —H | —H | —H | —H | 1H-NMR (DMSO-d6) δppm: 1.0-1.2 (2H, m), 1.3-1.45 (1H, m), 1.49 (3H, s), 1.51 (3H, s), 1.6-1.85 (3H, m), 1.9-2.1 (2H, m), 2.73 (1H, d, J = 12.8 Hz), 3.41 (1H, d, J = 12.8 Hz), 3.45-3.55 (1H, m), 3.75-3.9 (1H, m), 7.05-7.15 (1H, m), 7.17 (1H, dd, J = 1.4, 8.0 Hz), 7.25-7.35 (1H, m), 7.44 (1H, d, J = 1.5, 8.0 Hz), 8.09 (1H, br), 9.7-9.9 (1H, m). | Hydrochloride |
| 166 | —H | —H | —Cl | —$OCH_3$ | —H | —H | 1H-NMR (DMSO-d6) δppm: 1.15-1.45 (8H, m), 1.52 (3H, s), 1.6-1.9 (4H, m), 2.0-2.1 (1H, m), 2.92 (1H, d, J = 13.2 Hz), 3.19 (1H, d, J = 13.1 Hz), 3.7-3.8 (4H, m), 3.85-3.95 (1H, m), 5.9 (1H, br), 6.88 (1H, dd, J = 2.9, 9.0 Hz), 7.0-7.05 (1H, m), 8.15 (1H, br), 10.00 (1H, br). | Dihydrochloride |
| 167 | —H | —H | —H | —Cl | —H | —H | 1H-NMR (DMSO-d6) δppm: 1.2-1.45 (6H, m), 1.51 (3H, s), 1.6-2.1 (5H, m), 2.93 (1H, d, J = 13.7 Hz), 3.2-3.5 (1H, m), 3.66-3.85 (1H, m), 3.9-4.1 (1H, m), 6.96 (2H, d, J = 9.0 Hz), 7.24 (2H, d, J = 8.9 Hz), 8.14 (1H, br), 9.45-10.0 (1H, m). | Hydrochloride |
| 168 | —$CH_3$ | —H | —H | —Cl | —H | —H | 1H-NMR (DMSO-d6) δppm: 0.97 (3H, s), 1.05-1.2 (4H, m), 1.2-1.45 (4H, m), 1.6-1.75 (1H, m), 1.85-2.05 (2H, m), 2.14 (3H, s), 2.65-4.35 (4H, m), 6.61 (2H, s), 6.8-6.9 (2H, m), 7.1-7.2 (2H, m), 12.9 (2H, br). | Fumarate |
| 169 | —H | —Cl | —Cl | —H | —H | —H | 1H-NMR (DMSO-d6) δppm: 1.05-1.25 (2H, m), 1.35-1.45 (1H, m), 1.47 (3H, s), 1.49 (3H, s), 1.6-1.85 (3H, m), 1.9-2.05 (2H, m), 2.76 (1H, d, J = 12.8 Hz), 3.42 (1H, d, J = 13.0 Hz), 3.5-3.6 (1H, m), 3.8-3.9 (1H, m), 7.18 (1H, dd, J = 1.6, 7.9 Hz), 7.31 (1H, dd, J = 8.0, 8.0 Hz), 7.37 (1H, dd, J = 1.5, 8.0 Hz), 8.02 (1H, br), 9.61 (1H, br). | Hydrochloride |
| 170 | —H | —H | —Cl | —Cl | —H | —H | 1H-NMR (DMSO-d6) δppm: 1.2-1.45 (6H, m), 1.51 (3H, s), 1.8-2.1 (5H, m), 2.95 (1H, d, J = 13.7 Hz), 3.49 (1H, d, J = 13.7 Hz), 3.65-3.8 (1H, m), 4.0-4.15 (1H, m), 6.95 (1H, dd, J = 3.0, 9.1 Hz), 7.18 (1H, d, J = 2.9 Hz), 7.40 (1H, d, J = 9.0 Hz), 7.95-8.35 (1H, m), 9.6-10.05 (1H, m). | Hydrochloride |

TABLE 25-continued

Absolute configuration

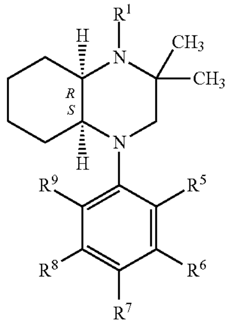

| Example | $R^1$ | $R^5$ | $R^6$ | $R^7$ | $R^8$ | $R^9$ | NMR | Salt |
|---|---|---|---|---|---|---|---|---|
| 171 | —$CH_3$ | —H | —Cl | —Cl | —H | —H | 1H-NMR (DMSO-d6) δppm: 0.95 (3H, s), 1.05-1.2 (4H, m), 1.2-1.5 (4H, m), 1.55-1.75 (1H, m), 1.85-2.05 (2H, m), 2.13 (3H, s), 2.75-2.9 (2H, m), 3.17 (1H, d, J = 12.4 Hz), 3.75-3.85 (1H, m), 6.62 (3H, s), 6.87 (1H, dd, J = 2.9, 9.1 Hz), 7.04 (1H, d, J = 2.9 Hz), 7.33 (1H, d, J = 9.0 Hz), 11.0 (3H, br). | ½ Fumarate |
| 172 | —H | —H | —Cl | —F | —H | —H | 1H-NMR (DMSO-d6) δppm: 1.1-1.45 (6H, m), 1.50 (3H, s), 1.6-1.9 (4H, m), 1.9-2.1 (1H, s), 2.00 (1H, d, J = 8.2 Hz), 3.25-3.45 (1H, m), 3.65-3.85 (1H, m), 3.9-4.1 (1H, m), 6.85-7.0 (1H, m), 7.12 (1H, dd, J = 3.0, 6.3 Hz), 7.25 (1H, dd, J = 9.1, 9.1 Hz), 8.12 (1H, br), 9.82 (1H, br). | Hydrochloride |
| 173 | —H | —H | —F | —Cl | —H | —H | 1H-NMR (DMSO-d6) δppm: 1.2-1.45 (6H, m), 1.50 (3H, s), 1.6-2.1 (5H, m), 2.94 (1H, d, J = 13.8 Hz), 3.51 (1H, d, J = 13.9 Hz), 3.65-3.85 (1H, m), 3.95-4.15 (1H, m), 6.80 (1H, dd, J = 2.5, 8.9 Hz), 7.91 (1H, dd, J = 2.8, 13.4 Hz), 7.34 (1H, dd, J = 9.0, 9.0 Hz), 8.16 (1H, br), 9.77 (1H, br). | Hydrochloride |
| 174 | —H | —H | —$OCH_3$ | —Cl | —H | —H | 1H-NMR (DMSO-d6) δppm: 1.2-1.5 (6H, m), 1.53 (3H, s), 1.65-1.95 (4H, m), 1.95-2.1 (1H, m), 2.95 (1H, d, J = 13.5 Hz), 3.3-3.45 (1H, m), 3.7-3.8 (1H, m), 3.84 (3H, s), 4.0-4.1 (1H, m), 6.52 (1H, dd, J = 2.7, 8.9 Hz), 6.63 (1H, d, J = 2.6 Hz), 7.19 (1H, d, J = 8.8 Hz), 8.18 (1H, br), 9.88 (1H, br). | Hydrochloride |

TABLE 26

Relative configuration

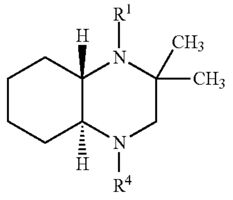

| Example | $R^1$ | $R^4$ | NMR | Salt |
|---|---|---|---|---|
| 175 | —H | 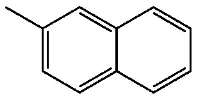 | 1H-NMR (CDCl3) δppm: 1.04-1.21 (1H, m), 1.25-1.46 (2H, m), 1.64-1.88 (3H, m), 1.67 (3H, s), 1.77 (3H, s), 2.00-2.12 (1H, m), 2.34-2.40 (1H, m), 2.88 (1H, d, J = 12.5 Hz), 3.13-3.29 (2H, m), 3.42 (1H, d, J = 12.5 Hz), 7.29-7.34 (1H, m), 7.41-7.51 (2H, m), 7.60 (1H, s), 7.77-7.82 (3H, m), 9.51 (1H, brs), 9.79 (1H, brs) | Hydrochloride |
| 176 | —H | 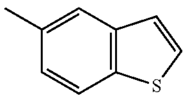 | 1H-NMR (CDCl3) δppm: 1.0-1.11 (1H, m), 1.25-1.39 (2H, m), 1.58-1.81 (3H, m), 1.65 (3H, s), 1.75 (3H, s), 1.96-2.10 (1H, m), 2.32-2.37 (1H, m), 2.82 (1H, d, J = 12.5 Hz), 3.06-3.15 (1H, m), 3.18-3.36 (2H, m), 3.39 (1H, d, J = 12.5 Hz), 7.19 (1H, d, J = 8.5 Hz), 7.291H, d, J = 5.4 Hz), 7.47 (1H, d, J = 5.4 Hz), 7.84 (1H, s), 7.81 (1H, d, J = 8.5 Hz), 9.46 (1H, brs), 9.75 (1H, brs) | Hydrochloride |
| 177 | —H | 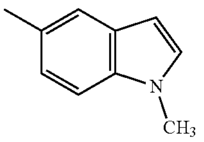 | 1H-NMR (DMSO) δppm: 0.92-1.37 (3H, m), 1.27 (3H, s), 1.40-1.60 (3H, m), 1.52 (3H, s), 1.60-1.75 (1H, m), 1.80-1.90 (1H, m), 2.60-2.73 (1H, m), 2.78 (1H, d, J = 12.1 Hz), 2.97 (1H, d, J = 12.1 Hz), 3.00-3.12 (1H, m), 3.13-3.69 (3H, br), 3.76 (3H, s), 6.36 (2H, d, J = 3.0 Hz), 6.50 (2H, s), 6.94 (1H, dd, J = 8.6, 1.6 Hz), 7.28 (1H, d, J = 1.6 Hz), 7.30 (1H, d, J = 3.0 Hz), 7.36 (1H, d, J = 8.6 Hz) | Fumarate |

TABLE 26-continued

Relative configuration

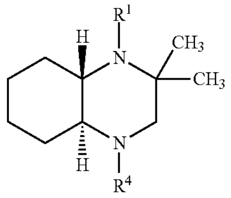

| Example | $R^1$ | $R^4$ | NMR | Salt |
|---|---|---|---|---|
| 178 | —H | 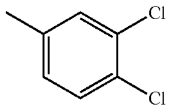 | 1H-NMR (CDCl3) δppm: 0.97-1.09 (1H, m), 1.23-1.38 (2H, m), 1.62-1.68 (3H, m), 1.83 (3H, s), 1.68 (3H, s), 1.92-2.05 (1H, m), 2.29-2.36 (1H, m), 2.73 (1H, d, J = 12.4 Hz), 2.94-3.03 (1H, m), 3.11-3.22 (1H, m), 3.28 (1H, d, J = 12.4 Hz) 7.02 (1H, dd, J = 8.5, 2.4 Hz), 7.25 (1H, d, J = 2.4 Hz), 7.39 (1H, d, J = 8.5 Hz), 9.50 (1H, brs), 9.78 (1H, brs) | Hydrochloride |

TABLE 27

Absolute configuration

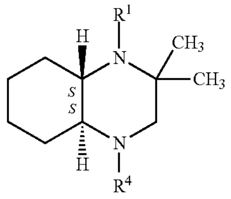

| Example | $R^1$ | $R^4$ | NMR | Salt |
|---|---|---|---|---|
| 179 | —H | 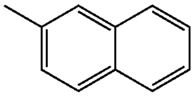 | 1H-NMR (CDCl3) δppm: 1.26-2.30 (8H, m), 1.79 (3H, s), 2.17 (3H, s), 2.51-2.57 (1H, m), 3.36 (1H, d, J = 13.2 Hz), 3.90-4.30 (2H, m), 4.08 (1H, d, J = 13.2 Hz), 7.56-7.69 (2H, m), 7.83-8.01 (4H, m), 8.50 (1H, brs), 10.07 (1H, brs), 10.25 (1H, brs) | Dihydro-chloride |
| 180 | —$CH_3$ | 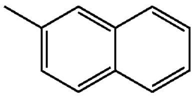 | 1H-NMR (CDCl3) δppm: 1.20-1.38 (1H, m), 1.42-1.76 (4H, m), 1.76 (3H, s), 1.91-1.93 (1H, m), 2.03-2.18 (1H, m), 2.16 (3H, s), 2.30-2.53 (2H, m), 2.85 (3H, d, J = 4.9 Hz), 3.49 (1H, d, J = 13.6 Hz), 4.06-4.21 (1H, m), 4.68 (1H, d, J = 13.6 Hz), 4.95-5.05 (1H, m), 7.55-7.67 (2H, m), 7.89-8.05 (4H, m), 8.95 (1H, br), 13.17 (1H, brs) | Dihydro-chloride |
| 181 | —H | 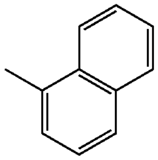 | 1H-NMR (DMSO-d6) δppm: 0.94-1.25 (2H, m), 1.25-1.45 (5H, m), 1.45-1.65 (1H, m), 1.55-1.80 (5H, m), 1.95-2.10 (1H, m), 2.82 (1H, d, J = 12.4 Hz), 2.97-3.11 (2H, m), 3.36-3.51 (1H, m), 7.40 (1H, d, J = 7.3 Hz), 7.50-7.59 (3H, m), 7.79 (1H, d, J = 8.2 Hz), 7.89-7.96 (1H, m), 8.42-8.48 (1H, m), 8.97-9.24 (1H, br), 9.50-9.80 (1H, br). | Hydro-chloride |
| 182 | —H | 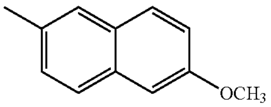 | 1H-NMR (CDCl3) δppm: 1.21-2.12 (8H, m), 1.77 (3H, s), 2.11 (3H, s), 2.49-2.55 (1H, m), 3.27 (1H, d, J = 13.1 Hz), 3.64-4.22 (3H, m), 3.94 (3H, s), 7.15-7.25 (2H, m), 7.68-7.85 (3H, m), 8.25 (1H, brs), 10.04 (2H, brs) | Dihydro-chloride |
| 183 | —$CH_3$ | 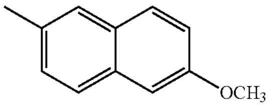 | 1H-NMR (CDCl3) δppm: 1.20-1.50 (2H, m), 1.63-2.28 (7H, m), 1.70 (3H, s), 1.95 (3H, s), 2.81 (3H, d, J = 4.9 Hz), 3.27 (1H, d, J = 13.2 Hz), 3.49-3.85 (1H, m), 3.94 (3H, s), 4.22-4.70 (2H, br), 7.14-7.25 (2H, m), 7.68-7.82 (3H, m), 7.97-8.60 (1H, br), 12.21 (1H, brs) | Dihydro-chloride |
| 184 | —H | 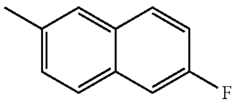 | 1H-NMR (DMSO-d6) δppm: 1.01-1.48 (6H, m), 1.48-1.85 (7H, m), 1.95-2.12 (1H, m), 2.88-3.33 (4H, m), 4.45-5.45 (1H, br), 7.30-7.48 (2H, m), 7.62-7.75 (2H, m), 7.89 (1H, d, J = 8.8 Hz), 7.99 (1H, dd, J = 5.8, 9.1 Hz), 9.07-9.38 (1H, br), 9.60-9.88 (1H, br). | Dihydro-chloride |

TABLE 28

Absolute configuration

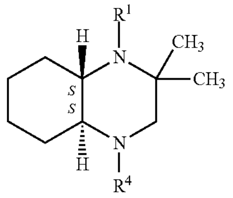

| Example | $R^1$ | $R^4$ | NMR | Salt |
|---|---|---|---|---|
| 185 | —H | 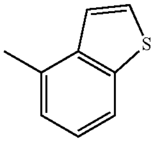 | $^1$H-NMR (CDCl3) δ ppm: 0.96-1.07 (1H, m), 1.25-1.33 (2H, m) 1.48-1.86 (3H, m), 1.85 (3H, s), 1.85 (3H, s), 1.95-2.12 (1H, m), 2.37-2.42 (1H, m), 2.86 (1H, d, J = 12.7 Hz), 3.20-3.35 (2H, m), 3.32 (1H, d, J = 12.7 Hz), 7.26 (1H, d, J = 7.7 Hz), 7.35 (1H, dd, J = 7.7, 7.7 Hz), 7.41 (1H, d, J = 5.5 Hz), 7.53 (1H, d, J = 5.5 Hz), 7.72 (1H, d, J = 7.7 Hz), 9.57 (1H, brs), 9.87 (1H, brs) | Hydrochloride |
| 186 | —H | 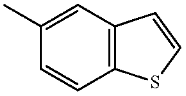 | 1H-NMR (CDCl3) δ ppm: 1.18-2.18 (8H, m), 1.76 (3H, s), 2.17 (3H, s), 2.47-2.54 (1H, m), 3.26 (1H, d, J = 12.9 Hz), 3.72-4.05 (2H, m), 3.92 (1H, d, J = 12.9 Hz), 7.41 (1H, d, J = 5.5 Hz), 7.59 (1H, d, J = 5.5 Hz), 7.65-7.80 (1H, m), 7.96 (1H, d, J = 8.7 Hz), 8.34 (1H, brs), 10.15 (2H, brs) | Dihydrochloride |
| 187 | —$CH_3$ | 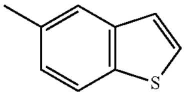 | 1H-NMR (CDCl3) δ ppm: 1.23-1.76 (5H, m), 1.75 (3H, s), 1.84-2.21 (2H, m), 2.14 (3H, s) 2.24-2.44 (2H, m), 2.86 (3H, d, J = 4.9 Hz), 3.49 (1H, d, J = 13.6 Hz), 4.05-4.20 (1H, m), 4.65 (1H, d, J = 13.6 Hz), 4.90-5.01 (1H, m), 7.46 (1H, d, J = 5.5 Hz), 7.65 (1H, d, J = 5.5 Hz), 7.74-9.30 (2H, br), 7.97-8.10 (1H, m), 13.12 (1H, brs) | Dihydrochloride |
| 188 | —H | 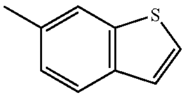 | 1H-NMR (CDCl3) δ ppm: 1.26-2.05 (8H, m), 1.75 (3H, s), 2.05 (3H, s), 2.46-2.52 (1H, m), 3.23 (1H, d, J = 13.4 Hz), 3.70-4.05 (2H, br), 3.86 (1H, d, J = 13.4 Hz), 7.36 (1H, d, J = 5.5 Hz), 7.56 (1H, d, J = 5.5 Hz), 7.67 (1H, brs), 7.89 (1H, d, J = 8.6 Hz), 8.36 (1H, brs), 10.03 (2H, brs) | Dihydrochloride |
| 189 | —$CH_3$ | 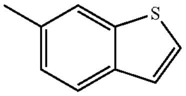 | 1H-NMR (CDCl3) δ ppm: 1.18-1.35 (1H, m), 1.39-1.53 (1H, m), 1.55-1.75 (2H, m), 1.74 (3H, s), 1.84-1.96 (1H, m), 2.02-2.39 (4H, m), 2.06 (3H, s), 2.84 (3H, d, J = 4.9 Hz), 3.42 (1H, d, J = 13.5 Hz), 3.96-4.07 (1H, m), 4.56 (1H, d, J = 13.5 Hz) 4.76-4.54 (1H, m), 7.39 (1H, d, J = 5.5 Hz), 7.63 (1H, d, J = 5.5 Hz), 7.90-7.99 (2H, m), 8.780 (1H, br), 13.05 (1H, brs) | Dihydrochloride |
| 190 | —H | 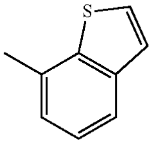 | 1H-NMR (DMSO-d6) δ ppm: 0.95-1.48 (6H, m), 1.48-1.80 (7H, m), 1.90-2.07 (1H, m) 2.67-3.16 (3H, m), 3.16-3.32 (1H, m), 7.23 (1H, d, J = 7.5 Hz), 7.40-7.52 (2H, m), 7.67-7.79 (2H, m), 8.92-9.22 (1H, br), 9.40-9.70 (1H, br). | Hydrochloride |

TABLE 29

Absolute configuration

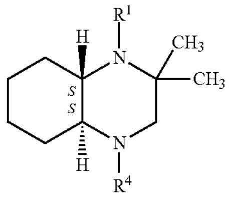

| Example | $R^1$ | $R^4$ | NMR | Salt |
|---|---|---|---|---|
| 191 | —H | 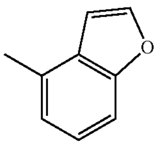 | 1H-NMR (DMSO-d6) δ ppm: 0.95-1.46 (6H, m), 1.46-1.85 (7H, m), 1.95-2.12 (1H, m), 2.80-3.40 (4H, m), 5.50-6.60 (1H, br), 6.75-7.20 (2H, m), 7.20-7.37 (1H, m), 7.37-1.53 (1H, m), 7.99 (1H, s), 9.00-9.50 (1H, br), 9.60-10.05 (1H, br). | Dihydrochloride |

TABLE 29-continued

Absolute configuration

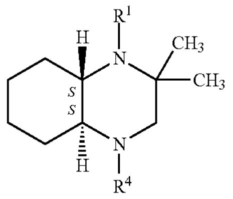

| Example | $R^1$ | $R^4$ | NMR | Salt |
|---|---|---|---|---|
| 192 | —H | 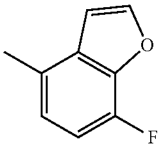 | 1H-NMR (DMSO-d6) δ ppm at 80° C.: 0.96-1.25 (2H, m), 1.26-1.51 (5H, m), 1.51-1.61 (1H, m), 1.61-1.78 (5H, m), 1.99-2.08 (1H, m), 2.80 (1H, d, J = 12.3 Hz), 3.05-3.32 (3H, m), 3.58-4.12 (1H, br), 7.01 (1H, dd, J = 3.8, 8.5 Hz), 7.08-7.18 (2H, m), 8.01 (1H, d, J = 2.1 Hz), 9.10-9.35 (1H, br), 9.38-9.75 (1H, br). | Dihydro-chloride |
| 193 | —H | 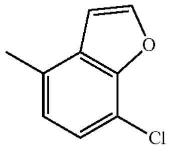 | 1H-NMR (DMSO-d6) δ ppm at 80° C.: 0.98-1.27 (2H, m), 1.27-1.46 (4H, m), 1.46-1.60 (2H, m), 1.60-1.80 (5H, m), 1.98-2.10 (1H, m), 2.84 (1H, d, J = 12.4 Hz), 3.05-3.35 (3H, m), 3.45-3.90 (1H, br), 7.05 (1H, d, J = 8.2 Hz), 7.08-7.13 (1H, br), 7.36 (1H, d, J = 8.2 Hz), 8.03 (1H, d, J = 2.2 Hz), 8.98-9.35 (1H, br), 9.35-9.72 (1H, br). | Dihydro-chloride |
| 194 | —H | 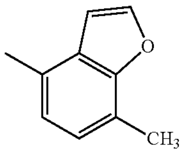 | 1H-NMR (CDCl3) δ ppm: 0.82-1.05 (2H, m), 1.07 (3H, s), 1.19-1.43 (3H, m), 1.49 (3H, s), 1.56-1.68 (1H, m), 1.68-1.90 (3H, m), 2.35-2.51 (4H, m), 2.51-2.70 (1H, m), 2.78-2.92 (2H, m), 6.83-6.89 (2H, m), 7.01 (1H, d, J = 7.8 Hz), 7.56 (1H, d, J = 2.1 Hz). | — |
| 195 | —H | 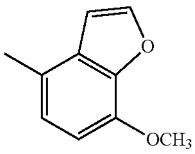 | 1H-NMR (DMSO-d6) δ ppm at 80° C. 0.96-1.25 (2H, m), 1.25-1.60 (6H, m), 1.60-1.79 (5H, m), 1.98-2.10 (1H, m), 2.76 (1H, d, J = 12.3 Hz), 2.99-3.37 (3H, m), 3.93 (3H, s), 4.52-4.86 (1H, br), 6.86 (1H, d, J = 8.4 Hz), 6.95 (1H, d = 8.4 Hz), 6.98-7.09 (1H, br), 7.87 (1H, d, J = 2.1 Hz), 9.02-9.40 (1H, br), 9.40-9.75 (1H, br). | Dihydro-chloride |
| 196 | —H | 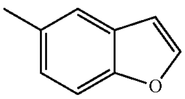 | 1H-NMR (CDCl3) δ ppm: 1.18-1.36 (1H, m), 1.41-1.63 (2H, m), 1.73-2.10 (5H, m), 1.78 (3H,s), 2.17 (3H, s), 2.36-2.69 (1H, m), 3.36 (1H, d, J = 12.8 Hz), 3.82-4.40 (2H, br), 4.09 (1H, d, J = 12.8 Hz), 6.88 (1H, d, J = 2.0 Hz), 7.62 (1H, d, J = 8.7 Hz), 7.74 (1H, d, J = 2.0 Hz), 7.70-8.76 (2H, br), 9.50-10.65 (2H, br) | Dihydro-chloride |
| 197 | —H | 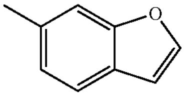 | 1H-NMR (DMSO-d6) δ ppm at 80° C.: 1.03-1.44 (6H, m), 1.51-1.79 (7H, m), 2.00-2.10 (1H, m), 2.87 (1H, d, J = 12.4 Hz), 2.94-3.05 (1H, m), 3.10-3.23 (2H, m), 4.64-5.12 (1H, br), 6.88 (1H, d, J = 1.4 Hz), 7.05-7.09 (1H, m), 7.33-7.36 (1H, br), 7.59 (1H, d, J = 8.2 Hz), 7.89 (1H, J = 2.2 Hz), 8.97-9.25 (1H, br), 9.45-9.82 (1H, br). | Dihydro-chloride |

TABLE 30
Absolute configuration
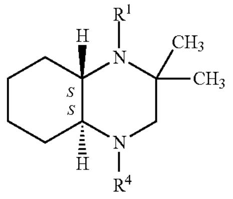
| Example | $R^1$ | $R^4$ | NMR | Salt |
| --- | --- | --- | --- | --- |
| 198 | —H | 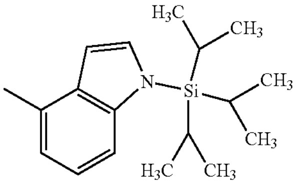 | 1H-NMR (CDCl3) δ ppm: 0.93-1.80 (35H, m), 1.80-2.05 (1H, br), 2.40-2.70 (2H, m), 2.81-2.95 (1H, m), 3.00-3.15 (1H, m), 6.72 (1H, d, J = 2.7 Hz), 6.80 (1H, d, J = 7.4 Hz), 7.00-7.13 (1H, m), 7.17 (1H, d, J = 3.2 Hz), 7.23-7.34 (1H, m). | — |
| 199 | —H | 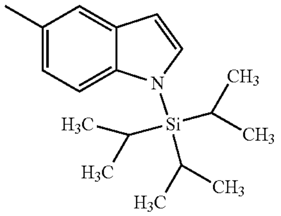 | 1H-NMR (CDCl3) δ ppm: 0.99-1.50 (5H, m), 1.07 (3H, s), 1.13 (9H, s), 1.15 (9H, s), 1.42 (3H, s), 1.58-1.73 (7H, m), 2.23-2.31 (1H, m), 2.68 (1H, d, J = 11.2 Hz), 2.73-2.79 (1H, m), 2.83 (1H, d, J = 11.2 Hz), 6.55 (1H, dd, J = 3.2, 0.7 Hz), 6.92 (1H, dd, J = 8.8, 2.1 Hz), 7.21 (1H, d, J = 3.2 Hz), 7.34 (1H, d, J = 2.1 Hz), 7.37 (1H, d, J = 8.8 Hz) | — |
| 200 | —H | 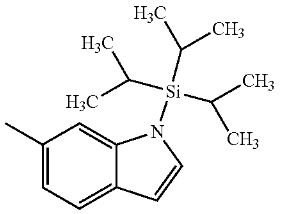 | 1H-NMR (CDCl3) δ ppm: 0.85-1.85 (36H, m), 2.25-2.39 (1H, m), 2.60 (1H, d, J = 11.2 Hz), 2.76-2.90 (2H, m), 6.54-6.60 (1H, m), 6.90 (1H, dd, J = 1.7, 8.3 Hz), 7.17-7.32 (2H, m), 7.50 (1H, d, J = 8.3 Hz). | — |
| 201 | —H | 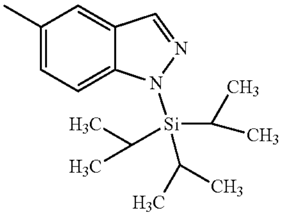 | 1H-NMR (CDCl3) δ ppm: 1.01-1.44 (5H, m), 1.08 (3H, s), 1.13 (9H, s), 1.15 (9H, s), 1.42 (3H, s), 1.56-1.83 (7H, m), 2.25-2.33 (1H, m), 2.67 (1H, d, J = 11.3 Hz), 2.77-2.83 (1H, m), 2.82 (1H, d, J = 11.3 Hz), 7.13 (1H, dd, J = 8.9, 2.0 Hz), 7.43 (1H, d, J = 2.0 Hz), 7.45 (1H, d, J = 8.9 Hz), 8.15 (1H, d, J = 0.8 Hz) | — |

TABLE 31

Absolute configuration

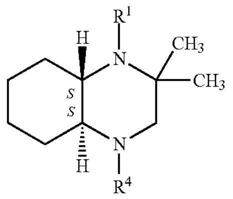

| Example | $R^1$ | $R^4$ | NMR | Melting point (° C.) | Salt |
| --- | --- | --- | --- | --- | --- |
| 202 | —H | 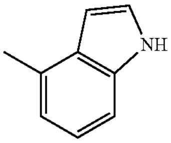 | 1H-NMR (CDCl3) δ ppm: 0.80-1.18 (5H, m), 1.18-1.46 (3H, m), 1.46-1.66 (4H, m), 1.66-2.05 (3H, m), 2.40-2.70 (2H, m), 2.80-2.98 (1H, m), 3.03 (1H, d, J = 11.3 Hz), 6.64-6.72 (1H, m), 6.83 (1H, dd, J = 1.6, 6.6 Hz), 7.07-7.20 (3H, m), 8.16-8.35 (1H, br). | | — |
| 203 | —H | 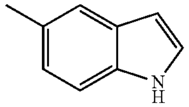 | 1H-NMR (CDCl3) δ ppm: 0.95-1.08 (1H, m), 1.07 (3H, s), 1.13-1.37 (4H, m), 1.43 (3H, s), 1.55-1.73 (4H, m), 2.25-2.33 (1H, m), 2.68 (1H, d, J = 11.1 Hz), 2.75-2.83 (1H, m), 2.81 (1H, d, J = 11.1 Hz), 6.48-6.50 (1H, m), 7.01 (1H, dd, J = 8.6, 1.9 Hz), 7.17-7.20 (1H, m), 7.30 (1H, d, J = 8.6 Hz), 7.38 (1H, d, J = 1.9 Hz), 8.11 (1H, brs) | | — |
| 204 | —$CH_3$ | 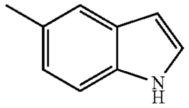 | 1H-NMR (CDCl3) δ ppm: 1.01-1.30 (3H, m), 1.09 (3H, s), 1.22 (3H, s), 1.50-1.75 (4H, m), 1.99-2.15 (1H, m), 2.25 (3H, s), 2.27-2.36 (1H, m), 2.54-2.64 (1H, m), 2.70 (1H, d, J = 11.2 Hz), 2.91 (1H, d, J = 11.2 Hz), 6.46-6.50 (1H, m), 7.02 (1H, dd, J = 8.6, 1.5 Hz), 7.17-7.20 (1H, m), 7.31 (1H, d, J = 8.6 Hz), 7.39 (1H, s), 8.10 (1H, brs) | | — |
| 205 | —H | 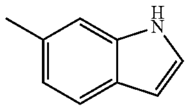 | 1H-NMR (CDCl3) δ ppm: 0.80-1.40 (8H, m), 1.43 (3H, s), 1.55-1.86 (4H, m), 2.27-2.40 (1H, m), 2.68 (1H, d, J = 11.3 Hz), 2.75-2.91 (2H, m), 6.48-6.56 (1H, m), 6.94 (1H, dd, J = 1.8, 8.4 Hz), 7.13-7.22 (2H, m), 7.53 (1H, d, J = 8.4 Hz), 8.15-8.48 (1H, br). | | — |
| 206 | —H | 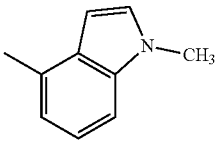 | 1H-NMR (MeOH-d4) δ ppm: 0.87-1.95 (14H, m), 2.66-3.02 (3H, m), 3.09-3.30 (3H, m), 3.69 (3H, s), 6.43 (1H, s), 6.58 (1H, s), 6.77 (1H, d, J = 7.6 Hz), 6.93-7.20 (3H, m). | | Hemi-fumarate |
| 207 | —$CH_3$ | 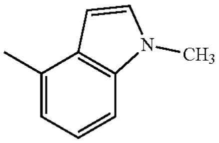 | 1H-NMR (DMSO-d6) δ ppm: 0.85-1.55 (11H, m), 1.63-1.85 (2H, m), 2.05-2.20 (1H, m), 2.41 (3H, brs), 2.60-3.00 (4H, m), 3.00-4.80 (5H, m), 6.36-6.52 (1H, br), 6.56 (2H, s), 6.79 (1H, d, J = 7.5 Hz), 7.03-7.15 (1H, m), 7.15-7.30 (2H, m). | | Fumarate |
| 208 | —$CH_3$ | 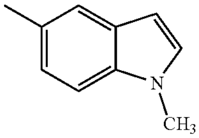 | 1H-NMR (DMSO-d6) δ ppm: 0.89-1.40 (10H, m), 10.40-10.58 (2H, m), 10.63-10.80 (1H, m), 2.01-2.27 (1H, m), 2.39 (3H, s), 2.55-2.78 (3H, m), 2.92-3.06 (1H, m), 4.65 (5H, m), 6.35 (1H, d, J = 2.6 Hz), 6.55 (2H, s), 6.90-7.00 (1H, m), 7.24-7.32 (2H, m), 7.34 (1H, d, J = 8.6 Hz). | | Fumarate |
| 209 | —H | 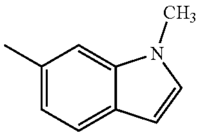 | 1H-NMR (DMDSO-d6) δ ppm: 0.90-1.63 (12H, m), 1.63-1.77 (1H, m), 1.82-1.99 (1H, m), 2.60-2.88 (2H, m), 2.91-3.14 (2H, m), 3.75 (3H, s), 3.80-5.30 (2H, br), 6.36 (1H, d, J = 3.0 Hz), 6.48 (2H, s), 6.85 (1H, d, J = 8.4 Hz), 7.14 (1H, s), 7.27 (1H, d, J = 3.0 Hz), 7.46 (1H, d, J = 8.4 Hz), 8.76-10.00 (1H, br). | | Fumarate |
| 210 | —$CH_3$ | 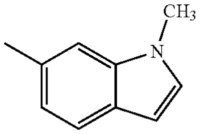 | 1H-NMR (DMSO-d6) δ ppm: 0.90-1.35 (10H, m), 1.40-1.55 (2H, m), 1.55-1.80 (1H, m), 2.02-2.16 (1H, m), 2.39 (3H, s), 2.55-2.80 (3H, m), 2.90-3.08 (1H, m), 3.15-4.70 (5H, m), 6.32-6.40 (1H, m), 6.56 (2H, s), 6.85 (1H, dd, J = 1.5, 8.4 Hz), 7.14 (1H, s), 7.26 (1H, d, J = 3.1 Hz), 7.45 (1H, d, 8.4 Hz). | | Fumarate |

TABLE 31-continued

Absolute configuration

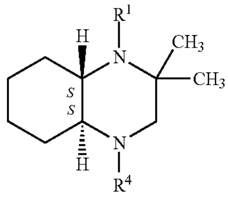

| Example | $R^1$ | $R^4$ | NMR | Melting point (° C.) | Salt |
|---|---|---|---|---|---|
| 211 | —H | 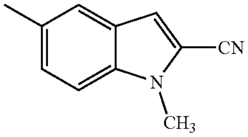 | | 209.8-214.2 | Fumarate |
| 212 | —H | 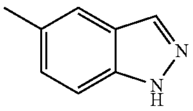 | 1H-NMR (CDCl3) δ ppm: 0.96-1.16 (1H, m), 1.09 (3H, s), 1.19-1.39 (4H, m), 1.44 (3H, s), 1.52-1.62 (2H, m), 1.69-1.82 (2H, m), 2.27-2.35 (1H, m), 2.68 (1H, d, J = 11.1 Hz), 2.75-2.85 (1H, m), 2.81 (1H, d, J = 11.1 Hz), 7.22 (1H, dd, J = 8.8, 1.9 Hz), 7.37-7.46 (2H, m), 8.01 (1H, s), 9.54-10.80 (1H, br) | | — |
| 213 | —$CH_3$ | 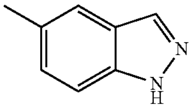 | 1H-NMR (CDCl3) δ ppm: 0.99-1.30 (4H, m), 1.10 (3H, s), 1.22 (3H, s), 1.41-1.67 (2H, br), 1.70-1.80 (1H, m), 1.98-2.16 (1H, m), 2.26 (3H, s), 2.20-2.37 (1H, m), 2.57-2.64 (1H, m), 2.59 (1H, d, J = 11.1 Hz), 2.89 (1H, d, J = 11.1 Hz), 5.85 (1H, s), 7.21-7.28 (1H, m), 7.40-7.53 (2H, m), 8.01 (1H, s) | | — |
| 214 | —H | 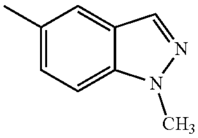 | 1H-NMR (DMSO-d6) δ ppm: 1.00-1.51 (7H, m), 1.51-1.85 (6H, m), 1.92-2.20 (1H, brs), 2.60-3.70 (4H, m), 4.04 (3H, s), 6.85-7.90 (3H, m), 7.90-8.18 (1H, brs), 8.75-10.40 (3H, brm). | | Dihydrochloride |
| 215 | —H | 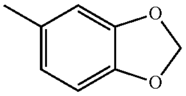 | 1H-NMR (DMSO-d6) δ ppm: 0.95-1.40 (6H, m), 1.40-1.65 (6H, m), 1.65-1.80 (1H, m), 1.85-2.00 (1H, m), 2.65-2.80 (2H, m), 2.85-3.00 (1H, m), 3.00-3.21 (1H, m), 3.98-4.55 (1H, br), 6.00 (2H, s), 6.55-6.65 (1H, m), 6.73 (1H, d, J = 1.6 Hz), 6.86 (1H, d, J = 8.2 Hz), 8.65-8.95 (1H, br), 9.22-9.52 (1H, br). | | Dihydrochloride |
| 216 | —H | 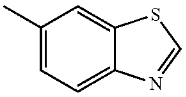 | 1H-NMR (DMSO) δ ppm: 1.04-1.46 (4H, m), 1.35 (3H, s), 1.50-1.75 (4H, m), 1.59 (3H, s), 1.94-1.99 (1H, m), 2.82-2.92 (1H, m), 2.97 (1H, d, J = 12.3 Hz), 3.07 (1H, d, J = 12.3 Hz), 3.13-3.28 (1H, m), 7.28 (1H, dd, J = 8.5, 1.8 Hz), 7.81 (1H, d, J = 1.8 Hz), 8.12 (1H, d, J = 8.5 Hz), 8.85-9.05 (1H, br), 9.41 (1H, s), 9.48-9.56 (1H, br) | | Dihydrochloride |

TABLE 32

Absolute configuration

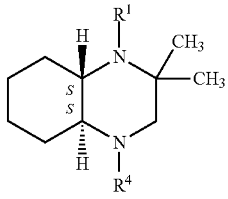

| Example | $R^1$ | $R^4$ | NMR | Melting point (° C.) | Salt |
|---|---|---|---|---|---|
| 217 | —H | 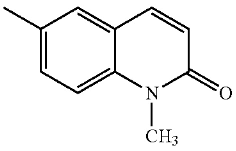 | 1H-NMR (DMSO-d6) δ ppm: 1.00-1.44 (6H, m), 1.50-1.79 (7H, m), 1.96-2.08 (1H, m), 2.82-3.00 (2H, m), 3.00-3.25 (2H, m), 3.61 (3H, s), 6.62 (1H, d, J = 9.5 Hz), 7.38-7.46 (1H, m), 7.48-7.58 (2H, m), 7.91 (1H, d, J = 9.5 Hz), 7.98-8.62 (1H, br), 9.14-9.37 (1H, br), 9.65-9.88 (1H, br). | | Dihydro-chloride |
| 218 | —H | 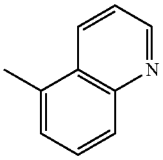 | 1H-NMR (CDCl3) δ ppm: 0.87-1.03 (1H, m), 1.09 (3H, m), 1.15-1.46 (4H, m), 1.46-1.65 (5H, m), 1.65-1.88 (2H, m), 2.47-2.60 (1H, m), 2.65 (1H, d, J = 11.3 Hz), 2.76 (1H, d, J = 11.3 Hz), 2.90-3.04 (1H, m), 7.25 (1H, d, J = 7.3 Hz), 7.40 (1H, dd, J = 4.2, 8.5 Hz), 7.65-7.72 (1H, m), 7.91 (1H, d, J = 8.5 Hz), 8.85 (1H, d, J = 8.5 Hz), 8.90 (1H, dd, J = 1.7, 4.2 Hz). | | — |
| 219 | —H | 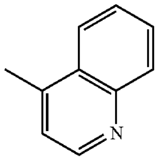 | 1H-NMR (CDCl3) δ ppm: 0.93-1.12 (5H, m), 1.22-1.48 (3H, m), 1.55-1.70 (4H, m), 1.73-1.90 (3H, m), 2.50 (1H, d, J = 11.5 Hz), 2.55-2.65 (1H, m), 2.92-3.05 (2H, m), 7.09 (1H, d, J = 4.8 Hz), 7.49-7.55 (1H, m), 7.65-7.72 (1H, m), 8.05-8.10 (1H, m), 8.36 (1H, dd, J = 1.0, 8.4 Hz), 8.84 (1H, d, J = 4.8 Hz). | | — |
| 220 | —H | 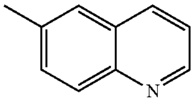 | 1H-NMR (CDCl3) δ ppm: 0.80-1.17 (5H, m), 1.21-1.50 (6H, m), 1.61-1.88 (4H, m), 2.42-2.50 (1H, m), 2.74 (1H, d, J = 11.4 Hz), 2.80-2.90 (1H, m), 2.96 (1H, d, J = 11.4 Hz), 7.31-7.39 (2H, m), 7.50 (1H, dd, J = 2.4, 9.0 Hz), 8.01 (1H, d, J = 9.0 Hz), 8.06 (1H, dd, J = 1.1, 8.3 Hz), 8.81 (1H, dd, J = 1.7, 4.2 Hz). | | — |
| 221 | —H | 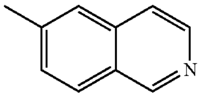 | 1H-NMR (CDCl3) δ ppm: 1.04-1.20 (4H, m), 1.20-1.48 (7H, m), 1.67-1.86 (3H, m), 1.96 (1H, dd, J = 3.0, 13.0), 2.61-2.70 (1H, m), 2.82-2.95 (2H, m), 3.07 (1H, d, J = 12.0 Hz), 7.20 (1H, d, J = 1.8 Hz), 7.32 (1H, dd, J = 2.1, 8.8 Hz), 7.50 (1H, d, J = 5.8 Hz), 7.84 (1H, d, J = 8.8 Hz), 8.41 (1H, d, J = 5.8 Hz), 9.09 (1H, s). | | — |

TABLE 33

Absolute configuration

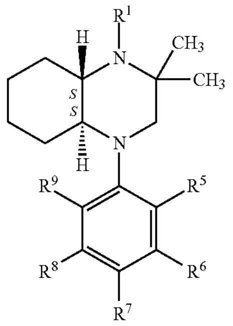

| Example | $R^1$ | $R^5$ | $R^6$ | $R^7$ | $R^8$ | $R^9$ | NMR | Salt |
|---|---|---|---|---|---|---|---|---|
| 222 | —H | —H | —H | —F | —H | —H | 1H-NMR (CDCl3) δ ppm: 1.21-1.36 (1H, m), 1.44-1.61 (2H, m), 1.68-2.00 (3H, m), 1.78 (3H, s), 2.09-2.33 (1H, m), 2.22 (3H, s), 2.51-2.55 (1H, m), 3.42 (1H, d, J = 13.2 Hz), 3.92-4.12 (1H, m), 4.15 (1H, d, J = 13.2 Hz), 4.37-4.44 (1H, m), 7.22-7.27 (4H, m), 7.90-8.46 (1H, br), 9.90-10.18 (1H, m), 10.32-10.60 (1H, brs) | Dihydro-chloride |
| 223 | —$CH_3$ | —H | —H | —F | —H | —H | 1H-NMR (CDCl3) δ ppm: 0.90-1.10 (1H, m), 1.14-1.38 (2H, m), 1.40-1.75 (2H, m), 1.53 (3H, s), 1.59 (3H, s), 1.85-1.95 (1H, m), 2.01-2.23 (2H, m), 2.72 (3H, d, J = 5.0 Hz), 2.75 (1H, d, J = 12.9 Hz), 2.87-3.06 (1H, m), 3.40-3.50 (1H, m), 3.80 (1H, d, J = 12.9 Hz), 6.98-7.04 (2H, m), 7.18-7.23 (2H, m), 12.10 (1H, brs) | Dihydro-chloride |
| 224 | —H | —H | —F | —F | —H | —H | 1H-NMR (CDCl3) δ ppm: 1.17-1.46 (3H, m), 1.53-1.74 (2H, m), 1.66 (3H, s), 1.79 (3H, s), 1.79 (1H, brs), 1.88-2.05 (1H, m), 2.24-2.46 (1H, m), 2.88 (1H, d, J = 12.5 Hz), 3.10-3.40 (2H, m), 3.43 (1H, d, J = 12.5 Hz), 7.13-7.18 (2H, m), 7.20-7.28 (1H, m), 9.40-9.75 (1H, br), 9.76-10.08 (1H, br) | Hydro-chloride |
| 225 | —$CH_3$ | —H | —F | —F | —H | —H | 1H-NMR (CDCl3) δ ppm: 1.19-1.41 (3H, m), 1.61 (8H, brs), 1.80-2.02 (1H, m), 2.04-2.24 (2H, m), 2.74 (3H, d, J = 5.0 Hz), 2.87 (1H, d, J = 12.8 Hz), 3.08-3.20 (1H, m), 3.62-3.78 (1H, m), 3.92 (1H, d, J = 12.8 Hz), 7.11-7.19 (2H, m), 7.27-7.32 (1H, m), 12.08 (1H, brs) | Hydro-chloride |
| 226 | —H | —H | —Cl | —F | —H | —H | 1H-NMR (CDCl3) δ ppm: 1.13-1.42 (3H, m), 1.47-1.81 (3H, m), 1.65 (3H, s), 1.74 (3H, s), 1.88-2.05 (1H, m), 2.32-2.38 (1H, m), 2.80 (1H, d, J = 12.5 Hz), 3.07-3.16 (1H, m), 3.19-3.29 (1H, m), 3.36 (1H, d, J = 12.5 Hz), 7.07-7.21 (2H, m), 7.34 (1H, dd, J = 6.5, 2.3 Hz), 9.56 (1H, brs), 9.82-9.86 (1H, br) | Hydro-chloride |
| 227 | —H | —H | —$CH_3$ | —F | —H | —H | 1H-NMR (DMSO-d6) δ ppm: 1.00-1.45 (6H, m), 1.45-1.81 (7H, m), 1.81-2.10 (1H, m), 2.22 (3H, d, J = 1.5 Hz), 2.78-3.00 (2H, m), 3.00-3.27 (2H, m), 4.10-4.98 (1H, br), 6.96-7.23 (3H, m), 9.00-9.40 (1H, br), 9.58-9.92 (1H, br). | Dihydro-chloride |
| 228 | —H | —H | —$OCH_2$ | —F | —H | —H | 1H-NMR (DMSO-d6) δ ppm at 80° C.: 1.00-1.43 (6H, m), 1.49-1.77 (7H, m), 1.97-2.08 (1H, m), 2.81 (1H, d, J = 12.3 Hz), 2.84-2.93 (1H, m), 3.04-3.18 (2H, m), 3.83 (3H, s), 4.30-4.57 (1H, br), 6.58-6.74 (1H, m), 6.86 (1H, dd, J = 2.5, 7.9 Hz), 7.11 (1H, dd, J = 8.6, 11.4 Hz), 8.94-9.25 (1H, br), 9.49-9.80 (1H, br). | Dihydro-chloride |
| 229 | —H | —H | —F | —$CH_3$ | —H | —H | 1H-NMR (CDCl3) δ ppm: 1.21-1.51 (2H, m), 1.62-1.97 (5H, m), 1.72 (3H, s), 2.03 (3H, s), 2.29 (3H, s), 2.44-2.49 (1H, m), 3.21 (1H, d, J = 12.9 Hz) 3.66-3.87 (2H, m), 3.21 (1H, d, J = 12.9 Hz), 7.25-7.31 (1H, m), 7.47-7.62 (2H, m), 10.00 (2H, brs) | Hydro-chloride |
| 230 | —$CH_2$ | —H | —F | —$CH_3$ | —H | —H | 1H-NMR (CDCl3) δ ppm: 1.20-1.40 (3H, m) 1.48-1.75 (2H, m), 1.61 (3H, s), 1.64 (3H, s), 1.84-1.93 (1H, m), 2.11-2.16 (2H, m), 2.26 (3H, d, J = 1.9 Hz), 2.73 (3H, d, J = 5.0 Hz), 2.90 (1H, d, J = 12.9 Hz), 3.12-3.24 (1H, m), 3.55-3.80 (1H, m), 3.92 (1H, d, J = 12.9 Hz), 7.09-7.21 (3H, m), 12.33 (1H, brs) | Hydro-chloride |
| 231 | —H | —H | —F | —Cl | —H | —H | 1H-NMR (CDCl3) δ ppm: 1.01-1.12 (1H, m), 1.20-1.39 (2H, m), 1.56-2.04 (4H, m), 1.63 (3H, s), 1.69 (3H, s), 2.31-2.36 (1H, m), 2.76 (1H, d, J = 12.4 Hz), 2.97-3.04 (1H, m), 3.13-3.24 (1H, m), 3.29 (1H, d, J = 12.4 Hz), 6.91-7.01 (2H, m), 7.34 (1H, dd, J = 8.4, 8.3 Hz), 9.50 (1H, brs), 9.80 (1H, brs) | Hydro-chloride |

TABLE 33-continued

Absolute configuration

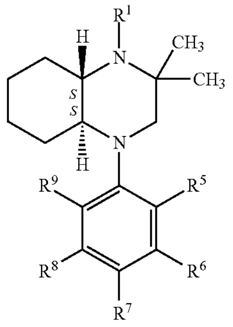

| Example | $R^1$ | $R^5$ | $R^6$ | $R^7$ | $R^8$ | $R^9$ | NMR | Salt |
|---|---|---|---|---|---|---|---|---|
| 232 | —$CH_3$ | —H | —F | —Cl | —H | —H | 1H-NMR (CDCl3) δ ppm: 1.00-1.13 (1H, m), 1.17-1.40 (2H, m), 1.53 (3H, s), 1.60 (3H, s), 1.60-1.81 (3H, m), 1.90-1.94 (1H, m), 2.04-2.25 (1H, m), 2.72 (3H, d, J = 4.9 Hz), 2.78 (1H, d, J = 12.8 Hz), 2.92-3.04 (1H, m), 3.46-3.55 (1H, m), 3.81 (1H, d, J = 12.8 Hz), 7.00-7.08 (2H, m), 7.32-7.39 (1H, m), 12.26 (1H, brs) | Hydro-chloride |
| 233 | —H | —H | —F | —$CCH_3$ | —F | —H | 1H-NMR (DMSO-d6) δ ppm: 1.02-1.34 (3H, m), 1.33 (3H, s), 1.51 (3H, s), 1.54-1.73 (4H, m), 1.96-2.01 (1H, m), 2.76-2.83 (1H, m), 2.89 (1H, d, J = 12.5 Hz), 2.98 (1H, d, J = 12.5 Hz), 3.08-3.18 (1H, m), 3.87 (3H, s), 4.76 (1H, s), 6.85-6.96 (2H, m), 9.01-9.09 (1H, m), 9.70-9.75 (1H, m) | Dihydro-chloride |
| 234 | —H | —H | —F | —$CCH_3$ | —H | —H | 1H-NMR (DMSO-d6) δ ppm: 1.05-1.45 (6H, m), 1.45-1.80 (7H, m), 1.95-2.08 (1H, m), 2.70-2.90 (2H, m), 2.95-3.23 (2H, m), 3.81 (3H, s), 4.65-5.40 (1H, br), 6.88-7.08 (2H, m), 7.08-7.22 (1H, m), 8.90-9.25 (1H, br), 9.55-9.85 (1H, br). | Dihydro-chloride |
| 235 | —H | —H | —Cl | —H | —H | —H | 1H-NMR (CDCl3) δ ppm: 1.05-1.13 (1H, m), 1.23-1.35 (2H, m), 1.50-1.78 (3H, m), 1.63 (3H, s), 1.71 (3H, s), 1.92-2.08 (1H, m), 2.31-2.36 (1H, m), 2.78 (1H, d, J = 12.7 Hz), 3.00-3.09 (1H, m), 3.15-3.26 (1H, m), 3.31 (1H, d, J = 12.7 Hz), 7.07-7.10 (1H, m), 7.15-7.19 (2H, m), 7.23-7.29 (1H, m), 9.50 (1H, brs), 9.79 (1H, brs) | Hydro-chloride |
| 236 | —$CH_3$ | —H | —Cl | —H | —H | —H | 1H-NMR (CDCl3) δ ppm: 1.18-1.50 (2H, m), 1.60-1.81 (2H, m), 1.71 (3H, s), 1.91-2.30 (5H, m), 2.00 (3H, s), 2.80 (3H, d, J = 4.9 Hz), 3.32 (1H, d, J = 13.4 Hz), 3.81-3.94 (1H, m), 4.42 (1H, d, J = 13.4 Hz), 4.61-4.70 (1H, m), 7.42-7.50 (2H, m), 7.97 (1H, brs), 8.13 (1H, brs), 13.7 (1H, brs) | Dihydro-chloride |
| 237 | —H | —H | —Cl | —CN | —H | —H | 1H-NMR (CDCl3) δ ppm: 1.05-1.20 (1H, m), 1.23-1.44 (2H, m), 1.54-2.10 (4H, m), 1.63 (3H, s), 1.68 (3H, s), 2.35-2.40 (1H, m), 2.89 (1H, d, J = 12.7 Hz), 3.19 (2H, br), 3.34 (1H, d, J = 12.7 Hz), 7.06 (1H, dd, J = 8.4, 2.0 Hz), 7.20 (1H, d, J = 2.0 Hz), 7.61 (1H, d, J = 8.4 Hz), 9.62 (1H, brs), 9.90 (1H, br) | Hydro-chloride |
| 238 | —$CH_3$ | —H | —Cl | —CN | —H | —H | 1H-NMR (CDCl3) δ ppm: 1.01-1.15 (1H, m), 1.23-1.46 (2H, m), 1.50 (3H, s), 1.61 (3H, s), 1.61-1.98 (3H, m), 2.09-2.27 (2H, m), 2.72 (2H, d, J = 4.9 Hz), 2.87 (1H, d, J = 13.0 Hz), 2.91-3.03 (1H, m), 3.63-3.72 (1H, m), 3.84 (1H, d, J = 13.0 Hz), 7.14 (1H, dd, J = 8.4, 2.1 Hz), 7.26 (1H, d, J = 2.1 Hz), 7.62 (1H, d, J = 8.4 Hz), 12.38 (1H, brs) | Hydro-chloride |
| 239 | —H | —H | —Cl | —$CH_2$ | —H | —H | 1H-NMR (CDCl3) δ ppm: 1.25-2.04 (7H, m), 1.75 (3H, s), 2.13 (3H, s), 2.40 (3H, s), 2.48-2.53 (1H, m), 3.33 (1H, d, J = 13.1 Hz), 3.88-3.92 (1H, m), 3.97 (1H, d, J = 13.1 Hz), 4.10-4.17 (1H, m), 7.36 (1H, d, J = 8.4 Hz), 7.78 (1H, d, J = 8.4 Hz), 8.00 (1H, s), 10.03-10.07 (1H, m), 10.20-10.30 (1H, m) | Hydro-chloride |
| 240 | —$CH_3$ | —H | —Cl | —$CH_3$ | —H | —H | 1H-NMR (CDCl3) δ ppm: 1.14-1.41 (3H, m), 1.47-1.74 (2H, m) 1.58 (3H, s), 1.60 (3H, s), 1.89-1.93 (1H, m), 2.10-2.22 (2H, m), 2.35 (3H, s), 2.72 (3H, d, J = 4.9 Hz), 2.83 (1H, d, J = 12.9 Hz), 3.00-3.15 (1H, m), 3.45-3.67 (1H, m), 3.85 (1H, d, J = 12.9 Hz), 7.11-7.22 (2H, m), 7.32 (1H, s), 12.24 (1H, brs) | Hydro-chloride |
| 241 | —H | —H | —Cl | —$OCH_2$ | —H | —H | 1H-NMR (DMSO-d6) δ ppm: 0.95-1.41 (6H, m), 1.41-1.80 (7H, m), 1.88-2.05 (1H, m), 2.69-2.90 (2H, m), 2.93-3.05 (1H, m), 3.05-3.24 (1H, m), 3.83 (3H, s), 4.15-5.35 (1H, br), 7.02-7.25 (3H, m), 8.87-9.18 (1H, br), 9.40-9.72 (1H, br). | Dihydro-chloride |

TABLE 33-continued

Absolute configuration

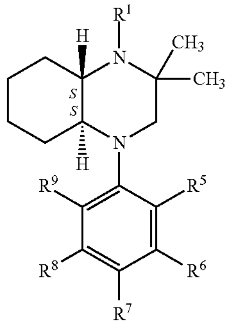

| Example | $R^1$ | $R^5$ | $R^6$ | $R^7$ | $R^8$ | $R^9$ | NMR | Salt |
|---|---|---|---|---|---|---|---|---|
| 242 | —H | —H | —H | —Cl | —H | —H | 1H-NMR (CDCl3) δ ppm: 1.13-1.24 (1H, m), 1.25-1.36 (2H, m), 1.60-1.83 (3H, m), 1.64 (3H, s), 1.74 (3H, s), 1.89-2.02 (1H, m), 2.32-2.37 (1H, m), 2.80 (1H, d, J = 12.5 Hz), 3.12-3.16 (1H, m), 3.22-3.29 (1H, m), 3.36 (1H, d, J = 12.5 Hz), 7.19-7.22 (2H, m), 7.29-7.33 (2H, m), 9.52 (1H, brs), 9.81 (1H, brs) | Hydro-chloride |
| 243 | —$CH_3$ | —H | —H | —Cl | —H | —H | 1H-NMR (CDCl3) δ ppm: 1.02-1.40 (3H, m), 1.48-1.75 (2H, m), 1.61 (3H, s), 1.63 (3H, s), 1.80-2.02 (1H, m), 2.11-2.16 (2H, m), 2.74 (3H, d, J = 5.0 Hz), 2.88 (1H, d, J = 12.9 Hz), 3.10-3.22 (1H, m), 3.56-3.78 (1H, m), 3.93 (1H, d, J = 12.9 Hz), 7.30-7.38 (4H, m), 12.28 (1H, brs) | Hydro-chloride |
| 244 | —H | —H | —$CH_3$ | —Cl | —H | —H | 1H-NMR (DMSO-d6) δ ppm: 0.90-1.79 (13H, m), 1.79-1.95 (1H, m), 2.29 (3H, s), 2.58-3.08 (4H, m), 3.10-4.90 (3H, br), 6.48 (2H, s), 6.89-7.00 (1H, m), 7.07 (1H, d, J = 2.3 Hz), 7.33 (1H, d, J = 8.5 Hz). | Fumarate |
| 245 | —H | —H | —$OCH_3$ | —Cl | —H | —H | 1H-NMR (DMSO-d6) δ ppm: 1.00-1.45 (6H, m), 1.45-1.82 (7H, m), 1.95-2.10 (1H, m), 2.78-3.10 (3H, m), 3.10-3.27 (1H, m), 3.85 (3H, s), 4.00-4.55 (1H, br), 6.73 (1H, dd, J = 2.1, 8.4 Hz), 6.80 (1H, d, J = 2.1 Hz), 7.37 (1H, d, J = 8.4 Hz), 8.90-9.19 (1H, br), 9.51-9.85 (1H, br). | Dihydro-chloride |
| 246 | —H | —H | —Cl | —Cl | —H | —H | 1H-NMR (CDCl3) δ ppm: 1.15-1.45 (3H, m), 1.58-1.81 (3H, m), 1.65 (3H, s), 1.75 (3H, s), 1.88-2.04 (1H, m), 2.32-2.38 (1H, m), 2.82 (1H, d, J = 12.6 Hz), 3.12-3.31 (2H, m), 3.38 (1H, d, J = 12.6 Hz), 7.15 (1H, dd, J = 8.5, 2.3 Hz), 7.40 (1H, d, J = 2.3 Hz), 7.42 (1H, d, J = 8.5 Hz), 9.57 (1H, br), 9.82 (1H, br) | Hydro-chloride |
| 247 | —$CH_3$ | —H | —Cl | —Cl | —H | —H | 1H-NMR (CDCl3) δ ppm: 1.23-1.49 (2H, m), 1.50-1.75 (2H, m), 1.69 (3H, s), 1.91 (3H, s), 1.91-2.15 (3H, m), 2.22-2.28 (1H, m), 2.79 (3H, d, J = 4.9 Hz), 3.23 (1H, d, J = 13.2 Hz), 3.54-3.76 (1H, m), 4.33 (1H, d, J = 13.2 Hz), 4.43-4.52 (1H, m), 7.56 (1H, d, J = 8.7 Hz), 7.82 (1H, dd, J = 8.7, 2.3 Hz), 8.14 (1H, d, J = 2.3 Hz), 12.88 (1H, brs) | Hydro-chloride |
| 248 | —H | —H | —H | —$OCH_3$ | —H | —H | 1H-NMR (DMSO-d6) δ ppm: 1.02-1.50 (7H, m), 1.50-1.82 (6H, m), 1.96-2.18 (1H, m), 2.60-3.60 (4H, m), 3.76 (3H, s), 6.85-7.10 (2H, m), 7.10-7.68 (2H, m), 8.60-10.90 (3H, m). | Dihydro-chloride |
| 249 | —H | —H | —$OCH_3$ | —F | —H | —H | 1H-NMR (DMSO-d6) δ ppm: at 80° C.: 1.00-1.43 (6H, m), 1.49-1.77 (7H, m), 1.97-2.08 (1H, m), 2.81 (1H, d, J = 12.3 Hz), 2.84-2.93 (1H, m), 3.04-3.18 (2H, m), 3.83 (3H, s), 4.30-4.57 (1H, br), 6.68-6.74 (1H, m), 6.86 (1H, dd, J = 2.5, 7.9 Hz), 7.11 (1H, dd, J = 8.6, 11.4 Hz), 8.94-9.25 (1H, br), 9.49-9.80 (1H, br). | Dihydro-chloride |

TABLE 34

Absolute configuration

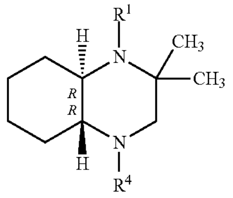

| Example | $R^1$ | $R^4$ | NMR | Salt |
|---|---|---|---|---|
| 250 | —H | 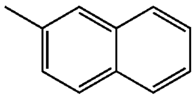 | 1H-NMR (CDCl3) δ ppm: 1.10-1.47 (3H, m), 1.48-2.16 (4H, m), 1.69 (3H, s), 1.78 (3H, s), 2.30-2.54 (1H, m), 2.95 (1H, d, J = 12.5 Hz), 3.20-3.50 (2H, br), 3.52 (1H, d, J = 12.5 Hz), 7.37-7.52 (2H, m), 7.60-8.00 (4H, m), 9.18-10.05 (2H, br) | Hydrochloride |
| 251 | —$CH_3$ | 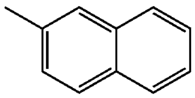 | 1H-NMR (CDCl3) δ ppm: 1.20-1.35 (1H, m), 1.41-1.55 (1H, m), 1.59-1.82 (2H, m), 1.75 (3H, s), 1.91-2.01 (1H, m), 2.02-2.15 (2H, m), 2.14 (3H, s), 2.30-2.44 (2H, m), 2.85 (3H, d, J = 4.8 Hz), 3.49 (1H, d, J = 13.5 Hz), 4.07-4.19 (1H, m), 4.66 (1H, d, J = 13.5 Hz), 4.92-5.01 (1H, m), 7.59-7.66 (2H, m), 7.89-8.04 (4H, m), 8.87 (1H, br), 13.11 (1H, brs) | Dihydrochloride |
| 252 | —H | 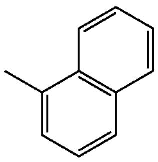 | 1H-NMR (DMSO-d6) δ ppm: 0.94-1.25 (2H, m), 1.25-1.45 (5H, m), 1.45-1.55 (1H, m), 1.55-1.80 (5H, m), 1.95-2.10 (1H, m), 2.82 (1H, d, J = 12.4 Hz), 2.97-3.11 (2H, m), 3.36-3.51 (1H, m), 7.40 (1H, d, J = 7.3 Hz), 7.50-7.59 (3H, m), 7.79 (1H, d, J = 8.2 Hz), 7.89-7.96 (1H, m), 8.42-8.48 (1H, m), 8.97-9.24 (1H, br), 9.50-9.80 (1H, br). | Hydrochloride |
| 253 | —H | 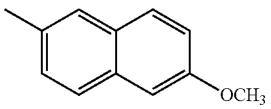 | 1H-NMR (CDCl3) δ ppm: 1.23-2.17 (8H, m), 1.76 (3H, s), 2.09 (3H, s), 2.48-2.53 (1H, m), 3.27 (1H, d, J = 1.23 Hz), 3.66-4.18 (3H, m), 3.94 (3H, s), 7.15 (1H, d, J = 2.4 Hz), 7.23 (1H, dd, J = 9.0, 2.4 Hz), 7.74 (1H, brs), 7.79-7.85 (2H, m), 8.24 (1H, brs), 9.87-10.19 (2H, br) | Dihydrochloride |
| 254 | —H | 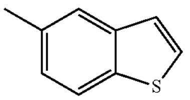 | 1H-NMR (CDCl3) δ ppm: 1.20-2.05 (8H, m), 1.73 (3H, s), 2.00 (3H, s), 2.44-2.48 (1H, m), 3.15 (1H, d, J = 10.7 Hz), 3.55-3.88 (3H, br), 7.38 (1H, d, J = 5.5 Hz), 7.49-7.69 (1H, m), 7.55 (1H, d, J = 5.5 Hz), 7.92 (1H, d, J = 8.6 Hz), 8.14 (1H, brs), 9.94 (2H, brs) | Dihydrochloride |

TABLE 35

Absolute configuration

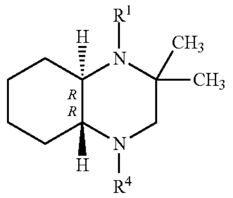

| Example | $R^1$ | $R^4$ | NMR | Salt |
|---|---|---|---|---|
| 255 | —H | 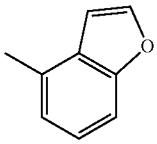 | 1H-NMR (DMSO-d6) δ ppm: 0.95-1.82 (13H, m), 1.97-2.12 (1H, m), 2.80-3.35 (4H, m), 6.07-6.72 (1H, br), 6.72-7.20 (2H, m), 7.23-7.35 (1H, m), 7.35-7.53 (1H, m), 7.99 (1H, brs), 9.00-9.50 (lH, br), 9.55-10.10 (1H, br). | Dihydrochloride |
| 256 | —H | 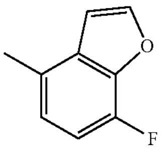 | 1H-NMR (DMSO-d6) δ ppm at 80° C.: 0.96-1.25 (2H, m), 1.26-1.51 (5H, m), 1.51-1.61 (1H, m, 1.61-1.78 (5H, m), 1.99-2.08 (1H, m), 2.80 (1H, d, J = 12.3 Hz), 3.05-3.32 (3H, m), 3.58-4.12 (1H, br), 7.01 (1H, dd, J = 3.8, 8.5 Hz), 7.08-7.18 (2H, m), 8.01 (1H, d, J = 2.1 Hz), 9.10-9.35 (1H, br), 9.38-9.75 (1H, br). | Dihydrochloride |

TABLE 35-continued

Absolute configuration

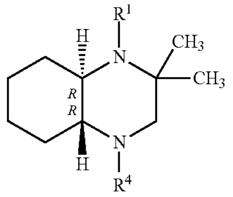

| Example | R[1] | R[4] | NMR | Salt |
| --- | --- | --- | --- | --- |
| 257 | —H | 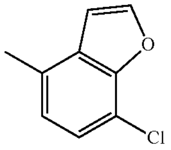 | 1H-NMR (DMSO-d6) δ ppm at 80° C.: 0.98-1.27 (2H, m), 1.27-1.46 (4H, m), 1.46-1.60 (2H, m), 1.60-1.80 (5H, m), 1.98-2.10 (1H, m), 2.84 (1H, d, J = 12.4 Hz), 3.05-3.35 (3H, m), 3.45-3.90 (1H, br), 7.05 (1H, d, J = 8.2 Hz), 7.08-7.13 (1H, br), 7.36 (1H, d, J = 8.2 Hz), 8.03 (1H, d, J = 2.2 Hz), 8.98-9.35 (1H, br), 9.35-9.72 (1H, br). | Dihydrochloride |
| 258 | —H | 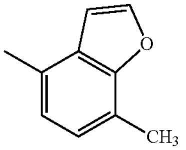 | 1H-NMR (CDCl3) δ ppm: 0.82-1.05 (2H, m), 1.07 (3H, s), 1.19-1.43 (3H, m), 1.49 (3H, s), 1.56-1.68 (1H, m), 1.58-1.90 (3H, m), 2.35-2.51 (4H, m), 2.51-2.70 (1H, m), 2.78-2.92 (2H, m), 6.83-6.89 (2H, m), 7.01 (1H, d, J = 7.8 Hz), 7.56 (1H, d, J = 2.1 Hz). | — |
| 259 | —H | 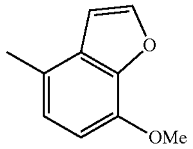 | 1H-NMR (DMSO-d6) δ ppm at 80° C.: 0.96-1.25 (2H, m), 1.25-1.60 (6H, m), 1.60-1.79 (5H, m), 1.96-2.10 (1H, m), 2.76 (1H, d, J = 12.3 Hz), 2.99-3.37 (3H, m), 3.93 (3H, s), 4.52-4.86 (1H, br), 6.86 (1H, d, J = 8.4 Hz), 6.95 (1H, d, =8.4 Hz), 6.98-7.09 (1H, br), 7.87 (1H, d, J = 2.1 Hz), 9.02-9.40 (1H, br), 9.40-9.75 (1H, br). | Dihydrochloride |
| 260 | —H | 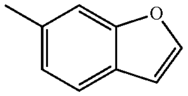 | 1H-NMR (DMSO-d6) δ ppm at 80° C.: 1.03-1.44 (6H, m), 1.51-1.79 (7H, m), 2.00-2.10 (1H, m), 2.87 (1H, d, J = 12.4 Hz), 2.94-3.05 (1H, m), 3.10-3.23 (2H, m), 4.64-5.12 (1H, br), 6.88 (1H, d, J = 1.4 Hz), 7.05-7.09 (1H, m), 7.33-7.36 (1H, br), 7.59 (1H, d, J = 8.2 Hz), 7.89 (1H, J = 2.2 Hz), 8.97-9.26 (1H, br), 9.45-9.82 (1H, br). | Dihydrochloride |

TABLE 36

Absolute configuration

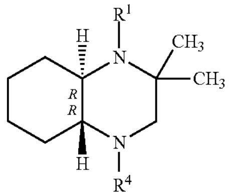

| Example | R[1] | R[4] | NMR | Melting point (° C.) | Salt |
| --- | --- | --- | --- | --- | --- |
| 261 | —H | 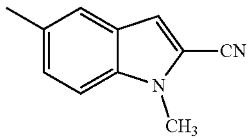 | | 209.8-214.2 | Fumarate |

TABLE 36-continued

Absolute configuration

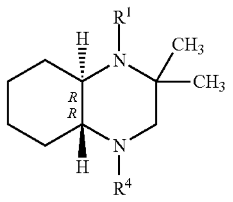

| Example | $R^1$ | $R^4$ | NMR | Melting point (° C.) | Salt |
|---|---|---|---|---|---|
| 262 | —H | 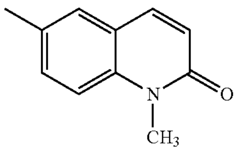 | 1H-NMR (DMSO-d6) δ ppm: 1.00-1.44 (5H, m), 1.50-1.79 (7H, m), 1.96-2.08 (1H, m), 2.82-3.00 (2H, m), 3.00-3.25 (2H, m), 3.61 (3H, s), 6.62 (1H, d, J = 9.5 Hz), 7.38-7.46 (1H, m), 7.48-7.58 (2H, m), 7.91 (1H, d, J = 9.5 Hz), 7.98-8.62 (1H, br), 9.14-9.37 (1H, br), 9.65-9.88 (1H, br). | | Dihydro-choloride |
| 263 | —H | 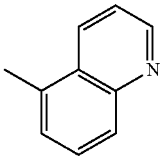 | 1H-NMR (CDCl3) δ ppm: 0.87-1.03 (1H, m), 1.09 (3H, m), 1.15-1.46 (4H, m), 1.46-1.65 (5H, m), 1.65-1.88 (2H, m), 2.47-2.60 (1H, m), 2.65 (1H, d, J = 11.3 Hz), 2.76 (1H, d, J = 11.3 Hz), 2.90-3.04 (1H, m), 7.25 (1H, d, J = 7.3 Hz), 7.40 (1H, dd, J = 4.2, 8.5 Hz), 7.65-7.72 (1H, m), 7.91 (1H, d, J = 8.5 Hz), 8.85 (1H, d, J = 8.5 Hz), 8.90 (1H, dd, J = 1.7, 4.2 Hz). | | — |
| 264 | —H | 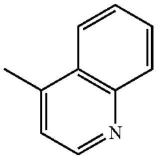 | 1H-NMR (CDCl3) δ ppm: 0.93-1.12 (5H, m), 1.22-1.48 (3H, m), 1.55-1.70 (4H, m), 1.73-1.90 (3H, m), 2.50 (1H, d, J = 11.5 Hz), 2.55-2.65 (1H, m), 2.92-3.05 (2H, m), 7.09 (1H, d, J = 4.8 Hz), 7.49-7.56 (1H, m), 7.65-7.72 (1H, m), 8.05-8.10 (1H, m), 8.36 (1H, dd, J = 1.0, 8.4 Hz), 8.84 (1H, d, J = 4.8 Hz). | | — |
| 265 | —H | 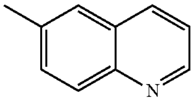 | 1H-NMR (CDCl3) δ ppm: 0.80-1.17 (5H, m), 1.21-1.50 (6H, m), 1.61-1.86 (4H, m), 2.42-2.50 (1H, m), 2.74 (1H, d, J = 11.4 Hz), 2.80-2.90 (1H, m), 2.96 (1H, d, J = 11.4 Hz), 7.31-7.39 (2H, m), 7.50 (1H, dd, J = 2.4, 9.0 Hz), 8.01 (1H, d, J = 9.0 Hz), 8.06 (1H, dd, J = 1.1, 8.3 Hz), 8.81 (1H, dd, J = 1.7, 4.2 Hz). | | — |
| 266 | —H | 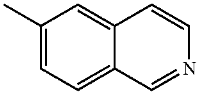 | 1H-NMR (CDCl3) δ ppm: 1.04-1.20 (4H, m), 1.20-1.48 (7H, m), 1.67-1.86 (3H, m), 1.96 (1H, dd, J = 3.0, 13.0), 2.61-2.70 (1H, m), 2.82-2.95 (2H, m), 3.07 (1H, d, J = 12.0 Hz), 7.20 (1H, d, J = 1.8 Hz), 7.32 (1H, dd, J = 2.1, 8.8 Hz), 7.50 (1H, d, J = 5.8 Hz), 7.84 (1H, d, J = 8.8 Hz), 8.41 (1H, d, J = 5.8 Hz), 9.09 (1H, s). | | — |

TABLE 37

Absolute configuration

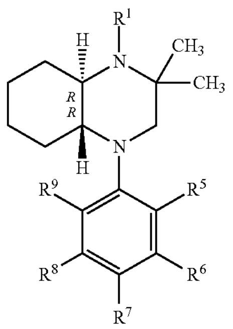

| Example | R1 | R5 | R6 | R7 | R8 | R9 | NMR | Salt |
|---|---|---|---|---|---|---|---|---|
| 267 | —H | —H | —H | —F | —H | —H | 1H-NMR (DMSO-d6) δ ppm: 0.99-1.44 (6H, m), 1.44-1.80 (7H, m), 1.93-2.10 (1H, m), 2.75-2.99 (2H, m), 2.99-3.28 (2H, m), 5.08-6.80 (1H, br), 7.10-7.33 (4H, m), 8.95-9.42 (1H, br), 9.58-9.94 (1H, br). | Dihydro-chloride |
| 268 | —H | —H | —$OCH_3$ | —F | —H | —H | 1H-NMR (DMSO-d6) δ ppm at 80° C.: 1.00-1.43 (6H, m), 1.49-1.77 (7H, m), 1.97-2.08 (1H, m), 2.81 (1H, d, J = 12.3 Hz), 2.84-2.93 (1H, m), 3.04-3.18 (2H, m), 3.83 (3H, s), 4.30-4.57 (1H, br), 6.68-6.74 (1H, m), 6.86 (1H, dd, J = 2.5, 7.9 Hz), 7.11 (1H, dd, J = 8.6, 11.4 Hz), 8.94-9.25 (1H, br), 9.49-9.80 (1H, br). | Dihydro-chloride |
| 269 | —H | —H | —Cl | —CN | —H | —H | 1H-NMR (CDCl3) δ ppm: 1.02-1.17 (1H, m), 1.25-1.44 (2H, m), 1.62-2.05 (4H, m), 1.63 (3H, s), 1.68 (3H, s), 2.35-2.41 (1H, m), 2.89 (1H, d, J = 12.8 Hz), 3.20 (2H, br), 3.35 (1H, d, J = 12.8 Hz), 7.07 (1H, dd, J = 8.4, 2.0 Hz), 7.20 (1H, d, J = 2.0 Hz), 7.61 (1H, d, J = 8.4 Hz), 9.61 (1H, brs), 9.89 (1H, br) | Hydro-chloride |
| 270 | —H | —H | —H | —Cl | —H | —H | 1H-NMR (DMSO-d6) δ ppm: 0.95-1.45 (6H, m), 1.45-1.80 (7H, m), 1.88-2.06 (1H, m), 2.70-3.05 (3H, m), 3.08-3.28 (1H, m), 3.50-3.94 (1H, br), 7.13 (2H, d, J = 8.7 Hz), 7.39 (2H, d, J = 8.7 Hz), 8.66-9.20 (1H, br), 9.20-9.80 (1H, br). | Dihydro-chloride |
| 271 | —H | —H | —$OCH_3$ | —Cl | —H | —H | 1H-NMR (DMSO-d6) δ ppm: 1.00-1.45 (6H, m), 1.45-1.83 (7H, m), 1.90-2.08 (1H, m), 2.70-2.87 (1H, m), 2.87-3.08 (2H, m), 3.08-3.28 (1H, m), 3.85 (3H, s), 6.72 (1H, dd, J = 2.2, 8.4 Hz), 6.79 (1H, d, J = 2.2 Hz), 7.36 (1H, d, J = 8.4 Hz), 8.73-9.10 (1H, br), 9.34-9.70 (1H, br). | Hydro-chloride |
| 272 | —H | —H | —Cl | —Cl | —H | —H | 1H-NMR (CDCl3) δ ppm: 0.98-1.14 (1H, m), 1.26-1.39 (2H, m), 1.55-1.78 (3H, m), 1.62 (3H, s), 1.68 (3H, s), 1.92-2.05 (1H, m), 2.30-2.35 (1H, m), 2.73 (1H, d, J = 12.5 Hz), 2.95-3.03 (1H, m), 3.11-3.23 (1H, m), 3.28 (1H, d, J = 12.5 Hz), 7.20 (1H, dd, J = 8.5, 2.4 Hz), 7.25 (1H, d, J = 2.4 Hz), 7.39 (1H, d, J = 8.5 Hz), 9.49 (1H, br), 9.79 (1H, br) | Hydro-chloride |
| 273 | —$CH_2$ | —H | —Cl | —Cl | —H | —H | 1H-NMR (CDCl3) δ ppm: 1.23-1.49 (2H, m), 1.60-1.74 (2H, m), 1.69 (3H, s), 1.87-2.15 (3H, m), 1.91 (3H, s), 2.21-2.28 (1H, m), 2.78 (3H, d, J = 4.9 Hz), 3.22 (1H, d, J = 13.2 Hz), 3.63-3.75 (1H, m), 4.32 (1H, d, J = 13.2 Hz), 4.42-4.51 (1H, m), 7.56 (1H, d, J = 8.7 Hz), 7.81 (1H, dd, J = 8.7, 2.0 Hz), 8.14 (1H, d, J = 2.0 Hz), 12.71 (1H, brs) | Hydro-chloride |

TABLE 38

Absolute configuration

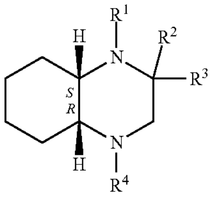

| Example | $R^1$ | $R^2$, $R^3$ | $R^4$ | NMR | Salt |
|---|---|---|---|---|---|
| 274 | 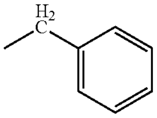 | —H, —H | 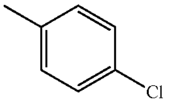 | 1H-NMR (CDCl3) δ ppm: 1.25-1.7 (5H, m), 1.75-1.9(1H, m), 2.05-2.2 (2H, m), 2.3-2.4 (1H, m), 2.6-2.7 (1H, m), 2.8-2.9 (1H, m), 2.92 (1H, d, J = 13.1 Hz), 3.0-3.15 (2H, m), 3.65-3.75 (1H, m), 4.20 (1H, d, J = 13.1 Hz), 6.7-6.8 (2H, m), 7.1-7.2 (2H, m), 7.2-7.3 (1H, m), 7.3-7.4 (4H, m). | — |
| 275 | —H | —H, —H | 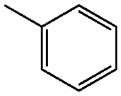 | 1H-NMR (DMSO-d6) δ ppm: 1.2-1.4 (2H, m), 1.4-1.5 (1H, m), 1.5-1.95 (4H, m), 1.95-2.05 (1H, m), 2.95-3.2 (2H, m), 3.25-3.4 (1H, m), 3.4-3.6 (2H, m), 3.95-4.1 (1H, m), 6.48 (1H, br), 6.80 (1H, dd, J = 7.2, 7.2 Hz), 6.9-7.0 (2H, m), 7.2-7.3 (2H, m), 9.22 (1H, br), 9.87 (1H, br). | Dihydrochloride |
| 276 | —H | $-(CH_2)_3-$ | 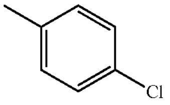 | 1H-NMR (DMSO-d6) δ ppm: 1.25-1.4 (2H, m), 1.4-2.35 (10H, m ), 2.3-2.6 (2H, m), 3.04 (1H, d, J = 13.3 Hz), 3.35-3.5 (1H, m), 3.67 (1H, d, J = 13.4 Hz), 3.7-4.3 (2H, m), 5.95-7.05 (2H, m), 7.2-7.3 (2H, m), 8.95-9.2 (1H, m), 10.1-10.3 (1H, m). | Dihydrochloride |
| 277 | —H | $-(CH_2)_3-$ | 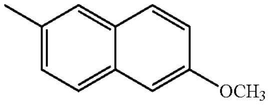 | 1H-NMR (CDCl3) δ ppm: 1.05-1.35 (3H, m), 1.35-1.45 (1H, m), 1.45-1.65 (3H, m), 1.65-1.9 (5H, m), 1.9-2.0 (1H, m), 2.0-2.1 (1H, m), 2.2-2.3 (1H, m), 2.93 (1H, d, J = 11.4 Hz), 3.25-3.35 (1H, m), 3.39 (1H, d, J = 11.4 Hz), 3.7-3.8 (1H, m), 3.89 (3H, s), 7.01 (1H, d, J = 2.4 Hz), 7.04 (1H, d, J = 2.5 Hz), 7.07 (1H, dd, J = 2.6, 6.8 Hz), 7.25-7.3 (1H, m), 7.58 (1H, d, J = 8.9 Hz), 7.61 (1H, d, J = 9.1 Hz). | — |
| 278 | —H | $-(CH_2)_3-$ | 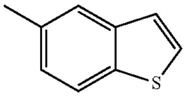 | 1H-NMR (DMSO-d6) δ ppm: 1.2-1.35 (2H, m), 1.4-2.15 (10H, m), 2.35-2.8 (2H, m), 3.14 (1H, d, J = 12.5 Hz), 3.4-3.55 (1H, m), 3.64 (1H, d, J = 13.1 Hz), 3.95-4.05 (1H, m), 4.05-4.4 (1H, m), 7.19 (1H, dd, J = 2.4, 8.9 Hz), 7.31 (1H, d, J = 5.3 Hz), 7.41 (1H, d, J = 2.0 Hz), 7.69 (1H, d, J = 5.4 Hz), 7.83 (1H, d, J = 8.9 Hz), 8.9-9.1 (1H, m), 11-12.5 (1H, m). | Dihydrochloride |

TABLE 39

Absolute configuration

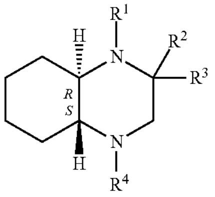

| Example | $R^1$ | $R^2$, $R^3$ | $R^4$ | NMR | Melting point (° C.) | Salt |
|---|---|---|---|---|---|---|
| 279 | 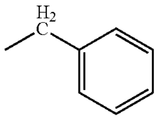 | —H, —H | 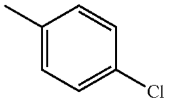 | 1H-NMR (CDCl3) δ ppm: 1.25-1.5 (4H, m), 1.55-1.7 (1H, m), 1.75-1.85 (1H, m), 2.05-2.2 (2H, m), 2.3-2.4 (1H, m), 2.6-2.7 (1H, m), 2.8-2.9 (1H, m), 2.82 (1H, d, J = 13.2 Hz), 3.0-3.15 (2H, m), 3.65-3.8 (1H, m), 4.20 (1H, d, J = 13.1 Hz), 6.7-6.8 (2H, m), 7.1-7.2 (2H, m), 7.2-7.3 (1H, m), 7.3-7.4 (4H, m). | | — |
| 280 | —H | —H, —H | 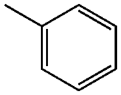 | 1H-NMR (DMSO-d6) δ ppm: 1.2-1.4 (2H, m), 1.4-1.5 (1H, m), 1.5-1.95 (4H, m), 1.95-2.05 (1H, m), 3.0-3.2 (2H, m), 3.25-3.4 (1H, m), 3.4-3.6 (2H, m), 3.95-4.1 (1H, m), 5.65 (1H, br), 6.79 (1H, dd, J = 7.2, 7.2 Hz), 6.9-7.0 (2H, m), 7.2-7.3 (2H, m), 9.16 (1H, br), 9.81 (1H, br). | | Dihydrochloride |
| 281 | —H | $—(CH_2)_3—$ | 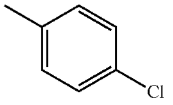 | 1H-NMR (DMSO-d6) δ ppm: 1.25-1.4 (2H, m), 1.4-2.15 (10H, m), 2.3-2.6 (2H, m), 3.03 (1H, d, J = 12.5 Hz), 3.35-3.5 (1H, m), 3.65-3.85 (2H, m), 3.9-4.0 (1H, m), 6.95-7.05 (2H, m), 7.2-7.3 (2H, m), 8.9-9.15 (1H, m), 10.05-12.5 (1H, m). | | Dihydrochloride |
| 282 | —H | $—(CH_2)_3—$ | 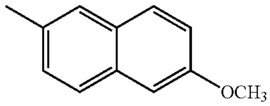 | 1H-NMR (CDCl3) δ ppm: 1.05-1.35 (3H, m), 1.35-1.45 (1H, m), 1.45-1.65 (3H, m), 1.65-1.9 (5H, m), 1.9-2.0 (1H, m), 2.0-2.1 (1H, m), 2.2-2.3 (1H, m), 2.93 (1H, d, J = 11.4 Hz), 3.25-3.35 (1H, m), 3.39 (1H, d, J = 11.4 Hz), 3.7-3.8 (1H, m), 3.89 (3H, s), 7.01 ( 1H, d, J = 2.4 Hz), 7.04 (1H, d, J = 2.5 Hz), 7.07 (1H, dd, J = 2.6, 8.8 Hz), 7.25-7.3 (1H, m), 7.58(1H, d, J = 8.8 Hz), 7.61 (1H, d, J = 9.0 Hz). | | — |
| 283 | —H | $—(CH_2)_3—$ | 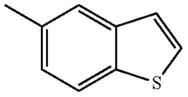 | 1H-NMR (DMSO-d6) δ ppm: 1.2-1.35 (2H, m), 1.4-2.15 (10H, m), 2.4-2.6 (2H, m), 3.15 (1H, d, J = 12.1 Hz), 3.4-3.55 (1H, m), 3.64 (1H, d, J = 13.0 Hz), 3.95-4.1 (1H, m), 4.2-4.6 (1H, m), 7.19 (1H, dd, J = 2.4, 8.9 Hz), 7.31 (1H, d, J = 5.2 Hz), 7.41(1H, d, J = 2.0 Hz), 7.69 (1H, d, J = 5.4 Hz), 7.83 (1H, d, J = 8.9 Hz), 8.9-9.1 (1H, m), 10.1-10.3 (1H, m). | | Dihydrochloride |

TABLE 40

Relative configuration

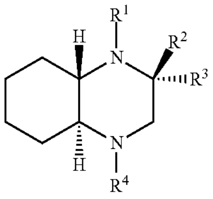

| Example | $R^1$ | $R^2$ | $R^3$ | $R^4$ | NMR | Salt |
|---|---|---|---|---|---|---|
| 284 | —H | —H | $-CH_3$ | 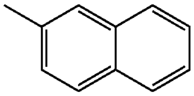 | 1H-NMR (CDCl3) δ ppm: 1.18-1.48 (2H, m), 1.62-2.08 (8H, m), 2.56-2.61 (1H, m), 3.63-3.66 (1H, m), 4.23 (1H, brs), 4.67 (3H, brs), 7.61-8.26 (7H, m), 9.60-9.81 (1H, m), 11.36 (1H, br), 14.02 (1H, brs) | Dihydro-chloride |
| 285 | —H | —H | $-CH_3$ | 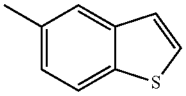 | 1H-NMR (DMSO) δ ppm: 1.02-1.43 (3H, m), 1.30 (3H, d, J = 6.4 Hz), 1.44-1.88 (4H, m), 1.95-2.20 (1H, m), 2.97-3.53 (6H, m), 7.26-7.46 (1H, br), 7.50 (1H, d, J = 5.4 Hz), 7.69-8.00 (1H, br), 7.86 (1H, d, J = 5.4 Hz), 8.09 (1H, d, J = 8.2 Hz), 9.28-10.12 (2H, br) | Dihydro-chloride |
| 286 | —H | —H | $-CH_3$ | 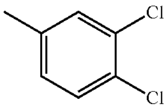 | 1H-NMR (DMSO) δ ppm: 0.87-1.06 (1H, m), 1.17-1.35 (2H, m), 1.24 (3H, d, J = 6.3 Hz), 1.41-1.84 (4H, m), 1.92-2.07 (1H, m), 2.88-3.08 (3H, m), 3.24 (1H, d, J = 12.4 Hz), 3.31-3.52 (1H, br), 7.16 (1H, dd, J = 8.6, 2.1 Hz), 7.40 (1H, d, J = 2.1 Hz), 7.60 (1H, d, J = 8.6 Hz), 9.02-9.33 (1H, br), 9.50-9.85 (1H, br) | Hydro-chloride |
| 287 | —H | —H | $-C_2H_5$ | 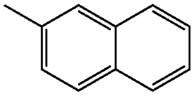 | 1H-NMR (CDCl3) δ ppm: 1.05 (3H, t, J = 7.3 Hz), 1.24-1.48 (2H, m), 1.51-2.14 (6H, br), 2.16-2.41 (1H, br), 2.43-2.75 (1H, m), 2.83-5.31 (5H, br), 7.33-6.24 (5H, br), 9.15-10.20 (1.3H, br), 11.04-11.76 (0.3H, br), 13.30-13.79 (0.4H, br) | Hydro-chloride |
| 288 | $-CH_2$ | —H | $-C_2H_5$ | 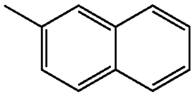 | 1H-NMR (CDCl3) δ ppm: 1.06 (3H, t, J = 7.5 Hz), 1.22-2.25 (10H, m), 2.26-2.45 (2H, m), 2.94 (3H, s), 3.31-4.97 (4H, br), 7.36-8.02 (7H, m), 12.47-13.27 (1H, br) | Dihydro-chloride |
| 289 | —H | $-C_2H_5$ | $-C_2H_5$ | 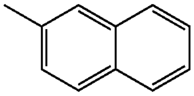 | 1H-NMR (CDCl3) δ ppm: 0.80-2.47 (11H, m), 0.99 (3H, t, J = 7.4 Hz), 1.17 (3H, t, J = 7.3 Hz), 2.66-2.76 (1H, m), 2.86-3.18 (1H, br), 3.38-3.43 (1H, m), 3.65-4.01 (2H, m), 4.02-4.36 (1H, m), 7.54-7.61 (2H, m), 7.80-7.96 (5H, m), 9.37 (1H, brs), 9.80-10.49 (1H, br) | Dihydro-chloride |
| 290 | —H | —H | $-C_2H_5$ | 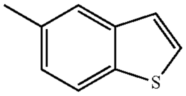 | 1H-NMR (CDCl3) δ ppm: 1.07 (3H, t, J = 7.5 Hz), 1.25-1.42 (2H, m), 1.48-1.85 (7H, m), 1.93-2.10 (2H, m), 2.16-2.40 (1H, m), 2.50-2.69 (1H, m), 2.91-5.05 (4H, br), 7.33-8.76 (4H, br & m), 9.19-9.85 (1H, br), 11.09-11.67 (0.4H, br), 13.40-13.82 (0.6H, br) | Dihydro-chloride |
| 291 | —H | $-C_2H_5$ | $-C_2H_5$ | 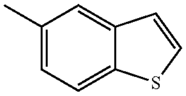 | 1H-NMR δ ppm: 0.80-2.44 (11H, m), 0.97 (3H, t, J = 7.4 Hz), 1.15 (3H, t, J = 7.4 Hz), 2.60-2.66 (1H, m), 2.78-3.09 (1H, m), 3.20-3.37 (1H, m), 3.45-4.16 (3H, m), 7.37 (1H, d, J = 5.4 Hz), 7.49-7.71 (1H, m), 7.55 (1H, d, J = 5.4 Hz), 7.86-7.96 (1H, m), 8.01-8.47 (1H, br), 9.02-9.48 (1H, br), 9.69-10.18 (1H, br) | Dihydro-chloride |
| 292 | —H | —H | $-C_2H_5$ | 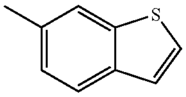 | 1H-NMR (CDCl3) δ ppm: 1.07 (3H, t, J = 7.5 Hz), 1.23-1.50 (3H, m), 1.51-2.13 (8H, m), 2.16-2.39 (1H, m), 2.50-2.71 (1H, m), 2.90-5.09 (4H, br), 7.30-7.46 (1H, m), 7.46-8.33 (3H, br), 9.10-9.91 (1H, br), 10.95-11.65 (0.4H, br), 13.37-13.92 (0.6H, br) | Dihydro-chloride |
| 293 | —H | $-C_2H_5$ | $-C_2H_5$ | 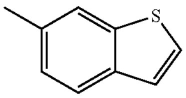 | 1H-NMR (CDCl3) δ ppm: 0.80-2.45 (10H, m), 0.97 (3H, t, J = 7.3 Hz), 1.45 (3H, t, J = 7.3 Hz), 2.60-2.66 (1H, m), 2.74-3.05 (1H, m), 3.11-3.42 (1H, m), 3.51-3.97 (3H, m), 7.37 (1H, d, J = 5.4 Hz), 7.50-7.68 (2H, m), 7.53 (1H, d, J = 5.5 Hz), 7.83-7.88 (1H, m), 8.02-8.53 (1H, br), 9.12-9.46 (1H, br), 9.66-10.18 (1H, br) | Dihydro-chloride |
| 294 | —H | $-C_2H_5$ | $-C_2H_5$ | 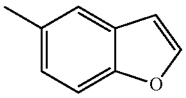 | 1H-NMR (CDCl3) δ ppm: 0.87-2.38 (11H, m), 0.98 (3H, t, J = 7.4 Hz), 1.14 (3H, t, J = 7.2 Hz), 2.49-2.73 (1H, m), 2.73-3.11 (1H, m), 3.31-3.42 (1H, m), 3.52-4.26 (3H, m), 6.82 (1H, d, J = 1.9 Hz), 7.54-7.68 (2H, m), 7.71 (1H, d, J = 1.9 Hz), 7.79-8.30 (1H, br), 8.94-9.51 (1H, br), 9.75-10.34 (1H, br) | Dihydro-chloride |

TABLE 40-continued

Relative configuration

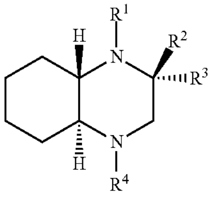

| Example | $R^1$ | $R^2$ | $R^3$ | $R^4$ | NMR | Salt |
|---|---|---|---|---|---|---|
| 295 | —H | —H | $—C_2H_5$ | 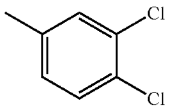 | 1H-NMR (CDCl3) δ ppm: 1.08 (3H, t, J = 7.5 Hz), 1.25-1.43 (2H, m), 1.54-2.05 (6H, m), 2.15-2.34 (1H, m), 2.50-2.64 (1H, m), 3.56 (1H, d, J = 11.1 Hz), 3.84-4.04 (1H, m), 4.10-4.46 (3H, m), 7.62 (1H, d, J = 8.6 Hz), 7.72 (1H, d, J = 8.6 Hz), 7.97 (1H, s), 9.25-9.53 (1H, br), 10.75-11.16 (1H, br) | Hydrochloride |
| 296 | —H | —H | $—C_3H_7$ | 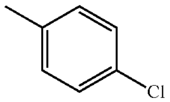 | 1H-NMR (DMSO-d6) δ ppm: 0.93 (3H, t, J = 7.3 Hz), 1.2-1.4 (2H, m), 1.4-1.6 (3H, m), 1.6-1.9 (6H, m), 2.05-2.15 (1H, m), 2.8-2.9 (1H, m), 3.25 (1H, br), 3.5-3.6 (2H, m), 4.0-4.1 (1H, m), 6.95-7.05 (2H, m), 7.2-7.3 (2H m), 8.35-8.6 (1H, m), 9.3-9.5 (1H, m). | Hydrochloride |

TABLE 41

Relative configuration

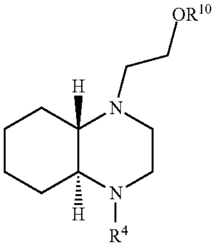

| Example | $R^{10}$ | $R^4$ | NMR | Salt |
|---|---|---|---|---|
| 297 | 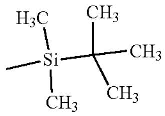 | 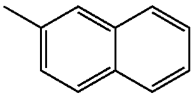 | 1H-NMR (CDCl3) δ ppm: 0.08 (6H, s), 0.91 (9H, s), 1.04-1.35 (4H, m), 1.53-1.80 (3H, m), 2.18-2.33 (2H, m), 2.60-2.76 (2H, m), 2.80-3.01 (3H, m), 3.09-3.13 (2H, m), 3.69-3.85 (2H, m), 7.29-7.48 (3H, m), 7.52-7.53 (1H, m), 7.73-7.80 (3H, m) | — |
| 298 | 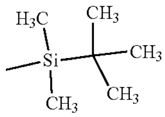 | 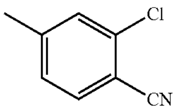 | 1H-NMR (CDCl3) δ ppm: 0.06 (6H, s), 0.90 (9H, s), 1.04-1.37 (5H, m), 1.61-1.75 (2H, m), 1.79-1.84 (2H, m), 2.15-2.20 (1H, m), 2.32-2.40 (1H, m), 2.58-2.68 (1H, m), 2.71-2.90 (3H, m), 2.97-3.14 (2H, m), 3.19-3.26 (1H, m), 3.64-3.79 (2H, m), 6.93 (1H, dd, J = 8.5, 2.1 Hz), 7.07 (1H, d, J = 2.1 Hz), 7.52 (1H, d, J = 8.5 Hz) | — |
| 299 | 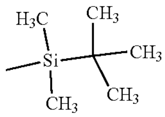 | 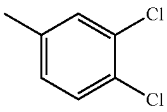 | 1H-NMR (CDCl3) δ ppm: 0.07 (6H, s), 0.81-1.90 (3H, m), 0.90 (9H, s), 1.55-1.78 (4H, m), 2.14-2.24 (2H, m), 2.46-2.54 (1H, m), 2.57-2.67 (1H, m), 2.72-2.82 (1H, m), 2.85-2.97 (4H, m), 3.66-3.81 (2H, m), 6.97 (1H, dd, J = 8.6, 2.4 Hz), 7.22 (1H, d, J = 2.4 Hz), 7.34 (1H, d, J = 8.6 Hz) | — |
| 300 | —H | 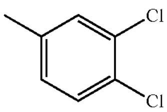 | 1H-NMR (CDCl3) δ ppm: 1.25-1.53 (2H, m), 1.61-1.70 (1H, m), 1.74-1.80 (2H, m), 1.89-2.04 (2H, m), 2.38-2.43 (1H, m), 3.08-3.16 (1H, m), 3.53-3.59 (1H, m), 3.66-3.73 (1H, m), 3.88-3.94 (1H, m), 4.06-4.14 (3H, m), 4.35-4.43 (2H, m), 4.61-4.78 (1H, m), 7.61 (1H, d, J = 6.7 Hz), 7.71 (1H, d, J = 8.7 Hz), 8.00 (1H, brs), 12.52 (1H, brs) | Hydrochloride |

TABLE 42

Relative configuration

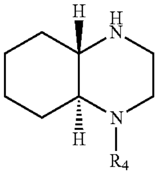

| Example | $R^4$ | NMR | Salt |
|---|---|---|---|
| 301 | 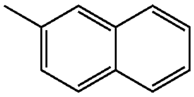 | 1H-NMR (CDCl3) δ ppm: 1.25-1.50 (2H, m), 1.60-2.05 (5H, m), 2.35-2.70 (1H, m), 2.81-5.38 (6H, br), 7.32-8.89 (7H, br), 9.47-10.31 (1H, br), 10.55-11.77 (0.45H, br), 13.51-14.36 (0.55H, br) | Hydro-chloride |
| 302 | 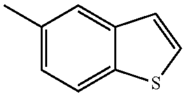 | 1H-NMR (CDCl3) δ ppm: 1.25-1.51 (2H, m), 1.63-2.09 (5H, m), 2.50-2.56 (1H, m), 3.56-3.91 (2H, m), 3.91-5.16 (4H, br), 7.46 (1H, d, J = 5.5 Hz), 7.55-8.76 (3H, br), 7.66 (1H, d, J = 5.5 Hz), 9.46-10.11 (1H, br), 10.94-11.83 (1H, br), 13.61-14.25 (1H, br) | Dihydro-chloride |
| 303 | 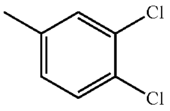 | 1H-NMR (CDCl3) δ ppm: 1.24-1.49 (2H, br), 1.51-2.00 (5H, m), 2.33-2.54 (1H, m), 3.30-3.79 (5H, m), 3.81-4.15 (1H, br), 7.34 (1H, d, J = 8.6 Hz), 7.50 (1H, d, J = 8.6 Hz), 7.59 (1H, s), 10.01 (1H, brs), 10.14-10.56 (1H, br) | Hydro-chloride |

TABLE 43

Relative configuration

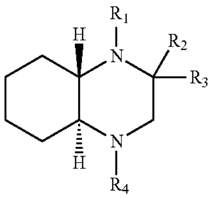

| Ex-ample | $R^1$ | $R^2$, $R^3$ | $R^4$ | NMR | Salt |
|---|---|---|---|---|---|
| 304 | —H | $-(CH_2)_3-$ | 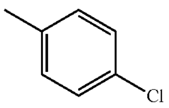 | 1H-NMR (DMSO-d6) δ ppm: 1.2-1.35 (2H, m), 1.4-2.1 (10H, m), 2.3-2.5 (2H, m), 3.03 (1H, d, J = 13.2 Hz), 3.35-3.45 (1H, m), 3.68 (1H, d, J = 13.4 Hz), 3.9-4.0 (1H, m), 4.35 (1H, br), 6.95-7.05 (2H, m), 7.2-7.3 (2H, m), 8.9-9.1 (1H, m), 10.0-10.15(1H, m). | Dihydro-chloride |
| 305 | —H | $-(CH_2)_4-$ | 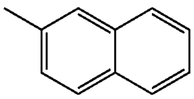 | 1H-NMR (CDCl3) δ ppm: 1.20-1.58 (2H, m), 1.60-2.17 (10H, m), 2.29-2.37 (1H, m), 2.46-2.67 (2H, m), 2.96-3.29 (1H, br), 3.33 (1H, d, J = 13.2 Hz), 3.60-3.98 (1H, br), 3.98-4.41 (2H, br), 7.56-7.60 (2H, m), 7.80-7.98 (4H, m), 8.11-8.71 (1H, br), 9.63-10.08 (1H, br), 10.13-10.87 (1H, br) | Hydro-chloride |
| 306 | —CH3 | $-(CH_2)_4-$ | 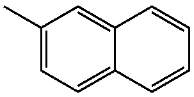 | 1H-NMR (CDCl3) δ ppm: 1.20-1.33 (1H, m), 1.40-2.08 (12H, m), 2.24-2.44 (2H, m), 2.58-2.69 (1H, m), 2.83 (3H, d, J = 4.8 Hz), 3.45 (1H, d, J = 13.4 Hz), 3.58-3.83 (1H, m), 3.87-4.14 (1H, m), 4.08 (1H, d, J = 13.4 Hz), 4.74-4.96 (1H, m), 7.55-7.65 (2H, m), 7.88-8.03 (4H, m), 8.42-9.20 (1H, br), 13.33 (1H, brs) | Dihydro-chloride |
| 307 | H | $-(CH_2)_4-$ | 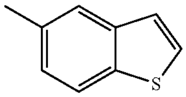 | 1H-NMR (CDCl3) δ ppm: 1.18-1.35 (1H, m), 1.41-2.17 (12H, m), 2.30-2.38 (1H, m), 2.51-2.67 (2H, m), 3.00-3.32 (1H, br), 3.36 (1H, d, J = 12.4 Hz), 3.65-4.47 (3H, br), 7.43 (1H, d, J = 5.5 Hz), 7.61 (1H, d, J = 5.5 Hz), 7.66-7.96 (1H, br), 7.99 (1H, d, J = 8.6 Hz), 8.12-8.19 (1H, br), 9.65-10.02 (1H, br), 10.29-10.83 (1H, br) | Dihydro-chloride |
| 308 | H | $-(CH_2)_4-$ | 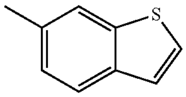 | 1H-NMR (CDCl3) δ ppm: 1.20-1.36 (1H, m), 1.41-2.21 (12H, m), 2.29-2.37 (1H, m), 2.49-2.58 (1H, m), 2.61-2.67 (1H, m), 3.07-3.30 (1H, br), 3.36 (1H, d, J = 13.1 Hz), 3.66-3.97 (1H, br), 3.98-4.32 (2H, br), 7.38 (1H, d, J = 5.5 Hz), 7.59 (1H, d, J = 5.5 Hz), 7.67-7.90 (1H, br), 7.93 (1H, d, J = 8.6 Hz), 8.11-8.93 (1H, br), 9.56-10.03 (1H, br), 10.20-10.81 (1H, br) | Dihydro-chloride |

TABLE 43-continued

Relative configuration

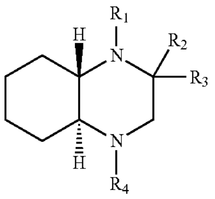

| Example | $R^1$ | $R^2$, $R^3$ | $R^4$ | NMR | Salt |
|---|---|---|---|---|---|
| 309 | H | —$(CH_2)_4$— | 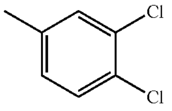 | 1H-NMR (CDCl3) δ ppm: 0.91-1.13 (1H, m), 1.23-1.38 (2H, m), 1.46-2.12 (10H, m), 2.33-2.48 (3H, m), 2.76 (1H, d, J = 12.5 Hz), 2.94-3.12 (2H, m), 3.32 (1H, d, J = 12.5 Hz), 7.03 (1H, dd, J = 8.5, 2.4 Hz), 7.26 (1H, d, J = 2.4 Hz), 7.39 (1H, d, J = 8.5 Hz), 9.75 (2H, brs) | Hydro-chloride |
| 310 | H | —$(CH_2)_4$— | 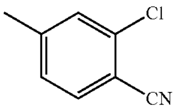 | 1H-NMR (DMSO) δ ppm: 0.96-2.27 (16H, m), 2.97-3.59 (4H, m), 7.10 (1H, d, J = 8.7 Hz), 7.31 (1H, s), 7.78 (1H, d, J = 8.7 Hz), 8.93-9.28 (1H, br), 9.32-9.67 (1H, br) | Hydro-chloride |
| 311 | H | —$(CH_2)_5$— | 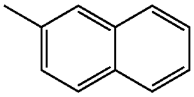 | 1H-NMR (CDCl3) δ ppm: 1.18-2.19 (16H, m), 2.30-2.35 (1H, m), 2.47-2.52 (1H, m), 3.04 (1H, br), 3.44-3.67 (3H, m), 7.47-7.61 (3H, m), 7.83-7.89 (4H, m), 9.64 (2H, br) | Hydro-chloride |
| 312 | H | —$(CH_2)_5$— | 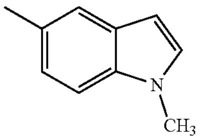 | 1H-NMR (CDCl3) δ ppm: 0.89-1.01 (1H, m), 1.08-1.70 (15H, m), 1.86-1.90 (1H, m), 2.42-2.47 (1H, m), 2.64-2.73 (1H, m), 2.79 (1H, d, J = 12.2 Hz), 3.00-3.08 (1H, m), 3.15 (1H, d, J = 12.2 Hz), 3.76 (3H, s), 3.47-4.70 (3H, br), 6.36 (1H, d, J = 3.0 Hz), 6.49 (2H, s), 6.93 (1H, dd, J = 8.6, 1.4 Hz), 7.27 (1H, d, J = 1.4 Hz), 7.29 (1H, d, J = 3.0 Hz), 7.36 (1H, d, J = 8.6 Hz) | Fumarate |
| 313 | H | —$(CH_2)_5$— | 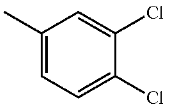 | 1H-NMR (CDCl3) δ ppm: 0.96-1.08 (1H, m), 1.23-1.45 (6H, m), 1.06-2.13 (8H, m), 2.20-2.25 (1H, m), 2.35-2.40 (1H, m), 2.62-2.67 (1H, m), 3.03-3.31 (4H, m), 7.03 (1H, dd, J = 8.5, 2.4 Hz), 7.26 (1H, d, J = 2.4 Hz), 7.40 (1H, d, J = 8.5 Hz), 9.49 (2H, brs) | Hydro-chloride |

TABLE 44

Absolute configuration

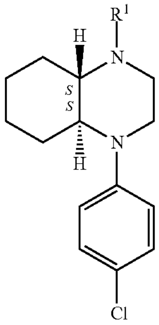

| Example | $R^1$ | NMR | Salt |
|---|---|---|---|
| 314 | 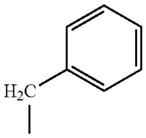 | 1H-NMR (CDCl3) δ ppm: 0.9-1.1 (1H, m), 1.15-1.4 (3H, m), 1.55-1.7 (2H, m), 1.75-1.85 (1H, m), 2.1-2.2 (1H, m), 2.25-2.45 (2H, m), 2.55-2.7 (1H, m), 2.7-2.8 (1H, m), 2.85-2.95 (2H, m), 3.21 (1H, d, J = 13.4 Hz), 4.18 (1H, d, J = 13.4 Hz), 7.05-7.1 (2H, m), 7.2-7.35(7H, m). | — |

TABLE 44-continued
Absolute configuration
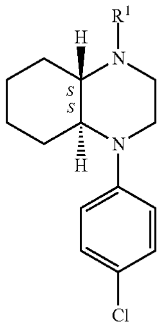
| Example | $R^1$ | NMR | Salt |
|---|---|---|---|
| 315 | —H | 1H-NMR (CDCl3) δ ppm: 0.9-1.4 (4H, m), 1.5-1.65 (2H, m), 1.7-1.9 (2H, m), 2.05-2.2 (1H, m), 2.32 (3H, s), 2.45-2.6 (2H, m), 2.8-2.9 (1H, m), 2.9-3.1 (2H, m), 7.0-7.1 (2H, m), 7.2-7.3 (2H, m). | — |
TABLE 45
Absolute configuration
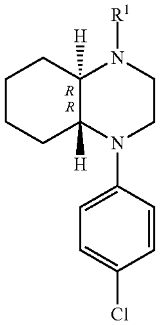
| Example | $R^1$ | NMR | Salt |
|---|---|---|---|
| 316 | 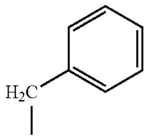 | 1H-NMR (CDCl3) δ ppm: 0.95-1.1 (1H, m), 1.15-1.45 (3H, m), 1.5-1.7 (2H, m), 1.75-1.85 (1H, m), 2.1-2.25 (1H, m), 2.25-2.45 (2H, m), 2.55-2.7 (1H, m), 2.7-2.8 1H, m), 2.85-3.0 (2H, m), 3.21 (1H, d, J = 13.3 Hz), 4.18 (1H, d, J = 13.4 Hz), 7.0-7.1 (2H, m), 7.2-7.35 (7H, m) | — |
| 317 | —H | 1H-NMR (DMSO-d6) δ ppm: 0.85-1.05 (1H, m), 1.1-1.4 (2H, m), 1.4-1.65 (3H, m), 1.65-1.8 (1H, m), 1.9-2.05 (1H, m), 2.8-3.0 (2H, m), 3.0-3.2 (3H, m), 3.2-3.5 (1H, m), 7.1-7.2 (2H, m), 7.35-7.45 (2H, m), 9.2-9.7 (2H, m). | Hydrochloride |
| 318 | $—CH_3$ | 1H-NMR (CDCl3) δ ppm: 0.9-1.4 (4H, m), 1.5-1.65 (2H, m), 1.7-1.9 (2H, m), 2.05-2.2 (1H, m), 2.32 (3H, s), 2.45-2.6 (2H, m), 2.8-2.9 (1H, m), 2.9-3.1 (2H, m), 7.0-7.15 (2H, m), 7.2-7.3 (2H, m). | — |

TABLE 46

Relative configuration

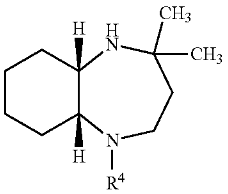

| Example | $R^4$ | NMR | Salt |
|---|---|---|---|
| 319 | 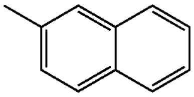 | 1H-NMR (DMSO-d6) δ ppm: 1.35 (3H, s), 1.45-1.67 (6H, m), 1.67-2.00 (4H, m), 2.16-2.30 (2H, m), 2.30-2.43 (1H, m), 3.39-3.48 (1H, m), 3.62-3.72 (1H, m), 3.88-3.96 (1H, m), 3.09-4.08 (1H, m), 6.05-6.75 (1H, br), 7.10 (1H, s), 7.20-7.25 (1H, m), 7.25-7.34 (1H, m), 7.33-7.40 (1H, m), 7.66-7.80 (3H, m), 8.22-8.35 (1H, br), 9.30-9.45 (1H, br). | Dihydrochloride |
| 320 | 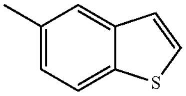 | 1H-NMR (DMSO-d6) δ ppm at 80° C.: 1.37-1.55 (5H, m), 1.55-1.70 (4H, m), 1.71-2.00 (4H, m), 2.19-2.40 (3H, m), 3.35-3.50 (1H, m), 3.52-3.66 (1H, m), 3.84-3.97 (2H, m), 5.53-5.86 (1H, br), 7.06 (1H, dd, J = 2.4, 8.9 Hz), 7.28 (1H, d, J = 5.4 Hz), 7.36 (1H, d, J = 2.4 Hz), 7.60 (1H, d, J = 5.4 Hz), 7.76 (1H, d, J = 8.9 Hz), 8.07-8.40 (1H, br), 9.20-9.57 (1H, br). | Dihydrochloride |
| 321 | 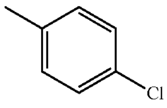 | 1H-NMR (DMSO-d6) δ ppm: 1.32 (3H, s), 1.43-1.61 (6H, m), 1.65-1.89 (4H, m), 2.07-2.17 (1H, m), 2.17-2.27 (1H, m), 2.27-2.40 (1H, m), 3.27-3.36 (1H, m), 3.40-3.55 (1H, m), 3.79-3.90 (2H, m), 5.00-6.60 (1H, br), 6.84 (2H, d, J = 8.9 Hz), 7.19 (2H, d, J = 8.9 Hz), 8.19-8.35 (1H, br), 9.25-9.44 (1H, br). | Dihydrochloride |
| 322 | 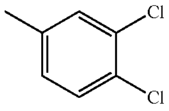 | 1H-NMR (DMSO-d6) δ ppm: 1.32 (3H, s), 1.40-1.63 (6H, m), 1.63-1.90 (4H, m), 2.07-2.25 (2H, m), 2.30-2.33 (1H, m), 3.27-3.38 (1H, m), 3.48-3.59 (1H, m), 3.78-3.86 (1H, m), 3.86-3.95 (1H, m), 5.30-6.75 (1H, br), 6.83 (1H, d, J = 3.0, 9.1 Hz), 7.02 (1H, d, J = 3.0 Hz), 7.35 (1H, d, J = 9.1 Hz), 8.23-8.40 (1H, br), 9.22-9.45 (1H, br). | Dihydrochloride |

TABLE 47

Relative configuration

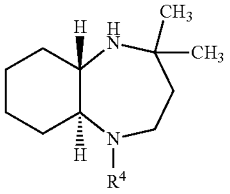

| Example | $R^4$ | NMR | Salt |
|---|---|---|---|
| 323 | 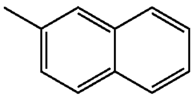 | 1H-NMR (DMSO-d6) δ ppm: 1.39 (3H, s), 1.43-1.65 (7H, m), 1.71-1.90 (4H, m), 1.93-2.06 (1H, m), 2.35-2.45 (1H, m), 3.60-3.79 (4H, m), 5.40-6.15 (1H, br), 6.90 (1H, s), 7.09-7.20 (2H, m), 7.30-7.40 (1H, m), 7.65-7.72 (2H, m), 7.75 (1H, d, J = 9.0 Hz), 8.60-8.80 (1H, br), 8.80-9.00 (1H, br). | Dihydrochloride |
| 324 | 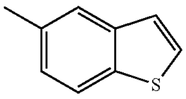 | 1H-NMR (DMSO-d6) δ ppm at 80° C.: 1.38-1.54 (10H, m), 1.69-2.02 (5H, m), 2.41-2.50 (1H, m), 3.55-3.85 (4H, m), 4.97-5.80 (1H, br), 6.94-7.10 (1H, br), 7.18-7.40 (2H, m), 7.59 (1H, d, J= 5.4 Hz), 7.78 (1H, d, J = 8.9 Hz), 8.75-8.92 (1H, br), 8.92-9.30 (1H, br). | Dihydrochloride |
| 325 | 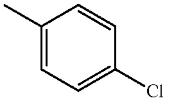 | 1H-NMR (DMSO-d6) δ ppm: 1.33-1.52 (10H, m), 1.64-1.82 (4H, m), 1.82-1.93 (1H, m), 2.30-2.40 (1H, m), 3.40-3.54 (2H, m), 3.54-3.70 (2H, m), 4.45-5.20 (1H, br), 6.66 (2H, d, J = 9.0 Hz), 7.19 (2H, d, J = 9.0 Hz), 8.55-8.70 (1H, br), 8.75-8.92 (1H, br). | Dihydrochloride |
| 326 | 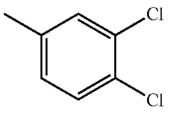 | 1H-NMR (DMSO-d6) δ ppm: 1.33-1.59 (10H, m), 1.61-1.90 (5H, m), 2.33-2.45 (1H, m), 3.45-3.56 (2H, m), 3.56-3.71 (2H, m), 5.05-6.00 (1H, br), 6.65 (1H, dd, J = 2.8, 9.1 Hz), 6.78 (1H, d, J = 2.8 Hz), 7.34 (1H, d, J = 9.1 Hz), 8.70-8.89 (1H, br), 9.00-9.15 (1H, br). | Dihydrochloride |

TABLE 48

Absolute configuration

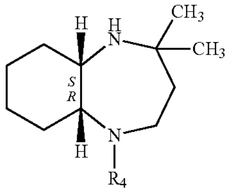

| Example | $R^4$ | NMR | Salt |
| --- | --- | --- | --- |
| 327 | 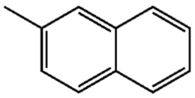 | 1H-NMR (DMSO-d6) δ ppm: 1.35 (3H, s), 1.45-1.67 (6H, m), 1.67-2.00 (4H, m), 2.16-2.30 (2H, m), 2.30-2.43 (1H, m), 3.39-3.48 (1H, m), 3.62-3.72 (1H, m), 3.88-3.96 (1H, m), 3.09-4.08 (1H, m), 6.05-6.75 (1H, br), 7.10 (1H, s), 7.20-7.25 (1H, m), 7.25-7.34 (1H, m), 7.33-7.40 (1H, m), 7.66-7.80 (3H, m), 8.22-8.35 (1H, br), 9.30-9.45 (1H, br). | Dihydro-chloride |
| 328 | 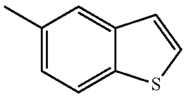 | 1H-NMR (DMSO-d6) δ ppm at 80° C.: 1.37-1.55 (5H, m), 1.55-1.70 (4H, m), 1.71-2.00 (4H, m), 2.19-2.40 (3H, m), 3.35-3.50 (1H, m), 3.52-3.66 (1H, m), 3.84-3.97 (2H, m), 5.53-5.86 (1H, br), 7.06 (1H, dd, J = 2.4, 8.9 Hz), 7.28 (1H, d, J = 5.4 Hz), 7.36 (1H, d, J = 2.4 Hz), 7.60 (1H, d, J = 5.4 Hz), 7.76 (1H, d, J = 8.9 Hz), 8.07-8.40 (1H, br), 9.20-9.57 (1H, br). | Dihydro-chloride |
| 329 | 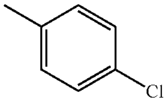 | 1H-NMR (DMSO-d6) δ ppm: 1.33-1.52 (10H, m), 1.64-1.82 (4H, m), 1.82-1.93 (1H, m), 2.30-2.40 (1H, m), 3.40-3.54 (2H, m), 3.54-3.70 (2H, m), 4.45-5.20 (1H, br), 6.66 (2H, d, J = 9.0 Hz), 7.19 (2H, d, J = 9.0 Hz), 8.55-8.70 (1H, br), 8.75-8.92 (1H, br). | Dihydro-chloride |
| 330 | 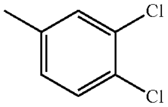 | 1H-NMR (DMSO-d6) δ ppm: 1.32 (3H, s), 1.40-1.63 (6H, m), 1.63-1.90 (4H, m), 2.07-2.25 (2H, m), 2.30-2.33 (1H, m), 3.27-3.38 (1H, m), 3.48-3.59 (1H, m), 3.78-3.86 (1H, m), 3.86-3.95 (1H, m), 5.30-6.75 (1H, br), 6.83 (1H, d, J = 3.0, 9.1 Hz), 7.02 (1H, d, J = 3.0 Hz), 7.35 (1H, d, J = 9.1 Hz), 8.23-8.40 (1H, br), 9.22-9.45 (1H, br). | Dihydro-chloride |

TABLE 49

Absolute configuration

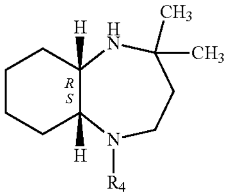

| Example | $R^4$ | NMR | Salt |
| --- | --- | --- | --- |
| 331 | 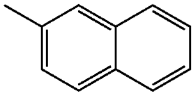 | 1H-NMR (DMSO-d6) δ ppm: 1.35 (3H, s), 1.45-1.67 (6H, m), 1.67-2.00 (4H, m), 2.16-2.30(2H, m), 2.30-2.43 (1H, m), 3.39-3.48 (1H, m), 3.62-3.72 (1H, m), 3.88-3.96 (1H, m), 3.09-4.08 (1H, m), 6.05-6.75 (1H, br), 7.10 (1H, s), 7.20-7.25 (1H, m), 7.25-7.34 (1H, m), 7.33-7.40 (1H, m), 7.66-7.80 (3H, m), 8.22-8.35 (1H, br), 9.30-9.45 (1H, br). | Di-hydro-chloride |
| 332 | 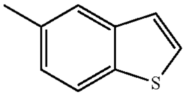 | 1H-NMR (DMSO-d6) δ ppm at 80° C.: 1.37-1.55 (5H, m), 1.55-1.70 (4H, m), 1.71-2.00 (4H, m), 2.19-2.40 (3H, m), 3.35-3.50 (1H, m), 3.52-3.66 (1H, m), 3.84-3.97 (2H, m), 5.53-5.86 (1H, br), 7.06 (1H, dd, J = 2.4, 8.9 Hz), 7.28 (1H, d, J = 5.4 Hz), 7.36 (1H, d, J = 2.4 Hz), 7.60(1H, d, J = 5.4 Hz), 7.76 (1H, d, J = 8.9 Hz), 8.07-8.40 (1H, br),9.20-9.57 (1H, br). | Di-hydro-chloride |
| 333 | 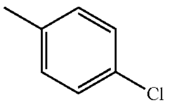 | 1H-NMR (DMSO-d6) δ ppm: 1.33-1.52 (10H, m), 1.64-1.82 (4H, m), 1.82-1.93 (1H, m), 2.30-2.40 (1H, m), 3.40-3.54 (2H, m), 3.54-3.70 (2H, m), 4.45-5.20 (1H, br), 6.66 (2H, d, J = 9.0 Hz), 7.19 (2H, d, J = 9.0 Hz), 8.55-8.70 (1H, br), 8.75-8.92 (1H, br). | Di-hydro-chloride |

TABLE 49-continued

Absolute configuration

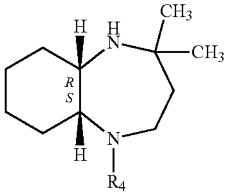

| Example | $R^4$ | NMR | Salt |
|---|---|---|---|
| 334 | 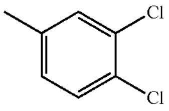 | 1H-NMR (DMSO-d6) δ ppm: 1.32 (3H, s), 1.40-1.63 (6H, m), 1.63-1.90 (4H, m), 2.07-2.25 (2H, m), 2.30-2.33 (1H, m), 3.27-3.38 (1H, m), 3.48-3.59 (1H, m), 3.78-3.86 (1H, m), 3.86-3.95 (1H, m), 5.30-6.75 (1H, br), 6.83 (1H, d, J = 3.0, 9.1 Hz), 7.02 (1H, d, J = 3.0 Hz), 7.35 (1H, d, J = 9.1 Hz), 8.23-8.40 (1H, br), 9.22-9.45 (1H, br). | Dihydrochloride |

TABLE 50

Absolute configuration

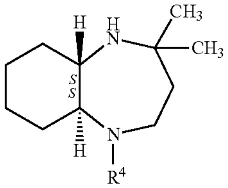

| Example | $R^4$ | NMR | Salt |
|---|---|---|---|
| 335 | 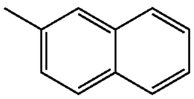 | 1H-NMR (DMSO-d6) δ ppm: 1.39 (3H, s), 1.43-1.65 (7H, m), 1.71-1.90 (4H, m), 1.93-2.06 (1H, m), 2.35-2.45 (1H, m), 3.60-3.79 (4H, m), 5.40-6.15 (1H, br), 6.90 (1H, s), 7.09-7.20 (2H, m), 7.30-7.40 (1H, m), 7.65-7.72 (2H, m), 7.75 (1H, d, J = 9.0 Hz), 8.60-8.80 (1H, br), 8.80-9.00 (1H, br). | Dihydrochloride |
| 336 | 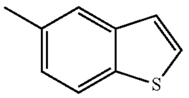 | 1H-NMR (DMSO-d6) δ ppm at 80° C.: 1.38-1.54 (10H, m), 1.69-2.02 (5H, m), 2.41-2.50 (1H, m), 3.55-3.85 (4H, m), 4.97-5.80 (1H, br), 6.94-7.10 (1H, br), 7.18-7.40 (2H, m), 7.59 (1H, d, J = 5.4 Hz), 7.78 (1H, d, J = 8.9 Hz), 8.75-8.92 (1H, br), 8.92-9.30 (1H, br). | Dihydrochloride |
| 337 | 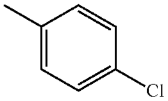 | 1H-NMR (DMSO-d6) δ ppm: 1.33-1.52 (10H, m), 1.64-1.82 (4H, m), 1.82-1.93 (1H, m), 2.30-2.40 (1H, m), 3.40-3.54 (2H, m), 3.54-3.70 (2H, m), 4.45-5.20 (1H, br), 6.66 (2H, d, J = 9.0 Hz), 7.19 (2H, d, J = 9.0 Hz), 8.55-8.70 (1H, br), 8.75-8.92 (1H, br). | Dihydrochloride |
| 338 | 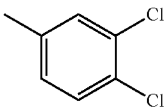 | 1H-NMR (DMSO-d6) δ ppm: 1.33-1.59 (10H, m), 1.61-1.90 (5H, m), 2.33-2.45 (1H, m), 3.45-3.56 (2H, m), 3.56-3.71 (2H, m), 5.05-6.00 (1H, br), 6.65 (1H, dd, J = 2.8, 9.1 Hz), 6.78 (1H, d, J = 2.8 Hz), 7.34 (1H, d, J = 9.1 Hz), 8.70-8.89 (1H, br), 9.00-9.15 (1H, br). | Dihydrochloride |

TABLE 51

Absolute configuration

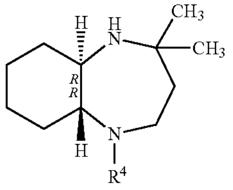

| Example | $R^4$ | NMR | Salt |
|---|---|---|---|
| 339 | 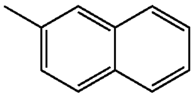 | 1H-NMR (DMSO-d6) δ ppm: 1.39 (3H, s), 1.43-1.65 (7H, m), 1.71-1.90 (4H, m), 1.93-2.06 (1H, m), 2.35-2.45 (1H, m), 3.60-3.79 (4H, m), 5.40-6.15 (1H, br), 6.90 (1H, s), 7.09-7.20 (2H, m), 7.30-7.40 (1H, m), 7.65-7.72 (2H, m), 7.75 (1H, d, J = 9.0 Hz), 8.60-8.80 (1H, br), 8.80-9.00 (1H, br). | Dihydro-chloride |
| 340 | 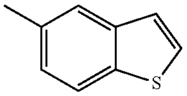 | 1H-NMR (DMSO-d6) δ ppm at 80° C.: 1.38-1.54 (10H, m), 1.69-2.02 (5H, m), 2.41-2.50 (1H, m), 3.55-3.85 (4H, m), 4.97-5.80 (1H, br), 6.94-7.10 (1H, br), 7.18-7.40 (2H, m), 7.59 (1H, d, J = 5.4 Hz), 7.78 (1H, d, J = 8.9 Hz), 8.75-8.92 (1H, br), 8.92-9.30 (1H, br). | Dihydro-chloride |
| 341 | 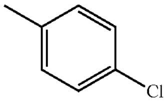 | 1H-NMR (DMSO-d6) δ ppm: 1.33-1.52 (10H, m), 1.64-1.82 (4H, m), 1.82-1.93 (1H, m), 2.30-2.40 (1H, m), 3.40-3.54 (2H, m), 3.54-3.70 (2H, m), 4.45-5.20 (1H, br), 6.66 (2H, d, J = 9.0 Hz), 7.19 (2H, d, J = 9.0 Hz), 8.55-8.70 (1H, br), 8.75-8.92 (1H, br). | Dihydro-chloride |
| 342 | 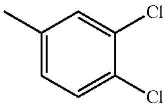 | 1H-NMR (DMSO-d6) δ ppm: 1.33-1.59 (10H, m), 1.61-1.90 (5H, m), 2.33-2.45 (1H, m), 3.45-3.56 (2H, m), 3.56-3.71 (2H, m), 5.05-6.00 (1H, br), 6.65 (1H, dd, J = 2.8, 9.1 Hz), 6.78 (1H, d, J = 2.8 Hz), 7.34 (1H, d, J = 9.1 Hz), 8.70-8.89 (1H, br), 9.00-9.15 (1H, br). | Dihydro-chloride |

TABLE 52

Relative configuration

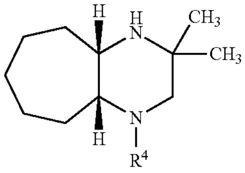

| Example | $R^4$ | NMR | Salt |
|---|---|---|---|
| 343 | 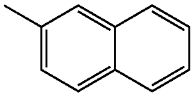 | 1H-NMR (DMSO-d6) δ ppm: 1.10-1.92 (14H, m), 2.23-2.44 (2H, m), 2.94 (1H, d, J = 13.3), 3.51 (1H, d, J = 13.3 Hz), 3.76-3.94 (1H, m), 4.10-4.22 (1H, m), 5.80-6.30 (1H, br), 7.11 (1H, d, J = 1.6 Hz), 7.22-7.31 (1H, m), 7.36-7.50 (2H, m), 7.66-7.85 (3H, m), 8.66-8.92 (1H, br), 9.80-9.08 (1H, br). | Dihydro-chloride |
| 344 | 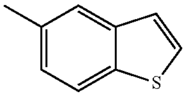 | 1H-NMR (DMSO-d6) δ ppm: 1.10-1.38 (3H, m), 1.38-1.65(8H, m), 1.65-1.92(3H, m), 2.15-2.40 (2H, m), 2.89 (1H, d, J = 13.3 Hz), 3.37 (1H, d, J = 13.3 Hz), 3.77-3.95 (1H, m), 4.00-4.14 (1H, m), 7.17 (1H, dd, J = 2.3, 8.9 Hz), 7.28-7.38 (2H, m), 7.68 (1H, d, J = 5.4 Hz), 7.83 (1H, d, J = 8.9 Hz), 8.44-8.74 (1H, br), 9.65-9.90 (1H, br). | Hydro-chloride |
| 345 | 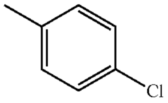 | 1H-NMR (DMSO-d6) δ ppm: 1.10-1.95 (14H, m), 2.16-2.45 (2H, m), 2.82 (1H, d, J = 13.5), 3.40 (1H, d, J = 13.5 Hz), 3.70-3.89 (1H, m), 3.89-4.07 (1H, m), 6.93(2H, d, J = 9.0 Hz), 7.26 (2H, d, J = 9.0 Hz), 8.54-8.88 (1H, br), 9.66-9.99 (1H, br). | Hydro-chloride |
| 346 | 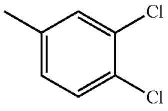 | 1H-NMR (DMSO-d6) δ ppm: 1.10-1.90 (14H, m), 2.19-2.45 (2H, m), 2.83 (1H, d, J = 13.6 Hz), 3.50 (1H, d, J = 13.6 Hz), 3.68-3.86 (1H, br), 3.94-4.07 (1H, br), 6.92 (1H, dd, J = 2.9, 9.0 Hz), 7.14 (1H, d, J = 2.9 Hz), 7.42 (1H, d, J = 9.0 Hz), 8.55-8.88 (1H, br), 9.62-9.98 (1H, br). | Hydro-chloride |

TABLE 53

Relative configuration

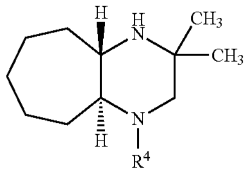

| Example | $R^4$ | NMR | Salt |
|---|---|---|---|
| 347 | 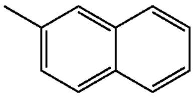 | 1H-NMR (DMSO-d6) δ ppm: 1.37 (3H, s), 1.42-1.88 (12H, m), 2.10-2.25 (1H, m), 3.13 (1H, d, J = 13.4 Hz), 3.28-3.63 (3H, m), 3.92-4.48 (1H, br), 7.26-7.51 (4H, m), 7.76-7.92 (3H, m), 8.85-9.15 (1H, br), 9.50-9.70 (1H, br). | Dihydrochloride |
| 348 | 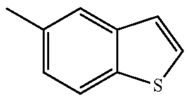 | 1H-NMR (DMSO-d6) δ ppm: 1.00 (3H, s), 1.20-1.70 (13H, m), 1.70-1.85 (1H, m), 2.70-2.95 (4H, m), 7.05 (1H, dd, J = 2.1, 8.7 Hz), 7.34 (1H, d, J = 5.4 Hz), 7.39 (1H, d, J = 2.1 Hz), 7.67 (1H, d, J = 5.4 Hz), 7.82 (1H, d, J = 8.7 Hz). | — |
| 349 | 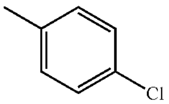 | 1H-NMR (DMSO-d6) δ ppm: 1.33 (3H, s), 1.37-1.81 (12H, m), 2.07-2.22 (1H, m), 3.00 (1H, d, J = 13.6 Hz), 3.21-3.50 (3H, m), 3.88-4.20 (1H, br), 6.97 (2H, d, J = 8.8 Hz), 7.31 (2H, d, J = 8.8 Hz), 8.66-9.00 (1H, br), 9.33-9.65 (1H, m). | Dihydrochloride |
| 350 | 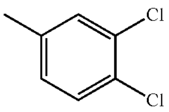 | 1H-NMR (DMSO-d6) δ ppm: 1.33 (3H, s), 1.36 (3H, s), 1.50-1.90 (9H, m), 2.07-2.28 (1H, m), 3.07 (1H, d, J = 14.2 Hz), 3.32-3.66 (3H, m), 6.88 (1H, dd, J = 2.8, 8.9 Hz), 7.09 (1H, d, J = 2.8 Hz), 7.43 (1H, d, J = 8.9 Hz), 8.70-8.92 (1H, br), 9.35-9.58 (1H, br). | Hydrochloride |

TABLE 54

Relative configuration

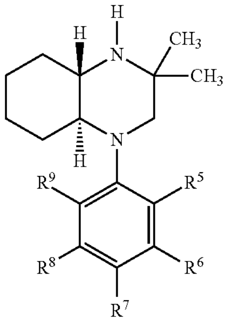

| Example | $R^5$ | $R^6$ | $R^7$ | $R^8$ | $R^9$ | MS (M + 1) |
|---|---|---|---|---|---|---|
| 351 | —H | —H | —H | —H | —H | 245 |
| 352 | —H | —H | $—CH_3$ | —H | —H | 259 |
| 353 | —H | $—CH_3$ | —H | —H | —H | 259 |
| 354 | —H | —F | —H | —H | —H | 263 |
| 355 | —H | —H | —CN | —H | —H | 270 |
| 356 | —H | $—CH_3$ | $—CH_3$ | —H | —H | 273 |
| 357 | —H | $—C_2H_5$ | —H | —H | —H | 273 |
| 358 | —H | $—CH_3$ | —H | $—CH_3$ | —H | 273 |
| 359 | —H | —H | $—C_2H_5$ | —H | —H | 273 |
| 360 | —H | $—OCH_3$ | —H | —H | —H | 275 |
| 361 | —H | —F | —H | —F | —H | 281 |
| 362 | —H | $—CH_3$ | —CN | —H | —H | 284 |
| 363 | —H | —H | $—(CH_2)_2CH_3$ | —H | —H | 287 |
| 364 | —H | $—CH(CH_3)_2$ | —H | —H | —H | 287 |
| 365 | —H | —H | $—CH(CH_3)_2$ | —H | —H | 287 |
| 366 | —H | —F | —CN | —H | —H | 288 |
| 367 | —H | —CN | —H | —F | —H | 288 |

TABLE 54-continued

Relative configuration

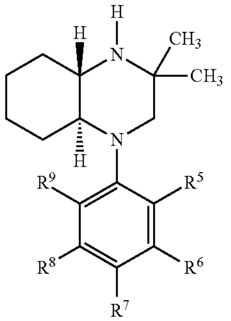

| Example | $R^5$ | $R^6$ | $R^7$ | $R^8$ | $R^9$ | MS (M + 1) |
|---|---|---|---|---|---|---|
| 368 | —H | $—N(CH_3)_2$ | —H | —H | —H | 288 |
| 369 | —H | —H | $—N(CH_3)_2$ | —H | —H | 288 |
| 370 | —H | $—OC_2H_5$ | —H | —H | —H | 289 |
| 371 | —H | $—CH_3$ | $—OCH_3$ | —H | —H | 289 |
| 372 | —H | —H | $—OCH_2CH_3$ | —H | —H | 289 |
| 373 | —H | $—CH_3$ | —F | $—CH_3$ | —H | 291 |
| 374 | —H | —H | $—SCH_3$ | —H | —H | 291 |
| 375 | —H | $—SCH_3$ | —H | —H | —H | 291 |
| 376 | $—OCH_3$ | —H | —H | —F | —H | 293 |
| 377 | —H | —F | —H | —Cl | —H | 297 |
| 378 | —H | —F | —F | —F | —H | 299 |
| 379 | —H | —H | $—C(CH_3)_3$ | —H | —H | 301 |
| 380 | —H | $—CH_3$ | $—OCH_3$ | $—CH_3$ | —H | 303 |
| 381 | —H | $—OCH(CH_3)_2$ | —H | —H | —H | 303 |
| 382 | —H | $—OCH_3$ | $—OCH_3$ | —H | —H | 305 |
| 383 | —H | —H | $—SCH_2CH_3$ | —H | —H | 305 |
| 384 | $—OCH_3$ | —H | —H | —Cl | —H | 309 |

TABLE 54-continued
Relative configuration
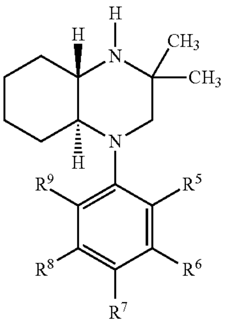
| Example | $R^5$ | $R^6$ | $R^7$ | $R^8$ | $R^9$ | MS (M + 1) |
|---|---|---|---|---|---|---|
| 385 | —H | —$OCH_3$ | —F | —F | —H | 311 |
| 386 | —H | —H | 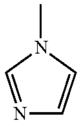 | —H | —H | 311 |
| 387 | —H | —$CF_3$ | —H | —H | —H | 313 |
| 388 | —H | —H | —$CF_3$ | —H | —H | 313 |
| 389 | —Cl | —H | —Cl | —H | —H | 313 |
| 390 | —H | —Cl | —H | —Cl | —H | 313 |
| 391 | —H | —$CF_3$ | —$CH_3$ | —H | —H | 327 |
| 392 | —H | —H | 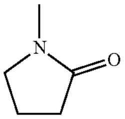 | —H | —H | 328 |
| 393 | —H | —H | —$OCF_3$ | —H | —H | 329 |
| 394 | —H | —$CF_3$ | —H | —F | —H | 331 |
| 395 | —F | —H | —$CF_3$ | —H | —H | 331 |
| 396 | —H | —F | —$CF_3$ | —H | —H | 331 |
| 397 | —F | —$CF_3$ | —H | —H | —H | 331 |
| 398 | —H | —$CF_3$ | —F | —H | —H | 331 |
| 399 | —H | —$CF_3$ | —$OCH_3$ | —H | —H | 343 |
| 400 | —H | —$CF_3$ | —Cl | —H | —H | 347 |
TABLE 55
Relative configuration
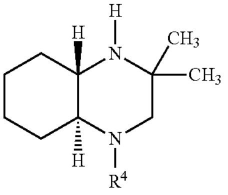
| Example | $R^4$ | MS(M + 1) |
|---|---|---|
| 401 | 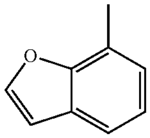 | 285 |
TABLE 55-continued
Relative configuration
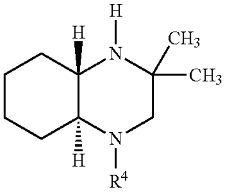
| Example | $R^4$ | MS(M + 1) |
|---|---|---|
| 402 | 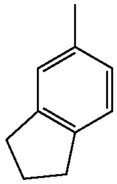 | 285 |
| 403 | 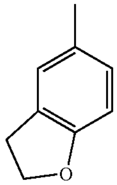 | 287 |
| 404 | 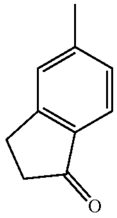 | 299 |
| 405 | 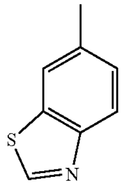 | 302 |
| 406 | 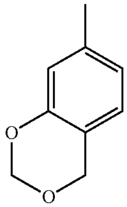 | 303 |
| 407 | 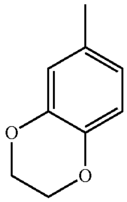 | 303 |

TABLE 55-continued
Relative configuration
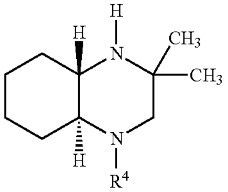
| Example | $R^4$ | MS(M + 1) |
|---|---|---|
| 408 | 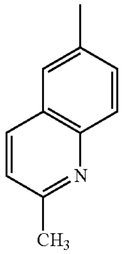 | 310 |
| 409 | 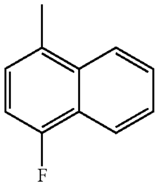 | 313 |
| 410 | 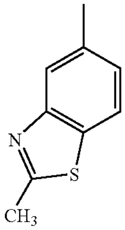 | 316 |
| 411 | 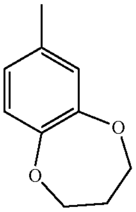 | 317 |
| 412 | 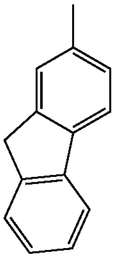 | 333 |
TABLE 56
Relative configuration
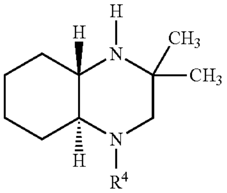
| Example | $R^4$ | MS(M + 1) |
|---|---|---|
| 413 | 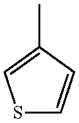 | 251 |
| 414 | 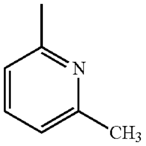 | 260 |
| 415 | 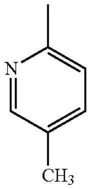 | 260 |
| 416 | 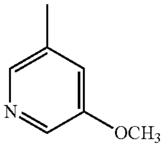 | 276 |
| 417 | 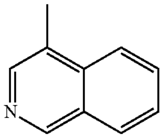 | 296 |
| 418 | 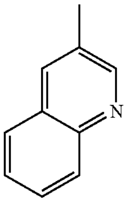 | 296 |
| 419 | 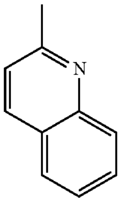 | 296 |

TABLE 56-continued
Relative configuration
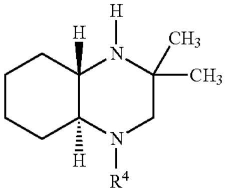
| Example | $R^4$ | MS(M + 1) |
|---|---|---|
| 420 | 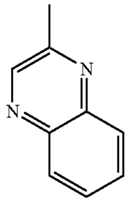 | 297 |
| 421 | 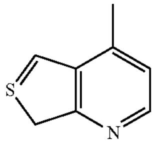 | 302 |
| 422 | 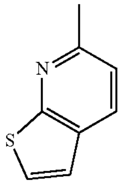 | 302 |
| 423 | 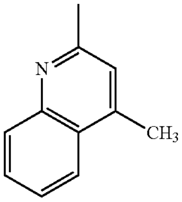 | 310 |
| 424 | 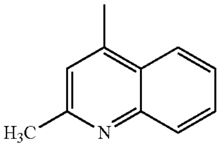 | 310 |
| 425 | 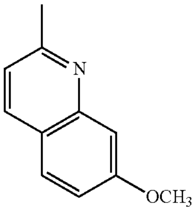 | 326 |
TABLE 56-continued
Relative configuration
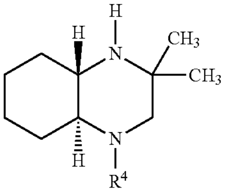
| Example | $R^4$ | MS(M + 1) |
|---|---|---|
| 426 | 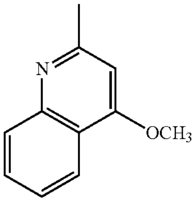 | 326 |
| 427 | 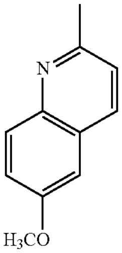 | 326 |
| 428 | 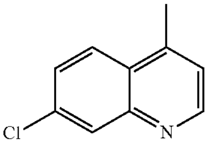 | 330 |
| 429 | 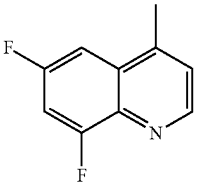 | 332 |
| 430 | 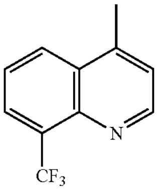 | 364 |

TABLE 57

Absolute configuration

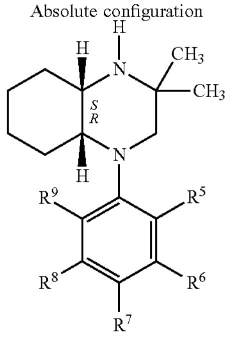

| Example | $R^5$ | $R^6$ | $R^7$ | $R^8$ | $R^9$ | MS(M + 1) |
|---|---|---|---|---|---|---|
| 431 | —H | —H | —H | —H | —H | 245 |
| 432 | —H | —H | $—CH_3$ | —H | —H | 259 |
| 433 | —H | $—CH_3$ | —H | —H | —H | 259 |
| 434 | $—CH_3$ | —H | —H | —H | —H | 259 |
| 435 | —H | —CN | —H | —H | —H | 270 |
| 436 | —CN | —H | —H | —H | —H | 270 |
| 437 | —H | —H | —CN | —H | —H | 270 |
| 438 | —H | $—CH_3$ | $—CH_3$ | —H | —H | 273 |
| 439 | —H | $—CH_3$ | —H | $—CH_3$ | —H | 273 |
| 440 | $—CH_3$ | $—CH_3$ | —H | —H | —H | 273 |
| 441 | —H | —H | $—C_2H_5$ | —H | —H | 273 |
| 442 | —H | $—OCH_3$ | —H | —H | —H | 275 |
| 443 | $—OCH_3$ | —H | —H | —H | —H | 275 |
| 444 | $—CH_3$ | —F | —H | —H | —H | 277 |
| 445 | —H | $—CH_3$ | —F | —H | —H | 277 |
| 446 | —F | —H | —H | $—CH_3$ | —H | 277 |
| 447 | —H | —F | $—CH_3$ | —H | —H | 277 |
| 448 | $—CH_3$ | —H | —F | —H | —H | 277 |
| 449 | —F | —H | —H | —F | —H | 281 |
| 450 | —F | —H | —F | —H | —H | 281 |
| 451 | —H | $—CH_3$ | —CN | —H | —H | 284 |
| 452 | —H | $—C(O)CH_3$ | —H | —H | —H | 287 |
| 453 | —H | —H | $—C(O)CH_3$ | —H | —H | 287 |
| 454 | $—CH_3$ | —H | $—CH_3$ | $—CH_3$ | —H | 287 |
| 455 | —H | —H | $—CH(CH_3)_2$ | —H | —H | 287 |
| 456 | —F | —H | —CN | —H | —H | 288 |
| 457 | —H | —F | —CN | —H | —H | 288 |
| 458 | —H | —CN | —F | —H | —H | 288 |
| 459 | —H | $—N(CH_3)_2$ | —H | —H | —H | 288 |
| 460 | —H | —H | $—N(CH_3)_2$ | —H | —H | 288 |
| 461 | $—CH_3$ | —H | $—OCH_3$ | —H | —H | 289 |
| 462 | —H | $—CH_3$ | $—OCH_3$ | —H | —H | 289 |
| 463 | —H | $—CH_3$ | —F | $—CH_3$ | —H | 291 |
| 464 | $—CH_3$ | —F | $—CH_3$ | —H | —H | 291 |
| 465 | —H | —H | $—SCH_3$ | —H | —H | 291 |
| 466 | —H | $—SCH_3$ | —H | —H | —H | 291 |
| 467 | $—OCH_3$ | —H | —H | —F | —H | 293 |
| 468 | $—CH_3$ | —Cl | —H | —H | —H | 293 |
| 469 | —H | $—CH_3$ | —Cl | —H | —H | 293 |
| 470 | —H | —Cl | $—CH_3$ | —H | —H | 293 |
| 471 | $—CH_3$ | —H | —Cl | —H | —H | 293 |
| 472 | —F | —H | —H | —Cl | —H | 297 |
| 473 | —H | —F | —H | —Cl | —H | 297 |
| 474 | —F | —H | —Cl | —H | —H | 297 |
| 475 | —F | —F | —H | —F | —H | 299 |
| 476 | —H | —H | $—(CH_2)_3CH_3$ | —H | —H | 301 |
| 477 | —H | —H | $—C(CH_3)_3$ | —H | —H | 301 |
| 478 | —H | —H | $—CH_2N(CH_3)_2$ | —H | —H | 302 |
| 479 | —H | $—CH_2N(CH_3)_2$ | —H | —H | —H | 302 |
| 480 | $—OCH(CH_3)_2$ | —H | —H | —H | —H | 303 |
| 481 | —H | $—CH_3$ | $—OCH_3$ | $—CH_3$ | —H | 303 |
| 482 | —H | —Cl | —CN | —H | —H | 304 |
| 483 | —H | $—OCH_3$ | —H | $—OCH_3$ | —H | 305 |
| 484 | —H | $—OCH_3$ | $—OCH_3$ | —H | —H | 305 |
| 485 | $—OCH_3$ | —H | —H | $—OCH_3$ | —H | 305 |
| 486 | $—OCH_3$ | —F | —H | —F | —H | 311 |
| 487 | —H | $—OCH_3$ | —F | —F | —H | 311 |
| 488 | $—OCH_3$ | —H | —F | —F | —H | 311 |
| 489 | —H | —H | $—OCHF_2$ | —H | —H | 311 |

TABLE 57-continued
Absolute configuration
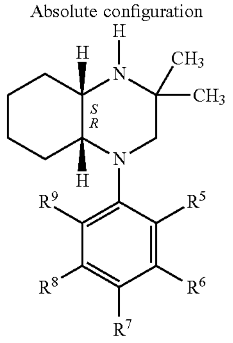
| Example | $R^5$ | $R^6$ | $R^7$ | $R^8$ | $R^9$ | MS(M + 1) |
|---|---|---|---|---|---|---|
| 490 | 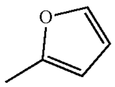 | —H | —H | —H | —H | 311 |
| 491 | —H | —H | 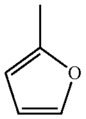 | —H | —H | 311 |
| 492 | —H | 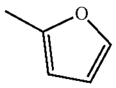 | —H | —H | —H | 311 |
| 493 | —H | 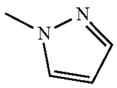 | —H | —H | —H | 311 |
| 494 | $—CF_3$ | —H | —H | —H | —H | 313 |
| 495 | —H | $—CF_3$ | —H | —H | —H | 313 |
| 496 | —H | —H | $—CF_3$ | —H | —H | 313 |
| 497 | —Cl | —H | —Cl | —H | —H | 313 |
| 498 | —H | —Cl | —H | —Cl | —H | 313 |
| 499 | —H | —H | 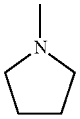 | —H | —H | 314 |
| 500 | —H | $—CH_3$ | $—N(CH_3)_2$ | $—CH_3$ | —H | 316 |
| 501 | 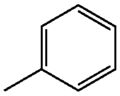 | —H | —H | —H | —H | 321 |
| 502 | —H | —H | 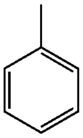 | —H | —H | 321 |
| 503 | —H | 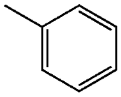 | —H | —H | —H | 321 |
| 504 | —H | —Cl | $—OC_2H_5$ | —H | —H | 323 |

TABLE 57-continued
Absolute configuration
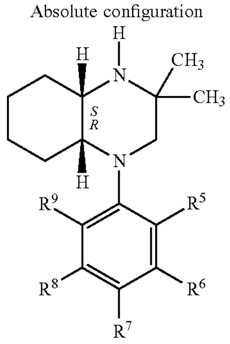
| Example | $R^5$ | $R^6$ | $R^7$ | $R^8$ | $R^9$ | MS(M + 1) |
|---|---|---|---|---|---|---|
| 505 | —H | —H | 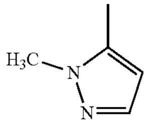 | —H | —H | 325 |
| 506 | —H | 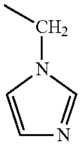 | —H | —H | —H | 325 |
| 507 | —H | —H | 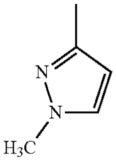 | —H | —H | 325 |
| 508 | —H | 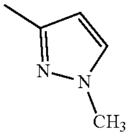 | —H | —H | —H | 325 |
| 509 | —H | —$CF_3$ | —$CH_3$ | —H | —H | 327 |
| 510 | —H | —H | 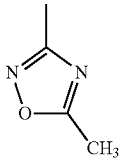 | —H | —H | 327 |
| 511 | —H | —H | 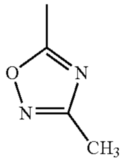 | —H | —H | 327 |
| 512 | —H | —H | 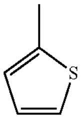 | —H | —H | 327 |

TABLE 57-continued
Absolute configuration
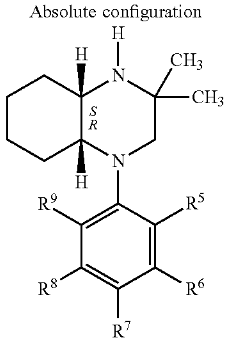
| Example | $R^5$ | $R^6$ | $R^7$ | $R^8$ | $R^9$ | MS(M + 1) |
|---|---|---|---|---|---|---|
| 513 | —H | —H | 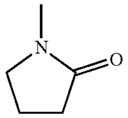 | —H | —H | 328 |
| 514 | —H | $—OCF_3$ | —H | —H | —H | 329 |
| 515 | $—OCF_3$ | —H | —H | —H | —H | 329 |
| 516 | —H | —H | $—OCF_3$ | —H | —H | 329 |
| 517 | —H | —F | $—CF_3$ | —H | —H | 331 |
| 518 | —H | $—CF_3$ | —F | —H | —H | 331 |
| 519 | —H | —H | $—O(CH_2)_2N(CH_3)_2$ | —H | —H | 332 |
| 520 | —H | $—OCH_3$ | $—OCH_3$ | $—OCH_3$ | —H | 335 |
| 521 | 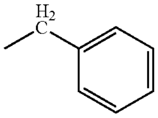 | —H | —H | —H | —H | 335 |
| 522 | —H | —H | 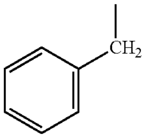 | —H | —H | 335 |
| 523 | —H | —H | 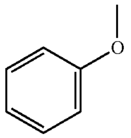 | —H | —H | 337 |
| 524 | —H | 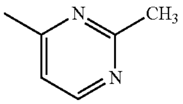 | —H | —H | —H | 337 |
| 525 | —H | —H | 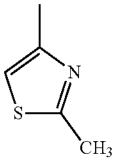 | —H | —H | 342 |
| 526 | —H | $—CF_3$ | $—OCH_3$ | —H | —H | 343 |
| 527 | —H | —H | $—O(CH_2)_5CH_3$ | —H | —H | 345 |
| 528 | —H | —H | $—O(CH_2)_3N(CH_3)_2$ | —H | —H | 346 |

TABLE 57-continued
Absolute configuration
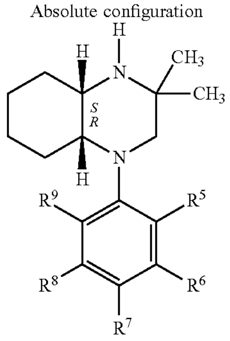
| Example | $R^5$ | $R^6$ | $R^7$ | $R^8$ | $R^9$ | MS(M + 1) |
|---|---|---|---|---|---|---|
| 529 | —H | —H | 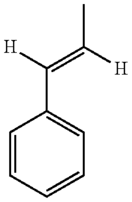 | —H | —H | 347 |
| 530 | —H | —Cl | $—CF_3$ | —H | —H | 347 |
| 531 | —H | $—CF_3$ | —Cl | —H | —H | 347 |
| 532 | —Cl | —Cl | —H | —Cl | —H | 347 |
| 533 | —H | 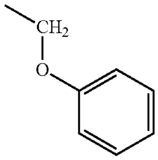 | —H | —H | —H | 351 |
| 534 | 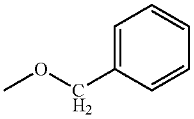 | —H | —H | —H | —H | 351 |
| 535 | —H | 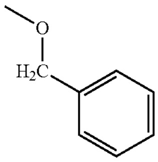 | —H | —H | —H | 351 |
| 536 | —H | —H | 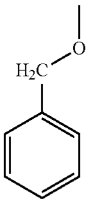 | —H | —H | 351 |
| 537 | —H | —H | $—SO_2N(CH_3)_2$ | —H | —H | 352 |
| 538 | —H | —H | 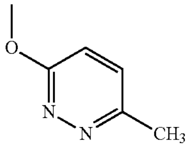 | —H | —H | 353 |

TABLE 57-continued
Absolute configuration
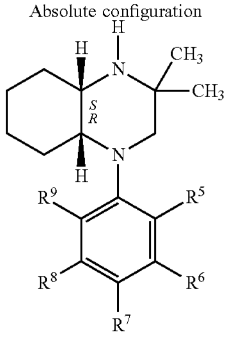
| Example | $R^5$ | $R^6$ | $R^7$ | $R^8$ | $R^9$ | MS(M + 1) |
|---|---|---|---|---|---|---|
| 539 | —H | 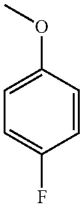 | —H | —H | —H | 355 |
| 540 | —H | —H | 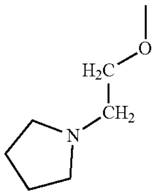 | —H | —H | 358 |
| 541 | —H | —H | $—CH_2N(i\text{-}Pr)_2$ | —H | —H | 358 |
| 542 | —H | $—CF_3$ | —H | $—CF_3$ | —H | 381 |
TABLE 58
Absolute configuration
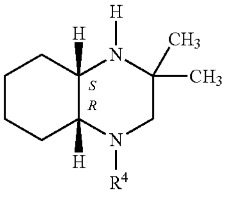
| Example | $R^4$ | MS(M + 1) |
|---|---|---|
| 543 | 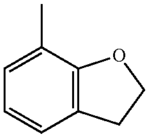 | 287 |
| 544 | 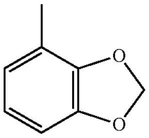 | 289 |
TABLE 58-continued
Absolute configuration
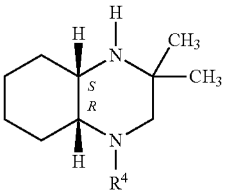
| Example | $R^4$ | MS(M + 1) |
|---|---|---|
| 545 | 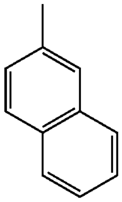 | 295 |
| 546 | 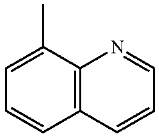 | 296 |

TABLE 58-continued
Absolute configuration
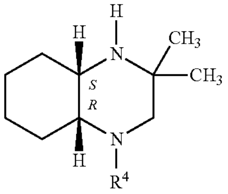
| Example | $R^4$ | MS(M + 1) |
|---|---|---|
| 547 | 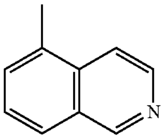 | 296 |
| 548 | 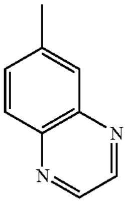 | 297 |
| 549 | 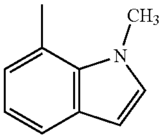 | 298 |
| 550 | 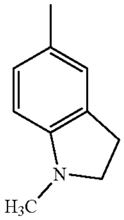 | 300 |
| 551 | 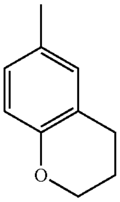 | 301 |
| 552 | 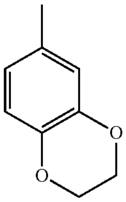 | 303 |
TABLE 58-continued
Absolute configuration
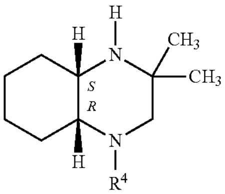
| Example | $R^4$ | MS(M + 1) |
|---|---|---|
| 553 | 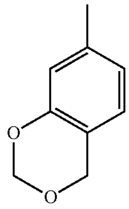 | 303 |
| 554 | 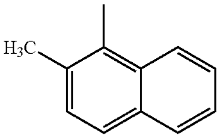 | 309 |
| 555 | 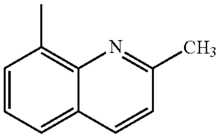 | 310 |
| 556 | 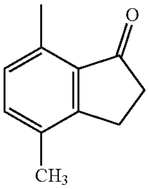 | 313 |
| 557 | 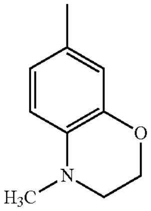 | 316 |
| 558 | 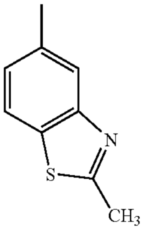 | 316 |

TABLE 58-continued
Absolute configuration
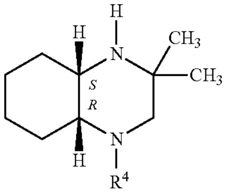
| Example | $R^4$ | MS(M + 1) |
|---|---|---|
| 559 | 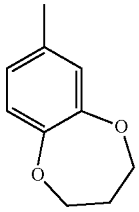 | 317 |
| 560 | 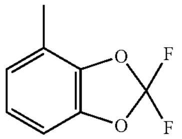 | 325 |
| 561 | 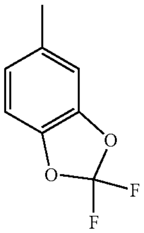 | 325 |
| 562 | 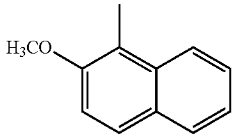 | 325 |
| 563 | 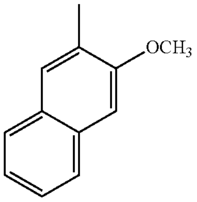 | 325 |
| 564 | 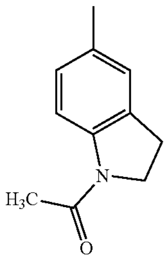 | 328 |
TABLE 58-continued
Absolute configuration
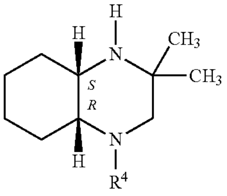
| Example | $R^4$ | MS(M + 1) |
|---|---|---|
| 565 | 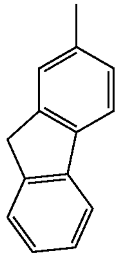 | 333 |
| 566 | 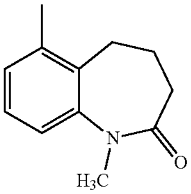 | 342 |
| 567 | 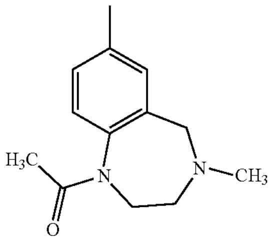 | 371 |
| 568 | 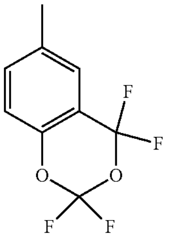 | 375 |
| 569 | 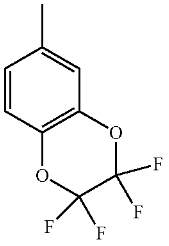 | 375 |

TABLE 59
Absolute configuration
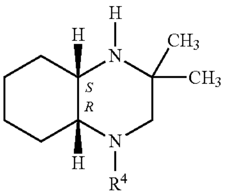
| Example | $R^4$ | MS(M + 1) |
|---|---|---|
| 570 | 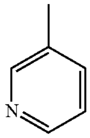 | 246 |
| 571 | 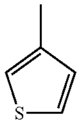 | 251 |
| 572 | 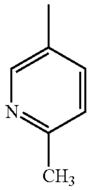 | 260 |
| 573 | 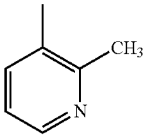 | 260 |
| 574 | 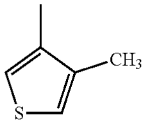 | 265 |
TABLE 59-continued
Absolute configuration
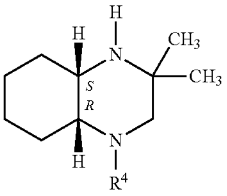
| Example | $R^4$ | MS(M + 1) |
|---|---|---|
| 575 | 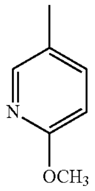 | 276 |
| 576 | 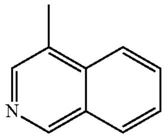 | 296 |
| 577 | 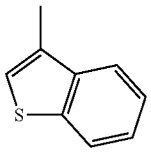 | 301 |
| 578 | 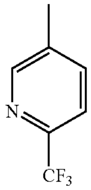 | 314 |
TABLE 63
relative configuration
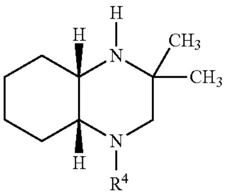
| Ex. No. | $R^4$ | NMR | Salt |
|---|---|---|---|
| 588 | 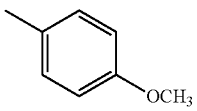 | 1H-NMR (DMSO-d6) δppm: 1.29-1.57 (3H, m), 1.46 (3H, s), 1.57 (3H, s), 1.69-1.91 (5H, m), 1.98-2.09 (1H, m), 3.07 (1H, d, J = 13.5 Hz), 3.51 (1H, d, J = 13.5 Hz), 3.73-3.92 (1H, m), 4.11-4.30 (1H, m), 7.18 (1H, d, J = 2.2 Hz), 7.22-7.28 (1H, m), 7.36-7.43 (2H, m), 7.68-7.80 (3H, m), 8.02-8.31 (1H, m), 9.62-9.91 (1H, br) | 2 Hydrochloride |

TABLE 64 absolute configuration

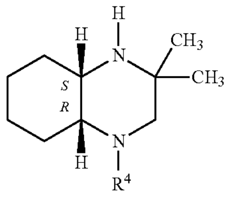

| Ex. No. | $R^4$ | NMR | Salt |
| --- | --- | --- | --- |
| 589 | 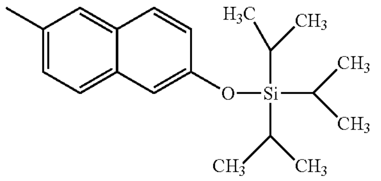 | 1H-NMR (CDCl3) δppm: 1.07-1.15 (18H, m), 1.17-1.34 (12H, m), 1.35-1.50 (2H, m), 1.64-1.86 (4H, m), 2.82 (1H, d, J = 11.6 Hz), 3.04 (1H, d, J = 11.7 Hz), 3.47-3.53 (1H, m), 3.69-3.78 (1H, m), 6.95 (1H, d, J = 2.3 Hz), 7.03 (1H, dd, J = 2.4, 8.8 Hz), 7.10 (1H, d, J = 2.4 Hz), 7.23 (1H, d, J = 2.4, 9.1 Hz), 7.51 (1H, d, J = 8.9 Hz), 7.55 (1H, d, J = 9.1 Hz). | — |
| 590 | 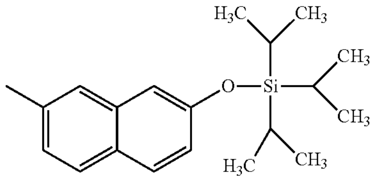 | 1H-NMR (CDCl3) δppm: 1.13 (18H, d, J = 7.3 Hz), 1.20-1.36 (12H, m), 1.36-1.64 (2H, m), 1.68-1.86 (4H, m), 2.83 (1H, d, J = 12.0 Hz), 3.12 (1H, d, J = 11.9 Hz), 3.45-3.55 (1H, m), 3.75-3.85 (1H, m), 6.82 (1H, d, J = 2.3 Hz), 6.86 (1H, dd, J = 2.4, 8.7 Hz), 7.02 (1H, d, J = 2.3 Hz), 7.10 (1H, dd, J = 2.4, 9.0 Hz), 7.53 (1H, d, J = 8.7 Hz), 7.59 (1H, d, J = 9.0 Hz). | — |
| 591 | 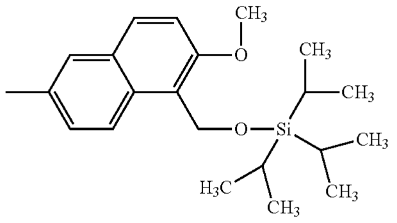 | 1H-NMR (CDCl3) δppm: 1.03-1.12 (18H, m), 1.12-1.32 (12H, m), 1.32-1.65 (2H, m), 1.66-1.84 (4H, m), 2.82 (1H, d, J = 11.7 Hz), 3.08 (1H, d, J = 11.8 Hz), 3.47-3.53 (1H, m), 3.73-3.81 (1H, m), 3.88 (3H, s), 5.17 (1H, d, J = 11.0 Hz), 5.24 (1H, d, J = 11.0 Hz), 6.94 (1H, d, J = 2.5 Hz), 7.16 (1H, d, J = 9.0 Hz), 7.31 (1H, dd, J = 2.5, 9.4 Hz), 7.58 (1H, d, J = 9.0 Hz), 8.12 (1H, d, J = 9.4 Hz). | — |
| 592 | 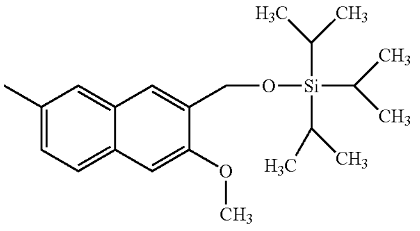 | 1H-NMR (CDCl3) δppm: 1.14 (18H, d, J = 6.6 Hz), 1.19-1.35 (13H, m), 1.35-1.65 (1H, m), 1.65-1.84 (4H, m), 2.83 (1H, d, J = 11.6 Hz), 3.04 (1H, d, J = 11.6 Hz), 3.5-3.6 (1H, m), 3.7-3.8 (1H, m), 3.87 (3H, s), 4.93 (2H, d, J = 1.0 Hz), 6.96 (1H, s), 6.99 (1H, d, J = 2.2 Hz), 7.21 (1H, dd, J = 2.4, 9.0 Hz), 7.59 (1H, d, J = 9.0 Hz), 7.77 (1H, s). | — |

TABLE 65 absolute configuration

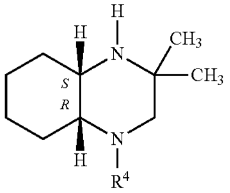

| Example. | $R^4$ | NMR | Salt |
|---|---|---|---|
| 593 | 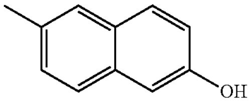 | 1H-NMR (CDCl3) δ ppm: 1.15-1.33 (9H, m), 1.33-1.50 (2H, m), 1.64-1.84 (4H, m), 2.82 (1H, d, J = 11.8 Hz), 3.04 (1H, d, J = 11.8 Hz), 3.49-3.56 (1H, m), 3.69-3.78 (1H, m), 6.96 (1H, d, J = 2.4 Hz), 6.99-7.06 (2H, m), 7.22-7.28 (1H, m), 7.52-7.58 (2H, m). | — |
| 594 | 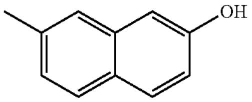 | 1H-NMR (CDCl3) δ ppm: 1.17-1.36 (9H, m), 1.36-1.52 (2H, m), 1.65-1.86 (4H, m), 2.83 (1H, d, J = 11.9 Hz), 3.13 (1H, d, J = 12.0 Hz), 3.45-3.55 (1H, m), 3.75-3.85 (1H, m), 6.8-6.85 (2H, m), 6.94 (1H, d, J = 2.4 Hz), 7.10 (1H, d, J = 2.4, 9.1 Hz), 7.57 (1H, d, J = 8.7 Hz), 7.60 (1H, d, J = 9.1 Hz). | — |
| 595 | 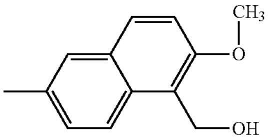 | 1H-NMR (DMSO-d6) δ ppm: 1.1-1.2 (1H, m), 1.2-1.4 (8H, m), 1.5-1.9 (5H, m), 2.89 (1H, d, J = 12.4 Hz), 3.22 (1H, d, J = 12.5 Hz), 3.62 (1H, br), 3.85 (3H, s), 3.95-4.05 (1H, m), 4.85 (2H, s), 6.53 (2H, s), 7.07 (1H, d, J = 2.4 Hz), 7.28 (1H, d, J = 9.1 Hz), 7.39 (1H, dd, J = 2.5, 9.5 Hz), 7.67 (1H, d, J = 9.0H), 7.98 (1H, d, J = 9.4 Hz). | Fumarate |
| 596 | 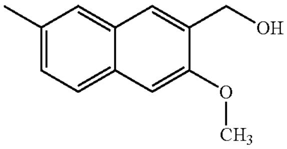 | 1H-NMR (CDCl3) δ ppm: 0.99 (1H, br), 1.15-1.35 (8H, m), 1.35-1.5 (2H, m), 1.5-1.85 (4H, m), 2.44 (1H, br), 2.81 (1H, d, J = 11.7 Hz), 3.05 (1H, d, J = 11.8H), 3.45-3.55 (1H, m), 3.7-3.8 (1H, m), 3.93 (3H, s), 4.79 (2H, s), 6.98 (1H, d, J = 2.4 Hz), 7.02 (1H, s), 7.21-7.28 (1H, m), 7.54 (1H, s), 7.60 (1H, d, J = 9.0 Hz). | — |

TABLE 66 absolute configuration

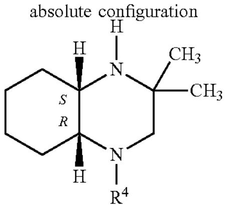

| Example. | $R^4$ | NMR | Salt |
|---|---|---|---|
| 597 | 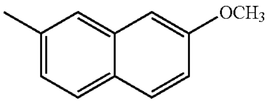 | 1H-NMR (CDCl3) δ ppm: 1.15-1.65 (11H, m), 1.65-1.9 (4H, m), 2.84 (1H, d, J = 12.0 Hz), 3.13 (1H, d, J = 11.9 Hz), 3.50 (1H, bs), 3.75-3.85 (1H, m), 3.89 (3H, s), 6.89 (1H, dd, J = 2.5, 8.8 Hz), 6.92 (1H, d, J = 2.3 Hz), 6.97 (1H, d, J = 2.4 Hz), 7.11 (1H, dd, J = 2.4, 9.0 Hz), 7.57 (1H, d, J = 8.8 Hz), 7.60 (1H, d, J = 9.0 Hz). | — |

TABLE 66-continued absolute configuration

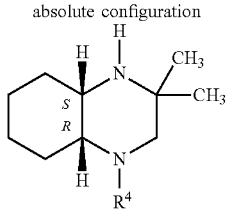

| Example. | $R^4$ | NMR | Salt |
|---|---|---|---|
| 598 | 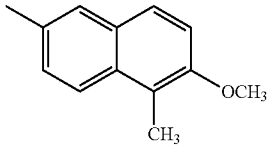 | 1H-NMR (CDCl3) δ ppm: 1.08 (1H, br), 1.15-1.35 (8H, m), 1.35-1.5 (2H, m), 1.65-1.85 (4H, m), 2.50 (3H, s), 2.82 (1H, d, J = 11.8 Hz), 3.07 (1H, d, J = 11.7 Hz), 3.45-3.55 (1H, m), 3.7-3.8 (1H, m), 3.90 (3H, s), 6.96 (1H, d, J = 2.6 Hz), 7.18 (1H, d, J = 9.0 Hz), 7.30 (1H, dd, J = 2.6, 9.4 Hz), 7.51 (1H, d, J = 8.9 Hz), 7.81 (1H, d, J = 9.4 Hz). | — |
| 599 | 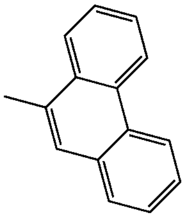 | 1H-NMR (CDCl3) δ ppm: 0.81-1.00 (1H, m), 1.03-1.13 (1H, m), 1.27 (3H, s), 1.33-1.43 (2H, m), 1.46 (3H, s), 1.54-1.72 (2H, m), 1.72-1.82 (1H, m), 1.85-2.0 (1H, m), 2.69 (1H, d, J = 11.1 Hz), 3.3-3.4 (2H, m), 3.75-3.85 (1H, m), 7.15 (1H, s), 7.5-7.55 (2H, m), 7.6-7.7 (2H, m), 7.7-7.8 (1H, m), 8.3-8.4 (1H, m), 8.55-8.65 (1H, m), 8.65-8.75 (1H, m). | — |
| 600 | 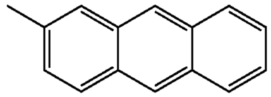 | 1H-NMR (CDCl3) δ ppm: 1.00 (1H, br), 1.19-1.37 (8H, m), 1.39-1.51 (2H, m), 1.68-1.79 (3H, m), 1.79-1.93 (1H, m), 2.90 (1H, d, J = 11.8 Hz), 3.18 (1H, d, J = 11.9 Hz), 3.5-3.6 (1H, m), 3.8-3.9 (1H, m), 7.05 (1H, d, J = 2.1 Hz), 7.3-7.45 (3H, m), 7.8-7.95 (3H, m), 8.15 (1H, s), 8.25 (1H, s). | — |
| 601 | 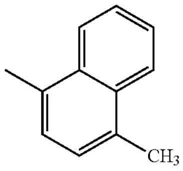 | 1H-NMR (DMSO-d6) δ ppm: 0.85-1.0 (1H, m), 1.0-1.1 (1H, m), 1.3-1.4 (1H, m), 1.5-1.65 (7H, m), 1.65-1.85 (2H, m), 1.85-2.1 (2H, m), 2.59 (3H, s), 2.76 (1H, d, J = 12.6 Hz), 3.3-3.5 (1H, m), 3.51 (1H, d, J = 13.1 Hz), 4.15-4.3 (1H, m), 7.02 (1H, d, J = 7.5 Hz), 7.28 (1H, d, J = 8.0 Hz), 7.5-7.65 (2H, m), 7.95-8.15 (2H, m), 8.25-8.35 (1H, m), 9.6-9.8 (1H, m). | Hydrochloride |
| 602 | 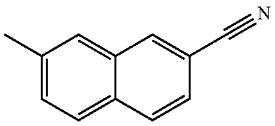 | 1H-NMR (DMSO-d6) δ ppm: 1.29-1.51 (6H, m), 1.56 (3H, s), 1.65-2.1 (5H, m), 3.09 (1H, d, J = 13.6 Hz), 3.62 (1H, d, J = 13.5 Hz), 3.8-3.9 (1H, m), 4.2-4.3 (1H, m), 7.32 (1H, d, J = 2.2 Hz), 7.50 (1H, dd, J = 1.6, 8.4 Hz), 7.63 (1H, dd, J = 2.5, 9.2 Hz), 7.87-7.98 (2H, m), 8.11-8.29 (2H, m), 9.74 (1H, br). | Hydrochloride |
| 603 | 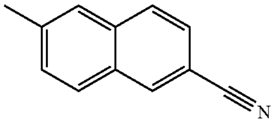 | 1H-NMR (DMSO-d6) δ ppm: 1.32-1.54 (6H, m), 1.58 (3H, s), 1.67-1.90 (3H, m), 1.90-2.14 (2H, m), 3.11 (1H, d, J = 13.8 Hz), 3.71 (1H, d, J = 13.8 Hz), 3.75-3.9 (1H, m), 4.25-4.35 (1H, m), 7.29 (1H, d, J = 2.2 Hz), 7.5-7.65 (2H, m), 7.81 (1H, d, J = 8.6 Hz), 7.91 (1H, d, J = 9.2 Hz), 8.25-8.45 (2H, m), 9.9-10.1 (1H, m). | Hydrochloride |
| 604 | 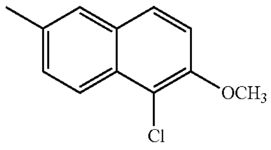 | 1H-NMR (CDCl3) δ ppm: 0.96 (1H, br), 1.15-1.35 (8H, m), 1.35-1.5 (2H, m), 1.65-1.9 (4H, m), 2.83 (1H, d, J = 11.8 Hz), 3.09 (1H, d, J = 11.8 Hz), 3.45-3.55 (1H, m), 3.75-3.85 (1H, m), 3.99 (3H, s), 6.95 (1H, d, J = 2.4 Hz), 7.20 (1H, d, J = 9.0 Hz), 7.37 (1H, dd, J = 2.5, 9.4 Hz), 7.56 (1H, d, J = 9.0 Hz), 8.06 (1H, d, J = 9.3 Hz). | — |

TABLE 66-continued absolute configuration

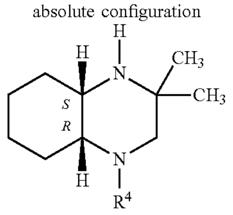

| Example. | $R^4$ | NMR | Salt |
|---|---|---|---|
| 605 | 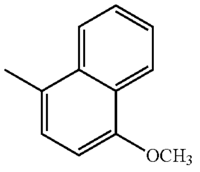 | 1H-NMR (DMSO-d6) δ ppm: 0.9-1.0 (1H, m), 1.1-1.2 (1H, m), 1.3-1.4 (1H, m), 1.52 (3H, s), 1.55-1.7 (4H, m), 1.7-1.85 (2H, m), 1.85-2.05 (2H, m), 2.73 (1H, d, J = 12.5 Hz), 3.3-3.6 (2H, m), 3.94 (3H, s), 4.15-4.3 (1H, m), 6.88 (1H, d, J = 8.2 Hz), 7.06 (1H, d, J = 8.1 Hz), 7.5-7.55 (1H, m), 7.55-7.6 (1H, m), 7.95 (1H, br), 8.16 (1H, dd, J = 1.0, 8.3 Hz), 8.24 (1H, d, J = 8.1 Hz), 9.45-9.6 (1H, m). | Hydrochloride |
| 606 | 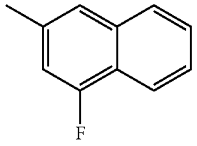 | 1H-NMR (DMSO-d6) δ ppm: 1.26-1.51 (6H, m), 1.57 (3H, s), 1.66-2.12 (5H, m), 3.06 (1H, d, J = 13.6 Hz), 3.57 (1H, d, J = 13.6 Hz), 3.74-3.86 (1H, m), 4.15-4.26 (1H, m), 7.05 (1H, d, J = 1.8 Hz), 7.28-7.37 (2H, m), 7.43-7.52 (1H, m), 7.75 (1H, d, J = 8.4 Hz), 7.84 (1H, d, J = 8.2 Hz), 8.23 (1H, br), 9.90 (1H, br). | Hydrochloride |
| 607 | 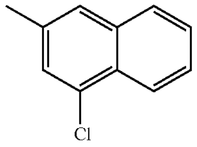 | 1H-NMR (DMSO-d6) δ ppm: 1.28-1.52 (6H, m), 1.57 (3H, s), 1.64-1.97 (4H, m), 2.02-2.16 (1H, m), 3.08 (1H, d, J = 13.5 Hz), 3.56 (1H, d, J = 13.6 Hz), 3.8-3.9 (1H, m), 3.95-4.1 (1H, m), 7.23 (1H, d, J = 2.0 Hz), 7.36-7.45 (1H, m), 7.45-7.54 (1H, m), 7.65 (1H, d, J = 2.3 Hz), 7.78 (1H, d, J = 8.1 Hz), 7.97 (1H, d, J = 8.3 Hz), 8.1-8.35 (1H, m), 9.90 (1H, br). | Hydrochloride |
| 608 | 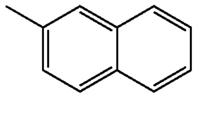 | 1H-NMR (DMSO-d6) δ ppm: 1.26-1.52 (6H, m), 1.57 (3H, s), 1.66-2.02 (4H, m), 2.02-2.12 (1H, m), 3.07 (1H, d, J = 13.4 Hz), 3.51 (1H, d, J = 13.4 Hz), 3.65-3.9 (2H, m), 4.15-4.25 (1H, m), 7.18 (1H, d, J = 2.2 Hz), 7.22-7.3 (1H, m), 7.35-7.47 (2H, m), 7.65-7.85 (3H, m), 8.1-8.3 (1H, m), 9.8-10.0 (1H, m). | 2 Hydrochloride |
| 609 | 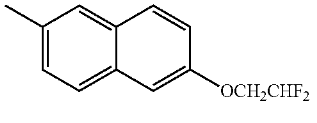 | 1H-NMR (DMSO-d6) δ ppm: 1.06-1.16 (1H, m), 1.16-1.39 (8H, m), 1.46-1.78 (4H, m), 1.78-1.93 (1H, m), 2.81 (1H, d, J = 12.2 Hz), 2.9-4.0 (5H, m), 4.30-4.42 (2H, m), 6.27-6.58 (2H, m), 7.06 (1H, d, J = 2.1 Hz), 7.10 (1H, dd, J = 2.6, 8.9 Hz), 7.26 (1H, d, J = 2.5 Hz), 7.35 (1H, dd, J = 2.6, 9.4 Hz), 7.61-7.68 (2H, m). | ½ Fumarate |
| 610 | 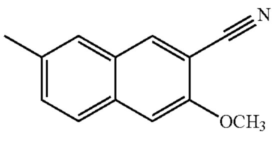 | 1H-NMR (DMSO-d6) δ ppm: 1.23-1.52 (6H, m), 1.59 (3H, s), 1.64-2.03 (4H, m), 2.03-2.16 (1H, m), 3.07 (1H, d, J = 13.3 Hz), 3.45 (1H, d, J = 14.0 Hz), 3.75-3.85 (1H, m), 3.95 (3H, s), 4.1-4.2 (1H, m), 4.77 (1H, br), 7.25 (1H, d, J = 2.2 Hz), 7.46 (1H, s), 7.58 (1H, dd, J = 2.4, 9.2 Hz), 7.81 (1H, d, J = 9.2 Hz), 8.23 (1H, s), 8.25-8.4 (1H, m), 10.13 (1H, br). | 2 Hydrochloride |
| 611 | 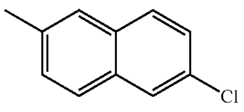 | 1H-NMR (DMSO-d6) δ ppm: 1.12-1.20 (1H, m), 1.21-1.39 (8H, m), 1.47-1.79 (4H, m), 1.79-1.95 (1H, m), 2.84 (1H, d, J = 12.3 Hz), 2.85-3.75 (5H, m), 3.9-4.0 (1H, m), 6.54 (2H, s), 7.12 (1H, d, J = 2.2 Hz), 7.34 (1H, dd, J = 2.2, 8.7 Hz), 7.43 (1H, dd, J = 2.4, 9.2 Hz), 7.65-7.75 (2H, m), 7.80 (1H, d, J = 2.1 Hz). | Fumarate |

TABLE 66-continued absolute configuration

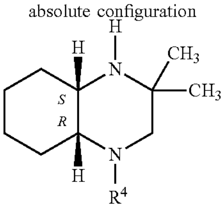

| Example. | $R^4$ | NMR | Salt |
|---|---|---|---|
| 612 | 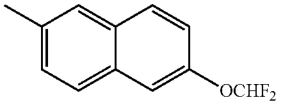 | 1H-NMR (DMSO-d6) δ ppm: 1.05-1.19 (1H, m), 1.19-1.40 (8H, m), 1.46-1.80 (4H, m), 1.80-1.96 (1H, m), 2.83 (1H, d, J = 12.3 Hz), 2.9-4.3 (5H, m), 6.51 (1H, s), 7.05-7.45 (4H, m), 7.49 (1H, d, J = 2.3 Hz), 7.7-7.8 (2H, m). | ½ Fumarate |
| 613 | 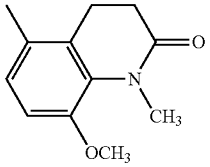 | 1H-NMR (DMSO-d6) δ ppm: 1.0-1.15 (2H, m), 1.3-1.4 (1H, m), 1.48 (3H, s), 1.50 (3H, s), 1.55-1.65 (1H, m), 1.7-1.8 (2H, m), 1.8-2.0 (2H, m), 2.25-2.35 (1H, m), 2.4-2.5 (1H, m), 2.6-2.75 (2H, m), 2.95-3.1 (2H, m), 3.21 (3H, s), 3.3-3.5 (1H, m), 3.78 (3H, s), 3.85-3.95 (1H, m), 6.78 (1H, d, J = 8.9 Hz), 6.93 (1H, d, J = 8.9 Hz), 7.99 (1H, br), 9.64 (1H, br). | Hydrochloride |
| 614 | 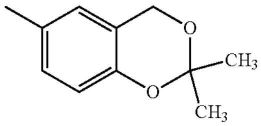 | 1H-NMR (DMSO-d6) δ ppm: 1.08-1.37 (9H, m), 1.42 (6H, s), 1.47-1.85 (5H, m), 2.76 (1H, d, J = 12.4 Hz), 2.95 (1H, d, J = 12.3 Hz), 3.53 (1H, br), 3.63-3.73 (1H, m), 4.74 (2H, s), 6.52 (2H, s), 6.58 (1H, d, J = 2.7 Hz), 6.65 (1H, d, J = 8.9 Hz), 6.76 (1H, dd, J = 2.8, 9.0 Hz). | Fumarate |

TABLE 67 absolute configuration

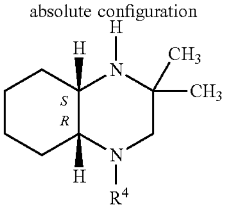

| Example. | $R^4$ | NMR | Salt |
|---|---|---|---|
| 615 | 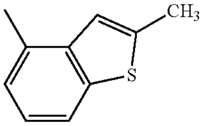 | 1H-NMR (CDCl3) δ ppm: 0.91-1.09 (3H, m), 1.20 (3H, s), 1.31-1.43 (5H, m), 1.54-1.78 (3H, m), 1.81-1.95 (1H, m), 2.55-2.65 (4H, m), 3.15 (1H, d, J = 11.2 Hz), 3.4-3.5 (1H, m), 3.65-3.7 (1H, m), 6.72-6.77 (1H, m), 7.05 (1H, s), 7.13 (1H, dd, J = 7.8, 7.8 Hz), 7.37 (1H, d, J = 8.0 Hz). | — |
| 616 | 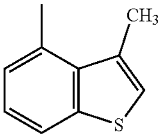 | 1H-NMR (CDCl3) δ ppm: 0.85-1.08 (3H, m), 1.21 (3H, s), 1.29-1.42 (5H, m), 1.52-1.68 (2H, m), 1.68-1.88 (2H, m), 2.58 (1H, d, J = 11.0 Hz), 2.77 (3H, d, J = 0.9 Hz), 3.02-3.12 (1H, m), 3.20 (1H, d, J = 11.0 Hz), 3.66 (1H, br), 6.91 (1H, d, J = 7.5 Hz), 6.98 (1H, d, J = 0.8 Hz), 7.19 (1H, dd, J = 7.8, 7.8 Hz), 7.52 (1H, dd, J = 0.7, 8.0 Hz). | — |
| 617 | 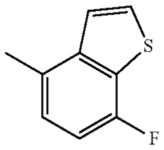 | 1H-NMR (CDCl3) δ ppm: 0.90-1.08 (3H, m), 1.20 (3H, s), 1.32-1.43 (5H, m), 1.45-1.78 (3H, m), 1.81-1.95 (1H, m), 2.57 (1H, d, J = 11.1 Hz), 3.14 (1H, d, J = 11.1 Hz), 3.33-3.42 (1H, m), 3.62-3.71 (1H, m), 6.71 (1H, dd, J = 4.1, 8.4 Hz), 6.92 (1H, dd, J = 8.9, 8.9 Hz), 7.41 (1H, d, J = 5.4 hz), 7.46 (1H, dd, J = 3.7, 5.4 Hz). | — |

TABLE 67-continued absolute configuration

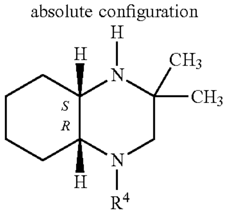

| Example. | $R^4$ | NMR | Salt |
|---|---|---|---|
| 618 | 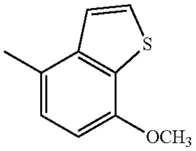 | 1H-NMR (CDCl3) δ ppm: 0.9-1.1 (2H, m), 1.20 (3H, s), 1.3-1.45 (5H, m), 1.45-1.8 (4H, m), 1.8-1.95 (1H, m), 2.56 (1H, d, J = 11.1 Hz), 3.14 (1H, d, J = 11.1 Hz), 3.3-3.4 (1H, m), 3.6-3.7 (1H, m), 3.96 (3H, s), 6.66 (1H, d, J = 8.2 Hz), 6.74 (1H, d, J = 8.2 Hz), 7.39 (1H, d, J = 5.4 Hz), 7.45 (1H, d, J = 5.4 Hz). | — |
| 619 | 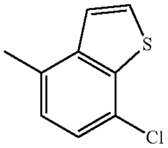 | 1H-NMR (CDCl3) δ ppm: 0.92-1.08 (3H, m), 1.20 (3H, s), 1.30-1.43 (5H, m), 1.47-1.78 (3H, m), 1.82-1.96 (1H, m), 2.61 (1H, d, J = 11.2 Hz), 3.13 (1H, d, J = 11.2 Hz), 3.42-3.52 (1H, m), 3.63-3.71 (1H, m), 6.74 (1H, d, J = 8.2 Hz), 7.21 (1H, d, J = 8.2 Hz), 7.43 (1H, d, J = 5.5 Hz), 7.47 (1H, d, J = 5.5 Hz). | — |
| 620 | 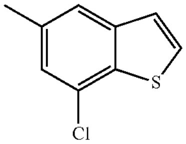 | 1H-NMR (CDCl3) δ ppm: 0.94 (1H, br), 1.14-1.33 (8H, m), 1.33-1.49 (2H, m), 1.65-1.85 (4H, m), 2.80 (1H, d, J = 11.7 Hz), 2.97 (1H, d, J = 11.6 Hz), 3.45-3.55 (1H, m), 3.6-3.7 (1H, m), 7.04 (1H, d, J = 2.1 Hz), 7.10 (1H, d, J = 2.2 Hz), 7.20 (1H, d, J = 5.4 Hz), 7.41 (1H, d, J = 5.5 Hz). | — |
| 621 | 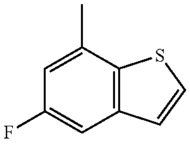 | 1H-NMR (DMSO-d6) δ ppm: 1.02-1.19 (2H, m), 1.32-1.44 (1H, m), 1.51 (3H, s), 1.52 (3H, s), 1.58-1.88 (3H, m), 1.92-2.09 (2H, m), 3.00 (1H, d, J = 13.0 Hz), 3.46 (1H, d, J = 13.1 Hz), 3.9-4.0 (1H, m), 3.95-4.08 (1H, m), 6.96 (1H, dd, J = 2.0, 11.0 Hz), 7.41 (1H, dd, J = 2.2, 9.1 Hz), 7.46 (1H, d, J = 5.4 Hz), 7.86 (1H, d, J = 5.4 Hz), 8.14 (1H, br), 9.76 (1H, br). | Hydrochloride |
| 622 | 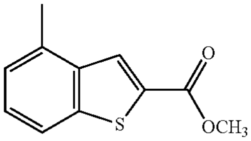 | 1H-NMR (CDCl3) δ ppm: 0.92-1.12 (2H, m), 1.13-2.02 (13H, m), 2.66 (1H, d, J = 11.6 Hz), 3.22 (1H, br), 3.45-3.6 (1H, m), 3.77 (1H, br), 3.96 (3H, s), 6.81 (1H, d, J = 7.6 Hz), 7.33 (1H, dd, J = 7.8, 7.8 Hz), 7.46 (1H, d, J = 7.8 Hz), 8.13 (1H, s). | — |
| 623 | 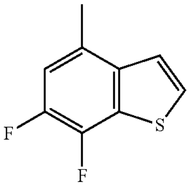 | 1H-NMR (DMSO-d6) δ ppm: 0.94-1.12 (2H, m), 1.28-1.43 (1H, m), 1.51 (3H, s), 1.53 (3H, s), 1.58-2.07 (5H, m), 2.84 (1H, d, J = 2.6 Hz), 3.41 (1H, d, J = 13.0 Hz), 3.6-3.7 (1H, m), 4.15-4.25 (1H, m), 7.11 (1H, dd, J = 6.5, 12.6 Hz), 7.77 (1H, dd, J = 3.8, 5.4 Hz), 7.84 (1H, d, J = 5.4 Hz), 8.05 (1H, br), 9.85 (1H, br). | Hydrochloride |
| 624 | 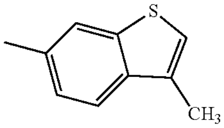 | 1H-NMR (DMSO-d6) δ ppm: 1.17-1.52 (6H, m), 1.52-1.63 (3H, m), 1.63-1.74 (1H, m), 1.74-1.98 (3H, m), 1.98-2.16 (1H, m), 2.33 (3H, d, J = 1.0 Hz), 3.03 (1H, d, J = 13.4 Hz), 3.33-3.5 (1H, m), 3.53-3.97 (2H, m), 4.03-4.18 (1H, m), 7.03-7.12 (1H, m), 7.15 (1H, dd, J = 2.1, 8.9 Hz), 7.4-7.5 (1H, m), 7.59 (1H, d, J = 8.8 Hz), 8.1-8.35 (1H, m), 9.8-10.1 (1H, m). | 2 Hydrochloride |

TABLE 67-continued absolute configuration

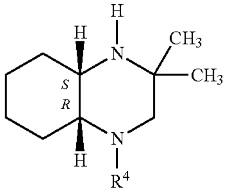

| Example. | $R^4$ | NMR | Salt |
|---|---|---|---|
| 625 | 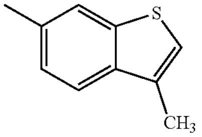 | 1H-NMR (DMSO-d6) δ ppm: 1.1-1.4 (9H, m), 1.49-1.93 (6H, m), 2.31 (3H, d, J = 1.2 Hz), 2.83 (1H, d, J = 12.4 Hz), 3.19 (1H, d, J = 12.4 Hz), 3.25-3.85 (3H, m), 3.85-3.95 (1H, m), 6.52 (2H, s), 7.01 (1H, d, J = 1.2 Hz), 7.10 (1H, dd, J = 2.3, 9.0 Hz), 7.34 (1H, d, J = 2.2 Hz), 7.55 (1H, d, J = 8.8 Hz). | Fumarate |
| 626 | 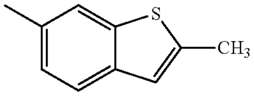 | 1H-NMR (DMSO-d6) δ ppm: 1.09-1.17 (1H, m), 1.17-1.41 (8H, m), 1.45-1.76 (4H, m), 1.76-1.89 (1H, m), 2.47 (3H, d, J = 1.1 Hz), 2.78 (1H, d, J = 12.2 Hz), 3.11 (1H, d, J = 12.2 Hz), 3.47 (3H, m), 3.75-3.85 (1H, m), 6.50 (1H, s), 6.90 (1H, s), 6.99 (1H, dd, J = 2.3, 8.9 Hz), 7.25 (1H, d, J = 2.2 Hz), 7.48 (1H, d, J = 8.8 Hz). | ½ Fumarate |

TABLE 68 absolute configuration

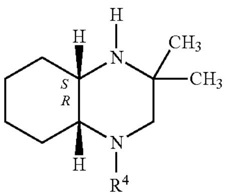

| Example. | $R^4$ | NMR | Salt |
|---|---|---|---|
| 627 | 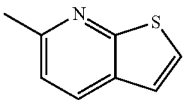 | 1H-NMR (CDCl3) δ ppm: 0.99 (1H, br), 1.20 (3H, s), 1.22 (3H, s), 1.29-1.51 (4H, m), 1.68-1.82 (3H, m), 1.82-1.95 (1H, m), 2.79 (1H, d, J = 12.8 Hz), 3.35-3.45 (1H, m), 3.91 (1H, d, J = 12.8 Hz), 4.2-4.3 (1H, m), 6.66 (1H, d, J = 9.0 Hz), 7.03 (2H, s), 7.77 (1H, d, J = 8.9 Hz). | — |
| 628 | 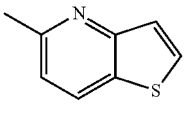 | 1H-NMR (DMSO-d6) δ ppm: 1.35-1.63 (9H, m), 1.69-1.97 (3H, m), 1.97-2.16 (2H, m), 3.05-3.35 (1H, m), 3.35-4.3 (2H, m), 4.3-4.8 (2H, m), 7.1-7.35 (1H, m), 7.4-7.75 (1H, m), 8.0-8.2 (1H, m), 8.25-8.7 (2H, m), 9.85-10.35 (1H, m). | 2 Hydrochloride |
| 629 | 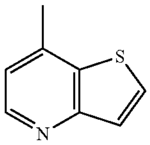 | 1H-NMR (DMSO-d6) δ ppm: 1.43-1.54 (5H, m), 1.64 (3H, s), 1.71-1.83 (2H, m), 1.83-2.06 (2H, m), 2.06-2.17 (1H, m), 2.4-2.6 (1H, m), 3.25-3.5 (2H, m), 3.56 (1H, d, J = 15.1 Hz), 3.85-4.0 (1H, m), 4.25 (1H, d, J = 15.0 Hz), 4.65-4.75 (1H, m), 7.28 (1H, d, J = 7.2 Hz), 7.69 (1H, d, J = 5.7 Hz), 8.5-8.6 (2H, m), 8.9-9.1 (1H, m), 10.35-10.65 (1H, m), 15.15 (1H, br). | 2 Hydrochloride |

TABLE 69 absolute configuration

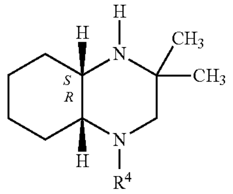

| Example. | $R^4$ | NMR | Salt |
|---|---|---|---|
| 630 | 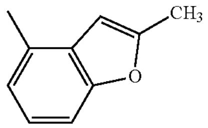 | 1H-NMR (CDCl3) δ ppm: 0.85-1.17 (3H, m), 1.20 (3H, s), 1.31 (3H, s), 1.33-1.45 (2H, m), 1.5-1.78 (3H, m), 1.81-1.95 (1H, m), 2.45 (3H, d, J = 1.0 Hz), 2.80 (1H, d, J = 11.5 Hz), 3.05 (1H, d, J = 11.5 Hz), 3.55-3.64 (2H, m), 6.39 (1H, s), 6.56 (1H, dd, J = 0.5, 7.7 Hz), 6.99 (1H, d, J = 8.2 Hz), 7.06 (1H, dd, J = 7.9, 7.9 Hz). | — |
| 631 | 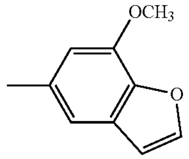 | 1H-NMR (CDCl3) δ ppm: 1.10-1.27 (5H, m), 1.29 (3H, s), 1.35-1.48 (2H, m), 1.48-1.83 (5H, m), 2.77-2.89 (2H, m), 3.49-3.55 (1H, m), 3.55-3.63 (1H, m), 4.01 (3H, s), 6.50 (1H, d, J = 2.0 Hz), 6.58 (1H, d, J = 2.1 Hz), 6.63 (1H, d, J = 2.1 Hz), 7.53 (1H, d, J = 2.0 Hz). | — |
| 632 | 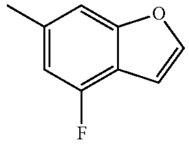 | 1H-NMR (DMSO-d6) δ ppm: 1.05-1.22 (2H, m), 1.34-1.45 (1H, m), 1.48 (3H, s), 1.53 (3H, s), 1.60-2.07 (5H, m), 3.13 (1H, d, J = 13.2 Hz), 3.28 (1H, d, J = 13.4 Hz), 3.88-3.89 (1H, m), 3.89-4.02 (1H, m), 6.62 (1H, dd, J = 2.1, 12.3 Hz), 7.09 (1H, dd, J = 1.3, 8.7 Hz), 7.22 (1H, dd, J = 0.7, 2.2 Hz), 7.96 (1H, d, J = 2.3 Hz), 8.05-8.2 (1H, m), 9.7-9.95 (1H, m). | Hydrochloride |
| 633 | 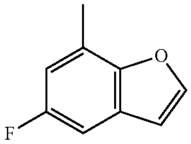 | 1H-NMR (DMSO-d6) δ ppm: 1.16-1.35 (2H, m), 1.35-1.45 (1H, m), 1.47 (3H, s), 1.54 (3H, s), 1.66-1.92 (3H, m), 1.92-2.14 (2H, m), 3.25 (1H, d, J = 13.5 Hz), 3.45 (1H, d, J = 13.4 Hz), 3.85-4.0 (1H, m), 4.2-4.35 (1H, m), 6.68 (1H, dd, J = 2.4, 12.1 Hz), 6.89-7.04 (2H, m), 8.02 (1H, d, J = 2.2 Hz), 8.26 (1H, br), 9.89 (1H, br). | Hydrochloride |
| 634 | 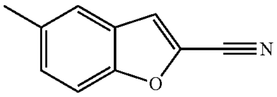 | 1H-NMR (DMSO-d6) δ ppm: 1.18-1.36 (2H, m), 1.36-1.49 (4H, m), 1.49-1.57 (3H, m), 1.62-1.94 (4H, m), 1.94-2.12 (1H, m), 3.03 (1H, d, J = 13.3 Hz), 3.25-3.4 (1H, m), 3.75-3.9 (1H, m), 3.95-4.15 (1H, m), 7.22 (1H, s), 7.37 (1H, dd, J = 2.5, 9.3 Hz), 7.62 (1H, d, J = 9.2 Hz), 7.95 (1H, s), 8.18 (1H, br), 9.6-10.1 (1H, m). | Hydrochloride |
| 635 | 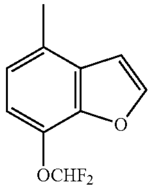 | 1H-NMR (DMSO-d6) δ ppm: 0.85-1.1 (2H, m), 1.2-1.35 (7H, m), 1.45-1.85 (4H, m), 1.85-2.05 (1H, m), 2.81 (1H, d, J = 12.0 Hz), 2.9-4.4 (5.5H, m), 6.52 (1.5H, s), 6.60 (1H, d, J = 8.6 Hz), 7.0-7.4 (3H, m), 8.00 (1H, d, J = 2.2 Hz). | Fumarate |
| 636 | 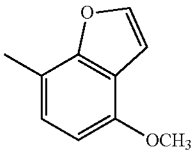 | 1H-NMR (DMSO-d6) δ ppm: 1.0-1.2 (2H, m), 1.35-1.44 (1H, m), 1.50 (3H, s), 1.53 (3H, s), 1.59-2.07 (5H, m), 3.05 (1H, d, J = 12.8 Hz), 3.27 (1H, d, J = 13.0 Hz), 3.84 (3H, s), 3.89-4.02 (2H, m), 6.66 (1H, d, J = 8.5 Hz), 6.75 (1H, d, J = 8.4 Hz), 6.93 (1H, J = 2.2 Hz), 7.92 (1H, d, J = 2.2 Hz), 8.0-8.2 (1H, m), 9.55-9.8 (1H, m). | Hydrochloride |

TABLE 69-continued absolute configuration

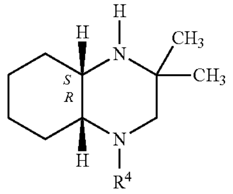

| Example. | $R^4$ | NMR | Salt |
|---|---|---|---|
| 637 | 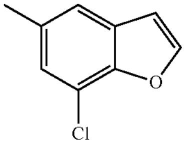 | 1H-NMR (DMSO-d6) δ ppm: 1.21-1.37 (2H, m), 1.37-1.49 (4H, m), 1.52 (3H, s), 1.63-1.92 (4H, m), 1.92-2.10 (1H, m), 3.02 (1H, d, J = 13.2 Hz), 3.29 (1H, d, J = 13.5 Hz), 3.75-3.9 (1H, m), 3.95-4.1 (1H, m), 6.92 (1H, d, J = 2.2 Hz), 7.12 (1H, d, J = 2.1 Hz), 7.16 (1H, d, J = 2.1 Hz), 8.01 (1H, d, J = 2.1 Hz), 8.06 (1H, br), 9.72 (1H, br) | Hydrochloride |
| 638 | 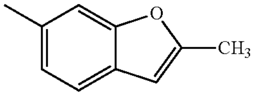 | 1H-NMR (DMSO-d6) δ ppm: 1.18-1.37 (2H, m), 1.37-1.48 (4H, m), 1.55 (3H, s), 1.61-1.98 (4H, m), 1.99-2.15 (1H, m), 2.38 (3H, s), 3.00 (1H, d, J = 13.3 Hz), 3.28 (1H, d, J = 13.2 Hz), 3.7-3.85 (1H, m), 3.95-4.05 (1H, m), 4.34 (1H, br), 6.40 (1H, s), 6.89 (1H, dd, J = 2.1, 8.6 Hz), 7.05 (1H, d, J = 1.4 Hz), 7.33 (1H, d, J = 8.5 Hz), 8.22 (1H, br), 10.07 (1H, br). | 2 Hydrochloride |
| 639 | 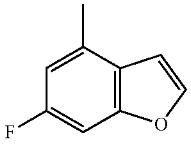 | 1H-NMR (DMSO-d6) δ ppm: 1.28-1.48 (6H, m), 1.52 (3H, s), 1.64-1.93 (4H, m), 1.95-2.06 (1H, m), 2.99 (1H, d, J = 13.6 Hz), 3.46 (1H, d, J = 13.4 Hz), 3.5-3.95 (2H, m), 4.05-4.15 (1H, m), 6.83-6.92 (2H, m), 7.01 (1H, s), 7.83 (1H, d, J = 2.1 Hz), 8.14 (1H, br), 9.82 (1H, br). | 2 Hydrochloride |
| 640 | 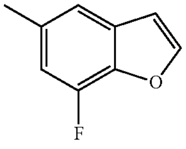 | 1H-NMR (DMSO-d6) δ ppm: 1.18-1.49 (6H, m), 1.53 (3H, s), 1.62-1.93 (4H, m), 1.95-2.12 (1H, m), 3.00 (1H, d, J = 13.2 Hz), 3.30 (1H, d, J = 13.2 Hz), 3.7-3.85 (1H, m), 3.95-4.1 (1H, m), 4.95 (1H, br), 6.91 (1H, dd, J = 2.1, 3.0 Hz), 6.94 (1H, d, J 2.1 Hz), 7.01 (1H, dd, J = 2.1, 14.3 Hz), 7.99 (1H, d, J = 2.1 Hz), 8.14 (1H, br), 9.89 (1H, br). | 2 Hydrochloride |
| 641 | 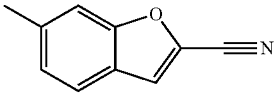 | 1H-NMR (DMSO-d6) δ ppm: 1.12-1.29 (8H, m), 1.29-1.40 (2H, m), 1.45-1.76 (4H, m), 1.82-1.96 (1H, m), 2.80 (1H, d, J = 12.6 Hz), 2.85-3.85 (4H, m), 3.85-3.95 (1H, m), 6.55 (2H, s), 7.08 (1H, s), 7.12 (1H, dd, J = 2.1, 9.0 Hz), 7.56 (1H, d, J = 8.9 Hz), 7.88 (1H, d, J = 0.6 Hz). | Fumarate |

TABLE 70 absolute configuration

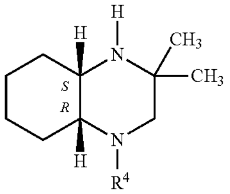

| Example. | $R^4$ | NMR | Salt |
|---|---|---|---|
| 642 | 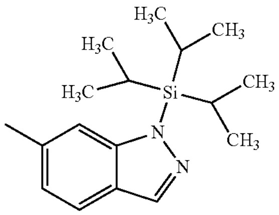 | 1H-NMR (CDCl3) δ ppm: 1.10-1.20 (20H, m), 1.22 (3H, s), 1.25-1.36 (4H, m), 1.37-1.50 (2H, m), 1.64-1.88 (7H, m), 2.82 (1H, d, J = 11.8 Hz), 3.02 (1H, d, J = 11.8 Hz), 3.45-3.55 (1H, m), 3.6-3.7 (1H, m), 6.82 (1H, s), 6.86 (1H, dd, J = 2.0, 8.9 Hz), 7.54 (1H, d, J = 8.8 Hz), 8.04 (1H, d, J = 0.9 Hz). | — |
| 643 | 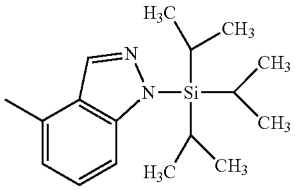 | 1H-NMR (CDCl3) δ ppm: 1.11-1.19 (19H, m), 1.21 (3H, s), 1.23-1.32 (2H, m), 1.35 (3H, s), 1.37-1.47 (2H, m), 1.63-1.86 (6H, m), 1.90-2.04 (1H, m), 3.04 (1H, d, J = 11.9 Hz), 3.09 (1H, d, J = 12.0 Hz), 3.55-3.65 (1H, m), 3.8-3.9 (1H, m), 6.41 (1H, d, J = 7.5 Hz), 7.05 (1H, d, J = 8.5 Hz), 7.16 (1H, dd, J = 7.6, 8.3 Hz), 8.26 (1H, d, J = 0.8 Hz). | — |
| 644 | 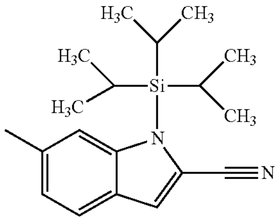 | 1H-NMR (CDCl3) δ ppm: 1.14-1.23 (21H, m), 1.23-1.33 (6H, m), 1.38-1.50 (2H, m), 1.63-1.88 (4H, m), 1.93-2.06 (3H, m), 2.82 (1H, d, J = 11.8 Hz), 3.00 (1H, d, J = 11.8 Hz), 3.44-3.50 (1H, m), 3.56-3.65 (1H, m), 6.88-6.94 (2H, m), 7.28 (1H, d, J = 0.4 Hz), 7.42-7.47 (1H, m). | — |
| 645 | 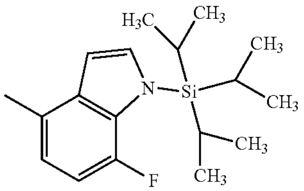 | 1H-NMR (CDCl3) δ ppm: 1.02-1.17 (21H, m), 1.19 (3H, s), 1.31-1.42 (5H, m), 1.59-1.77 (6H, m), 1.79-1.92 (1H, m), 2.67 (1H, d, J = 11.3 Hz), 3.09 (1H, d, J = 11.3 Hz), 3.45-3.6 (1H, m), 3.6-3.7 (1H, m), 6.39 (1H, dd, J = 3.4, 8.3 Hz), 6.65 (1H, dd, J = 3.2, 3.2 Hz), 6.72 (1H, d, J = 8.2, 12.7 Hz), 7.25 (1H, d, J = 3.2 Hz). | — |
| 646 | 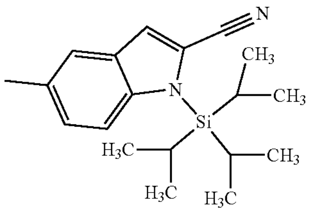 | 1H-NMR (CDCl3) δ ppm: 0.95 (1H, br), 1.15-1.30 (26H, m), 1.32-1.49 (2H, m), 1.63-1.82 (4H, m), 1.93-2.08 (3H, m), 2.78 (1H, d, J = 11.6 Hz), 2.93 (1H, d, J = 11.6 Hz), 3.45-3.55 (1H, m), 3.6-3.7 (1H, m), 6.92 (1H, d, J = 2.4 Hz), 7.07 (1H, dd, J = 2.6, 9.4 Hz), 7.23-7.28 (1H, m), 7.46 (1H, d, J = 9.4 Hz). | — |
| 647 | 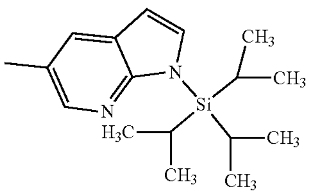 | 1H-NMR (CDCl3) δ ppm: 1.07-1.16 (19H, m), 1.17-1.32 (8H, m), 1.32-1.48 (2H, m), 1.61-1.89 (7H, m), 2.8-2.9 (2H, m), 3.5-3.55 (1H, m), 3.55-3.65 (1H, m), 6.40 (1H, d, J = 3.4 Hz), 7.21 (1H, d, J = 3.4 Hz), 7.31 (1H, d, J = 2.7 Hz), 8.06 (1H, d, J = 2.7 Hz). | — |

TABLE 70-continued absolute configuration

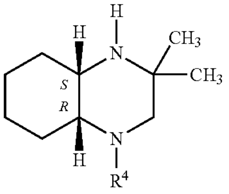

| Example. | $R^4$ | NMR | Salt |
|---|---|---|---|
| 648 | 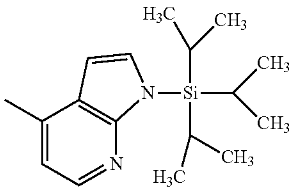 | 1H-NMR (CDCl3) δ ppm: 1.03-1.17 (19H, m), 1.19-1.36 (8H, m), 1.36-1.49 (2H, m), 1.63-1.90 (6H, m), 1.95-2.11 (1H, m), 3.05 (1H, d, J = 12.5 Hz), 3.38 (1H, d, J = 12.5 Hz), 3.45-3.55 (1H, m), 3.95-4.05 (1H, m), 6.33 (1H, d, J = 5.6 Hz), 6.54 (1H, d, J = 3.6 Hz), 7.10 (1H, d, J = 3.6 Hz), 7.98 (1H, d, J = 5.6 Hz). | — |
| 649 | 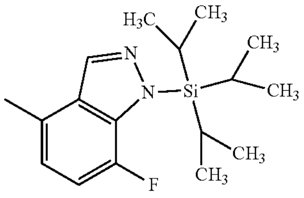 | 1H-NMR (CDCl3) δ ppm: 1.1-1.18 (19H, m), 1.18-1.22 (4H, m), 1.34 (3H, s), 1.36-1.44 (2H, m), 1.61-1.83 (7H, m), 1.85-1.98 (1H, m), 2.81 (1H, d, J = 11.5 Hz), 3.07 (1H, d, J = 11.4 Hz), 3.6-3.65 (1H, m), 3.65-3.75 (1H, m), 6.30 (1H, dd, J = 3.0, 8.2 Hz), 6.86 (1H, dd, J = 8.2, 12.0 Hz), 8.24 (1H, d, J = 3.1 Hz). | — |

TABLE 71 absolute configuration

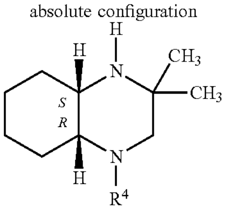

| Example. | $R^4$ | NMR | Salt |
|---|---|---|---|
| 650 | 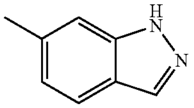 | 1H-NMR (CDCl3) δ ppm: 1.03 (1H, br), 1.15-1.34 (8H, m), 1.34-1.52 (2H, m), 1.62-1.90 (4H, m), 2.81 (1H, d, J = 11.8 Hz), 3.05 (1H, d, J = 11.8 Hz), 3.43-3.55 (1H, m), 3.69-3.81 (1H, m), 6.71 (1H, s), 6.92 (1H, d, J = 2.0, 9.0 Hz), 7.56 (1H, d, J = 8.8 Hz), 7.89 (1H, d, J = 0.9 Hz), 9.76 (1H, br). | — |
| 651 | 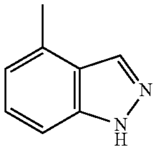 | 1H-NMR (CDCl3) δ ppm: 0.95-1.25 (6H, m), 1.33 (3H, s), 1.37-1.47 (2H, m), 1.64-1.80 (3H, m), 1.88-2.00 (1H, m), 3.02 (1H, d, J = 11.8 Hz), 3.09 (1H, d, J = 11.8 Hz), 3.62-3.68 (1H, m), 3.83-3.92 (1H, m), 6.4-6.45 (1H, m), 6.97 (1H, d, J = 8.3 Hz), 7.23 (1H, dd, J = 7.7, 8.1 Hz), 8.11 (1H, d, J = 1.0 Hz), 10.05 (1H, br). | — |
| 652 | 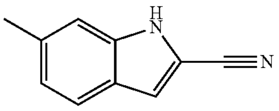 | 1H-NMR (CDCl3) δ ppm: 0.95 (1H, br), 1.15-1.33 (8H, m), 1.33-1.50 (2H, m), 1.64-1.88 (4H, m), 2.80 (1H, d, J = 11.8 Hz), 3.03 (1H, d, J = 11.8 Hz), 3.45-3.55 (1H, m), 3.65-3.75 (1H, m), 6.66 (1H, s), 6.95 (1H, dd, J = 2.1, 9.0 Hz), 7.06 (1H, dd, J = 0.8, 2.0 Hz), 7.46 (1H, d, J = 9.0 Hz), 8.22 (1H, bs). | — |

TABLE 71-continued

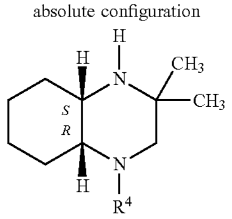

| Example. | $R^4$ | NMR | Salt |
|---|---|---|---|
| 653 | 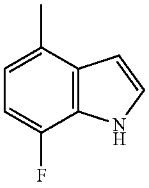 | 1H-NMR (CDCl3) δ ppm: 0.93-1.13 (3H, m), 1.20 (3H, s), 1.27-1.45 (5H, m), 1.58-1.79 (3H, m), 1.79-1.94 (1H, m), 2.70 (1H, d, J = 11.3 Hz), 3.08 (1H, d, J = 11.3 Hz), 3.6-3.7 (2H, m), 6.35 (1H, dd, J = 3.8, 8.3 Hz), 6.61 (1H, dd, J = 3.3, 5.5 Hz), 6.76 (1H, dd, J = 8.3, 10.7 Hz), 7.18 (1H, dd, J = 2.8, 2.8 Hz), 8.33 (1H, br). | — |
| 654 | 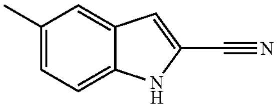 | 1H-NMR (CDCl3) δ ppm: 0.80-1.25 (6H, m), 1.28 (3H, s), 1.31-1.48 (2H, m), 1.63-1.82 (4H, m), 2.81 (1H, d, J = 11.6 Hz), 2.89 (1H, d, J = 11.6 Hz), 3.5-3.6 (1H, m), 3.6-3.7 (1H, m), 6.95 (1H, d, J = 2.1 Hz), 7.03 (1H, dd, J = 0.7, 2.0 Hz), 7.17 (1H, dd, J = 2.3, 9.1 Hz), 7.28 (1H, d, J = 9.0 Hz), 8.64 (1H, br). | — |
| 655 | 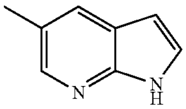 | 1H-NMR (DMSO-d6) δ ppm: 1.0-1.25 (2H, m), 1.25-1.35 (7H, m), 1.45-1.9 (5H, m), 2.55-4.35 (6H, m), 6.27 (1H, dd, J = 1.9, 3.3 Hz), 6.49 (1H, s), 7.33 (1H, dd, J = 2.9, 2.9 Hz), 7.40 (1H, d, J = 2.5 Hz), 8.04 (1H, d, J = 2.6 Hz), 11.30 (1H, s). | ½ Fumarate |
| 656 | 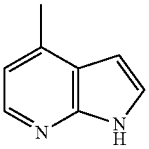 | 1H-NMR (CDCl3) δ ppm: 1.00 (1H, br), 1.18-1.36 (7H, m), 1.36-1.52 (3H, m), 1.64-1.83 (3H, m), 1.98-2.13 (1H, m), 3.09 (1H, d, J = 12.6 Hz), 3.43 (1H, d, J = 12.5 Hz), 3.52 (1H, br), 4.0-4.1 (1H, m), 6.36 (1H, d, J = 5.7 Hz), 6.51 (1H, d, J = 3.6 Hz), 7.13 (1H, d, J = 3.6 Hz), 8.03 (1H, d = 5.7 Hz), 9.99 (1H, br). | — |
| 657 | 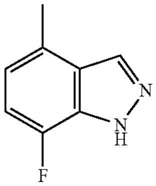 | 1H-NMR (CDCl3) δ ppm: 1.03-1.17 (2H, m), 1.22 (3H, s), 1.33 (3H, s), 1.36-1.45 (2H, m), 1.62-1.79 (3H, m), 1.83-1.96 (1H, m), 2.83 (1H, d, J = 11.5 Hz), 3.05 (1H, d, J = 11.5 Hz), 3.65-3.7 (1H, m), 3.7-3.8 (1H, m), 6.28 (1H, dd, J = 3.3, 8.3 Hz), 6.91 (1H, dd, J = 8.3, 10.3 Hz), 8.12 (1H, d, J = 3.3 Hz), 10.26 (1H, br). | — |

TABLE 72 absolute configuration

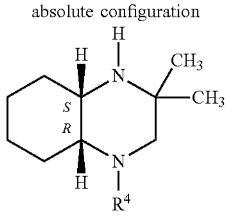

| Example. | $R^4$ | NMR | Salt |
| --- | --- | --- | --- |
| 658 | 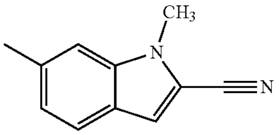 | 1H-NMR (CDCl3) δ ppm: 0.75-1.65 (11H, m), 1.65-1.9 (4H, m), 2.82 (1H, d, J = 11.7 Hz), 3.03 (1H, d, J = 11.7 Hz), 3.46-3.54 (1H, m), 3.71-3.79 (1H, m), 3.80 (3H, s), 6.51 (1H, d, J = 1.6 Hz), 6.96 (1H, dd, J = 2.1, 9.0 Hz), 7.02 (1H, s), 7.46 (1H, d, J = 9.0 Hz). | — |
| 659 | 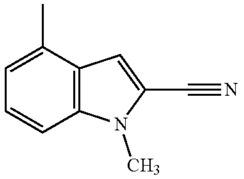 | 1H-NMR (CDCl3) δ ppm: 0.85-1.15 (3H, m), 1.20 (3H, s), 1.32 (3H, s), 1.35-1.45 (1H, m), 1.6-1.8 (4H, m), 1.85-2.0 (1H, m), 2.80 (1H, d, J = 11.5 Hz), 3.10 (1H, d, J = 11.6 Hz), 3.6-3.7 (1H, m), 3.7-3.8 (1H, m), 3.85 (3H, s), 6.52 (1H, d, J = 7.6 Hz), 6.89 (1H, d, J = 8.4 Hz) 7.20 (1H, s), 7.25-7.3 (1H, m). | — |
| 660 | 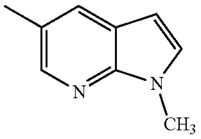 | 1H-NMR (DMSO-d6) δ ppm: 1.0-1.25 (2H, m), 1.25-1.4 (7H, m), 1.45-1.9 (5H, m), 2.93 (2H, s), 3.38 (3H, br), 3.63 (1H, br), 3.70-3.83 (4H, m), 6.28 (1H, d, J = 3.4 Hz), 6.53 (2H, s), 7.39 (1H, d, J = 3.3 Hz), 7.43 (1H, d, J = 2.6 Hz), 8.10 (1H, d, J = 2.6 Hz). | Fumarate |
| 661 | 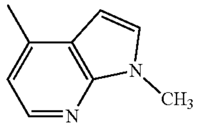 | 1H-NMR (DMSO-d6) δ ppm: 1.15-1.4 (9H, m), 1.5-1.8 (4H, m), 1.95-2.15 (1H, m), 3.09 (1H, d, J = 12.9 Hz), 3.43 (1H, d, J = 12.8 Hz), 3.55-3.65 (1H, m), 3.73 (3H, s), 4.05-4.15 (1H, m), 6.41 (1H, d, J = 5.6 Hz), 6.49 (1H, d, J = 3.6 Hz), 6.55 (2H, s), 7.26 (1H, d, J = 3.6 Hz), 7.93 (1H, d, J = 5.6 Hz). | Fumarate |
| 662 | 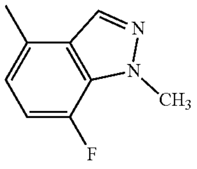 | 1H-NMR (DMSO-d6) δ ppm: 0.95-1.15 (2H, m), 1.30-1.42 (1H, m), 1.51 (3H, s), 1.54 (3H, s), 1.57-1.66 (1H, m), 1.69-1.98 (3H, m), 1.98-2.09 (1H, m), 2.99 (1H, d, J = 12.9 Hz), 3.26 (1H, d, J = 12.8 Hz), 3.9-4.0 (1H, m), 4.05-4.2 (4H, s), 6.39 (1H, dd, J = 3.0, 8.3 Hz), 7.05 (1H, dd, J = 8.2, 11.8 Hz), 8.14 (1H, br), 8.38 (1H, d, J = 2.3 Hz), 9.95 (1H, br). | Hydrochloride |
| 663 | 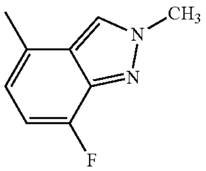 | 1H-NMR (DMSO-d6) δ ppm: 1.00-1.16 (2H, m), 1.34-1.44 (1H, m), 1.50 (3H, s), 1.52 (3H, s), 1.58-1.95 (4H, m), 1.98-2.09 (1H, m), 2.98 (1H, d, J = 13.0 Hz), 3.24 (1H, d, J = 13.0 Hz), 3.85-3.95 (1H, m), 3.95-4.1 (1H, m), 4.17 (3H, s), 6.24 (1H, dd, J = 3.2, 8.0 Hz), 6.85 (1H, dd, J = 8.0, 11.5 Hz), 7.95-8.2 (1H, m), 8.74 (1H, d, J = 2.7 Hz), 9.75-9.95 (1H, m). | Hydrochloride |
| 664 | 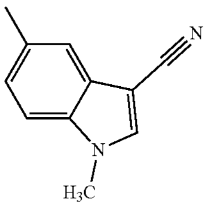 | 1H-NMR (DMSO-d6) δ ppm: 1.05-1.3 (2H, m), 1.3-1.45 (7H, m), 1.5-1.7 (2H, m), 1.7-1.9 (3H, m), 2.97 (1H, d, J = 12.4 Hz), 3.17 (1H, d, J = 12.7 Hz), 3.72 (1H, br), 3.81 (3H, s), 3.9-4.0 (1H, m), 6.58 (6H, s), 6.98 (1H, d, J = 2.0 Hz), 7.14 (1H, dd, J = 2.2, 9.1 Hz), 7.49 (1H, d, J = 9.0 Hz), 8.10 (1H, s). | 3 Fumarate |

TABLE 72-continued absolute configuration

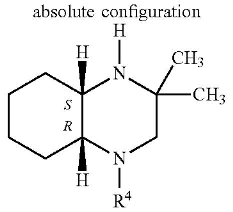

| Example. | $R^4$ | NMR | Salt |
|---|---|---|---|
| 665 | 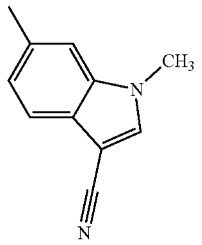 | 1H-NMR (DMSO-d6) δ ppm: 1.05-1.15 (1H, m), 1.15-1.35 (9H, m), 1.45-1.75 (3H, m), 1.75-1.9 (1H, m), 2.80 (1H, d, J = 11.9 Hz), 3.0-3.6 (4H, m), 3.77 (3H, s), 3.8-3.9 (1H, m), 6.51 (1H, s), 6.90 (1H, d, J = 1.8 Hz), 7.03 (1H, dd, J = 2.0, 8.9 Hz), 7.43 (1H, d, J = 8.8 Hz), 7.99 (1H, s). | ½ Fumarate |

TABLE 73 absolute configuration

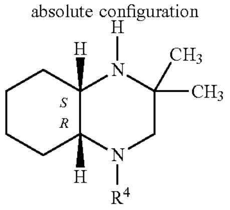

| Example. | $R^4$ | NMR | Salt |
|---|---|---|---|
| 666 | 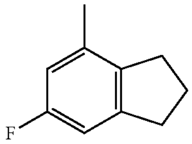 | 1H-NMR (DMSO-d6) δ ppm: 1.00-1.25 (2H, m), 1.31-1.42 (1H, m), 1.46 (3H, s), 1.49 (3H, s), 1.58-1.69 (1H, m), 1.69-1.84 (2H, m), 1.84-2.05 (3H, m), 2.05-2.2 (1H, m), 2.70-2.92 (5H, m), 3.24 (1H, d, J = 13.0 Hz), 3.45-3.57 (1H, m), 3.80-3.93 (1H, m), 6.53 (1H, dd, J = 2.0, 11.6 Hz), 6.66-6.76 (1H, m), 7.9-8.2 (1H, m), 9.7-10.0 (1H, m). | Hydrochloride |
| 667 | 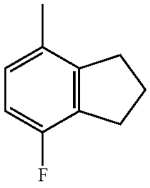 | 1H-NMR (DMSO-d6) δ ppm: 1.00-1.21 (2H, m), 1.29-1.41 (1H, m), 1.48 (6H, s), 1.55-1.67 (1H, m), 1.67-2.06 (5H, m), 2.07-2.21 (1H, m), 2.70 (1H, d, J = 12.7 Hz), 2.78-3.00 (4H, m), 3.21-3.39 (2H, m), 3.78-3.89 (1H, m), 6.74 (1H, dd, J = 4.4, 8.6 Hz), 6.88 (1H, dd, J = 8.6, 8.6 Hz), 8.01 (1H, br), 9.74 (1H, br). | Hydrochloride |
| 668 | 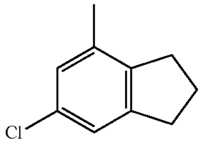 | 1H-NMR (DMSO-d6) δ ppm: 1.10-1.24 (1H, m), 1.34-1.42 (1H, m), 1.45 (3H, s), 1.48 (3H, s), 1.58-2.03 (6H, m), 2.03-2.19 (1H, m), 2.72-2.95 (5H, m), 3.27 (1H, d, J = 12.9 Hz), 3.38-3.55 (1H, m), 3.79-3.95 (1H, m), 4.28-4.11 (1H, m), 6.72 (1H, d, J = 1.5 Hz), 6.94 (1H, s), 7.9-8.1 (1H, m), 9.6-9.8 (1H, m). | Hydrochloride |
| 669 | 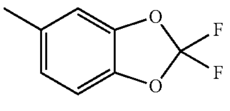 | 1H-NMR (DMSO-d6) δ ppm: 1.20-1.48 (6H, m), 1.51 (3H, s), 1.63-1.93 (4H, m), 1.93-2.10 (1H, m), 2.96 (1H, d, J = 13.4 Hz), 3.29 (1H, d, J = 14.0 Hz), 3.7-3.85 (1H, m), 3.9-4.05 (1H, m), 6.70 (1H, dd, J = 2.5, 8.9 Hz), 7.12 (1H, d, J = 2.4 Hz), 7.23 (1H, d, J = 8.9 Hz), 8.15 (1H, br), 9.86 (1H, br). | Hydrochloride |

TABLE 73-continued absolute configuration

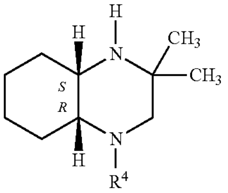

| Example. | $R^4$ | NMR | Salt |
|---|---|---|---|
| 670 | 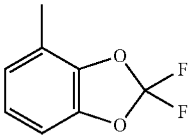 | 1H-NMR (DMSO-d6) δ ppm: 1.1-1.25 (9H, m), 1.25-1.4 (1H, m), 1.45-1.75 (4H, m), 1.9-2.05 (1H, m), 2.92 (1H, d, J = 12.2 Hz), 3.06 (1H, d, J = 12.3 Hz), 3.1-3.63 (3H, m), 3.63-3.70 (1H, m), 6.57 (2H, s), 6.71 (1H, d, J = 8.6 Hz), 6.75-6.81 (1H, m), 7.04 (1H, dd, J = 8.3, 8.3 Hz). | Fumarate |
| 671 | 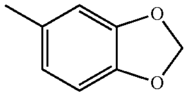 | 1H-NMR (DMSO-d6) δ ppm: 1.15-1.31 (2H, m), 1.35-1.46 (4H, m), 1.50 (3H, s), 1.61-1.87 (4H, m), 1.93-2.07 (1H, m), 2.92 (1H, d, J = 13.2 Hz), 3.11 (1H, d, J = 13.2 Hz), 3.7-3.8 (1H, m), 3.8-3.9 (1H, m), 5.88-5.95 (2H, m), 6.32 (1H, d, J = 2.4, 8.5 Hz), 6.71 (1H, d, J = 2.4 Hz), 6.76 (1H, d, J = 8.5 Hz), 7.9-8.15 (1H, m), 9.7-9.9 (1H, m). | Hydrochloride |

TABLE 74 absolute configuration

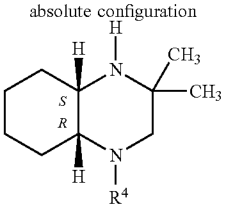

| Example | $R^4$ | NMR | Salt |
|---|---|---|---|
| 672 | 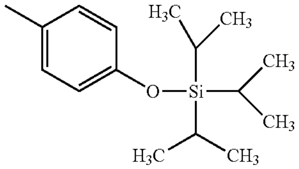 | 1H-NMR (CDCl3) δ ppm: 1.02-1.15 (19H, m), 1.15-1.28 (11 H, m), 1.29-1.46 (2H, m) 1.60-1.76 (4H, m), 2.67 (1H, d, J = 11.6 Hz), 2.83 (1H, d, J = 11.6 Hz), 3.4-3.55 (2H, m), 6.69-6.74 (2H, m), 6.74-6.79 (2H, m). | — |
| 673 | 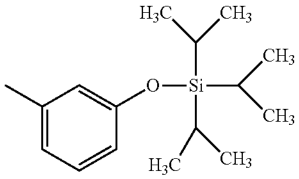 | 1H-NMR (CDCl3) δ ppm: 1.11 (18H, d, J = 7.0 Hz), 1.16-1.33 (11H, m), 1.33-1.59 (3H, m), 1.65-1.78 (4H, m), 2.68 (1H, d, J = 11.8 Hz), 2.97 (1H, d, J = 11.9 Hz), 3.4-3.45 (1H, m), 3.55-3.6 (1H, m), 6.28 (1H, dd, J = 1.9, 7.6 Hz), 6.37 (1H, dd, J = 2.3, 2.3 Hz), 6.43 (1H, dd, J = 2.4, 7.8 Hz), 7.03 (1H, dd, J = 8.1, 8.1 Hz). | — |
| 674 | 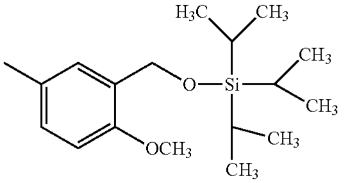 | 1H-NMR (CDCl3) δ ppm: 1.04-1.15 (19H, m), 1.15-1.30 (11H, m), 1.32-1.47 (2H, m), 1.47-1.77 (4H, m), 2.70 (1H, d, J = 11.7 Hz), 2.92 (1H, d, J = 11.7 Hz), 3.41-3.48 (1H, m) 3.54-3.63 (1H, m), 3.75 (3H, s), 4.78-4.88 (2H, m), 6.65 (1H, dd, J = 3.0, 8.7 Hz), 6.71 (1H, d, J = 8.8 Hz), 7.22 (1H, d, J = 2.9 Hz). | — |

TABLE 74-continued absolute configuration

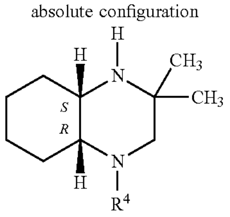

| Example | $R^4$ | NMR | Salt |
|---|---|---|---|
| 675 | 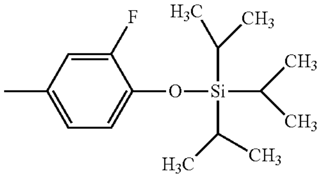 | 1H-NMR (CDCl3) δ ppm: 1.06-1.14 (18H, m), 1.15-1.29 (12H, m), 1.29-1.48 (2H, m), 1.58-1.76 (4H, m), 2.65 (1H, d, J = 11.8 Hz), 2.83 (1H, d, J = 11.6 Hz), 3.35-3.45 (1H, m), 3.45-3.55 (1H, m), 6.40-6.48 (1H, m), 6.55 (1H, dd, J = 2.9, 14.1 Hz), 6.79 (1H, dd, J = 9.4, 9.4 Hz). | — |
| 676 | 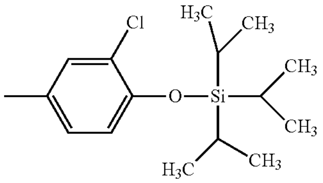 | 1H-NMR (CDCl3) δ ppm: 1.11 (18H, d, J = 7.3 Hz), 1.16-1.21 (4H, m), 1.21-1.33 (7H, m), 1.34-1.47 (2H, m), 1.47-1.78 (5H, m), 2.66 (1H, d, J = 11.6 Hz), 2.81 (1H, d, J = 11.6 Hz), 3.4-3.55 (2H, m), 6.61 (1H, d, J = 3.0, 8.9 Hz), 6.78 (1H, d, J = 8.9 Hz), 6.81 (1H, d, J = 3.0 Hz). | — |
| 677 | 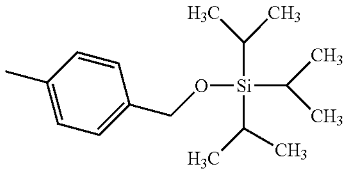 | 1H-NMR (CDCl3) δ ppm: 1.06-1.11 (18H, m), 1.11-1.22 (7H, m), 1.23 (3H, s), 1.25-1.80 (8H, m), 2.71 (1H, d, J = 11.8 Hz), 3.01 (1H, d, J = 11.9 Hz), 3.4-3.5 (1H, m), 3.6-3.7 (1H, m), 4.73 (2H, s), 6.79-6.85 (2H, m), 7.18-7.23 (2H, m), | — |
| 678 | 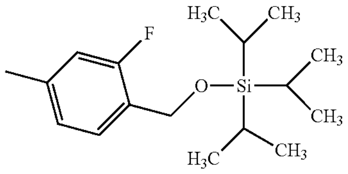 | 1H-NMR (CDCl3) δ ppm: 1.05-1.12 (18H, m), 1.12-1.48 (13H, m), 1.48-1.82 (5H, m), 2.70 (1H, d, J = 11.9 Hz), 2.99 (1H, d, J = 12.0 Hz), 3.35-3.45 (1H, m), 3.55-3.65 (1H, m), 4.77 (2H, s), 6.47 (1H, dd, J = 2.4, 13.9 Hz), 6.61 (1H, dd, J = 2.4, 8.6 Hz), 7.32 (1H, dd, J = 8.8, 8.8 Hz). | — |
| 679 | 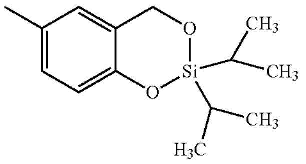 | 1H-NMR (CDCl3) δ ppm: 1.03 (18H, d, J = 2.4 Hz), 1.13-1.27 (9H, m), 1.27-1.77 (6H, m), 2.67 (1H, d, J = 11.5 Hz), 2.80 (1H, d, J = 11.5 Hz), 3.4-3.55 (2H, m), 4.96 (2H, s), 6.42 (1H, d, J = 2.8 Hz), 6.70 (1H, dd, J = 2.9, 8.8 Hz), 6.80 (1H, d, J = 8.8 Hz). | — |

TABLE 75 absolute configuration

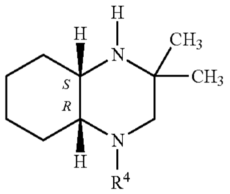

| Example | $R^4$ | NMR | Salt |
| --- | --- | --- | --- |
| 680 | 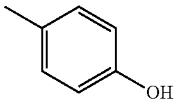 | 1H-NMR (CDCl3) δ ppm: 1.02-1.30 (9H, m), 1.30-1.49 (2H, m), 1.50-1.83 (4H, m), 2.70 (1H, d, J = 10.4 Hz), 2.81 (1H, d, J = 11.4 Hz), 3.4-3.6 (2H, m), 6.75 (4H, bs). | — |
| 681 | 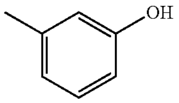 | 1H-NMR (CDCl3) δ ppm: 1.16-1.30 (8H, m), 1.30-1.49 (3H, m), 1.60-1.83 (4H, m), 2.71 (1H, d, J = 12.0 Hz), 3.03 (1H, d, J = 12.0 Hz), 3.38-3.45 (1H, m), 3.56-3.68 (1H, m), 6.17-6.23 (1H, m), 6.33 (1H, dd, J = 2.3, 2.3 Hz), 6.43 (1H, dd, J = 2.2, 8.3 Hz), 7.06 (1H, dd, J = 8.1, 8.1 Hz). | — |
| 682 | 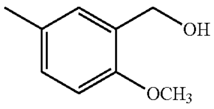 | 1H-NMR (DMSO-d6) δ ppm: 1.1-1.25 (2H, m), 1.3-1.4 (7H, m), 1.5-1.9 (5H, m) 2.87 (1H, d, J = 12.4 Hz), 2.97 (1H, d, J = 12.6 Hz) 3.63-3.78 (5H, m), 4.44 (2H, s), 6.54 (3H, s), 6.73 (1H, dd, J = 2.9, 8.8 Hz), 6.80 (1H, d, J = 8.8 Hz), 6.99 (1H, d, J = 2.8 Hz). | ½ Fumarate |
| 683 | 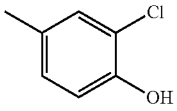 | 1H-NMR (CDCl3) δ ppm: 1.09-2.34 (16H, m), 2.81 (1H, d, J = 12.1 Hz), 2.85-3.1 (1H, m), 3.5-3.6 (1H, m), 3.6-3.75 (1H, m), 6.73 (1H, dd, J = 2.8, 8.9 Hz), 6.81 (1H, d, J = 2.8 Hz), 6.92 (1H, d, J = 8.8 Hz). | — |
| 684 | 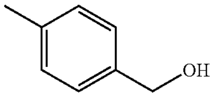 | 1H-NMR (CDCl3) δ ppm: 1.15-1.60 (12H, m), 1.61-1.83 (4H, m), 2.72 (1H, d, J = 12.0 Hz), 3.03 (1H, d, J = 11.9 Hz), 3.4-3.45 (1H, m), 3.6-3.7 (1H, m), 4.56 (2H, s), 6.80-6.86 (2H, m), 7.20-7.25 (2H, m). | — |
| 685 | 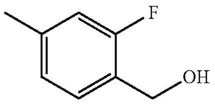 | 1H-NMR (CDCl3) δ ppm: 0.92 (1H, br), 1.16-1.36 (8H, m), 1.37-1.48 (2H, m), 1.57 (1H, br), 1.62-1.84 (4H, m), 2.71 (1H, d, J = 12.0 Hz), 3.02 (1H, d, J = 12.0 H), 3.35-3.45 (1H, m), 3.55-3.65 (1H, m), 4.62 (2H, s), 6.51 (1H, dd, J = 2.5, 14.0 Hz), 6.59 (1H, dd, J = 2.5, 8.5 Hz), 7.19 (1H, dd, J = 8.8, 8.8 Hz). | — |
| 686 | 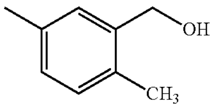 | 1H-NMR (CDCl3) δ ppm: 0.92-1.02 (1H, m), 1.02-1.18 (7H, m), 1.19-1.32 (1H, m), 1.35-1.66 (5H, m), 1.69-1.83 (1H, m), 2.60 (1H, d, J = 11.3 Hz), 2.69 (1H, d, J = 11.3 Hz), 3.32 (1H, br), 3.41-3.50 (1H, m), 4.43 (2H, d, J = 4.6 Hz), 4.88 (1H, t, J = 5.4 Hz), 6.55 (1H, dd, J = 2.9, 8.7 Hz), 6.60 (1H, d, J = 8.6 Hz), 6.83 (1H, d, J = 2.7 Hz), 8.55 (1H, s). | — |

TABLE 76 absolute configuration

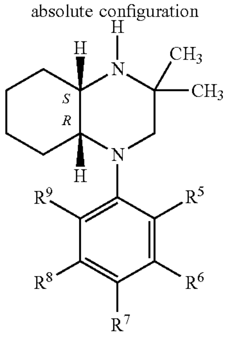

| Example | $R^5$ | $R^6$ | $R^7$ | $R^8$ | $R^9$ | NMR | Salt |
|---|---|---|---|---|---|---|---|
| 687 | —H | —H | —OCH3 | —H | —H | 1H-NMR (DMSO-d6) δ ppm: 1.1-1.3 (2H, m), 1.35-1.45 (4H, m), 1.52 (3H, s), 1.6-1.9 (4H, m), 1.95-2.1 (1H, m), 2.93 (1H, d, J = 13.1 Hz), 3.10 (1H, d, J = 13.0 Hz), 3.68 (3H, s), 3.7-3.9 (2H, m), 4.35-5.75 (1H, m), 6.75-6.85 (2H, m), 6.85-6.95 (2H, m), 8.11 (1H, br), 9.92 (1H, br). | 2 Hydrochloride |
| 688 | —CH3 | —Cl | —H | —H | —H | 1H-NMR (CDCl3) δ ppm: 0.93-1.1 (2H, m), 1.17 (3H, s), 1.31 (3H, s), 1.35-1.43 (2H, m), 1.55-1.75 (3H, m), 1.78-1.93 (1H, m), 2.37 (3H, s), 2.42 (1H, d, J = 11.0 Hz), 2.83-2.91 (1H, m), 3.10 (1H, d, J = 11.0 Hz), 3.5-3.6 (1H, m), 6.79 (1H, dd, J = 2.1, 7.1 Hz), 6.99-7.09 (2H, m). | — |
| 689 | —CH3 | —H | —H | —H | —H | 1H-NMR (DMSO-d6) δ ppm: 1.0-1.17 (2H, m), 1.3-1.43 (1H, m), 1.49 (3H, s), 1.52 (3H, s), 1.56-1.68 (1H, m), 1.68-1.87 (2H, m), 1.87-2.1 (2H, m), 2.30 (3H, s), 2.62 (1H, d, J = 12.6 Hz), 3.11-3.23 (1H, m), 3.25-3.45 (1H, m), 3.78-3.92 (1H, m), 6.92-7.04 (2H, m), 7.08-7.22 (2H, m), 8.03 (1H, br), 9.65-9.95 (1H, m). " | Hydrochloride |
| 690 | —H | —H | —CH3 | —H | —H | 1H-NMR (DMSO-d6) δ ppm: 1.18-1.35 (2H, m), 1.35-1.48 (4H, m), 1.52 (3H, s), 1.62-1.9 (4H, m), 1.98-2.04 (1H, m), 2.19 (3H, s), 2.91 (1H, d, J = 13.3 Hz), 3.25 (1H, d, J = 13.3 Hz), 3.7-3.8 (1H, m), 3.9- | 2 Hydrochloride |

TABLE 76-continued absolute configuration

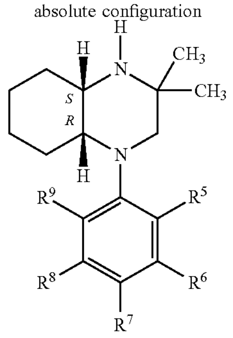

| Example | $R^5$ | $R^6$ | $R^7$ | $R^8$ | $R^9$ | NMR | Salt |
|---|---|---|---|---|---|---|---|
| | | | | | | 4.0 (1H, m), 4.1-4.45 (1H, m), 6.8-6.87 (2H, m), 6.98-7.07 (2H, m), 8.05-8.25 (1H, m), 9.8-10.05 (1H, m). " | |
| 691 | —CH3 | —CH3 | —H | —H | —H | 1H-NMR (DMSO-d6) δ ppm: 0.98-1.15 (2H, m), 1.3-1.42 (1H, m), 1.49 (3H, s), 1.52 (3H, s), 1.55-1.67 (1H, m), 1.67-1.83 (2H, m), 1.83-2.008 (2H, m), 2.20 (3H, s), 2.22 (3H, s), 2.59 (1H, d, J = 12.6 Hz), 3.05-3.15 (1H, m), 3.25-3.4 (1H, m), 3.82-3.96 (1H, m), 6.82 (1H, d, J = 7.8 Hz), 6.91 (1H, d, J = 7.4 Hz), 7.03 (1H, dd, J = 7.7, 7.7 Hz), 7.98 (1H, br), 9.65-9.8 (1H, m). | Hydrochloride |
| 692 | —H | —CH3 | —Cl | —H | —H | 1H-NMR (DMSO-d6) δ ppm: 1.22-1.47 (6H, m), 1.53 (3H, s), 1.63-1.93 (4H, m), 1.97-2.08 (1H, m), 2.27 (3H, s), 2.93 (1H, d, J = 13.6 Hz), 3.36 (1H, d, J = 13.5 Hz), 3.7-3.8 (1H, m), 3.8-4.1 (2H, m), 6.79 (1H, dd, J = 3.0, 8.9 Hz), 6.93 (1H, d, J = 2.9 Hz), 7.20 (1H, d, J = 8.8 Hz), 8.1-8.3 (1H, m), 9.85-10.05 (1H, m). | 2 Hydrochloride |
| 693 | —H | —CH3 | —F | —H | —H | 1H-NMR (DMSO-d6) δ ppm: 1.16-1.33 (2H, m), 1.36-1.45 (4H, m), 1.52 (3H, s), 1.62-1.9 (4H, m), 2.0-2.08 (1H, m), 2.18 (3H, d, J = 1.7 Hz), 2.93 (1H, d, J = 13.3 Hz), 3.21 (1H, d, J = 13.2 Hz), 3.7-3.8 (1H, m), 3.9-4.0 (1H, m), 4.15-4.55 (1H, m), 6.72-6.8 (1H, m), 6.81- | 2 Hydrochloride |

TABLE 76-continued absolute configuration

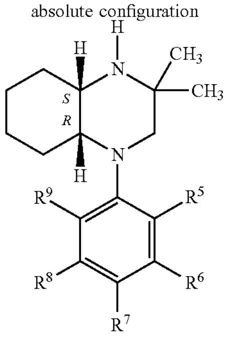

| Example | $R^5$ | $R^6$ | $R^7$ | $R^8$ | $R^9$ | NMR | Salt |
|---|---|---|---|---|---|---|---|
| | | | | | | 6.89 (1H, m), 6.97 (1H, dd, J = 9.1, 9.1 Hz), 8.05-8.25 (1H, m), 9.85-10.1 (1H, m). | |
| 694 | —CH3 | —F | —H | —H | —H | 1H-NMR (DMSO-d6) δ ppm: 1.0-1.2 (2H, m), 1.3-1.45 (1H, m), 1.49 ( 3H, s), 1.51 (3H, s), 1.56-1.84 (3H, m), 1.84-2.06 (2H, m), 2.20 (3H, d, J = 2.2 Hz), 2.67 (1H, d, J = 12.7 Hz), 3.15-3.25 (1H, m), 3.29-3.42 (1H, m), 3.85-4.0 (1H, m), 6.83 (1H, d, J = 8.0 Hz), 6.89 (1H, dd, J = 8.8, 8.8 Hz), 7.16 (1H, dd, J = 7.9, 15.3 Hz), 8.02 (1H, br), 9.72 (1H, br). | Hydrochloride |
| 695 | —H | —Cl | —H | —H | —H | 1H-NMR (DMSO-d6) δ ppm: 1.25-1.46 (6H, m), 1.52 (3H, s), 1.63-1.95 (4H, m), 1.95-2.1 (1H, m), 2.95 (1H, d, J = 13.7 Hz), 3.47 (1H, d, J = 13.6 Hz), 3.7-3.8 (1H, m), 4.0-4.1 (1H, m), 6.77 (1H, dd, J = 1.4, 7.8 Hz), 6.90 (1H, d, J = 2.2, 8.4 Hz), 6.96-7.01 (1H, m), 7.21 (1H, dd, J = 8.1, 8.1 Hz), 8.17 (1H, br), 9.85 (1H, br). | Hydrochloride |
| 696 | —CH3 | —OCH3 | —H | —H | —H | 1H-NMR (DMSO-d6) δ ppm: 1.0-1.2 (2H, m), 1.3-1.4 (1H, m), 1.48 (3H, s), 1.51 (3H, s), 1.55-1.65 (1H, m), 1.65-1.85 (2H, m), 1.85-2.05 (2H, m), 2.13 (3H, s), 2.62 (1H, d, J = 12.6 Hz), 3.1-3.2 (1H, m), 3.3-3.4 (1H, m), 3.76 (3H, s), 3.8-3.9 (1H, m), 6.61 (1H, d, J = 7.9 Hz), 6.72 (1H, d, J = 8.1 Hz), 7.10 (1H, dd, J = 8.1, | Hydrochloride |

TABLE 76-continued absolute configuration

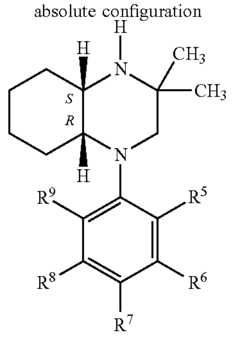

| Example | $R^5$ | $R^6$ | $R^7$ | $R^8$ | $R^9$ | NMR | Salt |
|---|---|---|---|---|---|---|---|
| | | | | | | 8.1 Hz), 8.01 (1H, br), 9.71 (1H, br). | |
| 697 | —H | —Cl | —CH3 | —H | —H | 1H-NMR (DMSO-d6) δ ppm: 1.24-1.47 (6H, m), 1.51 (3H, s), 1.63-1.91 (4H, m), 1.91-2.08 (1H, m), 2.20 (3H, s), 2.91 (1H, d, J = 13.5 Hz), 3.23-3.42 (1H, m), 3.66-3.80 (1H, m), 3.94-4.08 (1H, m), 6.84 (1H, dd, J = 2.6, 8.5 Hz), 6.97 (1H, d, J = 2.6 Hz), 7.16 (1H, d, J = 8.6 Hz), 8.12 (1H, br), 9.82 (1H, br). | Hydrochloride |
| 698 | —H | —F | —CH3 | —H | —H | 1H-NMR (DMSO-d6) δ ppm: 1.25-1.45 (6H, m), 1.51 (3H, s), 1.65-1.9 (4H, m), 2.0-2.05 (1H, m), 2.10 (3H, s), 2.91 (1H, d, J = 13.6 Hz), 3.3-3.45 (1H, m), 3.7-3.8 (1H, m), 3.95-4.05 (1H, m), 6.67 (1H, dd, J = 2.5, 8.5 Hz), 6.74 (1H, dd, J = 2.4, 13.5 Hz), 7.08 (1H, dd, J = 8.9, 8.9 Hz), 8.0-8.3 (1H, m), 9.75-10.0 (1H, m). | Hydrochloride |
| 699 | —H | —H | —OCHF2 | —H | —H | 1H-NMR (DMSO-d6 ) δ ppm: 1.21-1.35 (2H, m), 1.35-1.48 (4H, m), 1.53 (3H, s), 1.63-1.95 (4H, m), 1.98-2.12 (1H, m), 2.94 (1H, d, J = 13.4 Hz), 3.32 (1H, d, J = 13.3 Hz), 3.7-3.8 (1H, m), 3.9-4.05 (1H, m), 6.85-7.26 (5H, m), 8.20 (1H, br), 9.99 (1H, br). | Hydrochloride |
| 700 | —H | —H | —OCF3 | —H | —H | 1H-NMR (DMSO-d6) δ ppm: 1.25-1.49 (6H, m), 1.49-1.57 (3H, m), 1.65-1.95 (4H, m), 1.95-2.09 (1H, m), 2.96 (1H, d, J = 13.6 Hz), 3.39-3.48 (1H, m), 3.71-3.83 (1H, m), 3.98-4.09 | Hydrochloride |

TABLE 76-continued absolute configuration

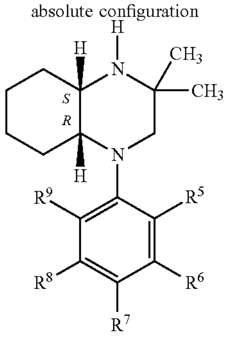

| Example | $R^5$ | $R^6$ | $R^7$ | $R^8$ | $R^9$ | NMR | Salt |
|---|---|---|---|---|---|---|---|
| | | | | | | (1H, m), 6.98-7.05 (2H, m), 7.16-7.24 (2H, m, 8.16 (1H, br), 9.65-10.1 (1H, m). | |
| 701 | —H | —Cl | —CN | —H | —H | 1H-NMR (DMSO-d6) δ ppm: 1.10 (3H, s), 1.15-1.25 (4H, m), 1.25-1.45 (2H, m), 1.45-1.7 (4H, m), 1.85-2.0 (1H, m), 2.76 (1H, d, J = 12.8 Hz), 2.85-3.85 (4H, m), 3.85-3.95 (1H, m), 6.56 (1H, s), 6.94 (1H, dd, J = 2.5, 9.1 Hz), 7.09 (1H, d, J = 2.4 Hz), 7.59 (1H, d, J = 9.0 Hz). | ½ Fumarate |
| 702 | —H | —F | —OCF3 | —H | —H | 1H-NMR (DMSO-d6) δ ppm: 1.25-1.5 (6H, m), 1.52 (3H, s), 1.65-2.1 (5H, m), 2.97 (1H, d, J = 13.8 Hz), 3.54 (1H, d, J = 13.6 Hz), 3.65-3.8 (1H, m), 4.0-4.15 (1H, m), 6.81 (1H, dd, J = 2.2, 9.3 Hz), 7.05 (1H, dd, J = 2.9, 14.4 Hz), 7.34 (1H, dd, J = 9.0, 9.0 Hz), 8.24 (1H, br), 9.92 (1H, br). | Hydrochloride |
| 703 | —H | —F | —OCHF2 | —H | —H | 1H-NMR (DMSO-d6) δ ppm: 1.10-1.37 (9H, m), 1.44-1.75 (4H, m), 1.75-1.90 (1H, m), 2.68 (1H, d, J = 12.4 Hz), 3.15 (1H, d, J = 12.4 Hz), 3.25-3.45 (1H, m), 3.7-3.8 (1H, m), 6.51 (1H, m), 6.67 (1H, d, J = 2.1, 9.1 Hz), 6.81-7.24 (3H, m) | ½ Fumarate |
| 704 | —H | —Cl | —OCHF2 | —H | —H | 1H-NMR (DMSO-d6) δ ppm: 1.07-1.36 (9H, m), 1.43-1.58 (1H, m), 1.58-1.72 (3H, m), 1.73-1.89 (1H, m), 2.67 (1H, d, J = 12.2 Hz), 3.0-3.7 (4H, m), 3.7-3.8 (1H, m), 6.52 (1H, s), 6.82-7.24 (4H, | ½ Fumarate |

TABLE 76-continued absolute configuration

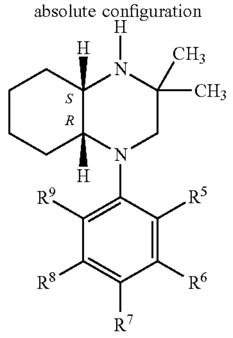

| Example | $R^5$ | $R^6$ | $R^7$ | $R^8$ | $R^9$ | NMR | Salt |
|---|---|---|---|---|---|---|---|
| | | | | | | m). | |
| 705 | —H | —CHF2 | —H | —H | —H | 1H-NMR (DMSO-d6) δ ppm: 1.15-1.41 (9H, m), 1.48-1.92 (5H, m), 2.75 (1H, d, J = 12.7 Hz), 2.8-4.4 (6H, m), 6.46 (1H, d, J = 7.8 Hz), 6.54 (2H, s), 6.62 (1H, s), 6.76 (1H, dd, J = 2.1, 8.5 Hz), 7.0-7.4 (2H, m). | Fumarate |
| 706 | —H | —OCHF2 | —F | —H | —H | 1H-NMR (DMSO-d6) δ ppm: 0.97-1.36 (9H, m), 1.43-1.73 (4H, m), 1.73-1.87 (1H, m), 2.67 (1H, d, J = 12.1 Hz), 2.95-3.8 (5H, m), 6.52 (1H, s), 6.7-6.8 (2H, m), 7.0-7.4 (2H, m). | ½ Fumarate |
| 707 | —H | —OCHF2 | —Cl | —H | —H | 1H-NMR (DMSO-d6) δ ppm: 1.11-1.37 (9H, m), 1.45-1.74 (4H, m), 1.77-1.91 (1H, m), 2.69 (1H, d, J = 12.3 Hz), 2.75-4.2 (5H, m), 6.52 (1H, s), 6.73-6.83 (2H, m), 7.03-7.43 (2H, m). | ½ Fumarate |
| 708 | —H | —CN | —OCHF2 | —H | —H | 1H-NMR (DMSO-d6) δ ppm: 1.06-1.21 (7H, m), 1.21-1.36 (2H, m), 1.41-1.70 (4H, m), 1.74-1.89 (1H, m), 2.68 (1H, d, J = 12.3 Hz), 2.9-3.75 (4H, m), 3.75-3.85 (1H, m), 6.54 (1H, s), 6.99-7.14 (4H, m). | ½ Fumarate |
| 709 | —H | —OCHF2 | —OCHF2 | —H | —H | 1H-NMR (DMSO-d6) δ ppm: 1.1-1.4 (9H, m), 1.45-1.75 (4H, m), 1.75-1.9 (1H, m), 2.69 (1H, d, J = 12.2 Hz), 2.8-4.3 (5H, m), 6.52 (1H, s), 6.71-7.38 (5H, m). | ½ Fumarate |
| 710 | —H | —F | —OCHF2 | —F | —H | 1H-NMR (DMSO-d6) δ ppm: 1.08-1.22 (7H, m), 1.25-1.40 (2H, m), 1.42-1.72 (4H, m), 1.76- | ½ Fumarate |

TABLE 76-continued absolute configuration

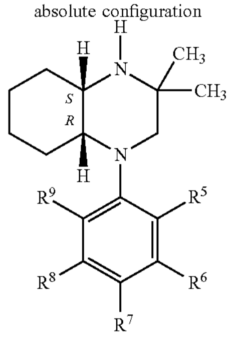

| Example | $R^5$ | $R^6$ | $R^7$ | $R^8$ | $R^9$ | NMR | Salt |
|---|---|---|---|---|---|---|---|
| | | | | | | 1.92 (1H, m), 2.66 (1H, d, J = 12.5 Hz), 2.8-4.35 (5H, m), 6.53 (1H, s), 6.66-6.76 (2H, m), 7.05 (1H, t, J = 72.9 Hz). | |
| 711 | —H | —H | —OCH2CHF2 | —H | —H | 1H-NMR (DMSO-d6) δ ppm: 1.15-1.31 (2H, m), 1.32-1.49 (4H, m), 1.52 (3H, s), 1.62-1.89 (4H, m), 1.98-2.08 (1H, m), 2.93 (1H, d, J = 13.1 Hz), 3.16 (1H, d, J = 13.2 Hz), 3.7-3.8 (1H, m), 3.80-4.27 (4H, m), 6.18-6.50 (1H, m), 6.90 (4H, s), 8.0-8.25 (1H, m), 9.8-10.1 (1H, m). | 2 Hydrochloride |
| 712 | —H | —F | —OCH2CF2 | —H | —H | 1H-NMR (DMSO-d6), δ ppm: 1.20-1.46 (6H, m), 1.51 (3H, s), 1.63-1.89 (4H m), 1.92-2.08 (1H, m), 2.91 (1H, d, J = 13.4 Hz), 3.29 (1H, d, J = 12.8 Hz), 3.67-3.79 (1H, m), 3.88-4.01 (1H, m), 4.20-4.33 (2H, m), 6.18-6.52 (1H, m), 6.68 (1H, dd, J = 1.8, 9.1 Hz), 6.91 (1H, dd, J = 2.9, 14.7 Hz), 7.10 (1H, dd, J = 9.5, 9.5 Hz), 8.0-8.2 (1H, m), 9.75-9.95 (1H, m). | Hydrochloride |
| 713 | —H | —CH3 | —OCHCF2 | —H | —H | 1H-NMR (DMSO-d6) δ ppm: 1.06-1.16 (1H, m), 1.16-1.37 (8H, m), 1.45-1.88 (5H, m), 2.17 (3H, s), 2.69 (1H, d, J = 12.0 Hz), 3.04 (1H, d, J = 12.0 Hz), 3.1-3.9 (4H, m), 6.50 (1H, s), 6.71 (1H, dd, J = 3.0, 8.9 Hz), 6.75-7.16 (3H, m). | ½ Fumarate |
| 714 | —H | —OCH3 | —OCHCF2 | —H | —H | 1H-NMR (DMSO d6) δ ppm: 1.08-1.18 (1H, m), 1.18-1.27 (7H, m), 1.27-1.38 (1H, m), 1.44- | ½ Fumarate |

TABLE 76-continued
absolute configuration
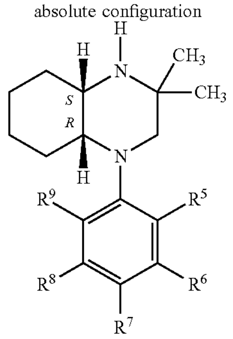
| Example | R5 | R6 | R7 | R8 | R9 | NMR | Salt |
|---|---|---|---|---|---|---|---|
| | | | | | | 1.60 (1H, m), 1.60-1.74 (3H, m), 1.74-1.88 (1H, m), 2.71 (1H, d, J = 12.1 Hz), 3.08 (1H, d, J = 12.2 Hz), 3.15-3.85 (7H, m), 6.40 (1H, dd, J = 2.7, 8.9 Hz), 6.50 (1H, s), 6.57 (1H, d, J = 2.6 Hz), 6.62-7.02 (2H, m). | |
| 715 | —OCHCF2 | —H | —H | —H | —H | 1H-NMR (DMSO-d6) δ ppm: 0.94-1.14 (1H, m), 1.14-1.15 (1H, m), 1.18 (3H, s), 1.26 (3H, s), 1.28-1.43 (2H, m), 1.48 (1H, br), 1.61-1.73 (3H, m), 1.76-1.90 (1H, m), 2.49 (1H, d, J = 11.2 Hz), 3.05 (1H, d, J = 11.2 Hz), 3.45-3.6 (2H, m), 6.55 (1H, dd, J = 70.2, 81.4 Hz), 6.91 (1H, dd, J = 1.4, 8.0 Hz), 6.93-6.99 (1H, m), 7.07-7.18 (2H, m) | — |
TABLE 77
absolute configuration
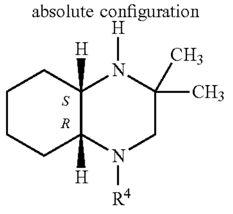
| Example | R4 | NMR | Salt |
|---|---|---|---|
| 716 | 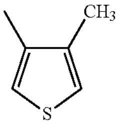 | 1H-NMR (DMSO-d6) δ ppm: 1.05-1.25 (2H, m), 1.35-1.45 (1H, m), 1.47 (3H, s), 1.50 (3H, s), 1.6-2.05 (5H, m), 2.15 (3H, d, J = 0.7 Hz), 2.70 (1H, d, J = 12.8 Hz), 3.20 (1H, d, J = 12.9 Hz), 3.25-3.4 (1H, m), 3.8-3.9 (1H, m), 6.77 (1H, d, J = 3.2 Hz), 7.09 (1H, dd, J = 1.0, 3.3 Hz), 7.9-8.1 (1H, m), 9.6-9.75 (1H, m). | — |

TABLE 77-continued absolute configuration

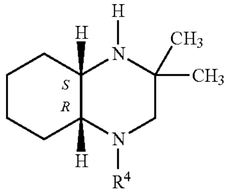

| Example | $R^4$ | NMR | Salt |
|---|---|---|---|
| 717 | 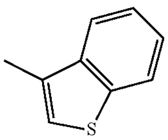 | 1H-NMR (DMSO-d6) δ ppm: 0.95-1.15 (2H, m), 1.3-1.45 (1H, m), 1.52 (3H, s), 1.56 (3H, s), 1.6-1.7 (1H, m), 1.7-2.1 (4H, m), 2.87 (1H, d, J = 12.8 Hz), 3.36 (1H, d, J = 13.1 Hz), 3.65-3.75 (1H, m), 4.1-4.2 (1H, m), 7.06 (1H, s), 7.35-7.45 (2H, m), 7.9-8.0 (2H, m), 8.0-8.15 (1H, m), 9.6-9.8 (1H, m). | Hydrochloride |

TABLE 78 absolute configuration

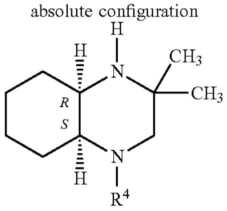

| Example | $R^4$ | NMR | Salt |
|---|---|---|---|
| 718 | 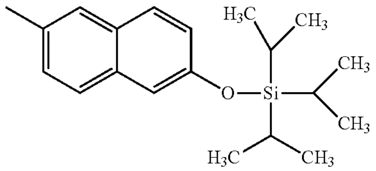 | 1H-NMR (CDCl3) δ ppm: 1.08-1.15 (18H, m), 1.19-1.34 (12H, m), 1.35-1.48 (2H, m), 1.64-1.85 (4H, m), 2.82 (1H, d, J = 11.6 Hz), 3.04 (1H, d, J = 11.7 Hz), 3.45-3.55 (1H, m), 3.7-3.8 (1H, m), 6.95 (1H, d, J = 2.2 Hz), 7.03 (1H, dd, J = 2.5, 8.8 Hz), 7.10 (1H, d, J = 2.4 Hz), 7.23 (1H, d, J = 2.5, 9.1 Hz), 7.51 (1H, d, J = 8.8 Hz), 7.55 (1H, d, J = 9.1 Hz). | — |
| 719 | 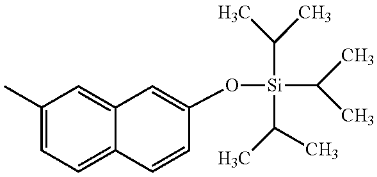 | 1H-NMR (CDCl3) δ ppm: 1.13 (18H, d, J = 7.3 Hz), 1.18-1.36 (12H, m), 1.36-1.65 (2H, m), 1.65-1.87 (4H, m), 2.83 (1H, d, J = 11.9 Hz), 3.12 (1H, d, J = 11.9 Hz), 3.45-3.55 (1H, m) , 3.75-3.85 (1H, m), 6.82 (1H, d, J = 2.3 Hz), 6.86 (1H, dd, J = 2.4, 8.7 Hz), 7.02 (1H, d, J = 2.3 Hz), 7.10 (1H, dd, J = 2.4, 9.0 Hz), 7.53 (1H, d, J = 8.7 Hz), 7.59 (1H, d, J = 9.0 Hz). | — |
| 720 | 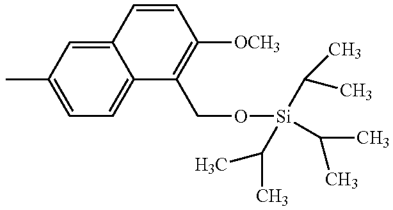 | 1H-NMR (CDCl3) δ ppm: 1.04-1.12 (18H, m), 1.12-1.32 (12H, m), 1.32-1.64 (2H, m), 1.65-1.86 (4H, m), 2.82 (1H, d, J = 11.8 Hz), 3.08 (1H, d, J = 11.8 Hz), 3.47-3.53 (1H, m), 3.73-3.81 (1H, m), 3.88 (3H, s), 5.17 (1H, d, J = 11.0 Hz), 5.24 (1H, d, J = 11.0 Hz), 6.94 (1H, d, J = 2.5 Hz), 7.16 (1H, d, J = 9.0 Hz), 7.31 (1H, dd, J = 2.5, 9.4 Hz), 7.58 (1H, d, J = 9.0 Hz), 8.12 (1H, d, J = 9.4 Hz). | — |

TABLE 78-continued absolute configuration

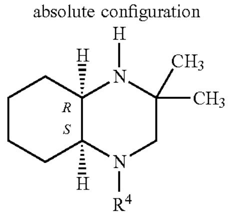

| Example | $R^4$ | NMR | Salt |
| --- | --- | --- | --- |
| 721 | 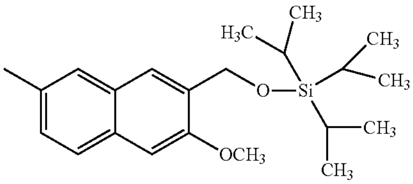 | 1H-NMR (CDCl3) δ ppm: 1.14 (18H, d, J = 6.7 Hz), 1.19-1.33 (13H, m), 1.33-1.65 (1H, m), 1.65-1.84 (4H, m), 2.83 (1H, d, J = 11.6 Hz), 3.04 (1H, d, J = 11.6 Hz), 3.5-3.6 (1H, m), 3.7-3.8 (1H, m), 3.87 (3H, s), 4.93 (2H, d, J = 0.9 Hz), 6.96 (1H, s), 6.99 (1H, d, J = 2.2 Hz), 7.21 (1H, dd, J = 2.4, 9.0 Hz), 7.59 (1H, d, J = 9.0 Hz), 7.77 (1H, s). | — |

TABLE 79 absolute configuration

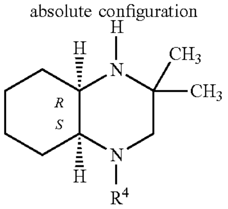

| Example | $R^4$ | NMR | Salt |
| --- | --- | --- | --- |
| 722 | 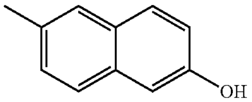 | 1H-NMR (CDCl3) δ ppm: 1.14-1.51 (11H, m), 1.65-1.85 (4H, m), 2.83 (1H, d, J = 11.7 Hz), 3.05 (1H, d, J = 11.8 Hz), 3.52-3.57 (1H, m), 3.69-3.79 (1H, m), 6.97 (1H, d, J = 2.3 Hz), 6.99-7.06 (2H, m), 7.22-7.28 (1H, m), 7.52-7.58 (2H, m). | — |
| 723 | 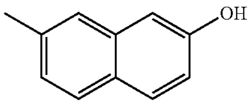 | 1H-NMR (CDCl3) δ ppm: 1.18-1.36 (9H, m), 1.35-1.51 (2H, m), 1.66-1.86 (4H, m), 2.84 (1H, d, J = 11.9 Hz), 3.13 (1H, d, J = 12.0 Hz), 3.45-3.55 (1H, m), 3.75-3.85 (1H, m), 6.8-6.85 (2H, m), 6.94 (1H, d, H = 2.4 Hz), 7.10 (1H, d, J = 2.4, 9.1 Hz), 7.57 (1H, d, J = 8.7 Hz), 7.60 (1H, d, J = 9.0 Hz). | — |
| 724 | 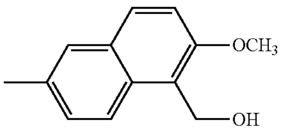 | 1H-NMR (DMSO-d6) δ ppm: 1.1-1.2 (1H, m), 1.2-1.4 (8H, m) 1.5-1.9 (5H, m), 2.86 (1H, d, J = 12.2 Hz), 3.20 (1H, d, J = 12.5 Hz), 3.58 (1H, br), 3.85 (3H, s), 3.9-4.0 (1H, m), 4.85 (2H, s), 6.54 (2H, s), 7.05 (1H, d, J = 2.4 Hz), 7.28 (1H, d, J = 9.1 Hz), 7.39 (1H, dd, J = 2.5, 9.5 Hz), 7.66 (1H, d, J = 9.0 H), 7.97 (1H, d, J = 9.4 Hz). | Fumarate |
| 725 | 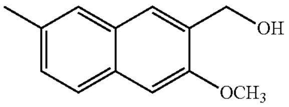 | 1H-NMR (CDCl3) δ ppm: 0.97 (1H, br), 1.15-1.35 (8H, m), 1.35-1.5 (2H, m), 1.65-1.85 (4H, m), 2.42 (1H, t, J = 6.5 Hz), 2.82 (1H, d, J = 11.8 Hz), 3.05 (1H, d, J = 11.7 H), 3.45-3.55 (1H, m), 3.7-3.8 (1H, m), 3.94 (3H, s), 4.79 (2H, d, J = 5.9 Hz), 6.98 (1H, d, J = 2.4 Hz), 7.02 (1H, s), 7.21-7.28 (1H, m), 7.54 (1H, s), 7.60 (1H, d, J = 9.0 Hz). | — |

TABLE 80 absolute configuration

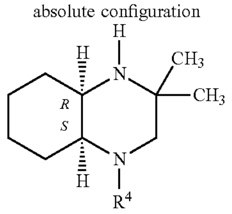

| Example | $R^4$ | NMR | Salt |
|---|---|---|---|
| 726 | 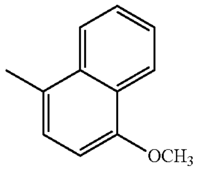 | 1H-NMR (DMSO-d6) δ ppm: 0.9-1.05 (1H, m), 1.05-1.2 (1H, m), 1.3-1.45 (1H, m), 1.52 (3H, s), 1.55-1.65 (4H, m), 1.65-1.85 (2H, m), 1.85-2.05 (2H, m), 2.73 (1H, d, J = 12.5 Hz), 3.25-3.6 (2H, m), 3.94 (3H, s), 4.15-4.3 (1H, m) 6.88, (1H, d, J = 8.2 Hz), 7.06 (1H, d, J = 8.0 Hz), 7.5-7.55 (1H, m), 7.55-7.6 (1H, m), 7.96 (1H, br), 8.16 (1H, dd, J = 1.0, 8.3 Hz), 8.24 (1H, d, J = 8.1 Hz), 9.4-9.6 (1H, m). | Hydrochloride |
| 727 | 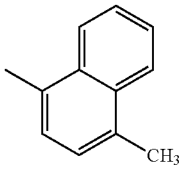 | 1H-NMR (DMSO-d6) δ ppm: 0.85-1.0 (1H, m), 1.0-1.15 (1H, m), 1.3-1.4 (1H, m), 1.5-1.65 (7H, m), 1.65-1.85 (2H, m), 1.85-2.1 (2H, m), 2.59 (3H, s), 2.76 (1H, d, J = 12.5 Hz), 3.3-3.45 (1H, m), 3.51 (1H, d, J = 12.5 Hz), 4.15-4.3 (1H, m), 7.02 (1H, d, J = 7.5 Hz), 7.28 (1H, d, J = 7.4 Hz), 7.5-7.65 (2H, m), 7.95-8.15 (2H, m), 8.25-8.35 (1H, m), 9.6-9.8 (1H, m). | Hydrochloride |
| 728 | 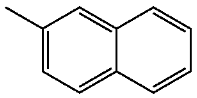 | 1H-NMR (DMSO-d6) δ ppm: 1.23-1.54 (6H, m), 1.58 (3H, s), 1.64-2.02 (4H, m), 2.02-2.15 (1H, m), 3.07 (1H, d, J = 13.4 Hz), 3.50 (1H, d, J = 13.4 Hz), 3.75-3.9 (1H, m), 3.9-4.53 (2H, m), 7.18 (1H, d, J = 2.2 Hz), 7.22-7.32 (1H, m), 7.32-7.46 (2H, m), 7.65-7.82 (3H, m), 8.26 (1H, br), 10.02 (1H, br). | 2 Hydrochloride |
| 729 | 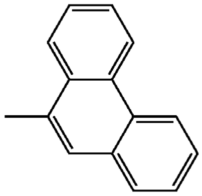 | 1H-NMR (CDCl3) δ ppm: 0.83-0.99 (1H, m), 1.021.13 (1H, m), 1.27 (3H, s), 1.32-1.42 (2H, m), 1.46 (3H, s), 1.54-1.71 (2H, m), 1.71-1.81 (1H, m), 1.85-1.99 (1H, m), 2.69 (1H, d, J = 11.1 Hz), 3.3-3.45 (2H, m), 3.75-3.85 (1H, m), 7.15 (1H, s), 7.5-7.55 (2H, m), 7.6-7.7 (2H, m), 7.7-7.8 (1H, m), 8.3-8.4 (1H, m), 8.55-8.65 (1H, m), 8.65-8.75 (1H, m). | — |
| 730 | 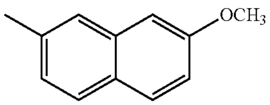 | 1H-NMR (CDCl3) δ ppm: 0.9-1.65 (11H, m), 1.65-1.9 (4H, m), 2.84 (1H, d, J = 12.0 Hz), 3.13 (1H, d, J = 11.9 Hz), 3.50 (1H, bs), 3.75-3.85 (1H, m), 3.89 (3H, s), 6.89 (1H, dd, J = 2.5, 8.8 Hz), 6.92 (1H, d, J = 2.4 Hz), 6.97 (1H, d, J = 2.4 Hz), 7.11 (1H, dd, J = 2.5, 9.0 Hz), 7.57 (1H, d, J = 8.8 Hz), 7.60 (1H, d, J = 9.0 Hz). | — |
| 731 | 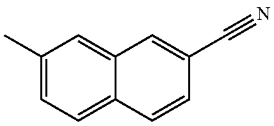 | 1H-NMR (DMSO-d6) δ ppm: 1.3-1.5 (6H, m), 1.55 (3H, s), 1.65-2.05 (5H, m), 3.08 (1H, d, J = 13.6 Hz), 3.62 (1H, d, J = 13.6 Hz), 3.8-3.9 (1H, m), 4.2-4.3 (1H, m), 7.32 (1H, d, J = 2.1 Hz), 7.50 (1H, dd, J = 1.6, 8.4 Hz), 7.63 (1H, dd, J = 2.5, 9.2 Hz), 7.85-8.0 (2H, m), 8.11-8.2 (1H, m), 8.26 (1H, s), 9.6-9.75 (1H, m). | Hydrochloride |

TABLE 80-continued absolute configuration

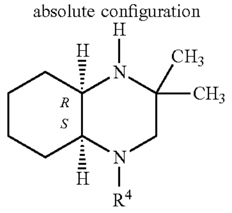

| Example | $R^4$ | NMR | Salt |
|---|---|---|---|
| 732 | 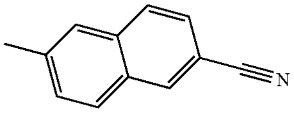 | 1H-NMR (DMSO-d6) δ ppm: 1.32-1.54 (6H, m), 1.57 (3H, s), 1.66-2.13 (5H, m), 3.10 (1H, d, J = 13.9 Hz), 3.72 (1H, d, J = 13.7 Hz), 3.75-3.9 (1H, m), 4.25-4.35 (1H, m), 7.29 (1H, d, J = 2.2 Hz), 7.5-7.65 (2H, m), 7.81 (1H, d, J = 8.6 Hz), 7.91 (1H, d, J = 9.2 Hz), 8.15-8.45 (2H, m), 9.92 (1H, br). | Hydrochloride |
| 733 | 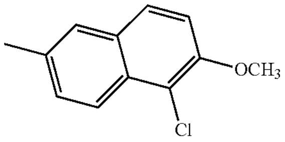 | 1H-NMR (DMSO) δ ppm: 1.0-1.35 (9H, m), 1.4-1.6 (2H, m), 1.6-1.7 (3H, m), 1.8-1.95 (1H, m), 2.72 (1H, d, J = 12.3 Hz), 3.12 (1H, d, J = 11.1 Hz), 3.3-3.4 (1H, m), 3.8-3.9 (1H, m), 3.92 (3H, s), 7.09 (1H, d, J = 1.8 Hz), 7.39 (1H, d, J = 9.2 Hz), 7.49 (1H, dd, J = 2.4, 9.5 Hz), 7.71 (1H, d, J = 9.0 Hz), 7.89 (1H, d, J = 9.4 Hz). | — |
| 734 | 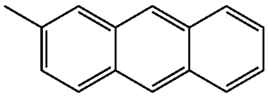 | 1H-NMR (CDCl3) δ ppm: 1.00 (1H, br), 1.19-1.37 (8H, m), 1.38-1.51 (2H, m), 1.67-1.79 (3H, m), 1.79-1.93 (1H, m), 2.90 (1H, d, J = 11.8 Hz), 3.18 (1H, d, J = 11.9 Hz), 3.53 (1H, br), 3.8-3.9 (1H, m), 7.05 (1H, d, J = 2.1 Hz), 7.3-7.45 (3H, m), 7.8-7.95 (3H, m), 8.15 (1H, s), 8.25 (1H, s). | — |
| 735 | 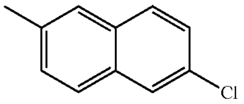 | 1H-NMR (DMSO-d6) δ ppm: 1.15-1.25 (1H, m), 1.25-1.4 (8H, m), 1.5-1.95 (5H, m), 2.88 (1H, d, J = 12.6 Hz), 3.31 (1H, d, J = 12.4 Hz), 3.54 (1H, br), 3.95-4.05 (1H, m), 6.54 (2H, s), 7.13 (1H, d, J = 2.1 Hz), 7.34 (1H, dd, J = 2.2, 8.7 Hz), 7.44 (1H, dd, J = 2.4, 9.2 Hz), 7.67-7.76 (2H, m), 7.81 (1H, d, J = 2.1 Hz). | Fumarate |
| 736 | 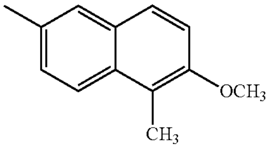 | 1H-NMR (CDCl3) δ ppm: 1.09 (1H, br), 1.15-1.35 (8H, m), 1.35-1.5 (2H, m), 1.65-1.85 (4H, m), 2.50 (3H, s), 2.82 (1H, d, J = 11.6 Hz), 3.07 (1H, d, J = 11.8 Hz), 3.45-3.55 (1H, m), 3.7-3.8 (1H, m), 3.90 (3H, s), (6.96 (1H, d, J = 2.5 Hz), 7.18 (1H, d, J = 9.0 Hz), 7.30 (1H, dd, J = 2.6, 9.4 Hz), 7.51 (1H, d, J = 9.0 Hz), 7.81 (1H, d, J = 9.3 Hz). | — |
| 737 | 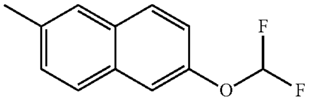 | 1H-NMR (DMSO-d6) δ ppm: 1.06-1.19 (1H, m), 1.19-1.39 (8H, m), 1.47-1.80 (4H, m), 1.80-1.96 (1H, m), 2.83 (1H, d, J = 12.2 Hz), 2.9-4.4 (5H, m), 6.51 (1H, s), 7.05-7.45 (4H, m), 7.49 (1H, d, J = 2.4 Hz), 7.7-7.8 (2H, m). | ½ Fumarate |
| 738 | 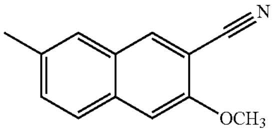 | 1H-NMR (DMSO-d6) δ ppm: 1.23-1.54 (6H, m), 1.60 (3H, s), 1.66-2.06 (4H, m), 2.06-2.20 (1H, m), 3.07 (1H, d, J = 13.4 Hz), 3.45 (1H, d, J = 13.9 Hz), 3.75-3.9 (1H, m), 3.95 (3H, s), 4.1-4.2 (1H, m), 4.77 (1H, br), 7.25 (1H, d, J = 2.2 Hz), 7.46 (1H, s), 7.58 (1H, dd, J = 2.4, 9.2 Hz), 7.81 (1H, d, J = 9.2 Hz), 8.23 (1H, s), 8.25-8.4 (1H, m), 10.18 (1H, br). | 2 Hydrochloride |

TABLE 80-continued absolute configuration

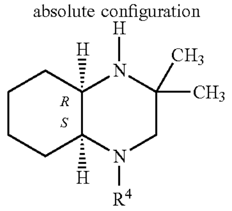

| Example | $R^4$ | NMR | Salt |
|---|---|---|---|
| 739 | 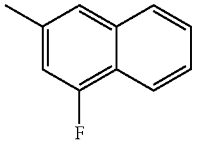 | 1H-NMR (DMSO-d6) δ ppm: 1.27-1.50 (6H, m), 1.58 (3H, s), 1.65-2.13 (5H, m), 3.06 (1H, d, J = 13.8 Hz), 3.56 (1H, d, J = 13.6 Hz), 3.73-3.87 (1H, m), 4.14-4.26 (1H, m), 7.05 (1H, d, J = 1.8 Hz), 7.28-7.38 (2H, m), 7.43-7.52 (1H, m), 7.75 (1H, d, J = 8.5 Hz), 7.84 (1H, d, J = 8.2 Hz), 8.15-8.4 (1H, m), 9.9-10.1 (1H, m). | Hydrochloride |
| 740 | 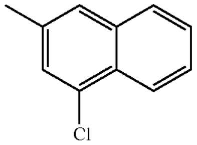 | 1H-NMR (DMSO-d6) δ ppm: 1.28-1.50 (6H, m), 1.57 (3H, s), 1.66-2.00 (4H, m), 2.00-2.18 (1H, m), 3.08 (1H, d, J = 13.5 Hz), 3.56 (1H, d, J = 13.5 Hz), 3.75-3.9 (1H, m), 3.95-4.1 (1H, m), 7.23 (1H, d, J = 2.0 Hz), 7.36-7.45 (1H, m), 7.45-7.54 (1H, m), 7.65 (1H, d, J = 2.4 Hz), 7.78 (1H, d, J = 8.1 Hz), 7.97 (1H, d, J = 8.4 Hz), 8.1-8.35 (1H, m), 9.8-10.1 (1H, m). | Hydrochloride |
| 741 | 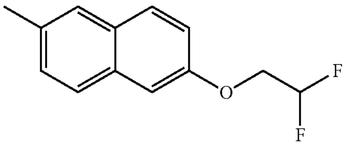 | 1H-NMR (DMSO-d6) δ ppm: 1.06-1.17 (1H, m), 1.17-1.39 (8H, m), 1.46-1.79 (4H, m), 1.79-1.92 (1H, m), 2.82 (1H, d, J = 12.1 Hz), 2.9-4.2 (5H, m), 4.30-4.41 (2H, m), 6.27-6.59 (2H, m), 7.06 (1H, d, J = 2.1 Hz), 7.10 (1H, dd, J = 2.6, 8.9 Hz), 7.26 (1H, d, J = 2.5 Hz), 7.36 (1H, dd, J = 2.4, 9.2 Hz), 7.60-7.68 (2H, m). | ½ Fumarate |

TABLE 81 absolute configuration

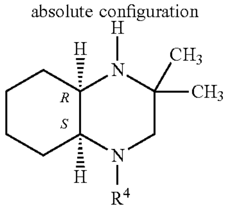

| Example | $R^4$ | NMR | Salt |
|---|---|---|---|
| 742 | 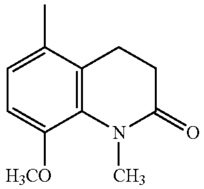 | 1H-NMR (DMSO-d6) δ ppm: 1.0-1.5 (2H, m), 1.3-1.45 (1H, m), 1.48 (3H, s), 1.50 (3H, s), 1.55-1.65 (1H, m), 1.65-1.8 (2H, m), 1.8-2.0 (2H, m), 2.25-2.35 (1H, m), 2.4-2.50 (1H, m), 2.6-2.75 (2H, m), 2.95-3.1 (2H, m), 3.21 (3H, s), 3.3-3.5 (1H, m), 3.78 (3H, s), 3.85-3.95 (1H, m), 6.78 (1H, d, J = 8.9 Hz), 6,93 (1H, d, J = 8.9 Hz), 7.97 (1H, br), 9.59 (1H, br). | Hydrochloride |

TABLE 81-continued absolute configuration

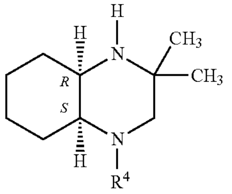

| Example | $R^4$ | NMR | Salt |
|---|---|---|---|
| 743 | 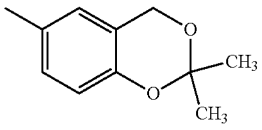 | 1H-NMR (DMSO-d6) δ ppm: 1.08-1.37 (9H, m), 1.42 (6H, s), 1,48-1.83 (5H, m), 2.74 (1H, d, J = 12.2 Hz), 2.94 (1H d, J = 12.3 Hz), 3.51 (1H, br), 3.6-3.75 (1H, m), 4,73 (2H, s), 6.53 (2H, s), 6,57 (1H, d, J = 2.6 Hz ), 6,65 (1H, d, J = 8.9 Hz), 6.75 (1H, dd, J = 2.8, 9.0 Hz). | Fumarate |

TABLE 82 absolute configuration

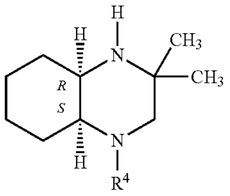

| Example | $R^4$ | NMR | Salt |
|---|---|---|---|
| 744 | 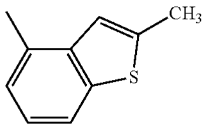 | 1H-NMR (CDC13 ) δ ppm: 0.94-1.09 (3H, m), 1.20 (3H, s), 1.34 (3H, s), 1.36-1.44 (2H, m), 1.45-1.79 (3H, m), 1.81-1.94 (1H, m), 2.55-2.65 (4H, m), 3.15 (1H, d, J = 11.2 Hz), 3,4-3,5 (1H, m), 3.65-3.7 (1H, m), 6.74 (1H, dd, J = 0.6, 7.6 Hz), 7,05 (1H, s), 7.13 (1H, dd, J = 7.8, 7.8 Hz), 7.38 (1H, d, J = 8.0 Hz). | — |
| 745 | 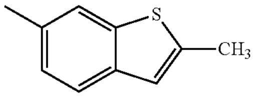 | 1H-NMR (DMSO-d6) δ ppm: 1.1-1.2 (1H, m), 1.2-1.4 (8H, m), 1.45-1.75 (4H, m), 1.75-1.9 (1H, m), 2,47 (3H, d, J = 1.2 Hz), 2.6-2.7 (6H, m), 6.49 (1H, s), 6.90 (1H, s), 6.99 (1H, dd, J = 2.3, 8.8 Hz), 7.25 (1H, d, J = 2.1 Hz), 7.48 (1H, d, J = 8.8 Hz), | 1/2 Fumarate |
| 746 | 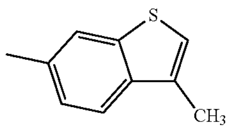 | 1H-NMR (DMSO-d6) δ ppm: 1.1-1.4 (9H, m), 1.5-1.95 (5H, m), 2.31 (3H, d, J = 1.2 Hz), 2.6-5.0 (7H, m), 6.52 (2H, s), 7.01 (1H, d, J = 1.2 Hz), 7,11 (1H, dd, J = 2.3, 8.9 Hz), 7.34 (1H, d, J = 2.2 Hz), 7.55 (1H, d, J = 8.8Hz). | 1/2 Fumarate |
| 747 | 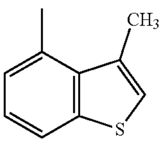 | 1H-NMR (DM80-d6) δ ppm: 0.93-1.10 (2H, m.), 1.28-1,42 (1H, m), 1.51-1.66 (7H, m), 1.70-2.00 (3H, m), 2.00-2,18 1H, m), 2.69 (3H, s), 2.80(1H, d, J = 12.5 Hz), 3.2-3.3 (1H, m), 3.48 (1H, d, J = 12,6 Hz), 3.85-3.95 (1H, m), 7.02 (1H, d, J = 7.5 Hz), 7.26 (1H, d, J = 7.8, 7.8 Hz), 7.36 (1H, d, J = 0.6 Hz), 7.69 (1H, d, J = 7.6 Hz), 7.95-8.15 (1H, m), 9.95-10.1 (1H, m). | Hydrochloride |

TABLE 82-continued absolute configuration

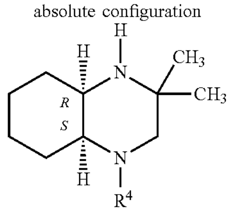

| Example | R⁴ | NMR | Salt |
| --- | --- | --- | --- |
| 748 | 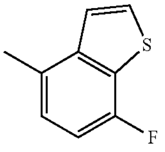 | 1H-NMR (CDC13) δ ppm: 0.92-1.08 (3H, m), 1.20 (3H, s), 1.32-1.43 (5H, m), 1,45-1.78 (3H, m), 1.81-1.94 (1H, m), 2.57 (1H, d, J = 11.1 Hz), 3.14 (H, d, J = 11.1 Hz), 3.33-3.41 (1H, m), 3.63-3.70 (1H, m), 6.71 (1H, dd, J = 4.1, 8.4 Hz), 6.92 (1H, dd, J = 8.9, 8.9 Hz) 7.41 (1H, d, J = 5.4 Hz), 7.46 (1H, dd, J = 3.7, 5.4 Hz). | — |
| 749 | 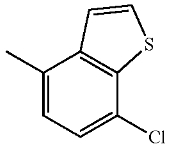 | 1H-NMR (CDC13) δ ppm: 0.92-1.08 (3H, m), 1.20 (3H, s), 1.29-1.42 (5H, m), 1.45-1.78 (3H, m), 1,82-1,96 (1H, m), 2,61 (1H, d, J = 11.2 Hz), 3.15 (1H, d, J = 11.1 Hz), 3,42-3,50 (1H, m) 3.64-3.71 (1H, m), 6,74 (1H, d, J = 8.2 Hz), 7.21 (1H, d, J = 8.21 Hz), 7.43 (1H, d, J = 5.5 Hz), 7.47 (1H, d, J = 5.5 Hz). | — |
| 750 | 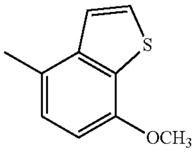 | 1H-NMR (CDC13) δ ppm: 0.9-1.1 (2H, m), 1.20 (3H, s), 1.3-1.45 (5H, m), 1.45-1.8 (4H, m), 1.8-1.95 (1H, m), 2.56 (1H, d, J = 11.1 Hz), 3.14 (1H, d, J = 11.1 Hz), 3.3-3.4 (1H, m), 3.6-3.7 (1H, m), 3.96 (3H, s), 6.66 (1H, d, J = 8.2 Hz), 6,74 (1H, d, J = 8.2 Hz), 7.39 (1H, d, J = 5.4 Hz), 7.45 (1H, d, J = 5.4 Hz) | — |
| 751 | 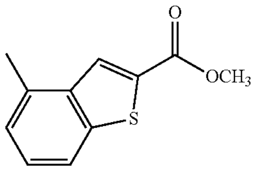 | 1H-NMR (CDC13) δ ppm: 0.95-1.1 (2H, m), 1.22 (3H, s), 1.3-1.45 (5H, m), 1.45-1.85 (4H, m), 1.85-2.0 (1H, m), 2.65 (1H, d, J = 11.2 Hz), 3.17 (1H, d, J = 11.2 Hz), 3.45-3.55 (1H, m), 3.7-3.8 (1H, m), 3.96 (3H, s), 6.77-6.82 (1H, m), 7.33 (1H, dd, J = 7.9, 7.9 Hz), 7.45 (1H, d, J = 8.1 Hz), 8.14 (1H, d, J = 0.5 Hz). | — |
| 752 | 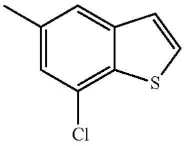 | 1H-NMR (CDC13) δ ppm: 0.93 (1H, br), 1.16-1.33 (8H, m), 1.33-1.49 (2H, m), 1.64-1.85 (4H, m), 2.80 (1H, d, J = 11.6 Hz), 2.97 (1H, d, J = 11.7 Hz), 3.48 (1H, br), 3.6-3.7 (1H, m), 7.04 (1H, d, J = 2.1 Hz), 7.10 (1H, d, J = 2.2 Hz), 7.20 (1H, d, J =5.4 Hz), 7.41 (1H, d, J = 5.5 Hz). | — |
| 753 | 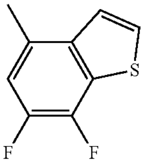 | 1H-NMR (DMSO-d6) δ ppm: 0.94-1.14 (2H, m), 1.29-1.44 (1H, m), 1.51 (3H, s), 1.53 (3H, s), 1.58-2.07 (5H, m), 2.84 (1H, d, J = 12.9 Hz), 3.41 (1H, d, J = 13.0 Hz), 3.6-3.7 (1H, m), 4.15-4.25 (1H, m), 7.11 (1H, dd, J = 12.6 Hz), 7.77 (1H, dd, J = 3.8, 5.4 Hz), 7.84 (1H d, J = 5.4 Hz), 8.04 (1H, br), 9.81 (1H, br). | Hydrochloride |
| 754 | 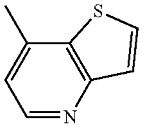 | 1H-NMR (DMSO-d6) δ ppm: 1.38-1.57 (5H, m), 1.64 (3H, s), 1.70-2.02 (4H, m), 2.03-2.14 (1H, m), 2.37-2.54 (1H, m), 3.55 (1H, d, J = 15.0 Hz), 3.9-4.0 (1H, m), 4.23 (1H, d, J = 15.3 Hz), 4.6-4.75 (1H, m), 7.27 (1H, d, J = 7.2 Hz), 7.67 (1H, d, J = 5.7 Hz), 8.45-8.6 (2H, m), 8.88 (1H, br), 10.33 (1H, m), 14.95 (1H, br). | 2 Hydrochloride |

TABLE 82-continued absolute configuration

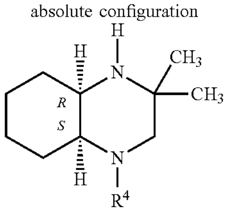

| Example | $R^4$ | NMR | Salt |
|---|---|---|---|
| 755 | 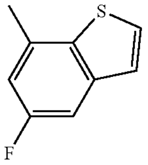 | 1H-NMR (DMSO-d6) δ ppm: 1.0-1.19 (2H, m), 1.31-1.46 (1H, m), 1.51 (3H, s), 1.52 (3H, s), 1.60-1.89 (3H, m), 1.93-2.08 (2H, m), 3.00 (1H, d, J = 12.9 Hz), 3.46 (1H, d, J = 13.0 Hz), 3.90-4.01 (1H, m), 3.95-4.08 (1H, m), 6.96 (1H, dd, J = 2.1, 11.0 Hz), 7.41 (1H, dd, J = 2.2, 9.1 Hz), 7.46 (1H, d, J = 5.4 Hz), 7.86 (1H, d, J = 5.4 Hz), 8.16 (1H, br), 9.78 (1H, br). | Hydrochloride |

TABLE 83 absolute configuration

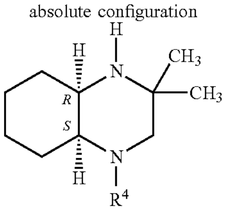

| Example | $R^4$ | NMR | Salt |
|---|---|---|---|
| 756 | 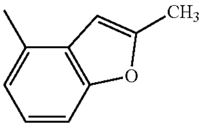 | 1H-NMR (CDCl3) δ ppm: 1.02-1.17 (3H, m), 1.20 (3H, s), 1.31 (3H, s), 1.34-1.46 (2H, m), 1.47-1.79 (3H, m), 1.81-1.95 (1H, m), 2.45 (3H, d, J = 1.0 Hz), 2.80 (1H, d, J = 11.5 Hz), 3.05 (1H, d, J = 11.5 Hz), 3.55-3.65 (2H, m), 6.39 (1H, dd, J = 1.0, 1.0 Hz), 6.56 (1H, dd, J = 0.8, 7.7 Hz), 6.95-7.05 (1H, m), 7.06 (1H, dd, J = 7.9, 7.9 Hz). | — |
| 757 | 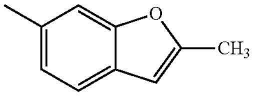 | 1H-NMR (DMSO-d6) δ ppm: 1.17-1.37 (2H, m), 1.37-1.52 (4H, s), 1.56 (3H, s),, 1.61-1.73 (1H, m), 1.73-1.99 (3H, m), 2.00-2.15 (1H, m), 2.37 (3H, d, J = 0.9 Hz), 3.00 (1H, d, J = 13.3 Hz), 3.28 (1H, d, J = 13.2 Hz), 3.7-3.85 (1H, m), 3.95-4.1 (1H, m), 4.92 (1H, br), 6.40 (1H, d, J = 0.8 Hz), 6.89 (1H, dd, J = 2.1, 8.6 Hz), 7.05 (1H, d, J = 1.5 Hz), 7.33 (1H, d, J = 8.5 Hz), 8.15-8.35 (1H, m), 10.0-10.2 (1H, m). | 2 Hydrochloride |
| 758 | 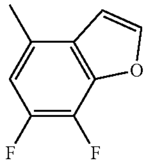 | 1H-NMR (DMSO-d6) δ ppm: 1.01-1.19 (2H, m), 1.33-1.44 (1H, m), 1.48 (3H, s), 1.51 (3H, s), 1.59-2.07 (5H, m), 3.01 (1H, d, J = 13.0 Hz), 3.28 (1H, d, J = 13.1 Hz), 3.75-3.9 (1H, m), 4.0-4.15 (1H, m), 6.83 (1H, dd, J = 5.9, 13.5 Hz), 7.36 (1H, dd, J = 2.6, 2.6 Hz), 8.0-8.2 (2H, m), 9.7-9.9 (1H, m). | Hydrochloride |
| 759 | 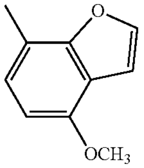 | 1H-NMR (DMSO-d6) δ ppm: 1.0-1.2 (2H, m), 1.34-1.44 (1H, m), 1.50 (3H, s), 1.53 (3H, s), 1.60-2.06 (5H, m), 3.05 (1H, d, J = 12.8 Hz), 3.27 (1H, d, J = 13.0 Hz), 3.84 (3H, s), 3.88-4.00 (2H, m), 6.66 (1H, d, J = 8.5 Hz), 6.75 (1H, d, J = 8.5 Hz), 6.93 (1H, d, J = 2.2 Hz), 7.92 (1H, d, J = 2.2 Hz), 8.0-8.25 (1H, m), 9.55-9.8 (1H, m). | Hydrochloride |

TABLE 83-continued absolute configuration

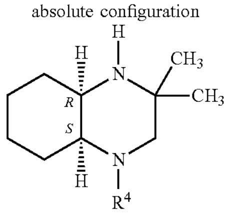

| Example | $R^4$ | NMR | Salt |
|---|---|---|---|
| 760 | 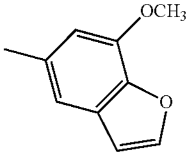 | 1H-NMR (DMSO-d6) δ ppm: 0.99-1.27 (5H, m), 1.28 (3H, s), 1.33-1.47 (2H, m), 1.48-1.84 (5H, m), 2.77-2.90 (2H, m), 3.45-3.55 (1H, m), 3.55-3.65 (1H, m), 4.01 (3H, s), 6.51 (1H, d, J = 2.0 Hz), 6.58 (1H, d, J = 2.1 Hz), 6.63 (1H, d, J = 2.1 Hz), 7.53 (1H, d, J = 2.0 Hz). | — |
| 761 | 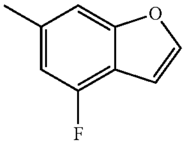 | 1H-NMR (DMSO-d6) δ ppm: 1.05-1.25 (2H, m), 1.35-1.45 (1H, m), 1.48 (3H, s), 1.52 (3H, s), 1.6-2.05 (5H, m), 3.13 (1H, d, J = 13.2 Hz), 3.28 (1H, d, J = 13.5 Hz), 3.9-4.0 (1H, m), 4.0-4.1 (1H, m), 6.63 (1H, dd, J = 2.1, 12.3 Hz), 7.09 (1H, dd, J = 1.3, 8.7 Hz), 7.22 (1H, dd, J = 0.7, 2.2 Hz), 7.96 (1H, d, J = 2.3 Hz), 8.0-8.2 (1H, m), 9.6-9.9 (1H, m). | Hydrochloride |
| 762 | 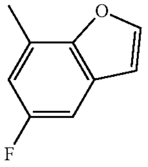 | 1H-NMR (DMSO-d6) δ ppm: 1.16-1.34 (2H, m), 1.35-1.45 (1H, m), 1.47 (3H, s), 1.54 (3H, s), 1.66-1.89 (3H, m), 1.92-2.11 (2H, m), 3.25 (1H, d, J = 13.6 Hz), 3.45 (1H, d, J = 13.4 Hz), 3.83-4.02 (1H, m), 4.02-4.38 (1H, m), 6.68 (1H, dd, J = 2.0, 12.2 Hz), 6.87-7.05 (2H, m), 8.02 (1H, d, J = 2.1 Hz), 8.24 (1H, br), 9.7-10.0 (1H, m). | Hydrochloride |
| 763 | 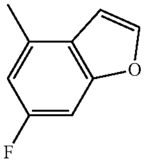 | 1H-NMR (DMSO-d6) δ ppm: 1.27-1.47 (6H, m), 1.53 (3H, s), 1.61-1.96 (4H, m), 1.97-2.09 (1H, m), 3.00 (1H, d, J = 13.6 Hz), 3.45 (1H, d, J = 13.5 Hz), 3.71-3.81 (1H, m), 4.05-4.15 (1H, m), 6.81-6.93 (2H, m), 6.98-7.04 (1H, m) , 7.83 (1H, d, J = 2.2 Hz), 8.1-8.3 (1H, m), 9.8-10.0 (1H, m). | Hydrochloride |
| 764 | 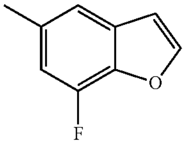 | 1H-NMR (DMSO-d6) δ ppm: 1.18-1.48 (6H, m), 1.53 (3H, s), 1.62-1.93 (4H, m), 1.95-2.13 (1H, m), 3.00 (1H, d, J = 13.3 Hz), 3.30 (1H, d, J = 13.2 Hz), 3.7-3.85 (1H, m), 3.95-4.1 (1H, m), 4.83 (1H, br), 6.91 (1H, dd, J = 2.2, 3.0 Hz), 6.94 (1H, d, J = 2.1 Hz), 7.01 (1H, dd, J = 2.1, 14.2 Hz), 7.99 (1H, d, J = 2.1 Hz), 8.12 (1H, br), 9.86 (1H, br). | 2 Hydrochloride |
| 765 | 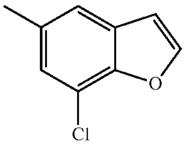 | 1H-NMR (DMSO-d6) δ ppm: 1.21-1.37 (2H, m), 1.37-1.47 (4H, m), 1.52 (3H, s), 1.62-1.90 (4H, m), 1.95-2.08 (1H, m), 3.02 (1H, d, J = 13.2 Hz), 3.29 (1H, d, J = 13.2 Hz), 3.75-3.9 (1H, m), 3.95-4.1 (1H, m), 6.92 (1H, d, J = 2.2 Hz), 7.12 (1H, d, J = 2.2 Hz), 7.16 (1H, d, J = 2.2 Hz), 8.01 (1H, d, J = 2.1 Hz), 8.06 (1H, br), 9.74 (1H, br) | Hydrochloride |
| 766 | 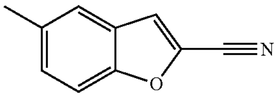 | 1H-NMR (DMSO-d6) δ ppm: 1.19-1.36 (2H, m), 1.38-1.48 (4H, m), 1.52 (3H, s), 1.62-1.89 (4H, m), 1.93-2.06 (1H, m), 3.03 (1H, d, J = 13.3 Hz), 3.25-3.4 (1H, m), 3.75-3.9 (1H, m), 4.0-4.1 (1H, m), 7.22 (1H, d, J = 2.4 Hz), 7.37 (1H, dd, J = 2.5, 9.3 Hz), 7.62 (1H, d, J = 9.2 Hz), 7.95 (1H, d, J = 0.7 Hz), 8.06 (1H, br), 9.64 (1H, br). | Hydrochloride |

TABLE 83-continued absolute configuration

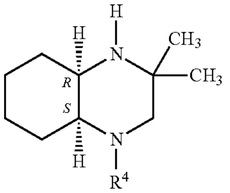

| Example | $R^4$ | NMR | Salt |
|---|---|---|---|
| 767 | 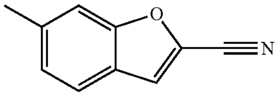 | 1H-NMR (DMSO-d6) δ ppm: 1.15-1.29 (8H, m), 1.29-1.40 (2H, m), 1.48-1.80 (4H, m), 1.80-1.96 (1H, m), 2.83 (1H, d, J = 12.8 Hz), 2.9-3.85 (4H, m), 3.9-4.0 (1H, m), 6.55 (2H, s), 7.09 (1H, s), 7.13 (1H, dd, J = 2.1, 8.9 Hz), 7.56 (1H, d, J = 8.9 Hz), 7.89 (1H, d, J = 0.6 Hz). | Fumarate |
| 768 | 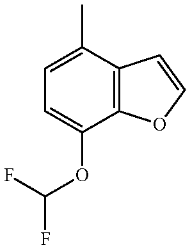 | 1H-NMR (DMSO-d6) δ ppm: 0.85-1.1 (2H, m), 1.2-1.35 (7H, m), 1.4-1.8 (4H, m), 1.85-2.05 (1H, m), 2.78 (1H, d, J = 11.8 Hz), 2.85-4.5 (5H, m), 6.5 (1H, s), 6.58 (1H, d, J = 8.6 Hz), 7.0-7.4 (3H, m), 7.92 (1H, d, J = 2.2 Hz). | 1/2 Fumarate |

TABLE 84 absolute configuration

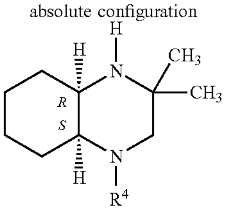

| Example | $R^4$ | NMR | Salt |
|---|---|---|---|
| 769 | 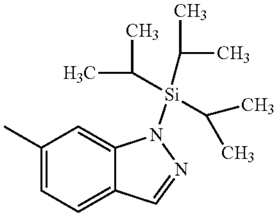 | 1H-NMR (CDCl3) δ ppm: 1.11-1.18 (20H, m), 1.22 (3H, s), 1.26-1.36 (4H, m), 1.37-1.47 (2H, m), 1.64-1.87 (7H, m), 2.82 (1H, d, J = 11.8 Hz), 3.02 (1H, d, J = 11.8 Hz), 3.45-3.55 (1H, m), 3.6-(1H, m), 6.82 (1H, s), 6.86 (1H, dd, J = 2.0, 8.9 Hz), 7.54 (1H, d, J = 8.8 Hz), 8.04 (1H, d, J = 0.8 Hz). | — |
| 770 | 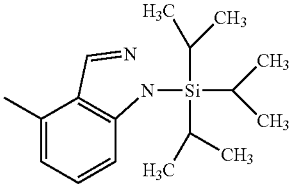 | 1H-NMR (CDCl3) δ ppm: 1.11-1.19 (19H, m), 1.21 (3H, s), 1.23-1.31 (2H, m), 1.35 (3H, s), 1.37-1.46 (2H, m), 1.62-1.85 (6H, m), 1.95-2.04 (1H, m), 3.03 (1H, d, J = 11.9 Hz), 3.09 (1H, d, J = 12.0 Hz), 3.55-3.65 (1H, m), 3.8-3.9 (1H, m), 6.41 (1H, d, J = 7.5 Hz), 7.05 (1H, d, J = 8.4 Hz), 7.16 (1H, d, J = 7.6, 8.3 Hz), 8.15 (1H, d, J = 0.8 Hz). | — |

TABLE 84-continued absolute configuration

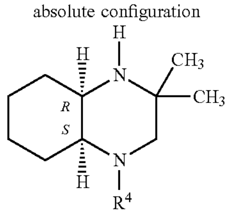

| Example | $R^4$ | NMR | Salt |
|---|---|---|---|
| 771 | 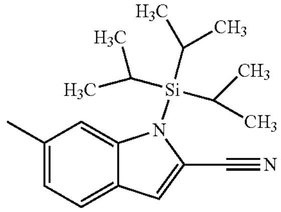 | 1H-NMR (CDCl3) δ ppm: 1.17-1.23 (21H, m), 1.25-1.33 (5H, m), 1.33-1.50 (3H, s), 1.62-1.90 (4H, m), 1.93-2.05 (3H, m), 2.82 (1H, d, J = 11.8 Hz), 3.00 (1H, d, J = 11.8 Hz), 3.45-3.50 (1H, m), 3.55-3.65 (1H, m), 6.88-6.95 (2H, m), 7.28 (1H, s), 7.41-7.48 (1H, m). | — |
| 772 | 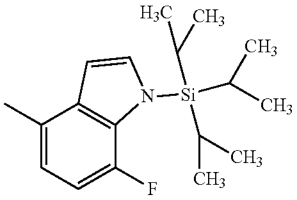 | 1H-NMR (CDCl3) δ ppm: 0.93-1.17 (21H, m), 1.19 (3H, s), 1.23-1.44 (5H, m), 1.58-1.78 (6H, m), 1.78-1.93(1H, m), 2.67 (1H, d, J = 11.2 Hz), 3.09 (1H, d, J = 11.2 Hz), 3.5-3.6 (1H, m), 3.67-3.7 (1H, m), 6.39 (1H, dd, J = 3.4, 8.3 Hz), 6.65 (1H, dd, J = 3.2, 3.2 Hz), 6.72 (c), (1H, d, J = 8.2, 12.7 Hz), 7.25 (1H, d, J = 3.2 Hz). | — |
| 773 | 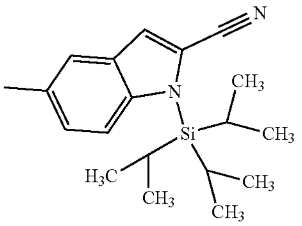 | 1H-NMR (CDCl3) δ ppm: 1.12-1.29 (27H, m), 1.30-1.48 (2H, s), 1.62-1.82 (4H, m), 1.93-2.07 (3H, m), 2.78 (1H, d, J = 11.6 Hz), 2.93 (1H, d, J = 11.6 Hz), 3.45-3.55 (1H, m), 3.63-3.7 (1H, m), 6.92 (1H, d, J = 2.4 Hz), 7.07 (1H, dd, J = 2.5, 9.4 Hz), 7.24 (1H, s), 7.46 (1H, d, J = 9.4 Hz). | — |
| 774 | 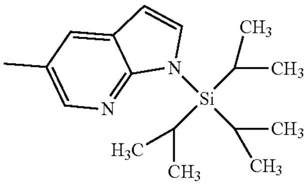 | 1H-NMR (CDCl3) δ ppm: 1.09-1.16 (19H, m), 1.20 (3H, s), 1.23-1.32 (5H, m), 1.33-1.48 (2H, m), 1.60-1.90 (7H, m), 2.81-2.91 (2H, m), 3.49-3.55 (1H, m), 3.55-3.63 (1H, m), 6.40 (1H, d, J = 3.4 Hz), 7.21 (1H, d, J = 3.4 Hz), 7.31 (1H, d, J = 2.8 Hz), 8.06 (1H, d, J = 2.7 Hz). | — |
| 775 | 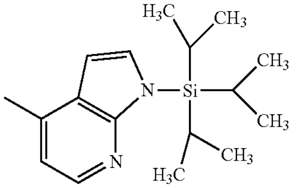 | 1H-NMR (DMSO-d6) δ ppm: 1.07-1.17 (19H, m), 1.21 (3H, s), 1.23-1.35 (5H, m), 1.37-1.49 (2H, m), 1.63-1.90 (6H, m), 1.96-2.09 (1H, m), 3.05 (1H, d, J = 12.6 Hz), 3.38 (1H, d, J = 12.5 Hz), 3.48-3.54 (1H, m), 3.94-4.02 (1H, m), 6.33 (1H, d, J = 5.6 Hz), 6.54 (1H, d, J = 3.6 Hz), 7.10 (1H, d, J = 3.6 Hz), 7.98 (1H, d, J = 5.5 Hz). | — |
| 776 | 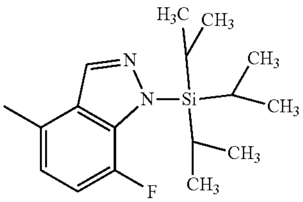 | 1H-NMR (DMSO-d6) δ ppm: 1.1-1.18 (19H, m), 1.18-1.22 (4H, m), 1.34 (3H, s), 1.36-1.44 (2H, m), 1.61-1.84 (7H, m), 1.86-1.98 (1H, m), 2.81 (1H, d, J = 11.4 Hz), 3.07 (1H, d, J = 11.4 Hz), 3.6-3.65 (1H, m), 3.65-3.75 (1H, m), 6.30 (1H, dd, J = 3.0, 8.2 Hz), 6.86 (1H, dd, J = 8.2, 12.0 Hz), 8.24 (1H, d, J = 3.1 Hz). | — |

TABLE 85 absolute configuration

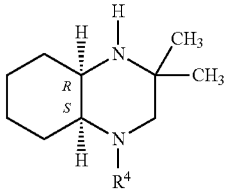

| Example | $R^4$ | NMR | Salt |
|---|---|---|---|
| 777 | 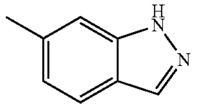 | 1H-NMR (CDCl3) δ ppm: 1.07 (1H, br), 1.16-1.33 (8H, s), 1.35-1.50 (2H, m), 1.64-1.88 (4H, m), 2.81 (1H, d, J = 11.8 Hz), 3.05 (1H, d, J = 11.4 Hz), 3.46-3.53 (1H, m), 3.68-3.79 (1H, m), 6.71 (1H, s), 6.92 (1H, d, J = 2.0, 9.0 Hz), 7.5-7.6 (1H, m), 7.89 (1H, d, J = 0.9 Hz), 9.7 (1H, br). | — |
| 778 | 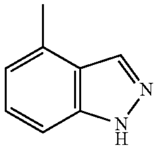 | 1H-NMR (CDCl3) δ ppm: 0.94-1.24 (6H, m), 1.33 (3H, s), 1.37-1.47 (2H, m), 1.63-1.80 (3H, m), 1.88-2.02 (1H, m), 3.02 (1H, d, J = 11.8 Hz), 3.09 (1H, d, J = 11.9 Hz), 3.62-3.68 (1H, m), 3.83-3.92 (1H, m), 6.43 (1H, d, J = 7.6 Hz), 6.97 (1H, d, J = 8.3 Hz), 7.23 (1H, dd, J = 7.7, 8.1 Hz), 8.10 (1H, d, J = 0.9 Hz), 9.96 (1H, br). | — |
| 779 | 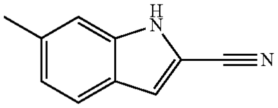 | 1H-NMR (CDCl3) δ ppm: 0.95 (1H, br), 1.15-1.35 (8H, m), 1.35-1.52 (2H, m), 1.52-1.90 (4H, m), 2.81 (1H, d, J = 11.9 Hz), 3.03 (1H, d, J = 11.8 Hz), 3.45-3.55 (1H, m), 3.5-3.8 (1H, m), 6.66 (1H, m), 6.95 (1H, dd, J = 2.1, 9.0 Hz), 7.06 (1H, dd, J = 0.8, 2.0 Hz), 7.46 (1H, d, J = 9.0 Hz), 8.23 (1H, bs). | — |
| 780 | 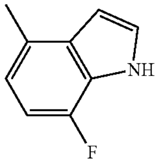 | 1H-NMR (CDCl3) δ ppm: 0.95-1.11 (3H, m), 1.20 (3H, 2), 1.28-1.44 (5H, m), 1.59-1.79 (3H, m), 1.79-1.93 (1H, m), 2.70 (1H, d, J = 11.3 Hz), 3.08 (1H, d, J = 11.3 Hz), 3.6-3.7 (2H, m), 6.35 (1H, dd, J = 3.8, 8.3 Hz), 6.61 (1H, d, J = 3.2, 5.6 Hz), 6.76 (1H, dd, J = 8.3, 10.7 Hz), 7.17 (1H, dd, J = 2.8, 2.8 Hz), 8.39 (1H, br). | — |
| 781 | 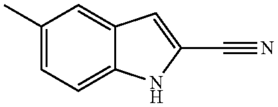 | 1H-NMR (CDCl3) δ ppm: 1.01 (1H, br), 1.10-1.26 (5H, s), 1.28 (3H, s), 1.31-1.48 (2H, m), 1.61-1.83 (4H, m), 2.81 (1H, d, J = 11.5 Hz), 2.89 (1H, d, J = 11.5 Hz), 3.5-3.6 (1H, m), 3.6-3.7 (1H, m), 6.95 (1H, d, J = 2.1 Hz), 7.04 (1H, dd, J = 0.8, 2.0 Hz), 7.17 (1H, d, J = 2.3, 9.1 Hz), 7.28 (1H, d, J = 2.0 Hz), 8.68(1H, br). | — |
| 782 | 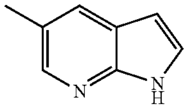 | 1H-NMR (CDCl3) δ ppm: 1.00-1.37 (9H, m), 1.47-1.9 (5H, m), 2.90 (2H, s), 2.95-4.35 (4H, m), 6.27 (1H, dd, J = 1.9, 3.3 Hz), 6.49 (1H, s), 7.34 (1H, dd, J = 2.9, 2.9 Hz), 7.40 (1H, d, J = 2.5 Hz), 8.04 (1H, d, J = 2.6 Hz), 11.30 (1H, s). | 1/2 Fumarate |
| 783 | 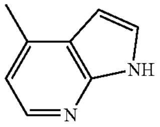 | 1H-NMR (CDCl3) δ ppm: 0.81-1.37 (8H, m), 1.37-1.51 (3H, m), 1.65-183 (3H, m), 1.98-2.13 (2H, m), 3.09 (1H, d, J = 12.6 Hz), 3.4-3.5 (1H, m), 3.5-3.55 (1H, m), 4.0-4.1 (1H, m), 6.36 (1H, d, J = 5.7 Hz), 6.50 (1H, d, J = 3.6 Hz), 7.1-7.2 (1H, m), 8.0-8.1 (1H, m), 9.7-10.6 (1H, m). | — |

TABLE 85-continued absolute configuration

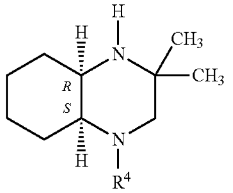

| Example | $R^4$ | NMR | Salt |
|---|---|---|---|
| 784 | 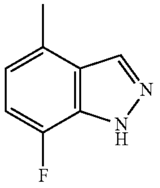 | 1H-NMR (DMSO-d6) δ ppm: 1.02-1.17 (2H, m), 1.22 (3H, s), 1.34 (3H, s), 1.36-1.45 (2H, m), 1.62-1.80 (3H, m), 1.83-1.96 (1H, m), 2.84 (1H, d, J = 11.5 Hz), 3.05 (1H, d, J = 11.5 Hz), 3.65-3.7 (1H, m), 3.7-3.8 (1H, s), 6.28 (1H, dd, J = 3.3, 8.3 Hz), 6.91 (1H, dd, J = 8.2, 10.4 Hz), 8.12 (1H, d, J = 3.4 Hz), 10.38 (1H, br). | — |

TABLE 86 absolute configuration

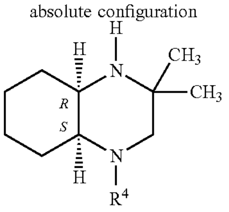

| Example | $R^4$ | NMR | Salt |
|---|---|---|---|
| 785 | 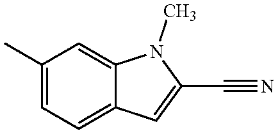 | 1H-NMR (CDCl3) δ ppm: 1.15-1.32 (9H, m), 1.33-1.50 (2H, m), 1.64-1.88 (4H, m), 2.82 (1H, d, J = 11.7 Hz), 3.03 (1H, d, J = 11.7 Hz), 3.46-3.54 (1H, m), 3.71-3.79 (1H, m), 3.80 (3H, s), 6.51 (1H, d, J = 1.7 Hz), 6.96 (1H, dd, J = 2.1, 9.0 Hz), 7.02 (1H, s), 7.46 (1H, d, J = 9.0 Hz). | — |
| 786 | 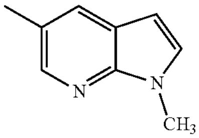 | 1H-NMR (DMSO-d6) δ ppm: 1.0-1.25 (2H, m), 1.25-1.4 (7H, m), 1.45-1.9 (5H, m), 2.94 (2H, s), 3.36 (3H, br), 3.66 (1H, br), 3.7-3.8 (4H, m), 6.29 (1H, d, J = 3.3 Hz), 6.54 (2H, s), 7.39 (1H, d, J = 3.3 Hz), 7.43 (1H, d, J = 2.5 Hz), 8.10 (1H, d, J = 2.5 Hz). | Fumarate |
| 787 | 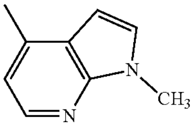 | 1H-NMR (DMSO-d6) δ ppm: 1.15-1.4 (9H, m), 1.5-1.8 (4H, m), 2.0-2.15 (1H, m), 3.09 (1H, d, J = 12.9 Hz), 3.43 (1H, d, J = 12.4 Hz), 3.55-3.65 (1H, m), 3.73 (3H, s), 4.05-4.15 (1H, m), 6.41 (1H, d, J = 5.6 Hz), 6.49 (1H, d, J = 3.6 Hz), 6.55 (2H, s), 7.26 (1H, d, J = 3.6 Hz), 7.93 (1H, d, J = 5.6 Hz). | Fumarate |
| 788 | 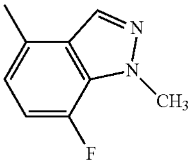 | 1H-NMR (DMSO-d6) δ ppm: 0.97-1.13 (2H, m), 1.33-1.44 (1H, m), 1.51 (3H, s), 1.53 (3H, s), 1.58-1.67 (1H, m), 1.67-1.96 (3H, m), 1.96-2.07 (1H, m), 3.00 (1H, d, J = 12.9 Hz), 3.26 (1H, d, J = 13.0 Hz), 3.85-4.0 (1H, m), 4.05-4.2 (4H, m), 6.40 (1H, dd, J = 3.0, 8.3 Hz), 7.05 (1H, dd, J = 8.2, 11.8 Hz), 8.0-8.2 (1H, m), 8.38 (1H, d, J = 2.3 Hz), 9.65-9.9 (1H, m). | Hydrochloride |

TABLE 86-continued absolute configuration

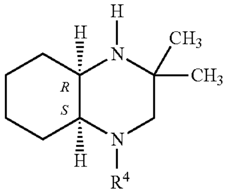

| Example | $R^4$ | NMR | Salt |
|---|---|---|---|
| 789 | 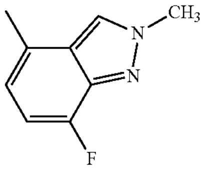 | 1H-NMR (DMSO-d6) δ ppm: 1.00-1.16 (2H, m), 1.34-1.44 (1H, m), 1.50 (3H, s), 1.53 (3H, s), 1.58-1.96 (4H, m), 1.98-2.09 (1H, m), 2.98 (1H, d, J = 12.9 Hz), 3.24 (1H, d, J = 13.0 Hz), 3.85-3.95 (1H, m), 3.95-4.08 (1H, m), 4.17 (3H, s), 6.24 (1H, dd, J = 3.2, 8.0 Hz), 6.85 (1H, dd, J = 8.0, 11.5 Hz), 7.95-8.2 (1H, m), 8.74 (1H, d, J = 2.8 Hz), 9.7-10.0 (1H, m). | Hydrochloride |

TABLE 87 absolute configuration

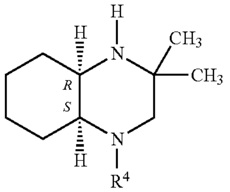

| Example | $R^4$ | NMR | Salt |
|---|---|---|---|
| 790 | 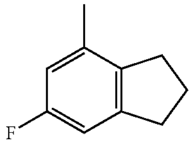 | 1H-NMR (DMSO-d6) δ ppm: 1.01-1.25 (2H, m), 1.32-1.42 (1H, m), 1.46 (3H, s), 1.48 (3H, s), 1.58-2.03 (6H, m), 2.05-2.18 (1H, m), 2.70-2.93 (5H, m), 3.24 (1H, d, J = 12.9 Hz), 3.45-3.57 (1H, m), 3.81-3.93 (1H, m), 6.53 (1H, d, J = 11.4 Hz), 6.70 (1H, d, J = 8.4 Hz), 8.02 (1H, br), 9.72 (1H, br). | Hydrochloride |
| 791 | 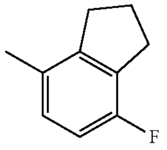 | 1H-NMR (DMSO-d6) δ ppm: 0.90-1.21 (2H, m), 1.28-1.41 (1H, m), 1.48 (6H, s), 1.57-1.67 (1H, m), 1.67-2.06 (5H, m), 2.08-2.21 (1H, m), 2.70 (1H, d, J = 12.4 Hz), 2.78-3.00 (4H, m), 3.22-3.42 (2H, m), 3.77-3.92 (1H, m), 6.74 (1H, dd, J = 4.3, 8.6 Hz), 6.88 (1H, dd, J = 8.6, 8.6 Hz), 8.01 (1H, br), 9.73 (1H, br). | Hydrochloride |
| 792 | 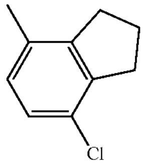 | 1H-NMR (CDCl3) δ ppm: 0.75-1.15 (3H, m), 1.17 (3H, s), 1.27 (3H, s), 1.3-1.45 (2H, m), 1.45-1.75 (3H, m), 1.75-1.95 (1H, m), 1.95-2.1 (1H, m), 2.1-2.25 (1H, m), 2.52 (1H, d, J = 11.2 Hz), 2.85-3.05 (5H, m), 3.1-3.2 (1H, m), 3.45-3.55 (1H, m), 6.58 (1H, d, J = 8.4 Hz), 7.03 (1H, d, J = 8.4 Hz). | — |
| 793 | 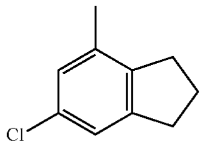 | 1H-NMR (DMSO-d6) δ ppm: 1.11-1.24 (1H, m), 1.34-1.42 (1H, m), 1.45 (3H, s), 1.47 (3H, s), 1.59-2.03 (6H, m), 2.05-2.17 (1H, m), 2.7-2.95 (5H, m), 3.27 (1H, d, J = 12.9 Hz), 3.38-3.55 (3H, m), 3.79-3.95 (1H, m), 4.28-4.11 (1H, m), 6.72 (1H, d, J = 1.5 Hz), 6.94 (1H, s), 7.9-8.1 (1H, m), 9.6-9.8 (1H, m). | Hydrochloride |

TABLE 87-continued absolute configuration

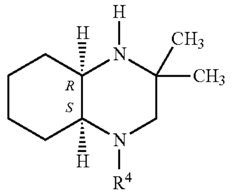

| Example | $R^4$ | NMR | Salt |
| --- | --- | --- | --- |
| 794 | 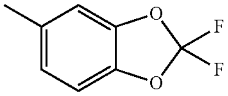 | 1H-NMR (DMSO-d6) δ ppm: 1.20-1.48 (6H, m), 1.52 (3H, s), 1.62-1.93 (4H, m), 1.96-2.12 (1H, m), 2.97 (1H, d, J = 13.4 Hz), 3.29 (1H, d, J = 13.4 Hz), 3.7-3.85 (1H, m), 3.9-4.05 (1H, m), 6.70 (1H, dd, J = 2.4 8.9 Hz), 7.12 (1H, d, J = 2.4 Hz), 7.23 (1H, d, J = 8.9 Hz), 8.18 (1H, br), 9.94 (1H, br). | Hydrochloride |
| 795 | 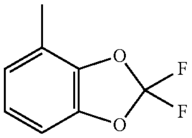 | 1H-NMR (DMSO-d6) δ ppm: 1.1-1.25 (9H, m), 1.25-1.35 (1H, m), 1.48-1.75 (4H, m), 1.9-2.05 (1H, m), 2.94 (1H, d, J = 12.2 Hz), 3.07 (1H, d, J = 12.3 Hz), 3.11-3.62 (3H, m), 3.63-3.71 (1H, m), 6.57 (2H, s), 6.72 (1H, d, J = 8.0 Hz), 6.75-6.81 (1H, m) 7.04 (1H, dd, J = 8.3, 8.3 Hz). | Fumarate |
| 796 | 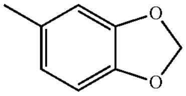 | 1H-NMR (CDCl3) δ ppm: 0.65-1.3 (9H, m), 1.3-1.95 (6H, m), 2.69 (1H, d, J = 11.5 Hz), 2.79 (1H, d, J = 11.6 Hz), 3.4-3.55 (2H, m), 5.84-5.90 (2H, m), 6.25 (1H, dd, J = 11.6 Hz), 6.51 (1H, d, J = 2.4 Hz), 6.69 (1H, d, J = 8.5 Hz). | — |

TABLE 88 absolute configuration

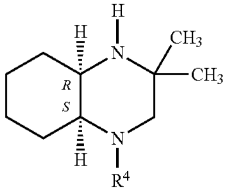

| Example | $R^4$ | NMR | Salt |
| --- | --- | --- | --- |
| 797 | 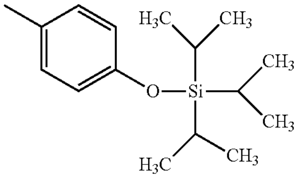 | 1H-NMR (CDCl3) δ ppm: 1.01-1.13 (19H, m), 1.14-1.28 (11H, m), 1.31-1.46 (2H, m), 1.60-1.76 (4H, m), 2.67 (1H, d, J = 11.6 Hz), 2.83 (1H, d, J = 11.5 Hz), 3.4-3.55 (2H, m), 6.69-6.74 (2H, m), 6.74-6.80 (2H, m). | — |
| 798 | 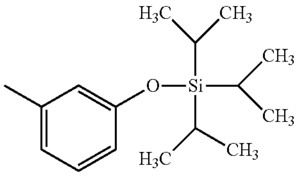 | 1H-NMR (CDCl3) δ ppm: 1.07-1.16 (19H, m), 1.16-1.33 (11H, m), 1.33-1.47 (2H, m), 1.62-1.80 (4H, m), 2.68 (1H, d, J = 12.0 Hz), 2.97 (1H, d, J = 11.9 Hz), 3.4-3.45 (1H, m), 3.55-3.6 (1H, m), 6.25-6.35 (1H, m), 6.37 (1H, dd, J = 2.4, 7.8 Hz), 6.43 (1H, dd, J = 1.9, 8.3 Hz), 7.03 (1H, dd, J = 8.1, 8.1 Hz). | — |

TABLE 88-continued absolute configuration

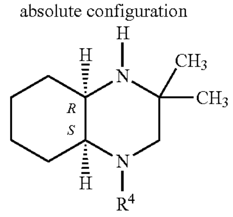

| Example | $R^4$ | NMR | Salt |
| --- | --- | --- | --- |
| 799 | 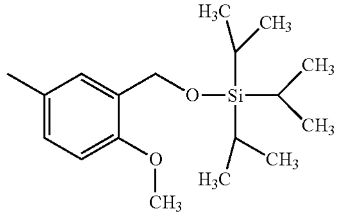 | 1H-NMR (CDCl3) δ ppm: 1.07-1.14 (19H, m), 1.14-1.29 (11H, m), 1.29-1.47 (2H, m), 1.58-1.77 (4H, m), 2.70 (1H, d, J = 11.7 Hz), 2.92 (1H, d, J = 11.7 Hz), 3.4-3.5 (1H, m), 3.55-3.65 (1H, m), 3.75 (3H, s), 4.78-4.89 (2H, m), 6.65 (1H, dd, J = 3.1, 8.8 Hz), 6.71 (1H, d, J = 8.8 Hz), 7.22 (1H, d, J = 3.0 Hz). | — |
| 800 | 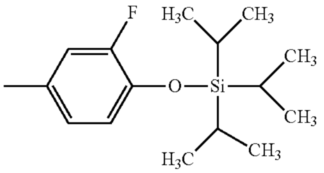 | 1H-NMR (CDCl3) δ ppm: 1.06-1.13 (18H, m), 1.14-1.29 (12H, m), 1.32-1.48 (2H, m), 1.48-1.76 (4H, m), 2.65 (1H, d, J = 11.8 Hz), 2.83 (1H, d, J = 11.6 Hz), 3.35-3.45 (1H, m), 3.45-3.55 (1H, m), 6.39-6.48 (1H, m), 6.55 (1H, dd, J = 2.9, 14.1 Hz), 6.79 (1H, dd, J = 9.4, 9.4 Hz). | — |
| 801 | 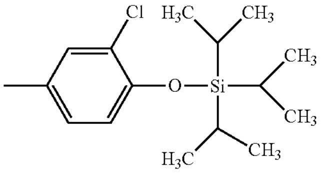 | 1H-NMR (CDCl3) δ ppm: 1.11 (18H, d, J = 7.2 Hz), 1.15-1.21 (4H, m), 1.21-1.33 (7H, m), 1.34-1.47 (2H, m), 1.47-1.77 (5H, m), 2.66 (1H, d, J = 11.5 Hz), 2.81 (1H, d, J = 11.6 Hz), 3.4-3.55 (2H, m), 6.61 (1H, d, J = 3.0, 8.9 Hz), 6.78 (1H, d, J = 8.9 Hz), 6.81 (1H, d, J = 3.0 Hz). | — |
| 802 | 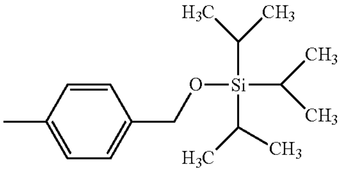 | 1H-NMR (CDCl3) δ ppm: 1.04-1.11 (18H, m), 1.11-1.22 (7H, m), 1.23 (3H, s), 1.26-1.49 (4H, m), 1.64-1.79 (4H, m), 2.71 (1H, d, J = 11.9 Hz), 3.01 (1H, d, J = 11.9 Hz), 3.4-3.5 (1H, m), 3.6-3.7 (1H, m), 4.73 (2H, s), 6.79-6.86 (2H, m), 7.18-7.23 (2H, m). | — |
| 803 | 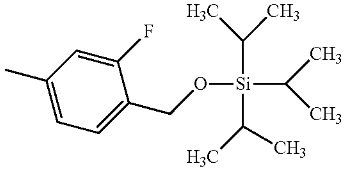 | 1H-NMR (CDCl3) δ ppm: 1.03-1.12 (18H, m), 1.12-1.48 (13H, m), 1.50-1.82 (5H, m), 2.70 (1H, d, J = 12.0 Hz), 2.99 (1H, d, J = 12.0 Hz), 3.35-3.45 (1H, m), 3.55-3.65 (1H, m), 4.77 (2H, s), 6.47 (1H, dd, J = 2.4, 14.0 Hz), 6.61 (1H, dd, J = 2.4, 8.6 Hz), 7.32 (1H, dd, J = 8.8, 8.8 Hz). | — |
| 804 | 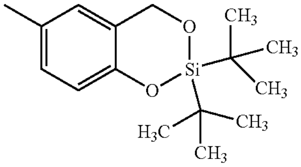 | 1H-NMR (CDCl3) δ ppm: 1.03 (18H, d, J = 2.4 Hz), 1.13-1.27 (9H, m), 1.27-1.77 (6H, m), 2.67 (1H, d, J = 11.6 Hz), 2.80 (1H, d, J = 11.5 Hz), 3.4-3.55 (2H, m), 4.96 (H, s), 6.42 (1H, d, J = 2.9 Hz), 6.70 (1H, dd, J = 2.9, 8.8 Hz), 6.80 (1H, d, J = 8.8 Hz), | — |

TABLE 89 absolute configuration

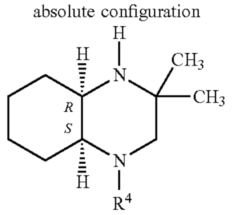

| Example | $R^4$ | NMR | Salt |
|---|---|---|---|
| 805 | 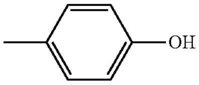 | 1H-NMR (CDCl3) δ ppm: 1.00-1.48 (11H, m), 1.54-1.87 (4H, m), 2.70 (1H, d, J = 10.4 Hz), 2.81 (1H, d, J = 11.5 Hz), 3.3-3.65 (2H, m), 6.75 (4H, bs). | — |
| 806 | 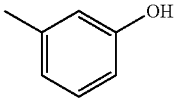 | 1H-NMR CDCl3) δ ppm: 1.14-1.49 (11H, m), 1.60-1.83 (4H, m), 2.71 (1H, d, J = 12.1Hz), 3.03 (1H, d, J = 12.0 Hz), 3.37-3.44 (1H, m), 3.56-3.67 (1H, m), 6.16-6.23 (1H, m), 6.33 (1H, dd, J = 2.3, 2.3 Hz), 6.43 (1H, dd, J = 2.1, 8.4 Hz), 7.06 (1H, dd, J = 8.1, 8.1 Hz). | — |
| 807 | 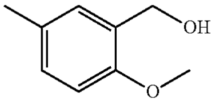 | 1H-NMR (DMSO-d6) δ ppm: 1.0-1.25 (2H, m), 1.25-1.4 (7H, m), 1.4-1.85 (5H, m), 2.78 (1H, d, J = 12.3 Hz), 2.90 (1H, d, J = 12.1 Hz), 2.95-4.1 (9H, m), 4.44 (2H, s), 6.50 (2H, s), 6.71 (1H, dd, J = 2.8, 8.8 Hz), 6.79 (1H, d, J = 8.9 Hz), 6.97 (1H, d, J = 2.7 Hz). | Fumarate |
| 808 | 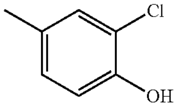 | 1H-NMR (CDCl3) δ ppm: 1.10-1.27 (9H, m), 1.31-1.48 (1H, m), 1.49-2.01 (6H, m), 2.68 (1H, d, J = 11.5 Hz), 2.78 (1H, d, J = 11.5 Hz), 3.4-3.55 (2H, m), 6.73 (1H, dd, J = 2.9, 8.8 Hz), 6.78 (1H, d, J = 2.8 Hz), 6.89 (1H, d, J = 8.9 Hz). | — |
| 809 | 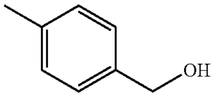 | 1H-NMR (CDCl3) δ ppm: 1.17-1.61 (12H, m), 1.62-1.83 (4H, m), 2.72 (1H, d, J = 11.9 Hz), 3.03 (1H, d, J = 11.9 Hz), 3.4-3.45 (1H, m), 3.6-3.7 (1H, m), 4.56 (2H, s), 6.80-6.86 (2H, m), 7.20-7.25 (2H, m). | — |
| 810 | 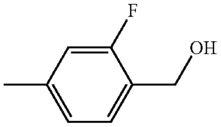 | 1H-NMR (CDCl3) δ ppm: 0.91 (1H, br), 1.17-1.48 (10H, m), 1.56 (1H, br), 1.62-1.84 (4H, m), 2.71 (1H, d, J = 12.1 Hz), 3.02 (1H, d, J = 12.0 H), 3.35-3.45 (1H, m), 3.55-3.65 (1H, m), 4.62 (2H, d, J = 3.2 Hz), 6.51 (1H, dd, J = 2.5, 14.0 Hz), 6.59 (1H, dd, J = 2.5, 8.5 Hz), 7.19 (1H, dd, J = 8.8, 8.8 Hz). | — |
| 811 | 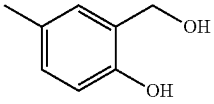 | 1H-NMR (CDCl3) δ ppm: 0.92-1.02 (1H, m), 1.02-1.13 (4H, m), 1.15 (3H, s), 1.21-1.30 (1H, m), 1.35-1.65 (3H, m), 1.69-1.83 (1H, m), 2.60 (1H, d, J = 11.3 Hz), 2.69 (1H, d, J = 11.3 Hz), 3.32 (1H, br), 3.41-3.49 (1H, m), 4.43 (2H, d, J = 4.6 Hz), 4.88 (1H, t, J = 5.4 Hz), 6.55 (1H, dd, J = 2.8, 8.7 Hz), 6.80 (1H, d, J = 8.6 Hz), 6.83 (1H, d, J = 2.7 Hz), 8.55 (1H, s). | — |

TABLE 90 absolute configuration

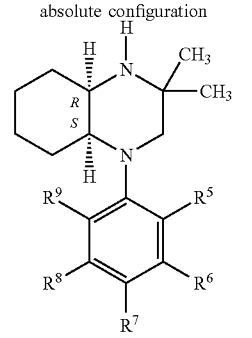

| Example | $R^5$ | $R^6$ | $R^7$ | $R^8$ | $R^9$ | NMR | Salt |
|---|---|---|---|---|---|---|---|
| 812 | —H | —H | —OCH3 | —H | —H | 1H-NMR (DMSO-d6) δppm: 1.1-1.3 (2H, m), 1.35-1.45 ( 4H, m), 1.52 (3H, s), 1.6-1.9 (4H, m), 1.95-2.1 (1H, m), 2.93 (1H, d, J = 13.1 Hz) 3.11 (1H, d, J = 13.0 Hz), 3,68 (3H, s), 3.7-3,9 (2H, m), 4.35-5,35 (1H, m), 6.75-6.85 (2H, m), 6.85-6.95 (2H, m), 8.09 (1H, br), 9.90 (1H, hr). | 2 Hydrochloride |
| 813 | —CH3 | —Cl | —H | —H | —H | 1H-NMR (CDCl3) δppm: 0.93-1.09 (3H, m), 1.16 (3H, s), 1.23-1.34 (4H, m), 1.34-1.44 (2H, m), 1.44-1.75 (2H, m), 1.79-1.92 (1H, m), 2.37 (3H, s), 2.41 (1H, d, J = 11.0 Hz), 2.83-2.91 (1H, m), 3,10 (1H, d, J = 11.1 Hz), 3.51-3,57 (1H, m), 6.79 (1H, dd, J = 2.1, 7.1 Hz), 6.99-7.08 (2H, m). | — |
| 814 | —CH3 | —H | —H | —H | —H | 1H-NMR (CDCl3) δppm: 0.78-1.13 (3H, m), 1.16 (3H, s), 1.28-1.42 (5H, m), 1.54-1.76 (4H, m), 1.81-1.95 (1H, m), 2.34 (3H, s), 2.43 (1H, d, J = 11.1 Hz), 2,87-2,96 (1H, m), 3.13 (1H, d, J = 11.1 Hz), 3,47-3.58 (1H, m), 6,88 (1H, dd. J = 1.0, 7.9 Hz), 6.91-6.97 (1H, m), 7.07-715 (1H, m), 7.1.7 (1H, dd, J = 0.7, 7.5 Hz). | Hydrochloride |
| 815 | —H | —H | —CH3 | —H | —H | 1H-NMR (DMSO-d6) δppm: 1.16-1.33 (2H, m), 1.34-1.48 (4H, m), 1.49-1.56 (3H, m), 1.61-1.93 (4H, m), 1.97-2.11 (1H, m), 2.19 (3H, s), 2,91 (1H, d, J = 13.2 Hz), 3.19-3.32, (1H, m), 3.68-3.80 (1H, m), 3.87-3.99 (1H, m), 4.35-6.4 (1H, m), 6.83 | 2 Hydrochloride |

TABLE 90-continued absolute configuration

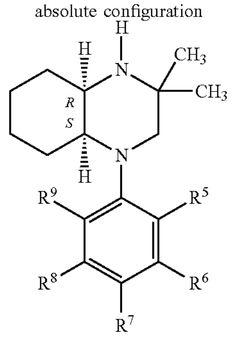

| Example | $R^5$ | $R^6$ | $R^7$ | $R^8$ | $R^9$ | NMR | Salt |
|---|---|---|---|---|---|---|---|
| | | | | | | (2H, d, J = 8.4 Hz), 7.02 (2H, d, J = 8.1 Hz), 8.0-8.35 (1H, m), 9.8-10.2 (1H, m). | |
| 816 | —CH3 | —CH3 | —H | —H | —H | 1H-NMR (DMSO-d6) δppm: 0.96-1.18 (2H, m), 1.28-1.45 (1H, m), 1.49 (3H, s), 1.52 (3H, s), 1.56-1.67 (1H, m), 1.67-1.83 (2H, m ), 1.83-2.10 (2H, m), 2,20 (3H, s), 2.22 (3H, s), 2,59 (1H, d, J = 12.6 Hz), 3.0-3,15 (1H, m), 3.25-3.4 (1H, m), 3.8-3.95 (1H, m), 6.82 (1H, d, J = 7.8 Hz), 6.90 (1H, d, J = 7.4 Hz), 7.03 (1H, dd, J = 7.7, 7.7 Hz), 8.02 (1H, br), 9.65-9.9 (1H, m). | Hydrochloride |
| 817 | —H | —CH3 | —Cl | —H | —H | 1H-NMR (DMSO-d6) δppm: 1.21-1.49 (6H, m), 1.53 (3H, s), 1.63-1.96 (4H, m), 1.96-2.16 (1H, m), 2.26 (3H, s), 2.93 (1H, d, J = 13.5 Hz), 3.36 (1H, d, J = 13.4Hz), 3.65-3.8 (1H, m), 3.95-4.05 (1H, m), 4.43 (1H, br), 6.79 (1H. dd, J = 2.9, 8.8 Hz), 6.93 (1H, d, J = 2.8 Hz), 7.20 (1H, d, J = 8.8 Hz), 8.1-8.4 (1H, m), 9.8-10.2 (1H, m). | Hydrochloride |
| 818 | —H | —CH3 | —F | —H | —H | 1H-NMR (DMSO-d6) δppm: 1.16-1.35 (2H, m), 1.35-1.48 (4H, m), 1.52 (3H, s), 1.62-1.95 (4H, m), 1.95-2.14 (1H, m), 2.18 (3H, d, J = 1.6 Hz), 2.93 (1H, d, J = 13.2 Hz), 3.21 (1H, d, J = 13.1 Hz), 3.7-3.8 (1H, m), 3.85-4.0 (1H, m), 4.05-5.8 (1H, m), 6.71-6.81 (1H, m), 6.85 (1H, dd, J = 2.9, 6.6 Hz), 6.97 (1H, dd, J = 9.1, 9.1 Hz), 8.05-8.3 (1H, m), 9.85-10,2 (1H, m). | Hydrochloride |

TABLE 90-continued absolute configuration

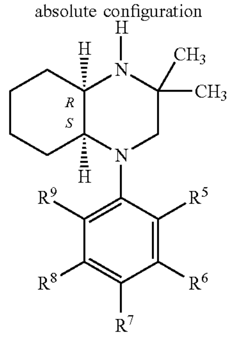

| Example | $R^5$ | $R^6$ | $R^7$ | $R^8$ | $R^9$ | NMR | Salt |
|---|---|---|---|---|---|---|---|
| 819 | —CH3 | —F | —H | —H | —H | 1H-NMR (DMSO-d6) δppm: 0.98-1.20 (214, m), 1.3-1.43 (1H, m), 1.50 (3H, s), 1.51 (3H, s), 1.56-1.69 (1H, m), 1.69-1.87 (2H, m), 1.87-2.08 (2H, m), 2,20 (3H, d, J = 2.3 Hz), 2.67 (1H, d, J = 12.6 Hz), 3.15-3.25 (1H, m), 3.36 (1H, d, J = 12.8 Hz), 3.8-4.0 (1H, m), 6.83 (1H, d, J = 8.0 Hz), 6.89 (1H, dd, J = 8.8, 8.8 Hz), 7.16 (1H, dd , J = 7.9, 15.2 Hz), 8.08 (1H, br), 9.7-10.0 (1H, m). | Hydrochloride |
| 820 | —H | —F | —CH3 | —H | —H | 1H-NMR (DMSO-d6) δppm: 1.14-1.41 (9H, m), 1.50-1.90 (5H, m), 2.09 (3H, d, J = 0.8 Hz), 2,78 (1H, d, J = 12.8 Hz), 3,5-3.6 (1H, m), 3.8-3.9 (1H, m), 6.52 (2H, s), 6.60-6.71 (2H, m), 7.05 (1H, dd, J = 8.9, 8.9 Hz). | Fumarate |
| 821 | —H | —Cl | —CH3 | —H | —H | 1H-NMR (DMSO-d6) δppm: 1.15-1.40 (9H, m), 1,5-1.9 (5H, m), 2.19 ( 3H, d, J = 0.8 Hz), 2.78 (1H, d, J = 12.7 Hz), 3.18 (1H. d, J = 12.7Hz), 3.5-3.6 (1H, m), 3.8-3.9 (1H, m), 6.54 (2H, s), 6.80 (1H, dd, J = 2.6, 8.5 Hz), 6.90 (1H, d, J = 2.6 Hz), 7.13 (1H, d, J = 8.5 Hz). | Fumarate |
| 822 | —H | —Cl | —H | —H | —H | 1H-NMR (DMSO-d6) δppm: 1.12-1.21 (4H, m), 1.22 (3H, s 1.24-1,37 (2H, m), 1.45-1.77 (4H, m), 1.77-1.92 (1H, m), 2.72 (1H, d, J = 12.5 Hz), 3.18 (1H, d, J = 12.4 Hz), 3.40 (1H, brs), 3.75-3.85 (1H, m), 6.50 (1H, s), 6.67 (1H, dd, J = 1.6, 7.7 Hz), 6.8-6.9 (2H, m), 7.16 (1H, dd, J = 8.1, 8.1 Hz). | 1/2 Fumarate |

TABLE 90-continued absolute configuration

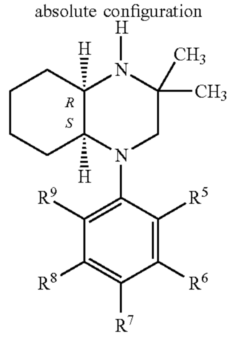

| Example | $R^5$ | $R^6$ | $R^7$ | $R^8$ | $R^9$ | NMR | Salt |
|---|---|---|---|---|---|---|---|
| 823 | —CH3 | —OCH3 | —H | —H | —H | 1H-NMR (DMSO-d6) δppm: 1.0-1.17 (2H, m), 1.29-1.43 (1H, m), 1.48 (3H, s), 1.51 (3H, s), 1.56-2.05 (5H, m), 2.12 (3H, s), 2.62 (1H, d, J = 12.6 Hz), 3.05-3.2 (1H, m), 3.3-3.4 (1H, m), 3.76 (3H, s), 3.85-3.95 (1H, m), 6.61 (1H, d, J = 7.9 Hz), 6.72 (1H, d, J = 8.2 Hz), 7.10 (1H, dd, J = 8.1, 8.1 Hz), 7.99 (1H. br), 9.5-9.8 (1H, m). | Hydrochloride |
| 824 | —H | —H | —OCHF2 | —H | —H | 1H-NMR (DMSO-d6) δppm: 1.21-1.36 (2H, m), 1.36-1.46 (4H, m), 1.52 (3H, s), 1.63-1.92 (4H, m), 1.93-2.09 (1H, m), 2.94 (1H, d, J = 13.4 Hz), 3.33 (1H, d, J = 13.3 Hz), 3.5-4.4 (2H, m), 6.84-7.26 (5H, m), 8.13 (1H, br), 9.84 (1H, br). | 2 Hydrochloride |
| 825 | —H | —H | —OCF3 | —H | —H | 1H-NMR (DMSO-d6) δppm: 1.26-1.48 (6H, m), 1.50 (3H, s), 1.63-1.92 (4H, m), 1.92-2.06 (1H, m), 2.96 (1H, d, J = 13.6 Hz), 3.44 (1H, d, J = 13.5 Hz), 3.72-3.83 (1H, m), 3.98-4.09 (1H, m), 6.96-7.07 (2H, m), 7.15-7.27 (2H, m), 8.08 (1H, br), 9.67 (1H, br). | Hydrochloride |
| 826 | —H | —Cl | —CN | —H | —H | 1H-NMR (DMSO-d6) δppm: 1.10 (3H, s), 1.15-1.25 (4H, m), 1.25-1.45 (2H, m), 1.45-1.75 (4H, m), 1.85-2.0 (1H, m), 2.75 (1H, d, J = 13.0 Hz), 2.9-3.85 (4H, m), 3.85-3.95 (1H, m), 6.56 (1H, s), 6.94 (1H, dd, J = 2.5, 9.1 Hz), 7.09 (1H, d, J = 2.4 Hz), 7.59 (1H, d, J = 9.0 Hz). | 1/2 Fumarate |
| 827 | —H | —F | —OCF3 | —H | —H | 1H-NMR (DMSO-d6) δppm: 1.28-1.46 (6H, m), 1.51 (3H, s), 1.63-2.10 (5H, m), 2.97 (1H, d, J = | Hydrochloride |

TABLE 90-continued absolute configuration

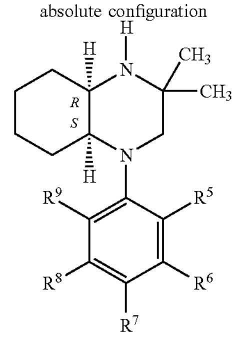

| Example | $R^5$ | $R^6$ | $R^7$ | $R^8$ | $R^9$ | NMR | Salt |
|---|---|---|---|---|---|---|---|
| | | | | | | 13.8 Hz), 3.54 (1H, d, J = 13.8 Hz), 3.65-3.8 (1H, m), 4.0-4.15 (1H, m), 6.81 (1H, dd, J = 2.2, 9.2 Hz), 7.05 (1H, dd, J = 2.9, 14.4 Hz), 7.34 (1H, dd, JJ = 9.2, 9.2 Hz), 8.22 (1H, br), 9.89 (1H, br). | |
| 828 | —H | —F | —OCHF2 | —H | —H | 1H-NMR (DMSO-d6) δppm: 1.09-1.37 (9H, m), 1.44-1.73 (4H, m), 1.75-1.90 (1H, m), 2.66 (1H. d, J = 12.1 Hz), 3,0-3,7 (4H, m), 3.7-3.8 (1H, m), 6.52 (1H, m), 6.67 (1H, d, J = 2.1, 9.3 Hz), 6,80-7,22 (3H, m) | 1/2 Fumarate |
| 829 | —H | —Cl | —OCHF2 | —H | —H | 1H-NMR (DMSO-d6) δppm: 1.08-1.37 (9H, m), 1.43-1.59 (1H, m), 1,59-1.74 (3H, m), 1.75-1.90 (1H, m), 2.69 (1H, d, J = 12.3 Hz), 2.8-4.2 (5H, m), 6,52 (1H, s), 6.82-7.25 (4H, m). | 1/2 Fumarate |
| 830 | —H | —OCHF2 | —H | —H | —H | 1H-NMR (DMSO-d6) δppm: 1.13-1.41 (9H, m), 1.46-1.93 (5H, m), 2.75 (1H, d, J = 12.5 Hz), 2.8-4.4 (6H, m), 6.46 (1H, d, J = 8.1 Hz), 6.54 (2H, s), 6.62 (1H, s), 6,76 (1H, dd, J = 8.4 Hz), 7.0-7.4 (2H, m), | 1/2 Fumarate |
| 831 | —H | —OCHF2 | —F | —H | —H | 1H-NMR (DMSO-d6) δppm: 1.02-1.36 (9H, m), 1.44-1.59 (1H, m), 1.59-1.74 (3H, m), 1.74-1.87 (1H, m), 2.65-4.5 (6H, m), 6.52 (1H, s), 6.7-6.8 (2H, m), 7.0-7.4 (2H, m). | 1/2 Fumarate |
| 832 | —H | —OCHF2 | —Cl | —H | —H | 1H-NMR (DMSO-d6) δppm: 1.10-1.38 (9H, m), 1.44-1.74 (4H, m), 1.76-1.91 (1H, m), 2.69 (1H, d, J = 12.3 Hz), 2.75-4.2 (5H, m), 6.53 (1H, s), 6.75-6,85 (2H, m), 7.05-7.45 (2H, m). | 1/2 Fumarate |

TABLE 90-continued absolute configuration

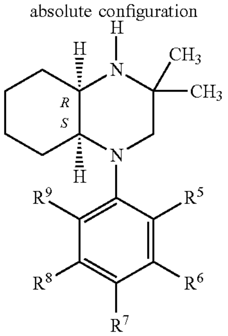

| Example | R5 | R6 | R7 | R8 | R9 | NMR | Salt |
|---|---|---|---|---|---|---|---|
| 833 | —H | —CN | —OCHF2 | —H | —H | 1H-NMR (DMSO-d6) δppm: 1.06-1.23 (7H, m), 1.23-1.37 (2H, m), 1.43-1.74 (4H, m), 1.75-1.89 (1H, m), 2.69 (1H, d, J = 12.4 Hz), 2.9-3.75 (4H, m), 3.75-3.85 (1H, m), 6.53 (1H, s), 7.00-7.41 (4H, m). | 1/2 Fumarate |
| 834 | —H | —OCHF2 | —OCHF2 | —H | —H | 1H-NMR (DMSO-d6) δppm: 1.1-1.4 (9H, m), 1.44-1,76 (4H, m), 1.76-1.90 (1H, m), 2.69 (1H, d, J = 12.2 Hz), 2.8-4.25 (5H, m), 6.52 (1H, s), 6.71-7.36 (5H, m). | 1/2 Fumarate |
| 835 | —H | —F | —OCHF2 | —F | —H | 1H-NMR (DMSO-d6) δppm: 1.08-1.23 (7H, m), 1.24-1.40 (2H, m), 1.43-1.73 (4H, m), 1.76-1.91 (1H, m), 2,67 (1H, d, J = 12.5 Hz), 2.8-4.2 (5H, m), 6.53 (1H, s), 6.67-6.77 (2H, m), 7.05 (1H, t, J = 72.9 Hz). | 1/2 Fumarate |
| 836 | —H | —H | —OCHF2 CHF2 | —H | —H | 1H-NMR (DMSO-d6) δppm: 1.13-1.31 (2H, m), 1.32-1.47 (4H, m), 1,53 (3H, s), 1.61-1.90 (4H, m), 1.97-2.12 (1H, m), 2.93 (1H, d, J = 13.1 Hz), 3.15 (1H, d, J = 13.1 Hz), 3.69-3.81 (1H, m), 3.83-3.93 (1H, m), 4.10-4.46 (3H, m), 6.12-6.53 (1H, m), 6.90 (4H, s), 8.0-8.25 (1H, m), 9.9-10.1 (1H, m). | 2 Hydrochloride |
| 837 | —H | —F | —OCH2 CHF2 | —H | —H | 1H-NMR (DMSO-d6) δppm: 1.20-1.46 (6H, m), 1.51 (3H, s), 1.63-1.91 (4H, m), 1.93-2.10 (1H, m) , 2.91 (1H, d, J = 13.4 Hz), 3.29 (1H, d, J = 13.2 Hz), 3.67-3.80 (1H, m), 3.89-4.01 (1H, m), 4.20-4.35 (2H, m), 6.18-6.51 (1H, m), 6,68 (1H, dd, J = 1.8, 9.1 Hz), 6.91 (1H, dd, J = 2.9, | Hydrochloride |

TABLE 90-continued
absolute configuration
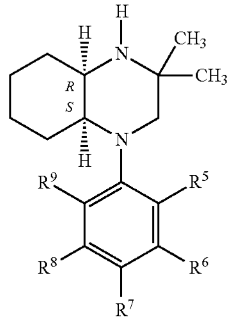
| Example | $R^5$ | $R^6$ | $R^7$ | $R^8$ | $R^9$ | NMR | Salt |
|---|---|---|---|---|---|---|---|
| | | | | | | 14.7 Hz), 7.10 (1H, dd, J = 9.5, 9.5 Hz), 8.05-8.2 (1H, m), 9.75-9.95 (1H, m). | |
| 838 | —H | —CH3 | —OCHF2 | —H | —H | 1H-NMR (DMSO-d6) δppm: 1.06-1.15 (1H, m), 1.15-1.38 (8H, m), 1.42-1.88 (5H, m), 2.17 (3H, s), 2.68 (1H, d, J = 11.9 Hz), 3.04 (1H, d, J = 12.1 Hz), 3.1-3.9 (4H, m), 6.50 (1H. s), 6.71 (1H, dd, J = 2.9, 8.9 Hz), 6.75-7.16 (3H, m). | 1/2 Fumarate |
| 839 | —H | —OCH3 | —OCHF2 | —H | —H | 1H-NMR (DMSO-d6) δppm: 1.10-1.39 (9H, m), 1.45-1.90 (5H, m), 2.72 (1H, d, J = 12.2 Hz), 2.95-4.1 (8H, m), 6.40 (1H, dd, J = 2.8, 8,9 Hz), 6,50 (1H, s), 6,57 (1H, d, J = 2.7 Hz), 6.63-7:03 (2H, m). | 1/2 Fumarate |
| 840 | —OCHF2 | —H | —H | —H | —H | 1H-NMR (DMSO-d6) δppm: 0.94-11.4 (1H, m), 1.14-1.17 (1H, m), 1.18 (3H, s), 1.26 (3H, s), 1.29-1.55 (3H, m), 1.59-1.73 (3H, m), 1.76-1.90 (1H, m), 2.49 (1H, d, J = 11.2 Hz), 3.04 (1H, d, J = 11.2 Hz), 3.5-3.6 (2H, m), 6.55 (1H, dd, J = 70.2, 81.4 Hz), 6.91 (1H, dd, J = 1.4, 8.0 Hz), 6.93-6.99 (1H, m), 7.07-7.18 (2H, m) | — |

TABLE 91 absolute configuration

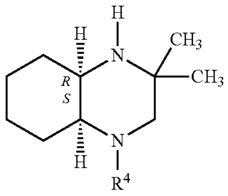

| Example | $R^4$ | NMR | Salt |
|---|---|---|---|
| 841 | 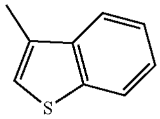 | 1H-NMR (DMSO-d6) δ ppm: 0.95-1.15 (2H, m), 1.35-1.45 (1H, m), 1.51 (3H, s), 1.56 (3H, s), 1.6-2.05 (5H, m), 2.87 (1H, d, J = 12.8 Hz), 3.3-3.4 (1H, m), 3.65-3.75 (1H, m), 4.1-4.2 (1H, m), 7.05 (1H, s), 7.35-7.45 (2H, m), 7.9-8.1 (3H, m), 9.5-9.7 (1H, m). | Hydrochloride |
| 842 | 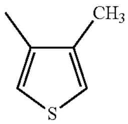 | 1H-NMR (CDCl3) δ ppm: 0.89-1.18 (5H, m), 1.25-1.74 (9H, m), 1.74-1.86 (1H, m), 2.19 (3H, d, J = 0.9 Hz), 2.52 (1H, d, J = 11.2 Hz), 2.93 (1H, d, J = 11.2 Hz), 3.03-3.10 (1H, m), 3.47-3.52 (1H, m), 6.35 (1H, d, J = 3.3 Hz), 6.84-6.88 (1H, m). | — |

TABLE 92 relative configuration

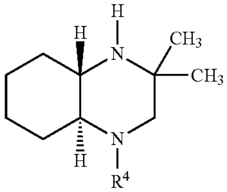

| Example | $R^4$ | NMR | Salt |
|---|---|---|---|
| 843 | 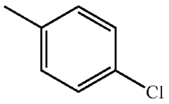 | 1H-NMR (CDCL3) δ ppm 0.97-1.09 (1H, m), 1.23-1.38 (2H, m), 1.62-1.68 (3H, m), 1.63 (3H, s), 1.68 (3H, s), 1.92-2.05 (1H, m), 2.29-2.36 (1H, m), 2.73 (1H, d, J = 12.4 Hz), 2.94-3.03 (1H, m), 3.11-3.22 (1H, m), 3.28 (1H, d, J = 12.4 Hz), 7.02 (1H, dd, J = 8.5, 2.4 Hz), 7.25 (1H, d, J = 2.4 Hz), 7.39 (1H, d, J = 8.5 Hz), 9.50 (1H, brs), 9.78 (1H, brs) | Hydrochloride |
| 844 | 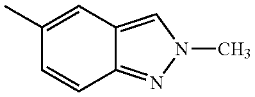 | 1H-NMR (DMSO-d6) δ ppm: 1.00-1.98 (13H, m), 1.98-2.28 (1H, br), 2.65-3.90 (4H, br), 4.18 (3H, s), 6.70-7.95 (3H, m), 8.22-8.60 (1H, br), 8.80-11.33 (3H, brm). | 2 Hydrochloride |

TABLE 93 absolute configuration

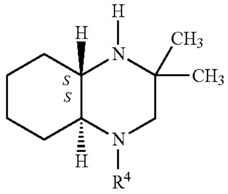

| Example | $R^4$ | NMR | Salt |
|---|---|---|---|
| 845 | 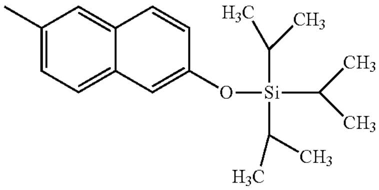 | 1H-NMR (CDCl3) δ ppm: 1.03-1.17 (23H, m), 1.17-1.41 (6H, m), 1.43 (3H, s), 1.59-1.68 (1H, m), 1.68-1.80 (3H, m), 2.32-2.40 (1H, m), 2.68 (1H, d, J = 11.3 Hz), 2.78-2.85 (1H, m), 2.88 (1H, d, J = 11.3 Hz), 7.08 (1H, dd, J = 2.4, 8.8 Hz), 7.16 (1H, d, J = 2.4 Hz), 7.22 (1H, dd, J = 2.1, 8.7 Hz), 7.37 (1H, d, J = 1.8 Hz), 7.57-7.64 (2H, m). | — |
| 846 | 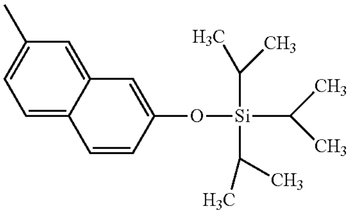 | 1H-NMR (CDCl3) δ ppm: 0.82-1.17 (23H, m), 1.20-1.46 (9H, m), 1.60-1.70 (1H, m), 1.70-1.85 (3H, m), 2.35-2.45 (1H, m), 2.69 (1H, d, J = 11.3 Hz), 2.77-2.86 (1H, m), 2.91 (1H, d, J = 11.3 Hz), 7.02 (1H, dd, J = 2.4, 8.8 Hz), 7.09-7.15 (2H, m), 7.27 (1H, d, J = 1.9 Hz), 7.60-7.68 (2H, m). | — |
| 847 | 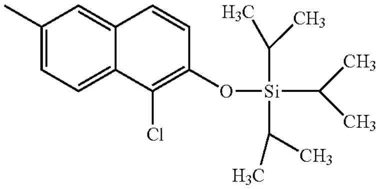 | 1H-NMR (CDCl3) δ ppm : 0.97-1.41 (29H, m), 1.43 (3H, s), 1.60-1.70 (1H, m), 1.70-1.80 (3H, m), 2.35-2.43 (1H, m), 2.69 (1H, d, J = 11.3 Hz), 2.78-2.87 (1H, m), 2.89 (1H, d, J = 11.3 Hz), 7.11 (1H, d, J =8.9 Hz), 7.34 (1H, dd, J = 2.1, 9.0 Hz), 7.37 (1H, d, J = 1.9 Hz), 7.53 (1H, d, J = 8.9 Hz), 8.10 (1H, d, J = 8.9 Hz). | — |
| 848 | 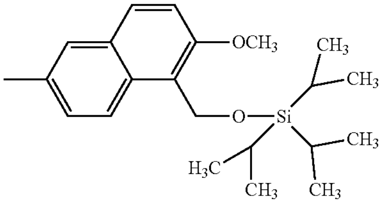 | 1H-NMR (CDCl3) δ ppm: 0.74-1.42 (29H, m), 1.44 (3H, s), 1.58-1.83 (4H, m), 2.35-2.43 (1H, m), 2.68 (1H, d, J = 11.3 Hz), 2.78-2.87 (1H, m), 2.91 (1H, d, J = 11.3 Hz), 3.91 (3H, s), 5.19-5.27 (2H, m), 7.21 (1H, d, J = 9.1 Hz), 7.29 (1H, d, J = 2.2, 9.1 Hz), 7.37 (1H, d, J = 2.1 Hz), 7.69 (1H, d, J = 9.0 Hz), 8.16 (1H, d, J = 9.1 Hz). | — |
| 849 | 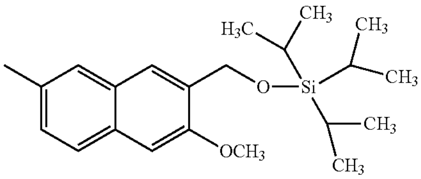 | 1H-NMR (CDCl3) δ ppm: 0.96-1.19 (23H, m), 1.19-1.42 (6H, m), 1.44 (3H, s), 1.57-1.78 (4H, m), 2.32-2.41 (1H, m), 2.71 (1H, d, J = 11.3 Hz), 2.77-2.86 (1H, m), 2.87 (1H, d, J = 11.3 Hz), 3.89 (3H, s), 4.94 (2H, d, J = 1.1 Hz), 7.02 (1H, s), 7.22 (1H, dd, J = 2.0, 8.6 Hz), 7.44 (1H, d, J = 1.8 Hz), 7.64 (1H, d, J = 8.6 Hz), 7.88 (1H, s). | — |

TABLE 94 absolute configuration

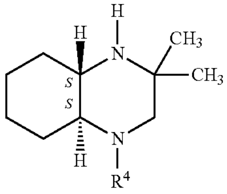

| Example | $R^4$ | NMR | Salt |
| --- | --- | --- | --- |
| 850 | 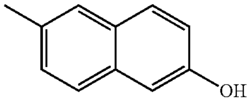 | 1H-NMR (DMSO-d6) δ ppm: 0.88-1.03 (4H, m), 1.11-1.37 (6H, m), 1.45-1.68 (5H, m), 2.26-2.35 (1H, m), 2.58 (1H, d, J = 10.9 Hz), 2.62-2.70 (1H, m), 2.73 (1H, d, J = 10.9 Hz), 7.02 (1H, dd, J = 2.4, 8.7 Hz), 7.05 (1H, d, J = 2.4 Hz), 7.16 (1H, dd, J = 2.1, 8.7 Hz), 7.37 (1H, d, J = 1.8 Hz), 7.58 (1H, d, J = 8.8 Hz), 7.67 (1H, d, J = 8.9 Hz), 9.57 (1H, brs). | — |
| 851 | 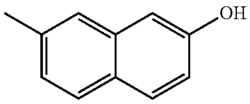 | 1H-NMR (DMSO-d6) δ ppm: 0.88-1.02 (4H, m), 1.10-1.37 (6H, m), 1.44-1.74 (5H, m), 2.32-2.41 (1H, m), 2.60 (1H, d, J = 11.1 Hz), 2.63-2.72 (1H, m), 2.80 (1H, d, J = 11.1 Hz), 6.94 (1H, dd, J = 2.4, 8.8 Hz), 7.00 (1H, dd, J = 2.0, 8.8 Hz), 7.02 (1H, d, J = 2.4 Hz), 7.21 (1H, d, J = 1.8 Hz), 7.64 (2H, d, J = 8.7 Hz), 9.63 (1H, s). | — |
| 852 | 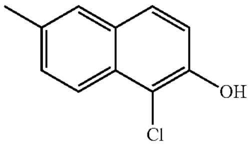 | 1H-NMR (DMSO-d6) δ ppm: 0.90-1.08 (4H, m), 1.15-1.40 (6H, m), 1.51-1.73 (4H, m), 2.35-2.47 (1H, m), 2.65 (1H, d, J = 11.2 H), 2.70-2.85 (2H, m), 2.90-3.75 (1H, br), 7.23 (1H, d, J = 8.9 Hz), 7.34 (1H, dd, J = 2.1, 9.0 Hz), 7.46 (1H, d, J = 2.0 Hz), 7.70 (1H, d, J = 8.9 Hz), 7.92 (1H, d, J = 9.0 Hz), 9.05-11.25 (1H, br). | — |
| 853 | 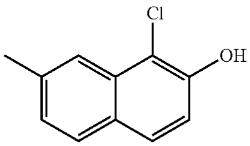 | 1H-NMR (DMSO-d6) δ ppm: 0.95-1.10 (4H, m), 1.17-1.40 (6H, m), 1.56-1.80 (4H, m), 2.49-2.60 (1H, m), 2.73-2.87 (2H, m), 2.92 (1H, d, J = 11.5 Hz), 3.18-3.46 (1H, br), 7.10-7.18 (2H, m), 7.50 (1H, d, J = 2.0 Hz), 7.67 (1H, d, J = 8.8 Hz), 7.75 (1H, d, J = 8.7 Hz), 9.95-10.75 (1H, br). | — |
| 854 | 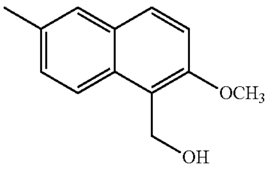 | 1H-NMR (DMSO-d6) δ ppm: 0.90-1.07 (4H, m), 1.13-1.37 (6H, m), 1.47-1.70 (5H, m), 2.30-2.40 (1H, m), 2.61 (1H, d, J = 11.0 Hz), 2.65-2.74 (1H, m), 2.77 (1H, d, J = 11.0 Hz), 3.88 (3H, s), 4.82 (1H, t, J = 5.1 Hz), 4.89 (2H, d, J = 5.1 Hz), 7.27 (1H, dd, J = 2.1, 9.1 Hz), 7.35 (1H, d, J = 9.1 Hz), 7.42 (1H, d, J = 2.1 Hz), 7.80 (1H, d, J = 9.1 Hz), 8.03 (1H, d, J = 9.1 Hz). | — |
| 855 | 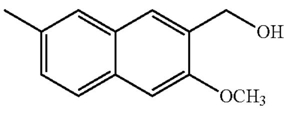 | 1H-NMR (DMSO-d6) δ ppm: 0.95-1.10 (1H, m), 1.10-1.50 (9H, m), 1.53-1.73 (3H, m), 1.77-1.87 (1H, m), 2.58-2.70 (1H, m), 2.85 (2H, s), 2.89-3.00 (1H, m), 3.87 (3H, s), 4.61 (2H, s), 6.46 (1H, s), 7.20 (1H, dd, J = 2.0, 8.7 Hz), 7.22 (1H, s), 7.46 (1H, d, J = 1.6 Hz), 7.73 (1H, d, J = 8.7 Hz), 7.79 (1H, s). | Fumarate |

TABLE 95 absolute configuration

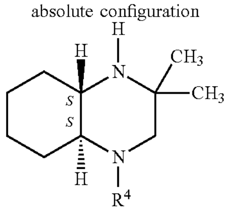

| Example | $R^4$ | NMR | Salt |
|---|---|---|---|
| 856 | 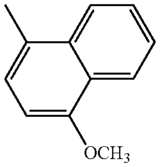 | 1H-NMR (CDCl3) δ ppm: 0.91-1.05 (1H, m), 1.08 (3H, s), 1.12-1.62 (9H, m), 1.68-1.78 (2H, m), 2.42-2.50 (1H, m), 2.62 (1H, d, J = 11.3 Hz), 2.75 (1H, d, J = 11.3 Hz), 2.91-3.00 (1H, m), 3.98 (3H, s), 6.78 (1H, d, J = 8.1 Hz), 7.20 (1H, d, J = 8.1 Hz), 7.43-7.54 (2H, m), 8.21-8.26 (1H, m), 8.50-8.54 (1H, m). | — |
| 857 | 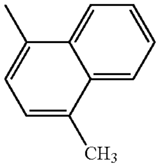 | 1H-NMR (DMSO-d6) δ ppm : 0.93-1.22 (2H, m), 1.26-1.44 (5H, m), 1.44-1.54 (1H, m), 1.56-1.77 (5H, m), 1.99-2.08 (1H, m), 2.62 (3H, s), 2.76 (1H, d, J = 12.4 Hz), 2.98-3.08 (2H, m), 3.33-3.50 (1H, m), 7.28 (1H, d, J = 7.5 Hz), 7.38 (1H, d, J = 7.5 Hz), 7.54-7.61 (2H, m), 7.97-8.03 (1H, m), 8.43-8.52 (1H, m), 9.10-9.25 (1H, br), 9.62-9.77 (1H, br). | Hydrochloride |
| 858 | 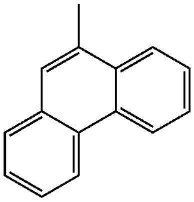 | 1H-NMR (DMSO-d6) δ ppm: 1.00-1.30 (2H, m), 1.30-1.45 (4H, m), 1.45-1.62 (2H, m), 1.62-1.81 (5H, m), 2.00-2.13 (1H, m), 2.91 (1H, d, J = 12.6 Hz), 3.05-3.20 (2H, m), 3.41-3.57 (1H, m), 3.75-4.30 (1H, br), 7.61-7.77 (5H, m), 7.98-8.05 (1H, m), 8.54-8.61 (1H, m), 8.77-8.88 (2H, m), 9.19-9.35 (1H, m), 9.669.81 (1H, m). | 2 Hydrochloride |
| 859 | 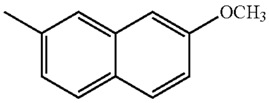 | 1H-NMR (DMSO-d6) δ ppm : 0.90-1.45 (6H, m), 1.53-1.80 (7H, m), 1.97-2.12 (1H, m), 2.83-3.40 (4H, m), 3.86 (3H, s), 7.05-7.25 (2H, m), 7.32 (1H, d, J = 2.4 Hz), 7.42-7.68 (1H, br), 7.75-7.87 (2H, m), 8.25-9.55 (2H, br), 9.55-10.02 (1H, br). | 2 Hydrochloride |
| 860 | 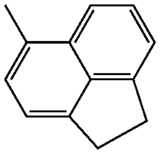 | 1H-NMR (DMSO-d6) δ ppm: 0.85-1.00 (1H, m), 1.10-1.70 (12H, m), 1.75-1.86 (1H, m), 2.65-2.80 (3H, m), 2.99-3.10 (1H, m), 3.25-3.43 (4H, m), 6.46 (1H, s), 7.20-7.34 (3H, m), 7.45 (1H, dd, J = 7.0, 8.2 Hz), 7.88 (1H, d, J = 8.2 Hz), 8.07-9.40 (1H, br). | ½ Fumarate |
| 861 | 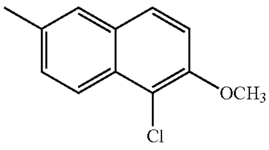 | 1H-NMR (DMSO-d6) δ ppm: 1.04-1.43 (6H, m), 1.54-1.80 (7H, m), 1.97-2.10 (1H, m), 2.86-3.07 (2H, m), 3.07-3.30 (2H, m), 3.98 (3H, s), 7.43 (1H, d, J = 9.1 Hz), 7.55 (1H, d, J = 9.2 Hz), 7.66 (1H, brs), 7.95 (1H, d, J = 9.1 Hz), 8.04 (1H, d, J = 9.1 Hz), 8.11-8.95 (1H, br), 9.08-9.35 (1H, m), 9.60-9.86 (1H, m). | 2 Hydrochloride |
| 862 | 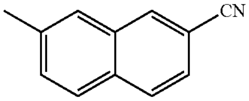 | 1H-NMR (CDCl3) δ ppm: 0.84-0.97 (1H, br), 1.03-1.17 (4H, m), 1.22-1.46 (6H, m), 1.61-1.74 (1H, m), 1.74-1.88 (3H, m), 2.45-2.55 (1H, m), 2.76 (1H, d, J = 11.5 Hz), 2.82-2.90 (1H, m), 2.98 (1H, d, J = 11.5 Hz), 7.38-7.43 (2H, m), 7.50 (1H, dd, J = 1.6, 8.4 Hz), 7.77-7.86 (2H, m), 8.12 (1H, s). | — |
| 863 | 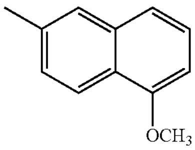 | 1H-NMR (DMSO-d6) δ ppm: 1.05-1.43 (6H, m), 1.54-1.80 (7H, m), 1.98-2.10 (1H, m), 2.90-3.32 (4H, m), 3.95 (3H, s), 6.91 (1H, d, J = 7.2 Hz), 7.24-7.36 (1H, br), 7.38-7.49 (2H, m), 7.50-7.68 (1H, br), 8.11 (1H, d, J = 8.9 Hz), 9.00-9.45 (1H, br), 9.55-9.98 (1H, br), 10.50-12.10 (1H, br). | 2 Hydrochloride |

TABLE 95-continued absolute configuration

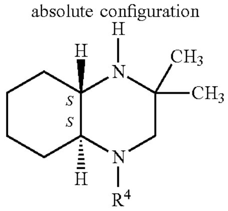

| Example | $R^4$ | NMR | Salt |
|---|---|---|---|
| 864 | 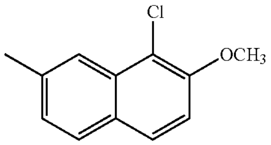 | 1H-NMR (DMSO-d6) δ ppm: 1.10-1.47 (6H, m), 1.54-1.80 (7H, m), 2.01-2.14 (1H, m), 2.95-3.37 (4H, m), 4.00 (3H, s), 7.30 (1H, d, J = 8.3 Hz), 7.51 (1H, d, J = 9.1 Hz), 7.73 (1H, brs), 7.95 (2H, d, J = 9.1 Hz), 9.39 (1H, brs), 9.90 (1H, brs), 11.80 (1H, brs). | 2 Hydrochloride |
| 865 | 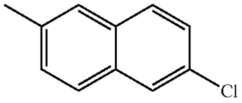 | 1H-NMR (DMSO-d6) δ ppm: 1.03-1.44 (6H, m), 1.53-1.79 (7H, m), 1.97-2.09 (1H, m), 2.92-3.06 (2H, m), 3.06-3.16 (1H, m), 3.16-3.30 (1H, m), 6.24-7.14 (1H, m), 7.36 (1H, dd, J = 2.1, 8.8 Hz), 7.49 (1H, dd, J = 2.1, 8.8 Hz), 7.64 (1H, brs), 7.88 (1H, d, J = 8.8 Hz), 7.94 (1H, d, J = 8.8 Hz), 8.00 (1H, d, J = 2.1 Hz), 9.10-9.39 (1H, brs), 9.63-9.87 (1H, brs). | 2 Hydrochloride |
| 866 | 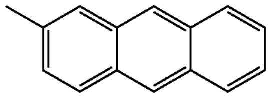 | 1H-NMR (CDCl3) δ ppm: 0.75-1.19 (5H, m), 1.24-1.43 (3H, m), 1.45 (3H, s), 1.64-1.73 (1H, m), 1.73-1.82 (2H, m), 1.90-2.00 (1H, m), 2.45-2.54 (1H, m), 2.72 (1H, d, J = 11.5 Hz), 2.83-2.92 (1H, m), 3.02 (1H, d, J = 11.5 Hz), 7.26 (1H, dd, J = 2.1, 9.0 Hz), 7.37-7.47 (2H, m), 7.50 (1H, brs), 7.91 (1H, d, J = 9.0 Hz), 7.94-7.99 (2H, m), 8.30 (1H, s), 8.34 (1H, s). | — |
| 867 | 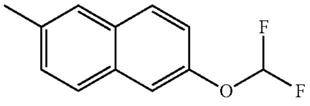 | 1H-NMR (DMSO-d6) δ ppm: 1.15-1.45 (6H, m), 1.53-1.80 (7H, m), 1.97-2.10 (1H, m), 2.94-3.09 (2H, m), 3.09-3.18 (1H, m), 3.18-3.31 (1H, m), 4.00-4.62 (1H, br), 7.16 (0.25H, s), 7.32-7.40 (2.5H, m), 7.53 (0.25H, s), 7.61-7.72 (2H, m), 7.90 (1H, d, J = 8.8 Hz), 7.98 (1H, d, J = 9.0 Hz).9.10-9.45 (1H, br), 9.61-9.90 (1H, br). | 2 Hydrochloride |
| 868 | 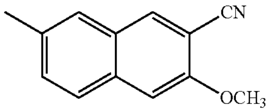 | 1H-NMR (DMSO-d6) δ ppm: 1.05-1.47 (6H, m), 1.55-1.80 (7H, m), 1.99-2.10 (1H, m), 2.41-3.05 (2H, m), 3.05-3.16 (1H, m), 3.16-3.30 (1H, m), 3.75-4.60 (4H, m), 7.45 (1H, dd, J = 2.0, 8.8 Hz), 7.57 (1H, s), 7.67 (1H, s), 7.90 (1H, d, J = 8.9 Hz), 8.48 (1H, s), 9.10-9.40 (1H, br), 9.61-9.90 (1H, br). | 3 Hydrochloride |
| 869 | 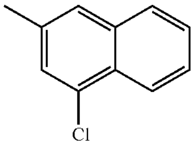 | 1H-NMR (DMSO-d6) δ ppm: 1.05-1.45 (6H, m), 1.54-1.80 (7H, m), 1.96-2.07 (1H, m), 2.93-3.04 (1H, m), 3.04-3.16 (2H, m), 3.18-3.32 1H, m), 4.23-4.51 (1H, br), 7.46-7.50 (1H, m), 7.58-7.67 (3H, m), 7.97-8.04 (1H, m), 8.08-8.14 (1H, m), 9.03-9.25 (1H, br), 9.51-9.75 (1H, br). | 2 Hydrochloride |
| 870 | 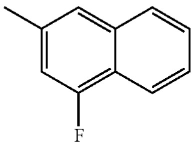 | 1H-NMR (DMSO-d6) δ ppm: 1.08-1.45 (6H, m), 1.52-1.80 (7H, m), 1.99-2.10 (1H, m), 2.96-3.17 (3H, m), 3.17-3.30 (1H, m), 4.45-4.55 (1H, br), 7.16 (1H, dd, J = 1.7, 12.3 Hz), 7.48 (1H, s), 7.51-7.64 (2H, m), 7.98 (2H, d, J = 8.2 Hz), 9.15-9.36 (1H, br), 9.70-9.90 (1H, br). | 2 Hydrochloride |
| 871 | 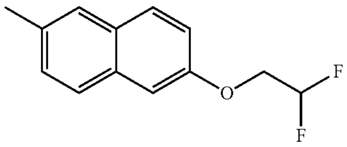 | 1H-NMR (CDCl3) δ ppm: 1.00-1.15 (4H, m), 1.15-1.52 (7H, m), 1.57-1.68 (1H, m), 1.68-1.79 (3H, m), 2.34-2.42 (1H, m), 2.69 (1H, d, J = 11.3 Hz), 2.77-2.86 (1H, m), 2.88 (1H, d, J = 11.3 Hz), 4.28 (2H, dt, J = 4.1, 13.1 Hz), 6.15 (1H, tt, J = 4.1, 55.2 Hz), 7.10 (1H, d, J = 2.5 Hz), 7.14 (1H, dd, J = 2.6, 8.9 Hz), 7.27 (1H, dd, J = 2.1, 8.7 Hz), 7.41 (1H, d, J = 2.0 Hz), 7.63-7.72 (2H, m). | — |

TABLE 95-continued absolute configuration

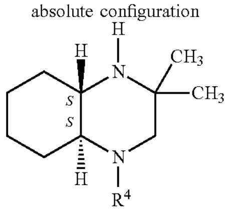

| Example | R$^4$ | NMR | Salt |
|---|---|---|---|
| 872 | 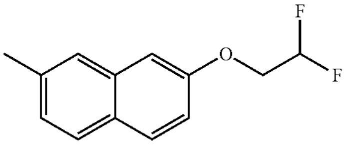 | 1H-NMR (CDCl3) δ ppm: 1.00-1.15 (4H, m), 1.20-1.70 (8H, m), 1.70-1.88 (3H, m), 2.39-2.48 (1H, m), 2.70 (1H, d, J = 11.4 Hz), 2.80-2.89 (1H, m), 2.93 (1H, d, J = 11.4 Hz), 4.29 (2H, dt, J = 4.2, 13.1 Hz), 6.15 (1H, tt, J = 4.1, 55.2 Hz), 7.03-7.11 (2H, m), 7.16 (1H, dd, J = 2.1, 8.7 Hz), 7.33 (1H, d, J = 2.0 Hz), 7.65-7.74 (2H, m). | — |
| 873 | 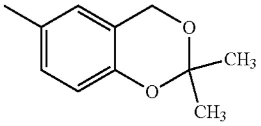 | 1H-NMR (DMSO-d6) δ ppm: 0.90-1.06 (1H, m), 1.06-1.64 (12H, m), 1.63-1.74 (1H, m), 1.80-1.83 (1H, m), 2.50-2.62 (1H, m), 2.71 (1H, d, J = 11.9 Hz), 2.86 (1H, d, J = 11.9 Hz), 2.92-3.02 (1H, m), 4.78 (2H, s), 6.48 (2H, s), 6.73 (1H, d, J = 8.6 Hz), 6.83 (1H, d, J = 2.2 Hz), 6.91 (1H, dd, J = 2.3, 8.6 Hz). 9.52-11.33 (1H, br), 9.37-11.61 (1H, br). | Fumarate |

TABLE 96 absolute configuration

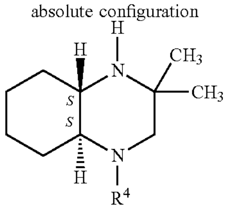

| Example | R$^4$ | NMR | Salt |
|---|---|---|---|
| 874 | 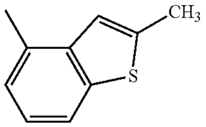 | 1H-NMR (DMSO-d6) δ ppm: 0.96-1.10 (1H, m), 1.10-1.25 (1H, m), 1.26-1.41 (4H, m), 1.47-1.78 (7H, m), 1.94-2.05 (1H, m), 2.56 (3H, s), 2.84 (1H, d, J = 12.4 Hz), 2.90-3.02 (2H, m), 3.23-3.35 (1H, m), 7.15 (1H, d, J = 7.6 Hz), 7.22-7.33 (2H, m), 7.68 (1H, d, J = 7.9 Hz), 8.91-9.09 (1H, brm), 9.54-9.70 (1H, brm). | Hydrochloride |
| 875 | 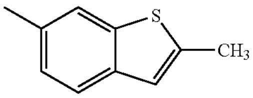 | 1H-NMR (DMSO-d6) δ ppm: (80° C.): 1.03-1.46 (6H, m), 1.51-1.78 (7H, m), 2.01-2.11 (1H, m), 2.53 (3H, s), 2.88 (1H, d, J = 12.4 Hz), 2.97-3.08 (1H, m), 3.10-3.25 (2H, m), 7.05 (1H, s), 7.13 (1H, d, J = 8.4 Hz), 7.60-7.68 (2H, m), 9.20 (1H, brs), 9.70 (1H, brs). | Hydrochloride |
| 876 | 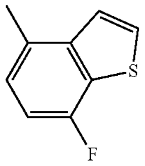 | 1H-NMR (DMSO-d6) δ ppm: 0.95-1.40 (6H, m), 1.40-1.78 (7H, m), 1.95-2.05 (1H, m), 2.85 (1H, d, J = 12.5 Hz), 2.90-3.00 (1H, m), 3.03 (1H, d, J = 12.5 Hz), 3.28-3.44 (1H, m), 7.26 (2H, d, J = 7.0 Hz), 7.64 (1H, dd, J = 4.0, 5.2 Hz), 7.86 (1H, d, J = 5.4 Hz), 9.07 (1H, brs), 9.64 (1H, brs). | Hydrochloride |
| 877 | 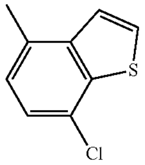 | 1H-NMR (DMSO-d6) δ ppm: 0.97-1.45 (6H, m), 1.45-1.80 (7H, m), 1.94-2.09 (1H, m), 2.88 (1H, d, J = 12.5 Hz), 2.93-3.05 (2H, m), 3.26-3.45 (1H, m), 7.28 (1H, d, J = 8.2 Hz), 7.50 (1H, d, J = 8.2 Hz), 7.64 (1H, d, J = 5.4 Hz), 7.88 (1H, d, J = 5.4 Hz), 9.06 (1H, brs), 9.59 (1H, brs). | Hydrochloride |

TABLE 96-continued absolute configuration

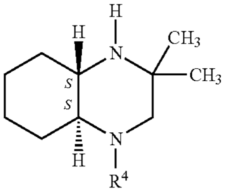

| Example | $R^4$ | NMR | Salt |
|---|---|---|---|
| 878 | 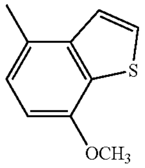 | 1H-NMR (DMSO-d6) δ ppm: 0.90-1.79 (13H, m), 1.35-2.06 (1H, m), 2.75-3.05 (4H, m), 3.94 (3H, s), 6.94 (1H, d, J = 7.9 Hz), 7.18 (1H, d, J = 7.9 Hz), 7.55 (1H, d, J = 5.4 Hz), 7.71 (1H, d, J = 5.4 Hz), 8.80 (1H, brs), 9.31 (1H, brs). | Hydrochloride |

TABLE 97 absolute configuration

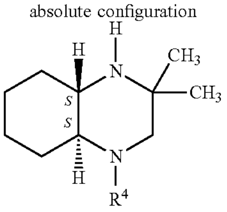

| Example | $R^4$ | NMR | Salt |
|---|---|---|---|
| 879 | 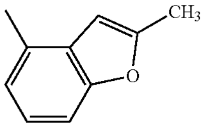 | 1H-NMR (DMSO-d6) δ ppm: 0.97-1.10 (1H, m), 1.10-1.41 (5H, m), 1.50-1.78 (7H, m), 1.94-2.05 (1H, m), 2.44 (3H, s), 2.75-3.09 (3H, m), 3.09-3.30 (1H, m), 6.58 (1H, brs), 6.98 (1H, d, J = 7.2 Hz), 7.19 (1H, t, J = 7.8 Hz), 7.31 (1H, d, J = 7.8 Hz), 9.00 (1H, brs), 9.59 (1H, brs). | Hydrochloride |
| 880 | 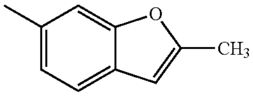 | 1H-NMR (DMSO-d6) δ ppm: 1.00-1.43 (6H, m), 1.44-1.78 (7H, m), 1.90-2.07 (1H, m), 2.42 (3H, d, J = 0.9 Hz), 2.75-3.30 (4H, m), 3.48-4.50 (1H, br), 6.54 (1H, s), 7.04 (1H, brs), 7.30 (1H, brs), 7.48 (1H, d, J = 8.6 Hz), 9.11 (1H, brs), 9.70 (1H, brs). | 2 Hydrochloride |
| 881 | 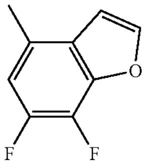 | 1H-NMR (DMSO-d6) δ ppm: 0.99-1.15 (1H, m), 1.15-1.42 (5H, m), 1.47-1.77 (7H, m), 1.93-2.05 (1H, m), 2.75-3.18 (3H, m), 3.27 (1H, brs), 7.08 (1H, brs), 7.22 (1H, brs), 8.14 (1H, s), 9.00 (1H, brs), 9.67 (1H, brs). | Hydrochloride |
| 882 | 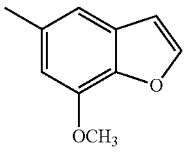 | 1H-NMR (CDCl3) δ ppm: 0.75-1.14 (5H, m), 1.14-1.40 (3H, m), 1.42 (3H, s), 1.56-1.68 (2H, m), 1.68-1.79 (2H, m), 2.20-2.30 (1H, m), 2.65 (1H, d, J = 11.1 Hz), 2.74-2.85 (2H, m), 3.99 (3H, s), 6.61 (1H, d, J = 1.7 Hz), 6.70 (1H, d, J = 2.1 Hz), 6.95 (1H, d, J = 1.7 Hz), 7.59 (1H, d, J = 2.1 Hz). | — |
| 883 | 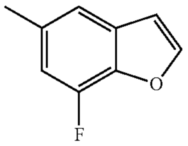 | 1H-NMR (DMSO-d6) δ ppm: 1.01-1.42 (6H, m), 1.49-1.68 (6H, m), 1.68-1.78 (1H, m), 1.95-2.05 (1H, m), 2.80-2.95 (2H, m), 3.01-3.10 (1H, m), 3.10-3.24 (1H, m), 6.50-7.80 (4H, m), 8.10 (1H, d, J = 2.1 Hz), 9.13 (1H, brs), 9.71 (1H, brs). | 2 Hydrochloride |

TABLE 97-continued absolute configuration

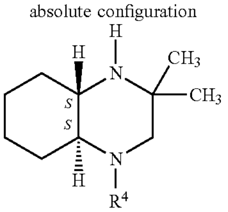

| Example | $R^4$ | NMR | Salt |
|---|---|---|---|
| 884 | 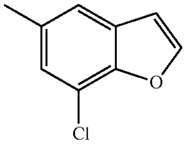 | 1H-NMR (DMSO-d6) δ ppm: 1.00-1.41 (6H, m), 1.45-1.67 (6H, m), 1.67-1.77 (1H, m), 1.92-2.03 (1H, m), 2.80-2.94 (2H, m), 3.01-3.10 (1H, m), 3.10-3.25 (1H, m), 3.65-4.00 (1H, br), 7.05 (1H, d, J = 2.1 Hz), 7.18 (1H, d, J = 1.7 Hz), 7.43 (1H, d, J = 1.7 Hz), 8.12 (1H, d, J = 2.1 Hz), 9.10 (1H, brs), 9.60 (1H, brs). | 2 Hydrochloride |
| 885 | 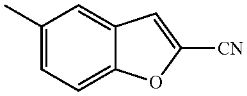 | 1H-NMR (DMSO-d6) δ ppm: 0.92-1.07 (1H, m), 1.07-1.88 (13H, m), 2.60-3.01 (3H, m), 3.10-4.92 (2H, br), 6.45 (3H, s), 7.35 (1H, dd, J = 2.1, 8.9 Hz), 7.54 (1H, d, J = 2.0 Hz), 7.68 (1H, d, J = 8.9 Hz), 8.04 (1H, d, J = 0.8 Hz). | Fumarate |
| 886 | 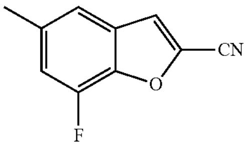 | 1H-NMR (CDCl3) δ ppm: 0.96-1.12 (4H, m), 1.16-1.44 (6H, m), 1.55-1.80 (5H, m), 2.20-2.30 (1H, m), 2.62 (1H, d, J = 11.2 Hz), 2.75-2.85 (2H, m), 7.04 (1H, dd, J = 1.8, 11.8 Hz), 7.15 (1H, d, J = 1.8 Hz), 7.42 (1H, d, J = 2.5 Hz). | — |
| 887 | 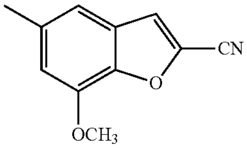 | 1H-NMR (CDCl3) δ ppm: 0.96-1.15 (4H, m), 1.15-1.39 (3H, m), 1.42 (3H, s), 1.55-1.69 (3H, m), 1.69-1.80 (2H, m), 2.23-2.34 (1H, m), 2.65 (1H, d, J = 11.1 Hz), 2.75-2.85 (2H, m), 4.01 (3H, s), 6.76 (1H, d, J = 1.7 Hz), 6.97 (1H, d, J = 1.7 Hz), 7.38 (1H, s). | — |
| 888 | 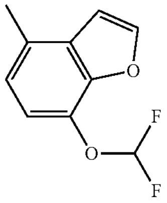 | 1H-NMR (DMSO-d6) δ ppm: 0.99-1.42 (7H, m), 1.50-1.78 (7H, m), 1.72-2.05 (1H, m), 2.75-3.11 (3H, m), 3.16-3.40 (1H, br), 4.95-6.80 (1H, br), 6.95-7.11 (2H, m), 7.12-7.21 (1.25H, m), 7.33 (0.5H, s), 7.51 (0.25H, s), 8.08 (1H, brs), 9.05 (1H, brs), 9.64 (1H, brs). | 2 Hydrochloride |
| 889 | 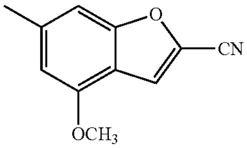 | 1H-NMR (CDCl3) δ ppm: 0.99-1.12 (4H, m), 1.20-1.43 (7H, m), 1.62-1.83 (4H, m), 2.34-2.42 (1H, m), 2.70 (1H, d, J = 11.5 Hz), 2.76-2.85 (1H, m), 2.91 (1H, d, J = 11.5 Hz), 3.92 (3H, s), 6.45 (1H, d, J = 1.4 Hz), 6.80-6.83 (1H, m), 7.45 (1H, d, J = 0.9 Hz). | — |
| 890 | 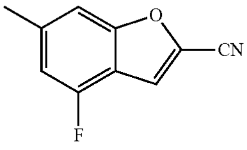 | 1H-NMR (CDCl3) δ ppm: 1.01-1.15 (4H, m), 1.20-1.45 (7H, m), 1.67-1.90 (4H, m), 2.44-2.53 (1H, m), 2.77-2.87 (2H, m), 2.98 (1H, d, J = 11.9 Hz), 6.74 (1H, dd, J = 1.6, 11.5 Hz), 6.90-6.94 (1H, m), 7.43 (1H, d, J = 0.9 Hz). | — |

TABLE 98
absolute configuration
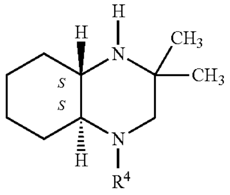
| Example | $R^4$ | NMR | Salt |
| --- | --- | --- | --- |
| 891 | 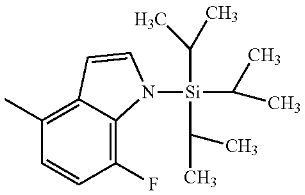 | 1H-NMR (CDCl3) δppm: 0.83-1.43 (26H, m), 1.52 (3H, s), 1.55-1.91 (7H, m), 2.34-2.61 (2H, m), 2.80-3.00 (2H, m), 6.69-6.84 (3H, m), 7.24 (1H, d, J = 3.2 Hz). | — |
| 892 | 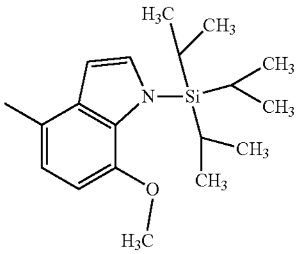 | 1H-NMR (CDCl3) δppm: 0.76-1.40 (26H, m), 1.52 (3H, s), 1.56-1.95 (7H, m), 2.36-2.64 (2H, m), 2.80-3.01 (2H, m), 3.88 (3H, s), 6.54 (1H, d, J = 8.1 Hz), 6.69 (1H, d, J = 3.1 Hz), 6.73 (1H, d, J = 8.1 Hz), 7.24 (1H, d, J = 3.1 Hz). | — |
| 893 | 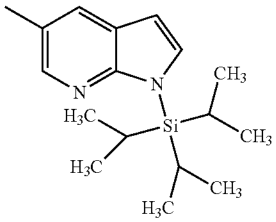 | 1H-NMR (CDCl3) δppm: 0.98-1.17 (23H, m), 1.17-1.40 (3H, m), 1.42 (3H, s), 1.55-1.66 (2H, m), 1.66-1.76 (2H, m), 1.84 (3H, quint, J = 7.5 Hz), 2.27-2.38 (1H, m), 2.72 (1H, d, J = 11.2 Hz), 2.77-2.85 (2H, m), 6.47 (1H, d, J = 3.4 Hz), 7.27 (1H, d, J = 3.4 Hz), 7.61 (1H, d, J = 2.4 Hz), 8.06 (1H, d, J = 2.4 Hz). | — |
| 894 | 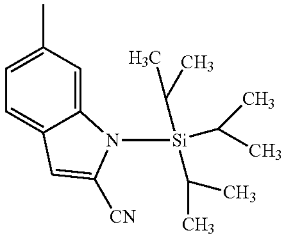 | 1H-NMR (CDCl3) δppm: 0.90-1.40 (26H, m), 1.43 (3H, s), 1.59-1.80 (4H, m), 1.95-2.06 (3H, m), 2.30-2.39 (1H, m), 2.58 (1H, d, J = 11.3 Hz), 2.79-2.89 (2H, m), 6.98 (1H, d, J = 1.5, 8.5 Hz), 7.31 (1H, s), 7.34 (1H, d, J = 0.6 Hz), 7.52 (1H, d, J = 8.5 Hz). | — |

TABLE 99 absolute configuration

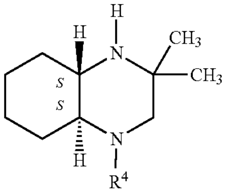

| Example | $R^4$ | NMR | Salt |
|---|---|---|---|
| 895 | 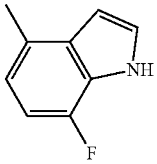 | 1H-NMR (DMSO-d6) δppm: 0.77-0.92 (1H, m), 0.95 (3H, s), 1.08-1.35 (3H, m), 1.40 (3H, s), 1.47-1.58 (2H, m), 1.58-1.82 (3H, m), 2.27-2.48 (2H, m), 2.60-2.85 (2H, m), 6.47 (1H, brs), 6.58-6.65 (1H, m), 6.81 (1H, dd, J = 8.3, 10.9 Hz), 7.30 (1H, t, J = 2.6 Hz), 11.47 (1H, s). | — |
| 896 | 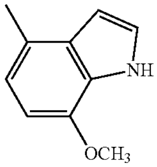 | 1H-NMR (CDCl3) δppm: 0.77-0.99 (4H, m), 1.08-1.90 (11H, m), 2.21-2.46 (2H, m), 2.58-2.85 (2H, m), 3.86 (3H, s), 6.38 (1H, brs), 6.47-6.63 (2H, m), 7.13 (1H, t, J = 2.6 Hz), 11.07 (1H, s). | — |
| 897 | 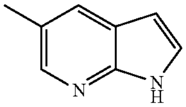 | 1H-NMR (DMSO-d6) δppm: 0.91-1.08 (1H, m), 1.08-1.60 (11H, m), 1.61-1.72 (1H, m), 1.78-1.90 (1H, m), 2.60-2.71 (1H, m), 2.75 (1H, d, J = 11.7 Hz), 2.90-3.05 (2H, m), 6.39 (1H, dd, J = 1.8, 3.4 Hz), 6.47 (1H, s), 7.42-7.49 (1H, m), 7.73 (1H, d, J = 2.0 Hz), 7.98 (1H, d, J = 2.2 Hz), 8.18-10.97 (2H, br), 11.59 (1H, s). | Fumarate |
| 898 | 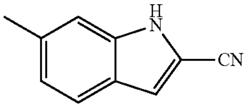 | 1H-NMR (DMSO-d6) δppm: 0.81-1.02 (4H, m), 1.10-1.36 (6H, n), 1.36-2.05 (5H, m), 2.25-2.35 (1H, m), 2.57 (1H, d, J = 11.0 Hz), 2.62-2.70 (1H, m), 2.75 (1H, d, J = 11.0 Hz), 6.91 (1H, dd, J = 1.7, 8.6 Hz), 7.03 (1H, s), 7.27 (1H, d, J = 0.6 Hz), 7.55 (1H, d, J = 8.6 Hz) 11.93-12.33 (1H, br). | — |

TABLE 100 absolute configuration

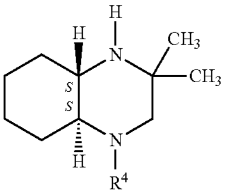

| Example | $R^4$ | NMR | Salt |
|---|---|---|---|
| 899 | 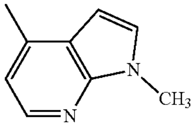 | 1H-NMR (CDCl3) δ ppm: 0.75-1.13 (5H, m), 1.25-1.45 (3H, m), 1.48 (3H, s), 1.62-1.85 (3H, m), 2.08-2.19 (1H, m), 2.66-2.78 (2H, m), 2.85-2.94 (1H, m), 3.27 (1H, d, J = 11.9 Hz), 3.85 (3H, s), 6.46 (1H, d, J = 3.5 Hz), 6.63 (1H, d, J = 5.4 Hz), 7.06 (1H, d, J = 3.5 Hz), 8.20 (1H, d, J = 5.4 Hz). | — |

TABLE 100-continued absolute configuration

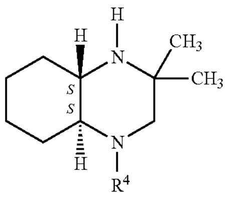

| Example | $R^4$ | NMR | Salt |
|---|---|---|---|
| 900 | 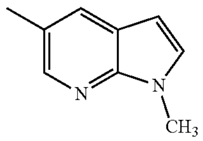 | 1H-NMR (DMSO-d6) δ ppm: 0.91-1.62 (11H, m), 1.62-1.84 (2H, m), 1.82-1.95 (1H, m), 2.65-2.83 (2H, m), 2.99-3.10 (2H, m), 3.79 (3H, s), 6.41 (1H, d, J = 3.4 Hz), 6.48 (2H, s), 7.50 (1H, d, J = 3.4 Hz), 7.76 (1H, d, J = 2.2 Hz), 8.04 (1H, d, J = 2.2 Hz), 8.35-11.00 (2H, br) | Fumarate |

TABLE 101 absolute configuration

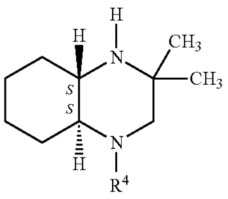

| Example | $R^4$ | NMR | Salt |
|---|---|---|---|
| 901 | 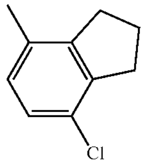 | 1H-NMR (DMSO-d6) δ ppm: 0.86-1.01 (1H, m), 1.12-1.40 (5H, m), 1.51-1.76 (7H, m), 1.72-2.10 (3H, m), 2.67-2.81 (2H, m), 2.81-3.00 (5H, m), 3.05-3.20 (1H, m), 6.65-7.10 (2H, m), 7.21 (1H, d, J = 8.4 Hz), 9.03-9.20 (1H, m), 9.59-9.77 (1H, m). | 2 Hydrochloride |
| 902 | 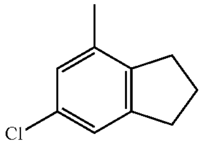 | 1H-NMR (DMSO-d6) δ ppm: 0.88-1.04 (1H, m), 1.15-1.41 (5H, m), 1.48-1.80 (7H, m), 1.90-2.10 (3H, m), 2.65-3.05 (7H, m), 3.05-3.22 (1H, m), 4.90-6.25 (1H, br), 6.94 (1H, s), 7.11 (1H, s), 9.21 (1H, brs), 9.70 (1H, brs). | 2 Hydrochloride |
| 903 | 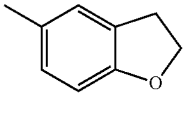 | 1H-NMR (DMSO-d6) δ ppm: 0.93-1.22 (2H, m), 1.22-1.43 (4H, m), 1.43-1.79 (7H, m), 1.90-2.10 (1H, m), 2.58-3.40 (6H, m), 4.52 (2H, t, J = 8.6 Hz), 5.30-6.20 (1H, br), 6.50-7.45 (3H, m), 8.65-9.38 (1H, br), 9.38-9.92 (1H, br). | 2 Hydrochloride |
| 904 | 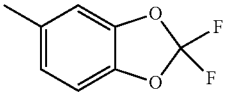 | 1H-NMR (DMSO-d6) δ ppm: 0.96-1.13 (1H, m), 1.13-1.42 (5H, m), 1.49-1.66 (6H, m), 1.66-1.77 (1H, m), 1.93-2.05 (1H, m), 2.74-2.90 (2H, m), 2.98 (1H, d, J = 12.5 Hz), 3.08-3.20 (1H, m), 4.35-4.68 (1H, br), 6.95 (1H, dd, J = 2.0, 8.6 Hz), 7.26 (1H, d, J = 2.0 Hz), 7.36 (1H, d, J = 8.6 Hz), 8.98-9.20 (1H, br), 9.60-9.85 (1H, br). | 2 Hydrochloride |

TABLE 102
absolute configuration
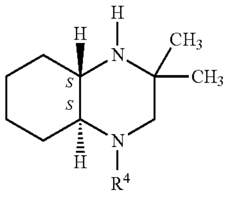
| Example | $R^4$ | NMR | Salt |
|---|---|---|---|
| 905 | 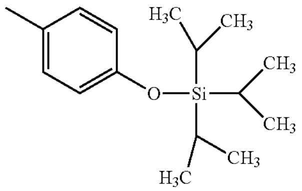 | 1H-NMR (CDCl3) δ ppm: 0.75-1.04 (2H, m) 1.04-1.13 (21H, m), 1.15-1.37 (6H, m), 1.38 (3H, s), 1.52-1.75 (4H, m), 2.12-2.20 (1H, m), 2.58 (1H, d, J = 11.1 Hz), 2.69-2.78 (2H, m), 6.76-6.81 (2H, m), 6.92-6.97 (2H, m). | |
| 906 | 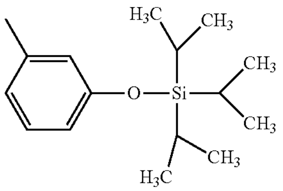 | 1H-NMR (CDCl3) δ ppm: 0.88-1.14 (23H, m), 1.16-1.37 (6H, m), 1.38 (3H, s), 1.60-1.77 (4H, m), 2.20-2.29 (1H, m), 2.57 (1H, d, J = 11.3 Hz), 2.72-2.82 (2H, m), 6.60-6.65 (2H, m), 6.65-6.70 (1H, m), 7.07-7.14 (1H, m). | |
| 907 | 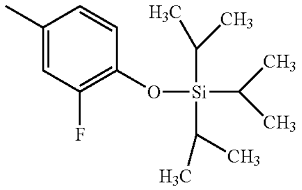 | 1H-NMR (CDCl3) δ ppm: 0.75-1.15 (23H, m), 1.17-1.40 (9H, m), 1.52-1.75 (4H, m), 2.10-2.17 (1H, m), 2.55 (1H, d, J = 11.1 Hz), 2.70-2.77 (2H, m), 6.69-6.74 (1H, m), 6.78-6.87 (2H, m). | |
| 908 | 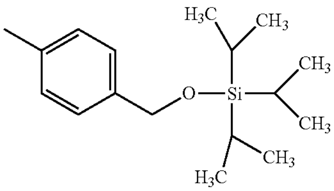 | 1H-NMR (CDCl3) δ ppm: 0.81-1.38 (29H, m), 1.39 (3H, s), 1.58-1.76 (4H, m), 2.23-2.32 (1H, m), 2.61 (1H, d, J = 11.2 Hz), 2.72-2.82 (2H, m), 4.79 (2H, s), 7.02-7.08 (2H, m), 7.24-7.30 (2H, m). | |
| 909 | 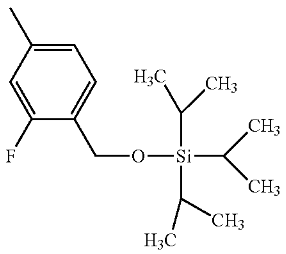 | 1H-NMR (CDCl3) δ ppm: 0.75-1.35 (29H, m), 1.37 (3H, s), 1.62-1.78 (4H, m), 2.22-2.30 (1H, m), 2.60 (1H, d, J = 11.4 Hz), 2.71-2.85 (2H, m), 5.30 (2H, s), 6.72 (1H, dd, J = 2.0, 12.0 Hz), 6.86 (1H, J = 2.0, 8.2 Hz), 7.44 (1H, t, J = 8.4 Hz). | |
| 910 | 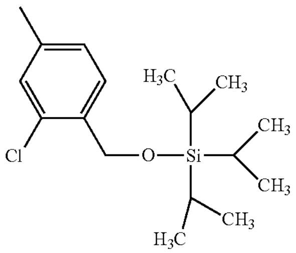 | 1H-NMR (CDCl3) δ ppm: 0.75-1.39 (32H, m), 1.53-1.75 (4H, m), 2.10-2.17 (1H, m), 2.56 (1H, d, J = 11.1 Hz), 2.68-2.77 (2H, m), 6.80 (1H, d, J = 8.6 Hz), 6.84 (1H, dd, J = 2.4, 8.6 Hz), 7.08 (1H, d, J = 2.4 Hz). | |

TABLE 102-continued absolute configuration

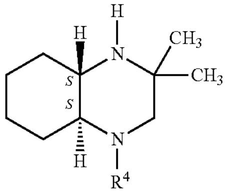

| Example | $R^4$ | NMR | Salt |
|---|---|---|---|
| 911 | 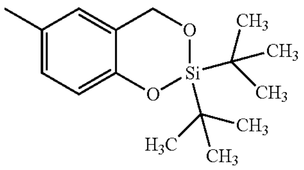 | 1H-NMR (CDCl3) δ ppm: 0.85-1.09 (23H, m), 1.09-1.36 (3H, m), 1.37 (3H, s), 1.50-1.75 (4H, m), 2.11-2.19 (1H, m), 2.57 (1H, d, J = 11.1 Hz), 2.67-2.77 (2H, m), 4.95 (2H, s), 6.67 (1H, d, J = 2.5 Hz), 6.82 (1H, d, J = 8.5 Hz), 6.91 (1H, dd, J = 2.5, 8.5 Hz). | |

TABLE 103 absolute configuration

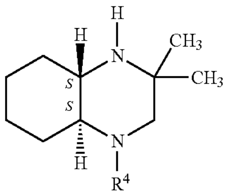

| Example | $R^4$ | NMR | Salt |
|---|---|---|---|
| 912 | 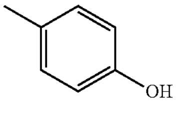 | 1H-NMR (CDCl3) δ ppm: 0.92-1.06 (1H, m), 1.09 (3H, s), 1.12-1.37 (3H, m), 1.40 (3H, s), 1.55-1.66 (2H, m), 1.66-1.78 (2H, m), 2.15-2.25 (1H, m), 2.57-2.65 (1H, m), 2.69-2.83 (2H, m), 3.15-4.30 (2H, br), 6.72-6.79 (2H, m), 6.95-7.01 (2H, m). | — |
| 913 | 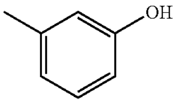 | 1H-NMR (DMSO-d6) δ ppm: 0.82-1.00 (4H, m), 1.09-1.35 (6H, m), 1.40-1.52 (1H, m), 1.52-1.70 (4H, m), 2.12-2.25 (1H, m), 2.45-2.55 (1H, m), 2.55-2.65 (1H, m), 2.66 (1H, d, J = 11.0 Hz), 6.40-6.51 (3H, m), 7.00-7.10 (1H, m), 9.21 (1H, s). | — |
| 914 | 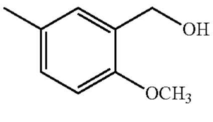 | 1H-NMR (DMSO-d6) δ ppm: 0.90-1.05 (1H, m), 1.05-1.38 (5H, m), 1.38-1.62 (6H, m), 1.64-1.74 (1H, m), 1.82-1.94 (1H, m), 2.53-2.62 (1H, m), 2.70 (1H, d, J = 12.0 Hz), 2.86 (1H, d, J = 12.0 Hz), 2.95-3.06 (1H, m), 3.74 (3H, s), 4.45 (2H, s), 4.65-5.60 (1H, br), 6.46 (1H, s), 6.87 (1H, d, J = 8.6 Hz), 6.94 (1H, dd, J = 2.5, 8.6 Hz), 7.15 (1H, d, J = 2.2 Hz), 8.59-10.40 (1H, br). | ½ Fumarate |
| 915 | 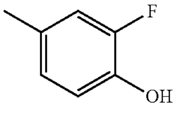 | 1H-NMR (DMSO-d6) δ ppm: 0.82-0.99 (4H, m), 1.05-1.32 (6H, m), 1.41-1.50 (1H, m), 1.50-1.65 (3H, m), 2.05-2.14 (1H, m), 2.47 (1H, d, J = 10.8 Hz), 2.53-2.62 (2H, m), 2.95-3.65 (1H, br), 6.67-6.72 (1H, m), 6.79-6.87 (2H, m), 8.65-10.50 (1H, m). | — |
| 916 | 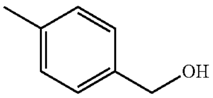 | 1H-NMR (CDCl3) δ ppm: 0.85-1.10 (5H, m), 1.15-1.42 (6H, m), 1.56-2.05 (5H, m), 2.25-2.15 (1H, m), 2.56-2.65 (1H, m), 2.72-2.84 (2H, m), 4.64 (2H, s), 7.04-7.10 (2H, m), 7.25-7.32 (2H, m). | — |

TABLE 103-continued absolute configuration

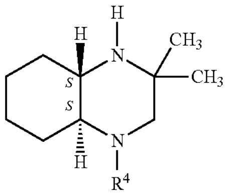

| Example | $R^4$ | NMR | Salt |
| --- | --- | --- | --- |
| 917 | 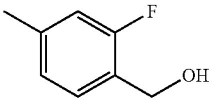 | 1H-NMR (CDCl3) δ ppm: 0.95-1.44 (11H, m), 1.44-2.20 (5H, m), 2.25-2.35 (1H, m), 2.61 (1H, d, J = 11.4 Hz), 2.72-2.86 (2H, m), 4.69 (2H, s), 6.75 (1H, dd, J = 2.0, 12.1 Hz), 6.83 (1H, dd, J = 2.0, 8.1 Hz), 7.29 (1H, t, J = 8.4 Hz). | — |
| 918 | 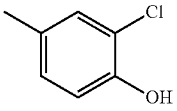 | 1H-NMR (CDCl3) δ ppm: 0.90-1.11 (4H, m), 1.14-1.42 (6H, m), 1.53-1.77 (4H, m), 2.12-2.21 (1H, m), 2.57 (1H, d, J = 11.2 Hz), 2.67-2.80 (2H, m), 2.81-3.38 (2H, br), 6.89-6.97 (2H, m), 7.07 (1H, dd, J = 0.5. 1.9 Hz). | — |
| 919 | 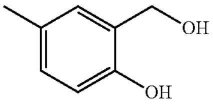 | 1H-NMR (DMSO-d6) δ ppm: 0.78-0.93 (1H, m), 0.95 (3H, s), 1.04-1.32 (6H, m), 1.37-1.66 (5H, m), 2.05-2.14 (1H, m), 2.45-2.62 (3H, m), 4.43 (2H, s), 4.65-5.20 (1H, br), 6.65 (1H, d, J = 8.4 Hz), 6.74 (1H, dd, J = 2.5, 8.4 Hz), 7.03 (1H, d, J = 2.5 Hz), 8.81-9.28 (1H, br). | — |

TABLE 104 absolute configuration

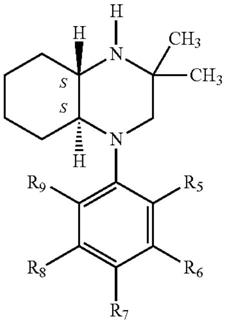

| Example | $R^5$ | $R^6$ | $R^7$ | $R^8$ | $R^9$ | NMR | Salt |
| --- | --- | --- | --- | --- | --- | --- | --- |
| 920 | —CH3 | —H | —H | —H | —H | 1H-NMR (DMSO-d6) δ ppm: 0.88-1.03 (1H, m), 1.10-1.25 (1H, m), 1.25-1.40 (4H, m), 1.45-1.66 (6H, m), 1.67-1.89 (1H, m), 1.92-2.03 (1H, m), 2.26 (3H, m), 2.65 (1H, d, J = 12.5 Hz), 2.80 (1H, d, J = 12.5 Hz), 2.88-3.00 (1H, m), 3.15-3.28 (1H, m), 7.06-7.17 (2H, m), 7.19-7.26 (2H, m), 9.04 (1H, brs), 9.58 (1H, brs). | Hydrochloride |

TABLE 104-continued absolute configuration

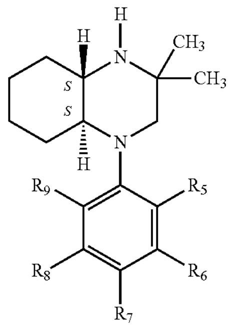

| Example | $R^5$ | $R^6$ | $R^7$ | $R^8$ | $R^9$ | NMR | Salt |
|---|---|---|---|---|---|---|---|
| 921 | —CH3 | —CH3 | —H | —H | —H | 1H-NMR (DMSO-d6) δ ppm: 0.87-1.02 (1H, m), 1.10-1.24 (1H, m), 1.24-1.40 (4H, m), 1.40-1.64 (6H, m), 1.67-1.77 (1H, m), 1.95-2.04 (1H, m), 2.21 (3H, s), 2.22 (3H, s), 2.59 (1H, d, J = 12.5 Hz), 2.82 (1H, d, J = 12.5 Hz), 2.86-2.95 (1H, m), 3.15-3.37 (1H, m), 6.97-7.03 (2H, m), 7.07-1.15 (1H, m), 9.11 (1H, brs), 9.65 (1H, brs). | Hydrochloride |
| 922 | —H | —F | —CN | —H | —H | 1H-NMR (DMSO-d6) δ ppm: 1.22-1.65 (10H, m), 1.65-1.84 (2H, m), 1.90-2.00 (1H, m), 2.10-2.20 (1H, m), 3.38-3.61 (4H, m), 3.78 (1H, d, J = 14.5 Hz), 6.83 (1H, dd, J = 2.3, 8.9 Hz), 6.97 (1H, dd, J = 2.0, 13.7 Hz), 7.65 (1H, t, J = 8.5 Hz), 8.93-9.15 (1H, m), 9.51-9.71 (1H, m). | 2 Hydrochloride |
| 923 | —H | —H | —OCF3 | —H | —H | 1H-NMR (DMSO-d6) δ ppm: 1.00-1.15 (1H, m), 1.15-1.41 (5H, m), 1.50-1.67 (6H, m), 1.67-1.77 (1H, m), 1.95-2.05 (1H, m), 2.81-2.95 (2H, m), 3.01 (1H, d, J = 12.5 Hz), 3.11-3.25 (1H, m), 5.42-6.30 (1H, br), 7.20-7.27 (2H, m), 7.31-7.37 (2H, m), 9.02-9.20 (1H, brm), 9.60-9.80 (1H, brm). | 2 Hydrochloride |
| 924 | —H | —F | —OCF3 | —H | —H | 1H-NMR (DMSO-d6) δ ppm: 1.04-1.20 (1H, m), 1.20-1.41 (5H, m), 1.49-1.78 (7H, m), 1.96-2.06 (1H, m), 2.85-3.11 (3H, m), 3.15-3.28 (1H, m), 5.10-6.60 (1H, br), 7.00-7.15 (1H, m), 7.22-7.29 (1H, m), 7.47-7.54 (1H, m), 9.09 (1H, brs), 9.71 (1H, brs). | 2 Hydrochloride |

TABLE 104-continued absolute configuration

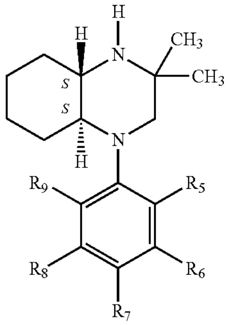

| Example | $R^5$ | $R^6$ | $R^7$ | $R^8$ | $R^9$ | NMR | Salt |
|---|---|---|---|---|---|---|---|
| 925 | —H | —H | —OCHF2 | —H | —H | 1H-NMR (DMSO-d6) δ ppm: 0.98-1.11 (1H, m), 1.11-1.25 (1H, m), 1.25-1.40 (4H, m), 1.48-1.65 (6H, m), 1.65-1.76 (1H, m), 1.92-2.03 (1H, m), 2.75-2.90 (2H, m), 2.99 (1H, d, J = 12.8 Hz), 3.10-3.23 (1H, m), 4.85-5.90 (1H, br), 7.01 (0.25H, s), 7.13-7.22 (4.5H, m), 7.38 (0.25H, s), 9.06 (1H, brs), 9.63 (1H, brs). | 2 Hydrochloride |
| 926 | —H | —Cl | —OCHF2 | —H | —H | 1H-NMR (DMSO-d6) δ ppm: 1.02-1.42 (6H, m), 1.50-1.66 (6H, m), 1.66-1.77 (1H, m), 1.95-2.05 (1H, m), 2.81-2.94 (2H, m), 3.02 (1H, d, J = 12.5 Hz), 3.10-3.23 (1H, m), 3.88-4.25 (1H, br), 7.15 (1H, dd, J = 2.6, 8.8 Hz), 7.24 (1H, t, J = 73.3 Hz), 7.32 (1H, d, J = 2.6 Hz), 7.34 (1H, d, J = 8.8 Hz), 9.05-9.22 (1H, m), 9.62-9.80 (1H, m). | 2 Hydrochloride |
| 927 | —H | —OCHF2 | —H | —H | —H | 1H-NMR (DMSO-d6) δ ppm: 1.02-1.16 (1H, m), 1.16-1.41 (5H, m), 1.50-1.67 (6H, m), 1.67-1.78 (1H, m), 1.96-2.06 (1H, m), 2.84-2.97 (2H, m), 3.04 (1H, d, J = 12.5 Hz), 3.11-3.25 (1H, m), 6.89 (1H, s), 6.96 (1H, dd, J = 2.1, 8.1 Hz), 7.00 (1H, d, J = 8.1 Hz), 7.27 (1H, t, J = 74.1 Hz), 7.39 (1H, t, J = 8.1 Hz), 8.30-9.30 (2H, br), 9.69-9.89 (1H, br). | 2 Hydrochloride |
| 928 | —H | —OCHF2 | —Cl | —H | —H | 1H-NMR (DMSO-d6) δ ppm: 1.04-1.40 (6H, m), 1.50-1.69 (6H, m), 1.69-1.79 (1H, m), 1.92-2.04 (1H, m), 2.78-2.89 (1H, m), 2.89-3.06 (2H, m), 3.15-3.27 (1H, m), 7.01-7.08 (2H, m), 7.32 (1H, t, J = 73,3 Hz), 7.54 (1H, d, J = 8.4 Hz), 8.81-9.11 (1H, m), 9.40-9.69 (1H, m). | Hydrochloride |

TABLE 104-continued absolute configuration

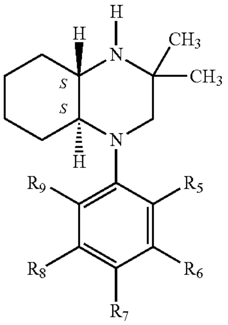

| Example | $R^5$ | $R^6$ | $R^7$ | $R^8$ | $R^9$ | NMR | Salt |
|---|---|---|---|---|---|---|---|
| 929 | —H | —OCHF2 | —F | —H | —H | 1H-NMR (DMSO-d6) δ ppm: 1.00-1.40 (6H, m), 1.47-1.65 (6H, m), 1.67-1.77 (1H. m), 1.90-2.00 (1H, m), 2.70-2.80 (1H, m), 2.87 (1H, d, J = 12.5 Hz), 2.96 (1H, d, J = 12.5 Hz), 3.10-3.24 (1H, m), 7.02-7.11 (2.25H, m), 7.27 (0.5H, s), 7.37 (1H, dd, J = 8.8, 10.5 Hz), 7.46 (0.25H, s), 8.80-9.00 (1H, br), 9.39-9.58 (1H, br). | Hydrochloride |
| 930 | —H | —CN | —OCHF2 | —H | —H | 1H-NMR (DMSO-d6) δ ppm: 1.03-1.15 (1H, m), 1.17-1.41 (5H, m), 1.48-1.82 (7H, m), 1.93-2.05 (1H, m), 2.82-2.91 (1H, m), 2.94 (1H, d, J = 12.7 Hz), 3.01 (1H, d, J = 12.7 Hz), 3.08-3.25 (1H, m), 4.00-4.60 (1H, br), 7.39 (1H, t, J = 72.6 Hz), 7.42 (1H, d, J = 8.9 Hz), 7.51 (1H, dd, J = 2.7, 9.0 Hz), 7.69 (1H, d, J = 2.7 Hz), 8.90-9.10 (1H, br), 9.40-9.65 (1H, br). | 2 Hydrochloride |
| 931 | —H | —F | —OCHF2 | —F | —H | 1H-NMR (DMSO-d6) δ ppm: 1.08-1.42 (6H, m), 1.42-1.80 (7H, m), 1.96-2.07 (1H, m), 2.90-3.00 (1H, m), 3.05 (1H, d, J = 13.0 Hz), 3.10 (1H, d, J = 13.0 Hz), 3.17-3.29 (1H, m), 3.55-3.85 (1H, br), 6.97-7.06 (2.25H, m), 7.19 (0.5H, s). 7.37 (0.25H, s), 8.90-9.07 (1H, br), 9.51-9.70 (1H, br). | 2 Hydrochloride |
| 932 | —H | —H | —OCH2CHF2 | —H | —H | 1H-NMR (DMSO-d6) δ ppm: 0.98-1.80 (13H, m), 1.91-2.14 (1H, m), 2.61-3.50 (4H, m), 4.20-4.40 (2H, m), 4.61-6.20 (1H, br), 6.39 (1H, tt, J = 3.4, 54.5 Hz), 6.85-7.65 (4H, brm), 8.84-10.20 (2H, br). | 2 Hydrochloride |

TABLE 104-continued absolute configuration

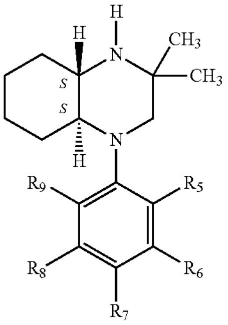

| Example | $R^5$ | $R^6$ | $R^7$ | $R^8$ | $R^9$ | NMR | Salt |
|---|---|---|---|---|---|---|---|
| 933 | —H | —F | —OCH2CHF2 | —H | —H | 1H-NMR (CDCl3) δ ppm: 0.95-1.09 (4H, m), 1.15-1.44 (7H, m), 1.57-1.78 (4H, m), 2.13-2.22 (1H, m), 2.56 (1H, d, J = 11.1 Hz), 2.70-2.79 (2H, m), 4.21 (2H, dt, J = 4.2, 13.1 Hz), 6.08 (1H, tt, J = 4.2, 55.1 Hz), 6.77-6.83 (1H. m), 6.84-6.95 (2H, m). | — |
| 934 | —H | —Cl | —OCH2CHF2 | —H | —H | 1H-NMR (CDCl3) δ ppm: 0.93-1.10 (4H, m), 1.15-1.41 (7H, m), 1.53-1.77 (4H, m), 2.14-2.23 (1H, m), 2.57 (1H, d, J = 11.0 Hz), 2.68-2.79 (2H, m), 4.20 (2H, dt, J = 4.2, 13.0 Hz), 6.12 (1H, tt, J = 4.2, 55.1 Hz), 6.87 (1H,d, J = 8.7 Hz), 6.96 (1H, dd, J = 2.5, 8.7 Hz), 7.13 (1H, d, J = 2.5 Hz). | — |
| 935 | —H | —CH3 | —OCHF2 | —H | —H | 1H-NMR (DMSO-d6) δ ppm: 0.96-1.10 (1H, m), 1.12-1.40 (5H, m), 1.47-1.63 (6H, m), 1.67-1.76 (1H, m), 1.90-2.01 (1H, m), 2.21 (3H, m), 2.70-2.87 (2H, m), 2.96 (1H, d, J = 12.1 Hz), 3.07-3.22 (1H, m), 4.40-6.50 (1H, br), 6.94 (0.25H, s), 6.97-7.03 (1H, m), 7.03-7.08 (1H, m), 7.09-7.15 (1.5H, m), 7.31 (0.25H, s), 9.01 (1H, brs), 9.56 (1H, brs). | 2 Hydrochloride |
| 936 | —H | —OCH3 | —OCHF2 | —H | —H | 1H-NMR (DMSO-d6) δ ppm: 1.02-1.40 (6H, m), 1.50-1.79 (7H, m), 1.96-2.06 (1H, m), 2.78-2.95 (2H, m), 2.98-3.22 (2H, m), 3.82 (3H, s), 6.75 (1H, d, J = 7.8 Hz), 6.80-6.93 (1.25H, m), 7.01 (0.5H. s), 7.11-7.21 (1.25H, m), 7.21-7.75 (1H, br), 9.14 (1H, brs), 9.77 (1H, brs). | 2 Hydrochloride |

TABLE 105 absolute configuration

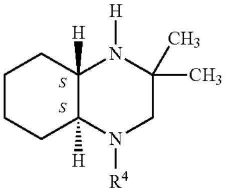

| Example | $R^4$ | NMR | Salt |
|---|---|---|---|
| 937 | 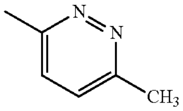 | 1H-NMR (DMSO-d6) δ ppm: 1.15-1.60 (10H, m), 1.60-1.86 (2H, m), 1.95-2.15 (2H, m), 2.47 (3H, s), 3.37 (1H, d, J = 14.2 Hz), 3.41-3.66 (2H, m), 3.88 (1H, d, J = 14.2 Hz), 5.32-7.05 (1.5H, br), 7.18 (1H, d, J = 9.2 Hz), 7.36 (1H, d, J = 9.2 Hz), 7.45-9.40 (1.5 H, br). | Oxalate |

TABLE 106 absolute configuration

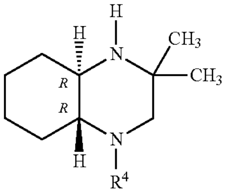

| Example | $R^4$ | NMR | Salt |
|---|---|---|---|
| 938 | 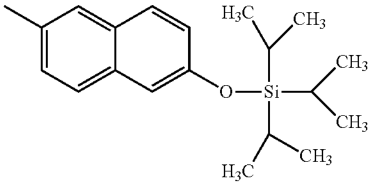 | 1H-NMR (CDCl3) δ ppm: 0.98-1.17 (23H, m), 1.17-1.40 (6H, m), 1.43 (3H, s), 1.59-1.68 (1H, m), 1.68-1.80 (3H, m), 2.32-2.41 (1H, m), 2.68 (1H, d, J = 11.3 Hz), 2.77-2.85 (1H, m), 2.88 (1H, d, J = 11.3 Hz), 7.08 (1H, dd, J = 2.4, 8.8 Hz), 7.16 (1H, d, J = 2.4 Hz), 7.22 (1H, dd, J = 2.1, 8.7 Hz), 7.37 (1H, d, J = 1.8 Hz), 7.57-7.64 (2H, m). | — |
| 939 | 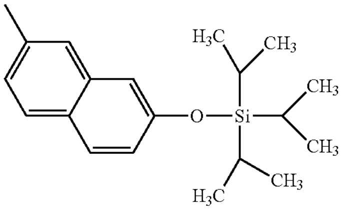 | 1H-NMR (CDCl3) δ ppm: 0.82-1.18 (23H, m), 1.20-1.40 (6H, m), 1.43 (3H, s), 1.59-1.70 (1H, m), 1.70-1.85 (3H, m), 2.35-2.45 (1H, m), 2.69 (1H, d, J = 11.3 Hz), 2.77-2.86 (1H, m), 2.91 (1H, d, J = 11.3 Hz), 7.02 (1H, dd, J = 2.4, 8.8 Hz), 7.09-7.15 (2H, m), 7.27 (1H, d, J = 1.9 Hz), 7.61-7.68 (2H, m). | — |
| 940 | 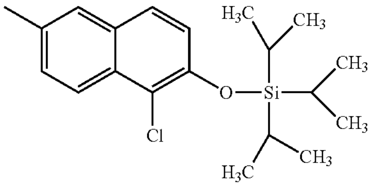 | 1H-NMR (CDCl3) δ ppm: 0.97-1.41 (29H, m), 1.43 (3H, s), 1.59-1.70 (1H, m), 1.70-1.80 (3H, m), 2.34-2.44 (1H, m), 2.69 (1H, d, J = 11.3 Hz), 2.78-2.87 (1H, m), 2.89 (1H, d, J = 11.3 Hz), 7.11 (1H, d, J = 8.9 Hz), 7.34 (1H, dd, J = 2.1, 9.0 Hz), 7.37 (1H, d, J = 1.9 Hz), 7.53 (1H, d, J = 8.9 Hz), 8.10 (1H, d, J = 8.9 Hz). | — |
| 941 | 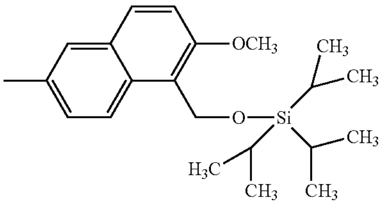 | 1H-NMR (CDCl3) δ ppm : 0.75-1.42 (29H, m), 1.44 (3H, s), 1.58-1.83 (4H, m), 2.34-2.42 (1H, m), 2.68 (1H, d, J = 11.3 Hz), 2.78-2.87 (1H, m), 2.91 (1H, d, J = 11.3 Hz), 3.91 (3H, s), 5.19-5.27 (2H, m), 7.21 (1H, d, J = 9.1 Hz), 7.29 (1H, d, J = 2.2, 9.1 Hz), 7.37 (1H, d, J = 2.1 Hz), 7.69 (1H, d, J = 9.0 Hz), 8.16 (1H, d, J = 9.1 Hz). | — |

TABLE 106-continued absolute configuration

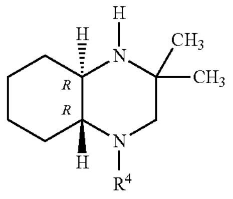

| Example | $R^4$ | NMR | Salt |
|---|---|---|---|
| 942 | 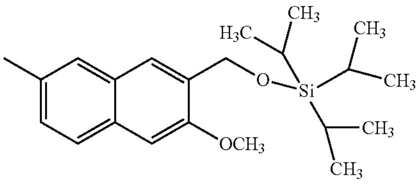 | 1H-NMR (CDCl3) δ ppm: 0.95-1.18 (23H, m), 1.18-1.40 (6H, m), 1.44 (3H, s), 1.57-1.77 (4H, m), 2.33-2.41 (1H, m), 2.71 (1H, d, J = 11.2 Hz), 2.77-2.85 (1H, m), 2.87 (1H, d, J = 11.2 Hz), 3.89 (3H, s), 4.94 (2H, d, J = 1.0 Hz), 7.02 (1H, s), 7.22 (1H, dd, J = 2.0, 8.6 Hz), 7.43 (1H, d, J = 1.8 Hz), 7.64 (1H, d, J = 8.6 Hz), 7.88 (1H, s). | — |

TABLE 107 absolute configuration

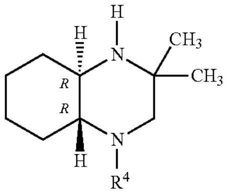

| Example | $R^4$ | NMR | Salt |
|---|---|---|---|
| 943 | 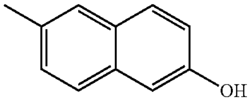 | 1H-NMR (DMSO-d6) δ ppm: 0.88-1.03 (4H, m), 1.10-1.37 (6H, m), 1.45-1.68 (5H, m), 2.25-2.36 (1H, m), 2.58 (1H, d, J = 10.9 Hz), 2.62-2.71 (1H, m), 2.73 (1H, d, J = 10.9 Hz), 7.02 (1H, dd, J = 2.4, 8.7 Hz), 7.05 (1H, d, J = 2.4 Hz), 7.16 (1H, dd, J = 2.1, 8.7 Hz), 7.37 (1H, d, J = 1.8 Hz), 7.58 (1H, d, J = 8.8 Hz), 7.67 (1H, d, J = 8.8 Hz), 9.57 (1H, brs). | — |
| 944 | 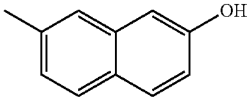 | 1H-NMR (DMSO-d6) δ ppm: 0.88-1.04 (4H, m), 1.12-1.37 (6H, m), 1.45-1.74 (5H, m), 2.32-2.41 (1H, m), 2.60 (1H, d, J = 11.1 Hz), 2.63-2.72 (1H, m), 2.80 (1H, d, J = 11.1 Hz), 6.94 (1H, dd, J = 2.4, 8.8 Hz). 6.97-7.04 (2H, m), 7.21 (1H, d, J = 1.8 Hz), 7.64 (2H, d, J = 8.8 Hz). 9.62 (1H, s). | — |
| 945 | 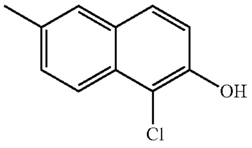 | 1H-NMR (DMSO-d6) δ ppm: 0.90-1.10 (4H, m), 1.15-1.40 (6H, m), 1.51-1.75 (4H, m), 2.35-2.48 (1H, m), 2.60-2.88 (3H, m), 2.96-3.88 (1H, br), 7.23 (1H, d, J = 8.9 Hz), 7.34 (1H, dd, J = 2.1, 9.0 Hz), 7.47 (1H, d, J = 2.0 Hz), 7.70 (1H, d, J = 8.9 Hz), 7.92 (1H, d, J = 9.0 Hz), 8.92-11.38 (1H, br). | — |
| 946 | 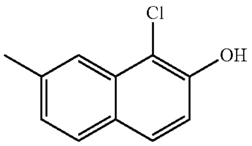 | 1H-NMR (DMSO-d6) δ ppm: 0.93-1.12 (4H, m), 1.15-1.41 (6H, m), 1.54-1.80 (4H, m), 2.48-2.60 (1H, m), 2.70-2.87 (2H, m), 2.92 (1H, d, J = 11.5 Hz), 3.03-4.36 (1H, br), 7.08-7.18 (2H, m), 7.50 (1H, d, J = 2.0 Hz), 7.67 (1H, d, J = 8.8 Hz), 7.75 (1H, d, J = 8.7 Hz), 8.89-11.11 (1H, br). | — |

TABLE 107-continued absolute configuration

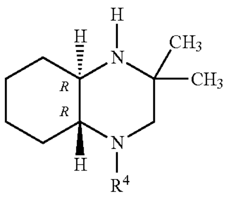

| Example | R4 | NMR | Salt |
|---|---|---|---|
| 947 | 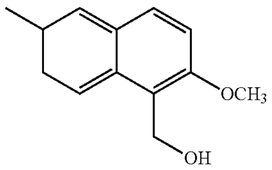 | 1H-NMR (DMSO-d6) δ ppm: 0.90-1.05 (4H, m), 1.13-1.37 (6H, m), 1.47-1.70 (5H, m), 2.30-2.39 (1H, m), 2.61 (1H, d, J = 11.0 Hz), 2.64-2.73 (1H, m), 2.78 (1H, d, J = 11.0 Hz), 3.88 (3H, s), 4.81 (1H, t, J = 5.2 Hz), 4.88 (2H, d, J = 5.2 Hz), 7.27 (1H, dd, J = 2.2, 9.1 Hz), 7.35 (1H, d, J = 9.1 Hz), 7.42 (1H, d, J = 2.1 Hz), 7.80 (1H, d, J = 9.1 Hz), 8.03 (1H, d, J = 9.1 Hz). | — |
| 948 | 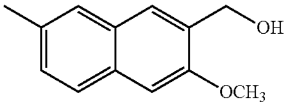 | 1H-NMR (DMSO-d6) δ ppm : 0.95-1.10 (1H, m), 1.10-1.50 (9H, m), 1.53-1.73 (3H, m), 1.77-1.87 (1H, m), 2.58-2.70 (1H, m), 2.85 (2H, s), 2.89-3.00 (1H, m), 3.87 (3H, s), 4,61 (2H, s), 6.46 (1H, s), 7.20 (1H, dd, J = 2.0, 8.7 Hz), 7.22 (1H, s), 7.46 (1H, d, J = 1.6 Hz), 7.73 (1H, d, J = 8.7 Hz), 7.79 (1H, s). | ½ Fumarate |

TABLE 108 absolute configuration

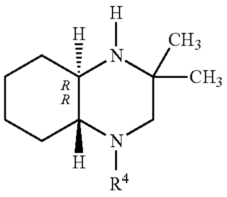

| Example | R4 | NMR | Salt |
|---|---|---|---|
| 949 | 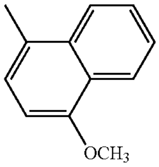 | 1H-NMR (CDCl3) δ ppm: 0.91-1.05 (1H, m), 1.08 (3H, s), 1.12-1.62 (9H, m), 1.68-1.78 (2H, m), 2.42-2.50 (1H, m), 2.62 (1H, d, J = 11.3 Hz), 2.75 (1H, d, J = 11.3 Hz), 2.91-3.00 (1H, m), 3.98 (3H, s), 6.78 (1H, d, J = 8.1 Hz), 7.20 (1H, d, J = 8.1 Hz), 7.43-7.54 (2H, m), 8.21-8.26 (1H, m), 8.50-8.54 (1H, m). | — |
| 950 | 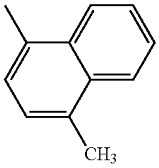 | 1H-NMR (DMSO-d6) δ ppm: 0.93-1.22 (2H, m), 1.26-1.44 (5H, m), 1.44-1.54 (1H, m), 1.56-1.77 (5H, m), 1.99-2.08 (1H, m), 2.62 (3H, s), 2.76 (1H, d, J = 12.4 Hz), 2.98-3.08 (2H, m), 3.33-3.50 (1H, m), 7.28 (1H, d, J = 7.5 Hz), 7.38 (1H, d, J = 7.5 Hz), 7.54-7.61 (2H, m), 7.97-8.03 (1H, m), 8.43-8.52 (1H, m), 9.10-9.25 (1H, br), 9.62-9.77 (1H, br). | Hydrochloride |
| 951 | 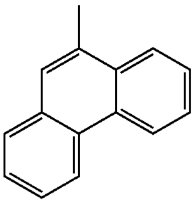 | 1H-NMR (DMSO-d6) δ ppm: 1.00-1.30 (2H, m), 1.30-1.45 (4H, m), 1.45-1.65 (2H, m), 1.65-1.85 (5H, m), 2.00-2.13 (1H, m), 2.91 (1H, d, J = 12.6 Hz), 3.05-3.20 (2H, m), 3.41-3.57 (1H, m), 3.93-4.29 (1H, br), 7.61-7.77 (5H, m), 7.98-8.05 (1H, m), 8.55-8.61 (1H, m), 8.77-8.88 (2H, m), 9.19-9.35 (1H, m), 9.669.81 (1H, m). | 2 Hydrochloride |

TABLE 108-continued absolute configuration

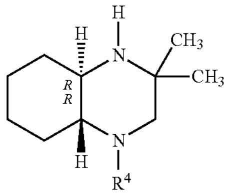

| Example | $R^4$ | NMR | Salt |
| --- | --- | --- | --- |
| 952 | 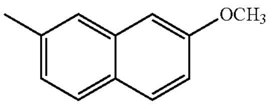 | 1H-NMR (DMSO-d6) δ ppm: 0.96-1.45 (6H, m), 1.55-1.80 (7H, m), 2.00-2.12 (1H, m), 2.85-3.40 (4H, m), 3.87 (3H, s), 7.05-7.26 (2H, m), 7.32 (1H, d, J = 2.5 Hz), 7.42-7.73 (1H, br), 7.73-7.90 (2H, m), 8.75-9.60 (2H, br), 9.60-10.15 (1H, br). | 2 Hydrochloride |
| 953 | 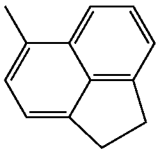 | 1H-NMR (DMSO-d6) δ ppm: 0.85-1.00 (1H, m), 1.10-1.70 (12H, m), 1.75-1.87 (1H, m), 2.62-2.81 (3H, m), 2.98-3.12 (1H, m), 3.20-3.45 (4H, m), 6.46 (1H, s), 7.15-7.35 (3H, m), 7.35-7.52 (1H, m), 7.88 (1H, d, J = 8.1 Hz), 8.05-9.35 (1H, br). | ½ Fumarate |
| 954 | 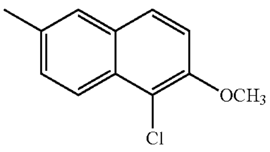 | 1H-NMR (DMSO-d6) δ ppm: 1.05-1.45 (6H, m), 1.55-1.80 (7H, m), 1.99-2.10 (1H, m), 2.91-3.08 (2H, m), 3.08-3.30 (2H, m), 3.98 (3H, s), 7.44 (1H, d, J = 9.0 Hz), 7.56 (1H, d, J = 9.2 Hz), 7.67 (1H, brs), 7.96 (1H, d, J = 9.1 Hz), 8.05 (1H, d, J = 9.1 Hz), 8.15-9.10 (1H, br), 9.17-9.40 (1H, m), 9.69-9.89 (1H, m). | 2 Hydrochloride |
| 955 | 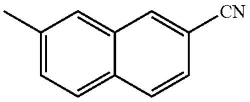 | 1H-NMR (CDCl3) δ ppm: 0.80-0.98 (1H, br), 1.03-1.17 (4H, m), 1.22-1.47 (6H, m), 1.63-1.74 (1H, m), 1.74-1.89 (3H, m), 2.45-2.55 (1H, m), 2.76 (1H, d, J = 11.5 Hz), 2.81-2.90 (1H, m), 2.98 (1H, d, J = 11.5 Hz), 7.38-7.44 (2H, m), 7.49 (1H, dd, J = 1.6, 8.4 Hz), 7.76-7.81 (1H, m), 7.83 (1H, d, J = 8.4 Hz), 8.12 (1H, s). | — |
| 956 | 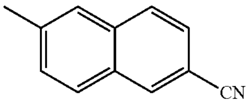 | 1H-NMR (DMSO-d6) δ ppm: 1.12-1.45 (6H, m), 1.55-1.90 (7H, m), 2.00-2.14 (1H, m), 3.08-3.40 (4H, m), 4.52-5.08 (1H, br), 7.45 (1H, dd, J = 2.0, 8.9 Hz), 7.64 (1H, d, J = 1.7 Hz), 7.73 (1H, dd, J = 1.6, 8.5 Hz), 8.00 (1H, d, J = 8.9 Hz), 8.04 (1H, d, J = 8.6 Hz), 8.49 (1H, s), 9.10-9.25 (1H, br), 9.60-9.75 (1H, br). | 2 Hydrochloride |
| 957 | 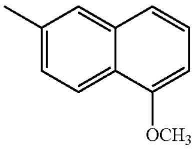 | 1H-NMR (DMSO-d6) δ ppm: 1.03-1.45 (6H, m), 1.50-1.80 (7H, m), 1.98-2.10 (1H, m), 2.90-3.30 (4H, m), 3.95 (3H, s), 6.91 (1H, d, J = 7.1 Hz), 7.23-7.34 (1H, br), 7.38-7.49 (2H, m), 7.48-7.65 (1H, br), 8.10 (1H, d, J = 8.9 Hz), 9.10-9.36 (1H, br), 9.60-9.88 (1H, br), 10.00-11.50 (1H, br). | 2 Hydrochloride |
| 958 | 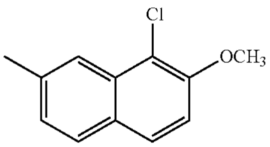 | 1H-NMR (DMSO-d6) δ ppm: 1.10-1.48 (6H, m), 1.55-1.80 (7H, m), 1.981-2.10 (1H, m), 2.95-3.10 (2H, m ), 3.10-3.21 (1H, m), 3.21-3.85 (1H, m), 3.99 (3H, s), 7.26 (1H, dd, J = 1.5, 8.7 Hz), 7.50 (1H, d, J = 9.1 Hz), 7.66 (1H, brs), 7.93 (2H, d, J = 9.1 Hz), 9.20 (1H, brs), 9.72 (1H, brs), 9.89-10.70 (1H, brs). | 2 Hydrochloride |
| 959 | 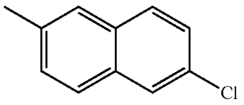 | 1H-NMR (DMSO-d6) δ ppm: 1.10-1.43 (6H, m), 1.56-1.80 (7H, m), 1.99-2.09 (1H, m), 2.95-3.06 (2H, m), 3.11 (1H, d, J = 12.5 Hz), 3.17-3.30 (1H, m), 6.05-7.25 (1H, br), 7.36 (1H, dd, J = 1.9, 8.8 Hz), 7.49 (1H, dd, J = 2.1, 8.8 Hz), 7.64 (1H, brs), 7.88 (1H, d, J = 8.9 Hz), 7.94 (1H, d, J = 8.9 Hz), 8.00 (1H, d, J = 1.8 Hz), 9.15-9.34 (1H, br), 9.69-9.85 (1H, br). | 2 Hydrochloride |

TABLE 108-continued absolute configuration

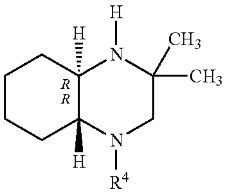

| Example | $R^4$ | NMR | Salt |
|---|---|---|---|
| 960 | 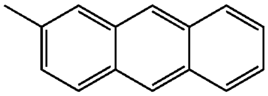 | 1H-NMR (CDCl3) δ ppm: 0.75-1.19 (5H, m), 1.24-1.44 (3H, m), 1.41 (3H, s), 1.59-1.73 (1H, m), 1.73-1.82 (2H, m), 1.90-2.00 (1H, m), 2.45-2.54 (1H, m), 2.73 (1H, d, J = 11.5 Hz), 2.81-2.92 (1H, m), 3.02 (1H, d, J = 11.5 Hz), 7.26 (1H, dd, J = 2.1, 9.0 Hz), 7.38-7.47 (2H, m), 7.51 (1H, d, J = 1.3 Hz), 7.91 (1H, d, J = 9.1 Hz), 7.94-7.99 (2H, m), 8.30 (1H, s), 8.34 (1H, s). | — |
| 961 | 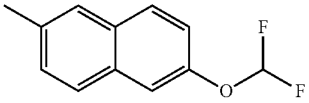 | 1H-NMR (DMSO-d6) δ ppm: 1.15-1.48 (6H, m), 1.55-1.80 (7H, m), 1.95-2.09 (1H, m), 2.91-3.05 (2H, m), 3.05-3.16 (1H, m), 3.16-3.30 (1H, m), 3.70-4.4.10 (1H, br), 7.16 (0.25H, s), 7.32-7.40 (2.5H, m), 7.53 (0.25H, s), 7.62-7.70 (2H, m), 7.90 (1H, d, J = 8.8 Hz), 7.98 (1H, d, J = 9.0 Hz).9.05-9.25 (1H, br), 9.54-9.78 (1H, br). | 2 Hydrochloride |
| 962 | 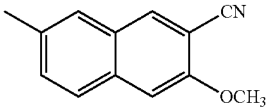 | 1H-NMR (DMSO-d6) δ ppm: 1.05-1.50 (6H, m), 1.55-1.80 (7H, m), 1.97-2.10 (1H, m), 2.40-3.05 (2H, m), 3.05-3.16 (1H, m), 3.16-3.31 (1H, m), 3.65-4.25 (4H, m), 7.44 (1H, dd, J = 2.0, 8.8 Hz), 7.56 (1H, s), 7.65 (1H, s), 7.89 (1H, d, J = 8.8 Hz), 8.47 (1H, s), 9.05-9.35 (1H, br), 9.53-9.84 (1H, br). | 2 Hydrochloride |
| 963 | 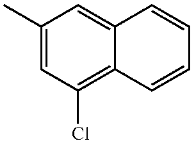 | 1H-NMR (DMSO-d6) δ ppm: 1.08-1.46 (6H, m), 1.54-1.80 (7H, m), 1.97-2.08 (1H, m), 2.95-3.17 (3H, m), 3.17-3.31 1H, m), 4.65-4.45 (1H, br), 7.46-7.50 (1H, m), 7.57-7.67 (3H, m), 7.97-8.04 (1H, m), 8.07-8.15 (1H, m), 9.13-9.35 (1H, br), 9.62-9.80 (1H, br). | 2 Hydrochloride |
| 964 | 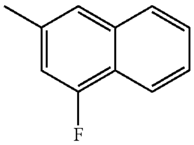 | 1H-NMR (DMSO-d6) δ ppm: 1.08-1.47 (6H, m), 1.53-1.82 (7H, m), 1.98-2.09 (1H, m), 2.93-3.17 (3H, m), 3.17-3.30 (1H, m), 4.30-4.85 (1H, br), 7.15 (1H, dd, J = 1.6, 12.4 Hz), 7.47 (1H, d, J = 1.3 Hz), 7.51-7.64 (2H, m), 7.97 (2H, d, J = 8.2 Hz), 9.10-9.30 (1H, br), 9.67-9.85 (1H, br). | 2 Hydrochloride |
| 965 | 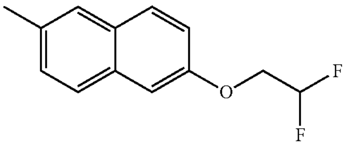 | 1H-NMR (CDCl3) δ ppm: 1.00-1.15 (4H, m), 1.17-1.52 (7H, m), 1.58-1.68 (1H, m), 1.68-1.79 (3H, m), 2.34-2.42 (1H, m), 2.69 (1H, d, J = 11.3 Hz), 2.77-2.86 (1H, m), 2.88 (1H, d, J = 11.3 Hz), 4.28 (2H, dt, J = 4.1, 13.1 Hz), 6.15 (1H, tt, J = 4.1, 55.2 Hz), 7.10 (1H, d, J = 2.5 Hz), 7.14 (1H, dd, J = 2.6, 8.9 Hz), 7.27 (1H, dd, J = 2.1, 8.7 Hz), 7.41 (1H, d, J = 2.0 Hz), 7.63-7.72 (2H, m). | — |
| 966 | 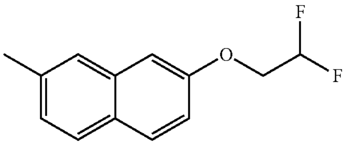 | 1H-NMR (CDCl3) δ ppm: 1.00-1.15 (4H, m), 1.20-1.70 (8H, m), 1.70-1.88 (3H, m), 2.39-2.48 (1H, m), 2.70 (1H, d, J = 11.4 Hz), 2.79-2.88 (1H, m), 2.93 (1H, d, J = 11.4 Hz), 4.29 (2H, dt, J = 4.2, 13.1 Hz), 6.15 (1H, tt, J = 4.1, 55.2 Hz), 7.03-7.11 (2H, m), 7.16 (1H, dd, J = 2.1, 8.6 Hz), 7.33 (1H, d, J = 2.0 Hz), 7.65-7.74 (2H, m). | — |

TABLE 108-continued absolute configuration

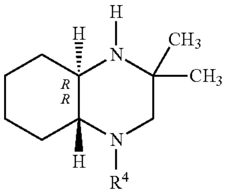

| Example | $R^4$ | NMR | Salt |
|---|---|---|---|
| 967 | 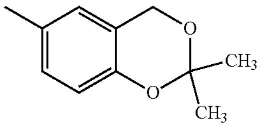 | 1H-NMR (DMSO-d6) δ ppm: 0.91-1.05 (1H, m), 1.07-1.36 (5H, m), 1.36-1.63 (12H, m), 1.63-1.74 (1H, m), 1.80-1.83 (1H, m), 2.50-2.62 (1H, m), 2.71 (1H, d, J = 12.0 Hz), 2.86 (1H, d, J = 12.0 Hz), 2.92-3.02 (1H, m), 4.78 (2H, s), 6.48 (2H, s), 6.73 (1H, d, J = 8.6 Hz), 6.83 (1H, d, J = 2.3 Hz), 6.91 (1H, dd, J = 2.3, 8.6 Hz). 9.52-11.33 (1H, br). | Fumarate |

TABLE 109 absolute configuration

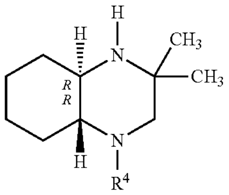

| Example. | $R^4$ | NMR | Salt |
|---|---|---|---|
| 968 | 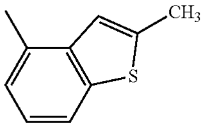 | 1H-NMR (DMSO-d6) δ ppm: 0.96-1.10 (1H, m), 1.10-1.25 (1H, m), 1.25-1.41 (4H, m), 1.47-1.78 (7H, m), 1.94-2.05 (1H, m), 2.56 (3H, s), 2.84 (1H, d, J = 12.4 Hz), 2.90-3.02 (2H, m), 3.23-3.35 (1H, m), 7.15 (1H, d, J = 7.6 Hz), 7.22-7.33 (2H, m), 7.68 (1H, d, J = 7.9 Hz), 8.91-9.09 (1H, brm), 9.54-9.70 (1H, brm). | Hydrochloride |
| 969 | 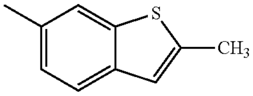 | 1H-NMR (DMSO-d6) δ ppm (80° C.): 1.03-1.46 (6H, m), 1.50-1.79 (7H, m), 2.02-2.12 (1H, m), 2.53 (3H, s), 2.88 (1H, d, J = 12.4 Hz), 3.02-3.12 (1H, m), 3.12-3.27 (2H, m), 7.05 (1H, s), 7.13 (1H, d, J = 8.6 Hz), 7.62-7.68 (2H, m), 9.25 (1H, brs), 9.75 (1H, brs). | Hydrochloride |
| 970 | 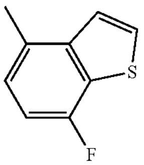 | 1H-NMR (DMSO-d6) δ ppm: 0.95-1.41 (6H, m), 1.40-1.76 (7H, m), 1.96-2.05 (1H, m), 2.84 (1H, d, J = 12.4 Hz), 2.93-3.01 (1H, m), 3.04 (1H, d, J = 12.4 Hz), 3.28-3.44 (1H, m), 7.25 (2H, d, J = 7.0 Hz), 7.64 (1H, dd, J = 4.0, 5.3 Hz), 7.86 (1H, d, J = 5.3 Hz), 9.04-9.19 (1H, brm), 9.63-9.75 (1H, brm). | Hydrochloride |
| 971 | 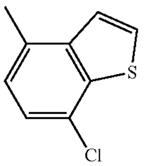 | 1H-NMR (DMSO-d6) δ ppm: 0.97-1.43 (6H, m), 1.45-1.78 (7H, m), 1.96-2.06 (1H, m), 2.87 (1H, d, J = 12.4 Hz), 2.94-3.06 (2H, m), 3.26-3.43 (1H, m), 7.28 (1H, d, J = 8.1 Hz), 7.50 (1H, d, J = 8.1 Hz), 7.64 (1H, d, J = 5.4 Hz), 7.88 (1H, d, J = 5.4 Hz), 9.12 (1H, brs), 9.66 (1H, brs). | Hydrochloride |

TABLE 109-continued absolute configuration

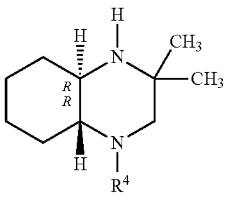

| Example. | $R^4$ | NMR | Salt |
| --- | --- | --- | --- |
| 972 | 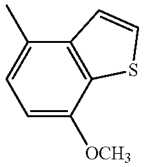 | 1H-NMR (DMSO-d6) δ ppm: 0.92-1.80 (13H, m), 1.36-2.05 (1H, m), 2.75-3.05 (4H, m), 3.94 (3H, s), 6.94 (1H, d, J = 7.9 Hz), 7.18 (1H, d, J = 7.9 Hz), 7.55 (1H, d, J = 5.4 Hz), 7.71 (1H, d, J = 5.4 Hz), 8.81 (1H, brs), 9.31 (1H, brs). | Hydrochloride |
| 973 | 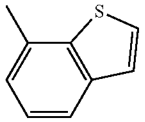 | 1H-NMR (DMSO-d6) δ ppm: 0.95-1.15 (1H, m), 1.15-1.3 (1H, m), 1.3-1.45 (5H, m), 1.5-1.7 (6H, m), 1.7, 1.8 (1H, m), 1.9-2.0 (1H m), 2.85-3.1 (3H, m), 3.2-3.4 (1H, m), 7.24 (1H, d, J = 7.2 Hz), 7.42 (1H, dd, J = 7.7, 7.7 Hz), 7.70-7.77 (2H, m), 8.84 (1H, br), 9.28 (1H, br). | Hydrochloride |

TABLE 110 absolute configuration

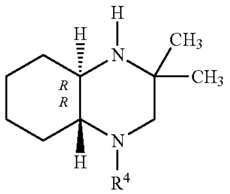

| Example | $R^4$ | NMR | Salt |
| --- | --- | --- | --- |
| 974 | 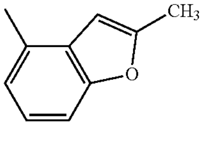 | 1H-NMR (DMSO-d6) δ ppm: 0.97-1.10 (1H, m), 1.10-1.41 (5H, m), 1.50-1.78 (7H, m), 1.94-2.05 (1H, m), 2.44 (3H, s), 2.75-3.09 (3H, m), 3.09-3.30 (1H, m), 6.58 (1H, brs), 6.98 (1H, d, J = 7.2 Hz), 7.19 (1H, t, J = 7.8 Hz), 7.31 (1H, d, J = 7.8 Hz), 9.00 (1H, brs), 9.59 (1H, brs). | Hydrochloride |
| 975 | 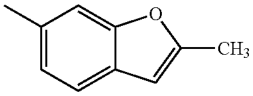 | 1H-NMR (DMSO-d6) δ ppm: 1.00-1.44 (6H, m), 1.44-1.79 (7H, m), 1.95-2.08 (1H, m), 2.42 (3H, d, J = 0.9 Hz), 2.78-3.30 (4H, m), 3.78-4.64 (1H, br), 6.55 (1H, s), 7.04 (1H, brs), 7.32 (1H, brs), 7.48 (1H, d, J = 8.6 Hz), 8.91-9.35 (1H, br), 9.54-9.90 (1H, br). | 2 Hydrochloride |
| 976 | 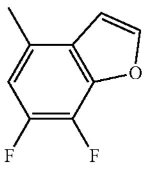 | 1H-NMR (DMSO-d6) δ ppm: 1.00-1.14 (1H, m), 1.14-1.42 (5H, m), 1.43-1.77 (7H, m), 1.93-2.03 (1H, m), 2.72-3.12 (3H, m), 3.27 (1H, brs), 7.08 (1H, brs), 7.24 (1H, brs), 8.14 (1H, s), 8.95 (1H, brs), 9.57 (1H, brs). | Hydrochloride |
| 977 | 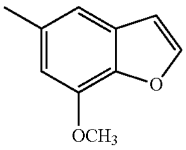 | 1H-NMR (CDCl3) δ ppm: 0.86-1.13 (5H, m), 1.13-1.40 (3H, m), 1.42 (3H, s), 1.57-1.68 (2H, m), 1.68-1.79 (2H, m), 2.20-2.30 (1H, m), 2.65 (1H, d, J = 11.1 Hz), 2.74-2.85 (2H, m), 3.99 (3H, s), 6.61 (1H, d, J = 1.8 Hz), 6.70 (1H, d, J = 2.1 Hz), 6.95 (1H, d, J = 1.8 Hz), 7.59 (1H, d, J = 2.1 Hz). | — |

TABLE 110-continued absolute configuration

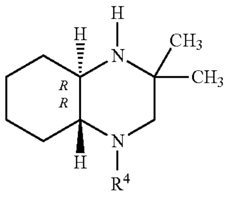

| Example | $R^4$ | NMR | Salt |
|---|---|---|---|
| 978 | 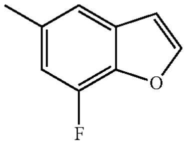 | 1H-NMR (DMSO-d6) δ ppm: 1.02-1.42 (6H, m), 1.49-1.78 (7H, m), 1.96-2.06 (1H, m), 2.82-2.97 (2H, m), 3.04-3.25 (2H, m), 6.55-7.25 (3H, m), 7.30 (1H, s), 8.11 (1H, d, J = 2.1 Hz), 9.11-9.30 (1H, m), 9.70-9.86 (1H, m). | 2 Hydrochloride |
| 979 | 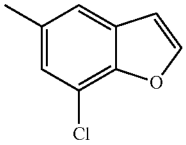 | 1H-NMR (DMSO-d6) δ ppm: 1.00-1.40 (6H, m), 1.45-1.78 (7H, m), 1.95-2.05 (1H, m), 2.82-2.95 (2H, m), 3.02-3.24 (2H, m), 3.78-4.47 (1H, br), 7.05 (1H, d, J = 2.2 Hz), 7.19 (1H, d, J = 1.7 Hz), 7.44 (1H, d, J = 1.7 Hz), 8.12 (1H, d, J = 2.2 Hz), 9.15 (1H, brs), 9.66 (1H, brs). | 2 Hydrochloride |
| 980 | 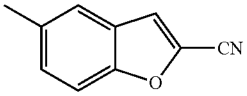 | 1H-NMR (DMSO-d6) δ ppm: 0.90-1.05 (1H, m), 1.12-1.84 (13H, m), 2.55-2.95 (4H, m), 3.10-4.75 (2H, br), 6.43 (3H, s), 7.34 (1H, dd, J = 2.1, 8.9 Hz), 7.53 (1H, d, J = 2.0 Hz), 7.68 (1H, d, J = 8.9 Hz), 8.03 (1H, d, J = 0.8 Hz). | Fumarate |
| 981 | 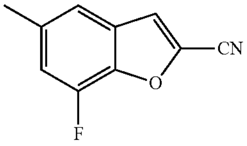 | 1H-NMR (CDCl3) δ ppm: 0.96-1.15 (4H, m), 1.15-1.45 (6H, m), 1.48-1.80 (5H, m), 2.21-2.30 (1H, m), 2.62 (1H, d, J = 11.1 Hz), 2.75-2.85 (2H, m), 7.04 (1H, dd, J = 1.8, 11.8 Hz), 7.15 (1H, d, J = 1.8 Hz), 7.42 (1H, d, J = 2.5 Hz). | — |
| 982 | 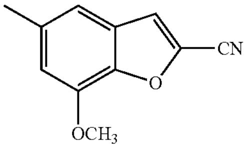 | 1H-NMR (CDCl3) δ ppm: 0.96-1.15 (4H, m), 1.15-1.40 (3H, m), 1.42 (3H, s), 1.55-1.70 (3H, m), 1.70-1.80 (2H, m), 2.23-2.35 (1H, m), 2.66 (1H, d, J = 11.1 Hz), 2.75-2.86 (2H, m), 4.01 (3H, s), 6.76 (1H, d, J = 1.7 Hz), 6.97 (1H, d, J = 1.7 Hz), 7.38 (1H, s). | — |
| 983 | 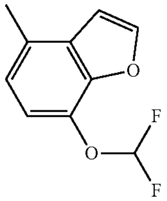 | 1H-NMR (DMSO-d6) δ ppm: 0.99-1.42 (6H, m), 1.50-1.78 (7H, m), 1.72-2.05 (1H, m), 2.75-3.11 (3H, m), 3.16-3.40 (1H, br), 4.95-6.80 (1H, br), 6.95-7.11 (2H, m), 7.12-7.21 (1.25H, m), 7.33 (0.5H, s), 7.51 (0.25H, s), 8.08 (1H, brs), 9.05 (1H, brs), 9.64 (1H, brs). | 2 Hydrochloride |
| 984 | 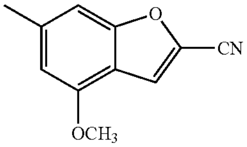 | 1H-NMR (CDC13) δ ppm: 0.99-1.12 (4H, m), 1.20-1.43 (7H, m), 1.62-1.83 (4H, m), 2.34-2.42 (1H, m), 2.70 (1H, d, J = 11.5 Hz), 2.76-2.85 (1H, m), 2.91 (1H, d, J = 11.5 Hz), 3.92 (3H, s), 6.45 (1H, d, J = 1.4 Hz), 6.80-6.83 (1H, m), 7.45 (1H, d, J = 0.9 Hz). | — |
| 985 | 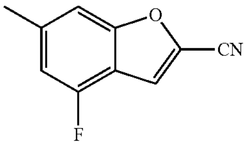 | 1H-NMR (CDCl3) δ ppm: 1.01-1.15 (4H, m), 1.20-1.45 (7H, m), 1.67-1.90 (4H, m), 2.44-2.53 (1H, m), 2.77-2.87 (2H, m), 2.98 (1H, d, J = 11.9 Hz), 6.74 (1H, dd, J = 1.6, 11.5 Hz), 6.90-6.94 (1H, m), 7.43 (1H, d, J = 0.9 Hz). | — |

TABLE 111 absolute configuration

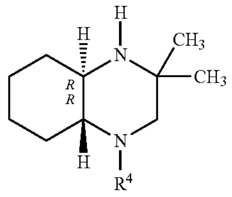

| Example | $R^4$ | NMR | Salt |
| --- | --- | --- | --- |
| 986 | 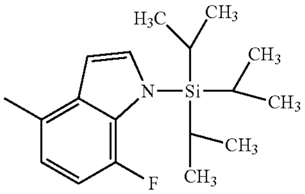 | 1H-NMR (CDCl3) δ ppm: 0.83-1.44 (26H, m), 1.52 (3H, s), 1.55-1.90 (7H, m), 2.36-2.62 (2H, m), 2.80-3.00 (2H, m), 6.69-6.84 (3H, m), 7.24 (1H, d, J = 3.2 Hz). | — |
| 987 | 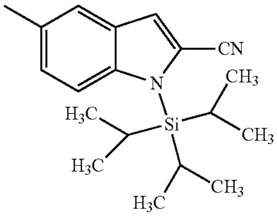 | 1H-NMR (CDCl3) δ ppm: 0.80-1.38 (26H, m), 1.42 (3H, s), 1.58-1.77 (4H, m), 2.01 (3H, sextet, J = 7.5 Hz), 2.25-2.34 (1H, m), 2.65 (1H, d, J = 11.2 Hz.), 2.75-2.85 (2H, m), 7.11 (1H, dd, J = 2.1, 9.1 Hz), 7.32 (1H, d, J = 2.1 Hz), 7.33 (1H, d, J = 0.5 Hz), 7.50 (1H, d, J = 9.1 Hz). | — |
| 988 | 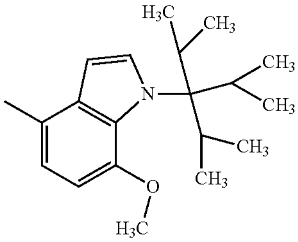 | 1H-NMR (CDCl3) δ ppm: 0.76-1.40 (26H, m), 1.52 (3H, s), 1.56-1.94 (7H, m), 2.35-2.64 (2H, m), 2.79-3.01 (2H, m), 3.88 (3H, s), 6.54 (1H, d, J = 8.1 Hz), 6.69 (1H, d, J = 3.1 Hz), 6.74 (1H, d, J = 8.1 Hz), 7.24 (1H, d, J = 3.2 Hz). | — |
| 989 | 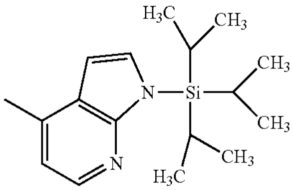 | 1H-NMR (CDCl3) δ ppm: 0.95-1.20 (22H, m), 1.20-1.45 (3H, m), 1.52 (3H, s), 1.62-1.90 (7H, m), 2.10-2.20 (1H, m), 2.57-2.68 (2H, m), 2.83-2.95 (1H, m), 3.26 (1H, d, J = 11.7 Hz), 6.55 (1H, d, J = 3.5 Hz), 6.63 (1H, d, J = 5.2 Hz), 7.18 (1H, d, J = 3.5 Hz), 8.12 (1H, d, J = 5.2 Hz). | — |
| 990 | 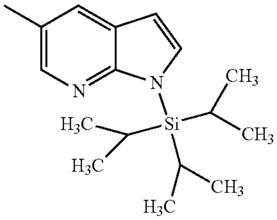 | 1H-NMR (CDCl3) δ ppm: 0.96-1.17 (23H, m), 1.17-1.40 (3H, m), 1.42 (3H, s), 1.55-1.66 (2H, m), 1.66-1.76 (2H, m), 1.84 (3H, quint, J = 7.5 Hz), 2.28-2.37 (1H, m), 2.72 (1H, d, J = 11.2 Hz), 2.76-2.85 (2H, m), 6.47 (1H, d, J = 3.4 Hz), 7.27 (1H, d, J = 3.4 Hz), 7.61 (1H, d, J = 2.4 Hz), 8.06 (1H, d, J = 2.4 Hz). | — |

TABLE 111-continued absolute configuration

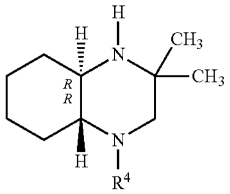

| Example | $R^4$ | NMR | Salt |
|---|---|---|---|
| 991 | 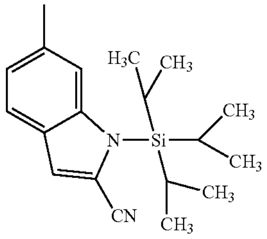 | 1H-NMR (CDCl3) δ ppm: 0.89-1.40 (26H, m), 1.43 (3H, s), 1.60-1.80 (4H, m), 1.95-2.07 (3H, m), 2.30-2.40 (1H, m), 2.58 (1H, d, J = 11.3 Hz), 2.80-2.90 (2H, m), 6.98 (1H, d, J = 1.6, 8.5 Hz), 7.31 (1H, s), 7.34 (1H, d, J = 0.6 Hz), 7.52 (1H, d, J = 8.5 Hz). | — |

TABLE 112 absolute configuration

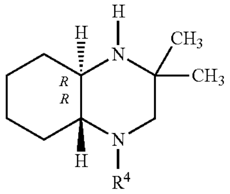

| Example | $R^4$ | NMR | Salt |
|---|---|---|---|
| 992 | 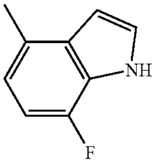 | 1H-NMR (DMSO-d6) δ ppm: 0.77-0.92 (1H, m), 0.95 (3H, s), 1.09-1.35 (3H, m), 1.40 (3H, s), 1.46-1.57 (2H, m), 1.58-1.83 (3H, m), 2.29-2.47 (2H, m), 2.60-2.85 (2H, m), 6.47 (1H, brs), 6.58-6.65 (1H, m), 6.81 (1H, dd, J = 8.3, 11.0 Hz), 7.30 (1H, t, J = 2.7 Hz), 11.47 (1H, s). | — |
| 993 | 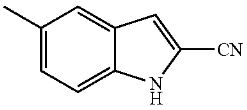 | 1H-NMR (DMSO-d6) δ ppm: 0.83-1.00 (4H, m), 1.08-1.34 (6H, m), 1.41-1.67 (5H, m), 2.19-2.27 (1H, m), 2.55 (1H, d, J = 10.8 Hz), 2.59-2.69 (2H, m), 7.11 (1H, dd, J = 1.8, 8.8 Hz), 7.26 (1H, d, J = 0.8 Hz), 7.32 (1H, d, J = 1.8 Hz), 7.32 (1H, d, J = 8.8 Hz), 12.25 (1H, brs). | — |
| 994 | 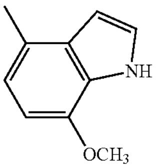 | 1H-NMR (CDCl3) δ ppm: 0.75-0.99 (4H, m), 1.08-1.90 (11H, m), 2.20-2.45 (2H, m), 2.58-2.86 (2H, m), 3.86 (3H, s), 6.38 (1H, brs), 6.47-6.66 (2H, m), 7.13 (1H, t, J = 2.5 Hz), 11.07 (1H, s). | — |
| 995 | 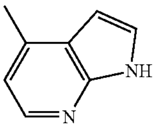 | 1H-NMR (DMSO-d6) δ ppm: 0.95-1.09 (1H, m), 1.21 (3H, s), 1.25-1.65 (7H, m), 1.69-1.79 (1H, m), 1.86-2.03 (2H, m), 2.88 (1H, d, J = 12.4 Hz), 2.96-3.21 (3H, m), 6.39 (1H, d, J = 2.6 Hz), 6.49 (2H, s), 6.72 (1H, d, J = 5.3 Hz), 7.33-7.38 (1H, m), 8.09 (1H, d, J = 5.3 Hz), 8.35-11.15 (1H, br), 11.58 (1H, s). | Fumarate |

TABLE 112-continued absolute configuration

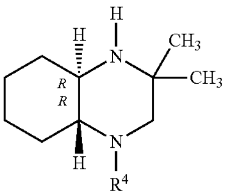

| Example | $R^4$ | NMR | Salt |
| --- | --- | --- | --- |
| 996 | 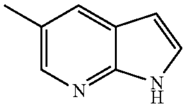 | 1H-NMR (DMSO-d6) δ ppm: 0.95-1.10 (1H, m), 1.10-1.23 (1H, m), 1.23-1.38 (4H, m), 1.38-1.60 (6H, m), 1.63-1.75 (1H, m), 1.84-1.95 (1H, m), 2.72-2.85 (2H, m), 3.00-3.13 (2H, m), 6.38-6.43 (1H, m), 6.50 (1H, s), 7.43-7.48 (1H, m), 7.75 (1H, d, J = 1.9 Hz), 7.99 (1H, d, J = 2.2 Hz), 8.35-11.30 (2H, br), 11.61 (1H, s). | ½ Fumarate |
| 997 | 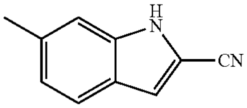 | 1H-NMR (DMSO-d6) δ ppm: 0.85-1.05 (4H, m), 1.10-1.36 (6H, m), 1.35-2.10 (5H, m), 2.25-2.35 (1H, m), 2.56 (1H, d, J = 11.0 Hz), 2.62-2.70 (1H, m), 2.75 (1H, d, J = 11.0 Hz), 6.91 (1H, dd, J = 1.2, 8.6 Hz), 7.02 (1H, s), 7.27 (1H, s), 7.55 (1H, d, J = 8.6 Hz) 11.93-12.33 (1H, br). | — |

TABLE 113 absolute configuration

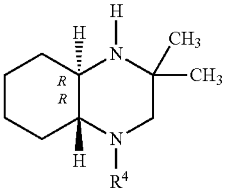

| Example | $R^4$ | NMR | Salt |
| --- | --- | --- | --- |
| 998 | 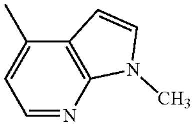 | 1H-NMR (CDCl3) δ ppm: 0.72-1.19 (5H, m), 1.25-1.45 (3H, m), 1.48 (3H, s), 1.65-1.82 (3H, m), 2.08-2.20 (1H, m), 2.65-2.80 (2H, m), 2.80-2.95 (1H, m), 3.27 (1H, d, J = 11.9 Hz), 3.85 (3H, s), 6.45 (1H, d, J = 3.5 Hz), 6.63 (1H, d, J = 5.3 Hz), 7.06 (1H, d, J = 3.5 Hz), 8.20 (1H, d, J = 5.3 Hz). | — |
| 999 | 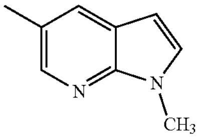 | 1H-NMR (DMSO-d6) δ ppm: 0.95-1.60 (11H, m), 1.60-1.83 (2H, m), 1.83-1.95 (1H, m), 2.65-2.83 (2H, m), 3.00-3.10 (2H, m), 3.79 (3H, s), 6.41 (1H, d, J = 3.4 Hz), 6.48 (2H, s), 7.50 (1H, d, J = 3.4 Hz), 7.77 (1H, d, J = 2.2 Hz), 8.04 (1H, d, J = 2.2 Hz), 8.35-10.85 (2H, br). | Fumarate |

TABLE 114 absolute configuration

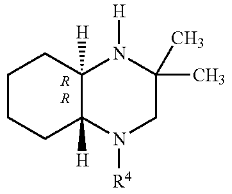

| Example | $R^4$ | NMR | Salt |
|---|---|---|---|
| 1000 | 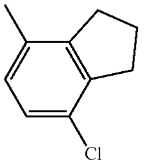 | 1H-NMR (DMSO-d6) δ ppm: 0.87-1.00 (1H, m), 1.15-1.40 (5H, m), 1.50-1.78 (7H, m), 1.90-2.11 (3H, m), 2.65-2.80 (2H, m), 2.80-3.05 (5H, m), 3.09-3.25 (1H, m), 3.48 (1H, brs), 6.99 (1H, d, J = 8.3 Hz), 7.21 (1H, d, J = 8.3 Hz), 8.90-9.10 (1H, m), 9.40-9.64 (1H, m). | 2 Hydrochloride |
| 1001 | 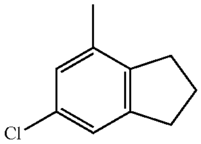 | 1H-NMR (DMSO-d6) δ ppm: 0.89-1.04 (1H, m), 1.20-1.40 (5H, m), 1.46-1.78 (7H, m), 1.88-2.09 (3H, m), 2.64-3.00 (7H, m), 3.05-3.25 (1H, m), 3.25-3.50 (1H, br), 6.96 (1H, s), 7.12 (1H, s), 8.70-9.10 (1H, brs), 9.15-9.55 (1H, brs). | 2 Hydrochloride |
| 1002 | 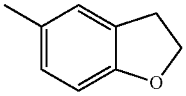 | 1H-NMR (DMSO-d6) δ ppm: 0.90-1.21 (2H, m), 1.22-1.43 (4H, m), 1.43-1.80 (7H, m), 1.90-2.10 (1H, m), 2.58-3.40 (6H, m), 4.52 (2H, t, J = 8.6 Hz), 5.35-6.40 (1H, br), 6.55-7.60 (3H, m), 8.60-10.20 (2H, br). | 2 Hydrochloride |
| 1003 | 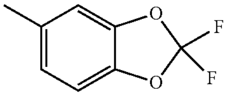 | 1H-NMR (DMSO-d6) δ ppm: 0.98-1.13 (1H, m), 1.13-1.40 (5H, m), 1.47-1.65 (6H, m), 1.65-1.77 (1H, m), 1.91-2.06 (1H, m), 2.74-2.90 (2H, m), 2.99 (1H, d, J = 12.5 Hz), 3.08-3.21 (1H, m), 4.05-5.00 (1H, br), 6.95 (1H, dd, J = 2.0, 8.6 Hz), 7.26 (1H, d, J = 2.0 Hz), 7.36 (1H, d, J = 8.6 Hz), 8.94-9.20 (1H, br), 9.55-9.85 (1H, br). | 2 Hydrochloride |

TABLE 115 absolute configuration

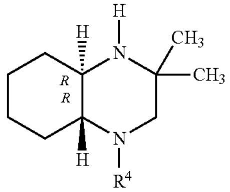

| Example | $R^4$ | NMR | Salt |
|---|---|---|---|
| 1004 | 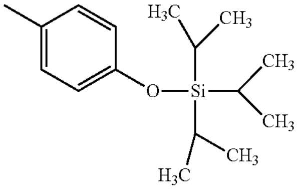 | 1H-NMR (CDCl3) δ ppm: 0.78-1.04 (2H, m), 1.04-1.14 (21H, m), 1.15-1.35 (6H, m), 1.38 (3H, s), 1.51-1.75 (4H, m), 2.12-2.20 (1H, m), 2.58 (1H, d, J = 11.1 Hz), 2.69-2.78 (2H, m), 6.76-6.81 (2H, m), 6.92-6.97 (2H, m). | — |

TABLE 115-continued
absolute configuration
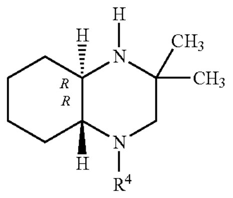
| Example | $R^4$ | NMR | Salt |
|---|---|---|---|
| 1005 | 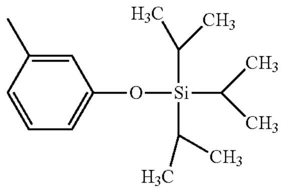 | 1H-NMR (CDCl3) δ ppm: 0.85-1.15 (23H, m), 1.15-1.37 (6H, m), 1.38 (3H, s), 1.60-1.77 (4H, m), 2.20-2.29 (1H, m), 2.58 (1H, d, J = 11.3 Hz), 2.72-2.82 (2H, m), 6.60-6.65 (2H, m), 6.65-6.70 (1H, m), 7.07-7.13 (1H, m). | — |
| 1006 | 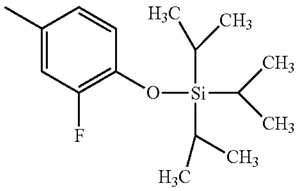 | 1H-NMR (CDCl3) δ ppm: 0.75-1.13 (23H, m), 1.13-1.39 (9H, m), 1.50-1.75 (4H, m), 2.08-2.18 (1H, m), 2.55 (1H, d, J = 11.2 Hz), 2.69-2.78 (2H, m), 6.68-6.74 (1H, m), 6.77-6.86 (2H, m). | — |
| 1007 | 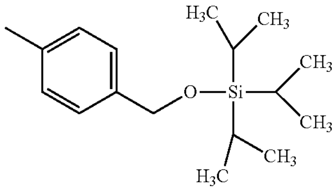 | 1H-NMR (CDCl3) δ ppm: 0.92-1.38 (29H, m), 1.39 (3H, s), 1.58-1.76 (4H, m), 2.23-2.31 (1H, m), 2.61 (1H, d, J = 11.3 Hz), 2.71-2.82 (2H, m), 4.79 (2H, s), 7.02-7.08 (2H, m), 7.22-7.31 (2H, m). | — |
| 1008 | 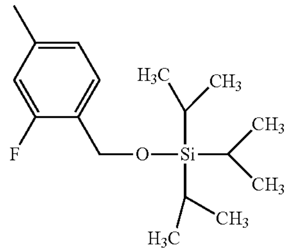 | 1H-NMR (CDCl3) δ ppm: 0.72-1.35 (29H, m), 1.36 (3H, s), 1.60-1.78 (4H, m), 2.21-2.30 (1H, m), 2.60 (1H, d, J = 12.1 Hz), 2.71-2.84 (2H, m), 5.30 (2H, s), 6.72 (1H, dd, J = 2.0, 12.0 Hz), 6.86 (1H, J = 2.0, 8.2 Hz), 7.44 (1H, t, J = 8.4 Hz). | — |
| 1009 | 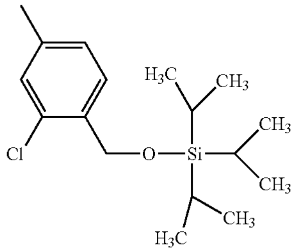 | 1H-NMR (CDCl3) δ ppm: 0.72-1.39 (32H, m), 1.52-1.75 (4H, m), 2.08-2.18 (1H, m), 2.56 (1H, d, J = 11.1 Hz), 2.67-2.77 (2H, m), 6.80 (1H, d, J = 8.6 Hz), 6.84 (1H, dd, J = 2.4, 8.6 Hz), 7.08 (1H, d, J = 2.4 Hz). | — |
| 1010 | 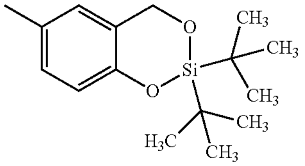 | 1H-NMR (CDCl3) δ ppm: 0.86-1.09 (23H, m), 1.09-1.36 (3H, m), 1.37 (3H, s), 1.50-1.75 (4H, m), 2.11-2.19 (1H, m), 2.57 (1H, d, J = 11.1 Hz), 2.67-2.77 (2H, m), 4.95 (2H, s), 6.67 (1H, d, J = 2.5 Hz), 6.82 (1H, d, J = 8.5 Hz), 6.91 (1H, dd, J = 2.5, 8.5 Hz). | — |

TABLE 116 absolute configuration

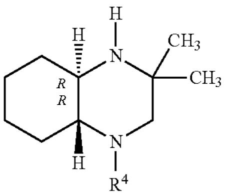

| Example | R4 | NMR | Salt |
|---|---|---|---|
| 1011 | 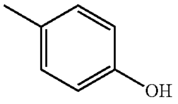 | 1H-NMR (CDCl3) δ ppm: 0.92-1.06 (1H, m), 1.09 (3H, s), 1.12-1.39 (3H, m), 1.41 (3H, s), 1.55-1.66 (2H, m), 1.66-1.79 (2H, m), 2.17-2.25 (1H, m), 2.61 (1H, d, J = 11.3 Hz), 2.70-2.83 (2H, m), 3.53-4.70 (2H, br), 6.73-6.79 (2H, m), 6.94-7.01 (2H, m). | — |
| 1012 | 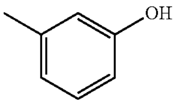 | 1H-NMR (DMSO-d6) δ ppm: 0.82-1.00 (4H, m), 1.09-1.35 (6H, m), 1.40-1.52 (1H, m), 1.52-1.70 (4H, m), 2.15-2.25 (1H, m), 2.44-2.55 (1H, m), 2.55-2.64 (1H, m), 2.66 (1H, d, J = 12.2 Hz), 6.39-6.51 (3H, m), 6.99-7.09 (1H, m), 9.21 (1H, s). | — |
| 1013 | 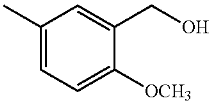 | 1H-NMR (DMSO-d6) δ ppm: 0.90-1.03 (1H, m), 1.05-1.53 (10H, m), 1.53-1.62 (1H, m), 1.62-1.74 (1H, m), 1.80-1.90 (1H, m), 2.48-2.59 (1H, m), 2.68 (1H, J = 11.8 Hz), 2.84 (1H, d, J = 11.8 Hz), 2.90-3.01 (1H, m), 3.74 (3H, s), 4.45 (2H, s), 6.45 (1H, s), 6.86 (1H, d, J = 8.6 Hz), 6.94 (1H, dd, J = 2.5, 8.6 Hz), 7.15 (1H, d, J = 2.5 Hz), 8.10-10.15 (1H, br). | ½ Fumarate |
| 1014 | 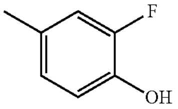 | 1H-NMR (DMSO-d6) δ ppm: 0.83-1.00 (4H, m), 1.05-1.31 (6H, m), 1.40-1.51 (1H, m), 1.51-1.65 (3H, m), 2.05-2.14 (1H, m), 2.47 (1H, d, J = 10.8 Hz), 2.53-2.62 (2H, m), 3.10-3.60 (1H, br), 6.67-6.73 (1H, m), 6.79-6.87 (2H, m), 9.00-10.10 (1H, m). | — |
| 1015 | 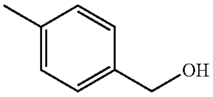 | 1H-NMR (CDCl3) δ ppm: 0.84-1.12 (5H, m), 1.16-1.45 (6H, m), 1.59-2.14 (5H, m), 2.25-2.35 (1H, m), 2.56-2.65 (1H, m), 2.72-2.85 (2H, m), 4.64 (2H, m), 7.07 (2H, dd, J = 1.3, 8.1 Hz), 7.29 (2H, d, J = 8.1 Hz). | — |
| 1016 | 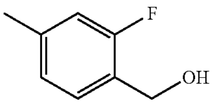 | 1H-NMR (CDCl3) δ ppm: 0.95-1.44 (11H, m), 1.44-2.22 (5H, m), 2.26-2.35 (1H, m), 2.62 (1H, d, J = 11.4 Hz), 2.72-2.87 (2H, m), 4.69 (2H, s), 6.75 (1H, dd, J = 2.0, 12.0 Hz), 6.81 (1H, dd, J = 2.0, 8.1 Hz), 7.29 (1H, t, J = 8.4 Hz). | — |
| 1017 | 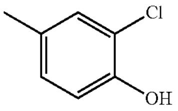 | 1H-NMR (CDCl3) δ ppm: 0.89-1.12 (4H, m), 1.14-1.43 (6H, m), 1.53-1.77 (4H, m), 2.12-2.21 (1H, m), 2.57 (1H, d, J = 11.2 Hz), 2.67-2.80 (2H, m), 2.80-3.30 (2H, br), 6.89-6.96 (2H, m), 7.05-7.09 (1H, m). | — |
| 1018 | 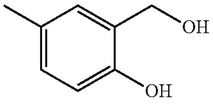 | 1H-NMR (DMSO-d6) δ ppm: 0.78-0.94 (1H, m), 0.95 (3H, s), 1.04-1.32 (6H, m), 1.39-1.66 (5H, m), 2.05-2.15 (1H, m), 2.45-2.62 (3H, m), 4.43 (2H, s), 4.70-5.15 (1H, br), 6.65 (1H, d, J = 8.4 Hz), 6.74 (1H, dd, J = 2.5, 8.4 Hz), 7.03 (1H, d, J = 2.5 Hz), 8.80-9.30 (1H, br). | — |

TABLE 117 absolute configuration

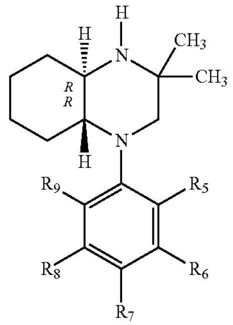

| Example | $R^5$ | $R^6$ | $R^7$ | $R^8$ | $R^9$ | NMR | Salt |
|---|---|---|---|---|---|---|---|
| 1019 | —CH3 | —H | —H | —H | —H | 1H-NMR (DMSO-d6) δ ppm: 0.88-1.03 (1H, m), 1.10-1.25 (1H, m), 1.25-1.40 (4H, m), 1.45-1.66 (6H, m), 1.67-1.89 (1H, m), 1.92-2.03 (1H, m), 2.26 (3H, m), 2.65 (1H, d, J = 12.5 Hz), 2.80 (1H, d, J = 12.5 Hz), 2.88-3.00 (1H, m), 3.15-3.28 (1H, m), 7.06-7.17 (2H, m), 7.19-7.26 (2H, m), 9.04 (1H, brs), 9.58 (1H, brs). | Hydrochloride |
| 1020 | —CH3 | —CH3 | —H | —H | —H | 1H-NMR (DMSO-d6) δ ppm: 0.89-1.02 (1H, m), 1.09-1.23 (1H, m), 1.24-1.40 (4H, m), 1.40-1.66 (6H, m), 1.67-1.76 (1H, m), 1.93-2.02 (1H, m), 2.21 (3H, s), 2.22 (3H, s), 2.60 (1H, d, J = 12.5 Hz), 2.76-2.95 (2H, m), 3.15-3.35 (1H, m), 6.97-7.03 (2H, m), 7.07-1.15 (1H, m), 9.07 (1H, brs), 9.61 (1H, brs). | Hydrochloride |
| 1021 | —H | —F | —CN | —H | —H | 1H-NMR (DMSO-d6) δ ppm: 1.21-1.65 (10H, m), 1.65-1.84 (2H, m), 1.90-2.00 (1H, m), 2.10-2.20 (1H, m), 3.38-3.61 (3H, m), 3.78 (1H, d, J = 14.5 Hz), 6.83 (1H, dd, J = 2.3, 8.9 Hz), 6.97 (1H, dd, J = 2.0, 13.7 Hz), 7.65 (1H, t, J = 8.5 Hz), 8.93-9.15 (1H, m), 9.51-9.71 (1H, m). | Fumarate |
| 1022 | —H | —H | —OCF3 | —H | —H | 1H-NMR (DMSO-d6) δ ppm: 1.00-1.15 (1H, m), 1.15-1.40 (5H, m), 1.50-1.67 (6H, m), 1.67-1.77 (1H, m), 1.95-2.05 (1H, m), 2.80-2.95 (2H, m), 3.01 (1H, d, J = 12.4 Hz), 3.11-3.25 (1H, m), 5.15-5.32 (1H, br), 7.20-7.27 (2H, m), | 2 Hydrochloride |

TABLE 117-continued absolute configuration

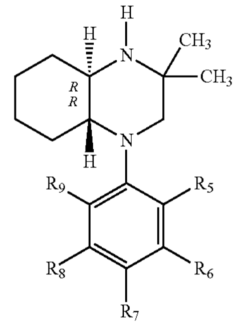

| Example | $R^5$ | $R^6$ | $R^7$ | $R^8$ | $R^9$ | NMR | Salt |
|---|---|---|---|---|---|---|---|
| | | | | | | 7.31-7.37 (2H, m), 9.10 (1H, brs), 9.68 (1H, brm). | |
| 1023 | —H | —F | —OCF3 | —H | —H | 1H-NMR (DMSO-d6) δ ppm: 1.04-1.20 (1H, m), 1.20-1.41 (5H, m), 1.479-1.78 (7H, m), 1.97-2.07 (1H, m), 2.86-3.11 (3H, m), 3.15-3.27 (1H, m), 4.45-6.85 (1H, br), 7.00-7.16 (1H, m), 7.22-7.29 (1H, m), 7.46-7.55 (1H, m), 9.12 (1H, brs), 9.77 (1H, brs). | 2 Hydrochloride |
| 1024 | —H | —H | —OCHF2 | —H | —H | 1H-NMR (DMSO-d6) δ ppm: 0.98-1.40 (6H, m), 1.49-1.77 (7H, m), 1.95-2.06 (1H, m), 2.76-2.95 (2H, m), 3.03 (1H, d, J = 12.3 Hz), 3.10-3.23 (1H, m), 6.20-6.90 (1H, br), 7.01 (0.25H, s), 7.13-7.23 (4.5H, m), 7.38 (0.25H, s), 9.17 (1H, brs), 9.74 (1H, brm). | 2 Hydrochloride |
| 1025 | —H | —F | —OCHF2 | —H | —H | 1H-NMR (DMSO-d6) δ ppm: 1.03-1.40 (6H, m), 1.50-1.67 (6H, m), 1.67-1.77 (1H, m), 1.96-2.05 (1H, m), 2.81-2.95 (2H, m), 3.02 (1H, d, J = 12.5 Hz), 3.10-3.23 (1H, m), 3.88-4.20 (1H, br), 6.96-7.01 (1H, m), 7.02 (0.25H, s), 7.17 (1H, dd, J = 2.5, 12.1 Hz), 7.20 (0.5H, s) 7.33 (1H, t, J = 8.9 Hz), 7.39 (0.25H, s), 9.08-9.22 (1H, m), 9.70-9.88 (1H, m). | 2 Hydrochloride |
| 1026 | —H | —Cl | —OCHF2 | —H | —H | 1H-NMR (DMSO-d6) δ ppm: 1.02-1.15 (1H, m), 1.15-1.41 (5H, m), 1.50-1.67 (6H, m), 1.67-1.78 (1H, m), 1.93-2.04 (1H, m), 2.78-2.95 (2H, m), 2.95-3.06 (1H, m), 3.10-3.25 (1H, m), 3.50-4.05 (1H, br), 7.15 | 2 Hydrochloride |

TABLE 117-continued absolute configuration

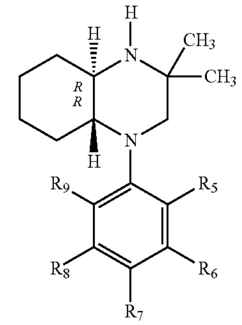

| Example | $R^5$ | $R^6$ | $R^7$ | $R^8$ | $R^9$ | NMR | Salt |
|---|---|---|---|---|---|---|---|
| | | | | | | (1H, dd, J = 2.5, 8.8 Hz), 7.24 (1H, t, J = 73.3 Hz), 7.32 (1H, d, J = 2.5 Hz), 7.34 (1H, d, J = 8.8 Hz), 8.90-9.20 (1H, br), 9.44-9.75 (1H, br). | |
| 1027 | —H | —OCHF2 | —H | —H | —H | 1H-NMR (DMSO-d6) δ ppm: 1.01-1.15 (1H, m), 1.15-1.42 (5H, m), 1.50-1.68 (6H, m), 1.68-1.78 (1H, m), 1.96-2.06 (1H, m), 2.83-2.96 (2H, m), 3.03 (1H, d, J = 12.7 Hz), 3.10-3.25 (1H, m), 6.89 (1H, s), 6.96 (1H, dd, J = 2.1, 8.1 Hz), 7.00 (1H, d, J = 8.1 Hz), 7.27 (1H, t, J = 74.1 Hz), 7.39 (1H, t, J = 8.1 Hz), 7.85-8.90 (1H, br), 9.00-9.25 (1H, br), 9.65-9.85 (1H, br). | 2 Hydrochloride |
| 1028 | —H | —OCHF2 | —Cl | —H | —H | 1H-NMR (DMSO-d6) δ ppm: 1.02-1.41 (6H, m), 1.49-1.80 (7H, m), 1.91-2.07 (1H, m), 2.78-2.90 (1H, m), 2.90-3.05 (2H, m), 3.10-3.27 (1H, m), 3.90-4.65 (1H, br), 7.01-7.08 (2H, m), 7.32 (1H, t, J = 73.3 Hz), 7.54 (1H, d, J = 8.4 Hz), 8.85-9.10 (1H, m), 9.39-9.70 (1H, m). | 2 Hydrochloride |
| 1029 | —H | —OCHF2 | —F | —H | —H | 1H-NMR (DMSO-d6) δ ppm: 1.00-1.40 (6H, m), 1.47-1.65 (6H, m), 1.67-1.77 (1H, m), 1.90-2.00 (1H, m), 2.70-2.80 (1H, m), 2.87 (1H, d, J = 12.5 Hz), 2.96 (1H, d, J = 12.5 Hz), 3.10-3.24 (1H, m), 7.02-7.11 (2.25H, m), 7.27 (0.5H, s), 7.37 (1H, dd, J = 8.8, 10.5 Hz), 7.46 (0.25H, s), 8.80-9.00 (1H, br), 9.39-9.58 (1H, br). | Hydrochloride |

TABLE 117-continued absolute configuration

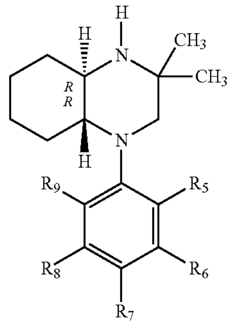

| Example | $R^5$ | $R^6$ | $R^7$ | $R^8$ | $R^9$ | NMR | Salt |
|---|---|---|---|---|---|---|---|
| 1030 | —H | —CN | —OCHF2 | —H | —H | 1H-NMR (DMSO-d6) δ ppm: 1.02-1.15 (1H, m), 1.17-1.40 (5H, m), 1.48-1.81 (7H, m), 1.93-2.07 (1H, m), 2.82-2.91 (1H, m), 2.94 (1H, d, J = 12.6 Hz), 3.01 (1H, d, J = 12.6 Hz), 3.08-3.25 (1H, m), 3.70-4.20 (1H, br), 7.39 (1H, t, J = 72.6 Hz), 7.42 (1H, d, J = 8.9 Hz), 7.51 (1H, dd, J = 2.7, 9.0 Hz), 7.69 (1H, d, J = 2.7 Hz), 8.90-9.10 (1H, br), 9.35-9.70 (1H, br). | 2 Hydrochloride |
| 1031 | —H | —F | —OCHF2 | —F | —H | 1H-NMR (DMSO-d6) δ ppm: 1.08-1.40 (6H, m), 1.43-1.80 (7H, m), 1.95-2.07 (1H, m), 2.88-2.99 (1H, m), 3.05 (1H, d, J = 13.1 Hz), 3.09 (1H, d, J = 13.1 Hz), 3.17-3.30 (1H, m), 3.48-3.70 (1H, br), 6.97-7.06 (2.25H, m), 7.19 (0.5H, s), 7.37 (0.25H, s), 8.81-9.04 (1H, br), 9.45-9.65 (1H, br). | 2 Hydrochloride |
| 1032 | —H | —H | —OCH2CHF2 | —H | —H | 1H-NMR (DMSO-d6) δ ppm: 0.98-1.85 (13H, m), 1.90-2.20 (1H, m), 2.60-3.80 (4H, m), 4.20-4.40 (2H, m), 4.40-5.40 (1H, br), 6.38 (1H, tt, J = 3.4, 54.5 Hz), 6.85-7.70 (4H, brm), 8.84-10.40 (2H, br). | 2 Hydrochloride |
| 1033 | —H | —F | OCH2CHF2 | —H | —H | 1H-NMR (CDCl3) δ ppm: 0.94-1.11 (4H, m), 1.14-1.41 (7H, m), 1.57-1.78 (4H, m), 2.13-2.22 (1H, m), 2.56 (1H, d, J = 11.1 Hz), 2.70-2.79 (2H, m), 4.21 (2H, dt, J = 4.2, 13.1 Hz), 6.08 (1H, tt, J = 4.2, 55.1 Hz), 6.77-6.83 (1H, m), 6.83-6.95 (2H, m). | — |

TABLE 117-continued absolute configuration

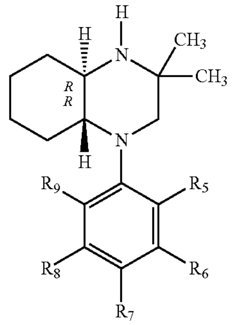

| Example | $R^5$ | $R^6$ | $R^7$ | $R^8$ | $R^9$ | NMR | Salt |
|---|---|---|---|---|---|---|---|
| 1034 | —H | Cl | OCH2CHF2 | —H | —H | 1H-NMR (CDCl3) δ ppm: 0.93-1.11 (4H, m), 1.15-1.41 (7H, m), 1.55-1.77 (4H, m), 2.14-2.23 (1H, m), 2.57 (1H, d, J = 11.0 Hz), 2.68-2.78 (2H, m), 4.20 (2H, dt, J = 4.2, 13.0 Hz), 6.12 (1H, tt, J = 4.2, 55.1 Hz), 6.87 (1H, d, J = 8.7 Hz), 6.96 (1H, dd, J = 2.5, 8.7 Hz), 7.13 (1H, d, J = 2.5 Hz). | |
| 1035 | —H | —CH3 | —OCHF2 | —H | —H | 1H-NMR (DMSO-d6) δ ppm: 0.97-1.10 (1H, m), 1.12-1.40 (5H, m), 1.47-1.63 (6H, m), 1.67-1.76 (1H, m), 1.90-2.01 (1H, m), 2.20 (3H, m), 2.70-2.80 (1H, m), 2.83 (1H, d, J = 12.3 Hz), 2.95 (1H, d, J = 12.3 Hz), 3.08-3.22 (1H, m), 4.60-5.40 (1H, br), 6.94 (0.25H, s), 6.99 (1H, dd, J = 2.5, 8.5 Hz), 7.05 (1H, d, J = 2.5 Hz), 7.09-7.15 (1.5H, m), 7.31 (0.25H, s), 8.85-9.01 (1H, m), 9.40-9.55 (1H, m). | 2 Hydrochloride |
| 1036 | —H | —OCH3 | —OCHF2 | —H | —H | 1H-NMR (DMSO-d6) δ ppm: 1.00-1.40 (6H, m), 1.50-1.80 (7H, m), 1.95-2.06 (1H, m), 2.75-2.94 (2H, m), 2.96-3.07 (1H, m), 3.09-3.22 (1H, m), 3.82 (3H, s), 6.08-6.65 (1H, br), 6.73 (1H, d, J = 8.2 Hz), 6.80-6.89 (1.25H, m), 7.01 (0.5H, s), 7.14 (1H, d, J = 8.4 Hz), 7.19 (0.25H, s), 9.09 (1H, brs), 9.72 (1H, brs). | 2 Hydrochloride |

TABLE 118 absolute configuration

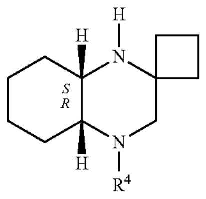

| Example | $R^4$ | NMR | Salt |
|---|---|---|---|
| 1037 | 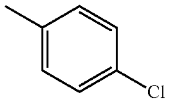 | 1H-NMR (DMSO-d6) δ ppm: 1.1-1.35 (3H, m), 1.4-1.55 (1H, m), 1.55-1.95 (8H, m), 1.95-2.05 (2H, m), 2.68 (1H, d, J = 11.9 Hz), 2.8-4.0 (5H, m), 6.55 (1H, s), 6.85-6.95 (2H, m), 7.14-7.22 (2H, m). | ½ Fumarate |
| 1038 | 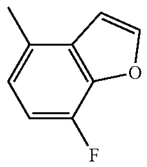 | 1H-NMR (CDCl3) δ ppm: 0.95-1.15 (2H, m), 1.3-1.4 (1H, m), 1.4-2.1 (11H, m), 2.25-2.4 (1H, m), 3.04 (1H, d, J = 11.1 Hz), 3.17 (1H, d, J = 10.9 Hz), 3.41 (1H, br), 3.45-3.58 (1H, m), 6.54 (1H, dd, J = 3.3, 8.4 Hz), 6.82 (1H, dd, J = 2.5, 2.5 Hz), 6.91 (1H, dd, J = 8.6, 10.4 Hz), 7.59 (1H, d, J = 2.1 Hz). | — |
| 1039 | 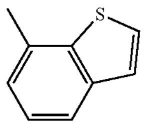 | 1H-NMR (DMSO-d6) δ ppm: 0.95-1.5 (3H, m), 1.5-1.7 (2H, m), 1.7-2.3 (6H, m), 2.3-2.7 (3H, m), 3.0-3.4 (1H, m), 3.59 (2H, br), 3.73 (1H, br), 7.07 (1H, br), 7.3-7.45 (1H, m), 7.48 (1H, d, J = 5.4 Hz), 7.64 (1H, br), 7.75 (1H, d, J = 5.4 Hz), 8.75-10.3 (2H, m). | Hydrochloride |

TABLE 119 absolute configuration

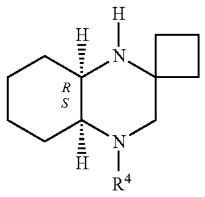

| Ex. No. | $R^4$ | NMR | Salt |
|---|---|---|---|
| 1040 | 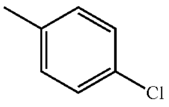 | 1H-NMR (DMSO-d6) δppm: 1.1-1.35 (3H, m), 1.4-1.55 (1H, m), 1.55-1.95 (8H, m), 1.95-2.05 (2H, m), 2.68 (1H, d, J = 11.9 Hz), 2.8-4.0 (5H, m), 6.55 (1H, s), 6.85-6.95 (2H, m), 7.14-7.22 (2H, m). | ½ Fumarate |
| 1041 | 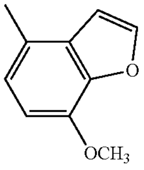 | 1H-NMR (CDCl3) δppm: 0.95-1.1 (2H, m), 1.3-1.4 (1H, m), 1.4-2.1 (11H, m), 2.25-2.4 (1H, m), 3.01 (1H, d, J = 11.0 Hz), 3.17 (1H, d, J = 11.1 Hz), 3.40 (1H, br), 3.45-3.5 (1H, m), 3.97 (3H, s), 6.58 (1H, d, J = 8.4 Hz), 6.70 (1H, d, J = 8.4 Hz), 6.80 (1H, d, J = 2.1 Hz), 7.58 (1H, d, J = 2.1 Hz). | — |
| 1042 | 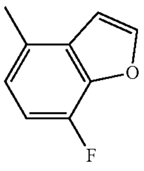 | 1H-NMR (CDCl3) δppm: 0.95-1.15 (2H, m), 1.3-1.4 (1H, m), 1.4-2.1 (11H, m), 2.25-2.4 (1H, m), 3.04 (1H, d, J = 11.1 Hz), 3.17 (1H, d, J = 10.9 Hz), 3.41 (1H, br), 3.45-3.58 (1H, m), 6.54 (1H, dd, J = 3.3, 8.4 Hz), 6.82 (1H, dd, J = 2.5, 2.5 Hz), 6.91 (1H, dd, J = 8.6, 10.4 Hz), 7.59 (1H, d, J = 2.1 Hz). | — |

TABLE 119-continued absolute configuration

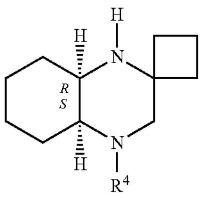

| Ex. No. | $R^4$ | NMR | Salt |
| --- | --- | --- | --- |
| 1043 | 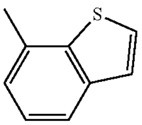 | 1H-NMR (DMSO-d6) δppm: 0.95-1.5 (3H, m), 1.5-1.7 (2H, m), 1.7-2.3 (6H, m), 2.3-2.7 (3H, m), 3.0-3.4 (1H, m), 3.59 (2H, br), 3.73 (1H, br), 7.07 (1H, br), 7.3-7.45 (1H, m), 7.48 (1H, d, J = 5.4 Hz), 7.64 (1H, br), 7.75 (1H, d, J = 5.4 Hz), 8.75-10.3 (2H, m). | Hydrochloride |

TABLE 120 relative configuration

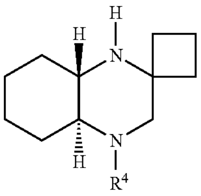

| Ex. No. | $R^4$ | NMR | Salt |
| --- | --- | --- | --- |
| 1044 | 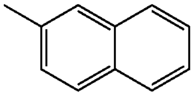 | 1H-NMR (CDCl3) δppm: 0.90-2.30 (10H, m), 2.36-3.40 (7H, m), 3.50-3.70 (1H, m), 7.30-7.55 (3H, m), 7.55-7.75 (1H, m), 7.75-7.90 (3H, m), 9.75-10.40 (2H, br). | 2 Hydrochloride |

TABLE 121 absolute configuration

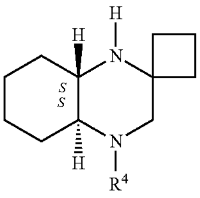

| Ex. No. | $R^4$ | NMR | Salt |
| --- | --- | --- | --- |
| 1045 | 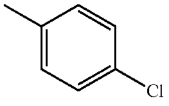 | 1H-NMR (DMSO-d6) δppm: 0.85-1.0 (1H, m), 1.12-1.40 (2H, m), 1.42-1.63 (3H, m), 1.65-1.78 (1H, m), 1.84-1.97 (3H, m), 1.97-2.06 (1H, m). 2.24-2.38 (2H, m), 2.39-2.49 (1H, m), 2.73-2.93 (2H, m), 3.03 (1H, d, J = 12.5 Hz), 3.23 (1H, d, J = 12.5 Hz), 3.6 (1H, br), 7.15-7.25 (2H, m), 7.37-7.46 (2H, m), 9.37 (1H, br), 9.87 (1H, br). | 2 Hydrochloride |
| 1046 | 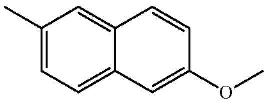 | 1H-NMR (CDCl3) δppm: 0.95-1.1 (1H, m), 1.15-1.45 (3H, m), 1.45-1.95 (10H, m), 2.45-2.7 (3H, m), 2.80 (1H, dd, J = 1.7, 11.2 Hz), 3.19 (1H, d, J = 11.1 Hz), 3.91 (3H, s), 7.08-7.15 (2H, m), 7.29 (1H, dd, J = 2.1, 8.7 Hz), 7.45 (1H, d, J = 2.0 Hz), 7.63-7.71 (2H, m). | — |

TABLE 121-continued absolute configuration

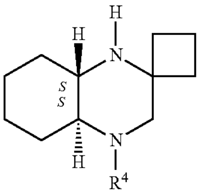

| Ex. No. | $R^4$ | NMR | Salt |
|---|---|---|---|
| 1047 | 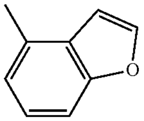 | 1H-NMR (DMSO-d6) δppm: 0.85-1.1 (1H, m), 1.1-1.45 (2H, m), 1.45-1.65 (3H, m), 1.65-1.8 (1H, m), 1.8-2.0 (3H, m), 2.0-2.15 (1H, m), 2.25-2.65 (3H, m), 2.85-3.35 (2H, m), 3.6-4.35 (3H, m), 6.9-7.2 (2H, m), 7.31 (1H, dd, J = 8.0, 8.0 Hz), 7.46 (1H, d, J = 8.2 Hz), 8.00 (1H, d, J = 1.6 Hz), 9.3-10.3 (2H, m). | 2 Hydrochloride |
| 1048 | 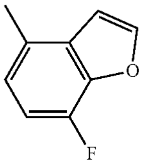 | 1H-NMR (DMSO-d6) δppm: 0.8-1.0 (1H, m), 1.1-1.6 (5H, m), 1.6-2.0 (5H, m), 2.1-2.5 (3H, m), 2.75-2.95 (2H, m), 2.95-3.13 (1H, m), 3.17 (1H, d, J = 12.6 Hz), 6.56 (4H, s), 6.99-7.14 (2H, m), 7.20 (1H, dd, J = 8.6, 10.7 Hz), 8.09 (1H, d, J = 2.0 Hz), 11.4 (5H, br). | 2 Fumarate |

TABLE 122 absolute configuration

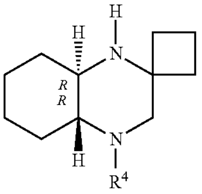

| Ex. No. | $R^4$ | NMR | Salt |
|---|---|---|---|
| 1049 | 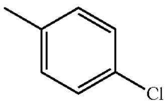 | 1H-NMR (DMSO-d6) δppm: 0.85-1.05 (1H, m), 1.1-1.4 (2H, m), 1.4-1.65 (3H, m), 1.65-1.8 (1H, m), 1.8-2.0 (3H, m), 2.0-2.1 (1H, m), 2.25-2.4 (2H, m), 2.4-2.6 (1H, m), 2.75-2.95 (2H, m), 3.0-3.1 (1H, m), 3.23 (1H, d, J = 12.6 Hz), 3.5-4.0 (1H, m), 7.15-7.25 (2H, m), 7.35-7.45 (2H, m), 9.3-9.6 (1H, m), 9.85-10.1 (1H, m). | 2 Hydrochloride |
| 1050 | 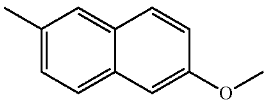 | 1H-NMR (CDCl3) δppm: 0.95-1.1 (1H, m), 1.1-1.45 (3H, m), 1.45-1.95 (10H, m), 2.45-2.7 (3H, m), 2.80 (1H, dd, J = 1.7, 11.2 Hz), 3.19 (1H, d, J = 11.2 Hz), 3.91 (3H, s), 7.07-7.15 (2H, m), 7.29 (1H, dd, J = 2.1, 8.7 Hz), 7.45 (1H, d, J = 2.0 Hz), 7.63-7.71 (2H, m). | — |
| 1051 | 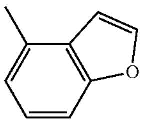 | 1H-NMR (DMSO-d6) δppm: 0.85-1.1 (1H, m), 1.1-1.4 (2H, m), 1.4-1.65 (3H, m), 1.65-1.8 (1H, m), 1.8-2.0 (3H, m), 2.0-2.15 (1H, m), 2.25-2.65 (3H, m), 2.8-3.45 (2H, m), 3.5-4.25 (3H, m), 6.9-7.2 (2H, m), 7.31 (1H, dd, J = 8.0, 8.0 Hz), 7.46 (1H, d, J = 8.2 Hz), 8.00 (1H, d, J = 1.8 Hz), 9.3-10.3 (2H, m). | 2 Hydrochloride |

TABLE 122-continued absolute configuration

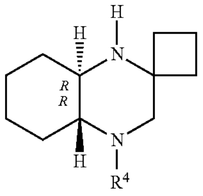

| Ex. No. | $R^4$ | NMR | Salt |
|---|---|---|---|
| 1052 | 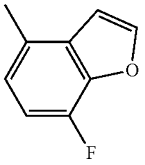 | 1H-NMR (DMSO-d6) δppm: 0.8-0.95 (1H, m), 1.1-1.4 (3H, m), 1.45-1.6 (2H, m), 1.6-1.7 (1H, m), 1.7-1.9 (4H, m), 2.0-2.15 (1H, m), 2.15-2.3 (1H, m), 2.35-2.5 (1H, m), 2.65-2.85 (2H, m), 2.85-3.0 (1H, m), 3.13 (1H, d, J = 11.7 Hz), 6.53 (3H, s), 7.0-7.1 (2H, m), 7.18 (1H, dd, J = 8.6, 10.8 Hz), 8.07 (1H, d, J = 2.1 Hz), 10.3 (4H, br). | 1.5 Fumarate |

TABLE 123 relative configuration

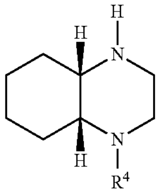

| Ex. No. | $R^4$ | NMR | Salt |
|---|---|---|---|
| 1053 | 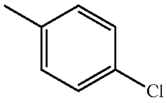 | 1H-NMR (CDCl3) δppm: 1.14-1.29 (1H, m), 1.29-1.38 (1H, m), 1.38-1.58 (3H, m), 1.62-1.86 (4H, m), 2.95-3.05 (2H, m), 3.1-3.25 (3H, m), 3.6-3.7 (1H, m), 6.74-6.82 (2H, m), 7.14-7.21 (2H, m). | — |
| 1054 | 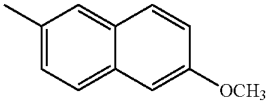 | 1H-NMR (CDCl3) δppm: 1.14-1.36 (2H, m), 1.37-1.65 (3H, m), 1.65-1.77 (2H, m), 1.77-1.91 (2H, m), 3.01-3.17 (2H, m), 3.19-3.28 (3H, m), 3.75-3.83 (1H, m), 3.88 (3H, s), 6.97-7.11 (3H, m), 7.23-7.30 (1H, m), 7.57 (1H, d, J = 8.8 Hz), 7.62 (1H, d, J = 9.0 Hz). | — |
| 1055 | 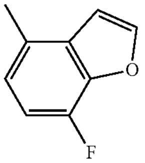 | 1H-NMR (DMSO-d6) δppm: 0.97-1.14 (2H, m), 1.32-1.43 (1H, m), 1.43-1.67 (2H, m), 1.68-2.03 (3H, m), 3.01-3.14 (2H, m), 3.25-3.43 (2H, m), 3.55-3.64 (1H, m), 3.66-3.77 (1H, m), 6.55 (4H, s), 6.68 (1H, br), 7.10 (1H, dd, J = 8.7, 10.7 Hz), 7.22 (1H, br), 8.05 (1H, d, J = 2.2 Hz), 11.27 (5H, br). | 2 Fumarate |
| 1056 | 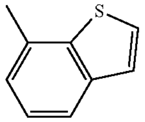 | 1H-NMR (DMSO-d6) δppm: 0.95-1.15 (2H, m), 1.28-1.40 (1H, m), 1.43-1.72 (3H, m), 1.94 (2H, br), 2.90-3.12 (2H, m), 3.19-3.30 (1H, m), 3.34-3.57 (2H, m), 3.70-3.87 (1H, br), 6.53 (2H, s), 7.00 (1H, br), 7.34 (1H, dd, J = 7.7, 7.7 Hz), 7.45 (1H, d, J = 5.4 Hz), 7.5-7.65 (1H, m), 7.72 (1H, d, J = 5.4 Hz), 10.5 (3H, br). | Fumarate |

TABLE 123-continued relative configuration

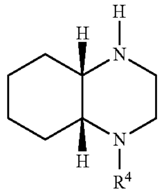

| Ex. No. | $R^4$ | NMR | Salt |
| --- | --- | --- | --- |
| 1057 | 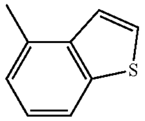 | 1H-NMR (CDCl3) δppm: 0.96-1.18 (2H, m), 1.33-1.72 (5H, m), 1.72-1.91 (1H, m), 1.92-2.07 (1H, m), 2.82-2.92 (1H, m), 3.03-3.17 (1H, m), 3.17-3.27 (1H, m), 3.38 (1H, br), 3.42-3.52 (1H, m), 3.52-3.61 (1H, m), 6.85 (1H, d, J = 7.6 Hz), 7.21-7.28 (1H, m), 7.37 (1H, d, J = 5.5 Hz), 7.40-7.47 (1H, m), 7.52 (1H, d, J = 8.0 Hz). | — |
| 1058 | 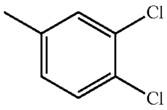 | 1H-NMR (DMSO-d6) δppm: 1.26-1.42 (2H, m), 1.42-1.63 (2H, m), 1.63-1.91 (3H, m), 1.91-2.04 (1H, m), 3.01-3.18 (2H, m), 3.24-3.42 (1H, m), 3.47-3.55 (1H, m), 3.55-3.65 (1H, m), 4.06-4.19 (1H, m), 6.95 (1H, dd, J = 2.9, 9.0 Hz), 7.18 (1H, d, J = 2.9 Hz), 7.43 (1H, d, J = 9.0 Hz), 9.00 (1H, br), 9.62 (1H, br). | Hydrochloride |
| 1059 | 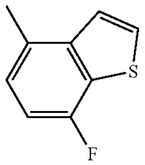 | 1H-NMR (DMSO-d6) δppm: 0.9-1.15 (2H, m), 1.25-1.4 (1H, m), 1.4-1.7 (3H, m), 1.91 (2H, br), 2.82-2.92 (1H, m), 2.97-3.10 (1H, m), 3.15-3.60 (7H, m), 6.52 (2H, s), 6.94 (1H, br), 7.15 (1H, dd, J = 8.9, 8.9 Hz), 7.59 (1H, br), 7.83 (1H, d, J = 5.3 Hz). | Fumarate |
| 1060 | 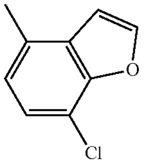 | 1H-NMR (DMSO-d6) δppm: 1.0-1.15 (2H, m), 1.28-1.40 (1H, m), 1.4-1.65 (2H, m), 1.65-1.77 (1H, m), 1.78-1.98 (2H, m), 2.95-3.15 (2H, m), 3.15-3.25 (1H, m), 3.25-3.4 (1H, m), 3.43 (1H, br), 3.7-3.8 (1H, m), 6.53 (2H, s), 6.68 (1H, d, J = 8.5 Hz), 7.19 (1H, bs), 7.26 (1H, d, J = 8.4 Hz), 8.04 (1H, d, J = 2.2 Hz). | Fumarate |
| 1061 | 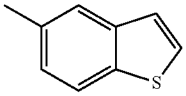 | 1H-NMR (DMSO-d6) δppm: 1.17-1.32 (2H, m), 1.34-1.56 (2H, m), 1.59-1.85 (3H, m), 1.86-1.96 (1H, m), 2.95-3.14 (2H, m), 3.23-3.40 (3H, m), 3.90-3.99 (1H, m), 6.51 (2H, s), 7.13 (1H, dd, J = 2.3, 8.9 Hz), 7.27-7.34 (2H, m), 7.66 (1H, d, J = 5.4 Hz), 7.80 (1H, d, J = 8.9 Hz). | Fumarate |
| 1062 | 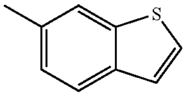 | 1H-NMR (DMSO-d6) δppm: 1.16-1.40 (3H, m), 1.40-1.55 (1H, m), 1.57-1.73 (2H, m), 1.73-1.87 (2H, m), 2.85-3.03 (3H, m), 3.04-3.83 (4H, m), 3.85-3.93 (1H, m), 6.49 (1H, s), 7.09 (1H, dd, J = 2.2, 8.9 Hz), 7.25 (1H, d, J = 5.3 Hz), 7.35-7.41 (2H, m), 7.67 (1H, d, J = 8.8 Hz). | ½ Fumarate |

TABLE 124 absolute configuration

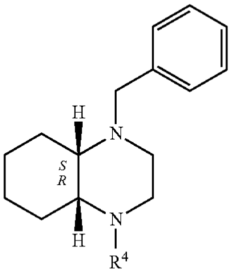

| Ex. No. | $R^4$ | NMR | Salt |
| --- | --- | --- | --- |
| 1063 | 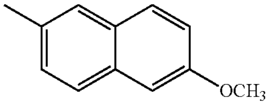 | 1H-NMR (CDCl3) δppm: 1.23-1.43 (3H m), 1.44-1.57 (1H, m), 1.58-1.72 (1H, m), 1.74-1.84 (1H, m), 2.08-2.27 (2H, m), 2.33-2.42 (1H, m), 2.72-2.79 (1H, m), 2.86-2.93 (1H, m), 2.97 (1H, d, J = 13.2 Hz), 3.14-3.25 (2H, m), 3.81-3.90 (4H, m), 4.22 (1H, d, J = 13.1 Hz), 6.97 (1H, bs), 7.02-7.09 (2H, m), 7.22-7.30 (2H, m), 7.31-7.38 (2H, m), 7.38-7.43 (2H, m), 7.55 (1H, d, J = 8.7 Hz), 7.61 (1H, d, J = 9.0 Hz). | — |
| 1064 | 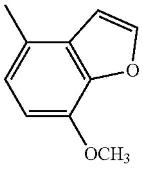 | 1H-NMR (CDCl3) δppm: 1.0-1.2 (2H, m), 1.2-1.4 (1H, m), 1.4-1.9 (3H, m), 2.0-2.5 (3H, m), 2.75-3.2 (4H, m), 3.38 (1H, br), 3.60 (1H, br), 3.96 (3H, s), 4.19 (1H, br), 6.54 (1H, br), 6.68 (1H, d, J = 8.2 Hz), 6.82 (1H, br), 7.22-7.29 (1H, m), 7.29-7.38 (2H, m), 7.38-7.44 (2H, m), 7.58 (1H, d, J = 2.2 Hz). | — |

TABLE 125 absolute configuration

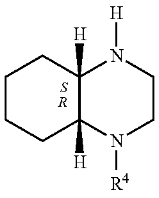

| Ex. No. | $R^4$ | NMR | Salt |
| --- | --- | --- | --- |
| 1065 | 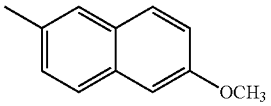 | 1H-NMR (CDCl3) δppm: 1.15-1.56 (5H, m), 1.65-1.76 (2H, m), 1.76-1.90 (2H, m), 3.01-3.18 (2H, m), 3.20-3.28 (3H, m), 3.76-3.83 (1H, m), 3.88 (3H, s), 7.01 (1H, d, J = 2.4 Hz), 7.04 (1H, d, J = 2.5 Hz), 7.07 (1H, dd, J = 2.6, 8.8 Hz), 7.25 (1H, dd, J = 2.5, 9.0 Hz), 7.57 (1H, d, J = 8.8 Hz), 7.62 (1H, d, J = 9.0 Hz). | — |
| 1066 | 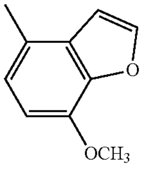 | 1H-NMR (DMSO-d6) δppm: 0.93-1.22 (2H, m), 1.33-1.47 (1H, m), 1.47-1.70 (1H, m), 1.70-1.94 (2H, m), 1.94-2.19 (1H, m), 2.88-3.22 (2H, m), 3.27-3.48 (2H, m), 3.59-3.78 (2H, m), 3.88 (3H, s), 6.69 (1H, br), 6.82 (1H, d, J = 8.3 Hz), 7.13 (1H, d, J = 1.9 Hz), 7.95 (1H, d, J = 2.1 Hz), 8.5 (1H, br), 9.00 (1H, br), 9.68 (1H, br). | 2 Hydrochloride |

TABLE 126 absolute configuration

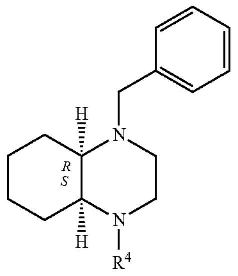

| Ex. No. | $R^4$ | NMR | Salt |
|---|---|---|---|
| 1067 | 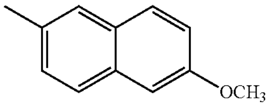 | 1H-NMR (CDCl3) δppm: 1.22-1.43 (3H m), 1.45-1.56 (1H, m), 1.58-1.72 (1H, m), 1.74-1.84 (1H, m), 2.08-2.27 (2H, m), 2.32-2.42 (1H, m), 2.73-2.79 (1H, m), 2.86-2.93 (1H, m), 2.97 (1H, d, J = 13.1 Hz), 3.14-3.25 (2H, m), 3.8-3.9 (4H, m), 4.22 (1H, d, J = 13.2 Hz), 6.97 (1H, bs), 7.02-7.09 (2H, m), 7.22-7.30 (2H, m), 7.31-7.37 (2H, m), 7.37-7.43 (2H, m), 7.55 (1H, d, J = 8.7 Hz), 7.61 (1H, d, J = 9.0 Hz). | — |
| 1068 | 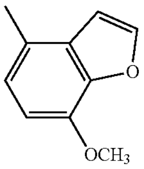 | 1H-NMR (CDCl3) δppm: 1.0-1.2 (2H, m), 1.2-1.4 (1H, m), 1.4-1.85 (3H, m), 2.05-2.5 (3H, m), 2.65-3.15 (4H, m), 3.2-3.5 (1H, m), 3.60 (1H, br), 3.96 (3H, s), 4.05-4.4 (1H, m), 6.54 (1H, br), 6.68 (1H, d, J = 8.2 Hz), 6.82 (1H, br), 7.22-7.29 (1H, m), 7.29-7.38 (2H, m), 7.38-7.44 (2H, m), 7.58 (1H, d, J = 2.2 Hz). | — |

TABLE 127 absolute configuration

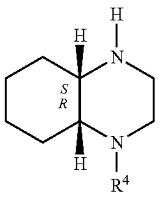

| Ex. No. | $R^4$ | NMR | Salt |
|---|---|---|---|
| 1069 | 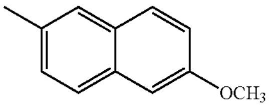 | 1H-NMR (CDCl3) δppm: 1.15-1.56 (5H, m), 1.65-1.76 (2H, m), 1.76-1.89 (2H, m), 3.00-3.20 (2H, m), 3.20-3.28 (3H, m), 3.76-3.83 (1H, m), 3.88 (3H, s), 7.01 (1H, d, J = 2.4 Hz), 7.04 (1H, d, J = 2.4 Hz), 7.07 (1H, dd, J = 2.6, 8.8 Hz), 7.26 (1H, dd, J = 2.5, 9.0 Hz), 7.57 (1H, d, J = 8.8 Hz), 7.62 (1H, d, J = 9.0 Hz). | — |
| 1070 | 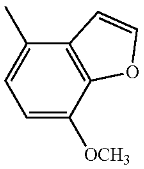 | 1H-NMR (DMSO-d6) δppm: 0.94-1.19 (2H, m), 1.35-1.47 (1H, m), 1.47-1.70 (1H, m), 1.70-1.91 (2H, m), 1.91-2.18 (1H, m), 3.0-3.25 (2H, m), 3.25-3.55 (2H, m), 3.6-3.8 (2H, m), 3.88 (3H, s), 6.69 (1H, br), 6.82 (1H, d, J = 8.4 Hz), 7.13 (1H, d, J = 2.2 Hz), 7.95 (1H, d, J = 2.1 Hz), 8.90 (1H, br), 9.56 (1H, br). | Hydrochloride |

TABLE 128
absolute configuration
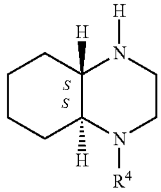
| Ex. No. | $R^4$ | NMR | Salt |
|---|---|---|---|
| 1071 | 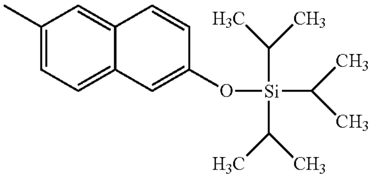 | 1H-NMR (CDCl3) δppm: 0.96-1.19 (19H, m), 1.19-1.41 (6H, m), 1.50-1.67 (2H, m), 1.67-1.82 (3H, m), 2.48-2.65 (2H, m), 2.94-3.09 (2H, m), 3.09-3.25 (2H, m), 7.09 (1H, dd, J = 2.4, 8.9 Hz), 7.17 (1H, d, J = 2.4 Hz), 7.28 (1H, dd, J = 2.1, 11.0 Hz), 7.45 (1H, d, J = 2.0 Hz), 7.59-7.66 (2H, m). | — |
| 1072 | 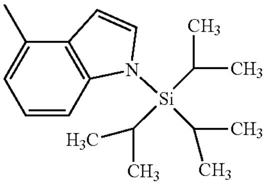 | 1H-NMR (CDCl3) δppm: 0.95-1.09 (1H, m), 1.14 (18H, d, J = 7.5 Hz), 1.20-1.45 (3H, m), 1.48-1.85 (8H, m), 2.58-2.74 (2H, m), 2.90-3.00 (1H, m), 3.00-3.08 (1H, m), 3.17-3.30 (2H, m), 6.74 (1H, dd, J = 0.7, 3.2 Hz), 6.85 (1H, d, J = 7.3 Hz), 7.03-7.10 (1H, m), 7.17 (1H, d, J = 3.2 Hz), 7.26 (1H, d, J = 8.3 Hz). | — |
| 1073 | 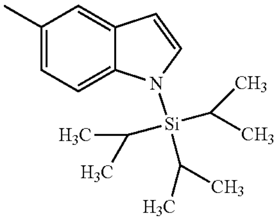 | 1H-NMR (CDCl3) δppm: 0.95-1.09 (1H, m), 1.09-1.42 (21H, m), 1.53-1.80 (8H, m), 2.41-2.50 (1H, m), 2.54-2.64 (1H, m), 2.95-3.10 (3H, m), 3.13-3.23 (1H, m), 6.56 (1H, d, J = 0.4, 3.1 Hz), 6.97 (1H, dd, J = 2.1, 8.8 Hz), 7.23 (1H, d, J = 3.1 Hz), 7.37-7.44 (2H, m). | — |
| 1074 | 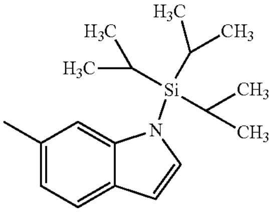 | 1H-NMR (CDCl3) δppm: 0.94-1.06 (1H, m), 1.05-1.25 (19H, m), 1.25-1.45 (2H, m), 1.53-1.80 (8H, m), 2.42-2.50 (1H, m), 2.55-2.65 (1H, m), 2.90-3.00 (1H, m), 3.00-3.13 (2H, m), 3.16-3.25 (1H, m), 6.56 (1H, dd, J = 0.7, 3.2 Hz), 6.97 (1H, dd, J = 1.7, 8.3 Hz), 7.20 (1H, d, J = 3.2 Hz), 7.32 (1H, s), 7.52 (1H, d, J = 8.3 Hz). | — |

TABLE 129 absolute configuration

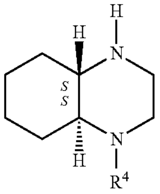

| Ex. No. | $R^4$ | NMR | Salt |
|---|---|---|---|
| 1075 | 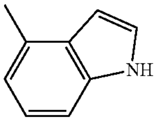 | 1H-NMR (CDCl3) δppm: 0.95-1.09 (1H, m), 1.20-1.55 (4H, m), 1.55-1.63 (1H, m), 1.66-1.86 (3H, m), 2.59-2.77 (2H, m), 2.81-3.01 (1H, m), 3.01-3.09 (1H, m), 3.18-3.30 (2H, m), 6.66-6.71 (1H, m), 6.87 (1H, dd, J = 1.1, 7.2 Hz), 7.10-7.21 (3H, m), 8.25 (1H, brs). | — |
| 1076 | 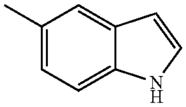 | 1H-NMR (CDCl3) δppm: 0.96-1.10 (1H, m), 1.10-1.43 (3H, m), 1.43-1.65 (3H, m), 1.65-1.84 (2H, m), 2.42-2.53 (1H, m), 2.53-2.66 (1H, m), 2.97-3.12 (3H, m), 3.15-3.26 (1H, m), 6.51 (1H, dd, J = 1.0, 2.1 Hz), 7.06 (1H, dd, J = 2.0, 8.6 Hz), 7.17-7.23 (1H, m), 7.32 (1H, d, J = 8.6 Hz), 7.44 (1H, d, J = 2.0 Hz), 8.36 (1H, brs). | — |
| 1077 | 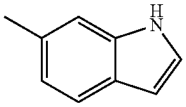 | 1H-NMR (DMSO-d6) δppm: 0.81-0.96 (1H, m), 1.06-1.35 (3H, m), 1.43-1.57 (2H, m), 1.58-1.74 (2H, m), 2.01 (1H, brs), 2.30-2.41 (2H, m), 2.75-2.97 (4H, m), 6.31-6.37 (1H, m), 6.80 (1H, dd, J = 1.8, 8.4 Hz), 7.10 (1H, s), 7.25 (1H, t, J = 2.7 Hz), 7.41 (1H, d, J = 8.4 Hz), 10.89 (1H, s). | — |
| 1078 | 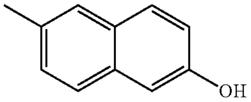 | 1H-NMR (DMSO-d6) δppm: 0.85-0.98 (1H, m), 1.12-1.35 (3H, m), 1.48-1.73 (4H, m), 2.17 (1H, brs), 2.32-2.50 (2H, m), 2.76-3.01 (4H, m), 6.99-7.08 (2H, m), 7.20 (1H, dd, J = 2.1, 8.7 Hz), 7.41 (1H, d, J = 1.8 Hz), 7.58 (1H, d, J = 8.8 Hz), 7.67 (1H, d, J = 8.8 Hz), 9.56 (1H, brs). | — |

TABLE 130 absolute configuration

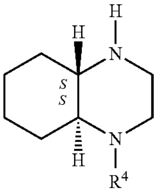

| Ex. No. | $R^4$ | NMR | Salt |
|---|---|---|---|
| 1079 | 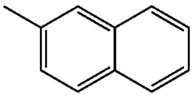 | 1H-NMR (CDCl3) δppm: 1.00-1.14 (1H, m), 1.20-1.45 (3H, m), 1.45-1.60 (1H, m), 1.60-1.68 (1H, m), 1.68-1.85 (3H, m), 2.53-2.66 (2H, m), 2.95-3.10 (2H, m), 3.15-3.26 (2H, m), 7.33 (1H, dd, J = 2.1, 8.8 Hz), 7.37-7.47 (2H, m), 7.51 (1H, d, J = 2.1 Hz), 7.74-7.82 (3H, m). | — |
| 1080 | 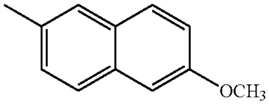 | 1H-NMR (CDCl3) δppm: 0.98-1.12 (1H, m), 1.17-1.82 (8H, m), 2.48-2.64 (2H, m), 2.95-3.25 (4H, m), 3.90 (3H, s), 7.08-7.14 (2H, m), 7.31 (1H, dd, J = 2.1, 8.7 Hz), 7.47 (1H, d, J = 2.0 Hz), 7.63-7.70 (2H, m). | — |

TABLE 130-continued absolute configuration

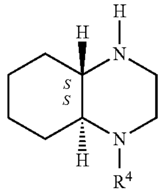

| Ex. No. | $R^4$ | NMR | Salt |
|---|---|---|---|
| 1081 | 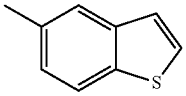 | 1H-NMR (CDCl3) δppm: 0.97-1.10 (1H, m), 1.15-1.69 (6H, m), 1.69-1.84 (2H, m), 2.45-2.54 (1H, m), 2.54-2.65 (1H, m), 2.93-3.13 (3H, m), 3.13-3.25 (1H, m), 7.19 (1H, dd, J = 2.0, 8.6 Hz), 5.27 (1H, d, J = 5.4 Hz), 7.42 (1H, d, J = 5.4 Hz), 7.59 (1H, d, J = 2.0 Hz), 7.79 (1H, d, J = 8.6 Hz). | — |
| 1082 | 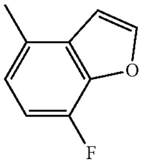 | 1H-NMR (DMSO-d6) δppm: 0.95-1.22 (2H, m), 1.22-1.37 (1H, m), 1.39-1.51 (1H, m), 1.51-1.68 (2H, m), 1.68-1.78 (1H, m), 1.99-2.11 (1H, m), 2.92-3.75 (6H, brm), 4.30-5.75 (1H, br), 7.00-7.30 (2H, m), 7.30-7.52 (1H, m), 8.15 (1H, s), 9.45-10.25 (2H, brm). | 2 Hydrochloride |
| 1083 | 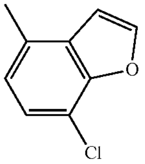 | 1H-NMR (DMSO-d6) δppm: 0.90-1.05 (1H, m), 1.10-1.38 (2H, m), 1.49-1.66 (3H, m), 1.67-1.78 (1H, m), 1.96-2.08 (1H, m), 2.94-3.10 (1H, m), 3.10-3.42 (5H, m), 3.53-4.15 (1H, br), 7.08 (1H, d, J = 8.3 Hz), 7.21 (1H, brs), 7.40 (1H, d, J = 8.3 Hz), 8.12 (1H, d, J = 2.1 Hz), 9.51 (2H, brs). | 2HC |
| 1084 | 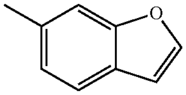 | 1H-NMR (DMSO-d6) δppm: 1.10-1.52 (4H, m), 1.52-1.69 (2H, m), 1.69-1.81 (1H, m), 2.03-2.22 (1H, m), 3.20-4.30 6H, m), 7.05 (1H, s), 7.25-7.70 (1H, m), 7.70-8.05 (2H, m), 8.14 (1H, s), 9.60-10.47 (2H, m). (1H not found) | 2HC |
| 1085 | 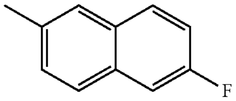 | 1H-NMR (CDCl3) δppm: 1.00-1.13 (1H, m), 1.19-1.45 (3H, m), 1.58-1.90 (5H, m), 2.52-2.65 (2H, m), 2.95-3.25 (4H, m), 7.22 (1H, dt, J = 2.5, 8.8 Hz), 7.36 (1H, dd, J = 2.0, 8.8 Hz), 7.40 (1H, dd, J = 2.5, 9.9 Hz), 7.51 (1H, d, J = 2.0 Hz), 7.69-7.78 (2H, m). | — |
| 1086 | 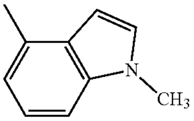 | 1H-NMR (DMSO-d6) δppm: 0.79-0.97 (1H, m), 1.05-1.56 (4H, m), 1.56-1.72 (2H, m), 1.77-1.90 (1H, m), 2.62-2.75 (1H, m), 2.79-3.19 (5H, m), 3.19-3.70 (1H, br), 3.75 (3H, s), 6.37-6.56 (2H, m), 6.78 (1H, d, J = 7.2 Hz), 7.30-7.14 (1H, m), 7.14-7.33 (2H, m). | Fumarate |
| 1087 | 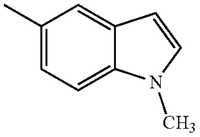 | 1H-NMR (DMSO-d6) δppm: 0.86-1.00 (1H, m), 1.04-1.47 (4H, m), 1.47-1.57 (1H, m), 1.61-1.71 (1H, m), 1.77-1.86 (1H, m), 2.55-2.72 (2H, m), 2.92-3.16 (4H, m), 3.75 (3H, s), 5.25-6.25 (1H, br), 6.35 (1H, dd, J = 0.4, 3.0 Hz), 6.96 (1H, dd, J = 1.9, 8.6 Hz), 7.25-7.33 (2H, m), 7.35 (1H, d, J = 8.6 Hz). (2H not found) | Oxalate |
| 1088 | 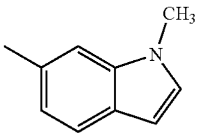 | 1H-NMR (CDCl3) δppm: 0.95-1.11 (1H, m), 1.11-1.42 (3H, m), 1.53-1.82 (5H, m), 2.45-2.55 (1H, m), 2.55-2.64 (1H, m), 2.98-3.12 (3H, m), 3.15-3.25 (1H, m), 3.75 (3H, s), 6.43 (1H, dd, J = 0.8, 3.1 Hz), 6.98-7.03 (2H, m), 7.12-7.15 (1H, m), 7.53 (1H, d, J = 8.4 Hz). | — |

TABLE 130-continued absolute configuration

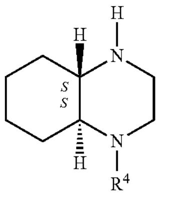

| Ex. No. | $R^4$ | NMR | Salt |
|---|---|---|---|
| 1089 | 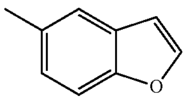 | 1H-NMR (DMSO-d6) δppm: 0.87-1.02 (1H, m), 1.08-1.50 (4H, m), 1.50-1.60 (1H, m), 1.62-1.72 (1H, m), 1.75-1.86 (1H, m), 2.57-2.76 (2H, m), 2.92-3.16 (4H, m), 3.20-4.38 (1H, br), 6.91 (1H, s), 7.09 (1H, dd, J = 1.9, 8.5 Hz), 7.41 (1H, d, J = 1.9 Hz), 7.52 (1H, d, J = 8.5 Hz), 7.97 (1H, d, J = 1.8 Hz). (2H not found) | Oxalate |

TABLE 131 absolute configuration

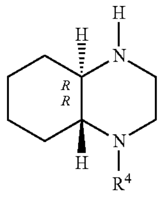

| Ex. No. | $R^4$ | NMR | Salt |
|---|---|---|---|
| 1090 | 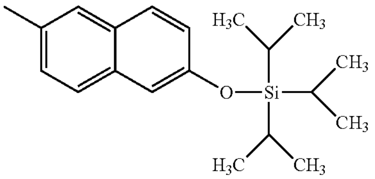 | 1H-NMR (CDCl3) δppm: 0.99-1.18 (19H, m), 1.20-1.41 (6H, m), 1.49-1.68 (2H, m), 1.68-1.82 (3H, m), 2.49-2.64 (2H, m), 2.94-3.10 (2H, m), 3.10-3.25 (2H, m), 7.09 (1H, dd, J = 2.4, 8.8 Hz), 7.17 (1H, d, J = 2.4 Hz), 7.28 (1H, dd, J = 2.1, 11.0 Hz), 7.45 (1H, d, J = 2.0 Hz), 7.59-7.66 (2H, m). | — |
| 1091 | 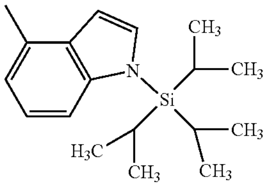 | 1H-NMR (CDCl3) δppm: 0.93-1.10 (1H, m), 1.14 (18H, d, J = 7.5 Hz), 1.20-1.45 (3H, m), 1.49-1.85 (8H, m), 2.58-2.74 (2H, m), 2.90-3.00 (1H, m), 3.00-3.08 (1H, m), 3.17-3.30 (2H, m), 6.74 (1H, dd, J = 0.7, 3.2 Hz), 6.85 (1H, d, J = 7.3 Hz), 7.03-7.10 (1H, m), 7.17 (1H, d, J = 3.2 Hz), 7.26 (1H, d, J = 8.3 Hz). | — |
| 1092 | 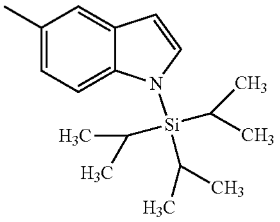 | 1H-NMR (CDCl3) δppm: 0.95-1.10 (1H, m), 1.10-1.41 (21H, m), 1.53-1.80 (8H, m), 2.41-2.50 (1H, m), 2.53-2.62 (1H, m), 2.95-3.10 (3H, m), 3.13-3.23 (1H, m), 6.56 (1H, d, J = 0.4, 3.1 Hz), 6.97 (1H, dd, J = 2.1, 8.8 Hz), 7.23 (1H, d, J = 3.1 Hz), 7.37-7.44 (2H, m). | — |

TABLE 131-continued absolute configuration

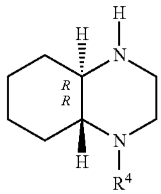

| Ex. No. | $R^4$ | NMR | Salt |
|---|---|---|---|
| 1093 | 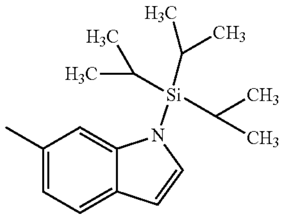 | 1H-NMR (CDCl3) δppm: 0.94-1.06 (1H, m), 1.05-1.25 (19H, m), 1.25-1.45 (2H, m), 1.53-1.80 (8H, m), 2.42-2.50 (1H, m), 2.55-2.65 (1H, m), 2.90-3.00 (1H, m), 3.00-3.13 (2H, m), 3.16-3.25 (1H, m), 6.56 (1H, dd, J = 0.7, 3.2 Hz), 6.97 (1H, dd, J = 1.7, 8.3 Hz), 7.20 (1H, d, J = 3.2 Hz), 7.32 (1H, s), 7.52 (1H, d, J = 8.3 Hz). | — |

TABLE 132 absolute configuration

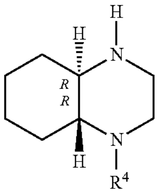

| Ex. No. | $R^4$ | NMR | Salt |
|---|---|---|---|
| 1094 | 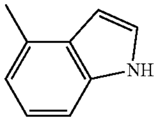 | 1H-NMR (CDCl3) δppm: 0.95-1.09 (1H, m), 1.18-1.55 (4H, m), 1.55-1.63 (1H, m), 1.66-1.85 (3H, m), 2.59-2.77 (2H, m), 2.81-3.01 (1H, m), 3.01-3.09 (1H, m), 3.18-3.30 (2H, m), 6.67-6.71 (1H, m), 6.87 (1H, dd, J = 1.1, 7.2 Hz), 7.10-7.20 (3H, m), 8.15-8.47 (1H, br). | — |
| 1095 | 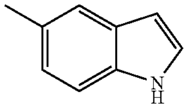 | 1H-NMR (CDCl3) δppm: 0.96-1.10 (1H, m), 1.11-1.43 (3H, m), 1.52-1.84 (5H, m), 2.42-2.52 (1H, m), 2.54-2.64 (1H, m), 2.97-3.10 (3H, m), 3.14-3.25 (1H, m), 6.51 (1H, dd, J = 1.0, 2.1 Hz), 7.06 (1H, dd, J = 2.0, 8.6 Hz), 7.17-7.23 (1H, m), 7.32 (1H, d, J = 8.6 Hz), 7.44 (1H, d, J = 2.0 Hz), 8.20 (1H, brs). | — |
| 1096 | 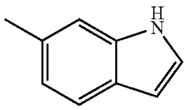 | 1H-NMR (DMSO-d6) δppm: 0.81-0.95 (1H, m), 1.05-1.35 (3H, m), 1.41-1.57 (2H, m), 1.58-1.74 (2H, m), 2.05 (1H, brs), 2.30-2.41 (2H, m), 2.75-2.97 (4H, m), 6.30-6.38 (1H, m), 6.80 (1H, dd, J = 1.8, 8.4 Hz), 7.10 (1H, s), 7.25 (1H, t, J = 2.7 Hz), 7.41 (1H, d, J = 8.4 Hz), 10.89 (1H, s). | — |
| 1097 | 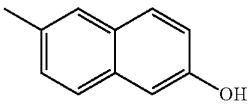 | 1H-NMR (DMSO-d6) δppm: 0.85-0.99 (1H, m), 1.12-1.36 (3H, m), 1.48-1.76 (4H, m), 2.17 (1H, brs), 2.31-2.50 (2H, m), 2.76-3.01 (4H, m), 6.99-7.08 (2H, m), 7.20 (1H, dd, J = 2.0, 8.7 Hz), 7.41 (1H, d, J = 1.6 Hz), 7.58 (1H, d, J = 8.8 Hz), 7.67 (1H, d, J = 8.8 Hz), 9.57 (1H, brs). | — |

TABLE 133 absolute configuration

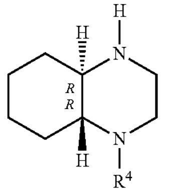

| Ex. No. | $R^4$ | NMR | Salt |
|---|---|---|---|
| 1098 | 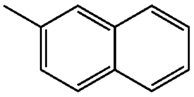 | 1H-NMR (CDCl3) δppm: 1.00-1.14 (1H, m), 1.20-1.45 (3H, m), 1.45-1.68 (2H, m), 1.68-1.85 (3H, m), 2.53-2.66 (2H, m), 2.95-3.10 (2H, m), 3.15-3.26 (2H, m), 7.33 (1H, dd, J = 2.1, 8.8 Hz), 7.37-7.47 (2H, m), 7.51 (1H, d, J = 2.1 Hz), 7.74-7.82 (3H, m). | — |
| 1099 | 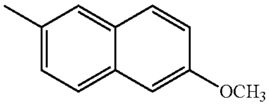 | 1H-NMR (CDCl3) δppm: 0.98-1.12 (1H, m), 1.17-1.45 (3H, m), 1.45-1.85 (5H, m), 2.49-2.64 (2H, m), 2.95-3.25 (4H, m), 3.90 (3H, s), 7.08-7.14 (2H, m), 7.31 (1H, dd, J = 2.1, 8.7 Hz), 7.47 (1H, d, J = 2.0 Hz), 7.63-7.70 (2H, m). | — |
| 1100 | 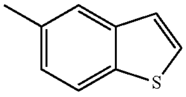 | 1H-NMR (CDCl3) δppm: 0.97-1.10 (1H, m), 1.15-1.69 (6H, m), 1.69-1.84 (2H, m), 2.45-2.54 (1H, m), 2.54-2.63 (1H, m), 2.93-3.13 (3H, m), 3.13-3.25 (1H, m), 7.19 (1H, dd, J = 2.0, 8.6 Hz), 5.27 (1H, d, J = 5.4 Hz), 7.42 (1H, d, J = 5.4 Hz), 7.59 (1H, d, J = 2.0 Hz), 7.79 (1H, d, J = 8.6 Hz). | — |
| 1101 | 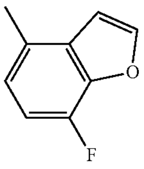 | 1H-NMR (DMSO-d6) δppm: 0.91-1.10 (1H, m), 1.10-1.37 (2H, m), 1.41-1.66 (3H, m), 1.66-1.79 (1H, m), 1.06-2.09 (1H, m), 2.95-3.55 (6H, m), 3.70-4.95 (1H, br), 7.00-7.17 (1H, m), 7.17-7.40 (2H, m), 8.08-8.19 (1H, m), 9.33-9.90 (2H, m). | 2 Hydrochloride |
| 1102 | 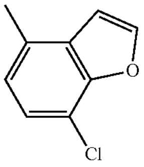 | 1H-NMR (DMSO-d6) δppm: 0.92-1.09 (1H, m), 1.10-1.39 (2H, m), 1.47-1.68 (3H, m), 1.68-1.78 (1H, m), 1.99-2.09 (1H, m), 2.94-3.14 (1H, br), 3.14-3.50 (5H, brm), 4.05-5.03 (1H, br), 7.08-7.19 (1H, m), 7.25-7.36 (1H, m), 7.41 (1H, d, J = 8.2 Hz), 8.14 (1H, d, J = 1.6 Hz), 9.70 (2H, brs). | 2 Hydrochloride |
| 1103 | 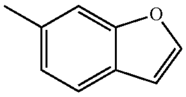 | 1H-NMR (DMSO-d6) δppm: 1.12-1.51 (4H, m), 1.53-1.68 (2H, m), 1.69-1.79 (1H, m), 2.07-2.19 (1H, m), 3.20-4.27 6H, m), 7.04 (1H, s), 7.30-7.65 (1H, m), 7.65-8.05 (2H, m), 8.13 (1H, s), 9.65-10.40 (2H, m). (1H not found) | 2 Hydrochloride |
| 1104 | 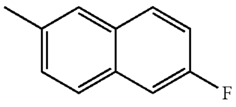 | 1H-NMR (CDCl3) δppm: 1.00-1.13 (1H, m), 1.18-1.45 (3H, m), 1.58-1.90 (5H, m), 2.52-2.65 (2H, m), 2.95-3.11 (2H, m), 3.11-3.25 (2H, m), 7.22 (1H, dt, J = 2.5, 8.8 Hz), 7.36 (1H, dd, J = 2.0, 8.8 Hz), 7.40 (1H, dd, J = 2.5, 9.9 Hz), 7.51 (1H, d, J = 2.0 Hz), 7.69-7.78 (2H, m). | — |
| 1105 | 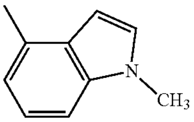 | 1H-NMR (DMSO-d6) δppm: 0.80-0.96 (1H, m), 1.05-1.56 (4H, m), 1.56-1.72 (2H, m), 1.77-1.90 (1H, m), 2.62-2.75 (1H, m), 2.77-2.90 (1H, m), 2.90-3.19 (4H, m), 3.19-3.70 (1H, br), 3.75 (3H, s), 6.37-6.54 (2H, m), 6.78 (1H, d, J = 7.3 Hz), 7.30-7.14 (1H, m), 7.14-7.31 (2H, m). | Fumarate |

TABLE 133-continued absolute configuration

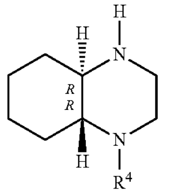

| Ex. No. | $R^4$ | NMR | Salt |
|---|---|---|---|
| 1106 | 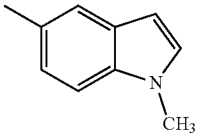 | 1H-NMR (DMSO-d6) δppm: 0.86-1.00 (1H, m), 1.04-1.47 (4H, m), 1.47-1.57 (1H, m), 1.61-1.70 (1H, m), 1.77-1.87 (1H, m), 2.55-2.72 (2H, m), 2.90-3.16 (4H, m), 3.75 (3H, s), 5.25-6.25 (1H, br), 6.35 (1H, d, J = 2.9 Hz), 6.96 (1H, dd, J = 1.7, 8.6 Hz), 7.25-7.33 (2H, m), 7.35 (1H, d, J = 8.6 Hz). (2H not found) | Oxalate |
| 1107 | 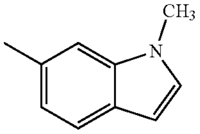 | 1H-NMR (CDCl3) δppm: 0.96-1.10 (1H, m), 1.10-1.44 (3H, m), 1.48-1.82 (5H, m), 2.45-2.55 (1H, m), 2.55-2.64 (1H, m), 2.98-3.12 (3H, m), 3.15-3.25 (1H, m), 3.75 (3H, s), 6.43 (1H, dd, J = 0.8, 3.1 Hz), 6.98-7.03 (2H, m), 7.12-7.15 (1H, m), 7.53 (1H, d, J = 8.5 Hz). | — |
| 1108 | 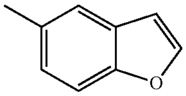 | 1H-NMR (DMSO-d6) δppm: 0.87-1.02 (1H, m), 1.08-1.50 (4H, m), 1.50-1.60 (1H, m), 1.62-1.72 (1H, m), 1.75-1.86 (1H, m), 2.54-2.76 (2H, m), 2.92-3.17 (4H, m), 3.20-5.40 (1H, br), 6.91 (1H, d, J = 1.2 Hz), 7.10 (1H, dd, J = 1.9, 8.6 Hz), 7.41 (1H, d, J = 1.9 Hz), 7.52 (1H, d, J = 8.6 Hz), 7.97 (1H, d, J = 2.0 Hz). (2H not found) | Oxalate |

TABLE 134 relative configuration

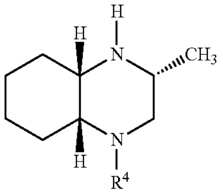

| Ex. No. | $R^4$ | NMR | Salt |
|---|---|---|---|
| 1109 | 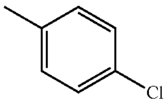 | 1H-NMR (DMSO-d6) δ ppm: 1.22-1.52 (6H, m), 1.56-1.97 (4H, m), 2.00-2.18 (1H, m), 2.75-2.95 (1H, m), 3.20-3.40 (1H, m), 3.40-3.60 (2H, m), 3.96-4.10 (1H, m), 4.20-4.57 (1H, br), 6.91-7.01 (2H, m), 7.19-7.31 (2H, m), 8.69 (1H, brs), 10.11 (1H, brs). | 2 Hydrochloride |
| 1110 | 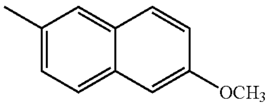 | 1H-NMR (CDCl3) δ ppm: 1.15-1.33 (6H, m), 1.48-1.58 (2H, m), 1.66-1.85 (4H, m), 2.68 (1H, t, J = 11.8 Hz), 3.02-3.12 (1H, m). 3.23 (1H, dd, J = 3.3, 11.4 Hz), 3.29-3.24 (1H, m), 3.76 (1H, td, J = 3.3, 11.4 Hz), 3.88 (3H, s), 7.00 (1H, d, J = 2.3 Hz), 7.02-7.30 (2H, m), 7.22-7.29 (1H, m), 7.57 (1H, d, J = 8.8 Hz), 7.61 (1H, d, J = 9.0 Hz). | — |
| 1111 | 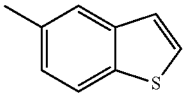 | 1H-NMR (DMSO-d6) δ ppm: 1.17-1.36 (2H, m), 1.36-1.51 (4H, m), 1.62-2.00 (4H, m), 2.06-2.17 (1H, m), 2.94-3.05 (1H, m), 3.30-3.50 (1H, m), 3.50-3.64 (2H, m), 4.04-4.13 (1H, m). 4.59-5.50 (1H, br), 7.17 (1H, d, J = 8.9 Hz), 7.31 (1H, d, J = 5.4 Hz), 7.38 (1H, brs), 7.62 (1H, d, J = 5.4 Hz), 7.83 (1H, d, J = 8.9 Hz), 8.68 (1H, brs), 10.12 (1H, brs). | 2 Hydrochloride |

TABLE 134-continued relative configuration

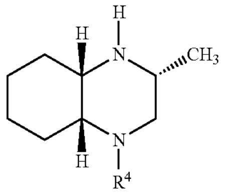

| Ex. No. | $R^4$ | NMR | Salt |
|---|---|---|---|
| 1112 | 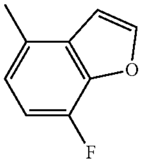 | 1H-NMR (DMSO-d6) δ ppm: 0.99-1.17 (2H, m), 1.30-1.49 (4H, m), 1.55-1.75 (2H, m), 1.75-1.98 (2H, m), 1.98-2.13 (1H, m), 3.12-3.28 (2H, m), 3.28-3.50 (1H, m), 3.67-3.85 (2H, m), 6.67 (1H, dd, J = 3.4, 8.6 Hz), 7.10 (1H, dd, J = 8.6. 10.7 Hz), 7.28 (1H, dd, J = 2.6, 2.6 Hz), 8.07 (1H, d, J = 2.2 Hz ), 8.43 (1H, br), 9.94 (1H, br). | Hydrochloride |
| 1113 | 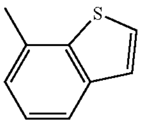 | 1H-NMR (DMSO-d6) δ ppm: 1.03-1.21 (2H, m), 1.37-1.48 (4H, m), 1.58-1.85 (3H, m), 1.95-2.14 (2H, m), 3.23 (1H, d, J = 10.6 Hz), 3.36-3.55 (2H, m), 3.64-3.76 (1H, m), 3.85-3.96 (1H, m), 7.01 (1H, d, J = 7.6 Hz), 7.34 (1H, dd, J = 7.7, 7.7 Hz ), 7.46 (1H, d, J = 5.4 Hz), 7.57-7.62 (1H, m), 7.75 (1H, d, J = 5.4 Hz), 8.35-8.6 (1H, m), 9.82 (1H, br). | Hydrochloride |

TABLE 134 absolute configuration

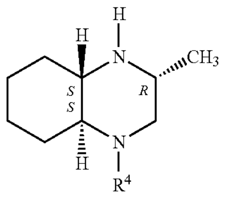

| Ex. No. | $R^4$ | NMR | Salt |
|---|---|---|---|
| 1114 | 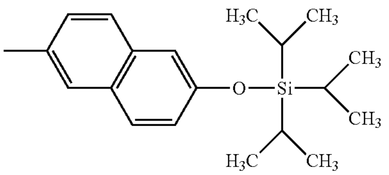 | 1H-NMR (CDCl3) δ ppm: 0.95-1.10 (4H, m), 1.13 (18H, d, J = 7.3 Hz), 1.19-1.47 (7H, m), 1.59-1.67 (1H, m), 1.70-1.84 (3H, m), 2.45-2.53 (1H, m), 2.57 (1H, dd, J = 10.3, 11.0 Hz), 2.62-2.70 (1H, m), 3.12 (1H, dd, J = 2.7, 11.2 Hz), 3.16-3.24 (1H, m), 7.09 (1H, dd, J = 2.4, 8.9 Hz), 7.17 (1H, d, J = 2.4 Hz), 7.27 (1H, dd, J = 2.1, 8.7 Hz), 7.44 (1H, d, J = 2.0 Hz), 7.59-7.65 (2H, m). | — |
| 1115 | 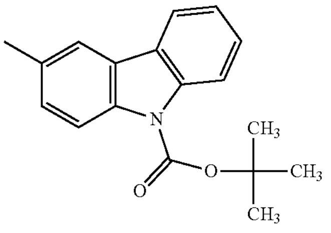 | 1H-NMR (CDCl3) δ ppm: 0.94-1.12 (4H, m), 1.15-1.46 (4H, m), 1.57-1.68 (2H, m), 1.68-1.85 (11H, m), 2.42-2.51 (1H, m), 2.59-2.70 (2H, m), 3.10 (1H, dd, J = 2.7, 11.2 Hz), 3.15-3.25 (1H, m), 7.29 (1H, dd, J = 2.2, 8.6 Hz), 7.30-7.37 (1H, m), 7.42-7.49 (1H, m), 7.76 (1H, d, J = 2.1 Hz), 7.93 (1H, d, J = 7.2 Hz), 8.21 (1H, d, J = 8.8 Hz), 8.29 (1H, d, J = 8.3 Hz). | — |

TABLE 135 absolute configuration

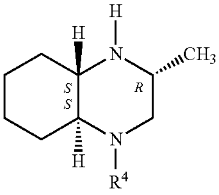

| Ex. No. | $R^4$ | NMR | Salt |
|---|---|---|---|
| 1116 | 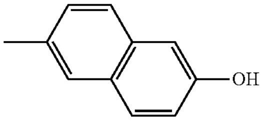 | 1H-NMR (DMSO-d6) δ ppm: 0.85-0.99 (4H, m), 1.13-1.35 (3H, m), 1.49-1.75 (4H, m), 1.99 (1H, brs), 2.32-2.50 (3H, m), 2.92-3.02 (2H, m), 7.00-7.09 (2H, m), 7.19 (1H, dd, J = 2.1, 8.7 Hz), 7.41 (1H, d, J = 1.8 Hz), 7.58 (1H, d, J = 8.8 Hz), 7.66 (1H, d, J = 8.8 Hz), 9.56 (1H, brs). | — |
| 1117 | 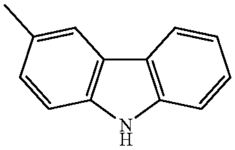 | 1H-NMR (DMSO-d6) δ ppm: 1.10-1.57 (7H, m), 1.57-1.71 (2H, m), 1.71-1.82 (1H, m), 2.11-2.22 (1H, m), 3.00-3.40 (6H, m), 7.22 (1H, t, J = 7.4 Hz), 7.35-7.85 (4H, m), 8.09 (1H, d, J = 7.8 Hz), 8.37 (1H, brs), 9.96 (2H, brs), 11.61 (1H, brs). | 2 Hydrochloride |

TABLE 136 absolute configuration

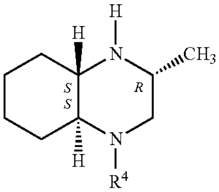

| Ex. No. | $R^4$ | NMR | Salt |
|---|---|---|---|
| 1118 | 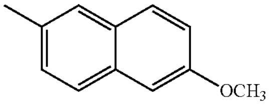 | 1H-NMR (CDCl3) δ ppm: 0.98-1.11 (4H, m), 1.17-1.58 (4H, m), 1.58-1.85 (4H, m), 2.44-2.53 (1H, m), 2.56-2.70 (2H, m), 3.12 (1H, dd, J = 2.8, 11.2 Hz), 3.15-3.25 (1H, m), 3.90 (3H, s), 7.08-7.16 (2H, m), 7.30 (1H, dd, J = 2.0, 8.7 Hz), 7.46 (1H, d, J = 2.0 Hz), 7.65 (1H, d, J = 4.8 Hz), 7.67 (1H, d, J = 4.9 Hz). | — |
| 1119 | 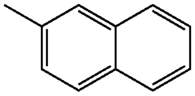 | 1H-NMR (DMSO-d6) δ ppm: 0.95-1.05 (1H, m), 1.11 (3H, d, J = 6.3Hz ), 1.15-1.5 (3H, m), 1.5-1.6 (1H, m), 1.65-1.75 (2H, m), 1.85-1.95 (1H, m), 2.65-2.85 (3H, m), 2.85-4.35 (4H, m ), 6.50 (1H, s), 7.33 (1H, dd, J = 2.1, 8.7 Hz), 7.4-7.5 (2H, m), 7.57 (1H, d, J = 1.8 Hz), 7.8-7.9 (3H, m). | ½ Fumarate |
| 1120 | 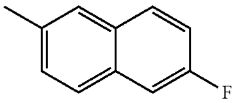 | 1H-NMR (CDCl3) δ ppm: 0.98-1.12 (4H, m), 1.18-1.48 (4H, m), 1.58-1.69 (1H, m), 1.69-1.85 (3H, m), 2.46-2.54 (1H, m), 2.57 (1H, dd, J = 10.2, 11.0 Hz), 2.62-2.70 (1H, m), 3.10-3.25 (2H, m), 7.22 (1H, dt, J = 2.6, 8.8 Hz), 7.35 (1H, dd, J = 1.8, 8.7 Hz), 7.40 (1H, dd, J = 2.5, 9.9 Hz), 7.50 (1H, d, J = 1.9 Hz), 7.68-7.77 (2H, m). | — |

TABLE 137 absolute configuration

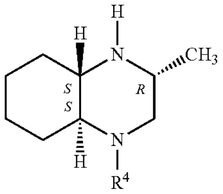

| Ex. No. | $R^4$ | NMR | Salt |
|---|---|---|---|
| 1121 | 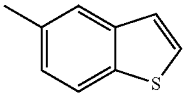 | 1H-NMR (CDCl3) δ ppm: 0.97-1.17 (4H, m), 1.17-1.49 (4H, m), 1.53-1.89 (4H, m), 2.42-2.55 (1H, m), 2.55-2.71 (2H, m), 3.08 (1H, dd, J = 2.8, 11.3 Hz), 3.13-3.26 (1H, m), 7.19 (1H, dd, J = 2.0, 8.6 Hz), 7.27 (1H, d, J = 5.4 Hz), 7.42 (1H, d. J = 5.4 Hz), 7.58 (1H, d, J = 2.0 Hz), 7.78 (1H, d, J = 8.6 Hz). | — |
| 1122 | 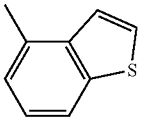 | 1H-NMR (CDCl3) δ ppm: 0.85-1.02 (1H, m), 1.05 (3H, d, J = 6.4 Hz), 1.17-1.54 (4H, m), 1,54-1.63 (1H, m), 1.63-1.83 (3H, m), 2.40-2.55 (1H, m), 2.55-2.65 (1H, m), 2.65-2.74 (1H, m), 3.10 (1H, dd, J = 2.8, 11.4 Hz), 3.15-3.26 (1H, m), 7.12 (1H, dd, J = 0.7, 7.6 Hz), 7.30 (1H, t, J = 7.8 Hz), 7.35 (1H, d, J = 5.5 Hz), 7.57 (1H, d, J = 5.5 Hz), 7.64 (1H, d, J = 8.0 Hz). | — |
| 1123 | 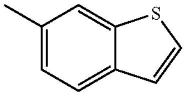 | 1H-NMR (DMSO-d6) δ ppm: 0.90-1.04 (1H, m), 1.12 (3H, d, J = 6.4 Hz), 1.17-1.35 (2H, m), 1.35-1.49 (1H, m), 1.50-1.62 (1H, m), 1.64-1.74 (1H, m), 1.84-1.94 (1H, m), 2.65-2.84 (3H, m), 3.10 (1H, dd, J = 2.9, 11.7 Hz), 3.21-3.34 (1H, m), 4.30-6.30 (1.5H, br), 6.49 (1.5H, s), 7.18 (1H, dd, J = 1.7, 8.4 Hz), 7.39 (1H, d, J = 5.4 Hz), 7.67 (1H, d, J = 5.4 Hz). 7.75 (1H, d, J = 17 Hz), 7.81 (1H, d, J = 8 4 Hz). | Fumarate |

TABLE 138 absolute configuration

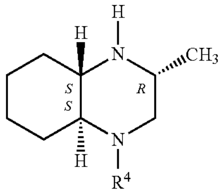

| Ex. No. | $R^4$ | NMR | Salt |
|---|---|---|---|
| 1124 | 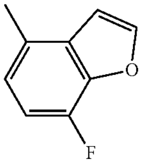 | 1H-NMR (DMSO-d6) δ ppm at 80° C.: 0.96-1.38 (6H, m), 1.40-1.50 (1H, m), 1.50-1.80 (3H, m), 2.06-2.17 (1H, m), 3.01-3.20 (2H, m), 3.27-3.40 (2H, m), 3.50-3.65 (1H, m), 5.90-6.39 (1H, br), 7.05-7.22 (2H, m), 7.32 (1H, brs), 8.03 (1H, d, J = 2.0 Hz), 9.64 (1H, brs), 9.81 (1H, brs). | 2 Hydrochloride |
| 1125 | 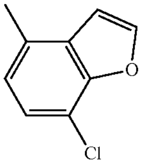 | 1H-NMR (DMSO-d6) δ ppm: 0.85-1.00 (1H, m), 1.05-1.38 (5H, m), 1.38-1.75 (4H, m), 1.87-2.00 (1H, m), 2.65-3.00 (3H, m), 3.12 (1H, dd, J = 2.8, 11.9 Hz), 3.30-3.47 (1H, m), 6.53 (2H, s), 7.04 (1H, d. J = 8.3 Hz), 7.14 (1H, brs), 7.37 (1H, d, J = 8.3 Hz), 8.08 (1H, d, J = 2.2 Hz). (3H, not found) | Fumarate |

TABLE 138-continued absolute configuration

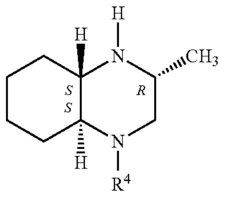

| Ex. No. | $R^4$ | NMR | Salt |
|---|---|---|---|
| 1126 | 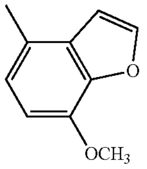 | 1H-NMR (DMSO-d6) δ ppm at 80° C.: 1.02-1.38 (6H, m), 1.38-1.50 (1H, m), 1.50-1.79 (3H, m), 2.05-2.16 (2H, m), 3.10-3.29 (2H, m), 3.29-3.57 (2H, br), 3.57-3.73 (1H, br), 3.94 (3H, s), 4.30-4.25 (1H, br), 6.91 (1H, d. J = 8.4 Hz), 7.16 (1H, brs), 7.31 (1H, brs), 7.93 (1H, s), 9.72 (1H, brs). | 2 Hydrochloride |
| 1127 | 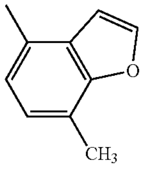 | 1H-NMR (DMSO-d6) δ ppm at 80° C.: 1.03-1.38 (6H, m), 1.40-1.79 (4H, m), 2.06-2.18 (1H, m), 2.45 (3H, s), 3.12-3.31 (2H, m), 3.31-3.56 (2H, m), 3.56-3.77 (1H, m), 5.39-6.13 (1H, br), 7.08-7.21 (2H, m), 7.21-7.40 (1H, m), 7.95 (1H, d, J = 2.0 Hz), 9.79 (2H, brs). | 2 Hydrochloride |
| 1128 | 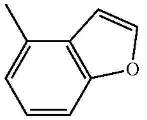 | 1H-NMR (DMSO-d6) δ ppm at 80° C.: 1.02-1.39 (6H, m), 1.45-1.80 (4H, m), 2.08-2.18 (1H, m), 3.10-3.30 (2H, m), 3.32-3.55 (2H, m), 3.55-3.74 (1H, m), 5.50-6.15 (1H, br), 7.16-7.25 (1H, m), 7.25-7.36 (2H, m), 7.47 (1H, d, J = 8.2 Hz), 7.94 (1H, d, J = 2.0 Hz), 9.55-10.05 (2H, brm). | 2 Hydrochloride |
| 1129 | 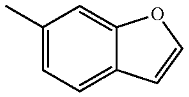 | 1H-NMR (DMSO-d6) δ ppm: 0.89-1.03 (1H, m), 1.08-1.35 (5H, m), 1.35-1.60 (3H, m), 1.63-1.73 (1H, m), 1.84-1.96 (1H, m), 2.62-2.85 (3H, m), 3.08 (1H, dd, J = 2.8, 11.8 Hz), 3.22-3.35 (1H, m), 6.50 (2H, s), 6.91 (1H, dd, J = 0.9, 2.1 Hz), 7.07 (1H, dd, J = 1.7, 8.3 Hz), 7.36 (1H, s), 7.58 (1H, d, J = 8.2 Hz), 7.95 (1H, d, J = 2.2 Hz). (3H not found) | Fumarate |
| 1130 | 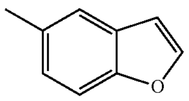 | 1H-NMR (DMSO-d6) δ ppm: 1.09-1.55 (7H, m), 1.55-1.80 (3H, m), 2.10-2.22 (1H, m), 3.35-4.13 (5H, m), 4.13-5.22 (1H, br), 7.12 (1H, s), 7.60 (1H, brs), 7.81 (1H, s), 7.98 (1H, brs), 8.15 (1H, s), 10.09 (2H, brs). | 2 Hydrochloride |
| 1131 | 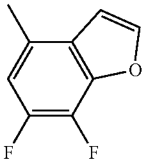 | 1H-NMR (DMSO-d6) δ ppm: 0.90-1.06 (1H, m), 1.15-1.38 (5H, m), 1.47-1.67 (3H, m), 1.67-1.80 (1H, m), 1.99-2.11 (1H, m), 2.80-3.30 (4H, m), 3.40-3.60 (1H, m), 4.40-5.10 (1H, br), 7.13-7.38 (2H, m), 8.15 (1H, d, J = 2.0 Hz), 9.05-9.58 (1H, br), 9.70-9.95 (1H, br). | 2 Hydrochloride |

TABLE 139 absolute configuration

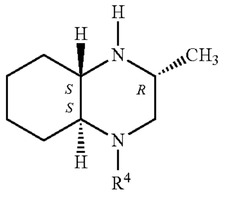

| Ex. No. | $R^4$ | NMR | Salt |
|---|---|---|---|
| 1132 | 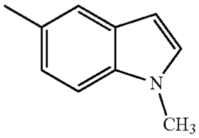 | 1H-NMR (CDCl3) δ ppm: 0.94-1.10 (4H, m), 1.13-1.65 (6H, m), 1.65-1.83 (2H, m), 2.37-2.47 (1H, m), 2.55-2.69 (2H, m), 3.05 (1H, dd, J = 2.8, 11.2 Hz), 3.12-3.23 (1H, m), 3.77 (3H, s), 6.42 (1H, d, J = 0.7, 3.1 Hz), 7.03 (1H, d, J = 3.1 Hz), 7.08 (1H, d, J = 2.0, 8.6 Hz), 7.22-7 30 (1H, m), 7.41 (1H, d, J = 18 Hz). | — |
| 1133 | 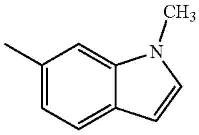 | 1H-NMR (DMSO-d6) δ ppm: 0.90-1.05 (1H, m), 1.09-1.35 (5H, m), 1.39-1.60 (3H, m), 1.64-1.76 (1H, m), 1.88-2.00 (1H, m), 2.68-2.79 (1H, m), 2.79-2.94 (2H, m), 3.01-3.11 (1H, m), 3.28-3.40 (1H, m), 3.75 (3H, s), 6.36 (1H, d, J = 0.6, 3.1 Hz), 6.51 (2H, s), 6.87 (1H, d, J = 1.7, 8.4 Hz), 7.18 (1H, s), 7.27 (1H, d, J = 3.1 Hz), 7.47 (1H, d, J = 8.3 Hz). (3H not found) | Fumarate |
| 1134 | 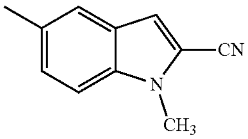 | 1H-NMR (CDCl3) δ ppm: 0.82-0.92 (1H, m), 0.94 (3H, d, J = 6.3 Hz), 1.06-1.34 (4H, m), 1.38-1.58 (2H, m), 1.59-1.75 (2H, m), 2.28-2.37 (1H, m), 2.37-2.49 (2H, m), 2.89 (1H, dd, J = 2.6, 10.8 Hz), 2.94-3.04 (1H, m), 3.86 (3H, s), 7.21 (1H, dd, J = 1.9, 8.9 Hz), 7.31 (1H, s), 7.36 (1H, d, J = 1.7 Hz), 7.51 (1H, d, J = 8.9 Hz). | — |
| 1135 | 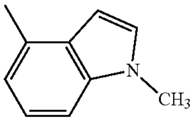 | 1H-NMR (DMSO-d6) δ ppm: 0.82-0.96 (1H, m), 1.01-1.35 (5H, m), 1.35-1.85 (4H, m), 1.85-1.96 (1H, m), 2.53-3.05 (3H, m), 3.05-3.23 (1H, m), 3.23-3.40 (1H, m), 3.76 (3H, s), 6.39-6.57 (3H, m), 6.79 (1H, d, J = 8.0 Hz), 7.09 (1H, t, J = 7.8 Hz), 7.17-7.28 (2H, m). (3H not found) | Fumarate |
| 1136 | 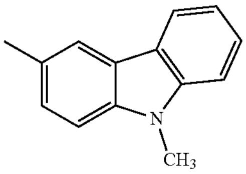 | 1H-NMR (DMSO-d6) δ ppm: 0.93-1.10 (1H, m), 1.10-1.35 (5H, m), 1.41-1.59 (3H, m), 1.64-1.78 (1H, m), 1.91-2.04 (1H, m), 2.75-3.04 (3H, m), 3.11 (1H, dd, J = 2.0, 12.0 Hz), 3.32-3.46 (1H, m), 3.85 (3H, s), 6.53 (2H, s), 7.15-7.23 (1H, m), 7.29 (1H, dd, J = 1.9. 8.6 Hz), 7.42-7.49 (1H, m), 7.53 (1H, d, J = 8.6 Hz), 7.56 (1H, d, J = 8.3 Hz), 7.94 (1H, d, J = 1.8 Hz), 8.15 (1H, d, J = 7.7 Hz). (3H, not found) | Fumarate |

TABLE 140 absolute configuration

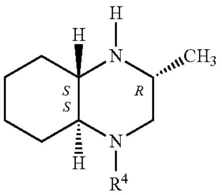

| Ex. No. | $R^4$ | NMR | Salt |
|---|---|---|---|
| 1137 | 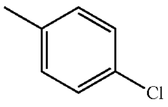 | 1H-NMR (CDCl3) δ ppm: 0.88-1.08 (4H, m), 1.15-1.57 (4H, m), 1.60-1.68 (2H, m), 1.68-1.80 (2H, m), 2.31-2.39 (1H, m), 2.46 (1H, dd, J = 10.4, 11.0 Hz), 2.55-2.63 (1H, m), 3.00 (1H, dd, J = 2.8, 11.2 Hz), 3.07-3.18 (1H, m), 7.03-7.09 (2H, m), 7.23-7.29 (2H, m). | — |

TABLE 140-continued absolute configuration

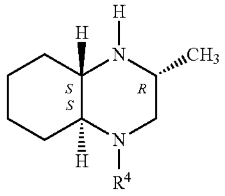

| Ex. No. | $R^4$ | NMR | Salt |
|---|---|---|---|
| 1138 | 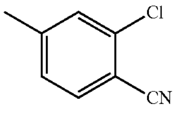 | 1H-NMR (CDCl3) δ ppm: 0.98-1.10 (4H, m), 1.20-1.46 (4H, m), 1.65-1.90 (4H, m), 2.46-2.67 (3H, m), 3.10-3.25 (2H, m), 6.98 (1H, dd, J = 2.1, 8.5 Hz), 7.12 (1H, d, J = 2.1 Hz), 7.54 (1H, d, J = 8.5 Hz) | — |
| 1139 | 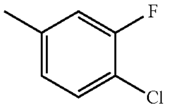 | 1H-NMR (DMSO-d6) δ ppm: 0.89-1.03 (1H, m), 1.11 (3H, d, J = 6.4 Hz), 1.17-1.34 (2H, m), 1.34-1.47 (1H, m), 1.51-1.74 (3H, m), 1.82-1.94 (1H, m), 2.64-2.74 (2H, m), 2.74-2.84 (1H, m), 3.14 (1H, dd, J = 3.0, 11.9 Hz), 3.20-3.33 (1H, m), 6.51 (2H, s), 6.97-7.04 (1H, m), 7.19 (1H, dd, J = 2.4, 11.3 Hz), 7.50 (1H, t, J = 8.7 Hz), 8.90-11.40 (2H, br). (1H not found) | Fumarate |
| 1140 | 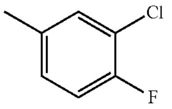 | 1H-NMR (DMSO-d6) δ ppm: 0.89-1.03 (1H, m), 1.10 (3H, d, J = 6.4 Hz), 1.14-1.45 (3H, m), 1.48-1.62 (2H, m), 1.65-1.73 (1H, m), 1.82-1.92 (1H, m), 2.58-2.81 (3H, m), 3.05 (1H, dd, J = 3.0, 11.7 Hz), 3.19-3.30 (1H, m), 6.51 (2H, s), 7.11-7.18 (1H, m), 7.31-7.41 (2H, m), 9.00-11.60 (2H, br). (1H not found) | Fumarate |

TABLE 141 absolute configuration

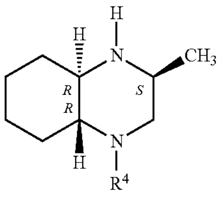

| Ex. No. | $R^4$ | NMR | Salt |
|---|---|---|---|
| 1141 | 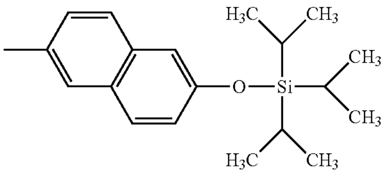 | 1H-NMR (CDCl3) δ ppm: 0.96-1.10 (4H, m), 1.13 (18H, d, J = 7.3 Hz), 1.19-1.50 (7H, m), 1.58-1.67 (1H, m), 1.68-1.84 (3H, m), 2.45-2.53 (1H, m), 2.57 (1H, dd, J = 10.3, 11.0 Hz), 2.62-2.70 (1H, m), 3.12 (1H, dd, J = 2.7, 11.2 Hz), 3.15-3.24 (1H, m), 7.09 (1H, dd, J = 2.4, 8.9 Hz), 7.17 (1H, d, J = 2.4 Hz), 7.27 (1H, dd, J = 2.1, 8.7 Hz), 7.44 (1H, d, J = 2.0 Hz), 7.59-7.65 (2H, m). | — |
| 1142 | 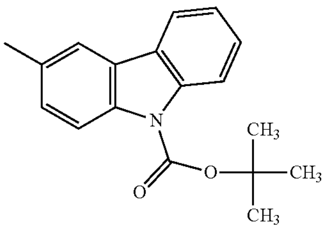 | 1H-NMR (CDCl3) δ ppm: 0.94-1.12 (4H, m), 1.15-1.46 (4H, m), 1.57-1.68 (2H, m), 1.68-1.85 (11H, m), 2.42-2.51 (1H, m), 2.59-2.70 (2H, m), 3.10 (1H, dd, J = 2.7, 11.2 Hz), 3.15-3.25 (1H, m), 7.29 (1H, dd, J = 2.2, 8.6 Hz), 7.30-7.37 (1H, m), 7.42-7.49 (1H, m), 7.76 (1H, d, J = 2.1 Hz), 7.93 (1H, d, J = 7.2 Hz), 8.21 (1H, d, J = 8.8 Hz), 8.29 (1H, d, J = 8.3 Hz). | — |

TABLE 142 absolute configuration

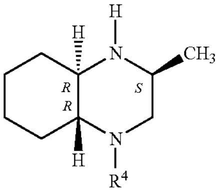

| Ex. No. | $R^4$ | NMR | Salt |
|---|---|---|---|
| 1143 | 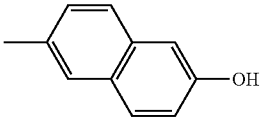 | 1H-NMR (DMSO-d6) δ ppm: 0.83-1.00 (4H, m), 1.12-1.35 (3H, m), 1.48-1.75 (4H, m), 1.99 (1H, brs), 2.31-2.50 (3H, m), 2.92-3.03 (2H, m), 6.99-7.09 (2H, m), 7.19 (1H, dd, J = 2.0, 8.7 Hz), 7.41 (1H, d, J = 1.7 Hz), 7.58 (1H, d, J = 8.8 Hz), 7.66 (1H, d, J = 8.8 Hz), 9.57 (1H, brs). | — |
| 1144 | 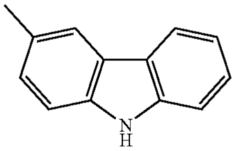 | 1H-NMR (DMSO-d6) δ ppm: 1.10-1.57 (7H, m), 1.57-1.71 (2H, m), 1.71-1.82 (1H, m), 2.11-2.22 (1H, m), 3.00-3.40 (6H, m), 7.22 (1H, t, J = 7.4 Hz). 7.35-7.85 (4H. m). 8.09 (1H, d, J = 7.8 Hz). 8.37 (1H, brs), 9.96 (2H, brs), 11.61 (1H, brs). | 2 Hydrochloride |

TABLE 143 absolute configuration

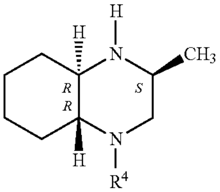

| Ex. No. | $R^4$ | NMR | Salt |
|---|---|---|---|
| 1145 | 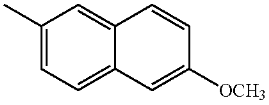 | 1H-NMR (CDCl3) δ ppm: 0.98-1.12 (4H, m), 1.18-1.58 (4H, m), 1.58-1.85 (4H, m), 2.45-2.53 (1H, m), 2.56-2.70 (2H, m), 3.12 (1H, dd, J = 2.8, 11.2 Hz), 3.16-3.25 (1H, m), 3.90 (3H, s), 7.08-7.16 (2H, m), 7.30 (1H, dd, J = 2.01, 8.7 Hz), 7.46 (1H, d, J = 2.0 Hz), 7.65 (1H, d, J = 4.9 Hz), 7.67 (1H, d, J = 4.9 Hz). | — |
| 1146 | 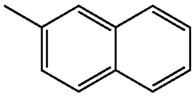 | 1H-NMR (DMSO-d6) δ ppm: 0.92-1.06 (1H, m), 1.11 (3H, d, J = 6.4 Hz), 1.16-1.51 ( 3H, m), 1.52-1.64 (1H, m), 1.64-1.78 (2H, m), 1.82-1.94 (1H, m), 2.65-2.85 (3H, m), 2.85-4.2 (4H, m), 6.50 (1H, s), 7.33 (1H, dd, J = 2.1, 8.7 Hz ), 7.39-7.51 (2H, m), 7.56 (1H, d, J = 1.9 Hz), 7.80-7.89 (3H, m). | ½ Fumarate |
| 1147 | 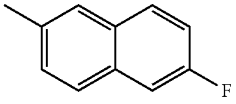 | 1H-NMR (CDCl3) δ ppm: 0.98-1.12 (4H, m), 1.18-1.48 (4H, m), 1.60-1.69 (1H, m), 1.69-1.85 (3H, m), 2.46-2.54 (1H, m), 2.57 (1H, dd, J = 10.2, 11.0 Hz), 2.62-2.71 (1H, m), 3.10-3.25 (2H, m), 7.22 (1H, dt, J = 2.6, 8.8 Hz), 7.35 (1H, dd, J = 1.8. 8.7 Hz), 7.40 (1H, dd, J = 2.5, 9.9 Hz), 7.50 (1H, d, J = 1.9 Hz), 7.68-7.77 (2H, m). | — |

TABLE 144 absolute configuration

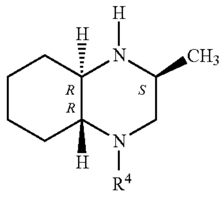

| Ex. No. | $R^4$ | NMR | Salt |
|---|---|---|---|
| 1148 | 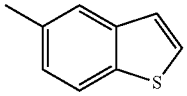 | 1H-NMR (CDCl3) δ ppm: 0.97-1.17 (4H, m), 1.17-1.89 (8H, m), 2.41-2.50 (1H, m), 2.53-2.69 (2H, m), 3.08 (1H, dd, J = 2.8, 11.2 Hz), 3.13-3.22 (1H, m), 7.18 (1H, dd, J = 2.0, 8.5 Hz), 7.27 (1H, d, J = 5.4 Hz), 7.42 (1H, d, J = 5.4 Hz), 7.58 (1H, d, J = 2.0 Hz), 7.78 (1H, d, J = 8 5 Hz). | — |
| 1149 | 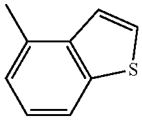 | 1H-NMR (CDCl3) δ ppm: 0.86-1.02 (1H, m), 1.05 (3H, d, J = 6.4 Hz), 1.17-1.54 (4H, m), 1.54-1.63 (1H, m), 1.63-1.83 (3H, m), 2.39-2.55 (1H, m), 2.55-2.65 (1H, m), 2.65-2.74 (1H, m), 3.10 (1H, dd, J = 2 8. 11.4 Hz). 3.15-3.26 (1H, m), 7.12 (1H, dd, J = 0.7, 7.6 Hz), 7.30 (1H, t, J = 7.8 Hz), 7.35 (1H, d, J = 5.5 Hz), 7.57 (1H, d, J = 5.5 Hz), 7.64 (1H, d, J = 8.0 Hz). | — |
| 1150 | 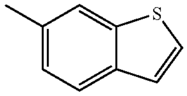 | 1H-NMR (DMS0-d6) δ ppm: 0.90-1.04 (1H, m), 1.10-1.35 (5H, m), 1.35-1.62 (2H, m), 1.64-1.74 (1H, m), 1.84-1.95 (1H, m), 2.65-2.84 (3H, m), 3.11 (1H, dd, J = 2.8, 11.8 Hz), 3.21-3.35 (1H, m), 6.49 (1.5H, s), 7.19 (1H, dd, J = 1.8, 8.5 Hz), 7.39 (1H, d, J = 5.4 Hz), 7.68 (1H, d, J = 5.4 Hz), 7.75 (1H, d, J = 1.8 Hz), 7.81 (1H, d, J = 8.5 Hz), 7.50-9.40 (1H, br). | Fumarate |

TABLE 145 absolute configuration

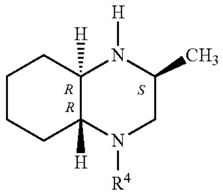

| Ex. No. | $R^4$ | NMR | Salt |
|---|---|---|---|
| 1151 | 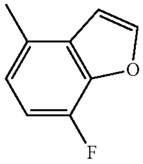 | 1H-NMR (DMSO-d6) δ ppm at 80° C.: 0.96-1.39 (6H, m), 1.40-1.50 (1H, m), 1.50-1.80 (3H, m), 2.05-2.15 (1H, m), 2.98-3.20 (2H, m), 3.20-3.40 (2H, m), 3.42-3.64 (1H, m), 5.23-6.05 (1H, br), 7.05-7.21 (2H, m), 7.30 (1H, brs), 8.03 (1H, s), 9.56 (1H, brs), 9.77 (1H, brs). | 2 Hydrochloride |
| 1152 | 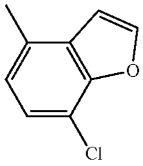 | 1H-NMR (DMSO-d6) δ ppm: 0.85-1.00 (1H, m), 1.05-1.38 (5H, m), 1.38-1.75 (4H, m), 1.87-2.00 (1H, m), 2.65-3.00 (3H, m), 3.12 (1H, dd, J = 2.8, 11.9 Hz), 3.30-3.47 (1H, m), 6.53 (2H, s), 7.04 (1H, d. J = 8.3 Hz), 7.14 (1H, brs), 7.37 (1H, d, J = 8 3 Hz), 8 08 (1H, d, J = 2.2 Hz). (3H, not found) | Fumarate |

TABLE 145-continued absolute configuration

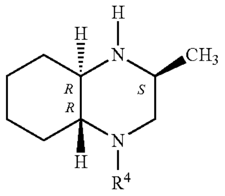

| Ex. No. | $R^4$ | NMR | Salt |
|---|---|---|---|
| 1153 | 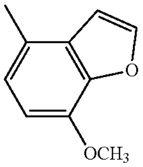 | 1H-NMR (DMSO-d6) δ ppm at 80° C.: 1.00-1.38 (6H, m), 1.38-1.50 (1H, m), 1.50-1.79 (3H, m), 2.05-2.14 (2H, m), 3.09-3.25 (2H, m), 3.25-3.50 (2H, br), 3.54-3.70 (1H, br), 3.94 (3H, s), 4.35-5.05 (1H, br), 6.90 (1H, d, J = 8.4 Hz), 7.07-7.20 (1H, m), 7.27 (1H, brs), 7.92 (1H, d, J = 18 Hz), 9.68 (1H, brs). | 2 Hydrochloride |
| 1154 | 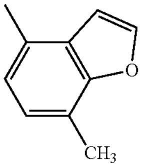 | 1H-NMR (DMSO-d6) δ ppm at 80° C.: 1.05-1.38 (6H, m), 1.38-1.52 (1H, m), 1.52-1.62 (1H, m), 1.62-1.79 (2H, m), 2.09-2.18 (1H, m), 2.46 (3H, s), 3.17-3.37 (2H, m), 3.37-3.66 (2H, m), 3.66-3.75 (1H, m), 6.25-7.10 (1H, br), 7.14 (1H, d, J = 7.8 Hz), 7.19-7.30 (1H, m), 7.40 (1H, brs), 7.97 (1H, d, J = 2.1 Hz), 9.88 (2H, brs). | 2 Hydrochloride |
| 1155 | 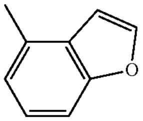 | 1H-NMR (DMSO-d6) δ ppm at 80° C.: 1.00-1.38 (6H, m), 1.45-1.80 (4H, m), 2.08-2.18 (1H, m), 3.06-3.27 (2H, m), 3.27-3.49 (2H, m), 3.53-3.70 (1H, m), 4.94-5.68 (1H, br), 7.13-7.22 (1H, m), 7.25-7.35 (2H, m), 7.45 (1H, d, J = 8.2 Hz), 7.93 (1H, d, J = 1.5 Hz), 9.45-10.00 (2H, brm). | 2 Hydrochloride |
| 1156 | 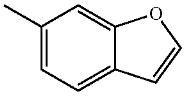 | 1H-NMR (DMSO-d6) δ ppm: 0.89-1.03 (1H, m), 1.05-1.35 (5H, m), 1.35-1.61 (3H, m), 1.61-1.75 (1H, m), 1.82-1.96 (1H, m), 2.62-2.86 (3H, m), 3.08 (1H, d, J = 11.6 Hz), 3.21-3.36 (1H, m), 6.50 (2H, s), 6.91 (1H, d, J = 2.0 Hz), 7.07 (1H, dd, J = 1.3, 8.3 Hz), 7.36 (1H, s), 7.58 (1H, d, J = 8.2 Hz), 7.95 (1H, d, J = 2.2 Hz). (3H not found) | Fumarate |
| 1157 | 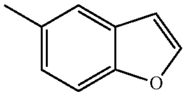 | 1H-NMR (DMSO-d6) δ ppm: 1.09-1.55 (7H, m), 1.55-1.80 (3H, m), 2.10-2.22 (1H, m), 3.30-4.10 (5H, m), 4.10-5.20 (1H, br), 7.11 (1H, s), 7.58 (1H, brs), 7.80 (1H, s), 7.97 (1H, brs), 8.15 (1H, s), 10.06 (2H, brs). | 2 Hydrochloride |
| 1158 | 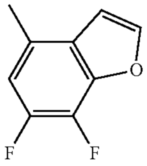 | 1H-NMR (DMSO-d6) δ ppm : 0.90-1.10 (1H, m), 1.15-1.38 (5H, m), 1.47-1.69 (3H, m), 1.69-1.80 (1H, m), 2.00-2.11 (1H, m), 2.80-3.40 (4H, m), 3.40-3.60 (1H, m), 5.35-6.36 (1H, br), 7.13-7.44 (2H, m), 8.15 (1H, d, J = 2.0 Hz), 9.08-9.66 (1H, br), 9.66-10.08 (1H, br). | 2 Hydrochloride |

TABLE 146 absolute configuration

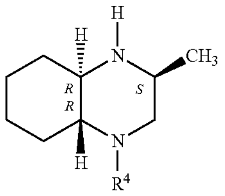

| Ex No. | $R^4$ | NMR | Salt |
| --- | --- | --- | --- |
| 1159 | 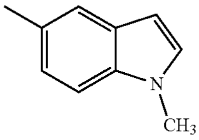 | 1H-NMR (CDCl3) δ ppm: 0.95-1.10 (4H, m), 1.10-1.54 (4H, m), 1.54-1.65 (2H, m), 1.65-1.83 (2H, m), 2.37-2.47 (1H, m), 2.55-2.69 (2H, m), 3.05 (1H, dd, J = 2.8, 11.2 Hz), 3.12-3.23 (1H, m), 3.77 (3H, s), 6.42 (1H, d, J = 0.7, 3.1 Hz), 7.03 (1H, d, J = 3.1 Hz), 7.08 (1H, d, J = 2.0, 8.6 Hz), 7.22-7.30 (1H, m), 7.41 (1H, d, J = 1.8 Hz). | — |
| 1160 | 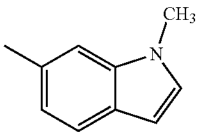 | 1H-NMR (DMSO-d6) δ ppm: 0.90-1.05 (1H, m), 1.09-1.35 (5H, m), 1.39-1.60 (3H, m), 1.64-1.75 (1H, m), 1.88-2.00 (1H, m), 2.67-2.95 (3H, m), 3.07 (1H, dd, J = 2.8, 12.0 Hz), 3.28-3.40 (1H, m), 3.75 (3H, s), 6.36 (1H, d, J = 0.6, 3.0 Hz), 6.51 (2H, s), 6.87 (1H, d, J = 1.6, 8.4 Hz), 7.18 (1H, s), 7.27 (1H, d, J = 3.0 Hz), 7.47 (1H, d, J = 8.3 Hz). (3H not found) | Fumarate |
| 1161 | 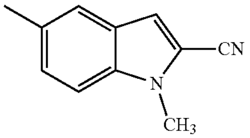 | 1H-NMR (CDCl3) δ ppm: 0.82-0.92 (1H, m), 0.94 (3H, d, J = 6.3 Hz), 1.06-1.34 (4H, m), 1.38-1.58 (2H, m), 1.59-1.75 (2H, m), 2.28-2.37 (1H, m), 2.37-2.49 (2H, m), 2.89 (1H, dd, J = 2.6, 10.8 Hz), 2.94-3.04 (1H, m), 3.86 (3H, s), 7.21 (1H, dd, J = 1.9, 8.9 Hz), 7.31 (1H, s), 7.36 (1H, d, J = 1.7 Hz), 7.51 (1H, d, J = 8.9 Hz). | — |
| 1162 | 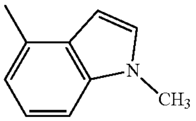 | 1H-NMR (DMSO-d6) δ ppm: 0.80-0.99 (1H, m), 1.00-1.35 (5H, m), 1.35-1.98 (5H, m), 2.53-3.25 (4H, m), 3.23-3.40 (1H, m), 3.76 (3H, s), 6.40-6.58 (3H, m), 6.79 (1H, d, J = 8.0 Hz), 7.09 (1H, t, J = 7.8 Hz), 7.17-7.28 (2H, m). (3H not found) | Fumarate |
| 1163 | 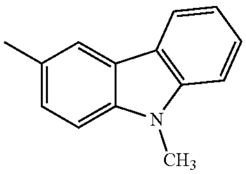 | 1H-NMR (DMSO-d6) δ ppm: 0.93-1.08 (1H, m), 1.10-1.35 (5H, m), 1.401-1.60 (3H, m), 1.64-1.75 (1H, m), 1.90-2.03 (1H, m), 2.72-3.00 (3H, m), 3.11 (1H, dd, J = 2.0, 12.0 Hz), 3.32-3.43 (1H, m), 3.85 (3H, s), 6.52 (2H, s), 7.15-7.23 (1H, m), 7.29 (1H, dd, J = 1.9, 8.6 Hz), 7.43-7.49 (1H, m), 7.53 (1H, d, J = 8.6 Hz), 7.56 (1H, d, J = 8.2 Hz), 7.94 (1H, d, J = 1.8 Hz), 8.14 (1H, d, J = 7.7 Hz). (3H, not found) | Fumarate |

TABLE 147 absolute configuration

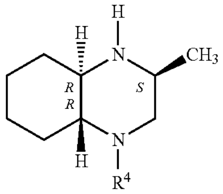

| Ex. No. | $R^4$ | NMR | Salt |
|---|---|---|---|
| 1164 | 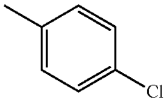 | 1H-NMR (CDCl3) δ ppm: 0.88-1.08 (4H, m), 1.15-1.42 (4H, m), 1.42-1.60 (1H, br), 1.60-1.69 (2H, m), 1.69-1.82 (2H, m), 2.31-2.39 (1H, m), 2.46 (1H, dd, J = 10.4, 11.0 Hz), 2.55-2.63 (1H, m), 3.00 (1H, dd, J = 2.8, 11.2 Hz), 3.07-3.18 (1H, m), 7.02-7.09 (2H, m). 7.23-7.29 (2H, m). | — |
| 1165 | 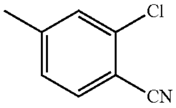 | 1H-NMR (CDl3) δ ppm: 0.98-1.10 (4H, m), 1.22-1.46 (4H, m), 1.65-1.90 (4H, m), 2.46-2.67 (3H, m), 3.10-3.25 (2H, m), 6.98 (1H, dd, J = 2.1, 8.6 Hz), 7.12 (1H, d, J = 2.1 Hz), 7.54 (1H, d, J = 8.6 Hz) | — |
| 1166 | 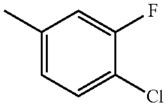 | 1H-NMR (DMSO-d6) δ ppm: 0.90-1.03 (1H, m), 1.12 (3H ,d, J = 6.4 Hz), 1.17-1.34 (2H, m), 1.34-1.48 (1H, m), 1.52-1.74 (3H, m), 1.84-1.94 (1H, m), 2.65-2.75 (2H, m), 2.74-2.84 (1H, m), 3.14 (1H, dd, J = 3.0, 11.9 Hz), 3.22-3.34 (1H, m), 6.51 (2H, s), 6.97-7.04 (1H, m), 7.19 (1H, dd, J = 2.4, 11.3 Hz), 7.51 (1H, t, J = 8.6 Hz), 8.60-11.75 (2H, br). (1H not found) | Fumarate |
| 1167 | 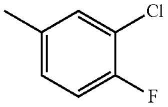 | 1H-NMR (DMSO-d6) δ ppm: 0.88-1.02 (1H, m), 1.11 (3H, d, J = 6.4 Hz), 1.14-1.45 (3H, m), 1.48-1.62 (2H, m), 1.65-1.73 (1H, m), 1.82-I.92 (1H, m), 2.60-2.81 (3H, m), 3.05 (1H, dd, J = 3.0, 11.8 Hz), 3.19-3.30 (1H, m), 6.51 (2H, s), 7.11-7.18 (1H, m), 7.30-7.41 (2H, m), 8.85-11.65 (2H, br). (1H not found) | Fumarate |

TABLE 148 absolute configuration

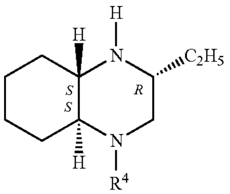

| Example | $R^4$ | NMR | Salt |
|---|---|---|---|
| 1168 | 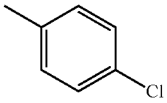 | 1H-NMR (DMSO-d6) δ ppm: 0.8-1.0 (4H, m), 1.1-1.6 (7H, m), 1.6-1.7 (1H, m), 1.8-1.9 (1H, m), 2.5-2.75 (3H, m), 2.85-3.9 (5H, m), 6.5-6.55 (2H, m), 7.1-7.2 (2H, m), 7.3-7.4 (2H, m). | Fumarate |
| 1169 | 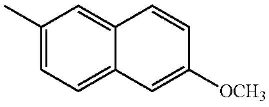 | 1H-NMR (CDCl3) δ ppm: 0.94 (3H, t, J = 7.5 Hz), 0.95-1.1 (1H, m), 1.15-1.5 (5H, m), 1.5-1.85 (5H, m), 2.46-2.69 (3H, m), 2.91-3.01 (1H, m), 3.18 (1H, dd, J = 2.7, 11.2 Hz), 3.91 (3H, s), 7.08-7.14 (2H, m), 7.31 (1H, dd, J = 2.1, 8.7 Hz), 7.47 (1H, d, J = 2.0 Hz), 7.64-7.71 (2H, m). | — |

TABLE 148-continued absolute configuration

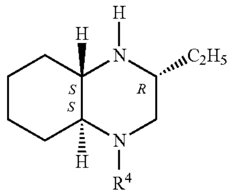

| Example | $R^4$ | NMR | Salt |
|---|---|---|---|
| 1170 | 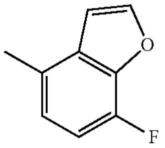 | 1H-NMR (DMSO-d6) δ ppm: 0.82-1.03 (4H, m), 1.09-1.36 (2H, m), 1.41-1.59 (4H, m), 1.59-1.75 (2H, m), 1.92-2.06 (1H, m), 2.71-3.07 (3H, m), 3.10-3.20 (1H, m), 3.20-3.32 (1H, m), 6.56 (4H, s), 6.97-7.26 (3H, m), 11.5 (5H, m). | 2 Fumarate |
| 1171 | 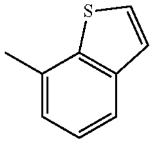 | 1H-NMR (DMSO-d6) δ ppm: 0.85-1.05 (4H, m), 1.1-1.4 (2H, m), 1.45-1.65 (4H, m), 1.65-1.85 (2H, m), 2.05-2.15 (1H, m), 2.85-3.22 (3H, m), 3.22-3.38 (2H, m), 4.09 (1H, br), 7.24 (1H, d, J = 7.5 Hz), 7.35-7.5 (2H, m), 7.7-7.8 (2H, m), 9.15-9.35 (1H, m), 9.35-9.55 (1H, m). | 2 Hydrochloride |
| 1172 | 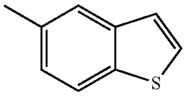 | 1H-NMR (CDCl3) δ ppm: 0.95 (3H, t, J = 7.5 Hz), 0.98-1.09 (1H, m), 1.14-1.50 (5H, m), 1.55-1.85 (5H, m), 2.44-2.53 (1H, m), 2.55-2.68 (2H, m), 2.91-3.00 (1H, m), 3.15 (1H, dd, J = 2.7, 11.1 Hz), 7.20 (1H, dd, J = 2.0, 8.6 Hz), 7.27 (1H, dd, J = 0.5, 5.4 Hz), 7.43 (1H, d, J = 5.4 Hz), 7.59 (1H, d, J = 2.0 Hz), 7.79 (1H, d, J = 8.6 Hz). | — |
| 1173 | 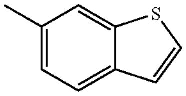 | 1H-NMR (DMSO-d6) δ ppm: 0.85-1.05 (4H, m), 1.15-1.35 (2H, m), 1.35-1.5 (2H, m), 1.5-1.6 (3H, m), 1.65-1.75 (1H, m), 1.85-1.95 (1H, m), 2.65-2.85 (3H, m), 3.05-3.2 (2H, m), 3.6 (3H, br), 6.51 (2H, s), 7.19 (1H, dd, J = 1.9, 8.5 Hz), 7.39 (1H, dd, J = 0.5, 5.4 Hz), 7.68 (1H, d, J = 5.4 Hz), 7.76 (1H, d, J = 1.8 Hz), 7.81 (1H, d, J = 8.5 Hz). | Fumarate |

TABLE 149 absolute configuration

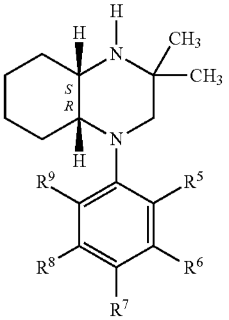

| Example | $R^5$ | $R^6$ | $R^7$ | $R^8$ | $R^9$ | MS(M + 1) |
|---|---|---|---|---|---|---|
| 1174 | —H | 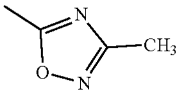 | —H | —H | —H | 327 |
| 1175 | —H | —H | 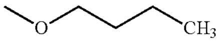 | —H | —H | 317 |

TABLE 149-continued
absolute configuration
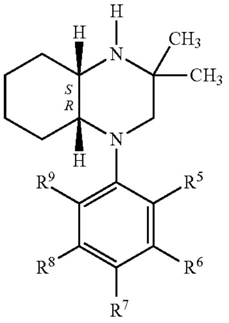
| Example | $R^5$ | $R^6$ | $R^7$ | $R^8$ | $R^9$ | MS(M + 1) |
|---|---|---|---|---|---|---|
| 1176 | —H | 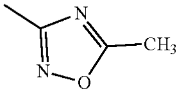 | —H | —H | —H | 327 |
| 1177 | —H | 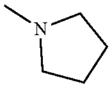 | —H | —H | —H | 314 |
| 1178 | —H | 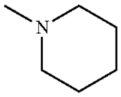 | —H | —H | —H | 328 |
| 1179 | —H | 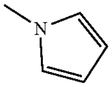 | —H | —H | —H | 310 |
| 1180 | —H | —H | 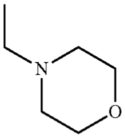 | —H | —H | 344 |
| 1181 | —H | 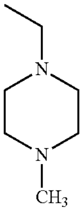 | —H | —H | —H | 357 |
| 1182 | —H | 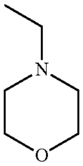 | —H | —H | —H | 344 |
| 1183 | —H | —H | 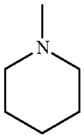 | —H | —H | 328 |

TABLE 149-continued
absolute configuration
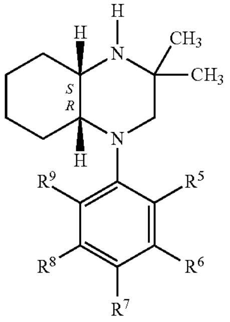
| Example | $R^5$ | $R^6$ | $R^7$ | $R^8$ | $R^9$ | MS(M + 1) |
|---|---|---|---|---|---|---|
| 1184 | —H | —H | 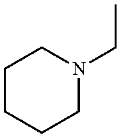 | —H | —H | 342 |
| 1185 | —H | 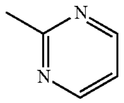 | —H | —H | —H | 323 |
| 1186 | —H | 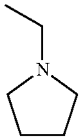 | —H | —H | —H | 328 |
| 1187 | —H | 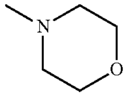 | —H | —H | —H | 330 |
| 1188 | —H | —Cl | 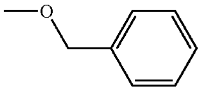 | —H | —H | 385 |
| 1189 | —H | —H | 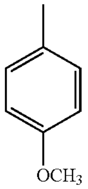 | —H | —H | 351 |
| 1190 | —H | 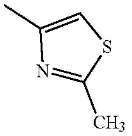 | —H | —H | —H | 342 |
| 1191 | —OCH3 | —OCH3 | —H | —H | —H | 305 |
| 1192 | —H | —H | —O(CH2)2CH3 | —H | —H | 303 |
| 1193 | —H | —H | 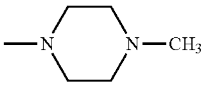 | —H | —H | 343 |
| 1194 | —F | —H | —OCH3 | —H | —H | 293 |
| 1195 | —Cl | —H | —H | —CF3 | —H | 347 |
| 1196 | —Cl | —H | —H | —H | —H | 297 |

TABLE 149-continued
absolute configuration
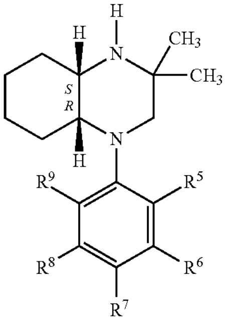
| Example | $R^5$ | $R^6$ | $R^7$ | $R^8$ | $R^9$ | MS(M + 1) |
|---|---|---|---|---|---|---|
| 1197 | —H | 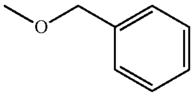 | —OCH3 | —H | —H | 381 |
| 1198 | —OCH3 | —H | —Cl | —H | —H | 309 |
| 1199 | —F | —Cl | —H | —H | —H | 297 |
| 1200 | —CH3 | —H | —OCH3 | —Cl | —H | 323 |
| 1201 | —H | —OCH3 | 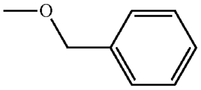 | —H | —H | 381 |
| 1202 | —H | —H | 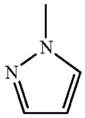 | —H | —H | 311 |
| 1203 | —H | 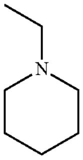 | —H | —H | —H | 342 |
| 1204 | —H | —H | 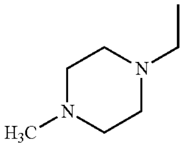 | —H | —H | 357 |
| 1205 | —H | —H | —OCH(CH3)2 | —H | —H | 303 |
| 1206 | —H | 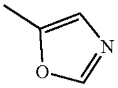 | —H | —H | —H | 312 |
| 1207 | —OCH2CH3 | —H | —H | —H | —H | 289 |
| 1208 | —H | 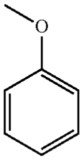 | —H | —H | —H | 337 |
| 1209 | —Cl | —CF3 | —H | —H | —H | 347 |
| 1210 | —H | —H | —CH2CH(CH3)2 | —H | —H | 301 |
| 1211 | —CN | —H | —Cl | —H | —H | 304 |

TABLE 149-continued
absolute configuration
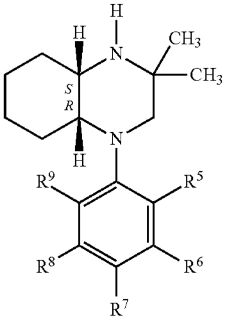
| Example | $R^5$ | $R^6$ | $R^7$ | $R^8$ | $R^9$ | MS(M + 1) |
|---|---|---|---|---|---|---|
| 1212 | —H | —H | 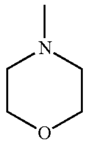 | —H | —H | 330 |
| 1213 | —H | —H | 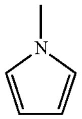 | —H | —H | 310 |
TABLE 150
absolute configuration
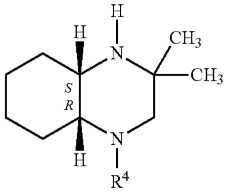
| Example | $R^4$ | MS(M + 1) |
|---|---|---|
| 1214 | 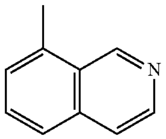 | 296 |
| 1215 | 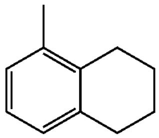 | 299 |
| 1216 | 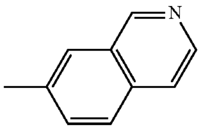 | 296 |
| 1217 | 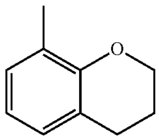 | 301 |
TABLE 150-continued
absolute configuration
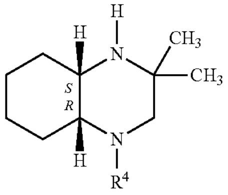
| Example | $R^4$ | MS(M + 1) |
|---|---|---|
| 1218 | 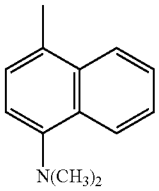 | 338 |
| 1219 | 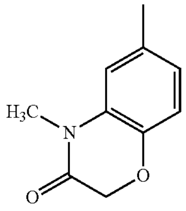 | 330 |
| 1220 | 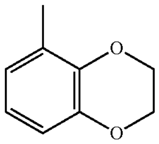 | 303 |

TABLE 150-continued
absolute configuration
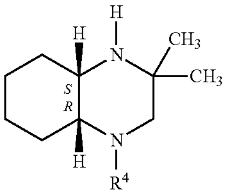
| Example | $R^4$ | MS(M + 1) |
|---|---|---|
| 1221 | 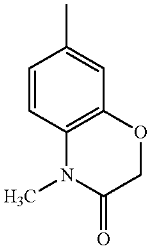 | 330 |
| 1222 | 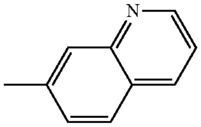 | 296 |
| 1223 | 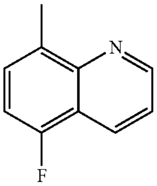 | 314 |
| 1224 | 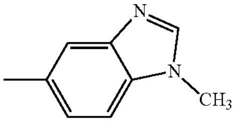 | 299 |
| 1225 | 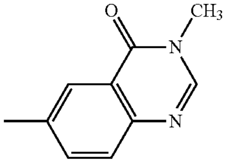 | 327 |
| 1226 | 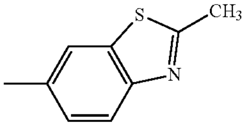 | 316 |
| 1227 | 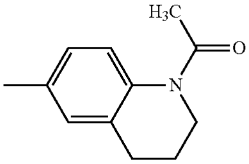 | 342 |
| 1228 | 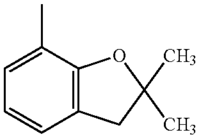 | 315 |
TABLE 150-continued
absolute configuration
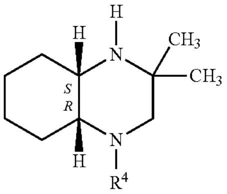
| Example | $R^4$ | MS(M + 1) |
|---|---|---|
| 1229 | 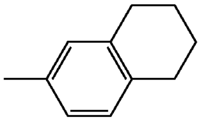 | 299 |
| 1230 | 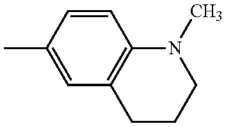 | 314 |
| 1231 | 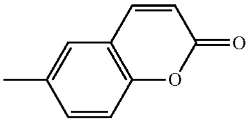 | 313 |
TABLE 151
absolute configuration
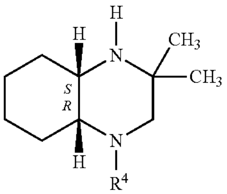
| Example | $R^4$ | MS(M + 1) |
|---|---|---|
| 1232 | 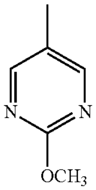 | 277 |
| 1233 | 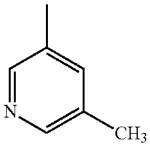 | 260 |
| 1234 | 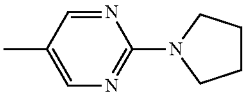 | 316 |
| 1235 | 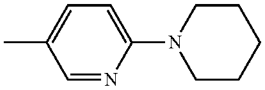 | 329 |

TABLE 151-continued
absolute configuration
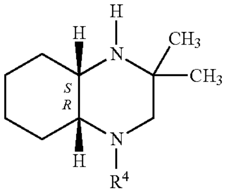
| Example | $R^4$ | MS(M + 1) |
|---|---|---|
| 1236 | 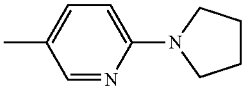 | 315 |
| 1237 | 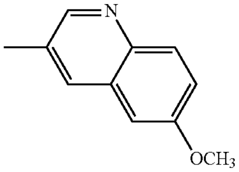 | 326 |
| 1238 | 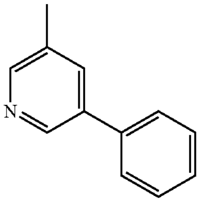 | 322 |
| 1239 | 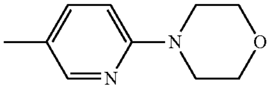 | 331 |
| 1240 | 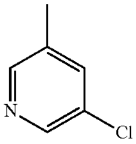 | 280 |
| 1241 | 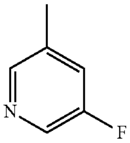 | 264 |
| 1242 | 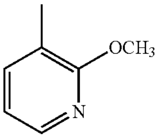 | 276 |
| 1243 | 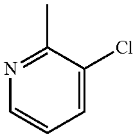 | 280 |
TABLE 151-continued
absolute configuration
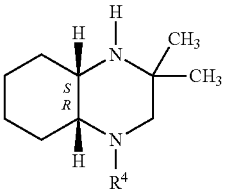
| Example | $R^4$ | MS(M + 1) |
|---|---|---|
| 1244 | 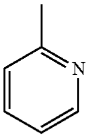 | 246 |
| 1245 | 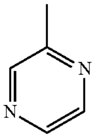 | 247 |
| 1246 | 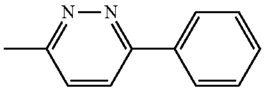 | 323 |
| 1247 | 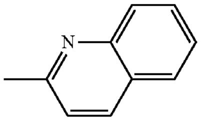 | 296 |
| 1248 | 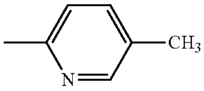 | 260 |
| 1249 | 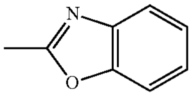 | 286 |
| 1250 | 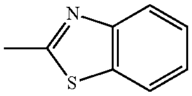 | 302 |
| 1251 | 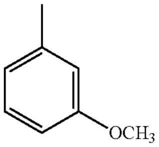 | 276 |
| 1252 | 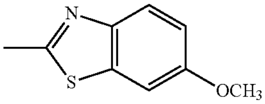 | 332 |
| 1253 | 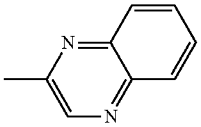 | 297 |

TABLE 151-continued
absolute configuration
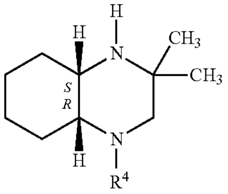
| Example | $R^4$ | MS(M + 1) |
|---|---|---|
| 1254 | 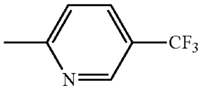 | 314 |
| 1255 | 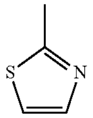 | 252 |
| 1256 | 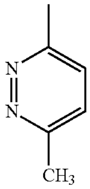 | 261 |
| 1257 | 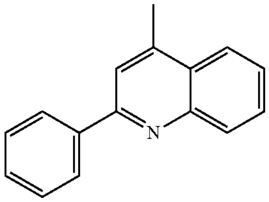 | 372 |
| 1258 | 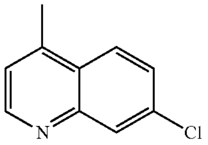 | 330 |
| 1259 | 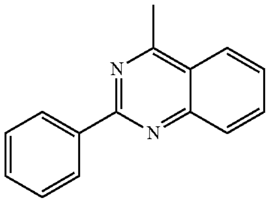 | 373 |
| 1260 | 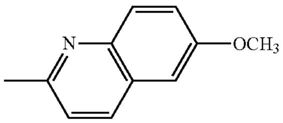 | 326 |
| 1261 | 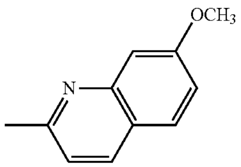 | 326 |
TABLE 151-continued
absolute configuration
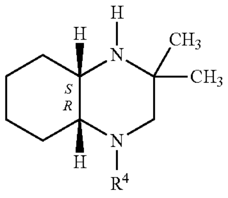
| Example | $R^4$ | MS(M + 1) |
|---|---|---|
| 1262 | 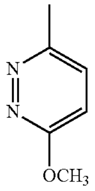 | 277 |
| 1263 | 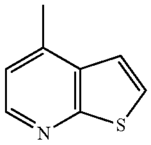 | 302 |
| 1264 | 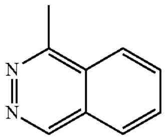 | 297 |
| 1265 | 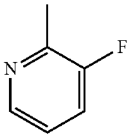 | 264 |
| 1266 | 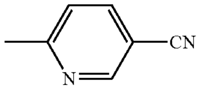 | 271 |
| 1267 | 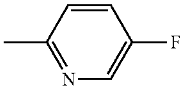 | 264 |
| 1268 | 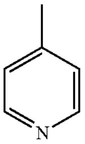 | 246 |
| 1269 | 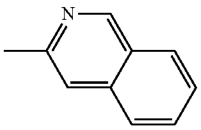 | 296 |

TABLE 151-continued
absolute configuration
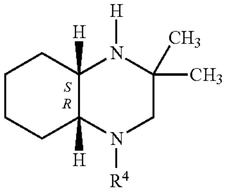
| Example | $R^4$ | MS(M + 1) |
| --- | --- | --- |
| 1270 | 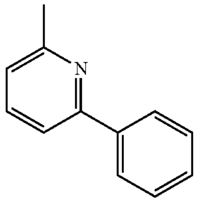 | 322 |
| 1271 | 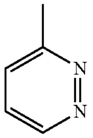 | 247 |
| 1272 | 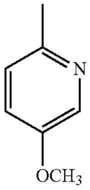 | 276 |
| 1273 | 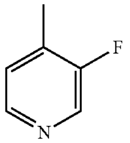 | 264 |
| 1274 | 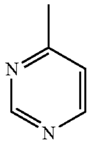 | 247 |
| 1275 | 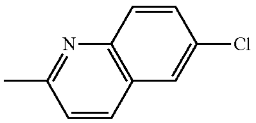 | 330 |
| 1276 | 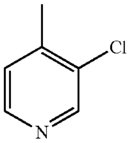 | 280 |
| 1277 | 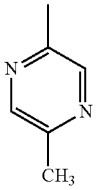 | 261 |
TABLE 151-continued
absolute configuration
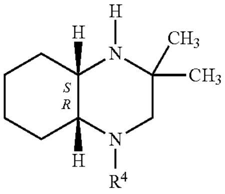
| Example | $R^4$ | MS(M + 1) |
| --- | --- | --- |
| 1278 | 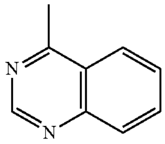 | 297 |
| 1279 | 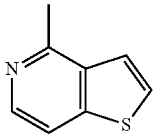 | 302 |
| 1280 | 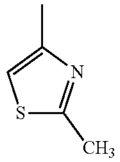 | 266 |
| 1281 | 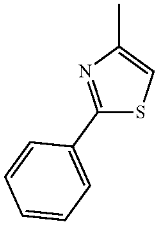 | 328 |
| 1282 | 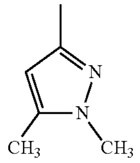 | 263 |
| 1283 | 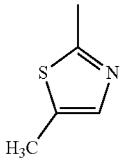 | 266 |

TABLE 152
absolute configuration
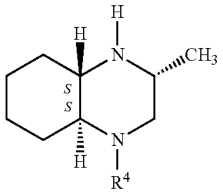
| Example | $R^4$ | MS(M + 1) |
|---|---|---|
| 1284 | 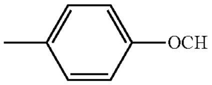 | 315 |
| 1285 | 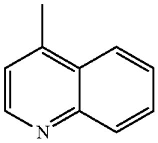 | 282 |
| 1286 | 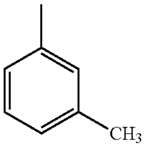 | 245 |
| 1287 | 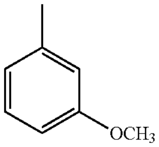 | 261 |
| 1288 | 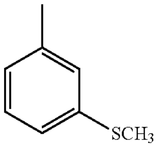 | 277 |
| 1289 | 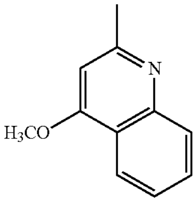 | 312 |
| 1290 | 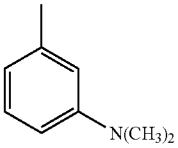 | 274 |
| 1291 | 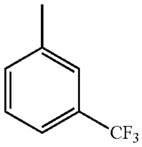 | 299 |
TABLE 152-continued
absolute configuration
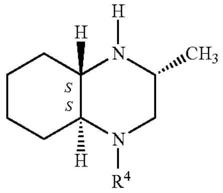
| Example | $R^4$ | MS(M + 1) |
|---|---|---|
| 1292 | 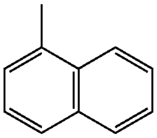 | 281 |
| 1293 | 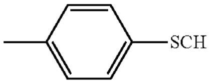 | 277 |
| 1294 | 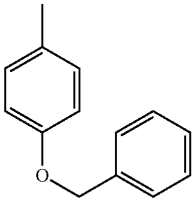 | 337 |
| 1295 | 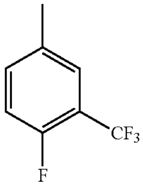 | 317 |
| 1296 | 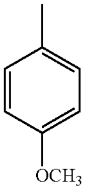 | 261 |
| 1297 | 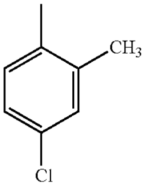 | 279 |
| 1298 | 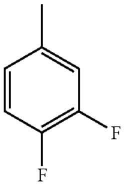 | 267 |

TABLE 152-continued
absolute configuration
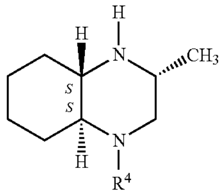
| Example | $R^4$ | MS(M + 1) |
|---|---|---|
| 1299 | 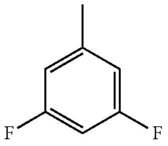 | 267 |
| 1300 | 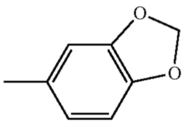 | 275 |
| 1301 | 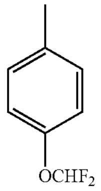 | 297 |
| 1302 | 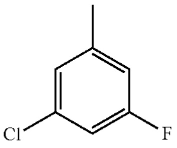 | 283 |
| 1303 | 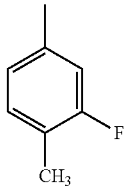 | 263 |
| 1304 | 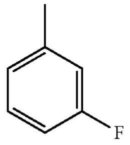 | 249 |
| 1305 | 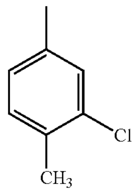 | 279 |
TABLE 152-continued
absolute configuration
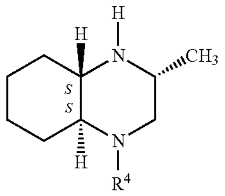
| Example | $R^4$ | MS(M + 1) |
|---|---|---|
| 1306 | 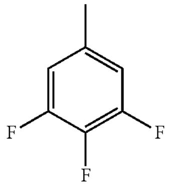 | 285 |
| 1307 | 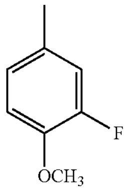 | 279 |
| 1308 | 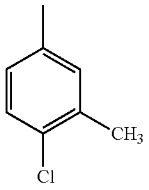 | 279 |
| 1309 | 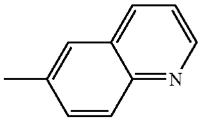 | 282 |
| 1310 | 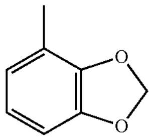 | 275 |
| 1311 | 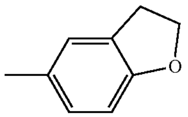 | 273 |
| 1312 | 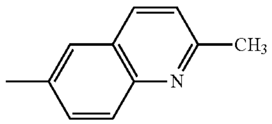 | 296 |
| 1313 | 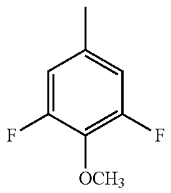 | 297 |

TABLE 152-continued
absolute configuration
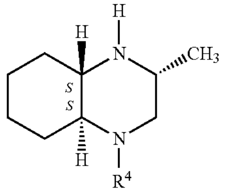
| Example | $R^4$ | MS(M + 1) |
|---|---|---|
| 1314 | 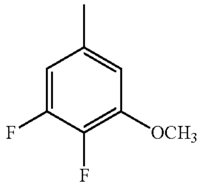 | 297 |
| 1315 | 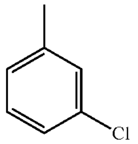 | 265 |
| 1316 | 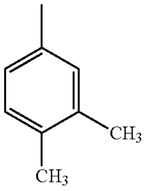 | 259 |
| 1317 | 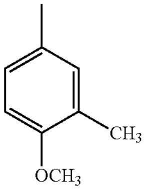 | 275 |
| 1318 | 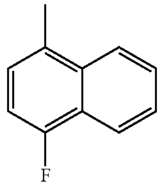 | 299 |
| 1319 | 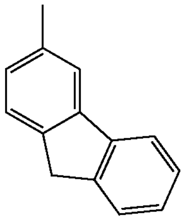 | 319 |
| 1320 | 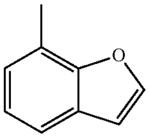 | 271 |
TABLE 152-continued
absolute configuration
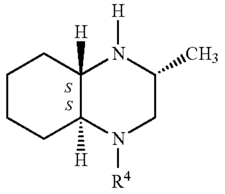
| Example | $R^4$ | MS(M + 1) |
|---|---|---|
| 1321 | 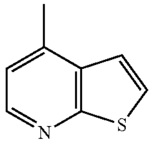 | 288 |
| 1322 | 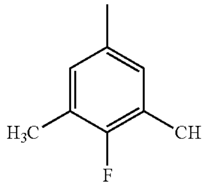 | 277 |
| 1323 | 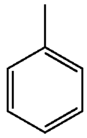 | 231 |
| 1324 | 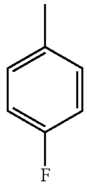 | 249 |
| 1325 | 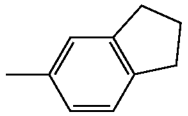 | 271 |
| 1326 | 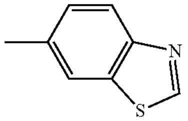 | 288 |
| 1327 | 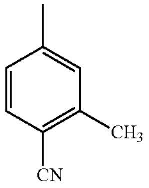 | 270 |

TABLE 152-continued
absolute configuration
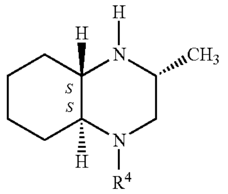
| Example | $R^4$ | MS(M + 1) |
| --- | --- | --- |
| 1328 | 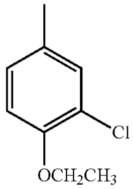 | 309 |
| 1329 | 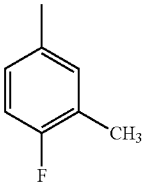 | 263 |
| 1330 | 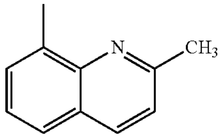 | 296 |
| 1331 | 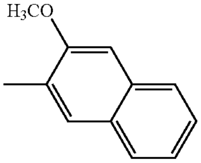 | 311 |
| 1332 | 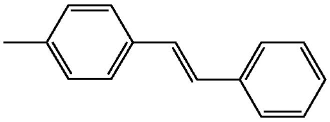 | 333 |
| 1333 | 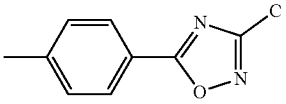 | 313 |
| 1334 | 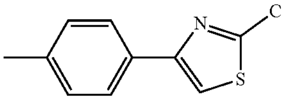 | 328 |
TABLE 152-continued
absolute configuration
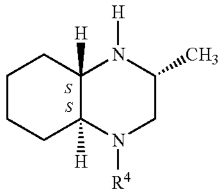
| Example | $R^4$ | MS(M + 1) |
| --- | --- | --- |
| 1335 | 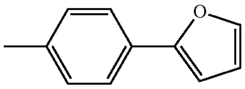 | 297 |
| 1336 | 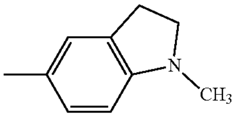 | 286 |
| 1337 | 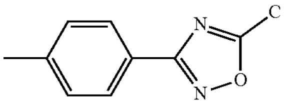 | 313 |
| 1338 | 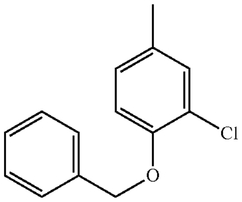 | 371 |
| 1339 | 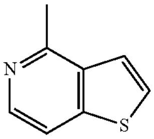 | 288 |
| 1340 | 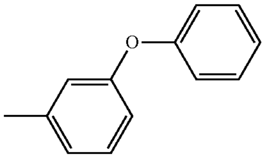 | 323 |
| 1341 | 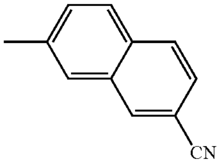 | 306 |

TABLE 153
absolute configuration
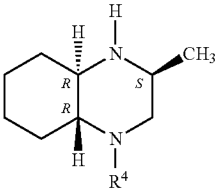
| Example | $R^4$ | MS (M + 1) |
|---|---|---|
| 1342 | 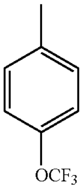 | 315 |
| 1343 | 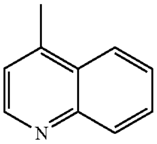 | 282 |
| 1344 | 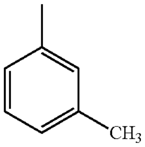 | 245 |
| 1345 | 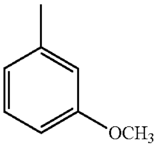 | 261 |
| 1346 | 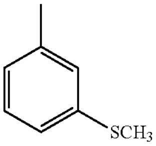 | 277 |
| 1347 | 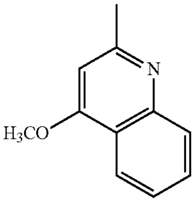 | 312 |
| 1348 | 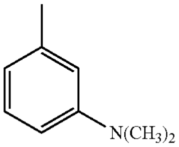 | 274 |
TABLE 153-continued
absolute configuration
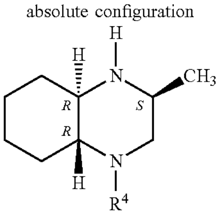
| Example | $R^4$ | MS (M + 1) |
|---|---|---|
| 1349 | 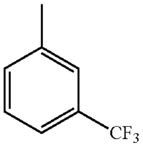 | 299 |
| 1350 | 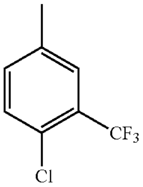 | 333 |
| 1351 | 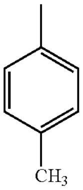 | 245 |
| 1352 | 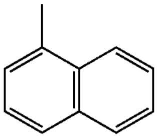 | 281 |
| 1353 | 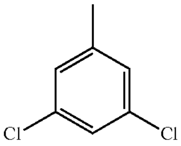 | 299 |
| 1354 | 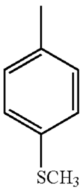 | 277 |
| 1355 | 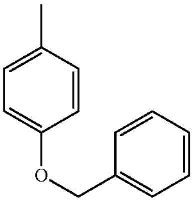 | 337 |

TABLE 153-continued
absolute configuration
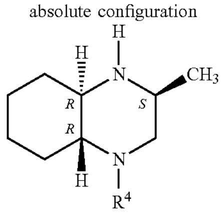
| Example | $R^4$ | MS (M + 1) |
|---|---|---|
| 1356 | 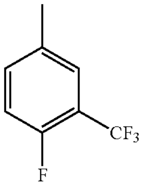 | 317 |
| 1357 | 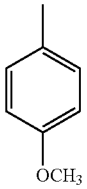 | 261 |
| 1358 | 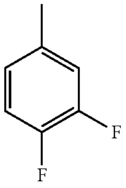 | 267 |
| 1359 | 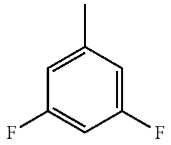 | 267 |
| 1360 | 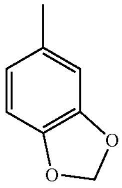 | 275 |
| 1361 | 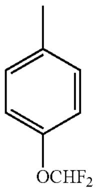 | 297 |
| 1362 | 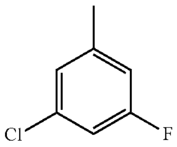 | 283 |
TABLE 153-continued
absolute configuration
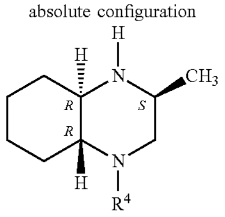
| Example | $R^4$ | MS (M + 1) |
|---|---|---|
| 1363 | 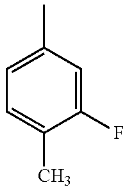 | 263 |
| 1364 | 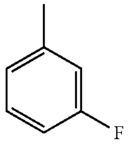 | 249 |
| 1365 | 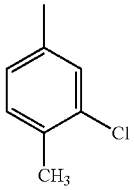 | 279 |
| 1366 | 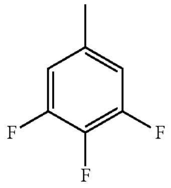 | 285 |
| 1367 | 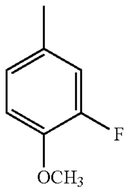 | 279 |
| 1368 | 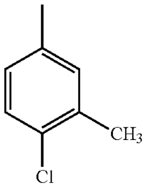 | 279 |
| 1369 | 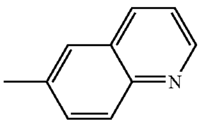 | 282 |

TABLE 153-continued
absolute configuration
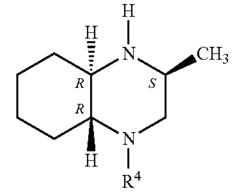
| Example | $R^4$ | MS (M + 1) |
|---|---|---|
| 1370 | 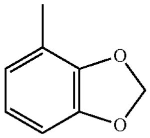 | 275 |
| 1371 | 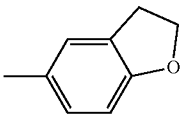 | 273 |
| 1372 | 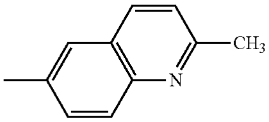 | 296 |
| 1373 | 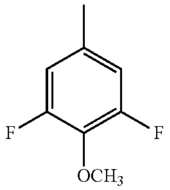 | 297 |
| 1374 | 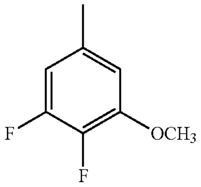 | 297 |
| 1375 | 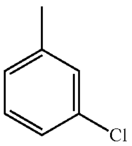 | 265 |
| 1376 | 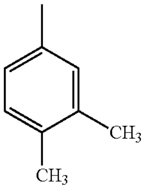 | 259 |
TABLE 153-continued
absolute configuration
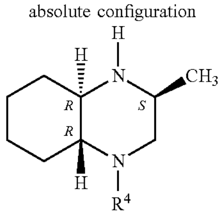
| Example | $R^4$ | MS (M + 1) |
|---|---|---|
| 1377 | 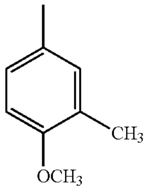 | 275 |
| 1378 | 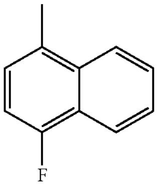 | 299 |
| 1379 | 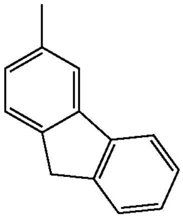 | 319 |
| 1380 | 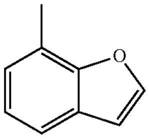 | 271 |
| 1381 | 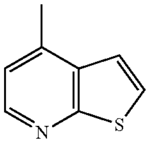 | 288 |
| 1382 | 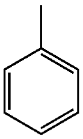 | 231 |
| 1383 | 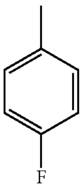 | 249 |

TABLE 153-continued
absolute configuration
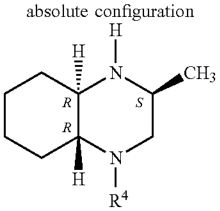
| Example | $R^4$ | MS (M + 1) |
| --- | --- | --- |
| 1384 | 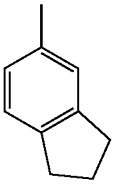 | 271 |
| 1385 | 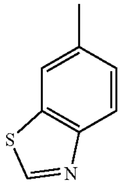 | 288 |
| 1386 | 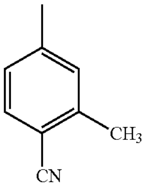 | 270 |
| 1387 | 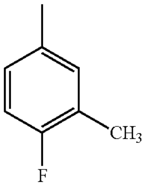 | 263 |
| 1388 | 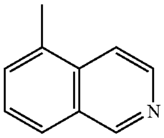 | 282 |
| 1389 | 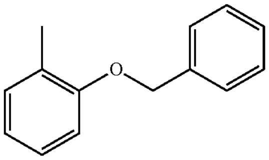 | 337 |
| 1390 | 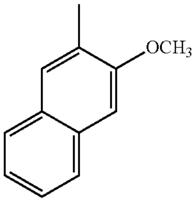 | 311 |
TABLE 153-continued
absolute configuration
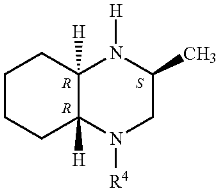
| Example | $R^4$ | MS (M + 1) |
| --- | --- | --- |
| 1391 | 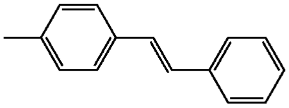 | 333 |
| 1392 | 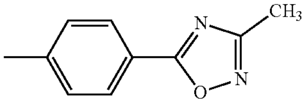 | 313 |
| 1393 | 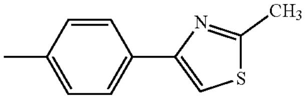 | 328 |
| 1394 | 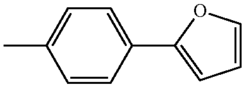 | 297 |
| 1395 | 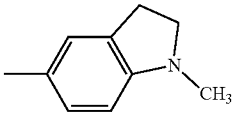 | 286 |
| 1396 | 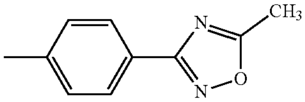 | 313 |
| 1397 | 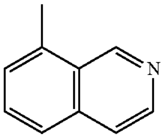 | 282 |
| 1398 | 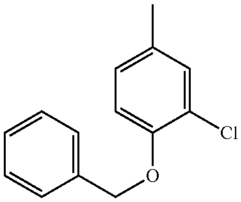 | 371 |
| 1399 | 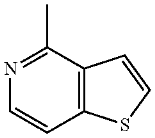 | 288 |

TABLE 153-continued
absolute configuration
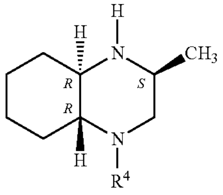
| Example | $R^4$ | MS (M + 1) |
|---|---|---|
| 1400 | 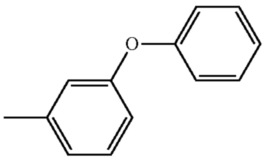 | 323 |
| 1401 | 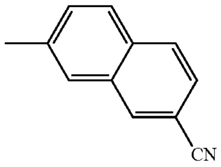 | 306 |
TABLE 154
absolute configuration
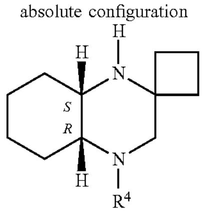
| Example | $R^4$ | MS(M + 1) |
|---|---|---|
| 1402 | 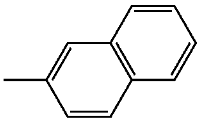 | 307 |
| 1403 | 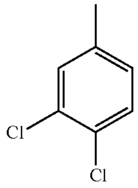 | 325 |
| 1404 | 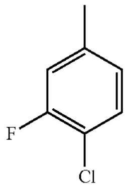 | 309 |
TABLE 154-continued
absolute configuration
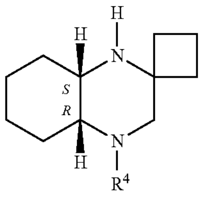
| Example | $R^4$ | MS(M + 1) |
|---|---|---|
| 1405 | 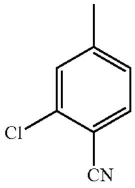 | 316 |
| 1406 | 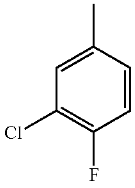 | 309 |
| 1407 | 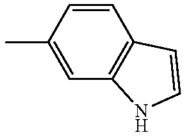 | 296 |
| 1408 | 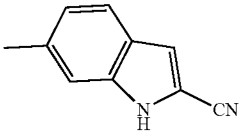 | 321 |
| 1409 | 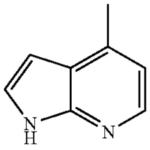 | 297 |
| 1410 | 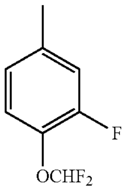 | 341 |
| 1411 | 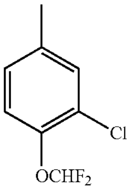 | 357 |

TABLE 154-continued
absolute configuration
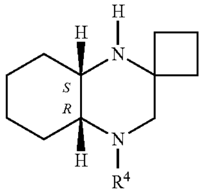
| Example | $R^4$ | MS(M + 1) |
|---|---|---|
| 1412 | 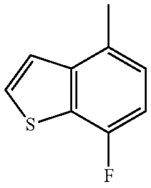 | 331 |
| 1413 | 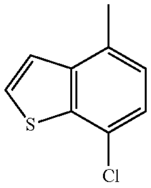 | 347 |
| 1414 | 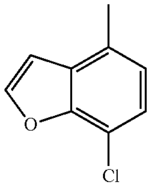 | 331 |
| 1415 | 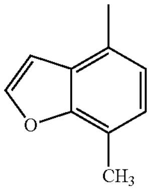 | 311 |
| 1416 | 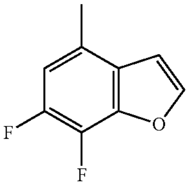 | 333 |
| 1417 | 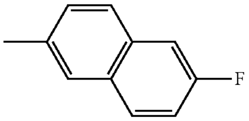 | 325 |
| 1418 | 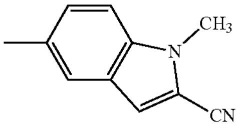 | 335 |
TABLE 154-continued
absolute configuration
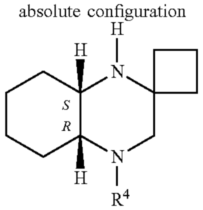
| Example | $R^4$ | MS(M + 1) |
|---|---|---|
| 1419 | 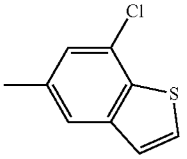 | 347 |
| 1420 | 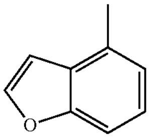 | 297 |
| 1421 | 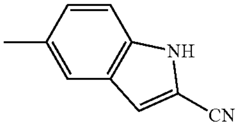 | 321 |
| 1422 | 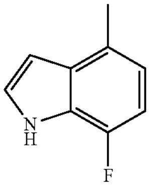 | 314 |
| 1423 | 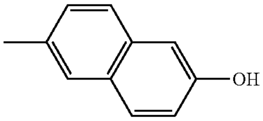 | 323 |
| 1424 | 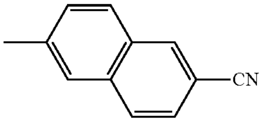 | 332 |
| 1425 | 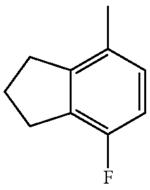 | 315 |
| 1426 | 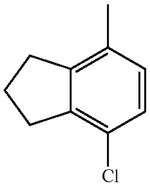 | 331 |

TABLE 155
absolute configuration
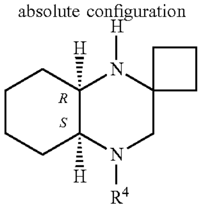
| Example | $R^4$ | MS(M + 1) |
|---|---|---|
| 1427 | 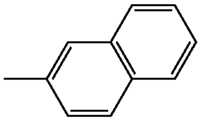 | 307 |
| 1428 | 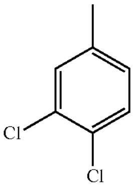 | 325 |
| 1429 | 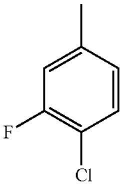 | 309 |
| 1430 | 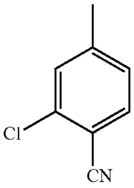 | 316 |
| 1431 | 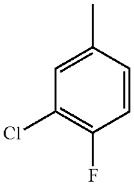 | 309 |
| 1432 | 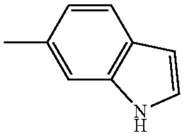 | 296 |
| 1433 | 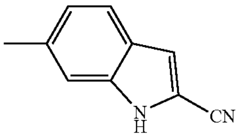 | 321 |
| 1434 | 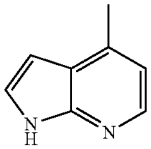 | 297 |
TABLE 155-continued
absolute configuration
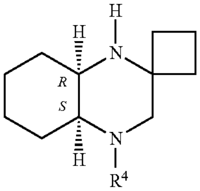
| Example | $R^4$ | MS(M + 1) |
|---|---|---|
| 1435 | 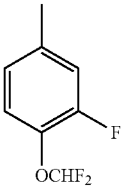 | 341 |
| 1436 | 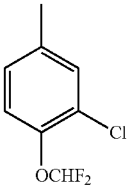 | 357 |
| 1437 | 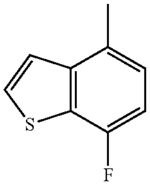 | 331 |
| 1438 | 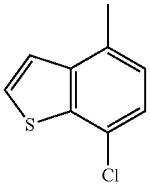 | 347 |
| 1439 | 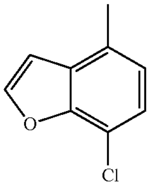 | 331 |
| 1440 | 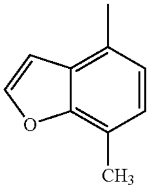 | 311 |

TABLE 155-continued
absolute configuration
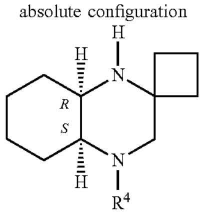
| Example | $R^4$ | MS(M + 1) |
|---|---|---|
| 1441 | 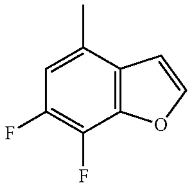 | 333 |
| 1442 | 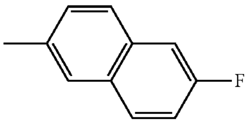 | 325 |
| 1443 | 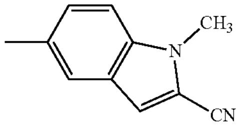 | 335 |
| 1444 | 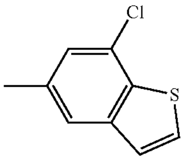 | 347 |
| 1445 | 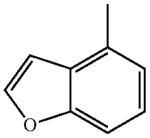 | 297 |
| 1446 | 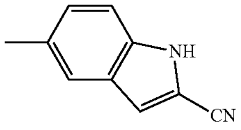 | 321 |
| 1447 | 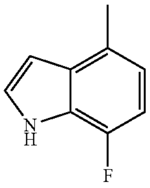 | 314 |
| 1448 | 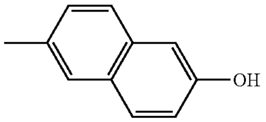 | 323 |
TABLE 155-continued
absolute configuration
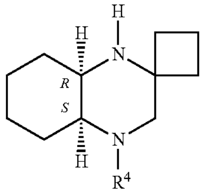
| Example | $R^4$ | MS(M + 1) |
|---|---|---|
| 1449 | 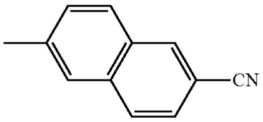 | 332 |
| 1450 | 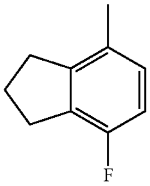 | 315 |
| 1451 | 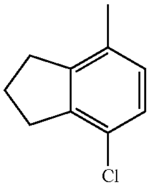 | 331 |
TABLE 156
absolute configuration
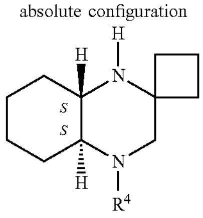
| Example | $R^4$ | MS(M + 1) |
|---|---|---|
| 1452 | 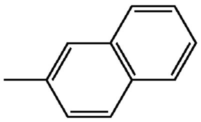 | 307 |
| 1453 | 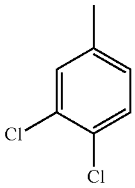 | 325 |

TABLE 156-continued
absolute configuration
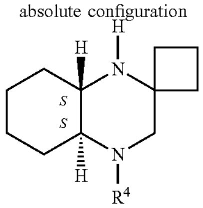
| Example | $R^4$ | MS(M + 1) |
|---|---|---|
| 1454 | 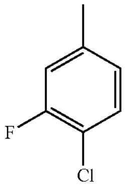 | 309 |
| 1455 | 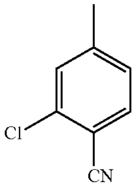 | 316 |
| 1456 | 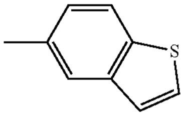 | 313 |
| 1457 | 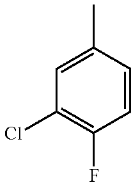 | 309 |
| 1458 | 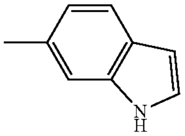 | 296 |
| 1459 | 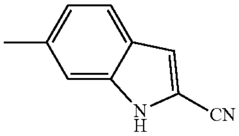 | 321 |
| 1460 | 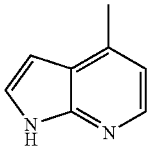 | 297 |
| 1461 | 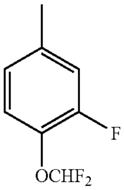 | 341 |
TABLE 156-continued
absolute configuration
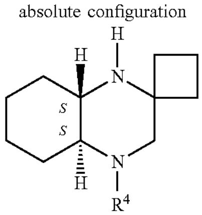
| Example | $R^4$ | MS(M + 1) |
|---|---|---|
| 1462 | 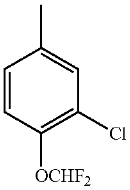 | 357 |
| 1463 | 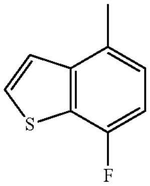 | 331 |
| 1464 | 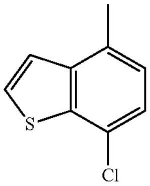 | 347 |
| 1465 | 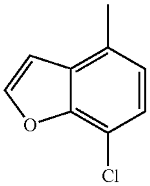 | 331 |
| 1466 | 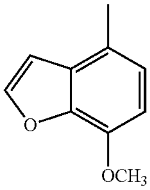 | 327 |
| 1467 | 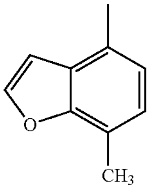 | 311 |

TABLE 156-continued
absolute configuration
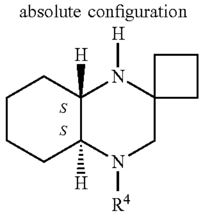
| Example | $R^4$ | MS(M + 1) |
| --- | --- | --- |
| 1468 | 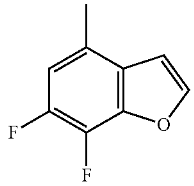 | 333 |
| 1469 | 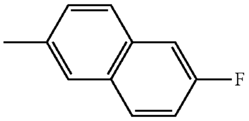 | 325 |
| 1470 | 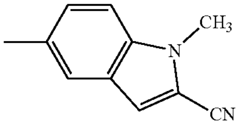 | 335 |
| 1471 | 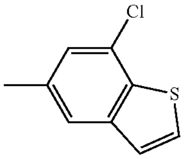 | 347 |
| 1472 | 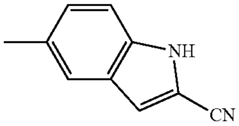 | 321 |
| 1473 | 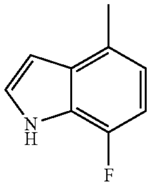 | 314 |
| 1474 | 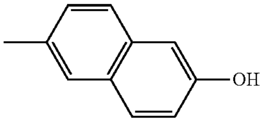 | 323 |
| 1475 | 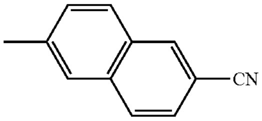 | 332 |
TABLE 156-continued
absolute configuration
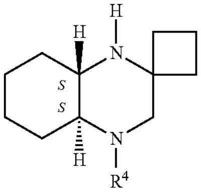
| Example | $R^4$ | MS(M + 1) |
| --- | --- | --- |
| 1476 | 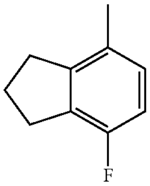 | 315 |
| 1477 | 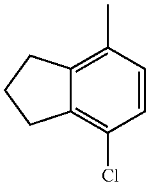 | 331 |
TABLE 157
absolute configuration
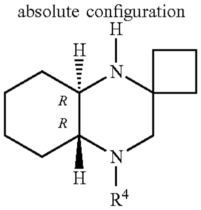
| Example | $R^4$ | MS(M + 1) |
| --- | --- | --- |
| 1478 | 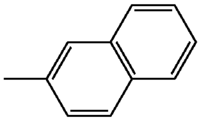 | 307 |
| 1479 | 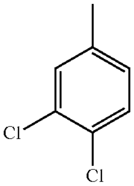 | 325 |
| 1480 | 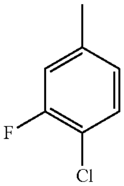 | 309 |

TABLE 157-continued
absolute configuration
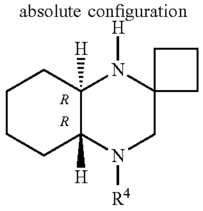
| Example | $R^4$ | MS(M + 1) |
|---|---|---|
| 1481 | 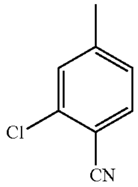 | 316 |
| 1482 | 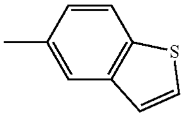 | 313 |
| 1483 | 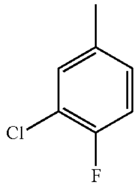 | 309 |
| 1484 | 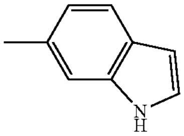 | 296 |
| 1485 | 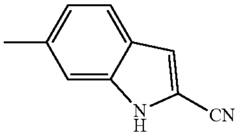 | 321 |
| 1486 | 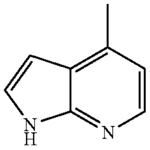 | 297 |
| 1487 | 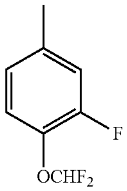 | 341 |
| 1488 | 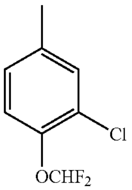 | 357 |
TABLE 157-continued
absolute configuration
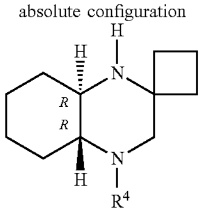
| Example | $R^4$ | MS(M + 1) |
|---|---|---|
| 1489 | 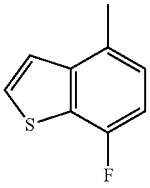 | 331 |
| 1490 | 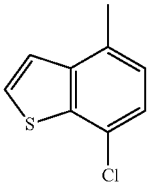 | 347 |
| 1491 | 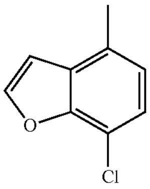 | 331 |
| 1492 | 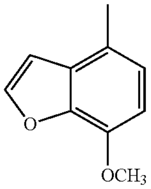 | 327 |
| 1493 | 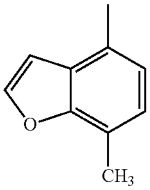 | 311 |
| 1494 | 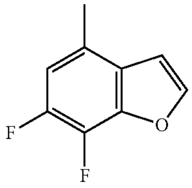 | 333 |
| 1495 | 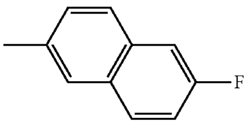 | 325 |

TABLE 157-continued
absolute configuration
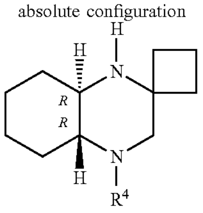
| Example | $R^4$ | MS(M + 1) |
|---|---|---|
| 1496 | 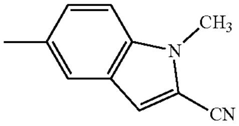 | 335 |
| 1497 | 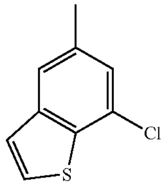 | 347 |
| 1498 | 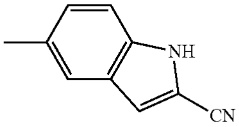 | 321 |
| 1499 | 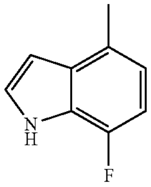 | 314 |
| 1500 | 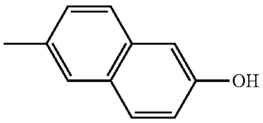 | 323 |
| 1501 | 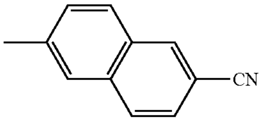 | 332 |
| 1502 | 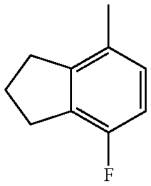 | 315 |
| 1503 | 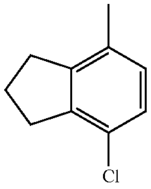 | 331 |
TABLE 158
relative configuration
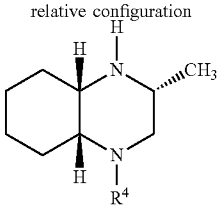
| Example | $R^4$ | MS(M + 1) |
|---|---|---|
| 1504 | 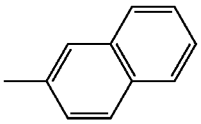 | 281 |
| 1505 | 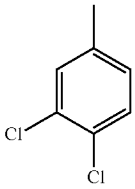 | 299 |
| 1506 | 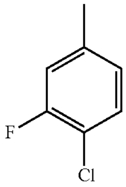 | 283 |
| 1507 | 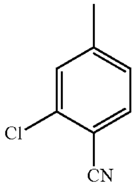 | 290 |
| 1508 | 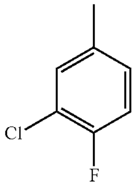 | 283 |
| 1509 | 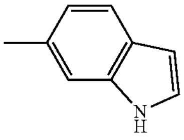 | 270 |
| 1510 | 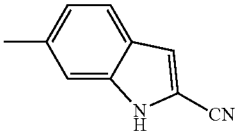 | 295 |
| 1511 | 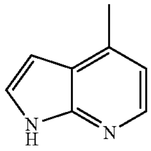 | 271 |

TABLE 158-continued
relative configuration
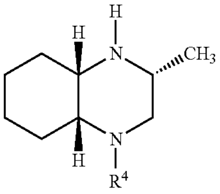
| Example | $R^4$ | MS(M + 1) |
|---|---|---|
| 1512 | 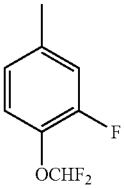 | 315 |
| 1513 | 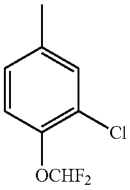 | 331 |
| 1514 | 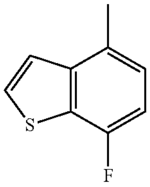 | 305 |
| 1515 | 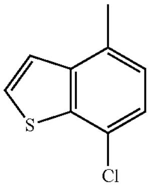 | 321 |
| 1516 | 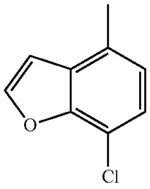 | 305 |
| 1517 | 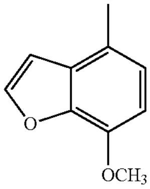 | 301 |
TABLE 158-continued
relative configuration
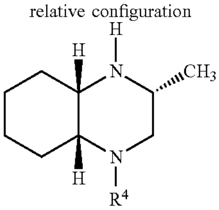
| Example | $R^4$ | MS(M + 1) |
|---|---|---|
| 1518 | 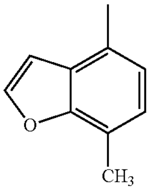 | 285 |
| 1519 | 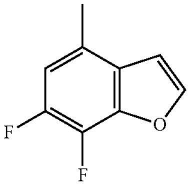 | 307 |
| 1520 | 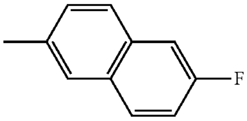 | 299 |
| 1521 | 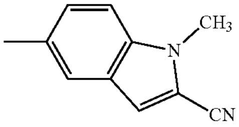 | 309 |
| 1522 | 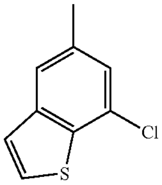 | 321 |
| 1523 | 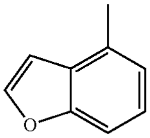 | 271 |
| 1524 | 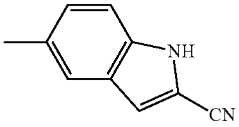 | 295 |
| 1525 | 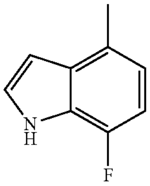 | 288 |

TABLE 158-continued
relative configuration
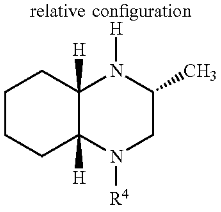
| Example | $R^4$ | MS(M + 1) |
|---|---|---|
| 1526 | 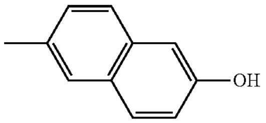 | 297 |
| 1527 | 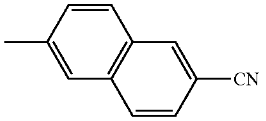 | 306 |
| 1528 | 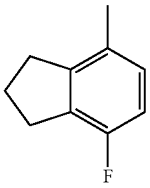 | 289 |
| 1529 | 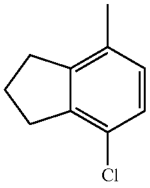 | 305 |
TABLE 159
absolute configuration
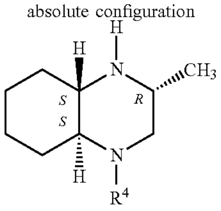
| Example. | $R^4$ | MS(M + 1) |
|---|---|---|
| 1530 | 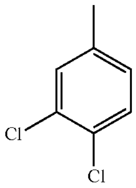 | 299 |
| 1531 | 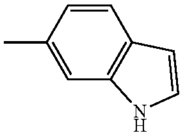 | 270 |
TABLE 159-continued
absolute configuration
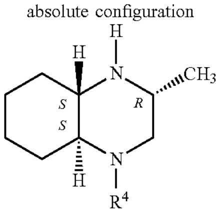
| Example. | $R^4$ | MS(M + 1) |
|---|---|---|
| 1532 | 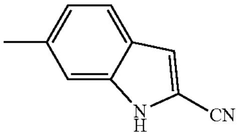 | 295 |
| 1533 | 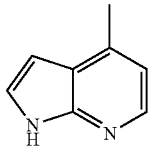 | 271 |
| 1534 | 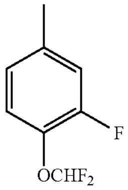 | 315 |
| 1535 | 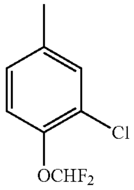 | 331 |
| 1536 | 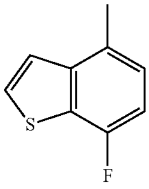 | 305 |
| 1537 | 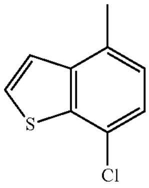 | 321 |
| 1538 | 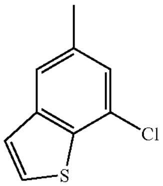 | 321 |

TABLE 159-continued
absolute configuration
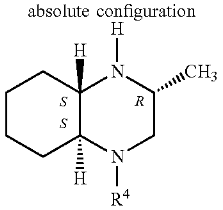
| Example. | $R^4$ | MS(M + 1) |
|---|---|---|
| 1539 | 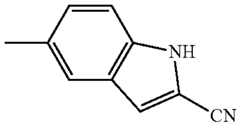 | 295 |
| 1540 | 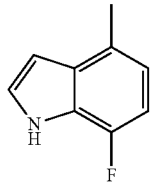 | 288 |
| 1541 | 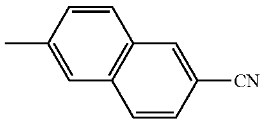 | 306 |
| 1542 | 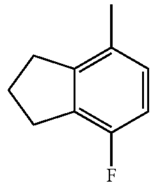 | 289 |
| 1543 | 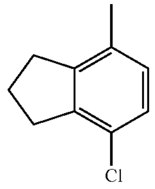 | 305 |
TABLE 160
absolute configuration
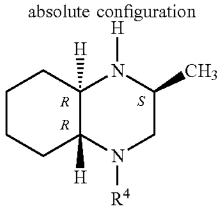
| Example. | $R^4$ | MS(M + 1) |
|---|---|---|
| 1544 | 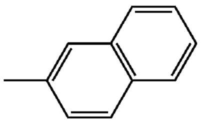 | 281 |
TABLE 160-continued
absolute configuration
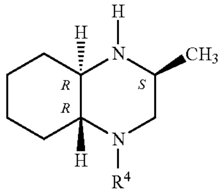
| Example. | $R^4$ | MS(M + 1) |
|---|---|---|
| 1545 | 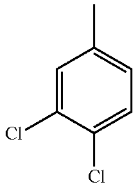 | 299 |
| 1546 | 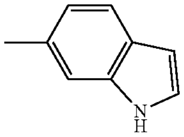 | 270 |
| 1547 | 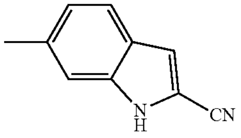 | 295 |
| 1548 | 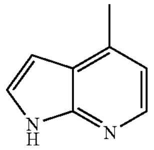 | 271 |
| 1549 | 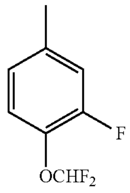 | 315 |
| 1550 | 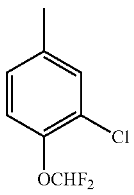 | 331 |
| 1551 | 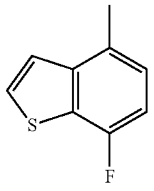 | 305 |

TABLE 160-continued
absolute configuration
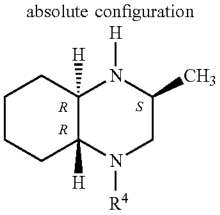
| Example. | $R^4$ | MS(M + 1) |
|---|---|---|
| 1552 | 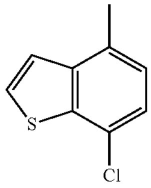 | 321 |
| 1553 | 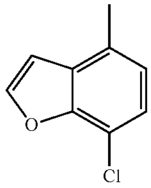 | 305 |
| 1554 | 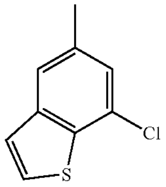 | 321 |
| 1555 | 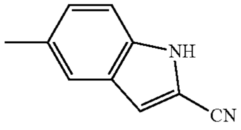 | 295 |
| 1556 | 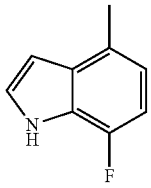 | 288 |
| 1557 | 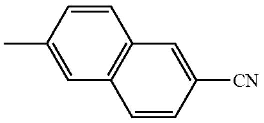 | 306 |
TABLE 160-continued
absolute configuration
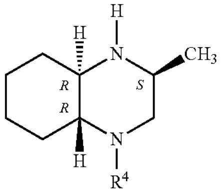
| Example. | $R^4$ | MS(M + 1) |
|---|---|---|
| 1558 | 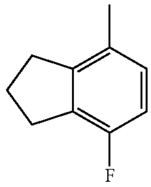 | 289 |
| 1559 | 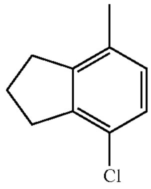 | 305 |
TABLE 161
relative configuration
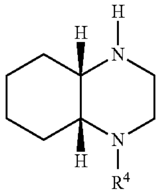
| Example. | $R^4$ | MS(M + 1) |
|---|---|---|
| 1560 | 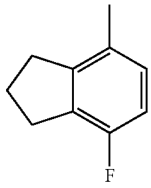 | 275 |
| 1561 | 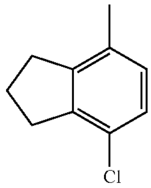 | 291 |

TABLE 162
absolute configuration
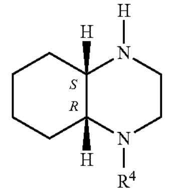
| Example. | $R^4$ | MS(M + 1) |
|---|---|---|
| 1562 | 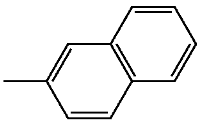 | 267 |
| 1563 | 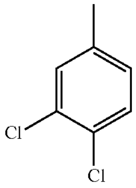 | 285 |
| 1564 | 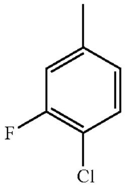 | 269 |
| 1565 | 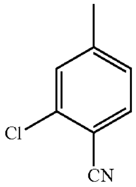 | 276 |
| 1566 | 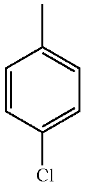 | 251 |
| 1567 | 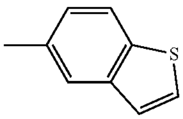 | 273 |
| 1568 | 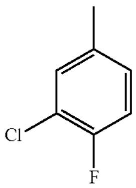 | 269 |
TABLE 162-continued
absolute configuration
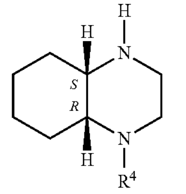
| Example. | $R^4$ | MS(M + 1) |
|---|---|---|
| 1569 | 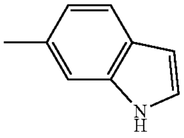 | 256 |
| 1570 | 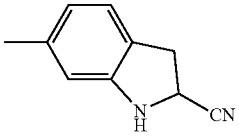 | 281 |
| 1571 | 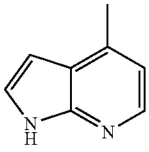 | 257 |
| 1572 | 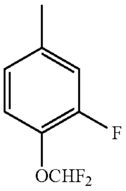 | 301 |
| 1573 | 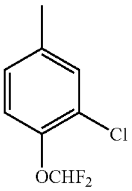 | 317 |
| 1574 | 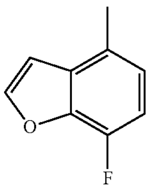 | 275 |
| 1575 | 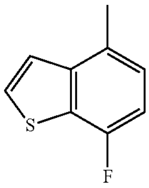 | 291 |

TABLE 162-continued
absolute configuration
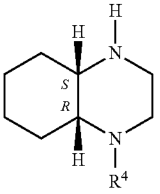
| Example. | $R^4$ | MS(M + 1) |
|---|---|---|
| 1576 | 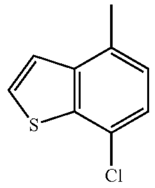 | 307 |
| 1577 | 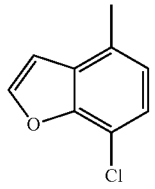 | 291 |
| 1578 | 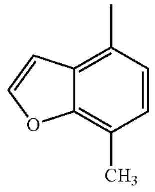 | 271 |
| 1579 | 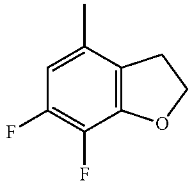 | 293 |
| 1580 | 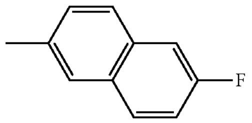 | 285 |
| 1581 | 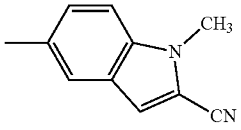 | 295 |
| 1582 | 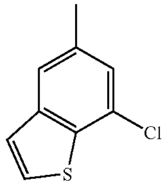 | 307 |
TABLE 162-continued
absolute configuration
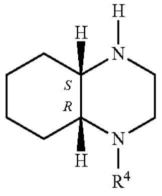
| Example. | $R^4$ | MS(M + 1) |
|---|---|---|
| 1583 | 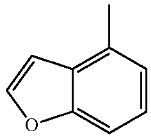 | 257 |
| 1584 | 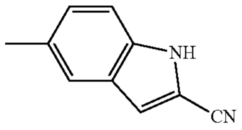 | 281 |
| 1585 | 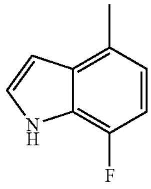 | 274 |
| 1586 | 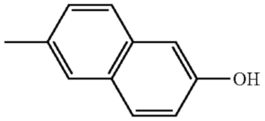 | 283 |
| 1587 | 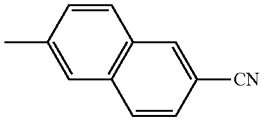 | 292 |
TABLE 163
absolute configuration
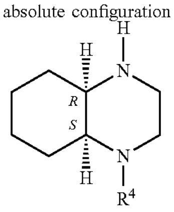
| Example. | $R^4$ | MS(M + 1) |
|---|---|---|
| 1588 | 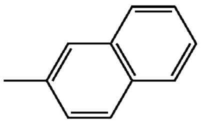 | 267 |

TABLE 163-continued
absolute configuration
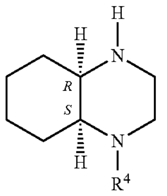
| Example. | $R^4$ | MS(M + 1) |
|---|---|---|
| 1589 | 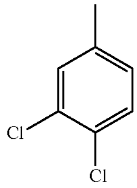 | 285 |
| 1590 | 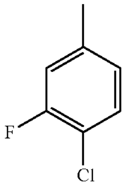 | 269 |
| 1591 | 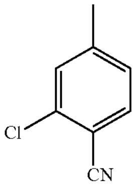 | 276 |
| 1592 | 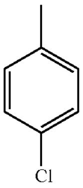 | 251 |
| 1593 | 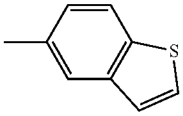 | 273 |
| 1594 | 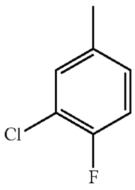 | 269 |
| 1595 | 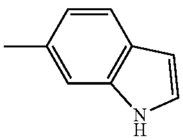 | 256 |
TABLE 163-continued
absolute configuration
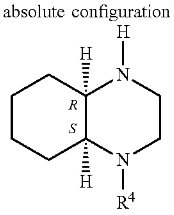
| Example. | $R^4$ | MS(M + 1) |
|---|---|---|
| 1596 | 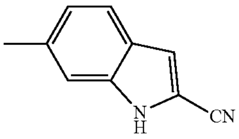 | 281 |
| 1597 | 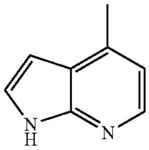 | 257 |
| 1598 | 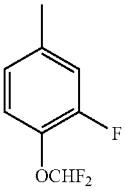 | 301 |
| 1599 | 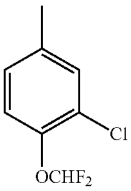 | 317 |
| 1600 | 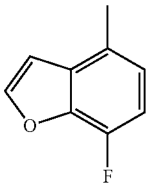 | 275 |
| 1601 | 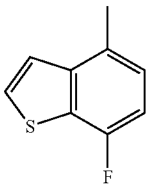 | 291 |
| 1602 | 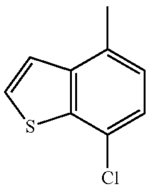 | 307 |

TABLE 163-continued
absolute configuration
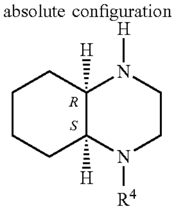
| Example. | $R^4$ | MS(M + 1) |
|---|---|---|
| 1603 | 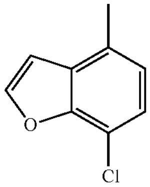 | 291 |
| 1604 | 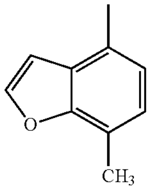 | 271 |
| 1605 | 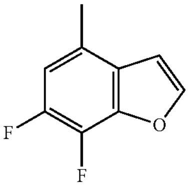 | 293 |
| 1606 | 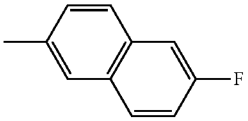 | 285 |
| 1607 | 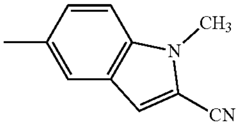 | 295 |
| 1608 | 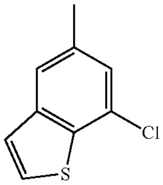 | 307 |
| 1609 | 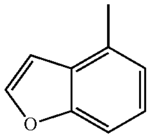 | 257 |
| 1610 | 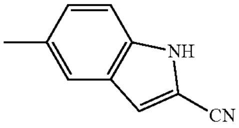 | 281 |
TABLE 163-continued
absolute configuration
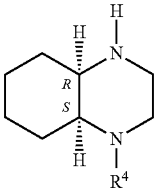
| Example. | $R^4$ | MS(M + 1) |
|---|---|---|
| 1611 | 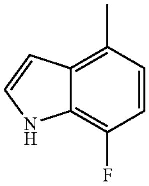 | 274 |
| 1612 | 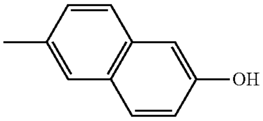 | 283 |
| 1613 | 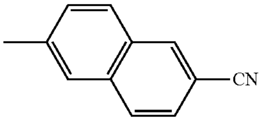 | 292 |
TABLE 164
absolute configuration
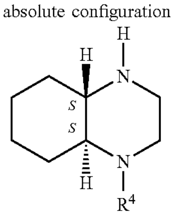
| Example. | $R^4$ | MS(M + 1) |
|---|---|---|
| 1614 | 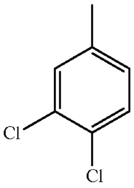 | 285 |
| 1615 | 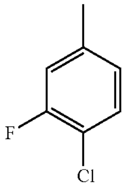 | 269 |

TABLE 164-continued
absolute configuration
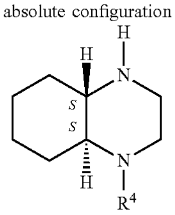
| Example. | $R^4$ | MS(M + 1) |
|---|---|---|
| 1616 | 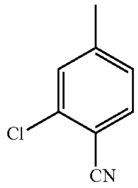 | 276 |
| 1617 | 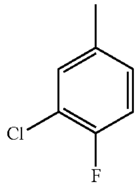 | 269 |
| 1618 | 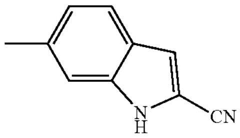 | 281 |
| 1619 | 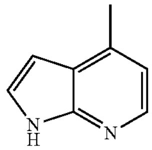 | 257 |
| 1620 | 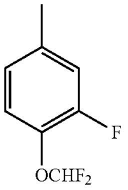 | 301 |
| 1621 | 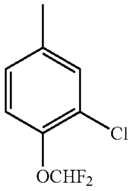 | 317 |
| 1622 | 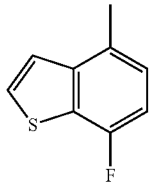 | 291 |
TABLE 164-continued
absolute configuration
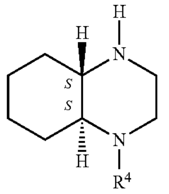
| Example. | $R^4$ | MS(M + 1) |
|---|---|---|
| 1623 | 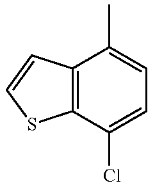 | 307 |
| 1624 | 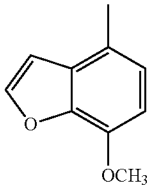 | 287 |
| 1625 | 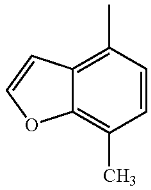 | 271 |
| 1626 | 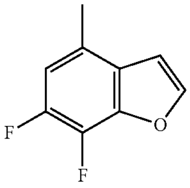 | 293 |
| 1627 | 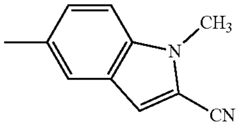 | 295 |
| 1628 | 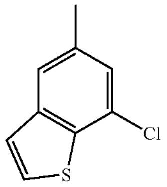 | 307 |
| 1629 | 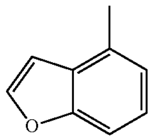 | 257 |

TABLE 164-continued
absolute configuration
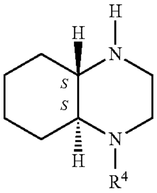
| Example. | $R^4$ | MS(M + 1) |
|---|---|---|
| 1630 | 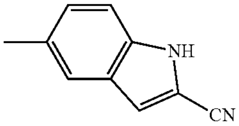 | 281 |
| 1631 | 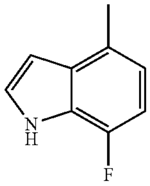 | 274 |
| 1632 | 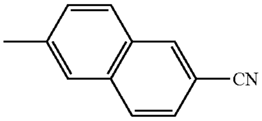 | 292 |
| 1633 | 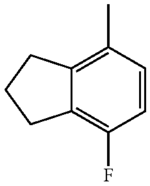 | 275 |
| 1634 | 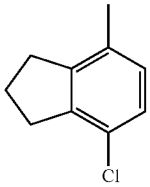 | 291 |
TABLE 165
absolute configuration
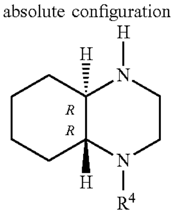
| Example. | $R^4$ | MS(M + 1) |
|---|---|---|
| 1635 | 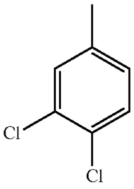 | 285 |
| 1636 | 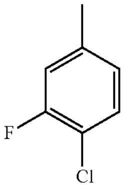 | 269 |
| 1637 | 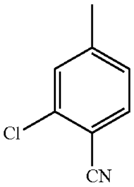 | 276 |
| 1638 | 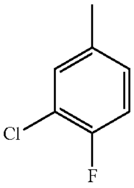 | 269 |
| 1639 | 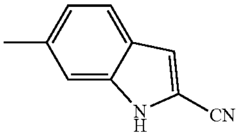 | 281 |
| 1640 | 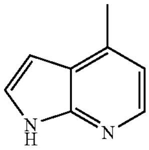 | 257 |
| 1641 | 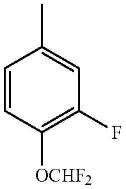 | 301 |

TABLE 165-continued
absolute configuration
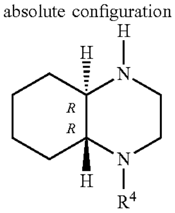
| Example. | $R^4$ | MS(M + 1) |
|---|---|---|
| 1642 | 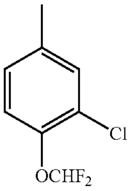 | 317 |
| 1643 | 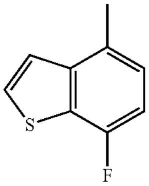 | 291 |
| 1644 | 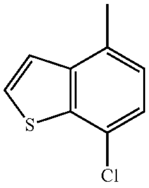 | 307 |
| 1645 | 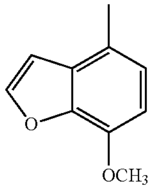 | 287 |
| 1646 | 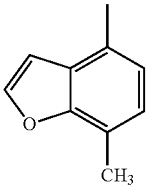 | 271 |
| 1647 | 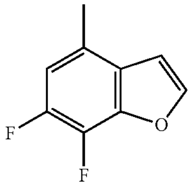 | 293 |
| 1648 | 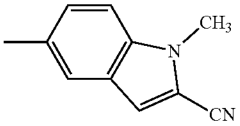 | 295 |
TABLE 165-continued
absolute configuration
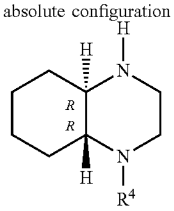
| Example. | $R^4$ | MS(M + 1) |
|---|---|---|
| 1649 | 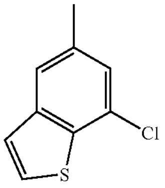 | 307 |
| 1650 | 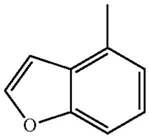 | 257 |
| 1651 | 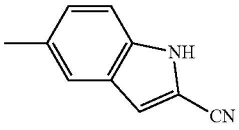 | 281 |
| 1652 | 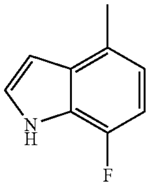 | 274 |
| 1653 | 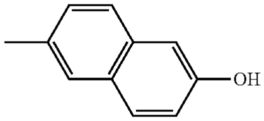 | 283 |
| 1654 | 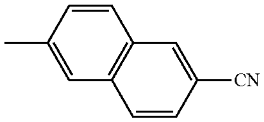 | 292 |
| 1655 | 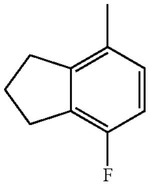 | 275 |
| 1656 | 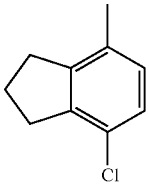 | 291 |

Pharmacological Study 1

Measurement of Serotonin (5-HT) Uptake Inhibitory Activity of Test Compound Using Rat Brain Synaptosome Male Wistar rats were decapitated, and their brains were removed and dissected to remove the frontal cortex. The separated frontal cortex was placed in a 20-fold weight of a 0.32 molarity (M) sucrose solution and homogenized with a potter homogenizer. The homogenate was centrifuged at 1000 g at 4° C. for 10 minutes, and the supernatant was further centrifuged at 20000 g at 4° C. for 20 minutes. The pellet was suspended in an incubation buffer (20 mM HEPES buffer (pH 7.4) containing 10 mM glucose, 145 mM sodium chloride, 4.5 mM potassium chloride, 1.2 mM magnesium chloride, and 1.5 mM calcium chloride). The suspension was used as a crude synaptosome fraction.

Uptake reaction was performed using each well of a 96-well round-bottom plate and a 200 μl volume in total of a solution containing pargyline (final concentration: 10 μM) and ascorbic acid (final concentration: 0.2 mg/ml).

Specifically, a solvent, unlabeled 5-HT, and serially diluted test compounds were separately added to the wells, and the synaptosome fraction was added in an amount 1/10 of the final volume to each well and preincubated at 37° C. for 10 minutes. Then, a tritium-labeled 5-HT solution (final concentration: 8 nM) was added thereto to initiate uptake reaction at 37° C. 10 minutes later, the uptake reaction was terminated by suction filtration through a 96-well glass fiber filter plate. Furthermore, the filter was washed with a cold saline and then sufficiently dried. MicroScint-O (PerkinElmer Co., Ltd.) was added thereto, and the residual radioactivity on the filter was measured.

An uptake value obtained by the addition of only the solvent was defined as 100%, and an uptake value (nonspecific uptake value) obtained by the addition of the unlabeled 5-HT (final concentration: 10 μM) was defined as 0%. A 50%, inhibitory concentration was calculated from the test compound concentrations and inhibitory activities thereat. The results are shown in Table 60.

TABLE 60

| Test compound | 50% Inhibitory concentration (nM) |
|---|---|
| Compound of Example 2 | 7.1 |
| Compound of Example 7 | 1.0 |
| Compound of Example 8 | 2.4 |
| Compound of Example 10 | 6.2 |
| Compound of Example 13 | 5.1 |
| Compound of Example 15 | 12.5 |
| Compound of Example 27 | 5.8 |
| Compound of Example 33 | 2.6 |
| Compound of Example 72 | 2.6 |
| Compound of Example 77 | 0.8 |
| Compound of Example 85 | 7.2 |
| Compound of Example 106 | 9.7 |
| Compound of Example 112 | 7.1 |
| Compound of Example 118 | 13.7 |
| Compound of Example 120 | 9.2 |
| Compound of Example 124 | 8.5 |
| Compound of Example 125 | 4.7 |
| Compound of Example 130 | 5.3 |
| Compound of Example 131 | 6.1 |
| Compound of Example 132 | 8.8 |
| Compound of Example 136 | 1.3 |
| Compound of Example 150 | 5.4 |
| Compound of Example 165 | 12.0 |
| Compound of Example 186 | 5.2 |
| Compound of Example 187 | 5.8 |
| Compound of Example 188 | 6.0 |
| Compound of Example 191 | 3.2 |

TABLE 60-continued

| Test compound | 50% Inhibitory concentration (nM) |
|---|---|
| Compound of Example 192 | 2.9 |
| Compound of Example 193 | 3.4 |
| Compound of Example 196 | 4.4 |
| Compound of Example 233 | 7.4 |
| Compound of Example 246 | 6.8 |
| Compound of Example 247 | 42.8 |
| Compound of Example 273 | 44.0 |
| Compound of Example 276 | 7.2 |
| Compound of Example 281 | 5.8 |
| Compound of Example 285 | 19.7 |
| Compound of Example 288 | 56.1 |
| Compound of Example 300 | 89.1 |
| Compound of Example 307 | 19.3 |
| Compound of Example 322 | 9.6 |
| Compound of Example 344 | 6.8 |
| Compound of Example 346 | 10.0 |
| Compound of Example 348 | 6.4 |
| Compound of Example 405 | 6.4 |
| Compound of Example 409 | 35.6 |
| Compound of Example 468 | 3.8 |
| Compound of Example 577 | 5.2 |
| Compound of Example 579 | 4.5 |
| Compound of Example 580 | 2.5 |
| Compound of Example 582 | 4.1 |
| Compound of Example 586 | 5.2 |
| Compound of Example 587 | 0.9 |
| Compound of Example 593 | 4.9 |
| Compound of Example 610 | 4.6 |
| Compound of Example 621 | 7.0 |
| Compound of Example 641 | 2.2 |
| Compound of Example 654 | 1.5 |
| Compound of Example 717 | 4.2 |
| Compound of Example 778 | 87.5 |
| Compound of Example 780 | 6.5 |
| Compound of Example 781 | 6.2 |
| Compound of Example 791 | 1.4 |
| Compound of Example 805 | 42.6 |
| Compound of Example 841 | 28.1 |
| Compound of Example 850 | 7.3 |
| Compound of Example 867 | 4.7 |
| Compound of Example 884 | 7.3 |
| Compound of Example 895 | 5.4 |
| Compound of Example 918 | 10.0 |
| Compound of Example 962 | 18.7 |
| Compound of Example 983 | 6.5 |
| Compound of Example 993 | 4.8 |
| Compound of Example 1026 | 2.4 |
| Compound of Example 1047 | 0.7 |
| Compound of Example 1083 | 5.1 |
| Compound of Example 1113 | 5.4 |
| Compound of Example 1121 | 8.5 |
| Compound of Example 1124 | 7.1 |
| Compound of Example 1318 | 40.7 |
| Compound of Example 1326 | 37.8 |
| Compound of Example 1333 | 84.2 |
| Compound of Example 1341 | 6.8 |
| Compound of Example 1534 | 38.1 |

Pharmacological Study 2

Measurement of Norepinephrine (NE) Uptake Inhibitory Activity of Test Compound Using Rat Brain Synaptosome Male Wistar rats were decapitated, and their brains were removed and dissected to remove the hippocampus. The separated hippocampus was placed in a 20-fold weight of a 0.32 molarity (M) sucrose solution and homogenized with a potter homogenizer. The homogenate was centrifuged at 1000 g at 4° C. for 10 minutes, and the supernatant was further centrifuged at 20000 g at 4° C. for 20 minutes. The pellet was suspended in an incubation buffer (20 mM HEPES buffer (pH 7.4) containing 10 mM glucose, 145 mM sodium chloride, 4.5 mM potassium chloride, 1.2 mM magnesium chloride, and 1.5 mM calcium chloride). The suspension was used as a crude synaptosome fraction.

Uptake reaction was performed using each well of a 96-well round-bottom plate and a 200 μl volume in total of a solution containing pargyline (final concentration: 10 μM) and ascorbic acid (final concentration: 0.2 mg/ml).

Specifically, a solvent, unlabeled NE, and serially diluted test compounds were separately added to the wells, and the synaptosome fraction was added in an amount 1/10 of the final volume to each well and preincubated at 37° C. for 10 minutes. Then, a tritium-labeled NE solution (final concentration: 12 nM) was added thereto to initiate uptake reaction at 37° C. Ten minutes later, the uptake reaction was terminated by suction filtration through a 96-well glass fiber filter plate. Furthermore, the filter was washed with a cold saline and then sufficiently dried. MicroScint-O (PerkinElmer Co., Ltd.) was added thereto, and the residual radioactivity on the filter was measured.

An uptake value obtained by the addition of only the solvent was defined as 100%, and an uptake value (nonspecific uptake value) obtained by the addition of the unlabeled NE (final concentration: 10 μM) was defined as 0%. A 50% inhibitory concentration was calculated from the test compound concentrations and inhibitory activities thereat. The results are shown in Table 61.

TABLE 61

| Test compound | 50% inhibitory concentration (nM) |
|---|---|
| Compound of Example 2 | 4.6 |
| Compound of Example 7 | 9.5 |
| Compound of Example 8 | 60.9 |
| Compound of Example 10 | 8.8 |
| Compound of Example 13 | 14.3 |
| Compound of Example 15 | 11.0 |
| Compound of Example 27 | 0.9 |
| Compound of Example 33 | 0.7 |
| Compound of Example 72 | 1.0 |
| Compound of Example 77 | 3.9 |
| Compound of Example 85 | 4.9 |
| Compound of Example 106 | 37.2 |
| Compound of Example 112 | 87.3 |
| Compound of Example 118 | 3.7 |
| Compound of Example 120 | 9.2 |
| Compound of Example 124 | 0.8 |
| Compound of Example 125 | 1.9 |
| Compound of Example 130 | 0.5 |
| Compound of Example 131 | 0.7 |
| Compound of Example 132 | 3.1 |
| Compound of Example 136 | 0.5 |
| Compound of Example 150 | 23.6 |
| Compound of Example 165 | 2.4 |
| Compound of Example 186 | 3.8 |
| Compound of Example 187 | 6.0 |
| Compound of Example 188 | 0.8 |
| Compound of Example 191 | 2.1 |
| Compound of Example 192 | 3.6 |
| Compound of Example 193 | 4.4 |
| Compound of Example 196 | 1.7 |
| Compound of Example 233 | 3.7 |
| Compound of Example 246 | 3.8 |
| Compound of Example 247 | 6.6 |
| Compound of Example 273 | 6.8 |
| Compound of Example 276 | 4.5 |
| Compound of Example 281 | 2.0 |
| Compound of Example 285 | 1.4 |
| Compound of Example 288 | 22.0 |
| Compound of Example 300 | 9.9 |
| Compound of Example 307 | 40.4 |
| Compound of Example 322 | 40.1 |
| Compound of Example 344 | 7.5 |
| Compound of Example 346 | 8.8 |
| Compound of Example 348 | 4.6 |
| Compound of Example 405 | 4.4 |

TABLE 61-continued

| Test compound | 50% inhibitory concentration (nM) |
|---|---|
| Compound of Example 409 | 9.1 |
| Compound of Example 468 | 7.5 |
| Compound of Example 577 | 5.9 |
| Compound of Example 579 | 5.1 |
| Compound of Example 580 | 5.4 |
| Compound of Example 582 | 6.0 |
| Compound of Example 586 | 4.0 |
| Compound of Example 587 | 1.9 |
| Compound of Exainple 593 | 3.1 |
| Compound of Example 610 | 5.9 |
| Compound of Example 621 | 0.7 |
| Compound of Example 641 | 76.0 |
| Compound of Example 654 | 1.0 |
| Compound of Example 717 | 4.8 |
| Compound of Example 778 | 4.2 |
| Compound of Example 780 | 0.6 |
| Compound of Example 781 | 3.0 |
| Compound of Example 791 | 0.7 |
| Compound of Example 805 | 30.4 |
| Compound of Example 841 | 0.9 |
| Compound of Example 850 | 1.0 |
| Compound of Example 867 | 11.7 |
| Compound of Example 884 | 4.8 |
| Compound of Example 895 | 3.0 |
| Compound of Example 918 | 0.8 |
| Compound of Example 962 | 31.9 |
| Compound of Example 983 | 47.6 |
| Compound of Example 993 | 8.7 |
| Compound of Example 1026 | 4.2 |
| Compound of Example 1047 | 0.7 |
| Compound of Example 1083 | 2.5 |
| Compound of Example 1113 | 1.7 |
| Compound of Example 1121 | 0.7 |
| Compound of Example 1124 | 0.8 |
| Compound of Example 1318 | 6.6 |
| Compound of Example 1326 | 1.8 |
| Compound of Example 1333 | 39.6 |
| Compound of Example 1341 | 42.7 |
| Compound of Example 1534 | 4.0 |

Pharmacological Study 3

Measurement of Dopamine (DA) Uptake Inhibitory Activity of Test Compound Using Rat Brain Synaptosome Male Wistar rats were decapitated, and their brains were removed and dissected to remove the corpus striatum. The separated corpus striatum was placed in a 20-fold weight of a 0.32 molarity (M) sucrose solution and homogenized with a potter homogenizer. The homogenate was centrifuged at 1000 g at 4° C. for 10 minutes, and the supernatant was further centrifuged at 20000 g at 4° C. for 20 minutes. The pellet was suspended in an incubation buffer (20 mM HEPES buffer (pH 7.4) containing 10 mM glucose, 145 mM sodium chloride, 4.5 mM potassium chloride, 1.2 mM magnesium chloride, and 1.5 mM calcium chloride). The suspension was used as a crude synaptosome fraction.

Uptake reaction was performed using each well of a 96-well round-bottom plate and a 200 μl volume in total of a solution containing pargyline (final concentration: 10 μM) and ascorbic acid (final concentration: 0.2 mg/mil).

Specifically, a solvent, unlabeled DA, and serially diluted test compounds were separately added to the wells, and the synaptosome fraction was added in an amount 1/10 of the final volume to each well and preincubated at 37° C. for 10 minutes. Then, a tritium-labeled DA solution (final concentration: 2 nM) was added thereto to initiate uptake reaction at 37° C. Ten minutes later, the uptake reaction was terminated by suction filtration through a 96-well glass fiber filter plate. Furthermore, the filter was washed with a cold saline and then sufficiently dried. MicroScint-O (PerkinElmer Co., Ltd.) was added thereto, and the residual radioactivity on the filter was measured.

An uptake value obtained by the addition of only the solvent was defined as 100%, and an uptake value (nonspecific uptake value) obtained by the addition of the unlabeled DA (final concentration: 10 μM) was defined as 0%. A 50% inhibitory concentration was calculated from the test compound concentrations and inhibitory activities thereat. The results are shown in Table 62.

TABLE 62

| Test compound | 50% Inhibitory concentration (nM) |
|---|---|
| Compound of Example 2 | 85.9 |
| Compound of Example 7 | 78.9 |
| Compound of Example 8 | 377.8 |
| Compound of Example 10 | 64.8 |
| Compound of Example 13 | 85.4 |
| Compound of Example 15 | 68.4 |
| Compound of Example 27 | 31.9 |
| Compound of Example 33 | 15.1 |
| Compound of Example 72 | 47.9 |
| Compound of Example 77 | 41.2 |
| Compound of Example 85 | 95.7 |
| Compound of Example 106 | 336.8 |
| Compound of Example 112 | 263.7 |
| Compound of Example 118 | 8.3 |
| Compound of Example 120 | 187.2 |
| Compound of Example 124 | 9.1 |
| Compound of Example 125 | 5.2 |
| Compound of Example 130 | 3.9 |
| Compound of Example 131 | 8.3 |
| Compound of Example 132 | 3.9 |
| Compound of Example 136 | 7.7 |
| Compound of Example 150 | 200.5 |
| Compound of Example 165 | 6.8 |
| Compound of Example 186 | 29.8 |
| Compound of Example 187 | 12.1 |
| Compound of Example 188 | 7.9 |
| Compound of Example 191 | 13.5 |
| Compound of Example 192 | 8.6 |
| Compound of Example 193 | 5.7 |
| Compound of Example 196 | 18.3 |
| Compound of Example 233 | 38.8 |
| Compound of Example 246 | 8.8 |
| Compound of Example 247 | 8.7 |
| Compound of Example 273 | 8.7 |
| Compound of Example 276 | 10.9 |
| Compound of Example 281 | 6.6 |
| Compound of Example 285 | 43.9 |
| Compound of Example 288 | 74.7 |
| Compound of Example 300 | 81.3 |
| Compound of Example 307 | 68.2 |
| Compound of Example 322 | 67.7 |
| Compound of Example 344 | 9.8 |
| Compound of Example 346 | 7.8 |
| Compound of Example 348 | 27.3 |
| Compound of Example 405 | 74.8 |
| Compound of Example 409 | 165.3 |
| Compound of Example 468 | 54.0 |
| Compound of Example 577 | 47.9 |
| Compound of Example 579 | 46.5 |
| Compound of Example 580 | 202.0 |
| Compound of Example 582 | 68.8 |
| Compound of Example 586 | 93.0 |
| Compound of Example 587 | 76.1 |
| Compound of Example 593 | 9.7 |
| Compound of Example 610 | 13.2 |
| Compound of Example 621 | 128.5 |
| Compound of Example 641 | 9.7 |
| Compound of Example 654 | 9.0 |
| Compound of Example 717 | 60.1 |
| Compound of Example 778 | 4.9 |
| Compound of Example 780 | 4.3 |

TABLE 62-continued

| Test compound | 50% Inhibitory concentration (nM) |
|---|---|
| Compound of Example 781 | 5.2 |
| Compound of Example 791 | 160.9 |
| Compound of Example 805 | 83.8 |
| Compound of Example 841 | 5.1 |
| Compound of Example 850 | 7.0 |
| Compound of Example 867 | 85.7 |
| Compound of Example 884 | 52.8 |
| Compound of Example 895 | 19.9 |
| Compound of Example 918 | 42.0 |
| Compound of Example 962 | 69.5 |
| Compound of Example 983 | 172.6 |
| Compound of Example 993 | 38.6 |
| Compound of Example 1026 | 12.3 |
| Compound of Example 1047 | 1.1 |
| Compound of Example 1083 | 53.7 |
| Compound of Example 1113 | 26.0 |
| Compound of Example 1121 | 29.9 |
| Compound of Example 1124 | 49.3 |
| Compound of Example 1318 | 83.5 |
| Compound of Example 1326 | 91.8 |
| Compound of Example 1333 | 73.0 |
| Compound of Example 1341 | 113.3 |
| Compound of Example 1534 | 214.8 |

Pharmacological Study 4

Forced Swimming Test

This test was conducted according to the method of Porsolt et al. (Porsolt, R. D., et al., Behavioural despair in mice: A primary screening test for antidepressants. Arch. int. Pharmacodyn. Ther., 229, pp 327-336 (1977)).

A test compound was suspended in a 5% gum arabic/saline (w/v), and this suspension was orally administered to male ICR mice (CLEA Japan, Inc. (JCL), 5 to 6 week old). One hour later, the mice were placed in a water tank having a water depth of 9.5 cm and a water temperature of 21 to 25° C. and immediately thereafter allowed to try to swim for 6 minutes. Then, a time during which the mouse was immobile (immobility time) was measured for the last 4 minutes. A SCANET MV-20 AQ system manufactured by Melquest Ltd. was used in the measurement and analysis of the immobility time.

In this experiment, the animals treated with the test compounds exhibited a reduction in immobility time. This demonstrates that the test compounds are useful as antidepressants.

The invention claimed is:

1. A method for treating anxiety caused by adjustment disorder, anxiety caused by various diseases and/or generalized anxiety disorder, comprising administering to a subject in need a compound represented by the formula (1) or a pharmaceutically acceptable salt thereof:

(1)

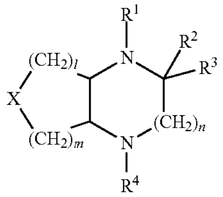

wherein m=2, l=1 and n=1;

X represents $CH_2$—;

$R^1$ represents hydrogen, a C1-C6 alkyl group, a hydroxy C1-C6 alkyl group, a protecting group selected from unsubstituted C1 alkanoyl, phthaloyl, C1-C6 alkoxycarbonyl, unsubstituted aralkyloxycarbonyl, 9-fluorenylmethoxycarbonyl, nitrophenylsulfenyl, aralkyl and C1-C6 alkylsilyl groups, or a tri C1-C6 alkylsilyloxy C1-C6 alkyl group;

$R^2$ and $R^3$, which are the same or different, each independently represent hydrogen or a C1-C6 alkyl group; or $R_2$ and $R_3$ are bonded to form a cyclo-C3-C8 alkyl group; and $R^4$ represents any of (1) a phenyl group,
(2) an indolyl group,
(3) a benzothienyl group,
(4) a naphthyl group,
(5) a benzofuryl group,
(6) a quinolyl group,
(7) an isoquinolyl group,
(8) a pyridyl group,
(9) a thienyl group,
(10) a dihydrobenzoxazinyl group,
(11) a dihydrobenzodioxinyl group,
(12) a dihydroquinolyl group,
(13) a chromanyl group,
(14) a quinoxalinyl group,
(15) a dihydroindenyl group,
(16) a dihydrobenzofuryl group,
(17) a benzodioxolyl group,
(18) an indazolyl group,
(19) a benzothiazolyl group,
(20) an indolinyl group,
(21) a thienopyridyl group,
(22) a tetrahydrobenzazepinyl group,
(23) a tetrahydrobenzodiazepinyl group,
(24) a dihydrobenzodioxepinyl group,
(25) a fluorenyl group,
(26) a pyridazinyl group,
(27) a tetrahydroquinolyl group,
(28) a carbazolyl group,
(29) a phenanthryl group,
(30) a dihydroacenaphthylenyl group,
(31) a pyrrolopyridyl group,
(32) an anthryl group,
(33) a benzodioxinyl group,
(34) a pyrrolidinyl group,
(35) a pyrazolyl group,
(36) an oxadiazolyl group,
(37) a pyrimidinyl group,
(38) a tetrahydronaphthyl group,
(39) a dihydroquinazolinyl group,
(40) a benzoxazolyl group,
(41) a thiazolyl group,
(42) a quinazolinyl group,
(43) a phthalazinyl group,
(44) a pyrazinyl group, and
(45) a chromenyl group, wherein these aromatic or heterocyclic groups may have one or more substituent(s) selected from (1-1) a halogen atom,
(1-2) a C1-C6 alkyl group,
(1-3) a C1-C6 alkanoyl group,
(1-4) a halogen-substituted C1-C6 alkyl group,
(1-5) a halogen-substituted C1-C6 alkoxy group,
(1-6) a cyano group,
(1-7) a C1-C6 alkoxy group,
(1-8) a C1-C6 alkylthio group,
(1-9) an imidazolyl group,
(1-10) a tri C1-C6 alkylsilyl group,
(1-11) an oxadiazolyl group which may have one or more C1-C6 alkyl group(s),
(1-12) a pyrrolidinyl group which may have one or more oxo group(s),
(1-13) a phenyl group which may have one or more C1-C6 alkoxy group(s),
(1-14) a C1-C6 alkylamino C1-C6 alkyl group,
(1-15) an oxo group,
(1-16) a pyrazolyl group which may have one or more C1-C6 alkyl group(s),
(1-17) a thienyl group,
(1-18) a furyl group,
(1-19) a thiazolyl group which may have one or more C1-C6 alkyl group(s),
(1-20) a C1-C6 alkylamino group,
(1-21) a pyrimidyl group which may have one or more C1-C6 alkyl group(s),
(1-22) a phenyl C2-C6 alkenyl group,
(1-23) a phenoxy group which may have one or more halogen atom(s),
(1-24) a phenoxy C1-C6 alkyl group,
(1-25) a pyrrolidinyl C1-C6 alkoxy group,
(1-26) a C1-C6 alkylsulfamoyl group,
(1-27) a pyridazinyloxy group which may have one or more C1-C6 alkyl group(s),
(1-28) a phenyl C1-C6 alkyl group,
(1-29) a C1-C6 alkylamino C1-C6 alkoxy group,
(1-30) an imidazolyl C1-C6 alkyl group,
(1-31) a phenyl C1-C6 alkoxy group,
(1-32) a hydroxy group,
(1-33) a C1-C6 alkoxycarbonyl group,
(1-34) a hydroxyl C1-C6 alkyl group,
(1-35) an oxazolyl group,
(1-36) a piperidyl group,
(1-37) a pyrrolyl group,
(1-38) a morpholinyl C1-C6 alkyl group,
(1-39) a piperazinyl C1-C6 alkyl group which may have one or more C1-C6 alkyl group(s),
(1-40) a piperidyl C1-C6 alkyl group,
(1-41) a pyrrolidinyl C1-C6 alkyl group,
(1-42) a morpholinyl group, and
(1-43) a piperazinyl group which may have one or more C1-C6 alkyl group(s).

2. The method according to claim 1, wherein the anxiety caused by various diseases is selected from the group consisting of anxiety caused by head injury, brain infection, inner ear impairment, cardiac failure, arrhythmia, hyperadrenalism, hyperthyroidism, asthma and chronic obstructive pulmonary disease.

3. The method according to claim 1, wherein in the compound represented by the formula (1) or a pharmaceutically acceptable salt thereof $R^4$ represents any of (1) a phenyl group,
(2) an indolyl group,
(3) a benzothienyl group,
(4) a naphthyl group,
(5) a benzofuryl group,
(6) a quinolyl group,
(7) an isoquinolyl group,
(8) a pyridyl group,
(9) a thienyl group,
(10) a dihydrobenzoxazinyl group,
(11) a dihydrobenzodioxinyl group,
(12) a dihydroquinolyl group,
(13) a chromanyl group,
(14) a quinoxalinyl group,

(15) a dihydroindenyl group,
(16) a dihydrobenzofuryl group,
(17) a benzodioxolyl group,
(18) an indazolyl group,
(19) a benzothiazolyl group,
(20) an indolinyl group,
(21) a thienopyridyl group,
(22) a tetrahydrobenzazepinyl group,
(23) a tetrahydrobenzodiazepinyl group,
(24) a dihydrobenzodioxepinyl group,
(25) a fluorenyl group,
(26) a pyridazinyl group,
(27) a tetrahydroquinolyl group,
(28) a carbazolyl group,
(29) a phenanthryl group,
(30) a dihydroacenaphthylenyl group,
(31) a pyrrolopyridyl group,
(32) an anthryl group,
(33) a benzodioxinyl group,
(34) a pyrrolidinyl group,
(35) a pyrazolyl group,
(36) an oxadiazolyl group,
(37) a pyrimidinyl group,
(38) a tetrahydronaphthyl group,
(39) a dihydroquinazolinyl group,
(40) a benzoxazolyl group,
(41) a thiazolyl group,
(42) a quinazolinyl group,
(43) a phthalazinyl group,
(44) a pyrazinyl group, and
(45) a chromenyl group, wherein these aromatic or heterocyclic groups may have 1 to 4 substituent(s) selected from
(1-1) a halogen atom,
(1-2) a C1-C6 alkyl group,
(1-3) a C1-C6 alkanoyl group,
(1-4) a halogen-substituted C1-C6 alkyl group,
(1-5) a halogen-substituted C1-C6 alkoxy group,
(1-6) a cyano group,
(1-7) a C1-C6 alkoxy group,
(1-8) a C1-C6 alkylthio group,
(1-9) an imidazolyl group,
(1-10) a tri C1-C6 alkylsilyl group,
(1-11) an oxadiazolyl group which may have 1 C1-C6 alkyl group,
(1-12) a pyrrolidinyl group which may have 1 oxo group,
(1-13) a phenyl group which may have 1 C1-C6 alkoxy group,
(1-14) a C1-C6 alkylamino C1-C6 alkyl group,
(1-15) an oxo group,
(1-16) a pyrazolyl group which may have 1 C1-C6 alkyl group,
(1-17) a thienyl group,
(1-18) a furyl group,
(1-19) a thiazolyl group which may have 1 C1-C6 alkyl group,
(1-20) a C1-C6 alkylamino group,
(1-21) a pyrimidyl group which may have 1 C1-C6 alkyl group,
(1-22) a phenyl C2-C6 alkenyl group,
(1-23) a phenoxy group which may have 1 halogen atom,
(1-24) a phenoxy C1-C6 alkyl group,
(1-25) a pyrrolidinyl C1-C6 alkoxy group,
(1-26) a C1-C6 alkylsulfamoyl group,
(1-27) a pyridazinyloxy group which may have 1 C1-C6 alkyl group,
(1-28) a phenyl C1-C6 alkyl group,
(1-29) a C1-C6 alkylamino C1-C6 alkoxy group,
(1-30) an imidazolyl C1-C6 alkyl group,
(1-31) a phenyl C1-C6 alkoxy group,
(1-32) a hydroxy group,
(1-33) a C1-C6 alkoxycarbonyl group,
(1-34) a hydroxy C1-C6 alkyl group,
(1-35) an oxazolyl group,
(1-36) a piperidyl group,
(1-37) a pyrrolyl group,
(1-38) a morpholinyl C1-C6 alkyl group,
(1-39) a piperazinyl C1-C6 alkyl group which may have 1 C1-C6 alkyl group,
(1-40) a piperidyl C1-C6 alkyl group,
(1-41) a pyrrolidinyl C1-C6 alkyl group,
(1-42) a morpholinyl group, and
(1-43) a piperazinyl group which may have 1 C1-C6 alkyl group.

4. The method according to claim 1, wherein in the compound represented by the formula (1) or a pharmaceutically acceptable salt thereof m represents 2; I and n respectively represent 1;

X represents —$CH_2$—;

$R^1$ represents hydrogen, a C1-C6 alkyl group, a hydroxy C1-C6 alkyl group, a benzyl group, or a tri C1-C6 alkylsilyloxy C1-C6 alkyl group; and $R^4$ represents any of
(1) a phenyl group,
(2) an indolyl group,
(4) a naphthyl group,
(5) a benzofuryl group, and
(31) a pyrrolopyridyl group, wherein these aromatic or heterocyclic groups may have 1 to 4 substituent(s) selected from
(1-1) a halogen atom,
(1-2) a C1-C6 alkyl group,
(1-3) a C1-C6 alkanoyl group,
(1-4) a halogen-substituted C1-C6 alkyl group,
(1-5) a halogen-substituted C1-C6 alkoxy group,
(1-6) a cyano group,
(1-7) a C1-C6 alkoxy group,
(1-8) a C1-C6 alkylthio group,
(1-9) an imidazolyl group,
(1-10) a tri C1-C6 alkylsilyl group,
(1-11) an oxadiazolyl group which may have 1 C1-C6 alkyl group,
(1-12) a pyrrolidinyl group which may have 1 oxo group,
(1-13) a phenyl group which may have 1 C1-C6 alkoxy group,
(1-14) a C1-C6 alkylamino C1-C6 alkyl group,
(1-15) an oxo group,
(1-16) a pyrazolyl group which may have 1 C1-C6 alkyl group,
(1-17) a thienyl group,
(1-18) a furyl group,
(1-19) a thiazolyl group which may have 1 C1-C6 alkyl group,
(1-20) a C1-C6 alkylamino group,
(1-21) a pyrimidyl group which may have 1 C1-C6 alkyl group,
(1-22) a phenyl C2-C6 alkenyl group,
(1-23) a phenoxy group which may have 1 halogen atom,
(1-24) a phenoxy C1-C6 alkyl group,
(1-25) a pyrrolidinyl C1-C6 alkoxy group,
(1-26) a C1-C6 alkylsulfamoyl group,
(1-27) a pyridazinyloxy group which may have 1 C1-C6 alkyl group,
(1-28) a phenyl C1-C6 alkyl group, (1-29) a C1-C6 alkylamino C1-C6 alkoxy group,
(1-30) an imidazolyl C1-C6 alkyl group,
(1-31) a phenyl C1-C6 alkoxy group,
(1-32) a hydroxy group,
(1-34) a hydroxy C1-C6 alkyl group,
(1-35) an oxazolyl group,
(1-36) a piperidyl group,
(1-37) a pyrrolyl group,
(1-38) a morpholinyl C1-C6 alkyl group,
(1-39) a piperazinyl C1-C6 alkyl group which may have 1 C1-C6 alkyl group(s),
(1-40) a piperidyl C1-C6 alkyl group,
(1-41) a pyrrolidinyl C1-C6 alkyl group,
(1-42) a morpholinyl group, and
(1-43) a piperazinyl group which may have 1 C1-C6 alkyl group.

5. The method according to claim 1, wherein in the compound represented by the formula (1) or a pharmaceutically acceptable salt thereof $R^1$ represents hydrogen;
$R^2$ and $R^3$, which are the same or different, each independently represent a C1-C6 alkyl group; or $R^2$ and $R^3$ are bonded to form a cyclo-C3-C8 alkyl group; and
$R^4$ represents any of
(1) a phenyl group,
(2) an indolyl group,
(4) a naphthyl group,
(5) a benzofuryl group, and
(31) a pyrrolopyridyl group, wherein
these aromatic or heterocyclic groups may have 1 to 2 substituent(s) selected from
(1-1) a halogen atom,
(1-2) a C1-C6 alkyl group,
(1-5) a halogen-substituted C1-C6 alkoxy group,
(1-6) a cyano group, and
(1-7) a C1-C6 alkoxy group.

6. The method according to claim 1, wherein the compound represented by the formula (1) or a pharmaceutically acceptable salt thereof is selected from (4aS,8aR)-1-(4-chlorophenyl)-3,3-dimethyldecahydroquinoxaline,
2-chloro-4-((4aS,8aS)-3,3-dimethyloctahydroquinoxalin-1(2H)-yl)benzonitrile,
(4aS,8aR)-1-(3-chloro-4-fluorophenyl)-3,3-dimethyldecahydroquinoxaline,
(4aS,8aR)-1-(7-fluorobenzofuran-4-yl)-3,3-dimethyldecahydroquinoxaline,
5-((4aR,8aS)-3,3-dimethyloctahydroquinoxalin-1(2H)-yl)-1-methyl-1H-indole-2-carbonitrile,
(4a'R, 8a'S)-4'-(7-m ethoxybenzofuran-4-yl)octahydro-1'H-spiro[cyclobutane-1,2'-quinoxaline],
(4aS,8aR)-1-(6,7-difluorobenzofuran-4-yl)-3,3-dimethyldecahydroquinoxaline,
5-((4aS,8aS)-3,3-dimethyloctahydroquinoxalin-1(2H)-yl)-1H-indole-2-carbonitrile,
(4aS,8aR)-1-(7-chloro-2,3-dihydro-1H-inden-4-yl)-3,3-dimethyldecahydroquinoxaline,
6-((4aS,8aS)-3,3-dimethyloctahydroquinoxalin-1(2H)-yl)-2-naphthonitrile,
(4aS,8aS)-3,3-dimethyl-1-(1H-pyrrolo[2,3-b]pyridin-4-yl)decahydroquinoxaline,
(4aS,8aS)-1-(4-(difluoromethoxy)-3-fluorophenyl)-3,3-dimethyldecahydroquinoxaline,
(4aS,8aS)-1-(4-(difluoromethoxy)phenyl-3,3-dimethyldecahydroquinoxaline, and
(4aR,8aR)-1-(4-difluoromethyoxy)-3-fluorophenyl-3,3-dimethyldecahydroquinoxaline.

* * * * *